(12) United States Patent
Abeliovich et al.

(10) Patent No.: US 11,661,585 B2
(45) Date of Patent: May 30, 2023

(54) GENE THERAPIES FOR LYSOSOMAL DISORDERS

(71) Applicant: Prevail Therapeutics, Inc., New York, NY (US)

(72) Inventors: Asa Abeliovich, New York, NY (US); Laura Heckman, New York, NY (US); Herve Rhinn, New York, NY (US)

(73) Assignee: Prevail Therapeutics, Inc., New York, NY (US)

( * ) Notice: Subject to any disclaimer, the term of this patent is extended or adjusted under 35 U.S.C. 154(b) by 334 days.

(21) Appl. No.: 16/841,539

(22) Filed: Apr. 6, 2020

(65) Prior Publication Data
US 2020/0282080 A1 Sep. 10, 2020

Related U.S. Application Data

(63) Continuation of application No. 16/753,322, filed as application No. PCT/US2018/054227 on Oct. 3, 2018.

(60) Provisional application No. 62/567,296, filed on Oct. 3, 2017, provisional application No. 62/567,311, filed on Oct. 3, 2017, provisional application No. 62/567,319, filed on Oct. 3, 2017, provisional application No. 62/567,301, filed on Oct. 3, 2017, provisional application No. 62/567,310, filed on Oct. 3, 2017.

(51) Int. Cl.

| | |
|---|---|
| *C12N 7/00* | (2006.01) |
| *C07K 14/47* | (2006.01) |
| *A61K 35/76* | (2015.01) |
| *C07K 14/005* | (2006.01) |
| *C07K 14/61* | (2006.01) |
| *C07K 14/705* | (2006.01) |
| *C07K 14/435* | (2006.01) |
| *A61K 35/761* | (2015.01) |
| *C12N 15/861* | (2006.01) |
| *C12N 15/86* | (2006.01) |
| *C12N 15/864* | (2006.01) |
| *A61P 25/28* | (2006.01) |
| *A61K 9/00* | (2006.01) |
| *A61K 48/00* | (2006.01) |
| *A61P 25/16* | (2006.01) |
| *A61K 39/23* | (2006.01) |
| *C07H 21/04* | (2006.01) |

(52) U.S. Cl.
CPC ............. *C12N 7/00* (2013.01); *A61K 9/0019* (2013.01); *A61K 9/0085* (2013.01); *A61K 35/76* (2013.01); *A61K 35/761* (2013.01); *A61K 48/0058* (2013.01); *A61K 48/0075* (2013.01); *A61P 25/16* (2018.01); *A61P 25/28* (2018.01); *C07K 14/005* (2013.01); *C07K 14/435* (2013.01); *C07K 14/47* (2013.01); *C07K 14/61* (2013.01); *C07K 14/70503* (2013.01); *C12N 15/861* (2013.01); *A61K 39/23* (2013.01); *C07H 21/04* (2013.01); *C12N 15/86* (2013.01); *C12N 15/8645* (2013.01); *C12N 2750/14022* (2013.01); *C12N 2750/14043* (2013.01); *C12N 2750/14121* (2013.01); *C12N 2750/14122* (2013.01); *C12N 2750/14143* (2013.01); *C12Y 302/01045* (2013.01)

(58) Field of Classification Search
CPC ................ A61K 9/0019; A61K 9/0085; A61K 35/761; A61K 48/0075; A61P 25/16; C07K 14/435
See application file for complete search history.

(56) References Cited

U.S. PATENT DOCUMENTS

| | | |
|---|---|---|
| 5,879,680 A | 3/1999 | Ginns et al. |
| 6,521,225 B1 | 2/2003 | Srivasta et al. |
| 6,696,272 B1 | 2/2004 | Mahuran et al. |
| 7,172,893 B2 | 2/2007 | Rabinowitz |
| 7,452,716 B2 | 11/2008 | Yew |
| 8,389,487 B2 | 3/2013 | Bohn et al. |
| 8,454,954 B2 | 6/2013 | Schlossmacher et al. |
| 8,486,635 B2 | 7/2013 | Hutton et al. |
| 8,962,273 B2 | 2/2015 | Reczek |
| 9,034,836 B2 | 5/2015 | Dodge et al. |
| 9,290,759 B2 | 3/2016 | Abeliovich et al. |

(Continued)

FOREIGN PATENT DOCUMENTS

| | | |
|---|---|---|
| EP | 2687223 A1 | 1/2014 |
| EP | 3091087 A1 | 9/2016 |

(Continued)

OTHER PUBLICATIONS

Lazic and Barker, Cell-based therapies for disorders of the CNS, Expert Opin. Ther. Patents (2005) 15(10): 1361-1376.*
Molnar and Nemeth, Gene therapy in neurology: review of ongoing clinical trials, Clin. Invest. (2012) 2(6), 639-652 K.*
Hurdy, Therapeutic AAV Gene Transfer to the Nervous System: A Clinical Reality, Neuron 101, Mar. 6, 2019, 839-862.*

(Continued)

*Primary Examiner* — Gregory S Emch
(74) *Attorney, Agent, or Firm* — Wolf, Greenfield & Sacks, P.C.

(57) ABSTRACT

The disclosure relates, in some aspects, to compositions and methods for treatment of diseases associated with aberrant lysosomal function, for example Parkinson's disease (PD) and Gaucher disease. In some embodiments, the disclosure provides expression constructs comprising a transgene encoding beta-Glucocerebrosidase (GBA) or a portion thereof alone or in combination with one or more PD-associated genes. In some embodiments, the disclosure provides methods of Parkinson's disease by administering such expression constructs to a subject in need thereof.

19 Claims, 48 Drawing Sheets

Specification includes a Sequence Listing.

(56) References Cited

U.S. PATENT DOCUMENTS

| | | |
|---|---|---|
| 9,347,107 B2 | 5/2016 | Lai et al. |
| 9,427,438 B2 | 8/2016 | Alam |
| 9,486,541 B2 | 11/2016 | Hutton et al. |
| 10,213,494 B2 | 2/2019 | Schlossmacher et al. |
| 10,689,625 B2 | 6/2020 | Abeliovich et al. |
| 10,837,028 B2 | 11/2020 | Abeliovich et al. |
| 11,060,113 B2 | 7/2021 | Abeliovich et al. |
| 2003/0100115 A1 | 5/2003 | Raj et al. |
| 2003/0133924 A1 | 7/2003 | Canfield |
| 2006/0287358 A1 | 12/2006 | Wustman |
| 2006/0292117 A1 | 12/2006 | Loiler et al. |
| 2008/0003204 A1 | 1/2008 | Flotte et al. |
| 2013/0287736 A1 | 10/2013 | Passini et al. |
| 2015/0284472 A1 | 10/2015 | Sardi et al. |
| 2016/0060656 A1 | 3/2016 | Rebar |
| 2016/0120960 A1 | 5/2016 | McIvor et al. |
| 2017/0035860 A1 | 2/2017 | Flynn |
| 2018/0071373 A1 | 3/2018 | Melvor et al. |
| 2018/0147300 A1 | 5/2018 | Park et al. |
| 2019/0038773 A1 | 2/2019 | Esteves et al. |
| 2019/0055578 A1 | 2/2019 | Sah et al. |
| 2019/0282662 A1 | 9/2019 | Kay et al. |
| 2019/0328906 A1 | 10/2019 | Chen Plotkin et al. |
| 2019/0388507 A1 | 12/2019 | Kay |
| 2020/0071680 A1 | 3/2020 | Abeliovich et al. |
| 2020/0071726 A1 | 3/2020 | Abeliovich et al. |
| 2020/0231954 A1 | 7/2020 | Abeliovich et al. |
| 2020/0276335 A1 | 9/2020 | Abeliovich et al. |
| 2020/0318115 A1 | 10/2020 | Abeliovich et al. |
| 2021/0010032 A1 | 1/2021 | Abeliovich et al. |
| 2022/0211871 A1 | 7/2022 | Abeliovich et al. |

FOREIGN PATENT DOCUMENTS

| | | |
|---|---|---|
| EP | 3701030 A1 | 9/2020 |
| JP | 2015-516143 A | 6/2015 |
| WO | WO 2000/014113 A2 | 3/2000 |
| WO | WO 2002/24932 A2 | 3/2002 |
| WO | WO 2004/098648 A1 | 11/2004 |
| WO | WO 2003/029403 A3 | 8/2007 |
| WO | WO 2008/019187 A2 | 2/2008 |
| WO | WO 2009/079399 A2 | 6/2009 |
| WO | WO 2009/089635 A9 | 9/2009 |
| WO | WO 2009/120978 A2 | 10/2009 |
| WO | WO 2012/027558 A2 | 3/2012 |
| WO | WO 2012/027713 A2 | 3/2012 |
| WO | WO 2012/065248 A1 | 5/2012 |
| WO | WO 2013/151665 A2 | 10/2013 |
| WO | WO 2014/071282 A1 | 5/2014 |
| WO | WO 2014/186579 A1 | 11/2014 |
| WO | WO 2016/081927 A2 | 3/2016 |
| WO | WO 2016/179497 A1 | 11/2016 |
| WO | WO 2017/077451 A1 | 5/2017 |
| WO | WO 2017/136202 A1 | 8/2017 |
| WO | WO 2017/147509 A1 | 8/2017 |
| WO | WO 2019/070891 A1 | 4/2019 |
| WO | WO 2019/070893 A1 | 4/2019 |
| WO | WO 2019/070894 A1 | 4/2019 |
| WO | WO 2019/084068 A1 | 5/2019 |

OTHER PUBLICATIONS

Fumoto et al, Targeted Gene Delivery: Importance of Administration Routes, Chapter 1, Intech, 2013, pp. 3-31.*
Manno et al., Successful transduction of liver in hemophilia by AAV-Factor IX and limitations imposed by the host immune response, Nature Medicine, 2006, pp. 342-349 and 592.*
Niederkofler et al, Characterization of relevant mouse models for new biomarkers, Poster #141, 2019, QPS.*
Shanks et al, Are animal models predictive for humans?, Philosophy, Ethics, and Humanities in Medicine 2009, pp. 1-20.*
Wong et al, Lysosomal Trafficking Defects Link Parkinson's Disease With Gaucher's Disease, Movement Disorders, 2013, pp. 1610-1618.*
U.S. Appl. No. 16/753,322, filed Apr. 2, 2020, Abeliovich et al.
U.S. Appl. No. 16/838,993, filed Apr. 2, 2020, Abeliovich et al.
U.S. Appl. No. 17/601,984, filed Oct. 7, 2021, Abeliovich et al.
Extended European Search Report dated Jul. 2, 2021 in connection with Application No. 18864729.1.
Invitation to Pay Additional Fees mailed Dec. 4, 2018 in connection with Application No. PCT/US2018/054227.
International Search Report and Written Opinion dated Jan. 24, 2019 in connection with Application No. PCT/US2018/054227.
International Preliminary Report on Patentability dated Apr. 16, 2020 in connection with Application No. PCT/US2018/054227.
[No Author Listed] G0345 pFBAAVCAGmcsBgHpA Viral Vector Core updated Feb. 22, 2017 [retrieved from the internet on Jun. 10, 2022] https://medicine.uiowa.edu/vectorcore/sites/medicine.uiowa.edu.vectorcore/files/wysiwyg_uploads/Manual_ G0345_ pFBAAVCAGmesBgHpA_0.pdf, University of Iowa, Viral Vextor Core, 7 pages.
Anderson et al., Human pathology in NCL. Biochim Biophys Acta. Nov. 2013;1832(11):1807-26. doi: 10.1016/j.bbadis.2012.11.014. Epub Nov. 29, 2012.
Bond et al., Use of model organisms for the study of neuronal ceroid lipofuscinosis. Biochim Biophys Acta. Nov. 2013;1832(11):1842-65. doi: 10.1016/j.bbadis.2013.01.009. Epub Jan. 18, 2013.
Calcutt et al., Prosaposin gene expression and the efficacy of a prosaposin-derived peptide in preventing structural and functional disorders of peripheral nerve in diabetic rats. J Neuropathol Exp Neurol. Jun. 1999;58(6):628-36. doi: 10.1097/00005072-199906000-00007.
Chen-Plotkin et al., TMEM106B, the risk gene for frontotemporal dementia, is regulated by the microRNA-132/212 cluster and affects progranulin pathways. J Neurosci. Aug. 15, 2012;32(33):11213-27. doi: 10.1523/JNEUROSCI.0521-12.2012.
Choi et al., Optimization of AAV expression cassettes to improve packaging capacity and transgene expression in neurons. Mol Brain. Mar. 11, 2014;7:17. doi: 10.1186/1756-6606-7-17.
Daya et al., Gene therapy using adeno-associated virus vectors. Clin Microbiol Rev. Oct. 2008;21(4):583-93. doi: 10.1128/CMR.00008-08.
Franco et al., Glucocerebrosidase Mutations and Synucleinopathies. Potential Role of Sterylglucosides and Relevance of Studying Both GBA1 and GBA2 Genes. Front Neuroanat. Jun. 28, 2018;12:52. doi: 10.3389/fnana.2018.00052.
Francois et al., The cellular TATA binding protein is required for rep-dependent replication of a minimal adeno-associated virus type 2 p5 element. J Virol. Sep. 2005;79(17):11082-94. doi: 10.1128/JVI.79.17.11082-11094.2005.
Garcia-Gomez et al., Modelling gaucher disease through interference RNA technology. Human Gene Therapy, Sep. 1, 2015;26(9):A22-A23.
Ge et al., Optimization of eGFP expression using a modified baculovirus expression system. J Biotechnol. Mar. 10, 2014;173:41-6. doi: 10.1016/j.jbiotec.2014.01.003. Epub Jan. 18, 2014.
GenBank Accession No. AAA60303.1 "Prosaposin [*Homo sapiens*]" Jan. 9, 1995 [online].
GenBank Accession No. AAC37547.1 "cathepsin B [*Homo sapiens*]" Apr. 7, 1994 [online].
GenBank Accession No. AAF69824.1 "triggering receptor expressed on myeloid cells 2 [*Homo sapiens*]" May 23, 2000 [online].
GenBank Accession No. AAH01503.1 "Prosaposin [*Homo sapiens*]" Aug. 4, 2008 [online].
GenBank Accession No. AAH02585.1 "RAB7, member RAS oncogene family-like 1 [*Homo sapiens*]" Jul. 15, 2006 [online].
GenBank Accession No. AAH04275.1 "Prosaposin [*Homo sapiens*]" Aug. 4, 2008 [online].
GenBank Accession No. AAH07612.1 "Prosaposin [*Homo sapiens*]" Aug. 4, 2008 [online].
GenBank Accession No. AAH10240.1 "Cathepsin B [*Homo sapiens*]" Jul. 15, 2006 [online].
GenBank Accession No. AAH25415.1 "GTP cyclohydrolase 1 [*Homo sapiens*]" Aug. 7, 2008 [online].

(56) References Cited

OTHER PUBLICATIONS

GenBank Accession No. AAH29804.1 "Interleukin 34 [*Homo sapiens*]" Jun. 9, 2008 [online].
GenBank Accession No. AAH95408.1 "Cathepsin B [*Homo sapiens*]" Jul. 17, 2006 [online].
GenBank Accession No. AAP36904.1 "*Homo sapiens* glucosidase, beta; acid (includes glucosylceramidase), partial [synthetic construct]" Jul. 25, 2016 [online].
GenBank Accession No. BT008212.1 "Synthetic construct *Homo sapiens* glucosidase, beta; acid (includes glucosylceramidase) mRNA, partial eds" Jul. 25, 2016 [online].
GenBank Accession No. EAW68726.1 "sphingomyelin phosphodiesterase 1, acid lysosomal (acid sphingomyelinase), isoform CRA a [*Homo sapiens*]" Mar. 23, 2015 [online].
GenBank Accession No. EAW68727.1 "sphingomyelin phosphodiesterase 1, acid lysosomal (acid sphingomyelinase), isoform CRA b [*Homo sapiens*]" Mar. 23, 2015 [online].
GenBank Accession No. EAW68728.1 "sphingomyelin phosphodiesterase 1, acid lysosomal (acid sphingomyelinase), isoform CRA c [*Homo sapiens*]" Mar. 23, 2015 [online].
GenBank Accession No. EAW68729.1 "sphingomyelin phosphodiesterase 1, acid lysosomal (acid sphingomyelinase), isoform CRA d [*Homo sapiens*]" Mar. 23, 2015 [online].
GenBank Accession No. EAW81359.1 "galactosylceramidase, isoformCRA_a [*Homo sapiens*]" Mar. 23, 2015 [online].
GenBank Accession No. EAW81360.1 "galactosylceramidase, isoformCRA_b [*Homo sapiens*]" Mar. 23, 2015 [online].
GenBank Accession No. EAW81362.1 "galactosylceramidase, isoformCRA_c [*Homo sapiens*]" Mar. 23, 2015 [online].
GenBank Accession No. NP_000144.2 "galactocerebrosidase isoform a precursor [*Homo sapiens*]" Sep. 26, 2019 [online].
GenBank Accession No. NP_000148.2 "lysosomal acid glucosylceramidase isoform 1 precursor [*Homo sapiens*]" Jan. 8, 2020 [online].
GenBank Accession No. NP_000152.1 "GTP cyclohydrolase 1 isoform 1 [*Homo sapiens*]" Dec. 30, 2019 [online].
GenBank Accession No. NP_000534.3 "sphingomyelin phosphodiesterase isoform 1 precursor [*Homo sapiens*]" Jan. 13, 2020 [online].
GenBank Accession No. NP_001005742.1 "lysosomal acid glucosylceramidase isoform 1 precursor [*Homo sapiens*]" Nov. 11, 2019 [online].
GenBank Accession No. NP_001165282.1 "lysosomal acid glucosylceramidase isoform 2 [*Homo sapiens*]" Nov. 11, 2019 [online].
GenBank Accession No. NP_001165283.1 "lysosomal acid glucosylceramidase isoform 3 [*Homo sapiens*]" Nov. 11, 2019 [online].
GenBank Accession No. NP_001191184.1 "lysosome membrane protein 2 isoform 2 precursor [*Homo sapiens*]" Jan. 4, 2020 [online].
GenBank Accession No. NP_001317589.1 "non-lysosomal glucosylceramidase isoform 2 [*Homo sapiens*]" Aug. 7, 2019 [online].
GenBank Accession No. NP_001899.1 "cathepsinB isoform 1 preproprotein [*Homo sapiens*]" Jan. 27, 2020 [online].
GenBank Accession No. NP_002078.1 "progranulin precursor [*Homo sapiens*]" Jan. 21, 2020 [online].
GenBank Accession No. NP_002087.1 "general transcription factor IIF, polypeptide 1, 74kDa [*Homo sapiens*]" Jun. 3, 2007 [online].
GenBank Accession No. NP_002769.1 "prosaposin isoform a preproprotein [*Homo sapiens*]" Sep. 27, 2019 [online].
GenBank Accession No. NP_003920.1 "ras-related protein Rab-7L1 isoform 1 [*Homo sapiens*]" Dec. 31, 2019 [online].
GenBank Accession No. NP_005497.1 "lysosome membrane protein 2 isoform 1 precursor [*Homo sapiens*]" Jan. 1, 2020 [online].
GenBank Accession No. NP_060676.2 "vacuolar protein sorting-associated protein 35 [*Homo sapiens*]" Oct. 11, 2019 [online].
GenBank Accession No. NP_060844.2 "transmembrane protein 106B [*Homo sapiens*]" Jul. 28, 2019 [online].

GenBank Accession No. NP_061838.1 "triggering receptor expressed on myeloid cells 2 precursor isoform 1 precursor [*Homo sapiens*]" Feb. 2, 2020 [online].
GenBank Accession No. NP_065995.1 "non-lysosomal glucosylceramidase isoform 1 [*Homo sapiens*]" Aug. 22, 2019 [online].
GenBank Accession No. NP_689669.2 "interleukin-34 isoform 1 precursor [*Homo sapiens*]" Dec. 25, 2019 [online].
Geneseq Accession No. BDA66566. "Adeno-associated virus—2 (AAV2) ITR S-sequence, SEQ ID 3." Jul. 14, 2016 [online].
Gotz et al., Animal models for Alzheimer's disease and frontotemporal dementia: a perspective. ASN Neuro. Nov. 9, 2009;1(4):e00019. doi: 10.1042/AN20090042.
Ham, Prosaposin precursor protein: Functions and medical applications. Scripta Medica (BRNO). Jun. 2004;77(3):127-34.
Huang et al., Targeting Visceral Fat by Intraperitoneal Delivery of Novel AAV Serotype Vector Restricting Off-Target Transduction in Liver. Mol Ther Methods Clin Dev. Jun. 19, 2017;6:68-78. doi: 10.1016/j.omtm.2017.06.002.
Jian et al., Association Between Progranulin and Gaucher Disease. EBioMedicine. Sep. 2016;11:127-137. doi: 10.1016/j.ebiom.2016. 08.004. Epub Aug. 4, 2016.
Jiang et al., TREM2 in Alzheimer's disease. Mol Neurobiol. Aug. 2013;48(1):180-5. doi: 10.1007/S12035-013-8424-8. Epub Feb. 14, 2013.
Jiang et al., TREM2 modifies microglial phenotype and provides neuroprotection in P301S tau transgenic mice. Neuropharmacology. Jun. 2016;105:196-206. doi: 10.1016/j.neuropharm.2016.01.028. Epub Jan. 21, 2016.
Jiang et al., TREM2 Overexpression has No Improvement on Neuropathology and Cognitive Impairment in Aging APPswe/PS1dE9 Mice. Mol Neurobiol. Mar. 2017;54(2):855-865. doi: 10.1007/s12035-016-9704-x. Epub Jan. 16, 2016.
Khodr et al., Targeting alpha-synuclein with a microRNA-embedded silencing vector in the rat substantia nigra: positive and negative effects. Brain Res. Mar. 6, 2014;1550:47-60. doi: 10.1016/j.brainres.2014.01.010. Epub Jan. 21, 2014.
Ling et al., The Adeno-Associated Virus Genome Packaging Puzzle. J Mol Genet Med. Aug. 2015;9(3):175. doi: 10.4172/1747-0862. 1000175. Epub Jul. 15, 2015. Author Manuscript, 10 pages.
Naso et al., Adeno-Associated Virus (AAV) as a Vector for Gene Therapy. BioDrugs. Aug. 2017;31(4):317-334. doi: 10.1007/s40259-017-0234-5.
Rafi et al., Correction of sulfatide metabolism after transfer of prosaposin cDNA to cultured cells from a patient with SAP-1 deficiency. Am J Hum Genet. Jun. 1992;50(6):1252-8.
Renaud-Gabardos et al., Internal ribosome entry site-based vectors for combined gene therapy. World J Exp Med. Feb. 20, 2015;5(1):11-20. doi: 10.5493/wjem.v5.i1.11.
Rothaug et al., LIMP-2 expression is critical for β-glucocerebrosidase activity and α-synuclein clearance. Proc Natl Acad Sci U S A. Oct. 28, 2014;111(43):15573-8. doi: 10.1073/pnas.1405700111. Epub Oct. 14, 2014.
Salmon et al., Safety profile of recombinant adeno-associated viral vectors: focus on alipogene tiparvovec (Glybera®). Expert Rev Clin Pharmacol. Jan. 2014;7(1):53-65. doi: 10.1586/17512433.2014. 852065. Epub Nov. 25, 2013.
Savy et al., Impact of Inverted Terminal Repeat Integrity on rAAV8 Production Using the Baculovirus/Sf9 Cells System. Hum Gene Ther Methods. Oct. 2017;28(5):277-289. doi: 10.1089/hgtb.2016. 133.
Sikora et al., Neurolysosomal pathology in human prosaposin deficiency suggests essential neurotrophic function of prosaposin. Acta Neuropathol. Feb. 2007;113(2):163-75. doi: 10.1007/s00401-006-0148-7. Epub Oct. 6, 2006.
Sinclair et al., Synonymous codon usage bias and the expression of human glucocerebrosidase in the methylotrophic yeast, Pichia pastoris. Protein Expr Purif. Oct. 2002;26(1):96-105. doi: 10.1016/s1046-5928(02)00526-0.
Takahashi et al., TREM2-transduced myeloid precursors mediate nervous tissue debris clearance and facilitate recovery in an animal model of multiple sclerosis. PLoS Med. Apr. 2007;4(4):e124. doi: 10.1371/journal.pmed.0040124.

(56) References Cited

OTHER PUBLICATIONS

Tamargo et al., The role of saposin C in Gaucher disease. Mol Genet Metab. Jul. 2012;106(3):257-63. doi: 10.1016/j.ymgme.2012.04.024. Epub May 5, 2012.

Ulrich et al., Elucidating the Role of TREM2 in Alzheimer's Disease. Neuron. Apr. 19, 2017;94(2):237-248. doi: 10.1016/j.neuron.2017.02.042.

UniProtKB Submission; Accession No. Q14108. "SCARB2—Lysosome membrane protein 2" Nov. 1, 1997. [online].

Wang et al., Adeno-associated virus type 2 DNA replication in vivo: mutation analyses of the D sequence in viral inverted terminal repeats. J Virol. Apr. 1997;71(4):3077-82. doi: 10.1128/JVI.71.4.3077-3082.1997.

Wang et al., Enhancing Transgene Expression from Recombinant AAV8 Vectors in Different Tissues Using Woodchuck Hepatitis Virus Post-Transcriptional Regulatory Element. Int J Med Sci. Apr. 1, 2016;13(4):286-91. doi: 10.7150/ijms.14152.

Xu et al., Extracellular progranulin protects cortical neurons from toxic insults by activating survival signaling. Neurobiol Aging. Dec. 2011;32(12):2326.e5-16. doi: 10.1016/j.neurobiolaging.2011.06.017. Epub Aug. 4, 2011. Author Manuscript, 20 pages.

Xu et al., Tau silencing by siRNA in the P301S mouse model of tauopathy. Curr Gene Ther. 2014;14(5):343-51. doi: 10.2174/1566523214051409 26160602.

Yu et al., The spectrum of mutations in progranulin: a collaborative study screening 545 cases of neurodegeneration. Arch Neurol. Feb. 2010;67(2):161-70. doi: 10.1001/archneurol.2009.328. Author Manuscript, 18 pages.

\* cited by examiner

PrevailVector_FP12_CMVe_CBA_GBA1_bGH_JetLong_IL34_SV40l_4503nt
11,459 bp

```
                       SEQUENCE LISTING

<160> NUMBER OF SEQ ID NOS: 78

<210> SEQ ID NO 1
<211> LENGTH: 10697
<212> TYPE: DNA
<213> ORGANISM: Artificial sequence
<220> FEATURE:
<223> OTHER INFORMATION: Synthetic polynucleotide
```

<400> SEQUENCE: 1

| | | | | | |
|---|---|---|---|---|---|
| ttggccactc | cctctctgcg | cgctcgctcg | ctcactgagg | ccgggcgacc | aaaggtcgcc | 60 |
| cgacgcccgg | gctttgcccg | ggcggcctca | gtgagcgagc | gagcgcgcag | agagggagtg | 120 |
| gccaactcca | tcactagggg | ttcctgctag | ctctgggtat | ttaagcccga | gtgagcacgc | 180 |
| agggtctcca | ttttgaagcg | ggaggttacg | cgttcgtcga | ctactagtgg | gtaccagagc | 240 |
| tccctaggtt | ctagaaccgg | tgacgtctcc | catggtgaag | cttggatctg | aattcggtac | 300 |
| cctagttatt | aatagtaatc | aattacgggg | tcattagttc | atagcccata | tatggagttc | 360 |
| cgcgttacat | aacttacggt | aaatggcccg | cctggctgac | cgcccaacga | cccccgccca | 420 |
| ttgacgtcaa | taatgacgta | tgttcccata | gtaacgccaa | tagggacttt | ccattgacgt | 480 |
| caatgggtgg | actatttacg | gtaaactgcc | cacttggcag | tacatcaagt | gtatcatatg | 540 |
| ccaagtacgc | cccctattga | cgtcaatgac | ggtaaatggc | ccgcctggca | ttatgcccag | 600 |
| tacatgacct | tatgggactt | tcctacttgg | cagtacatct | acgtattagt | catcgctatt | 660 |
| accatggtcg | aggtgagccc | cacgttctgc | ttcactctcc | ccatctcccc | ccctcccca | 720 |
| cccccaattt | tgtatttatt | tattttttaa | ttattttgtg | cagcgatggg | ggcggggggg | 780 |
| gggggggggc | gcgcgccagg | cggggcgggg | cggggcgagg | ggcggggcgg | ggcgaggcgg | 840 |
| agaggtgcgg | cggcagccaa | tcagagcggc | gcgctccgaa | agtttccttt | tatggcgagg | 900 |
| cggcggcggc | ggcggcccta | taaaaagcga | agcgcgcggc | gggcgggagt | cgctgcgacg | 960 |
| ctgccttcgc | cccgtgcccc | gctccgccgc | cgcctcgcgc | cgcccgcccc | ggctctgact | 1020 |
| gaccgcgtta | ctcccacagg | tgagcgggcg | ggacggccct | tctcctccgg | gctgtaatta | 1080 |
| gcgcttggtt | taatgacggc | ttgttttctg | tggctgcgtg | aaagccttga | ggggctccgg | 1140 |
| gagctagagc | ctctgctaac | catgttcatg | ccttcttctt | tttcctacag | ctcctgggca | 1200 |
| acgtgctggt | tattgtgctg | tctcatcatt | ttggcaaaga | attcctcgaa | gatccgaagg | 1260 |
| gaaagtcttc | cacgactgtg | ggatccgttc | gaagatatca | ccggttgagc | caccatggaa | 1320 |
| ttcagcagcc | ccagcagaga | ggaatgcccc | aagcctctga | gccgggtgtc | aatcatggcc | 1380 |
| ggatctctga | caggactgct | gctgcttcag | gccgtgtctt | gggcttctgg | cgctagacct | 1440 |
| tgcatcccca | agagcttcgg | ctacagcagc | gtcgtgtgcg | tgtgcaatgc | cacctactgc | 1500 |
| gacagcttcg | accctcctac | ctttcctgct | ctgggcacct | tcagcagata | cgagagcacc | 1560 |
| agatccggca | gacggatgga | actgagcatg | ggacccatcc | aggccaatca | cacaggcact | 1620 |
| ggcctgctgc | tgacactgca | gcctgagcag | aaattccaga | agtgaaaggc | ttcggcgga | 1680 |
| gccatgacag | atgccgccgc | tctgaatatc | ctggctctgt | ctccaccagc | tcagaacctg | 1740 |
| ctgctcaaga | gctacttcag | cgaggaaggc | atcggctaca | acatcatcag | agtgccatg | 1800 |
| gccagctgcg | acttcagcat | caggacctac | acctacgccg | acacacccga | cgatttccag | 1860 |
| ctgcacaact | tcagcctgcc | tgaagaggac | accaagctga | agatccctct | gatccacaga | 1920 |
| gccctgcagc | tggcacaaag | acccgtgtca | ctgctggcct | ctccatggac | atctcccacc | 1980 |
| tggctgaaaa | caaatggcgc | cgtgaatggc | aagggcagcc | tgaaaggcca | acctggcgac | 2040 |
| atctaccacc | agacctgggc | cagatacttc | gtgaagttcc | tggacgccta | tgccgagcac | 2100 |
| aagctgcagt | tttgggccgt | gacagccgag | aacgaacctt | ctgctggact | gctgagcggc | 2160 |
| tacccctttc | agtgcctggg | ctttacaccc | gagcaccagc | gggactttat | cgcccgtgat | 2220 |
| ctgggaccca | cactggccaa | tagcacccac | cataatgtgc | ggctgctgat | gctggacgac | 2280 |

-continued

```
cagagactgc ttctgcccca ctgggctaaa gtggtgctga cagatcctga ggccgccaaa    2340
tacgtgcacg gaatcgccgt gcactggtat ctggactttc tggcccctgc caaggccaca    2400
ctgggagaga cacacagact gttccccaac accatgctgt tcgccagcga agcctgtgtg    2460
ggcagcaagt tttgggaaca gagcgtgcgg ctcggcagct gggatagagg catgcagtac    2520
agccacagca tcatcaccaa cctgctgtac cacgtcgtcg gctggaccga ctggaatctg    2580
gccctgaatc ctgaaggcgg ccctaactgg gtccgaaact tcgtggacag ccccatcatc    2640
gtggacatca ccaaggacac cttctacaag cagcccatgt tctaccacct gggacacttc    2700
agcaagttca tccccgaggg ctctcagcgc gttggactgg tggcttccca gaagaacgat    2760
ctggacgccg tggctctgat gcaccctgat ggatctgctg tggtggtggt cctgaaccgc    2820
agcagcaaag atgtgcccct gaccatcaag gatcccgccg tgggattcct ggaaacaatc    2880
agccctggct actccatcca cacctacctg tggcgtagac agtgacaatt gttaattaag    2940
tttaaaccct cgaggccgca agcttatcga taatcaacct ctggattaca aaatttgtga    3000
aagattgact ggtattctta actatgttgc tccttttacg ctatgtggat acgctgcttt    3060
aatgcctttg tatcatgcta ttgcttcccg tatggctttc attttctcct ccttgtataa    3120
atcctggttg ctgtctcttt atgaggagtt gtggcccgtt gtcaggcaac gtggcgtggt    3180
gtgcactgtg tttgctgacg caaccccac tggttggggc attgccacca cctgtcagct    3240
cctttccggg actttcgctt tccccctccc tattgccacg gcggaactca tcgccgcctg    3300
ccttgcccgc tgctggacag gggctcggct gttgggcact gacaattccg tggtgttgtc    3360
ggggaaatca tcgtccttc cttggctgct cgcctgtgtt gccacctgga ttctgcgcgg    3420
gacgtccttc tgctacgtcc cttcggccct caatccagcg gaccttcctt cccgcggcct    3480
gctgccggct ctgcggcctc ttccgcgtct tcgccttcgc cctcagacga gtcggatctc    3540
cctttgggcc gcctccccgc atcgataccg tcgactagag ctcgctgatc agcctcgact    3600
gtgccttcta gttgccagcc atctgttgtt tgccctccc ccgtgccttc cttgaccctg    3660
gaaggtgcca ctcccactgt cctttcctaa taaaatgagg aaattgcatc gcattgtctg    3720
agtaggtgtc attctattct ggggggtggg gtggggcagg acagcaaggg ggaggattgg    3780
gaagacaata gcaggcatgc tggggagaga tccacgataa caaacagctt ttttggggtg    3840
aacatattga ctgaattccc tgcaggttgg ccactccctc tctgcgcgct cgctcgctca    3900
ctgaggccgc ccgggcaaag cccgggcgtc gggcgacctt tggtcgcccg gcctcagtga    3960
gcgagcgagc gcgcagagag ggagtggcca actccatcac taggggttcc tgcggccgct    4020
cgtacggtct cgaggaattc ctgcaggata acttgccaac ctcattctaa aatgtatata    4080
gaagcccaaa agacaataac aaaaatattc ttgtagaaca aaatgggaaa gaatgttcca    4140
ctaaatatca agatttagag caaagcatga gatgtgtggg gatagacagt gaggctgata    4200
aaatagagta gagctcagaa acagacccat tgatatatgt aagtgaccta tgaaaaaaat    4260
atggcatttt acaatgggaa aatgatggtc tttttctttt ttagaaaaac agggaaatat    4320
atttatatgt aaaaaataaa agggaaccca tatgtcatac catacacaca aaaaaattcc    4380
agtgaattat aagtctaaat ggagaaggca aaactttaaa tcttttagaa ataatatag    4440 aagcatgcag accagcctgg ccaacatgat gaaaccctct ctactaataa taaaatcagt    4500
agaactactc aggactactt tgagtgggaa gtccttttct atgaagactt ctttggccaa    4560
aattaggctc taaatgcaag gagatagtgc atcatgcctg gctgcactta ctgataaatg    4620
atgttatcac catctttaac caaatgcaca ggaacaagtt atggtactga tgtgctggat    4680
```

```
tgagaaggag ctctacttcc ttgacaggac acatttgtat caacttaaaa aagcagattt    4740
ttgccagcag aactattcat tcagaggtag gaaacttaga atagatgatg tcactgatta    4800
gcatggcttc cccatctcca cagctgcttc ccacccaggt tgcccacagt tgagtttgtc    4860
cagtgctcag ggctgcccac tctcagtaag aagccccaca ccagcccctc tccaaatatg    4920
ttggctgttc cttccattaa agtgacccca ctttagagca gcaagtggat ttctgtttct    4980
tacagttcag gaaggaggag tcagctgtga aacctggag cctgagatgc ttctaagtcc     5040
cactgctact ggggtcaggg aagccagact ccagcatcag cagtcaggag cactaagccc    5100
ttgccaacat cctgtttctc agagaaactg cttccattat aatggttgtc ctttttaag    5160 ctatcaagcc aaacaaccag tgtctaccat tattctcatc acctgaagcc aagggttcta    5220
gcaaaagtca agctgtcttg taatggttga tgtgcctcca gcttctgtct tcagtcactc    5280
cactcttagc ctgctctgaa tcaactctga ccacagttcc ctggagcccc tgccacctgc    5340
tgcccctgcc accttctcca tctgcagtgc tgtgcagcct tctgcactct tgcagagcta    5400
ataggtggag acttgaagga agaggaggaa agtttctcat aatagccttg ctgcaagctc    5460
aaatgggagg tgggcactgt gcccaggagc cttggagcaa aggctgtgcc caacctctga    5520
ctgcatccag gtttggtctt gacagagata agaagccctg gcttttggag ccaaaatcta    5580
ggtcagactt aggcaggatt ctcaaagttt atcagcagaa catgaggcag aagacccttt    5640
ctgctccagc ttcttcaggc tcaaccttca tcagaataga tagaaagaga ggctgtgagg    5700
gttcttaaaa cagaagcaaa tctgactcag agaataaaca acctcctagt aaactacagc    5760
ttagacagag catctggtgg tgagtgtgct cagtgtccta ctcaactgtc tggtatcagc    5820
cctcatgagg acttctcttc tttccctcat agacctccat ctctgttttc cttagcctgc    5880
agaaatctgg atggctattc acagaatgcc tgtgctttca gagttgcatt ttttctctgg    5940
tattctggtt caagcatttg aaggtaggaa aggttctcca agtgcaagaa agccagccct    6000
gagcctcaac tgcctggcta gtgtggtcag taggatgcaa aggctgttga atgccacaag    6060
gccaaacttt aacctgtgta ccacaagcct agcagcagag gcagctctgc tcactggaac    6120
tctctgtctt cttctcctg agccttttct tttcctgagt tttctagctc tcctcaacct     6180
tacctctgcc ctacccagga caaacccaag agccactgtt tctgtgatgt cctctccagc    6240
cctaattagg catcatgact tcagcctgac cttccatgct cagaagcagt gctaatccac    6300
ttcagatgag ctgctctatg caacacaggc agagcctaca aacctttgca ccagagccct    6360
ccacatatca gtgtttgttc atactcactt caacagcaaa tgtgactgct gagattaaga    6420
ttttacacaa gatggtctgt aatttcacag ttagttttat cccattaggt atgaaagaat    6480
tagcataatt ccccttaaac atgaatgaat cttagatttt ttaataaata gttttggaag    6540
taaagacaga gacatcagga gcacaaggaa tagcctgaga ggacaaacag aacaagaaag    6600
agtctggaaa tacacaggat gttcttggcc tcctcaaagc aagtgcaagc agatagtacc    6660
agcagcccca ggctatcaga gcccagtgaa gagaagtacc atgaaagcca cagctctaac    6720
caccctgttc cagagtgaca gacagtcccc aagacaagcc agcctgagcc agagagagaa    6780
ctgcaagaga aagtttctaa tttaggttct gttagattca gacaagtgca ggtcatcctc    6840
tctccacagc tactcacctc tccagcctaa caaagcctgc agtccacact ccaaccctgg    6900
tgtctcacct cctagcctct cccaacatcc tgctctctga ccatcttctg catctctcat    6960
ctcaccatct cccactgtct acagcctact cttgcaacta ccatctcatt ttctgacatc    7020
```

```
ctgtctacat cttctgccat actctgccat ctaccatacc acctcttacc atctaccaca    7080
ccatcttta  tctccatccc tctcagaagc ctccaagctg aatcctgctt tatgtgttca    7140
tctcagcccc tgcatggaaa gctgaccccca gaggcagaac tattcccaga gagcttggcc   7200
aagaaaaaca aaactaccag cctggccagg ctcaggagta gtaagctgca gtgtctgttg    7260
tgttctagct tcaacagctg caggagttcc actctcaaat gctccacatt tctcacatcc    7320
tcctgattct ggtcactacc catcttcaaa gaacagaata tctcacatca gcatactgtg    7380
aaggactagt catgggtgca gctgctcaga gctgcaaagt cattctggat ggtggagagc    7440
ttacaaacat ttcatgatgc tccccccgct ctgatggctg gagcccaatc cctacacaga    7500
ctcctgctgt atgtgttttc ctttcactct gagccacagc cagagggcag gcattcagtc    7560
tcctcttcag gctggggctg gggcactgag aactcaccca acaccttgct ctcactcctt    7620
ctgcaaaaca agaaagagct ttgtgctgca gtagccatga agaatgaaag gaaggcttta    7680
actaaaaaat gtcagagatt attttcaacc ccttactgtg gatcaccagc aaggaggaaa    7740
cacaacacag agacattttt tcccctcaaa ttatcaaaag aatcactgca tttgttaaag    7800
agagcaactg aatcaggaag cagagttttg aacatatcag aagttaggaa tctgcatcag    7860
agacaaatgc agtcatggtt gttgctgca taccagccct aatcattaga agcctcatgg     7920
acttcaaaca tcattccctc tgacaagatg ctctagccta actccatgag ataaaataaa    7980
tctgcctttc agagccaaag aagagtccac cagcttcttc tcagtgtgaa caagagctcc    8040
agtcaggtta gtcagtccag tgcagtagag gagaccagtc tgcatcctct aattttcaaa    8100
ggcaagaaga tttgtttacc ctggacacca ggcacaagtg aggtcacaga gctcttagat    8160
atgcagtcct catgagtgag gagactaaag cgcatgccat caagacttca gtgtagagaa    8220
aacctccaaa aaagcctcct cactacttct ggaatagctc agaggccgag gcggcctcgg    8280
cctctgcata aataaaaaaa attagtcagc catggggcgg agaatgggcg gaactgggcg    8340
gagttagggg cgggatgggc ggagttaggg gcgggactat ggttgctgac taattgagat    8400
gcatgctttg catacttctg cctgctgggg agcctgggga cttccacac ctggttgctg     8460
actaattgag atgcatgctt tgcatacttc tgcctgctgg ggagcctggg gacttccac    8520
accctaactg acacacattc cacagctgca ttaatgaatc ggccaacgcg cggggagagg    8580
cggtttgcgt attgggcgct cttccgcttc ctcgctcact gactcgctgc gctcggtcgt    8640
tcggctgcgg cgagcggtat cagctcactc aaaggcggta atacggttat ccacagaatc    8700
aggggataac gcaggaaaga acatgtgagc aaaaggccag caaaaggcca ggaaccgtaa    8760
aaaggccgcg ttgctggcgt ttttccatag gctccgcccc cctgacgagc atcacaaaaa    8820
tcgacgctca agtcagaggt ggcgaaaccc gacaggacta taaagatacc aggcgtttcc    8880
ccctggaagc tccctcgtgc gctctcctgt tccgaccctg ccgcttaccg gatacctgtc    8940
cgcctttctc ccttcgggaa gcgtggcgct ttctcatagc tcacgctgta ggtatctcag    9000
ttcggtgtag gtcgttcgct ccaagctggg ctgtgtgcac gaaccccccg ttcagcccga    9060
ccgctgcgcc ttatccggta actatcgtct tgagtccaac ccggtaagac acgacttatc    9120
gccactggca gcagccactg gtaacaggat tagcagagcg aggtatgtag gcggtgctac    9180
agagttcttg aagtggtggc ctaactacgg ctacactaga agaacagtat ttggtatctg    9240
cgctctgctg aagccagtta ccttcggaaa aagagttggt agctcttgat ccggcaaaca    9300
aaccaccgct ggtagcggtg gtttttttgt ttgcaagcag cagattacgc gcagaaaaaa    9360
aggatctcaa gaagatcctt tgatcttttc tacggggtct gacgctcagt ggaacgaaaa    9420
```

| | |
|---|---:|
| ctcacgttaa gggatttttgg tcatgagatt atcaaaaagg atcttcacct agatccttt | 9480 |
| aaattaaaaa tgaagtttta aatcaatcta aagtatatat gagtaaactt ggtctgacag | 9540 |
| ttaccaatgc ttaatcagtg aggcacctat ctcagcgatc tgtctatttc gttcatccat | 9600 |
| agttgcctga ctcctgcaaa ccacgttgtg tctcaaaatc tctgatgtta cattgcacaa | 9660 |
| gataaaaata tatcatcatg aacaataaaa ctgtctgctt acataaacag taatacaagg | 9720 |
| ggtgttatga gccatattca acgggaaacg tcttgctcga ggccgcgatt aaattccaac | 9780 |
| atggatgctg atttatatgg gtataaatgg gctcgcgata atgtcgggca atcaggtgcg | 9840 |
| acaatctatc gattgtatgg gaagcccgat gcgccagagt tgtttctgaa acatggcaaa | 9900 |
| ggtagcgttg ccaatgatgt tacagatgag atggtcagac taaactggct gacggaattt | 9960 |
| atgcctcttc cgaccatcaa gcattttatc cgtactcctg atgatgcatg gttactcacc | 10020 |
| actgcgatcc ccgggaaaac agcattccag gtattagaag aatatcctga ttcaggtgaa | 10080 |
| aatattgttg atgcgctggc agtgttcctg cgccggttgc attcgattcc tgtttgtaat | 10140 |
| tgtcctttta acagcgatcg cgtatttcgt ctcgctcagg cgcaatcacg aatgaataac | 10200 |
| ggtttggttg atgcgagtga ttttgatgac gagcgtaatg gctggcctgt tgaacaagtc | 10260 |
| tggaaagaaa tgcataagct tttgccattc tcaccggatt cagtcgtcac tcatggtgat | 10320 |
| ttctcacttg ataaccttat ttttgacgag gggaaattaa taggttgtat tgatgttgga | 10380 |
| cgagtcggaa tcgcagaccg ataccaggat cttgccatcc tatggaactg cctcggtgag | 10440 |
| ttttctcctt cattacagaa acggcttttt caaaaatatg gtattgataa tcctgatatg | 10500 |
| aataaattgc agtttcattt gatgctcgat gagttttct aagggcggcc tgccaccata | 10560 |
| cccacgccga aacaagcgct catgagcccg aagtggcgag cccgatcttc cccatcggtg | 10620 |
| atgtcggcga tataggcgcc agcaaccgca cctgtggcgc cggtgatgag ggcgcgccaa | 10680 |
| gtcgacgtcc ggcagtc | 10697 |

<210> SEQ ID NO 2
<211> LENGTH: 11355
<212> TYPE: DNA
<213> ORGANISM: Artificial sequence
<220> FEATURE:
<223> OTHER INFORMATION: Synthetic polynucleotide

<400> SEQUENCE: 2

| | |
|---|---:|
| ttggccactc cctctctgcg cgctcgctcg ctcactgagg cccggcgacc aaaggtcgcc | 60 |
| cgacgcccgg gctttgcccg gcggcctca gtgagcgagc gagcgcgcag agagggagtg | 120 |
| gccaactcca tcactagggg ttcctgctag ctctgggtat ttaagcccga gtgagcacgc | 180 |
| agggtctcca ttttgaagcg ggaggttacg cgttcgtcga ctactagtgg gtaccagagc | 240 |
| tccctaggtt ctagaaccgg tgacgtctcc catggtgaag cttggatctg agggcggagt | 300 |
| tagggcggag ccaatcagcg tgcgccgttc gaaagttgc cttttatggc tgggcggaga | 360 |
| atgggcggtg aacgccgatg attatataag gacgcgccgg gtgtggcaca gctagttccg | 420 |
| tcgcagccgg gatttgggtc gcggttcttg tttgtggatc cctgtgatcg tcacttggta | 480 |
| agtcactgac tgtctatgcc tggaaagggt gggcaggaa tggggcagt gcaggaaaag | 540 |
| tggcactatg aaccctgcag ccctaggaat gcatctagac aattgtacta accttcttct | 600 |
| cttcctctc ctgacagtcc ggaaagccac catgggccgc tgctgcttct acaccgccgg | 660 |
| caccctgagc ctgctgctgc tggtgaccag cgtgaccctg ctggtggccc gcgtgttcca | 720 |

-continued

```
gaaggccgtg gaccagagca tcgagaagaa gatcgtgctg cgcaacggca ccgaggcctt      780
cgacagctgg gagaagcccc ccctgcccgt gtacacccag ttctacttct tcaacgtgac      840
caaccccgag gagatcctgc gcggcgagac ccccgcgtg gaggaggtgg cccctacac       900
ctaccgcgag ctgcgcaaca aggccaacat ccagttcggc gacaacggca ccaccatcag      960
cgccgtgagc aacaaggcct acgtgttcga gcgcgaccag agcgtgggcg accccaagat     1020
cgacctgatc cgcaccctga acatccccgt gctgaccgtg atcgagtgga gccaggtgca     1080
cttcctgcgc gagatcatcg aggccatgct gaaggcctac cagcagaagc tgttcgtgac     1140
ccacaccgtg gacgagctgc tgtggggcta caaggacgag atcctgagcc tgatccacgt     1200
gttccgcccc gacatcagcc cctacttcgg cctgttctac gagaagaacg gcaccaacga     1260
cggcgactac gtgttcctga ccggcgagga cagctacctg aacttcacca agatcgtgga     1320
gtggaacggc aagaccagcc tggactggtg gatcaccgac aagtgcaaca tgatcaacgg     1380
caccgacggc gacagcttcc accccctgat caccaaggac gaggtgctgt acgtgttccc     1440
cagcgacttc tgccgcagcg tgtacatcac cttcagcgac tacgagagcg tgcagggcct     1500
gcccgccttc cgctacaagg tgcccgccga gatcctggcc aacaccagcg acaacgccgg     1560
cttctgcatc cccgagggca actgcctggg cagcggcgtg ctgaacgtga gcatctgcaa     1620
gaacggcgcc cccatcatca tgagcttccc ccacttctac caggccgacg agcgcttcgt     1680
gagcgccatc gagggcatgc accccaacca ggaggaccac gagaccttcg tggacatcaa     1740
cccctgacc ggcatcatcc tgaaggccgc caagcgcttc cagatcaaca tctacgtgaa     1800
gaagctggac gacttcgtgg agaccggcga catccgcacc atggtgttcc ccgtgatgta     1860
cctgaacgag agcgtgcaca tcgacaagga ccgccagc cgcctgaaga gcatgatcaa     1920
caccaccctg atcatcacca acatccccta catcatcatg ccctgggcg tgttcttcgg     1980
cctggtgttc acctggctgg cctgcaaggg ccagggcagc atggacgagg caccgccga     2040
cgagcgcgcc cccctgatcc gcacctgatt gtggccgaac cgccgaactc agaggccggc     2100
cccagaaaac ccgagcgagt aggggggcgg cgcaggagg gaggagaact gggggcgcgg     2160
gaggctggtg ggtgtgggg gtggagatgt agaagatgtg acgccgcggc ccggcgggtg     2220
ccagattagc ggacgcggtg cccgcggttg caacgggatc ccgggcgctg cagcttggga     2280
ggcggctctc cccaggcggc gtccgcggag acacccatcc gtgaaccca ggtcccgggc     2340
cgccggctcg ccgcgcacca ggggccggcg acagaagag cggccgagcg gctcgaggct     2400
gggggaccgc gggcgcggcc gcgcgctgcc gggcgggagg ctgggggcc ggggccgggg     2460
ccgtgccccg gagcgggtcg gaggccgggg ccggggccgg gggacggcgg ctccccgcgc     2520
ggctccagcg gctcggggat ccggccgggg ccccgcaggg accatgatgg aattcagcag     2580
ccccagcaga gaggaatgcc ccaagcctct gagccgggtg tcaatcatgg ccggatctct     2640
gacaggactg ctgctgcttc aggccgtgtc ttgggcttct ggcgctagac cttgcatccc     2700
caagagcttc ggctacagca gcgtcgtgtg cgtgtgcaat gccacctact gcgacagctt     2760
cgaccctcct acctttcctg ctctgggcac cttcagcaga tacgagagca ccagatccgg     2820
cagacggatg gaactgagca tgggacccat ccaggccaat cacacaggca ctggcctgct     2880
gctgacactg cagcctgagc agaaattcca gaaagtgaaa ggcttcggcg agccatgac     2940
agatgccgcc gctctgaata tcctggctct gtctccacca gctcagaacc tgctgctcaa     3000
gagctacttc agcgaggaag gcatcggcta caacatcatc agagtgccca tggccagctg     3060
cgacttcagc atcaggacct acacctacgc cgacacaccc gacgatttcc agctgcacaa     3120
```

```
cttcagcctg cctgaagagg acaccaagct gaagatccct ctgatccaca gagccctgca    3180
gctggcacaa agacccgtgt cactgctggc ctctccatgg acatctccca cctggctgaa    3240
aacaaatggc gccgtgaatg gcaagggcag cctgaaaggc caacctggcg acatctacca    3300
ccagacctgg gccagatact tcgtgaagtt cctggacgcc tatgccgagc acaagctgca    3360
gttttgggcc gtgacagccg agaacgaacc ttctgctgga ctgctgagcg gctacccctt    3420
tcagtgcctg ggctttacac ccgagcacca gcgggacttt atcgcccgtg atctgggacc    3480
cacactggcc aatagcaccc accataatgt gcggctgctg atgctggacg accagagact    3540
gcttctgccc cactgggcta agtggtgct gacagatcct gaggccgcca atacgtgca     3600 cggaatcgcc gtgcactggt atctggactt tctggcccct gccaaggcca cactgggaga    3660
gacacacaga ctgttcccca acaccatgct gttcgccagc gaagcctgtg tgggcagcaa    3720
gttttgggaa cagagcgtgc ggctcggcag ctgggataga ggcatgcagt acagccacag    3780
catcatcacc aacctgctgt accacgtcgt cggctggacc gactggaatc tggccctgaa    3840
tcctgaaggc ggccctaact gggtccgaaa cttcgtggac agccccatca tcgtggacat    3900
caccaaggac accttctaca gcagcccat gttctaccac ctgggacact tcagcaagtt     3960
catccccgag ggctctcagc gcgttggact ggtggcttcc cagaagaacg atctggacgc    4020
cgtggctctg atgcaccctg atggatctgc tgtggtggtg gtcctgaacc gcagcagcaa    4080
agatgtgccc ctgaccatca aggatcccgc cgtgggattc ctggaaacaa tcagccctgg    4140
ctactccatc cacacctacc tgtggcgtag acagtgacaa ttgttaatta agtttaaacc    4200
ctcgaggccg caagccgcat cgataccgtc gactagagct cgctgatcag cctcgactgt    4260
gccttctagt tgccagccat ctgttgtttg cccctcccc gtgccttcct tgaccctgga     4320
aggtgccact cccactgtcc tttcctaata aaatgaggaa attgcatcgc attgtctgag    4380
taggtgtcat tctattctgg ggggtggggt ggggcaggac agcaaggggg aggattggga    4440
agacaatagc aggcatgctg gggagagatc cacgataaca aacagctttt ttggggtgaa    4500
catattgact gaattccctg caggttggcc actccctctc tgcgcgctcg ctcgctcact    4560
gaggccgccc gggcaaagcc cgggcgtcgg gcgacctttg gtcgcccggc ctcagtgagc    4620
gagcgagcgc gcagagaggg agtggccaac tccatcacta ggggttcctg cggccgctcg    4680
tacggtctcg aggaattcct gcaggataac ttgccaacct cattctaaaa tgtatataga    4740
agcccaaaag acaataacaa aaatattctt gtagaacaaa atgggaaaga atgttccact    4800
aaatatcaag atttagagca aagcatgaga tgtgtgggga tagacagtga ggctgataaa    4860
atagagtaga gctcagaaac agacccattg atatatgtaa gtgacctatg aaaaaaatat    4920
ggcattttac aatgggaaaa tgatggtctt tttctttttt agaaaaacag ggaaatatat    4980
ttatatgtaa aaaataaaag gaacccata tgtcatacca tacacacaaa aaattccag     5040 tgaattataa gtctaaatgg agaaggcaaa actttaaatc ttttagaaaa taatatagaa    5100
gcatgcagac cagcctggcc aacatgatga aaccctctct actaataata aaatcagtag    5160
aactactcag gactactttg agtgggaagt ccttttctat gaagacttct ttggccaaaa    5220
ttaggctcta aatgcaagga gatagtgcat catgcctggc tgcacttact gataaatgat    5280
gttatcacca tctttaacca aatgcacagg aacaagttat ggtactgatg tgctggattg    5340
agaaggagct ctacttcctt gacaggacac atttgtatca acttaaaaaa gcagattttt    5400
gccagcagaa ctattcattc agaggtagga aacttagaat agatgatgtc actgattagc    5460
```

-continued

```
atggcttccc catctccaca gctgcttccc acccaggttg cccacagttg agtttgtcca      5520
gtgctcaggg ctgcccactc tcagtaagaa gccccacacc agcccctctc caaatatgtt      5580
ggctgttcct tccattaaag tgaccccact ttagagcagc aagtggattt ctgtttctta      5640
cagttcagga aggaggagtc agctgtgaga acctggagcc tgagatgctt ctaagtccca      5700
ctgctactgg ggtcagggaa gccagactcc agcatcagca gtcaggagca ctaagccctt      5760
gccaacatcc tgtttctcag agaaactgct tccattataa tggttgtcct tttttaagct      5820
atcaagccaa acaaccagtg tctaccatta ttctcatcac ctgaagccaa gggttctagc      5880
aaaagtcaag ctgtcttgta atggttgatg tgcctccagc ttctgtcttc agtcactcca      5940
ctcttagcct gctctgaatc aactctgacc acagttccct ggagccctg ccacctgctg       6000 cccctgccac cttctccatc tgcagtgctg tgcagccttc tgcactcttg cagagctaat      6060
aggtggagac ttgaaggaag aggaggaaag tttctcataa tagccttgct gcaagctcaa      6120
atgggaggtg ggcactgtgc ccaggagcct tggagcaaag gctgtgccca acctctgact      6180
gcatccaggt ttggtcttga cagagataag aagccctggc ttttggagcc aaaatctagg      6240
tcagacttag gcaggattct caaagtttat cagcagaaca tgaggcagaa gacccttct      6300 gctccagctt cttcaggctc aaccttcatc agaatagata gaaagagagg ctgtgagggt      6360
tcttaaaaca gaagcaaatc tgactcagag aataaacaac ctcctagtaa actacagctt      6420
agacagagca tctggtggtg agtgtgctca gtgtcctact caactgtctg gtatcagccc      6480
tcatgaggac ttctcttctt tccctcatag acctccatct ctgttttcct tagcctgcag      6540
aaatctggat ggctattcac agaatgcctg tgctttcaga gttgcatttt ttctctggta      6600
ttctggttca agcatttgaa ggtaggaaag gttctccaag tgcaagaaag ccagccctga      6660
gcctcaactg cctggctagt gtggtcagta ggatgcaaag gctgttgaat gccacaaggc      6720
caaactttaa cctgtgtacc acaagcctag cagcagaggc agctctgctc actggaactc      6780
tctgtcttct ttctcctgag cctttctctt tcctgagttt tctagctctc ctcaaccttta     6840 cctctgccct acccaggaca aacccaagag ccactgtttc tgtgatgtcc tctccagccc      6900
taattaggca tcatgacttc agcctgacct tccatgctca gaagcagtgc taatccactt      6960
cagatgagct gctctatgca acacaggcag agcctacaaa cctttgcacc agagccctcc      7020
acatatcagt gtttgttcat actcacttca acagcaaatg tgactgctga gattaagatt      7080
ttacacaaga tggtctgtaa tttcacagtt agttttatcc cattaggtat gaaagaatta      7140
gcataattcc ccttaaacat gaatgaatct tagatttttt aataaatagt tttggaagta      7200
aagacagaga catcaggagc acaaggaata gcctgagagg acaaacagaa caagaaagag      7260
tctggaaata cacaggatgt tcttggcctc ctcaaagcaa gtgcaagcag atagtaccag      7320
cagccccagg ctatcagagc ccagtgaaga gaagtaccat gaaagccaca gctctaacca      7380
ccctgttcca gagtgacaga cagtccccaa gacaagccag cctgagccag agagagaact      7440
gcaagagaaa gtttctaatt taggttctgt tagattcaga caagtgcagg tcatcctctc      7500
tccacagcta ctcacctctc cagcctaaca aagcctgcag tccacactcc aaccctggtg      7560
tctcacctcc tagcctctcc caacatcctg ctctctgacc atcttctgca tctctcatct      7620
caccatctcc cactgtctac agcctactct tgcaactacc atctcatttt ctgacatcct      7680
gtctacatct tctgccatac tctgccatct accataccac ctcttaccat ctaccacacc      7740
atcttttatc tccatccctc tcagaagcct ccaagctgaa tcctgcttta tgtgttcatc      7800
tcagcccctg catggaaagc tgaccccaga ggcagaacta ttcccagaga gcttggccaa      7860
```

-continued

```
gaaaaacaaa actaccagcc tggccaggct caggagtagt aagctgcagt gtctgttgtg      7920
ttctagcttc aacagctgca ggagttccac tctcaaatgc tccacatttc tcacatcctc      7980
ctgattctgg tcactaccca tcttcaaaga acagaatatc tcacatcagc atactgtgaa      8040
ggactagtca tgggtgcagc tgctcagagc tgcaaagtca ttctggatgg tggagagctt      8100
acaaacattt catgatgctc cccccgctct gatggctgga gcccaatccc tacacagact      8160
cctgctgtat gtgttttcct ttcactctga gccacagcca gagggcaggc attcagtctc      8220
ctcttcaggc tggggctggg gcactgagaa ctcacccaac accttgctct cactccttct      8280
gcaaaacaag aaagagcttt gtgctgcagt agccatgaag aatgaaagga aggctttaac      8340 taaaaatgt cagagattat tttcaaccc ttactgtgga tcaccagcaa ggaggaaaca       8400
caacacagag acatttttc ccctcaaatt atcaaaagaa tcactgcatt tgttaaagag      8460
agcaactgaa tcaggaagca gagttttgaa catatcagaa gttaggaatc tgcatcagag      8520
acaaatgcag tcatggttgt ttgctgcata ccagccctaa tcattagaag cctcatggac      8580
ttcaaacatc attccctctg acaagatgct ctagcctaac tccatgagat aaaataaatc      8640 tgccttttcag agccaaagaa gagtccacca gcttcttctc agtgtgaaca agagctccag      8700
tcaggttagt cagtccagtg cagtagagga gaccagtctg catcctctaa ttttcaaagg      8760
caagaagatt tgtttaccct ggacaccagg cacaagtgag gtcacagagc tcttagatat      8820
gcagtcctca tgagtgagga gactaaagcg catgccatca agacttcagt gtagagaaaa      8880
cctccaaaaa agcctcctca ctacttctgg aatagctcag aggccgaggc ggcctcggcc      8940
tctgcataaa taaaaaaaat tagtcagcca tggggcggag aatgggcgga actgggcgga      9000 gttagggcg ggatgggcgg agttaggggc gggactatgg ttgctgacta attgagatgc       9060
atgctttgca tacttctgcc tgctggggag cctggggact ttccacacct ggttgctgac      9120
taattgagat gcatgctttg catacttctg cctgctgggg agcctgggga cttttccacac      9180 cctaactgac acacattcca cagctgcatt aatgaatcgg ccaacgcgcg gggagaggcg      9240
gtttgcgtat tgggcgctct tccgcttcct cgctcactga ctcgctgcgc tcggtcgttc      9300
ggctgcggcg agcggtatca gctcactcaa aggcggtaat acggttatcc acagaatcag      9360
gggataacgc aggaaagaac atgtgagcaa aaggccagca aaaggccagg aaccgtaaaa      9420
aggccgcgtt gctggcgttt ttccataggc tccgccccc tgacgagcat cacaaaaatc       9480
gacgctcaag tcagaggtgg cgaaacccga caggactata agataccag gcgtttcccc       9540 ctggaagctc cctcgtgcgc tctcctgttc cgaccctgcc gcttaccgga tacctgtccg      9600
cctttctccc ttcgggaagc gtggcgcttt ctcatagctc acgctgtagg tatctcagtt      9660
cggtgtaggt cgttcgctcc aagctgggct gtgtgcacga accccccgtt cagcccgacc      9720
gctgcgcctt atccggtaac tatcgtcttg agtccaaccc ggtaagacac gacttatcgc      9780
cactggcagc agccactggt aacaggatta gcagagcgag gtatgtaggc ggtgctacag      9840
agttcttgaa gtggtggcct aactacggct acactagaag aacagtattt ggtatctgcg      9900
ctctgctgaa gccagttacc ttcggaaaaa gagttggtag ctcttgatcc ggcaaacaaa      9960
ccaccgctgg tagcggtggt ttttttgttt gcaagcagca gattacgcgc agaaaaaaag     10020
gatctcaaga agatcctttg atcttttcta cggggtctga cgctcagtgg aacgaaaact     10080
cacgttaagg gattttggtc atgagattat caaaaaggat cttcacctag atccttttaa     10140
attaaaaatg aagttttaaa tcaatctaaa gtatatatga gtaaacttgg tctgacagtt     10200
```

```
accaatgctt aatcagtgag gcacctatct cagcgatctg tctatttcgt tcatccatag    10260
ttgcctgact cctgcaaacc acgttgtgtc tcaaaatctc tgatgttaca ttgcacaaga    10320
taaaaatata tcatcatgaa caataaaact gtctgcttac ataaacagta atacaagggg    10380
tgttatgagc catattcaac gggaaacgtc ttgctcgagg ccgcgattaa attccaacat    10440
ggatgctgat ttatatgggt ataaatgggc tcgcgataat gtcgggcaat caggtgcgac    10500
aatctatcga ttgtatggga agcccgatgc gccagagttg tttctgaaac atggcaaagg    10560
tagcgttgcc aatgatgtta cagatgagat ggtcagacta aactggctga cggaatttat    10620
gcctcttccg accatcaagc attttatccg tactcctgat gatgcatggt tactcaccac    10680
tgcgatcccc gggaaaacag cattccaggt attagaagaa tatcctgatt caggtgaaaa    10740
tattgttgat gcgctggcag tgttcctgcg ccggttgcat tcgattcctg tttgtaattg    10800
tccttttaac agcgatcgcg tatttcgtct cgctcaggcg caatcacgaa tgaataacgg    10860
tttggttgat gcgagtgatt ttgatgacga gcgtaatggc tggcctgttg aacaagtctg    10920
gaaagaaatg cataagcttt tgccattctc accggattca gtcgtcactc atggtgattt    10980
ctcacttgat aaccttattt ttgacgaggg gaaattaata ggttgtattg atgttggacg    11040
agtcggaatc gcagaccgat accaggatct tgccatccta tggaactgcc tcggtgagtt    11100
ttctccttca ttacagaaac ggctttttca aaaatatggt attgataatc ctgatatgaa    11160
taaattgcag tttcatttga tgctcgatga gttttttcta a gggcggcctg ccaccatacc    11220
cacgccgaaa caagcgctca tgagcccgaa gtggcgagcc cgatcttccc catcggtgat    11280
gtcggcgata taggcgccag caaccgcacc tgtggcgccg gtgatgaggg cgcgccaagt    11340
cgacgtccgg cagtc                                                     11355
```

<210> SEQ ID NO 3
<211> LENGTH: 11420
<212> TYPE: DNA
<213> ORGANISM: Artificial sequence
<220> FEATURE:
<223> OTHER INFORMATION: Synthetic polynucleotide

<400> SEQUENCE: 3

```
ttggccactc cctctctgcg cgctcgctcg ctcactgagg ccgggcgacc aaaggtcgcc     60
cgacgcccgg gctttgcccg gcggcctca gtgagcgagc gagcgcgcag agagggagtg    120
gccaactcca tcactagggg ttcctgctag ctctgggtat ttaagcccga gtgagcacgc    180
agggtctcca ttttgaagcg ggaggttacg cgttcgtcga ctactagtgg gtaccagagc    240
tccctaggtt ctagaaccgg tgacgtctcc catggtgaag cttggatctg agggcggagt    300
tagggcggag ccaatcagcg tgcgccgttc cgaaagttgc cttttatggc tgggcggaga    360
atgggcggtg aacgccgatg attatataag gacgcgccgg gtgtggcaca gctagttccg    420
tcgcagccgg gatttgggtc gcggttcttg tttgtggatc cctgtgatcg tcacttggta    480
agtcactgac tgtctatgcc tgggaaaggg tgggcaggag atggggcagt gcaggaaaag    540
tggcactatg aaccctgcag ccctaggaat gcatctagac aattgtacta accttcttct    600
ctttcctctc ctgacagtcc ggaaagccac catggaattc agcagcccca gcagagagga    660
atgccccaag cctctgagcc gggtgtcaat catggccgga tctctgacag gactgctgct    720
gcttcaggcc gtgtcttggg cttctggcgc tagaccttgc atccccaaga gcttcggcta    780
cagcagcgtc gtgtgcgtgt gcaatgccac ctactgcgca agcttcgacc ctcctaccct    840
tcctgctctg ggcaccttca gcagatacga gagcaccaga tccggcagac ggatggaact    900
```

```
gagcatggga cccatccagg ccaatcacac aggcactggc ctgctgctga cactgcagcc    960
tgagcagaaa ttccagaaag tgaaaggctt cggcggagcc atgacagatg ccgccgctct   1020
gaatatcctg gctctgtctc caccagctca gaacctgctg ctcaagagct acttcagcga   1080
ggaaggcatc ggctacaaca tcatcagagt gcccatggcc agctgcgact tcagcatcag   1140
gacctacacc tacgccgaca cacccgacga tttccagctg cacaacttca gcctgcctga   1200
agaggacacc aagctgaaga tccctctgat ccacagagcc ctgcagctgg cacaaagacc   1260
cgtgtcactg ctggcctctc catggacatc tcccacctgg ctgaaaacaa atggcgccgt   1320
gaatggcaag ggcagcctga aaggccaacc tggcgacatc taccaccaga cctgggccag   1380
atacttcgtg aagttcctgg acgcctatgc cgagcacaag ctgcagtttt gggccgtgac   1440
agccgagaac gaaccttctg ctggactgct gagcggctac ccctttcagt gcctgggctt   1500
tacacccgag caccagcggg actttatcgc ccgtgatctg ggacccacac tggccaatag   1560
cacccaccat aatgtgcggc tgctgatgct ggacgaccag agactgcttc tgccccactg   1620
ggctaaagtg gtgctgacag atcctgaggc cgccaaatac gtgcacggaa tcgccgtgca   1680
ctggtatctg gactttctgg cccctgccaa ggccacactg ggagagacac acagactgtt   1740
ccccaacacc atgctgttcg ccagcgaagc ctgtgtgggc agcaagtttt gggaacagag   1800
cgtgcggctc ggcagctggg atagaggcat gcagtacagc cacagcatca tcaccaacct   1860
gctgtaccac gtcgtcggct ggaccgactg gaatctggcc ctgaatcctg aaggcggccc   1920
taactgggtc cgaaacttcg tggacagccc catcatcgtg acatcacca aggacacctt   1980
ctacaagcag cccatgttct accacctggg acacttcagc aagttcatcc ccgagggctc   2040
tcagcgcgtt ggactggtgg cttcccagaa gaacgatctg gacgccgtgg ctctgatgca   2100
ccctgatgga tctgctgtgg tggtggtcct gaaccgcagc agcaaagatg tgcccctgac   2160
catcaaggat cccgccgtgg gattcctgga acaatcagc cctggctact ccatccacac   2220
ctacctgtgg cgtagacagt gacaattgtt aattaagttt catcgatacc gtcgactaga   2280
gctcgctgat cagcctcgac tgtgccttct agttgccagc catctgttgt ttgcccctcc   2340
cccgtgcctt ccttgaccct ggaaggtgcc actcccactg tcctttccta ataaaatgag   2400
gaaattgcat cgcattgtct gagtaggtgt cattctattc tggggggtgg ggtggggcag   2460
gacagcaagg gggaggattg gaagacaat agcaggcatg ctgggagag atccacgata   2520
acaaacagct ttttgggggg gcggagtta gggcggagcc aatcagcgtg cgccgttccg   2580
aaagttgcct tttatggctg gcggagaat gggcggtgaa cgccgatgat tatataagga   2640
cgcgccgggt gtggcacagc tagttccgtc gcagccggga tttgggtcgc ggttcttgtt   2700
tgtggatccc tgtgatcgtc acttggtaag tcactgactg tctatgcctg ggaaagggtg   2760
ggcaggagat ggggcagtgc aggaaaagtg gcactatgaa ccctgcagcc ctaggaatgc   2820
atctagacaa ttgtactaac cttcttctct ttcctctcct gacagtccgg aaagccacca   2880
tgggccgctg ctgcttctac accgccggca ccctgagcct gctgctgctg gtgaccagcg   2940
tgacctgct ggtggcccgc gtgttccaga aggccgtgga ccagagcatc gagaagaaga   3000
tcgtgctgcg caacggcacc gaggccttcg acagctggga agcccccc ctgccgtgt   3060
acacccagtt ctacttcttc aacgtgacca ccccgagga gatcctgcgc ggcgagaccc   3120
cccgcgtgga ggaggtgggc cctacacct ccgcgagct cgcaacaag gccaacatcc   3180
agttcggcga caacggcacc accatcagcg ccgtgagcaa caaggcctac gtgttcgagc   3240
```

```
gcgaccagag cgtgggcgac cccaagatcg acctgatccg caccctgaac atccccgtgc    3300
tgaccgtgat cgagtggagc caggtgcact tcctgcgcga gatcatcgag gccatgctga    3360
aggcctacca gcagaagctg ttcgtgaccc acaccgtgga cgagctgctg tggggctaca    3420
aggacgagat cctgagcctg atccacgtgt ccgccccga catcagcccc tacttcggcc    3480
tgttctacga gaagaacggc accaacgacg gcgactacgt gttcctgacc ggcgaggaca    3540
gctacctgaa cttcaccaag atcgtggagt ggaacggcaa gaccagcctg gactggtgga    3600
tcaccgacaa gtgcaacatg atcaacggca ccgacggcga cagcttccac cccctgatca    3660
ccaaggacga ggtgctgtac gtgttcccca gcgacttctg ccgcagcgtg tacatcacct    3720
tcagcgacta cgagagcgtg cagggcctgc ccgccttccg ctacaaggtg cccgccgaga    3780
tcctggccaa caccagcgac aacgccggct ctgcatccc cgagggcaac tgcctgggca    3840
gcggcgtgct gaacgtgagc atctgcaaga acggcgcccc catcatcatg agcttccccc    3900
acttctacca ggccgacgag cgcttcgtga gcgccatcga gggcatgcac cccaaccagg    3960
aggaccacga gaccttcgtg gacatcaacc ccctgaccgg catcatcctg aaggccgcca    4020
agcgcttcca gatcaacatc tacgtgaaga agctggacga cttcgtggag accggcgaca    4080
tccgcaccat ggtgttcccc gtgatgtacc tgaacgagag cgtgcacatc gacaaggaga    4140
ccgccagccg cctgaagagc atgatcaaca ccaccctgat catcaccaac atcccctaca    4200
tcatcatggc cctgggcgtg ttcttcggcc tggtgttcac ctggctggcc tgcaagggcc    4260
agggcagcat ggacgagggc accgccgacg agcgcgcccc cctgatccgc acctgaccca    4320
ggggactcaa tcagcctcga agacatgata agatacattg atgagtttgg acaaaccaca    4380
acaagaatgc agtgaaaaaa atgctttatt tgtgaaattt gtgatgctat tgctttattt    4440
gtaaccatta taagctgcaa taaacaagtt aacaacaaca attgcattca ttttatgttt    4500
caggttcagg gggagatgtg ggaggttttt taaagcaagt aaaacctcta caaatgtggt    4560
atgaacatat tgactgaatt ccctgcaggt tggccactcc ctctctgcgc gctcgctcgc    4620
tcactgaggc cgcccgggca agcccgggc gtcgggcgac cttggtcgc ccggcctcag    4680 tgagcgagcg agcgcgcaga gagggagtgg ccaactccat cactagggt tcctgcggcc    4740 gctcgtacgg tctcgaggaa ttcctgcagg ataacttgcc aacctcattc taaaatgtat    4800
atagaagccc aaaagacaat aacaaaaata ttcttgtaga acaaaatggg aaagaatgtt    4860
ccactaaata tcaagattta gagcaaagca tgagatgtgt ggggatagac agtgaggctg    4920
ataaaataga gtagagctca gaaacagacc cattgatata tgtaagtgac ctatgaaaaa    4980
aatatggcat tttacaatgg gaaaatgatg gtctttttct tttttagaaa aacagggaaa    5040
tatatttata tgtaaaaaat aaagggaac ccatatgtca taccatacac acaaaaaaat    5100
tccagtgaat tataagtcta atggagaag gcaaaacttt aaatctttta gaaaataata    5160
tagaagcatg cagaccagcc tggccaacat gatgaaaccc tctctactaa taataaaatc    5220
agtagaacta ctcaggacta ctttgagtgg gaagtccttt tctatgaaga cttctttggc    5280
caaaattagg ctctaaatgc aaggagatag tgcatcatgc ctggctgcac ttactgataa    5340
atgatgttat caccatcttt aaccaaatgc acaggaacaa gttatggtac tgatgtgctg    5400
gattgagaag gagctctact tccttgacag gacacatttg tatcaactta aaaaagcaga    5460
tttttgccag cagaactatt cattcagagg taggaaactt agaatagatg atgtcactga    5520
ttagcatggc ttccccatct ccacagctgc ttcccaccca ggttgccac agttgagttt    5580 gtccagtgct cagggctgcc cactctcagt aagaagcccc acaccagccc ctctccaaat    5640
```

```
atgttggctg ttccttccat taaagtgacc ccactttaga gcagcaagtg gatttctgtt    5700
tcttacagtt caggaaggag gagtcagctg tgagaacctg gagcctgaga tgcttctaag    5760
tcccactgct actggggtca gggaagccag actccagcat cagcagtcag gagcactaag    5820
cccttgccaa catcctgttt ctcagagaaa ctgcttccat tataatggtt gtcctttttt    5880
aagctatcaa gccaaacaac cagtgtctac cattattctc atcacctgaa gccaagggtt    5940
ctagcaaaag tcaagctgtc ttgtaatggt tgatgtgcct ccagcttctg tcttcagtca    6000
ctccactctt agcctgctct gaatcaactc tgaccacagt tccctggagc ccctgccacc    6060
tgctgcccct gccaccttct ccatctgcag tgctgtgcag ccttctgcac tcttgcagag    6120
ctaataggtg gagacttgaa ggaagaggag gaaagtttct cataatagcc ttgctgcaag    6180
ctcaaatggg aggtgggcac tgtgcccagg agccttggag caaaggctgt gcccaacctc    6240
tgactgcatc caggtttggt cttgacagag ataagaagcc ctggcttttg gagccaaaat    6300
ctaggtcaga cttaggcagg attctcaaag tttatcagca gaacatgagg cagaagaccc    6360
tttctgctcc agcttcttca ggctcaacct tcatcagaat agatagaaag agaggctgtg    6420
agggttctta aaacagaagc aaatctgact cagagaataa acaacctcct agtaaaactac    6480 agcttagaca gagcatctgg tggtgagtgt gctcagtgtc ctactcaact gtctggtatc    6540
agccctcatg aggacttctc ttctttccct catagacctc catctctgtt ttccttagcc    6600
tgcagaaatc tggatggcta ttcacagaat gcctgtgctt tcagagttgc atttttctc     6660 tggtattctg gttcaagcat ttgaaggtag gaaaggttct ccaagtgcaa gaaagccagc    6720
cctgagcctc aactgcctgg ctagtgtggt cagtaggatg caaaggctgt tgaatgccac    6780
aaggccaaac tttaacctgt gtaccacaag cctagcagca gaggcagctc tgctcactgg    6840
aactctctgt cttctttctc ctgagccttt tcttttcctg agttttctag ctctcctcaa    6900
ccttacctct gccctaccca ggacaaaccc aagagccact gtttctgtga tgtcctctcc    6960
agccctaatt aggcatcatg acttcagcct gaccttccat gctcagaagc agtgctaatc    7020
cacttcagat gagctgctct atgcaacaca ggcagagcct acaaaccttt gcaccagagc    7080
cctccacata tcagtgtttg ttcatactca cttcaacagc aaatgtgact gctgagatta    7140
agattttaca caagatggtc tgtaatttca cagttagttt tatcccatta ggtatgaaag    7200
aattagcata attcccctta aacatgaatg aatcttagat tttttaataa atagtttgg    7260 aagtaaagac agagacatca ggagcacaag gaatagcctg agaggacaaa cagaacaaga    7320
aagagtctgg aaatacacag gatgttcttg gcctcctcaa agcaagtgca agcagatagt    7380
accagcagcc ccaggctatc agagcccagt gaagagaagt accatgaaag ccacagctct    7440
aaccaccctg ttccagagtg acagacagtc cccaagacaa gccagcctga gccagagaga    7500
gaactgcaag agaaagtttc taatttaggt tctgttagat tcagacaagt gcaggtcatc    7560
ctctctccac agctactcac ctctccagcc taacaaagcc tgcagtccac actccaaccc    7620
tggtgtctca cctcctagcc tctcccaaca tcctgctctc tgaccatctt ctgcatctct    7680
catctcacca tctcccactg tctacagcct actcttgcaa ctaccatctc atttttctgac   7740 atcctgtcta catcttctgc catactctgc catctaccat accacctctt accatctacc    7800
acaccatctt ttatctccat ccctctcaga agcctccaag ctgaatcctg ctttatgtgt    7860
tcatctcagc ccctgcatgg aaagctgacc ccagaggcag aactattccc agagagcttg    7920
gccaagaaaa acaaaactac cagcctggcc aggctcagga gtagtaagct gcagtgtctg    7980
```

```
ttgtgttcta gcttcaacag ctgcaggagt tccactctca aatgctccac atttctcaca   8040
tcctcctgat tctggtcact acccatcttc aaagaacaga atatctcaca tcagcatact   8100
gtgaaggact agtcatgggt gcagctgctc agagctgcaa agtcattctg gatggtggag   8160
agcttacaaa catttcatga tgctcccccc gctctgatgg ctggagccca atccctacac   8220
agactcctgc tgtatgtgtt ttcctttcac tctgagccac agccagaggg caggcattca   8280
gtctcctctt caggctgggg ctggggcact gagaactcac ccaacacctt gctctcactc   8340
cttctgcaaa acaagaaaga gctttgtgct gcagtagcca tgaagaatga aggaaggct    8400 ttaactaaaa aatgtcagag attattttca accccttact gtggatcacc agcaaggagg   8460
aaacacaaca cagagacatt ttttcccctc aaattatcaa aagaatcact gcatttgtta   8520
aagagagcaa ctgaatcagg aagcagagtt ttgaacatat cagaagttag gaatctgcat   8580
cagagacaaa tgcagtcatg gttgtttgct gcataccagc cctaatcatt agaagcctca   8640
tggacttcaa acatcattcc ctctgacaag atgctctagc ctaactccat gagataaaat   8700
aaatctgcct ttcagagcca aagaagagtc caccagcttc ttctcagtgt gaacaagagc   8760
tccagtcagg ttagtcagtc cagtgcagta gaggagacca gtctgcatcc tctaattttc   8820
aaaggcaaga agatttgttt accctggaca ccaggcacaa gtgaggtcac agagctctta   8880
gatatgcagt cctcatgagt gaggagacta aagcgcatgc catcaagact tcagtgtaga   8940
gaaaacctcc aaaaaagcct cctcactact tctggaatag ctcagaggcc gaggcggcct   9000
cggcctctgc ataaataaaa aaaattagtc agccatgggg cggagaatgg gcggaactgg   9060
gcggagttag gggcgggatg ggcggagtta ggggcgggac tatggttgct gactaattga   9120
gatgcatgct ttgcatactt ctgcctgctg gggagcctgg ggactttcca cacctggttg   9180
ctgactaatt gagatgcatg ctttgcatac ttctgcctgc tggggagcct ggggactttc   9240
cacaccctaa ctgacacaca ttccacagct gcattaatga atcggccaac gcgcggggag   9300
aggcggtttg cgtattgggc gctcttccgc ttcctcgctc actgactcgc tgcgctcggt   9360
cgttcggctg cggcgagcgg tatcagctca ctcaaaggcg gtaatacggt tatccacaga   9420
atcaggggat aacgcaggaa agaacatgtg agcaaaaggc cagcaaaagg ccaggaaccg   9480
taaaaaggcc gcgttgctgg cgttttttcca taggctccgc cccccctgacg agcatcacaa   9540 aaatcgacgc tcaagtcaga ggtggcgaaa cccgacagga ctataaagat accaggcgtt   9600
tccccctgga agctccctcg tgcgctctcc tgttccgacc ctgccgctta ccggatacct   9660
gtccgccttt ctcccttcgg gaagcgtggc gctttctcat agctcacgct gtaggtatct   9720
cagttcggtg taggtcgttc gctccaagct gggctgtgtg cacgaacccc ccgttcagcc   9780
cgaccgctgc gccttatccg gtaactatcg tcttgagtcc aacccggtaa gacacgactt   9840
atcgccactg gcagcagcca ctggtaacag gattagcaga gcgaggtatg taggcggtgc   9900
tacagagttc ttgaagtggt ggcctaacta cggctacact agaagaacag tatttggtat   9960
ctgcgctctg ctgaagccag ttaccttcgg aaaaagagtt ggtagctctt gatccggcaa  10020
acaaaccacc gctggtagcg gtggtttttt tgtttgcaag cagcagatta cgcgcagaaa  10080
aaaaggatct caagaagatc ctttgatctt ttctacgggg tctgacgctc agtggaacga  10140
aaactcacgt taagggattt tggtcatgag attatcaaaa aggatcttca cctagatcct  10200
tttaaattaa aaatgaagtt ttaaatcaat ctaaagtata tatgagtaaa cttggtctga  10260
cagttaccaa tgcttaatca gtgaggcacc tatctcagcg atctgtctat ttcgttcatc  10320
catagttgcc tgactccctgc aaaccacgtt gtgtctcaaa atctctgatg ttacattgca  10380
```

```
caagataaaa atatatcatc atgaacaata aaactgtctg cttacataaa cagtaataca    10440
aggggtgtta tgagccatat tcaacgggaa acgtcttgct cgaggccgcg attaaattcc    10500
aacatggatg ctgatttata tgggtataaa tgggctcgcg ataatgtcgg gcaatcaggt    10560
gcgacaatct atcgattgta tgggaagccc gatgcgccag agttgtttct gaaacatggc    10620
aaaggtagcg ttgccaatga tgttacagat gagatggtca gactaaactg gctgacggaa    10680
tttatgcctc ttccgaccat caagcatttt atccgtactc ctgatgatgc atggttactc    10740
accactgcga tccccgggaa aacagcattc caggtattag aagaatatcc tgattcaggt    10800
gaaaatattg ttgatgcgct ggcagtgttc ctgcgccggt tgcattcgat tcctgttttgt   10860
aattgtcctt ttaacagcga tcgcgtattt cgtctcgctc aggcgcaatc acgaatgaat    10920
aacggtttgg ttgatgcgag tgattttgat gacgagcgta atggctggcc tgttgaacaa    10980
gtctggaaag aaatgcataa gcttttgcca ttctcaccgg attcagtcgt cactcatggt    11040
gatttctcac ttgataacct tatttttgac gaggggaaat taataggttg tattgatgtt    11100
ggacgagtcg gaatcgcaga ccgataccag gatcttgcca tcctatggaa ctgcctcggt    11160
gagttttctc cttcattaca gaaacggctt tttcaaaaat atggtattga taatcctgat    11220
atgaataaat tgcagtttca tttgatgctc gatgagtttt tctaagggcg gcctgccacc    11280
atacccacgc cgaaacaagc gctcatgagc ccgaagtggc gagcccgatc ttccccatcg    11340
gtgatgtcgg cgatataggc gccagcaacc gcacctgtgg cgccggtgat gagggcgcgc    11400
caagtcgacg tccggcagtc                                                11420

<210> SEQ ID NO 4
<211> LENGTH: 11171
<212> TYPE: DNA
<213> ORGANISM: Artificial sequence
<220> FEATURE:
<223> OTHER INFORMATION: Synthetic polynucleotide
<400> SEQUENCE: 4
ttggccactc cctctctgcg cgctcgctcg ctcactgagg ccgggcgacc aaaggtcgcc      60
cgacgcccgg gctttgcccg gcgcggcctca gtgagcgagc gagcgcgcag agagggagtg    120
gccaactcca tcactagggg ttcctgctag ctctgggtat ttaagcccga gtgagcacgc     180
agggtctcca ttttgaagcg ggaggttacg cgttcgtcga ctactagtgg gtaccagagc     240
tccctaggtt ctagaaccgg tgacgtctcc catggtgaag cttggatctg agggcggagt     300
tagggcggag ccaatcagcg tgcgccgttc cgaaagttgc ctttatggc tgggcggaga     360
atgggcggtg aacgccgatg attatataag gacgcgccgg gtgtggcaca gctagttccg    420
tcgcagccgg gatttgggtc gcggttcttg tttgtggatc cctgtgatcg tcacttggta     480
agtcactgac tgtctatgcc tgggaaaggg tgggcaggag atgggcagt gcaggaaaag     540
tggcactatg aaccctcctg gtggcgaggg gaggggggtg gtcctcgaac gccttgcaga    600
actggcctgg atacagagtg gaccggctgg ccccatctgg aagacttcga gatacactgt    660
tgtcttactg cgctcaacag tgtatctcga agtcttccaa atggtgccag ccatcgcagc    720
ggggtgcagg aaatgggggc agcccccctt tttggctatc cttccacgtg ttcttttttg    780
tatcttttgt gtttcctaga aaacatctca gtcaccaccg cagccctagg aatgcatcta    840
gacaattgta ctaaccttct tctctttcct ctcctgacag tccggaaagc caccatgggc    900
cgctgctgct tctacaccgc cggcaccctg agcctgctgc tgctggtgac cagcgtgacc    960
```

```
ctgctggtgg cccgcgtgtt ccagaaggcc gtggaccaga gcatcgagaa gaagatcgtg      1020
ctgcgcaacg gcaccgaggc cttcgacagc tgggagaagc cccccctgcc cgtgtacacc      1080
cagttctact tcttcaacgt gaccaacccc gaggagatcc tgcgcggcga accccccgc       1140 gtggaggagg tgggccccta cacctaccgc gagctgcgca acaaggccaa catccagttc      1200
ggcgacaacg gcaccaccat cagcgccgtg agcaacaagg cctacgtgtt cgagcgcgac      1260
cagagcgtgg gcgaccccaa gatcgacctg atccgcaccc tgaacatccc cgtgctgacc      1320
gtgatcgagt ggagccaggt gcacttcctg cgcgagatca tcgaggccat gctgaaggcc      1380
taccagcaga agctgttcgt gacccacacc gtggacgagc tgctgtgggg ctacaaggac      1440
gagatcctga gcctgatcca cgtgttccgc cccgacatca gcccctactt cggcctgttc      1500
tacgagaaga acggcaccaa cgacggcgac tacgtgttcc tgaccggcga ggacagctac      1560
ctgaacttca ccaagatcgt ggagtggaac ggcaagacca gcctggactg gtggatcacc      1620
gacaagtgca acatgatcaa cggcaccgac ggcgacagct ccacccccct gatcaccaag      1680
gacgaggtgc tgtacgtgtt ccccagcgac ttctgccgca gcgtgtacat caccttcagc      1740
gactacgaga gcgtgcaggg cctgcccgcc ttccgctaca aggtgcccgc cgagatcctg      1800
gccaacacca gcgacaacgc cggcttctgc atccccgagg gcaactgcct gggcagcggc      1860
gtgctgaacg tgagcatctg caagaacggc gcccccatca tcatgagctt cccccacttc      1920
taccaggccg acgagcgctt cgtgagcgcc atcgagggca tgcaccccaa ccaggaggac      1980
cacgagacct tcgtggacat caaccccctg accggcatca tcctgaaggc cgccaagcgc      2040
ttccagatca acatctacgt gaagaagctg gacgacttcg tggagaccgg cgacatccgc      2100
accatggtgt tccccgtgat gtacctgaac gagagcgtgc acatcgacaa ggagaccgcc      2160
agccgcctga gagcatgat caacaccacc ctgatcatca ccaacatccc ctacatcatc      2220
atggccctgg gcgtgttctt cggcctggtg ttcacctggc tggcctgcaa gggccagggc      2280
agcatggacg agggcaccgc cgacgagcgc gcccccctga tccgcaccga gggcagagga      2340
agtcttctga catgcggaga cgtggaagag aatcccggcc ctatggaatt cagcagcccc      2400
agcagagagg aatgccccaa gcctctgagc cgggtgtcaa tcatggccgg atctctgaca      2460
ggactgctgc tgcttcaggc cgtgtcttgg gcttctggcg ctagaccttg catccccaag      2520
agcttcggct acagcagcgt cgtgtgcgtg tgcaatgcca cctactgcga cagcttcgac      2580
cctcctacct ttcctgctct gggcaccttc agcagatacg agagcaccag atccggcaga      2640
cggatggaac tgagcatggg accccatccag gccaatcaca caggcactgg cctgctgctg      2700
acactgcagc ctgagcagaa attccagaaa gtgaaaggct cggcggagc catgacagat      2760 gccgccgctc tgaatatcct ggctctgtct ccaccagctc agaacctgct gctcaagagc      2820
tacttcagcg aggaaggcat cggctacaac atcatcagag tgcccatggc cagctgcgac      2880
ttcagcatca ggacctacac ctacgccgac acacccgacg atttccagct gcacaacttc      2940
agcctgcctg aagaggacac caagctgaag atccctctga ccacagagc cctgcagctg      3000 gcacaaagac ccgtgtcact gctggcctct ccatggacat ctcccacctg ctgaaaaaca      3060
aatggcgccg tgaatggcaa gggcagcctg aaaggccaac ctggcgacat ctaccaccag      3120
acctgggcca gatacttcgt gaagttcctg gacgcctatg ccgagcacaa gctgcagttt      3180
tgggccgtga cagccgagaa cgaaccttct gctggactgc tgagcggcta cccctttcag      3240
tgcctgggct ttacacccga gcaccagcgg gactttatcg cccgtgatct gggacccaca      3300
ctggccaata gcacccacca taatgtgcgg ctgctgatgc tggacgacca gagactgctt      3360
```

```
ctgccccact gggctaaagt ggtgctgaca gatcctgagg ccgccaaata cgtgcacgga    3420
atcgccgtgc actggtatct ggactttctg cccctgcca aggccacact gggagagaca     3480
cacagactgt tccccaacac catgctgttc gccagcgaag cctgtgtggg cagcaagttt    3540
tgggaacaga gcgtgcggct cggcagctgg gatagaggc tgcagtacag ccacagcatc     3600
atcaccaacc tgctgtacca cgtcgtcggc tggaccgact ggaatctggc cctgaatcct    3660
gaaggcggcc ctaactgggt ccgaaacttc gtggacagcc ccatcatcgt ggacatcacc    3720
aaggacacct tctacaagca gcccatgttc taccacctgg acacttcag caagttcatc     3780
cccgagggct ctcagcgcgt ggactggtg gcttcccaga gaacgatct ggacgccgtg      3840
gctctgatgc accctgatgg atctgctgtg gtggtggtcc tgaaccgcag cagcaaagat    3900
gtgcccctga ccatcaagga tcccgccgtg ggattcctgg aaacaatcag ccctggctac    3960
tccatccaca cctacctgtg gcgtagacag tgacaattgt taattaagtt taaaccctcg    4020
aggccgcaag ccgcatcgat accgtcgact agagctcgct gatcagcctc gactgtgcct    4080
tctagttgcc agccatctgt tgtttgcccc tcccccgtgc cttccttgac cctggaaggt    4140
gccactccca ctgtcctttc ctaataaaat gaggaaattg catcgcattg tctgagtagg    4200
tgtcattcta ttctgggggg tggggtgggg caggacagca aggggagga ttgggaagac     4260
aatagcaggc atgctgggga gagatccacg ataacaaaca gctttttgg ggtgaacata     4320
ttgactgaat tccctgcagg ttggccactc cctctctgcg cgctcgctcg ctcactgagg    4380
ccgcccgggc aaagcccggg cgtcgggcga cctttggtcg cccggcctca gtgagcgagc    4440
gagcgcgcag agagggagtg gccaactcca tcactagggg ttcctgcggc cgctcgtacg    4500
gtctcgagga attcctgcag gataacttgc caacctcatt ctaaaatgta tatagaagcc    4560
caaaagacaa taacaaaaat attcttgtag aacaaaatgg gaaagaatgt tccactaaat    4620
atcaagattt agagcaaagc atgagatgtg tggggataga cagtgaggct gataaaatag    4680
agtagagctc agaaacagac ccattgatat atgtaagtga cctatgaaaa aaatatggca    4740
ttttacaatg ggaaaatgat ggtctttttc tttttagaa aaacagggaa atatatttat     4800
atgtaaaaaa taaagggaa cccatatgtc ataccataca cacaaaaaaa ttccagtgaa     4860
ttataagtct aaatggagaa ggcaaaactt taaatctttt agaaaataat atagaagcat    4920
gcagaccagc ctggccaaca tgatgaaacc ctctctacta ataataaaat cagtagaact    4980
actcaggact actttgagtg ggaagtcctt ttctatgaag acttctttgg ccaaaattag    5040
gctctaaatg caaggagata gtgcatcatg cctggctgca cttactgata aatgatgtta    5100
tcaccatctt taaccaaatg cacaggaaca agttatggta ctgatgtgct ggattgagaa    5160
ggagctctac ttccttgaca ggacacattt gtatcaactt aaaaaagcag attttgcca    5220
gcagaactat tcattcagag gtaggaaact tagaatagat gatgtcactg attagcatgg    5280
cttccccatc tccacagctg cttcccaccc aggttgccca cagttgagtt tgtccagtgc    5340
tcagggctgc ccactctcag taagaagccc cacaccagcc cctctccaaa tatgttggct    5400
gttccttcca ttaaagtgac cccactttag agcagcaagt ggatttctgt ttcttacagt    5460
tcaggaagga ggagtcagct gtgagaacct ggagcctgag atgcttctaa gtcccactgc    5520
tactggggtc agggaagcca gactccagca tcagcagtca ggagcactaa gcccttgcca    5580
acatcctgtt tctcagagaa actgcttcca ttataatggt tgtccttttt taagctatca    5640
agccaaacaa ccagtgtcta ccattattct catcacctga agccaagggt tctagcaaaa    5700
```

-continued

```
gtcaagctgt cttgtaatgg ttgatgtgcc tccagcttct gtcttcagtc actccactct   5760
tagcctgctc tgaatcaact ctgaccacag ttccctggag cccctgccac ctgctgcccc   5820
tgccaccttc tccatctgca gtgctgtgca gccttctgca ctcttgcaga gctaataggt   5880
ggagacttga aggaagagga ggaaagtttc tcataatagc cttgctgcaa gctcaaatgg   5940
gaggtgggca ctgtgcccag gagccttgga gcaaaggctg tgcccaacct ctgactgcat   6000
ccaggtttgg tcttgacaga gataagaagc cctggctttt ggagccaaaa tctaggtcag   6060
acttaggcag gattctcaaa gtttatcagc agaacatgag gcagaagacc ctttctgctc   6120
cagcttcttc aggctcaacc ttcatcagaa tagatagaaa gagaggctgt gagggttctt   6180
aaaacagaag caaatctgac tcagagaata acaacctcc tagtaaacta cagcttagac    6240
agagcatctg gtggtgagtg tgctcagtgt cctactcaac tgtctggtat cagccctcat   6300
gaggacttct cttcttccc tcatagacct ccatctctgt tttccttagc ctgcagaaat    6360
ctggatggct attcacagaa tgcctgtgct ttcagagttg cattttttct ctggtattct   6420
ggttcaagca tttgaaggta ggaaaggttc tccaagtgca agaaagccag ccctgagcct   6480
caactgcctg gctagtgtgg tcagtaggat gcaaaggctg ttgaatgcca caaggccaaa   6540
cttaacctg tgtaccacaa gcctagcagc agaggcagct ctgctcactg gaactctctg    6600
tcttctttct cctgagcctt ttcttttcct gagttttcta gctctcctca accttacctc   6660
tgccctaccc aggacaaacc caagagccac tgtttctgtg atgtcctctc cagccctaat   6720
taggcatcat gacttcagcc tgaccttcca tgctcagaag cagtgctaat ccacttcaga   6780
tgagctgctc tatgcaacac aggcagagcc tacaaacctt gcaccagag ccctccacat    6840
atcagtgttt gttcatactc acttcaacag caaatgtgac tgctgagatt aagattttac   6900
acaagatggt ctgtaatttc acagttagtt ttatcccatt aggtatgaaa gaattagcat   6960
aattccccctt aaacatgaat gaatcttaga ttttttaata aatagttttg gaagtaaaga   7020
cagagacatc aggagcacaa ggaatagcct gagaggacaa acagaacaag aaagagtctg   7080
gaaatacaca ggatgttctt ggcctcctca aagcaagtgc aagcagatag taccagcagc   7140
cccaggctat cagagcccag tgaagagaag taccatgaaa gccacagctc taaccaccct   7200
gttccagagt gacagacagt ccccaagaca agccagcctg agccagagag agaactgcaa   7260
gagaaagttt ctaatttagg ttctgttaga ttcagacaag tgcaggtcat cctctctcca   7320
cagctactca cctctccagc ctaacaaagc ctgcagtcca cactccaacc ctggtgtctc   7380
acctcctagc ctctcccaac atcctgctct ctgaccatct tctgcatctc tcatctcacc   7440
atctcccact gtctacagcc tactcttgca actaccatct catttctga catcctgtct    7500
acatcttctg ccatactctg ccatctacca taccacctct taccatctac cacaccatct   7560
tttatctcca tccctctcag aagcctccaa gctgaatcct gctttatgtg ttcatctcag   7620
cccctgcatg gaaagctgac cccagaggca gaactattcc cagagagctt ggccaagaaa   7680
aacaaaacta ccagcctggc caggctcagg agtagtaagc tgcagtgtct gttgtgttct   7740
agcttcaaca gctgcaggag ttccactctc aaatgctcca catttctcac atcctcctga   7800
ttctggtcac tacccatctt caaagaacag aatatctcac atcagcatac tgtgaaggac   7860
tagtcatggg tgcagctgct cagagctgca aagtcattct ggatggtgga gagcttacaa   7920
acatttcatg atgctccccc cgctctgatg gctggagccc aatccctaca cagactcctg   7980
ctgtatgtgt tttcctttca ctctgagcca cagccagagg gcaggcattc agtctcctct   8040
tcaggctggg gctggggcac tgagaactca cccaacacct tgctctcact ccttctgcaa   8100
```

```
aacaagaaag agctttgtgc tgcagtagcc atgaagaatg aaaggaaggc tttaactaaa    8160
aaatgtcaga gattattttc aaccccttac tgtggatcac cagcaaggag gaaacacaac    8220
acagagacat ttttccccct caaattatca aaagaatcac tgcatttgtt aaagagagca    8280
actgaatcag gaagcagagt tttgaacata tcagaagtta ggaatctgca tcagagacaa    8340
atgcagtcat ggttgtttgc tgcataccag ccctaatcat tagaagcctc atggacttca    8400
aacatcattc cctctgacaa gatgctctag cctaactcca tgagataaaa taaatctgcc    8460
tttcagagcc aaagaagagt ccaccagctt cttctcagtg tgaacaagag ctccagtcag    8520
gttagtcagt ccagtgcagt agaggagacc agtctgcatc ctctaatttt caaaggcaag    8580
aagatttgtt taccctggac accaggcaca agtgaggtca cagagctctt agatatgcag    8640
tcctcatgag tgaggagact aaagcgcatg ccatcaagac ttcagtgtag agaaaacctc    8700 caaaaagcc tcctcactac ttctggaata gctcagaggc cgaggcggcc tcggcctctg    8760
cataaataaa aaaaattagt cagccatggg gcggagaatg gcggaactg gcggagtta    8820 ggggcgggat gggcggagtt aggggcggga ctatggttgc tgactaattg agatgcatgc    8880
tttgcatact tctgcctgct ggggagcctg gggactttcc acacctggtt gctgactaat    8940
tgagatgcat gctttgcata cttctgcctg ctggggagcc tggggacttt ccacacccta    9000
actgacacac attccacagc tgcattaatg aatcggccaa cgcgcgggga gaggcggttt    9060
gcgtattggg cgctcttccg cttcctcgct cactgactcg ctgcgctcgg tcgttcggct    9120
gcggcgagcg gtatcagctc actcaaaggc ggtaatacgg ttatccacag aatcaggga    9180 taacgcagga aagaacatgt gagcaaaagg ccagcaaaag gccaggaacc gtaaaaaggc    9240
cgcgttgctg gcgtttttcc ataggctccg ccccctgac gagcatcaca aaatcgacg    9300 ctcaagtcag aggtggcgaa acccgacagg actataaaga taccaggcgt ttccccctgg    9360
aagctccctc gtgcgctctc ctgttccgac cctgccgctt accggatacc tgtccgcctt    9420
tctcccttcg ggaagcgtgg cgctttctca tagctcacgc tgtaggtatc tcagttcggt    9480
gtaggtcgtt cgctccaagc tgggctgtgt gcacgaaccc cccgttcagc ccgaccgctg    9540
cgccttatcc ggtaactatc gtcttgagtc caacccggta agacacgact tatcgccact    9600
ggcagcagcc actggtaaca ggattagcag agcgaggtat gtaggcggtg ctacagagtt    9660
cttgaagtgg tggcctaact acggctacac tagaagaaca gtatttggta tctgcgctct    9720
gctgaagcca gttaccttcg gaaaaagagt tggtagctct tgatccggca aacaaaccac    9780
cgctggtagc ggtggttttt ttgtttgcaa gcagcagatt acgcgcagaa aaaaaggatc    9840
tcaagaagat cctttgatct tttctacggg gtctgacgct cagtggaacg aaaactcacg    9900
ttaagggatt ttggtcatga gattatcaaa aaggatcttc acctagatcc ttttaaatta    9960
aaaatgaagt tttaaatcaa tctaaagtat atatgagtaa acttggtctg acagttacca   10020
atgcttaatc agtgaggcac ctatctcagc gatctgtcta tttcgttcat ccatagttgc   10080
ctgactcctg caaaccacgt tgtgtctcaa aatctctgat gttacattgc acaagataaa   10140
aatatatcat catgaacaat aaaactgtct gcttacataa acagtaatac aagggtgtt   10200 atgagccata ttcaacggga aacgtcttgc tcgaggccgc gattaaattc caacatggat   10260
gctgatttat atgggtataa atgggctcgc gataatgtcg ggcaatcagg tgcgacaatc   10320
tatcgattgt atgggaagcc cgatgcgcca gagttgtttc tgaaacatgg caaaggtagc   10380
gttgccaatg atgttacaga tgagatggtc agactaaact ggctgacgga atttatgcct   10440
```

```
cttccgacca tcaagcattt tatccgtact cctgatgatg catggttact caccactgcg    10500
atccccggga aaacagcatt ccaggtatta gaagaatatc ctgattcagg tgaaaatatt    10560
gttgatgcgc tggcagtgtt cctgcgccgg ttgcattcga ttcctgtttg taattgtcct    10620
tttaacagcg atcgcgtatt tcgtctcgct caggcgcaat cacgaatgaa taacggtttg    10680
gttgatgcga gtgattttga tgacgagcgt aatggctggc ctgttgaaca agtctggaaa    10740
gaaatgcata agcttttgcc attctcaccg gattcagtcg tcactcatgg tgatttctca    10800
cttgataacc ttatttttga cgaggggaaa ttaataggtt gtattgatgt tggacgagtc    10860
ggaatcgcag accgatacca ggatcttgcc atcctatgga actgcctcgg tgagttttct    10920
ccttcattac agaaacggct ttttcaaaaa tatggtattg ataatcctga tatgaataaa    10980
ttgcagtttc atttgatgct cgatgagttt ttctaagggc ggcctgccac catacccacg    11040
ccgaaacaag cgctcatgag cccgaagtgg cgagcccgat cttccccatc ggtgatgtcg    11100
gcgatatagg cgccagcaac cgcacctgtg gcgccggtga tgagggcgcg ccaagtcgac    11160
gtccggcagt c                                                        11171

<210> SEQ ID NO 5
<211> LENGTH: 11309
<212> TYPE: DNA
<213> ORGANISM: Artificial sequence
<220> FEATURE:
<223> OTHER INFORMATION: Synthetic polynucleotide

<400> SEQUENCE: 5
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctgctag ctctgggtat ttaagcccga gtgagcacgc     180
agggtctcca ttttgaagcg ggaggttacg cgttcgtcga ctactagtgg gtaccagagc     240
tccctaggtt ctagaaccgg tgacgtctcc catggtgaag cttggatctg agggcggagt     300
tagggcggag ccaatcagcg tgcgccgttc cgaaagttgc cttttatggc tgggcggaga     360
atgggcggtg aacgccgatg attatataag gacgcgccgg gtgtggcaca gctagttccg     420
tcgcagccgg gatttgggtc gcggttcttg tttgtggatc cctgtgatcg tcacttggta     480
agtcactgac tgtctatgcc tgggaaaggg tgggcaggag atgggcagt gcaggaaaag     540 tggcactatg aaccctcctg gtggcgaggg gaggggggtg gtcctcgaac gccttgcaga     600
actggcctgg atacagagtg gaccggctgg ccccatctgg aagacttcga gatacactgt     660
tgtcttactg cgctcaacag tgtatctcga agtcttccaa atggtgccag ccatcgcagc     720
ggggtgcagg aaatggggc agccccccctt tttggctatc cttccacgtg ttcttttttg     780
tatcttttgt gtttcctaga aaacatctca gtcaccaccg cagccctagg aatgcatcta     840
gacaattgta ctaaccttct tctctttcct ctccctgacag tccggaaagc caccatgtac     900
gccctgttcc tgctggccag cctgctgggc cgccctggg ccggccccgt gctgggcctg     960
aaggagtgca cccgcggcag cgccgtgtgg tgccagaacg tgaagaccgc cagcgactgc    1020
ggcgccgtga gcactgcct gcagaccgtg tggaacaagc ccaccgtgaa gagcctgccc    1080
tgcgacatct gcaaggacgt ggtgaccgcc gccggcgaca tgctgaagga caacgccacc    1140
gaggaggaga tcctggtgta cctggagaag acctgcgact ggctgcccaa gcccaacatg    1200
agcgccagct gcaaggagat cgtggacagc tacctgcccg tgatcctgga catcatcaag    1260
ggcgagatga gccgccccgg cgaggtgtgc agcgccctga acctgtgcga gagcctgcag    1320
```

```
aagcacctgg ccgagctgaa ccaccagaag cagctggaga gcaacaagat ccccgagctg    1380
gacatgaccg aggtggtggc ccccttcatg gccaacatcc ccctgctgct gtaccccag     1440 gacggccccc gcagcaagcc ccagcccaag gacaacggcg acgtgtgcca ggactgcatc    1500
cagatggtga ccgacatcca gaccgccgtg cgcaccaaca gcaccttcgt gcaggccctg    1560
gtggagcacg tgaaggagga gtgcgaccgc ctgggccccg gcatggccga catctgcaag    1620
aactacatca gccagtacag cgagatcgcc atccagatga tgatgcacat gcagcccaag    1680
gagatctgcg ccctggtggg cttctgcgac gaggtgaagg agatgcccat gcagaccctg    1740
gtgcccgcca aggtggccag caagaacgtg atccccgccc tggagctggt ggagcccatc    1800
aagaagcacg aggtgcccgc caagagcgac gtgtactgcg aggtgtgcga gttcctggtg    1860
aaggaggtga ccaagctgat cgacaacaac aagaccgaga aggagatcct ggacgccttc    1920
gacaagatgt gcagcaagct gcccaagagc ctgagcgagg agtgccagga ggtggtggac    1980
acctacggca gcagcatcct gagcatcctg ctggaggagg tgagccccga gctggtgtgc    2040
agcatgctgc acctgtgcag cggcacccgc ctgcccgccc tgaccgtgca cgtgacccag    2100
cccaaggacg gcggcttctg cgaggtgtgc aagaagctgg tgggctacct ggaccgcaac    2160
ctggagaaga acagcaccaa gcaggagatc ctggccgccc tggagaaggg ctgcagcttc    2220
ctgcccgacc cctaccagaa gcagtgcgac cagttcgtgg ccgagtacga gcccgtgctg    2280
atcgagatcc tggtggaggt gatggacccc agcttcgtgt gcctgaagat cggcgcctgc    2340
cccagcgccc acaagcccct gctgggcacc gagaagtgca tctggggccc cagctactgg    2400
tgccagaaca ccgagaccgc cgcccagtgc aacgccgtgg agcactgcaa cgccacgtg     2460 tggaacgagg gcagaggaag tcttctgaca tgcggagacg tggaagagaa tcccggccct    2520
atggaattca gcagccccag cagagaggaa tgccccaagc ctctgagccg ggtgtcaatc    2580
atggccggat ctctgacagg actgctgctg cttcaggccg tgtcttgggc ttctggcgct    2640
agaccttgca tccccaagag cttcggctac agcagcgtcg tgtgcgtgtg caatgccacc    2700
tactgcgaca gcttcgaccc tcctaccttt cctgctctgg gcaccttcag cagatacgag    2760
agcaccagat ccggcagacg gatggaactg agcatgggac ccatccaggc caatcacaca    2820
ggcactggcc tgctgctgac actgcagcct gagcagaaat ccagaaaagt gaaaggcttc    2880
ggcggagcca tgacagatgc cgccgctctg aatatcctgg ctctgtctcc accagctcag    2940
aacctgctgc tcaagagcta cttcagcgag gaaggcatcg gctacaacat catcagagtg    3000
cccatggcca gctgcgactt cagcatcagg acctacacct acgccgacac acccgacgat    3060
ttccagctgc acaacttcag cctgcctgaa gaggacacca agctgaagat ccctctgatc    3120
cacagagccc tgcagctggc acaaagaccc gtgtcactgc tggcctctcc atggacatct    3180
cccacctggc tgaaaacaaa tggcgccgtg aatggcaagg gcagcctgaa aggccaacct    3240
ggcgacatct accaccagac ctgggccaga tacttcgtga agttcctgga cgcctatgcc    3300
gagcacaagc tgcagttttg gccgtgaca gccgagaacg aaccttctgc tggactgctg    3360
agcggctacc cctttcagtg cctgggcttt acacccgagc accagcggga ctttatcgcc    3420
cgtgatctgg acccacact ggccaatagc acccaccata atgtgcggct gctgatgctg    3480
gacgaccaga gactgcttct gccccactgg gctaaagtgg tgctgacaga tcctgaggcc    3540
gccaaatacg tgcacggaat cgccgtgcac tggtatctgg actttctggc ccctgccaag    3600
gccacactgg gagagacaca cagactgttc cccaacacca tgctgttcgc cagcgaagcc    3660
```

```
tgtgtgggca gcaagttttg ggaacagagc gtgcggctcg gcagctggga tagaggcatg    3720
cagtacagcc acagcatcat caccaacctg ctgtaccacg tcgtcggctg gaccgactgg    3780
aatctggccc tgaatcctga aggcggccct aactgggtcc gaaacttcgt ggacagcccc    3840
atcatcgtgg acatcaccaa ggacaccttc tacaagcagc ccatgttcta ccacctggga    3900
cacttcagca agttcatccc cgagggctct cagcgcgttg gactggtggc ttcccagaag    3960
aacgatctgg acgccgtggc tctgatgcac cctgatggat ctgctgtggt ggtggtcctg    4020
aaccgcagca gcaaagatgt gcccctgacc atcaaggatc ccgccgtggg attcctggaa    4080
acaatcagcc ctggctactc catccacacc tacctgtggc gtagacagtg acaattgtta    4140
attaagttta aaccctcgag gccgcaagcc gcatcgatac cgtcgactag agctcgctga    4200
tcagcctcga ctgtgccttc tagttgccag ccatctgttg tttgcccctc cccgtgcct     4260 tccttgaccc tggaaggtgc cactcccact gtcctttcct aataaaatga ggaaattgca    4320
tcgcattgtc tgagtaggtg tcattctatt ctgggggtg gggtggggca ggacagcaag     4380
ggggaggatt gggaagacaa tagcaggcat gctggggaga gatccacgat aacaaacagc    4440
ttttttgggg tgaacatatt gactgaattc cctgcaggtt ggccactccc tctctgcgcg    4500
ctcgctcgct cactgaggcc gcccgggcaa agcccgggcg tcgggcgacc tttggtcgcc    4560
cggcctcagt gagcgagcga gcgcgcagag agggagtggc caactccatc actaggggtt    4620
cctgcggccg ctcgtacggt ctcgaggaat tcctgcagga taacttgcca acctcattct    4680
aaaatgtata tagaagccca aaagacaata acaaaaatat tcttgtagaa caaatgggaa    4740
aagaatgttc cactaaatat caagatttag agcaaagcat gagatgtgtg gggatagaca    4800
gtgaggctga taaaatagag tagagctcag aaacagaccc attgatatat gtaagtgacc    4860
tatgaaaaaa atatggcatt ttacaatggg aaaatgatgg tcttttttctt ttttagaaaa    4920 acagggaaat atatttatat gtaaaaaata aagggaacc catatgtcat accatacaca     4980
caaaaaaatt ccagtgaatt ataagtctaa atggagaagg caaaacttta aatcttttag    5040
aaaataatat agaagcatgc agaccagcct ggccaacatg atgaaaccct ctctactaat    5100
aataaaatca gtagaactac tcaggactac tttgagtggg aagtcctttt ctatgaagac    5160
ttctttggcc aaaattaggc tctaaatgca aggagatagt gcatcatgcc tggctgcact    5220
tactgataaa tgatgttatc accatcttta accaaatgca caggaacaag ttatggtact    5280
gatgtgctgg attgagaagg agctctactt ccttgacagg acacatttgt atcaacttaa    5340
aaaagcagat ttttgccagc agaactattc attcagaggt aggaaactta gaatagatga    5400
tgtcactgat tagcatggct tccccatctc cacagctgct tcccacccag gttgcccaca    5460
gttgagtttg tccagtgctc agggctgccc actctcagta agaagcccca caccagcccc    5520
tctccaaata tgttggctgt tccttccatt aaagtgaccc cactttagag cagcaagtgg    5580
atttctgttt cttacagttc aggaaggagg agtcagctgt gagaacctgg agcctgagat    5640
gcttctaagt cccactgcta ctgggtcag ggaagccaga ctccagcatc agcagtcagg     5700
agcactaagc ccttgccaac atcctgtttc tcagagaaac tgcttccatt ataatggttg    5760
tcctttttta agctatcaag ccaaacaacc agtgtctacc attattctca tcacctgaag    5820
ccaagggttc tagcaaaagt caagctgtct tgtaatggtt gatgtgcctc cagcttctgt    5880
cttcagtcac tccactctta gcctgctctg aatcaactct gaccacagtt ccctggagcc    5940
cctgccacct gctgccctg ccaccttctc catctgcagt gctgtgcagc cttctgcact    6000
cttgcagagc taataggtgg agacttgaag gaagaggagg aaagtttctc ataatagcct    6060
```

-continued

```
tgctgcaagc tcaaatggga ggtgggcact gtgcccagga gccttggagc aaaggctgtg   6120
cccaacctct gactgcatcc aggtttggtc ttgacagaga taagaagccc tggcttttgg   6180
agccaaaatc taggtcagac ttaggcagga ttctcaaagt ttatcagcag aacatgaggc   6240
agaagaccct ttctgctcca gcttcttcag gctcaacctt catcagaata gatagaaaga   6300
gaggctgtga gggttcttaa aacagaagca aatctgactc agagaataaa caacctccta   6360
gtaaactaca gcttagacag agcatctggt ggtgagtgtg ctcagtgtcc tactcaactg   6420
tctggtatca gccctcatga ggacttctct tctttccctc atagacctcc atctctgttt   6480
tccttagcct gcagaaatct ggatggctat tcacagaatg cctgtgcttt cagagttgca   6540
ttttttctct ggtattctgg ttcaagcatt tgaaggtagg aaaggttctc caagtgcaag   6600
aaagccagcc ctgagcctca actgcctggc tagtgtggtc agtaggatgc aaaggctgtt   6660
gaatgccaca aggccaaact ttaacctgtg taccacaagc ctagcagcag aggcagctct   6720
gctcactgga actctctgtc ttctttctcc tgagcctttt cttttcctga gttttctagc   6780
tctcctcaac cttacctctg ccctacccag acaaacccca agagccactg tttctgtgat   6840
gtcctctcca gccctaatta ggcatcatga cttcagcctg accttccatg ctcagaagca   6900
gtgctaatcc acttcagatg agctgctcta tgcaacacag gcagagccta caaacctttg   6960
caccagagcc ctccacatat cagtgtttgt tcatactcac ttcaacagca aatgtgactg   7020
ctgagattaa gattttacac aagatggtct gtaatttcac agttagtttt atcccattag   7080
gtatgaaaga attagcataa ttccccttaa acatgaatga atcttagatt ttttaataaa   7140
tagttttgga agtaaagaca gagacatcag gagcacaagg aatagcctga gaggacaaac   7200
agaacaagaa agagtctgga aatacacagg atgttcttgg cctcctcaaa gcaagtgcaa   7260
gcagatagta ccagcagccc caggctatca gagcccagtg aagagaagta ccatgaaagc   7320
cacagctcta accaccctgt tccagagtga cagacagtcc caagacaag ccagcctgag   7380
ccagagagag aactgcaaga gaaagtttct aatttaggtt ctgttagatt cagacaagtg   7440
caggtcatcc tctctccaca gctactcacc tctccagcct aacaaagcct gcagtccaca   7500
ctccaacccct ggtgtctcac ctcctagcct ctcccaacat cctgctctct gaccatcttc   7560
tgcatctctc atctcaccat ctcccactgt ctacagccta ctcttgcaac taccatctca   7620
ttttctgaca tcctgtctac atcttctgcc atactctgcc atctaccata ccacctctta   7680
ccatctacca caccatcttt tatctccatc cctctcagaa gcctccaagc tgaatcctgc   7740
tttatgtgtt catctcagcc cctgcatgga aagctgaccc cagaggcaga actattccca   7800
gagagcttgg ccaagaaaaa caaaactacc agcctggcca ggctcaggag tagtaagctg   7860
cagtgtctgt tgtgttctag cttcaacagc tgcaggagtt ccactctcaa atgctccaca   7920
tttctcacat cctcctgatt ctggtcacta cccatcttca aagaacagaa tatctcacat   7980
cagcatactg tgaaggacta gtcatgggtg cagctgctca gagctgcaaa gtcattctgg   8040
atggtggaga gcttacaaac atttcatgat gctccccccg ctctgatggc tggagcccaa   8100
tccctacaca gactcctgct gtatgtgttt tcctttcact ctgagccaca gccagagggc   8160
aggcattcag tctcctcttc aggctggggc tgggcactg agaactcacc caacaccttg   8220
ctctcactcc ttctgcaaaa caagaaagag ctttgtgctg cagtagccat gaagaatgaa   8280
aggaaggctt taactaaaaa atgtcagaga ttatttcaa ccccttactg tggatcacca   8340
gcaaggagga aacacaacac agagacattt tttcccctca aattatcaaa agaatcactg   8400
```

```
catttgttaa agagagcaac tgaatcagga agcagagttt tgaacatatc agaagttagg    8460
aatctgcatc agagacaaat gcagtcatgg ttgtttgctg cataccagcc ctaatcatta    8520
gaagcctcat ggacttcaaa catcattccc tctgacaaga tgctctagcc taactccatg    8580
agataaaata aatctgcctt tcagagccaa agaagagtcc accagcttct tctcagtgtg    8640
aacaagagct ccagtcaggt tagtcagtcc agtgcagtag aggagaccag tctgcatcct    8700
ctaattttca aaggcaagaa gatttgttta ccctggacac caggcacaag tgaggtcaca    8760
gagctcttag atatgcagtc ctcatgagtg aggagactaa agcgcatgcc atcaagactt    8820
cagtgtagag aaaacctcca aaaagcctc ctcactactt ctggaatagc tcagaggccg     8880
aggcggcctc ggcctctgca taaataaaaa aaattagtca gccatggggc ggagaatggg    8940
cggaactggg cggagttagg ggcgggatgg gcggagttag gggcgggact atggttgctg    9000
actaattgag atgcatgctt tgcatacttc tgcctgctgg ggagcctggg gactttccac    9060
acctggttgc tgactaattg agatgcatgc tttgcatact tctgcctgct ggggagcctg    9120
gggactttcc acaccctaac tgacacacat tccacagctg cattaatgaa tcggccaacg    9180
cgcggggaga ggcggtttgc gtattgggcg ctcttccgct tcctcgctca ctgactcgct    9240
gcgctcggtc gttcggctgc ggcgagcggt atcagctcac tcaaaggcgg taatacggtt    9300
atccacagaa tcaggggata acgcaggaaa gaacatgtga gcaaaaggcc agcaaaaggc    9360
caggaaccgt aaaaaggccg cgttgctggc gtttttccat aggctccgcc ccctgacga    9420
gcatcacaaa aatcgacgct caagtcagag gtggcgaaac ccgacaggac tataaagata    9480
ccaggcgttt ccccctggaa gctccctcgt gcgctctcct gttccgaccc tgccgcttac    9540
cggatacctg tccgcctttc tcccttcggg aagcgtggcg ctttctcata gctcacgctg    9600
taggtatctc agttcggtgt aggtcgttcg ctccaagctg ggctgtgtgc acgaaccccc    9660
cgttcagccc gaccgctgcg ccttatccgg taactatcgt cttgagtcca acccggtaag    9720
acacgactta tcgccactgg cagcagccac tggtaacagg attagcagag cgaggtatgt    9780
aggcggtgct acagagttct tgaagtggtg gcctaactac ggctacacta agaacagt     9840
atttggtatc tgcgctctgc tgaagccagt taccttcgga aaaagagttg gtagctcttg    9900
atccggcaaa caaaccaccg ctggtagcgg tggtttttttt gtttgcaagc agcagattac    9960
gcgcagaaaa aaggatctc aagaagatcc tttgatcttt tctacggggt ctgacgctca    10020
gtggaacgaa aactcacgtt aagggatttt ggtcatgaga ttatcaaaaa ggatcttcac    10080
ctagatcctt ttaaattaaa aatgaagttt taaatcaatc taaagtatat atgagtaaac    10140
ttggtctgac agttaccaat gcttaatcag tgaggcacct atctcagcga tctgtctatt    10200
tcgttcatcc atagttgcct gactcctgca accacgttg tgtctcaaaa tctctgatgt     10260
tacattgcac aagataaaaa tatatcatca tgaacaataa aactgtctgc ttacataaac    10320
agtaatacaa ggggtgttat gagccatatt caacgggaaa cgtcttgctc gaggccgcga    10380
ttaaattcca acatggatgc tgatttatat gggtataaat gggctcgcga taatgtcggg    10440
caatcaggtg cgacaatcta tcgattgtat gggaagcccg atgcgccaga gttgtttctg    10500
aaacatggca aaggtagcgt tgccaatgat gttacagatg agatggtcag actaaactgg    10560
ctgacggaat ttatgcctct tccgaccatc aagcatttta tccgtactcc tgatgatgca    10620
tggttactca ccactgcgat ccccgggaaa acagcattcc aggtattaga agaatatcct    10680
gattcaggtg aaaatattgt tgatgcgctg gcagtgttcc tgcgccggtt gcattcgatt    10740
cctgtttgta attgtccttt taacagcgat cgcgtatttc gtctcgctca ggcgcaatca    10800
```

| | |
|---|---|
| cgaatgaata acggtttggt tgatgcgagt gattttgatg acgagcgtaa tggctggcct | 10860 |
| gttgaacaag tctggaaaga aatgcataag cttttgccat tctcaccgga ttcagtcgtc | 10920 |
| actcatggtg atttctcact tgataacctt attttgacg aggggaaatt aataggttgt | 10980 |
| attgatgttg gacgagtcgg aatcgcagac cgataccagg atcttgccat cctatggaac | 11040 |
| tgcctcggtg agttttctcc ttcattacag aaacggcttt ttcaaaaata tggtattgat | 11100 |
| aatcctgata tgaataaatt gcagtttcat ttgatgctcg atgagttttt ctaagggcgg | 11160 |
| cctgccacca tacccacgcc gaaacaagcg ctcatgagcc cgaagtggcg agcccgatct | 11220 |
| tccccatcgg tgatgtcggc gatataggcg ccagcaaccg cacctgtggc gccggtgatg | 11280 |
| agggcgcgcc aagtcgacgt ccggcagtc | 11309 |

<210> SEQ ID NO 6
<211> LENGTH: 11293
<212> TYPE: DNA
<213> ORGANISM: Artificial sequence
<220> FEATURE:
<223> OTHER INFORMATION: Synthetic polynucleotide

<400> SEQUENCE: 6

| | |
|---|---|
| ttggccactc cctctctgcg cgctcgctcg ctcactgagg ccgggcgacc aaaggtcgcc | 60 |
| cgacgcccgg gctttgcccg ggcggcctca gtgagcgagc gagcgcgcag agagggagtg | 120 |
| gccaactcca tcactagggg ttcctgctag ctctgggtat ttaagcccga gtgagcacgc | 180 |
| agggtctcca ttttgaagcg ggaggttacg cgttcgtcga ctactagtgg gtaccagagc | 240 |
| tccctaggtt ctagaaccgg tgacgtctcc catggtgaag cttggatctg agggcggagt | 300 |
| tagggcggag ccaatcagcg tgcgccgttc cgaaagttgc cttttatggc tgggcggaga | 360 |
| atgggcggtg aacgccgatg attatataag gacgcgccgg gtgtggcaca gctagttccg | 420 |
| tcgcagccgg gatttgggtc gcggttcttg tttgtggatc cctgtgatcg tcacttggta | 480 |
| agtcactgac tgtctatgcc tgggaaaggg tgggcaggag atgggcagt gcaggaaaag | 540 |
| tggcactatg aaccctgcag ccctaggaat gcatctagac aattgtacta accttcttct | 600 |
| ctttcctctc ctgacagtcc ggaaagccac catgtacgcc ctgttcctgc tggccagcct | 660 |
| gctgggcgcc gccctggccg gccccgtgct gggcctgaag gagtgcaccc gcggcagcgc | 720 |
| cgtgtggtgc cagaacgtga agaccgccag cgactgcggc gccgtgaagc actgcctgca | 780 |
| gaccgtgtgg aacaagccca ccgtgaagag cctgccctgc gacatctgca aggacgtggt | 840 |
| gaccgccgcc ggcgacatgc tgaaggacaa cgccaccgag gaggagatcc tggtgtacct | 900 |
| ggagaagacc tgcgactggc tgcccaagcc caacatgagc gccagctgca aggagatcgt | 960 |
| ggacagctac ctgcccgtga tcctggacat catcaagggc gagatgagcc gccccggcga | 1020 |
| ggtgtgcagc gccctgaacc tgtgcgagag cctgcagaag cacctggccg agctgaacca | 1080 |
| ccagaagcag ctggagagca caagatccc gagctggac atgaccgagg tggtggcccc | 1140 |
| cttcatggcc aacatccccc tgctgctgta ccccaggac ggccccgca gcaagcccca | 1200 |
| gcccaaggac aacggcgacg tgtgccagga ctgcatccag atggtgaccg acatccagac | 1260 |
| cgccgtcgc accaacagca ccttcgtgca ggccctggtg gagcacgtga aggagagtg | 1320 |
| cgaccgcctg ggccccggca tggccgacat ctgcaagaac tacatcagcc agtacagcga | 1380 |
| gatcgccatc cagatgatga tgcacatgca gcccaaggga atctgcgccc tggtgggctt | 1440 |
| ctgcgacgag gtgaaggaga tgcccatgca gaccctggtg cccgccaagg tggccagcaa | 1500 |

```
gaacgtgatc cccgccctgg agctggtgga gcccatcaag aagcacgagg tgcccgccaa    1560
gagcgacgtg tactgcgagg tgtgcgagtt cctggtgaag gaggtgacca agctgatcga    1620
caacaacaag accgagaagg agatcctgga cgccttcgac aagatgtgca gcaagctgcc    1680
caagagcctg agcgaggagt gccaggaggt ggtggacacc tacggcagca gcatcctgag    1740
catcctgctg gaggaggtga gccccgagct ggtgtgcagc atgctgcacc tgtgcagcgg    1800
cacccgcctg cccgccctga ccgtgcacgt gacccagccc aaggacggcg gcttctgcga    1860
ggtgtgcaag aagctggtgg gctacctgga ccgcaacctg gagaagaaca gcaccaagca    1920
ggagatcctg gccgccctgg agaagggctg cagcttcctg cccgacccct accagaagca    1980
gtgcgaccag ttcgtggccg agtacgagcc cgtgctgatc gagatcctgg tggaggtgat    2040
ggaccccagc ttcgtgtgcc tgaagatcgg cgcctgcccc agcgcccaca gcccctgct    2100
gggcaccgag aagtgcatct ggggccccag ctactggtgc cagaacaccg agaccgccgc    2160
ccagtgcaac gccgtggagc actgcaagcg ccacgtgtgg aactgattgt ggccgaaccg    2220
ccgaactcag aggccggccc cagaaaaccc gagcgagtag gggcggcgc gcaggaggga    2280
ggagaactgg gggcgcggga ggctggtggg tgtgggggggt ggagatgtag aagatgtgac    2340
gccgcggccc ggcgggtgcc agattagcgg acgcggtgcc cgcggttgca acgggatccc    2400
gggcgctgca gcttgggagg cggctctccc caggcggcgt ccgcggagac acccatccgt    2460
gaaccccagg tcccgggccg ccggctcgcc gcgcaccagg ggccggcgga cagaagagcg    2520
gccgagcggc tcgaggctgg gggaccgcgg gcgcggccgc gcgctgccgg gcgggaggct    2580
ggggggccgg ggccggggcc gtgccccgga gcgggtcgga ggccggggcc ggggccgggg    2640
gacggcggct ccccgcgcgg ctccagcggc tcggggatcc cggccgggcc ccgcagggac    2700
catgatggaa ttcagcagcc ccagcagaga ggaatgcccc aagcctctga gccgggtgtc    2760
aatcatggcc ggatctctga caggactgct gctgcttcag gccgtgtctt gggcttctgg    2820
cgctagacct tgcatcccca agagcttcgg ctacagcagc gtcgtgtgcg tgtgcaatgc    2880
cacctactgc gacagcttcg accctcctac ctttcctgct ctgggcacct tcagcagata    2940
cgagagcacc agatccggca gacgatgga actgagcatg ggacccatcc aggccaatca    3000
cacaggcact ggcctgctgc tgacactgca gcctgagcag aaattccaga aagtgaaagg    3060
cttcggcgga gccatgacag atgccgccgc tctgaatatc ctggctctgt ctccaccagc    3120
tcagaacctg ctgctcaaga gctacttcag cgaggaaggc atcggctaca acatcatcag    3180
agtgcccatg gccagctgcg acttcagcat caggacctac acctacgccg acacacccga    3240
cgatttccag ctgcacaact tcagcctgcc tgaagaggac accaagctga agatccctct    3300
gatccacaga gccctgcagc tggcacaaag acccgtgtca ctgctggcct ctccatggac    3360
atctcccacc tggctgaaaa caaatggcgc cgtgaatggc aagggcagcc tgaaaggcca    3420
acctggcgac atctaccacc agacctgggc cagatacttc gtgaagttcc tggacgccta    3480
tgccgagcac aagctgcagt tgggccgt gacagccgag aacgaaccgt ctgctggact    3540
gctgagcggc tacccctttc agtgcctggg ctttacaccc gagcaccagc gggactttat    3600
cgcccgtgat ctgggaccca cactggccaa tagcacccac cataatgtgc ggctgctgat    3660
gctggacgac cagagactgc ttctgcccca ctgggctaaa gtggtgctga cagatcctga    3720
ggccgccaaa tacgtgcacg gaatcgccgt gcactggtat ctggactttc tggcccctgc    3780
caaggccaca ctgggagaga cacacagact gttcccaac accatgctgt cgccagcga    3840
agcctgtgtg ggcagcaagt tttgggaaca gagcgtgcgg ctcggcagct gggatagagg    3900
```

```
catgcagtac agccacagca tcatcaccaa cctgctgtac cacgtcgtcg gctggaccga   3960
ctggaatctg gccctgaatc ctgaaggcgg ccctaactgg gtccgaaact tcgtggacag   4020
ccccatcatc gtggacatca ccaaggacac cttctacaag cagcccatgt tctaccacct   4080
gggacacttc agcaagttca tccccgaggg ctctcagcgc gttggactgg tggcttccca   4140
gaagaacgat ctggacgccg tggctctgat gcaccctgat ggatctgctg tggtggtggt   4200
cctgaaccgc agcagcaaag atgtgcccct gaccatcaag gatcccgccg tgggattcct   4260
ggaaacaatc agccctggct actccatcca cacctacctg tggcgtagac agtgacaatt   4320
gttaattaag tttaaaccct cgaggccgca agcaataaaa tatctttatt ttcattacat   4380
ctgtgtgttg gttttttgtg tggagatcca cgataacaaa cagcttttt ggggtgaaca    4440 tattgactga attccctgca ggttggccac tccctctctg cgcgctcgct cgctcactga   4500
ggccgcccgg gcaaagcccg ggcgtcgggc gacctttggt cgcccggcct cagtgagcga   4560
gcgagcgcgc agagagggag tggccaactc catcactagg ggttcctgcg gccgctcgta   4620
cggtctcgag gaattcctgc aggataactt gccaacctca ttctaaaatg tatatagaag   4680
cccaaaagac aataacaaaa atattcttgt agaacaaaat gggaaagaat gttccactaa   4740
atatcaagat ttagagcaaa gcatgagatg tgtggggata gacagtgagg ctgataaaat   4800
agagtagagc tcagaaacag acccattgat atatgtaagt gacctatgaa aaaatatgg    4860 cattttacaa tgggaaaatg atggtctttt tcttttttag aaaaacaggg aaatatattt   4920
atatgtaaaa aataaaaggg aacccatatg tcataccata cacacaaaaa aattccagtg   4980
aattataagt ctaaatggag aaggcaaaac tttaaatctt ttagaaaata atatagaagc   5040
atgcagacca gcctggccaa catgatgaaa ccctctctac taataataaa atcagtagaa   5100
ctactcagga ctactttgag tgggaagtcc ttttctatga agacttcttt ggccaaaatt   5160
aggctctaaa tgcaaggaga tagtgcatca tgcctggctg cacttactga taaatgatgt   5220
tatcaccatc tttaaccaaa tgcacaggaa caagttatgg tactgatgtg ctggattgag   5280
aaggagctct acttccttga caggacacat ttgtatcaac ttaaaaaagc agattttgc    5340 cagcagaact attcattcag aggtaggaaa cttagaatag atgatgtcac tgattagcat   5400
ggcttcccca tctccacagc tgcttcccac ccaggttgcc cacagttgag tttgtccagt   5460
gctcagggct gcccactctc agtaagaagc cccacaccag cccctctcca aatatgttgg   5520
ctgttccttc cattaaagtg accccacttt agagcagcaa gtggatttct gtttcttaca   5580
gttcaggaag gaggagtcag ctgtgagaac ctggagcctg agatgcttct aagtcccact   5640
gctactgggg tcagggaagc cagactccag catcagcagt caggagcact aagcccttgc   5700
caacatcctg tttctcagag aaactgcttc cattataatg gttgtccttt tttaagctat   5760
caagccaaac aaccagtgtc taccattatt ctcatcacct gaagccaagg gttctagcaa   5820
aagtcaagct gtcttgtaat ggttgatgtg cctccagctt ctgtcttcag tcactccact   5880
cttagcctgc tctgaatcaa ctctgaccac agttccctgg agccctgcc acctgctgcc    5940 cctgccacct tctccatctg cagtgctgtg cagccttctg cactcttgca gagctaatag   6000
gtggagactt gaaggaagag gaggaaagtt tctcataata gccttgctgc aagctcaaat   6060
gggaggtggg cactgtgccc aggagccttg agcaaaggc tgtgcccaac ctctgactgc    6120
atccaggttt ggtcttgaca gagataagaa gccctggctt ttggagccaa aatctaggtc   6180
agacttaggc aggattctca aagtttatca gcagaacatg aggcagaaga cccttctctgc  6240
```

```
tccagcttct tcaggctcaa ccttcatcag aatagataga aagagaggct gtgagggttc    6300
ttaaaacaga agcaaatctg actcagagaa taaacaacct cctagtaaac tacagcttag    6360
acagagcatc tggtggtgag tgtgctcagt gtcctactca actgtctggt atcagccctc    6420
atgaggactt ctcttctttc cctcatagac ctccatctct gttttcctta gcctgcagaa    6480
atctggatgg ctattcacag aatgcctgtg cttccagagt tgcatttttt ctctggtatt    6540
ctggttcaag catttgaagg taggaaaggt tctccaagtg caagaaagcc agccctgagc    6600
ctcaactgcc tggctagtgt ggtcagtagg atgcaaaggc tgttgaatgc cacaaggcca    6660
aactttaacc tgtgtaccac aagcctagca gcagaggcag ctctgctcac tggaactctc    6720
tgtcttcttt ctcctgagcc ttttcttttc ctgagttttc tagctctcct caaccttacc    6780
tctgccctac ccaggacaaa cccaagagcc actgtttctg tgatgtcctc tccagcccta    6840
attaggcatc atgacttcag cctgaccttc catgctcaga agcagtgcta atccacttca    6900
gatgagctgc tctatgcaac acaggcagag cctacaaacc tttgcaccag agccctccac    6960
atatcagtgt ttgttcatac tcacttcaac agcaaatgtg actgctgaga ttaagatttt    7020
acacaagatg gtctgtaatt tcacagttag ttttatccca ttaggtatga aagaattagc    7080
ataattcccc ttaaacatga atgaatctta gattttttaa taaatagttt tggaagtaaa    7140
gacagagaca tcaggagcac aaggaatagc ctgagaggac aaacagaaca agaaagagtc    7200
tggaaataca caggatgttc ttggcctcct caaagcaagt gcaagcagat agtaccagca    7260
gccccaggct atcagagccc agtgaagaga agtaccatga aagccacagc tctaaccacc    7320
ctgttccaga gtgacagaca gtccccaaga caagccagcc tgagccagag agagaactgc    7380
aagagaaagt ttctaattta ggttctgtta gattcagaca agtgcaggtc atcctctctc    7440
cacagctact cacctctcca gcctaacaaa gcctgcagtc cacactccaa ccctggtgtc    7500
tcacctccta gcctctccca acatcctgct ctctgaccat cttctgcatc tctcatctca    7560
ccatctccca ctgtctacag cctactcttg caactaccat ctcatttcct gacatccctgt    7620
ctacatcttc tgccatactc tgccatctac ataccaccct cttaccatct accacaccat    7680
cttttatctc catccctctc agaagcctcc aagctgaatc ctgctttatg tgttcatctc    7740
agccccctgca tggaaagctg accccagagg cagaactatt cccagagagc ttggccaaga    7800
aaaacaaaac taccagcctg gccaggctca ggagtagtaa gctgcagtgt ctgttgtgtt    7860
ctagcttcaa cagctgcagg agttccactc tcaaatgctc cacatttctc acatcctcct    7920
gattctggtc actacccatc ttcaaagaac agaatatctc acatcagcat actgtgaagg    7980
actagtcatg ggtgcagctg ctcagagctg caaagtcatt ctggatggtg gagagcttac    8040
aaacatttca tgatgctccc cccgctctga tggctggagc ccaatcccta cacagactcc    8100
tgctgtatgt gttttccttt cactctgagc cacagccaga gggcaggcat tcagtctcct    8160
cttcaggctg gggctgggc actgagaact cacccaacac cttgctctca ctccttctgc    8220
aaaacaagaa agagctttgt gctgcagtag ccatgaagaa tgaaaggaag ctttaacta    8280
aaaaatgtca gagattattt tcaaccccctt actgtggatc accagcaagg aggaaacaca    8340
acacagagac attttttccc ctcaaattat caaaagaatc actgcatttg ttaaagagag    8400
caactgaatc aggaagcaga gttttgaaca tatcagaagt taggaatctg catcagagac    8460
aaatgcagtc atggttgttt gctgcatacc agccctaatc attagaagcc tcatggactt    8520
caaacatcat tccctctgac aagatgctct agcctaactc catgagataa aataaatctg    8580
cctttcagag ccaaagaaga gtccaccagc ttcttctcag tgtgaacaag agctccagtc    8640
```

```
aggttagtca gtccagtgca gtagaggaga ccagtctgca tcctctaatt ttcaaaggca    8700
agaagatttg tttaccctgg acaccaggca caagtgaggt cacagagctc ttagatatgc    8760
agtcctcatg agtgaggaga ctaaagcgca tgccatcaag acttcagtgt agagaaaacc    8820
tccaaaaaag cctcctcact acttctggaa tagctcagag gccgaggcgg cctcggcctc    8880
tgcataaata aaaaaaatta gtcagccatg gggcggagaa tgggcggaac tgggcggagt    8940
tagggggcggg atgggcggag ttaggggcgg gactatggtt gctgactaat tgagatgcat    9000
gctttgcata cttctgcctg ctggggagcc tggggacttt ccacacctgg ttgctgacta    9060
attgagatgc atgctttgca tacttctgcc tgctggggag cctggggact ttccacaccc    9120
taactgacac acattccaca gctgcattaa tgaatcggcc aacgcgcggg gagaggcggt    9180
ttgcgtattg ggcgctcttc cgcttcctcg ctcactgact cgctgcgctc ggtcgttcgg    9240
ctgcggcgag cggtatcagc tcactcaaag gcggtaatac ggttatccac agaatcaggg    9300
gataacgcag gaaagaacat gtgagcaaaa ggccagcaaa aggccaggaa ccgtaaaaag    9360
gccgcgttgc tggcgttttt ccataggctc cgcccccctg acgagcatca caaaaatcga    9420
cgctcaagtc agaggtggcg aaacccgaca ggactataaa gataccaggc gtttccccct    9480
ggaagctccc tcgtgcgctc tcctgttccg accctgccgc ttaccggata cctgtccgcc    9540
tttctccctt cgggaagcgt ggcgctttct catagctcac gctgtaggta tctcagttcg    9600
gtgtaggtcg ttcgctccaa gctgggctgt gtgcacgaac ccccgttca gcccgaccgc    9660
tgcgccttat ccggtaacta tcgtcttgag tccaacccgg taagacacga cttatcgcca    9720
ctggcagcag ccactggtaa caggattagc agagcgaggt atgtaggcgg tgctacagag    9780
ttcttgaagt ggtggcctaa ctacggctac actagaagaa cagtatttgg tatctgcgct    9840
ctgctgaagc cagttacctt cggaaaaaga gttggtagct cttgatccgg caaacaaacc    9900
accgctggta gcggtggttt ttttgtttgc aagcagcaga ttacgcgcag aaaaaaagga    9960
tctcaagaag atcctttgat cttttctacg gggtctgacg ctcagtggaa cgaaaactca   10020
cgttaaggga ttttggtcat gagattatca aaaaggatct tcacctagat ccttttaaat   10080
taaaaatgaa gttttaaatc aatctaaagt atatatgagt aaacttggtc tgacagttac   10140
caatgcttaa tcagtgaggc acctatctca gcgatctgtc tatttcgttc atccatagtt   10200
gcctgactcc tgcaaaccac gttgtgtctc aaaatctctg atgttacatt gcacaagata   10260
aaaatatatc atcatgaaca ataaaactgt ctgcttacat aaacagtaat acaaggggtg   10320
ttatgagcca tattcaacgg gaaacgtctt gctcgaggcc gcgattaaat tccaacatgg   10380
atgctgattt atatgggtat aaatgggctc gcgataatgt cgggcaatca ggtgcgacaa   10440
tctatcgatt gtatgggaag cccgatgcgc cagagttgtt tctgaaacat ggcaaaggta   10500
gcgttgccaa tgatgttaca gatgagatgg tcagactaaa ctggctgacg gaatttatgc   10560
ctcttccgac catcaagcat tttatccgta ctcctgatga tgcatggtta ctcaccactg   10620
cgatccccgg gaaaacagca ttccaggtat tagaagaata tcctgattca ggtgaaaata   10680
ttgttgatgc gctggcagtg ttcctgcgcc ggttgcattc gattcctgtt tgtaattgtc   10740
cttttaacag cgatcgcgta tttcgtctcg ctcaggcgca atcacgaatg aataacggtt   10800
tggttgatgc gagtgatttt gatgacgagc gtaatggctg gcctgttgaa caagtctgga   10860
aagaaatgca taagcttttg ccattctcac cggattcagt cgtcactcat ggtgatttct   10920
cacttgataa ccttattttt gacgagggga aattaatagg ttgtattgat gttggacgag   10980
```

-continued

| | |
|---|---|
| tcggaatcgc agaccgatac caggatcttg ccatcctatg gaactgcctc ggtgagtttt | 11040 |
| ctccttcatt acagaaacgg cttttttcaaa aatatggtat tgataatcct gatatgaata | 11100 |
| aattgcagtt tcatttgatg ctcgatgagt ttttctaagg gcggcctgcc accataccca | 11160 |
| cgccgaaaca agcgctcatg agcccgaagt ggcgagcccg atcttcccca tcggtgatgt | 11220 |
| cggcgatata ggcgccagca accgcacctg tggcgccggt gatgagggcg cgccaagtcg | 11280 |
| acgtccggca gtc | 11293 |

<210> SEQ ID NO 7
<211> LENGTH: 10700
<212> TYPE: DNA
<213> ORGANISM: Artificial sequence
<220> FEATURE:
<223> OTHER INFORMATION: Synthetic polynucleotide

<400> SEQUENCE: 7

| | |
|---|---|
| ttggccactc cctctctgcg cgctcgctcg ctcactgagg ccgcccgggc aaagcccggg | 60 |
| cgtcgggcga cctttggtcg cccggcctca gtgagcgagc gagcgcgcag agagggagtg | 120 |
| gccaactcca tcactagggg ttcctgctag ctctgggtat ttaagcccga gtgagcacgc | 180 |
| agggtctcca ttttgaagcg ggaggttacg cgttcgtcga ctactagtgg gtaccagagc | 240 |
| tccctaggtt ctagaaccgg tgacgtctcc catggtgaag cttggatctg aattcggtac | 300 |
| ctagttatta atagtaatca attacgggt cattagttca tagcccatat atggagttcc | 360 |
| gcgttacata acttacggta aatggcccgc ctggctgacc gcccaacgac ccccgcccat | 420 |
| tgacgtcaat aatgacgtat gttcccatag taacgccaat agggactttc cattgacgtc | 480 |
| aatgggtgga gtatttacgg taaactgccc acttggcagt acatcaagtg tatcatatgc | 540 |
| caagtacgcc ccctattgac gtcaatgacg gtaaatggcc cgcctggcat tatgcccagt | 600 |
| acatgacctt atgggacttt cctacttggc agtacatcta cgtattagtc atcgctatta | 660 |
| ccatggtcga ggtgagcccc acgttctgct tcactctccc catctccccc cctccccac | 720 |
| ccccaatttt gtatttattt attttttaat tattttgtgc agcgatgggg gcggggggg | 780 |
| ggggggggcg cgcgccaggc ggggcggggc ggggcgaggg gcgggcggg gcgaggcgga | 840 |
| gaggtgcggc ggcagccaat cagagcggcg cgctccgaaa gtttcctttt atggcgaggc | 900 |
| ggcggcggcg gcggccctat aaaaagcgaa gcgcgcggcg gcgggagtc gctgcgacgc | 960 |
| tgccttcgcc ccgtgccccg ctccgccgcc gcctcgcgcc gcccgccccg gctctgactg | 1020 |
| accgcgttac tcccacaggt gagcgggcgg gacggccctt ctcctccggg ctgtaattag | 1080 |
| cgcttggttt aatgacggct tgtttctttt ctgtggctgc gtgaaagcct tgaggggctc | 1140 |
| cgggagctag agcctctgct aaccatgttc atgccttctt ctttttccta cagctcctgg | 1200 |
| gcaacgtgct ggttattgtg ctgtctcatc attttggcaa agaattcctc gaagatccga | 1260 |
| agggaaagtc ttccacgact gtgggatccg ttcgaagata tcaccggttg agccaccatg | 1320 |
| gaattcagca gccccagcag agaggaatgc cccaagcctc tgagccgggt gtcaatcatg | 1380 |
| gccggatctc tgacaggact gctgctgctt caggccgtgt cttgggcttc tggcgctaga | 1440 |
| ccttgcatcc ccaagagctt cggctacagc agcgtcgtgt gcgtgtgcaa tgccacctac | 1500 |
| tgcgacagct tcgaccctcc tacctttcct gctctgggca ccttcagcag atacgagagc | 1560 |
| accagatccg gcagacggat ggaactgagc atgggaccca tccaggccaa tcacacaggc | 1620 |
| actggcctgc tgctgacact gcagcctgag cagaaattcc agaaagtgaa aggcttcggc | 1680 |
| ggagccatga cagatgccgc cgctctgaat atcctggctc tgtctccacc agctcagaac | 1740 |

```
ctgctgctca agagctactt cagcgaggaa ggcatcggct acaacatcat cagagtgccc    1800
atggccagct gcgacttcag catcaggacc tacacctacg ccgacacacc cgacgatttc    1860
cagctgcaca acttcagcct gcctgaagag gacaccaagc tgaagatccc tctgatccac    1920
agagccctgc agctggcaca aagacccgtg tcactgctgg cctctccatg gacatctccc    1980
acctggctga aaacaaatgg cgccgtgaat ggcaagggca gcctgaaagg ccaacctggc    2040
gacatctacc accagacctg gccagatac ttcgtgaagt tcctggacgc ctatgccgag     2100
cacaagctgc agttttgggc cgtgacagcc gagaacgaac cttctgctgg actgctgagc    2160
ggctacccct tcagtgcct gggctttaca cccgagcacc agcgggactt tatcgcccgt     2220
gatctgggac ccacactggc caatagcacc caccataatg tgcggctgct gatgctggac    2280
gaccagagac tgcttctgcc ccactgggct aaagtggtgc tgacagatcc tgaggccgcc    2340
aaatacgtgc acggaatcgc cgtgcactgg tatctggact ttctggcccc tgccaaggcc    2400
acactgggag agacacacag actgttcccc aacaccatgc tgttcgccag cgaagcctgt    2460
gtgggcagca gttttgggga acagagcgtg cggctcggca gctgggatag aggcatgcag    2520
tacagccaca gcatcatcac caacctgctg taccacgtcg tcggctggac cgactggaat    2580
ctggccctga atcctgaagg cggccctaac tgggtccgaa acttcgtgga cagccccatc    2640
atcgtggaca tcaccaagga caccttctac aagcagccca tgttctacca cctgggacac    2700
ttcagcaagt tcatccccga gggctctcag cgcgttggac tggtggcttc ccagaagaac    2760
gatctggacg ccgtggctct gatgcaccct gatggatctg ctgtggtggt ggtcctgaac    2820
cgcagcagca aagatgtgcc cctgaccatc aaggatcccg ccgtgggatt cctggaaaca    2880
atcagccctg gctactccat ccacacctac ctgtggcgta cacagtgaca attgttaatt    2940
aagtttaaac cctcgaggcc gcaagcttat cgataatcaa cctctggatt acaaaatttg    3000
tgaaagattg actggtattc ttaactatgt tgctcctttt acgctatgtg gatacgctgc    3060
tttaatgcct ttgtatcatg ctattgcttc ccgtatggct ttcattttct cctccttgta    3120
taaatcctgg ttgctgtctc tttatgagga gttgtggccc gttgtcaggc aacgtggcgt    3180
ggtgtgcact gtgtttgctg acgcaacccc cactggttgg ggcattgcca ccacctgtca    3240 gctccttttcc gggactttcg ctttccccct ccctattgcc acggcggaac tcatcgccgc    3300
ctgccttgcc cgctgctgga caggggctcg gctgttgggc actgacaatt ccgtggtgtt    3360
gtcggggaaa tcatcgtcct ttccttggct gctcgcctgt gttgccacct ggattctgcg    3420
cgggacgtcc ttctgctacg tcccttcggc cctcaatcca gcggacctttc cttcccgcgg    3480 cctgctgccg gctctgcggc ctcttccgcg tcttcgcctt cgccctcaga cgagtcggat    3540
ctccctttgg gccgcctccc cgcatcgata ccgtcgacta gagctcgctg atcagcctcg    3600
actgtgcctt ctagttgcca gccatctgtt gtttgcccct cccccgtgcc ttccttgacc    3660
ctggaaggtg ccactcccac tgtcctttcc taataaaatg aggaaattgc atcgcattgt    3720
ctgagtaggt gtcattctat tctggggggt ggggtggggc aggacagcaa ggggaggat    3780 tgggaagaca atagcaggca tgctggggag agatccacga taacaaacag ctttttggg    3840 gtgaacatat tgactgaatt ccctgcaggt tggccactcc ctctctgcgc gctcgctcg    3900 tcactgaggc cgcccgggca aagcccgggc gtcgggcgac ctttggtcgc ccggcctcag   3960
tgagcgagcg agcgcgcaga gagggagtgg ccaactccat cactagggggt tcctgcggcc   4020 gctcgtacgg tctcgaggaa ttcctgcagg ataacttgcc aacctcattc taaaatgtat    4080
```

| | |
|---|---|
| atagaagccc aaaagacaat aacaaaaata ttcttgtaga acaaaatggg aaagaatgtt | 4140 |
| ccactaaata tcaagattta gagcaaagca tgagatgtgt ggggatagac agtgaggctg | 4200 |
| ataaaataga gtagagctca gaaacagacc cattgatata tgtaagtgac ctatgaaaaa | 4260 |
| aatatggcat tttacaatgg gaaaatgatg gtctttttct tttttagaaa acagggaaa | 4320 |
| tatatttata tgtaaaaaat aaaagggaac ccatatgtca taccatacac acaaaaaaat | 4380 |
| tccagtgaat tataagtcta aatggagaag gcaaaacttt aaatctttta gaaataata | 4440 |
| tagaagcatg cagaccagcc tggccaacat gatgaaaccc tctctactaa taataaaatc | 4500 |
| agtagaacta ctcaggacta cttttgagtgg gaagtccttt tctatgaaga cttctttggc | 4560 |
| caaaattagg ctctaaatgc aaggagatag tgcatcatgc ctggctgcac ttactgataa | 4620 |
| atgatgttat caccatcttt aaccaaatgc acaggaacaa gttatggtac tgatgtgctg | 4680 |
| gattgagaag gagctctact tccttgacag gacacatttg tatcaactta aaaaagcaga | 4740 |
| ttttgccag cagaactatt cattcagagg taggaaactt agaatagatg atgtcactga | 4800 |
| ttagcatggc ttccccatct ccacagctgc ttcccaccca ggttgccac agttgagttt | 4860 |
| gtccagtgct cagggctgcc cactctcagt aagaagcccc acaccagccc ctctccaaat | 4920 |
| atgttggctg ttccttccat taaagtgacc ccactttaga gcagcaagtg gatttctgtt | 4980 |
| tcttacagtt caggaaggag gagtcagctg tgagaacctg gagcctgaga tgcttctaag | 5040 |
| tcccactgct actggggtca gggaagccag actccagcat cagcagtcag gagcactaag | 5100 |
| cccttgccaa catcctgttt ctcagagaaa ctgcttccat tataatggtt gtccttttt | 5160 |
| aagctatcaa gccaaacaac cagtgtctac cattattctc atcacctgaa gccaagggtt | 5220 |
| ctagcaaaag tcaagctgtc ttgtaatggt tgatgtgcct ccagcttctg tcttcagtca | 5280 |
| ctccactctt agcctgctct gaatcaactc tgaccacagt tccctggagc ccctgccacc | 5340 |
| tgctgcccct gccaccttct ccatctgcag tgctgtgcag ccttctgcac tcttgcagag | 5400 |
| ctaataggtg gagacttgaa ggaagaggag gaaagtttct cataatagcc ttgctgcaag | 5460 |
| ctcaaatggg aggtgggcac tgtgcccagg agccttggag caaaggctgt gcccaacctc | 5520 |
| tgactgcatc caggttttggt cttgacagag ataagaagcc ctggcttttg gagccaaaat | 5580 |
| ctaggtcaga cttaggcagg attctcaaag tttatcagca gaacatgagg cagaagaccc | 5640 |
| tttctgctcc agcttcttca ggctcaacct tcatcagaat agatagaaag agaggctgtg | 5700 |
| agggttctta aaacagaagc aaatctgact cagagaataa acaacctcct agtaaactac | 5760 |
| agcttagaca gagcatctgg tggtgagtgt gctcagtgtc ctactcaact gtctggtatc | 5820 |
| agccctcatg aggacttctc ttctttccct catagacctc catctctgtt ttccttagcc | 5880 |
| tgcagaaatc tggatggcta ttcacagaat gcctgtgctt tcagagttgc attttttctc | 5940 |
| tggtattctg gttcaagcat ttgaaggtag gaaaggttct ccaagtgcaa gaaagccagc | 6000 |
| cctgagcctc aactgcctgg ctagtgtggt cagtaggatg caaaggctgt tgaatgccac | 6060 |
| aaggccaaac tttaacctgt gtaccacaag cctagcagca gaggcagctc tgctcactgg | 6120 |
| aactctctgt cttctttctc ctgagccttt tcttttcctg agttttctag ctctcctcaa | 6180 |
| ccttacctct gccctaccca ggacaaaccc aagagccact gtttctgtga tgtcctctcc | 6240 |
| agccctaatt aggcatcatg acttcagcct gaccttccat gctcagaagc agtgctaatc | 6300 |
| cacttcagat gagctgctct atgcaacaca ggcagagcct acaaaccttt gcaccagagc | 6360 |
| cctccacata tcagtgtttg ttcatactca cttcaacagc aaatgtgact gctgagatta | 6420 |
| agattttaca caagatggtc tgtaatttca cagttagttt tatcccatta ggtatgaaag | 6480 |

```
aattagcata attcccctta aacatgaatg aatcttagat tttttaataa atagttttgg    6540
aagtaaagac agagacatca ggagcacaag gaatagcctg agaggacaaa cagaacaaga    6600
aagagtctgg aaatacacag gatgttcttg gcctcctcaa agcaagtgca agcagatagt    6660
accagcagcc ccaggctatc agagcccagt gaagagaagt accatgaaag ccacagctct    6720
aaccaccctg ttccagagtg acagacagtc cccaagacaa gccagcctga gccagagaga    6780
gaactgcaag agaaagtttc taatttaggt tctgttagat tcagacaagt gcaggtcatc    6840
ctctctccac agctactcac ctctccagcc taacaaagcc tgcagtccac actccaaccc    6900
tggtgtctca cctcctagcc tctcccaaca tcctgctctc tgaccatctt ctgcatctct    6960
catctcacca tctcccactg tctacagcct actcttgcaa ctaccatctc attttctgac    7020
atcctgtcta tcttctgc catactctgc catctaccat accacctctt accatctacc      7080
acaccatctt ttatctccat ccctctcaga agcctccaag ctgaatcctg ctttatgtgt    7140
tcatctcagc ccctgcatgg aaagctgacc ccagaggcag aactattccc agagagcttg    7200
gccaagaaaa acaaaactac cagcctggcc aggctcagga gtagtaagct gcagtgtctg    7260
ttgtgttcta gcttcaacag ctgcaggagt tccactctca aatgtccac atttctcaca     7320 tcctcctgat tctggtcact acccatcttc aaagaacaga atatctcaca tcagcatact    7380
gtgaaggact agtcatgggt gcagctgctc agagctgcaa agtcattctg gatggtggag    7440
agcttacaaa catttcatga tgctccccccc gctctgatgg ctggagccca tccctacac    7500 agactcctgc tgtatgtgtt ttcctttcac tctgagccac agccagaggg caggcattca    7560
gtctcctctt caggctgggg ctggggcact gagaactcac ccaacaccctt gctctcactc   7620 cttctgcaaa acaagaaaga gctttgtgct gcagtagcca tgaagaatga aggaaggct     7680 ttaactaaaa aatgtcagag attattttca accccttact gtggatcacc agcaaggagg    7740
aaacacaaca cagagacatt ttttcccctc aaattatcaa aagaatcact gcatttgtta    7800
aagagagcaa ctgaatcagg aagcagagtt ttgaacatat cagaagttag gaatctgcat    7860
cagagacaaa tgcagtcatg gttgtttgct gcataccagc cctaatcatt agaagcctca    7920
tggacttcaa acatcattcc ctctgacaag atgctctagc ctaactccat gagataaaat    7980
aaatctgcct ttcagagcca aagaagagtc caccagcttc ttctcagtgt gaacaagagc    8040
tccagtcagg ttagtcagtc cagtgcagta gaggagacca gtctgcatcc tctaattttc    8100
aaaggcaaga agatttgttt accctggaca ccaggcacaa gtgaggtcac agagctctta    8160
gatatgcagt cctcatgagt gaggagacta aagcgcatgc catcaagact tcagtgtaga    8220
gaaaacctcc aaaaaagcct cctcactact tctggaatag ctcagaggcc gaggcggcct    8280
cggcctctgc ataaataaaa aaaattagtc agccatgggg cggagaatgg gcggaactgg    8340
gcggagttag gggcgggatg ggcggagtta ggggcgggac tatggttgct gactaattga    8400
gatgcatgct ttgcatactt ctgcctgctg gggagcctgg ggactttcca cacctggttg    8460
ctgactaatt gagatgcatg ctttgcatac ttctgcctgc tggggagcct ggggactttc    8520 cacacccctaa ctgacacaca ttccacagct gcattaatga atcggccaac gcgcggggag   8580
aggcggtttg cgtattgggc gctcttccgc ttcctcgctc actgactcgc tgcgctcggt    8640
cgttcggctg cggcgagcgg tatcagctca ctcaaaggcg gtaatacggt tatccacaga    8700 atcagggggat aacgcaggaa agaacatgtg agcaaaaggc cagcaaaagg ccaggaaccg    8760
taaaaaggcc gcgttgctgg cgttttttcca taggctccgc ccccctgacg agcatcacaa    8820
```

| | | | | | |
|---|---|---|---|---|---|
| aaatcgacgc | tcaagtcaga | ggtggcgaaa | cccgacagga | ctataaagat | accaggcgtt | 8880 |
| tccccctgga | agctccctcg | tgcgctctcc | tgttccgacc | ctgccgctta | ccggatacct | 8940 |
| gtccgccttt | ctcccttcgg | gaagcgtggc | gctttctcat | agctcacgct | gtaggtatct | 9000 |
| cagttcggtg | taggtcgttc | gctccaagct | gggctgtgtg | cacgaacccc | ccgttcagcc | 9060 |
| cgaccgctgc | gccttatccg | gtaactatcg | tcttgagtcc | aacccggtaa | gacacgactt | 9120 |
| atcgccactg | gcagcagcca | ctggtaacag | gattagcaga | gcgaggtatg | taggcggtgc | 9180 |
| tacagagttc | ttgaagtggt | ggcctaacta | cggctacact | agaagaacag | tatttggtat | 9240 |
| ctgcgctctg | ctgaagccag | ttaccttcgg | aaaaagagtt | ggtagctctt | gatccggcaa | 9300 |
| acaaaccacc | gctggtagcg | gtggtttttt | tgtttgcaag | cagcagatta | cgcgcagaaa | 9360 |
| aaaaggatct | caagaagatc | ctttgatctt | ttctacgggg | tctgacgctc | agtggaacga | 9420 |
| aaactcacgt | taagggattt | tggtcatgag | attatcaaaa | aggatcttca | cctagatcct | 9480 |
| tttaaattaa | aaatgaagtt | ttaaatcaat | ctaaagtata | tatgagtaaa | cttggtctga | 9540 |
| cagttaccaa | tgcttaatca | gtgaggcacc | tatctcagcg | atctgtctat | ttcgttcatc | 9600 |
| catagttgcc | tgactcctgc | aaaccacgtt | gtgtctcaaa | atctctgatg | ttacattgca | 9660 |
| caagataaaa | atatatcatc | atgaacaata | aaactgtctg | cttacataaa | cagtaataca | 9720 |
| aggggtgtta | tgagccatat | tcaacgggaa | acgtcttgct | cgaggccgcg | attaaattcc | 9780 |
| aacatggatg | ctgatttata | tgggtataaa | tgggctcgcg | ataatgtcgg | gcaatcaggt | 9840 |
| gcgacaatct | atcgattgta | tgggaagccc | gatgcgccag | agttgtttct | gaaacatggc | 9900 |
| aaaggtagcg | ttgccaatga | tgttacagat | gagatggtca | gactaaactg | gctgacggaa | 9960 |
| tttatgcctc | ttccgaccat | caagcatttt | atccgtactc | ctgatgatgc | atggttactc | 10020 |
| accactgcga | tccccgggaa | aacagcattc | caggtattag | aagaatatcc | tgattcaggt | 10080 |
| gaaaatattg | ttgatgcgct | ggcagtgttc | ctgcgccggt | tgcattcgat | tcctgtttgt | 10140 |
| aattgtcctt | ttaacagcga | tcgcgtattt | cgtctcgctc | aggcgcaatc | acgaatgaat | 10200 |
| aacggtttgg | ttgatgcgag | tgattttgat | gacgagcgta | atggctggcc | tgttgaacaa | 10260 |
| gtctggaaag | aaatgcataa | gcttttgcca | ttctcaccgg | attcagtcgt | cactcatggt | 10320 |
| gatttctcac | ttgataacct | tatttttgac | gaggggaaat | taataggttg | tattgatgtt | 10380 |
| ggacgagtcg | gaatcgcaga | ccgataccag | gatcttgcca | tcctatggaa | ctgcctcggt | 10440 |
| gagttttctc | cttcattaca | gaaacggctt | tttcaaaaat | atggtattga | taatcctgat | 10500 |
| atgaataaat | tgcagtttca | tttgatgctc | gatgagtttt | tctaagggcg | gcctgccacc | 10560 |
| atacccacgc | cgaaacaagc | gctcatgagc | ccgaagtggc | gagcccgatc | ttccccatcg | 10620 |
| gtgatgtcgg | cgatataggc | gccagcaacc | gcacctgtgg | cgccggtgat | gagggcgcgc | 10680 |
| caagtcgacg | tccggcagtc | | | | | 10700 |

<210> SEQ ID NO 8
<211> LENGTH: 10700
<212> TYPE: DNA
<213> ORGANISM: Artificial sequence
<220> FEATURE:
<223> OTHER INFORMATION: Synthetic polynucleotide

<400> SEQUENCE: 8

| | | | | | |
|---|---|---|---|---|---|
| ttggccactc | cctctctgcg | cgctcgctcg | ctcactgagg | ccgggcgacc | aaaggtcgcc | 60 |
| cgacgcccgg | gctttgcccg | ggcggcctca | gtgagcgagc | gagcgcgcag | agagggagtg | 120 |
| gccaactatt | agatctgatg | gccgcgctag | ctctgggtat | ttaagcccga | gtgagcacgc | 180 |

```
agggtctcca ttttgaagcg ggaggttacg cgttcgtcga ctactagtgg gtaccagagc    240
tccctaggtt ctagaaccgg tgacgtctcc catggtgaag cttggatctg aattcggtac    300
ctagttatta atagtaatca attacggggt cattagttca tagcccatat atggagttcc    360
gcgttacata acttacggta aatggcccgc ctggctgacc gcccaacgac ccccgcccat    420
tgacgtcaat aatgacgtat gttcccatag taacgccaat agggactttc cattgacgtc    480
aatgggtgga gtatttacgg taaactgccc acttggcagt acatcaagtg tatcatatgc    540
caagtacgcc ccctattgac gtcaatgacg gtaaatggcc cgcctggcat tatgcccagt    600
acatgacctt atgggacttt cctacttggc agtacatcta cgtattagtc atcgctatta    660
ccatggtcga ggtgagcccc acgttctgct tcactctccc catctccccc cctccccac    720 ccccaatttt gtatttattt attttttaat tattttgtgc agcgatgggg gcggggggg    780 gggggggggcg cgcgccaggc ggggcgggc ggggcgaggg gcgggcggg gcgaggcgga    840 gaggtgcggc ggcagccaat cagagcgcg cgctccgaaa gtttccttttt atggcgaggc    900 ggcggcggcg gcggccctat aaaaagcgaa gcgcgcggcg ggcgggagtc gctgcgacgc    960
tgccttcgcc ccgtgccccg ctccgccgcc gcctcgcgcc gcccgccccg gctctgactg   1020
accgcgttac tcccacaggt gagcgggcgg gacggccctt ctcctccggg ctgtaattag   1080
cgcttggttt aatgacggct tgtttctttt ctgtggctgc gtgaaagcct tgaggggctc   1140
cgggagctag agcctctgct aaccatgttc atgccttctt cttttttccta cagctcctgg   1200 gcaacgtgct ggttattgtg ctgtctcatc attttggcaa agaattcctc gaagatccga   1260
agggaaagtc ttccacgact gtgggatccg ttcgaagata tcaccggttg agccaccatg   1320
gaattcagca gccccagcag agaggaatgc cccaagcctc tgagccgggt gtcaatcatg   1380
gccggatctc tgacaggact gctgctgctt caggccgtgt cttgggcttc tggcgctaga   1440
ccttgcatcc ccaagagctt cggctacagc agcgtcgtgt gcgtgtgcaa tgccacctac   1500
tgcgacagct tcgaccctcc tacctttcct gctctgggca ccttcagcag atacgagagc   1560
accagatccg gcagacggat ggaactgagc atgggaccca tccaggccaa tcacacaggc   1620
actggcctgc tgctgacact gcagcctgag cagaaattcc agaaagtgaa aggcttcggc   1680
ggagccatga cagatgccgc cgctctgaat atcctggctc tgtctccacc agctcagaac   1740
ctgctgctca gagctacttt cagcgaggaa ggcatcggct acaacatcat cagagtgccc   1800
atggccagct gcgacttcag catcaggacc tacacctacg ccgacacacc cgacgatttc   1860
cagctgcaca acttcagcct gcctgaagag gacaccaagc tgaagatccc tctgatccac   1920
agagccctgc agctggcaca aagacccgtg tcactgctgg cctctccatg gacatctccc   1980
acctggctga aaacaaatgg cgccgtgaat ggcaagggca gcctgaaagg ccaacctggc   2040
gacatctacc accagacctg gccagatac ttcgtgaagt tcctggacgc ctatgccgag   2100
cacaagctgc agttttgggc cgtgacagcc gagaacgaac cttctgctgg actgctgagc   2160 ggctaccect ttcagtgcct gggctttaca cccgagcacc agcgggactt tatcgcccgt   2220
gatctgggac ccacactggc caatagcacc caccataatg tgcggctgct gatgctggac   2280
gaccagagac tgcttctgcc ccactgggct aaagtggtgc tgacagatcc tgaggccgcc   2340
aaatacgtgc acggaatcgc cgtgcactgg tatctggact ttctggcccc tgccaaggcc   2400
acactggagg agacacacag actgttcccc aacaccatgc tgttcgccag cgaagcctgt   2460
gtgggcagca agttttggga acagagcgtg cggctcggca gctgggatag aggcatgcag   2520
```

```
tacagccaca gcatcatcac caacctgctg taccacgtcg tcggctggac cgactggaat    2580
ctggccctga atcctgaagg cggccctaac tgggtccgaa acttcgtgga cagccccatc    2640
atcgtggaca tcaccaagga caccttctac aagcagccca tgttctacca cctgggacac    2700
ttcagcaagt tcatccccga gggctctcag cgcgttggac tggtggcttc ccagaagaac    2760
gatctggacg ccgtggctct gatgcaccct gatggatctg ctgtggtggt ggtcctgaac    2820
cgcagcagca aagatgtgcc cctgaccatc aaggatcccg ccgtgggatt cctgaaaaca    2880
atcagccctg gctactccat ccacacctac ctgtggcgta gacagtgaca attgttaatt    2940
aagtttaaac cctcgaggcc gcaagctatt cgataatcaa cctctggatt acaaaatttg    3000
tgaaagattg actggtattc ttaactatgt tgctcctttt acgctatgtg gatacgctgc    3060
tttaatgcct ttgtatcatg ctattgcttc ccgtatggct ttcattttct cctccttgta    3120
taaatcctgg ttgctgtctc tttatgagga gttgtggccc gttgtcaggc aacgtggcgt    3180
ggtgtgcact gtgtttgctg acgcaacccc cactggttgg ggcattgcca ccacctgtca    3240
gctccttttcc gggactttcg ctttcccccct ccctattgcc acggcggaac tcatcgccgc    3300
ctgccttgcc cgctgctgga caggggctcg gctgttgggc actgacaatt ccgtggtgtt    3360
gtcggggaaa tcatcgtcct ttccttggct gctcgcctgt gttgccacct ggattctgcg    3420
cgggacgtcc ttctgctacg tcccttcggc cctcaatcca gcggaccttc cttcccgcgg    3480
cctgctgccg gctctgcggc ctcttccgcg tcttcgcctt cgccctcaga cgagtcggat    3540
ctcccttggg gccgcctccc cgcatcgata ccgtcgacta gagctcgctg atcagcctcg    3600
actgtgcctt ctagttgcca gccatctgtt gtttgcccct cccccgtgcc ttccttgacc    3660
ctggaaggtg ccactcccac tgtccttttcc taataaaatg aggaaattgc atcgcattgt    3720
ctgagtaggt gtcattctat tctggggggt ggggtggggc aggacagcaa ggggaggat    3780
tgggaagaca atagcaggca tgctggggag agatccacga taacaaacag cttttttggg    3840
gtgaacatat tgactgaatt ccctgcaggt tggccactcc ctctctgcgc gctcgctcgc    3900
tcactgaggc cgcccgggca agcccgggc gtcgggcgac ctttggtcgc ccggcctcag    3960
tgagcgagcg agcgcgcaga gagggagtgg ccaactccat cactagggt tcctgcggcc    4020
gctcgtacgg tctcgaggaa ttcctgcagg ataacttgcc aacctcattc taaaatgtat    4080
atagaagccc aaaagacaat aacaaaaata ttcttgtaga caaaatggg aaagaatgtt    4140
ccactaaata tcaagattta gagcaaagca tgagatgtgt ggggatagac agtgaggctg    4200
ataaaataga gtagagctca gaaacagacc cattgatata tgtaagtgac ctatgaaaaa    4260
aatatggcat tttacaatgg gaaaatgatg gtctttttct tttttagaaa aacagggaaa    4320
tatatttata tgtaaaaaat aaagggaac ccatatgtca taccatacac acaaaaaaat    4380
tccagtgaat tataagtcta aatggagaag gcaaaacttt aaatctttta gaaaataata    4440
tagaagcatg cagaccagcc tggccaacat gatgaaaccc tctctactaa taataaaatc    4500
agtagaacta ctcaggacta cttttgagtgg gaagtccttt tctatgaaga cttctttggc    4560
caaaattagg ctctaaatgc aaggagatag tgcatcatgc ctggctgcac ttactgataa    4620
atgatgttat caccatctttt aaccaaatgc acaggaacaa gttatggtac tgatgtgctg    4680
gattgagaag gagctctact tccttgacag gacacatttg tatcaactta aaaagcaga    4740
tttttgccag cagaactatt cattcagagg taggaaactt agaatagatg atgtcactga    4800
ttagcatggc ttccccatct ccacagctgc ttcccacccca ggttgccac agttgagttt    4860
gtccagtgct cagggctgcc cactctcagt aagaagcccc acaccagccc ctctccaaat    4920
```

-continued

```
atgttggctg ttccttccat taaagtgacc ccactttaga gcagcaagtg gatttctgtt    4980
tcttacagtt caggaaggag gagtcagctg tgagaacctg gagcctgaga tgcttctaag    5040
tcccactgct actggggtca gggaagccag actccagcat cagcagtcag gagcactaag    5100
cccttgccaa catcctgttt ctcagagaaa ctgcttccat tataatggtt gtcctttttt    5160
aagctatcaa gccaaacaac cagtgtctac cattattctc atcacctgaa gccaagggtt    5220
ctagcaaaag tcaagctgtc ttgtaatggt tgatgtgcct ccagcttctg tcttcagtca    5280
ctccactctt agcctgctct gaatcaactc tgaccacagt ccctggagc ccctgccacc     5340 tgctgcccct gccaccttct ccatctgcag tgctgtgcag ccttctgcac tcttgcagag    5400
ctaataggtg gagacttgaa ggaagaggag gaaagtttct cataatagcc ttgctgcaag    5460
ctcaaatggg aggtgggcac tgtgcccagg agccttggag caaaggctgt gcccaacctc    5520
tgactgcatc caggtttggt cttgacagag ataagaagcc ctggcttttg gagccaaaat    5580
ctaggtcaga cttaggcagg attctcaaag tttatcagca gaacatgagg cagaagaccc    5640
tttctgctcc agcttcttca ggctcaacct tcatcagaat agatagaaag agaggctgtg    5700
agggttctta aaacagaagc aaatctgact cagagaataa acaacctcct agtaaactac    5760
agcttagaca gagcatctgg tggtgagtgt gctcagtgtc ctactcaact gtctggtatc    5820
agccctcatg aggacttctc ttctttccct catagacctc catctctgtt ttccttagcc    5880
tgcagaaatc tggatggcta ttcacagaat gcctgtgctt tcagagttgc attttttctc    5940
tggtattctg gttcaagcat ttgaaggtag gaaaggttct ccaagtgcaa gaaagccagc    6000
cctgagcctc aactgcctgg ctagtgtggt cagtaggatg caaaggctgt tgaatgccac    6060
aaggccaaac tttaacctgt gtaccacaag cctagcagca gaggcagctc tgctcactgg    6120
aactctctgt cttctttctc ctgagccttt tcttttcctg agttttctag ctctcctcaa    6180
ccttacctct gccctaccca ggacaaaccc aagagccact gtttctgtga tgtcctctcc    6240
agccctaatt aggcatcatg acttcagcct gaccttccat gctcagaagc agtgctaatc    6300
cacttcagat gagctgctct atgcaacaca ggcagagcct acaaaccttt gcaccagagc    6360
cctccacata tcagtgtttg ttcatactca cttcaacagc aaatgtgact gctgagatta    6420
agattttaca caagatggtc tgtaatttca cagttagttt tatcccatta ggtatgaaag    6480
aattagcata attcccctta aacatgaatg aatcttagat ttttaataa atagttttgg     6540 aagtaaagac agagacatca ggagcacaag gaatagcctg agaggacaaa cagaacaaga    6600
aagagtctgg aaatacacag gatgttcttg gcctcctcaa agcaagtgca agcagatagt    6660
accagcagcc ccaggctatc agagcccagt gaagagaagt accatgaaag ccacagctct    6720
aaccaccctg ttccagagtg acagacagtc cccaagacaa gccagcctga gcagagaga    6780 gaactgcaag agaaagtttc taatttaggt tctgttagat tcagacaagt gcaggtcatc    6840
ctctctccac agctactcac ctctccagcc taacaaagcc tgcagtccac actccaaccc    6900
tggtgtctca cctcctagcc tctcccaaca tcctgctctc tgaccatctt ctgcatctct    6960
catctcacca tctcccactg tctacagcct actcttgcaa ctaccatctc attttctgac    7020
atcctgtcta catcttctgc catactctgc catctaccat accacctctt accatctacc    7080
acaccatctt ttatctccat ccctctcaga agcctccaag ctgaatcctg ctttatgtgt    7140
tcatctcagc ccctgcatgg aaagctgacc ccagaggcag aactattccc agagagcttg    7200
gccaagaaaa acaaaactac cagcctggcc aggctcagga gtagtaagct gcagtgtctg    7260
```

```
ttgtgttcta gcttcaacag ctgcaggagt tccactctca aatgctccac atttctcaca   7320
tcctcctgat tctggtcact acccatcttc aaagaacaga atatctcaca tcagcatact   7380
gtgaaggact agtcatgggt gcagctgctc agagctgcaa agtcattctg gatggtggag   7440
agcttacaaa catttcatga tgctcccccc gctctgatgg ctggagccca atccctacac   7500
agactcctgc tgtatgtgtt ttcctttcac tctgagccac agccagaggg caggcattca   7560
gtctcctctt caggctgggg ctggggcact gagaactcac ccaacaccTt gctctcactc   7620
cttctgcaaa acaagaaaga ctttgtgct gcagtagcca tgaagaatga aggaaggct    7680
ttaactaaaa aatgtcagag attattttca accccttact gtggatcacc agcaaggagg   7740
aaacacaaca cagagacatt ttttcccctc aaattatcaa aagaatcact gcatttgtta   7800
aagagagcaa ctgaatcagg aagcagagtt ttgaacatat cagaagttag gaatctgcat   7860
cagagacaaa tgcagtcatg gttgtttgct gcataccagc cctaatcatt agaagcctca   7920
tggacttcaa acatcattcc ctctgacaag atgctctagc ctaactccat gagataaaat   7980
aaatctgcct ttcagagcca aagaagagtc caccagcttc ttctcagtgt gaacaagagc   8040
tccagtcagg ttagtcagtc cagtgcagta gaggagacca gtctgcatcc tctaattttc   8100
aaaggcaaga agatttgttt accctggaca ccaggcacaa gtgaggtcac agagctctta   8160
gatatgcagt cctcatgagt gaggagacta aagcgcatgc catcaagact tcagtgtaga   8220
gaaaacctcc aaaaagcct cctcactact tctggaatag ctcagaggcc gaggcggcct    8280
cggcctctgc ataaataaaa aaattagtc agccatgggg cggagaatgg gcggaactgg   8340
gcggagttag gggcgggatg ggcggagtta ggggcgggac tatggttgct gactaattga   8400
gatgcatgct ttgcatactt ctgcctgctg gggagcctgg ggactttcca cacctggttg   8460
ctgactaatt gagatgcatg cttTgcatac ttctgcctgc tggggagcct ggggactttc   8520
cacaccctaa ctgacacaca ttccacagct gcattaatga atcggccaac gcgcgggag    8580
aggcggtttg cgtattgggc gctcttccgc ttcctcgctc actgactcgc tgcgctcggt   8640
cgttcggctg cggcgagcgg tatcagctca ctcaaaggcg gtaatacggt tatccacaga   8700
atcagggat aacgcaggaa agaacatgtg agcaaaaggc cagcaaaagg ccaggaaccg    8760
taaaaaggcc gcgttgctgg cgttttTcca taggctccgc cccectgacg agcatcacaa   8820
aaatcgacgc tcaagtcaga ggtggcgaaa cccgacagga ctataaagat accaggcgtt   8880
tccccctgga agctccctcg tgcgctctcc tgttccgacc ctgccgctta ccggatacct   8940
gtccgccttt ctcccttcgg gaagcgtggc gctttctcat agctcacgct gtaggtatct   9000
cagttcggtg taggtcgttc gctccaagct gggctgtgtg cacgaaccec ccgttcagcc   9060
cgaccgctgc gccttatccg gtaactatcg tcttgagtcc aacccggtaa gacacgactt   9120
atcgccactg gcagcagcca ctggtaacag gattagcaga gcgaggtatg taggcggtgc   9180
tacagagttc ttgaagtggt ggcctaacta cggctacact agaagaacag tatttggtat   9240
ctgcgctctg ctgaagccag ttaccttcgg aaaaagagtt ggtagctctt gatccggcaa   9300
acaaaccacc gctggtagcg gtggtttTtt tgtttgcaag cagcagatta cgcgcagaaa   9360
aaaaggatct caagaagatc ctttgatctt ttctacgggg tctgacgctc agtggaacga   9420
aaactcacgt taagggattt tggtcatgag attatcaaaa aggatcttca cctagatcct   9480
tttaaattaa aaatgaagtt ttaaatcaat ctaaagtata tatgagtaaa cttggtctga   9540
cagttaccaa tgcttaatca gtgaggcacc tatctcagcg atctgtctat ttcgttcatc   9600
catagttgcc tgactccctgc aaaccacgtt gtgtctcaaa atctctgatg ttacattgca   9660
```

```
caagataaaa atatatcatc atgaacaata aaactgtctg cttacataaa cagtaataca      9720 agggqtgtta tgagccatat tcaacgggaa acgtcttgct cgaggccgcg attaaattcc      9780
aacatggatg ctgatttata tgggtataaa tgggctcgcg ataatgtcgg gcaatcaggt      9840
gcgacaatct atcgattgta tgggaagccc gatgcgccag agttgtttct gaaacatggc      9900
aaaggtagcg ttgccaatga tgttacagat gagatggtca gactaaactg gctgacggaa      9960
tttatgcctc ttccgaccat caagcatttt atccgtactc ctgatgatgc atggttactc     10020
accactgcga tccccgggaa aacagcattc caggtattag aagaatatcc tgattcaggt     10080
gaaaatattg ttgatgcgct ggcagtgttc ctgcgccggt tgcattcgat tcctgtttgt     10140
aattgtcctt ttaacagcga tcgcgtattt cgtctcgctc aggcgcaatc acgaatgaat     10200
aacggtttgg ttgatgcgag tgattttgat gacgagcgta atggctggcc tgttgaacaa     10260
gtctggaaag aaatgcataa gcttttgcca ttctcaccgg attcagtcgt cactcatggt     10320
gatttctcac ttgataacct tattttgac gaggggaaat taataggttg tattgatgtt      10380
ggacgagtcg gaatcgcaga ccgataccag gatcttgcca tcctatggaa ctgcctcggt     10440
gagttttctc cttcattaca gaaacggctt tttcaaaaat atggtattga taatcctgat     10500
atgaataaat tgcagtttca tttgatgctc gatgagtttt tctaagggcg gcctgccacc     10560
atacccacgc cgaaacaagc gctcatgagc ccgaagtggc gagcccgatc ttccccatcg     10620
gtgatgtcgg cgatataggc gccagcaacc gcacctgtgg cgccggtgat gagggcgcgc     10680
caagtcgacg tccggcagtc                                                 10700
```

<210> SEQ ID NO 9
<211> LENGTH: 10700
<212> TYPE: DNA
<213> ORGANISM: Artificial sequence
<220> FEATURE:
<223> OTHER INFORMATION: Synthetic polynucleotide

<400> SEQUENCE: 9

```
ttggccactc cctctctgcg cgctcgctcg ctcactgagg ccgggcgacc aaaggtcgcc        60
cgacgcccgg gctttgcccg ggcggcctca gtgagcgagc gagcgcgcag agagggagtg       120
gccaactcca tcactagggg ttcctgctag ctctgggtat ttaagcccga gtgagcacgc       180
agggtctcca ttttgaagcg ggaggttacg cgttcgtcga ctactagtgg gtaccagagc      240
tccctaggtt ctagaaccgg tgacgtctcc catggtgaag cttggatctg aattcggtac      300
ctagttatta atagtaatca attacggggt cattagttca tagcccatat atggagttcc     360
gcgttacata acttacggta aatggcccgc ctggctgacc gcccaacgac ccccgcccat      420
tgacgtcaat aatgacgtat gttcccatag taacgccaat agggactttc cattgacgtc      480
aatgggtgga gtatttacgg taaactgccc acttggcagt acatcaagtg tatcatatgc     540
caagtacgcc ccctattgac gtcaatgacg gtaaatggcc cgcctggcat tatgcccagt     600
acatgacctt atgggacttt cctacttggc agtacatcta cgtattagtc atcgctatta     660
ccatggtcga ggtgagcccc acgttctgct tcactctccc catctccccc cctccccac      720 ccccaatttt gtatttattt attttttaat tattttgtgc agcgatgggg gcggggggg      780 gggggggcg cgcgccaggc gggcggggc ggggcgaggg gcgggcggg gcgaggcgga      840 gaggtgcggc ggcagccaat cagagcgcg cgctccgaaa gtttccttt atggcgaggc      900 ggcggcggcg gcggccctat aaaaagcgaa gcgcgcgggg ggcgggagtc gctgcgacgc     960
```

-continued

| | |
|---|---|
| tgccttcgcc ccgtgccccg ctccgccgcc gcctcgcgcc gcccgccccg gctctgactg | 1020 |
| accgcgttac tcccacaggt gagcgggcgg gacggcccct tcctccgggg ctgtaattag | 1080 |
| cgcttggttt aatgacggct tgtttctttt ctgtggctgc gtgaaagcct tgagggctc | 1140 |
| cgggagctag agcctctgct aaccatgttc atgccttctt cttttcct cagctcctgg | 1200 |
| gcaacgtgct ggttattgtg ctgtctcatc attttggcaa agaattcctc gaagatccga | 1260 |
| agggaaagtc ttccacgact gtgggatccg ttcgaagata tcaccggttg agccaccatg | 1320 |
| gaattcagca gccccagcag agaggaatgc cccaagcctc tgagccgggt gtcaatcatg | 1380 |
| gccggatctc tgacaggact gctgctgctt caggccgtgt cttgggcttc tggcgctaga | 1440 |
| ccttgcatcc ccaagagctt cggctacagc agcgtcgtgt gcgtgtgcaa tgccacctac | 1500 |
| tgcgacagct tcgaccctcc tacctttcct gctctgggca ccttcagcag atacgagagc | 1560 |
| accagatccg gcagacggat ggaactgagc atgggaccca tccaggccaa tcacacaggc | 1620 |
| actggcctgc tgctgacact gcagcctgag cagaaattcc agaaagtgaa aggcttcggc | 1680 |
| ggagccatga cagatgccgc cgctctgaat atcctggctc tgtctccacc agctcagaac | 1740 |
| ctgctgctca agagctactt cagcgaggaa ggcatcggct acaacatcat cagagtgccc | 1800 |
| atggccagct gcgacttcag catcaggacc tacacctacg ccgacacacc cgacgatttc | 1860 |
| cagctgcaca acttcagcct gcctgaagag acaccaagc tgaagatccc tctgatccac | 1920 |
| agagccctga gctggcaca aagaccccgtg tcactgctgg cctctccatg acatctccc | 1980 |
| acctggctga aaacaaatgg cgccgtgaat ggcaagggca gcctgaaagg ccaacctggc | 2040 |
| gacatctacc accagacctg ggccagatac ttcgtgaagt tcctggacgc ctatgccgag | 2100 |
| cacaagctgc agttttgggc cgtgacagcc gagaacgaac cttctgctgg actgctgagc | 2160 |
| ggctacccct tcagtgcct gggctttaca cccgagcacc agcgggactt tatcgcccgt | 2220 |
| gatctgggac ccacactggc caatagcacc caccataatg tgcggctgct gatgctggac | 2280 |
| gaccagagac tgcttctgcc ccactgggct aaagtggtgc tgacagatcc tgaggccgcc | 2340 |
| aaatacgtgc acggaatcgc cgtgcactgg tatctggact ttctggcccc tgccaaggcc | 2400 |
| acactggag agacacacag actgttcccc aacaccatgc tgttcgccag cgaagcctgt | 2460 |
| gtgggcagca gttttggga acagagcgtg cggctcggca gctgggatag aggcatgcag | 2520 |
| tacagccaca gcatcatcac caacctgctg taccacgtcg tcggctggac cgactggaat | 2580 |
| ctggccctga atcctgaagg cggccctaac tgggtccgaa acttcgtgga cagccccatc | 2640 |
| atcgtggaca tcaccaagga caccttctac aagcagccca tgttctacca cctgggacac | 2700 |
| ttcagcaagt tcatccccga gggctctcag cgcgttggac tggtggcttc ccagaagaac | 2760 |
| gatctggacg ccgtggctct gatgcaccct gatggatctg ctgtggtggt ggtcctgaac | 2820 |
| cgcagcagca agatgtgcc cctgaccatc aaggatcccg ccgtgggatt cctggaaaca | 2880 |
| atcagccctg ctactccat ccacacctac ctgtggcgta cagtgaca attgttaatt | 2940 |
| aagtttaaac cctcgaggcc gcaagcttat cgataatcaa cctctggatt acaaaatttg | 3000 |
| tgaaagattg actggtattc ttaactatgt tgctcctttt acgctatgtg gatacgctgc | 3060 |
| tttaatgcct ttgtatcatg ctattgcttc ccgtatggct ttcattttct cctccttgta | 3120 |
| taaatcctgg ttgctgtctc tttatgagga gttgtggccc gttgtcaggc aacgtggcgt | 3180 |
| ggtgtgcact gtgtttgctg acgcaacccc cactggttgg ggcattgcca ccacctgtca | 3240 |
| gctccttttcc gggactttcg ctttccccct cccattgcc acggcggaac tcatcgccgc | 3300 |
| ctgccttgcc cgctgctgga caggggctcg gctgttgggc actgacaatt ccgtggtgtt | 3360 |

```
gtcggggaaa tcatcgtcct ttccttggct gctcgcctgt gttgccacct ggattctgcg    3420
cgggacgtcc ttctgctacg tcccttcggc cctcaatcca gcggaccttc cttcccgcgg    3480
cctgctgccg gctctgcggc ctcttccgcg tcttcgcctt cgccctcaga cgagtcggat    3540 ctcccttttgg gccgcctccc cgcatcgata ccgtcgacta gagctcgctg atcagcctcg    3600
actgtgcctt ctagttgcca gccatctgtt gtttgcccct cccccgtgcc ttccttgacc    3660
ctggaaggtg ccactcccac tgtccttttcc taataaaatg aggaaattgc atcgcattgt    3720
ctgagtaggt gtcattctat tctgggggggt ggggtggggc aggacagcaa ggggggaggat    3780 tgggaagaca atagcaggca tgctggggag agatccacga taacaaacag cttttttggg    3840
gtgaacatat tgactgaatt ccctgcaggt tggccactcc ctctctgcgc gctcgctcgc    3900
tcactgaggc cgcccgggca aagcccgggc gtcgggcgac ctttggtcgc ccggcctcag    3960
tgagcgagcg agcgcgcaga gagggagtgg ccaactccat cactagggt tcctgcggcc    4020 gctcgtacgg tctcgaggaa ttcctgcagg ataacttgcc aacctcattc taaaatgtat    4080
atagaagccc aaaagacaat aacaaaaata ttcttgtaga acaaaatggg aaagaatgtt    4140
ccactaaata tcaagattta gagcaaagca tgagatgtgt ggggatagac agtgaggctg    4200
ataaaataga gtagagctca gaaacagacc cattgatata tgtaagtgac ctatgaaaaa    4260
aatatggcat tttacaatgg gaaaatgatg gtcttttttct tttttagaaa acagggaaa    4320 tatatttata tgtaaaaaat aaaagggaac ccatatgtca taccatacac acaaaaaaat    4380
tccagtgaat tataagtcta aatggagaag gcaaaacttt aaatctttta gaaaataata    4440
tagaagcatg cagaccagcc tggccaacat gatgaaaccc tctctactaa taataaaatc    4500
agtagaacta ctcaggacta ctttgagtgg gaagtccttt tctatgaaga cttcttttggc    4560 caaaattagg ctctaaatgc aaggagatag tgcatcatgc ctggctgcac ttactgataa    4620
atgatgttat caccatcttt aaccaaatgc acaggaacaa gttatggtac tgatgtgctg    4680
gattgagaag gagctctact tccttgacag gacacatttg tatcaactta aaaaagcaga    4740
tttttgccag cagaactatt cattcagagg taggaaactt agaatagatg atgtcactga    4800
ttagcatggc ttccccatct ccacagctgc ttcccaccca ggttgcccac agttgagttt    4860
gtccagtgct cagggctgcc cactctcagt aagaagcccc acaccagccc ctctccaaat    4920
atgttggctg ttccttccat taaagtgacc ccactttaga gcagcaagtg gatttctgtt    4980
tcttacagtt caggaaggag gagtcagctg tgagaacctg gagcctgaga tgcttctaag    5040
tcccactgct actggggtca gggaagccag actccagcat cagcagtcag gagcactaag    5100
cccttgccaa catcctgttt ctcagagaaa ctgcttccat tataatggtt gtcctttttt    5160
aagctatcaa gccaaacaac cagtgtctac cattattctc atcacctgaa gccaagggtt    5220
ctagcaaaag tcaagctgtc ttgtaatggt tgatgtgcct ccagcttctg tcttcagtca    5280
ctccactctt agcctgctct gaatcaactc tgaccacagt tccctggagc ccctgccacc    5340
tgctgcccct gccaccttct ccatctgcag tgctgtgcag ccttctgcac tcttgcagag    5400
ctaataggtg gagacttgaa ggaagaggag gaaagtttct cataatagcc ttgctgcaag    5460
ctcaaatggg aggtgggcac tgtgcccagg agccttggag caaaggctgt gcccaacctc    5520
tgactgcatc caggtttggt cttgacagag ataagaagcc ctggcttttg gagccaaaat    5580
ctaggtcaga cttaggcagg attctcaaag tttatcagca gaacatgagg cagaagaccc    5640
tttctgctcc agcttcttca ggctcaacct tcatcagaat agatagaaag agaggctgtg    5700
```

```
agggttctta aaacagaagc aaatctgact cagagaataa acaacctcct agtaaactac    5760
agcttagaca gagcatctgg tggtgagtgt gctcagtgtc ctactcaact gtctggtatc    5820
agccctcatg aggacttctc ttcttcccct catagacctc catctctgtt ttccttagcc    5880
tgcagaaatc tggatggcta ttcacagaat gcctgtgctt tcagagttgc attttttctc    5940
tggtattctg gttcaagcat ttgaaggtag gaaaggttct ccaagtgcaa gaaagccagc    6000
cctgagcctc aactgcctgg ctagtgtggt cagtaggatg caaaggctgt tgaatgccac    6060
aaggccaaac tttaacctgt gtaccacaag cctagcagca gaggcagctc tgctcactgg    6120
aactctctgt cttctttctc ctgagccttt tcttttcctg agttttctag ctctcctcaa    6180
ccttacctct gccctaccca ggacaaaccc aagagccact gtttctgtga tgtcctctcc    6240
agccctaatt aggcatcatg acttcagcct gaccttccat gctcagaagc agtgctaatc    6300
cacttcagat gagctgctct atgcaacaca ggcagagcct acaaaccttt gcaccagagc    6360
cctccacata tcagtgtttg ttcatactca cttcaacagc aaatgtgact gctgagatta    6420
agattttaca caagatggtc tgtaatttca cagttagttt tatcccatta ggtatgaaag    6480
aattagcata attcccctta aacatgaatg aatcttagat tttttaataa atagttttgg    6540
aagtaaagac agagacatca ggagcacaag gaatagcctg agaggacaaa cagaacaaga    6600
aagagtctgg aaatacacag gatgttcttg gcctcctcaa agcaagtgca agcagatagt    6660
accagcagcc ccaggctatc agagcccagt gaagagaagt accatgaaag ccacagctct    6720
aaccaccctg ttccagagtg acagacagtc cccaagacaa gccagcctga gccagagaga    6780
gaactgcaag agaaagtttc taatttaggt tctgttagat tcagacaagt gcaggtcatc    6840
ctctctccac agctactcac ctctccagcc taacaaagcc tgcagtccac actccaaccc    6900
tggtgtctca cctcctagcc tctcccaaca tcctgctctc tgaccatctt ctgcatctct    6960
catctcacca tctcccactg tctacagcct actcttgcaa ctaccatctc attttctgac    7020
atcctgtcta catcttctgc catactctgc catctaccat accacctctt accatctacc    7080
acaccatctt ttatctccat ccctctcaga agcctccaag ctgaatcctg ctttatgtgt    7140
tcatctcagc ccctgcatgg aaagctgacc ccagaggcag aactattccc agagagcttg    7200
gccaagaaaa acaaaactac cagcctggcc aggctcagga gtagtaagct gcagtgtctg    7260
ttgtgttcta gcttcaacag ctgcaggagt tccactctca aatgctccac atttctcaca    7320
tcctcctgat tctggtcact acccatcttc aaagaacaga atatctcaca tcagcatact    7380
gtgaaggact agtcatgggt gcagctgctc agagctgcaa agtcattctg gatggtggag    7440
agcttacaaa catttcatga tgctcccccc gctctgatgg ctggagccca tccctacac     7500 agactcctgc tgtatgtgtt ttccttcac tctgagccac agccagaggg caggcattca    7560
gtctcctctt caggctgggg ctgggcact gagaactcac ccaacacctt gctctcactc     7620
cttctgcaaa acaagaaaga gctttgtgct gcagtagcca tgaagaatga aaggaaggct    7680
ttaactaaaa aatgtcagag attattttca acccttact gtggatcacc agcaaggagg     7740
aaacacaaca cagagacatt ttttcccctc aaattatcaa agaatcact gcatttgtta     7800 aagagagcaa ctgaatcagg aagcagagtt ttgaacatat cagaagttag gaatctgcat    7860
cagagacaaa tgcagtcatg gttgtttgct gcataccagc cctaatcatt agaagcctca    7920
tggacttcaa acatcattcc ctctgacaag atgctctagc ctaactccat gagataaaat    7980
aaatctgcct tcagagccaa agaagagtc caccagcttc ttctcagtgt gaacaagagc    8040
tccagtcagg ttagtcagtc cagtgcagta gaggagacca gtctgcatcc tctaattttc    8100
```

```
aaaggcaaga agatttgttt accctggaca ccaggcacaa gtgaggtcac agagctctta    8160
gatatgcagt cctcatgagt gaggagacta aagcgcatgc catcaagact tcagtgtaga    8220
gaaaacctcc aaaaaagcct cctcactact tctggaatag ctcagaggcc gaggcggcct    8280
cggcctctgc ataaataaaa aaaattagtc agccatgggg cggagaatgg gcggaactgg    8340
gcggagttag gggcgggatg ggcggagtta ggggcgggac tatggttgct gactaattga    8400
gatgcatgct ttgcatactt ctgcctgctg gggagcctgg ggactttcca cacctggttg    8460
ctgactaatt gagatgcatg ctttgcatac ttctgcctgc tggggagcct ggggactttc    8520
cacaccctaa ctgacacaca ttccacagct gcattaatga atcggccaac gcgcggggag    8580
aggcggtttg cgtattgggc gctcttccgc ttcctcgctc actgactcgc tgcgctcggt    8640
cgttcggctg cggcgagcgg tatcagctca ctcaaaggcg gtaatacggt tatccacaga    8700
atcaggggat aacgcaggaa agaacatgtg agcaaaaggc cagcaaaagg ccaggaaccg    8760
taaaaaggcc gcgttgctgg cgttttttcca taggctccgc ccccctgacg agcatcacaa    8820
aaatcgacgc tcaagtcaga ggtggcgaaa cccgacagga ctataaagat accaggcgtt    8880
tccccctgga agctccctcg tgcgctctcc tgttccgacc ctgccgctta ccggatacct    8940
gtccgccttt ctcccttcgg gaagcgtggc gctttctcat agctcacgct gtaggtatct    9000
cagttcggtg taggtcgttc gctccaagct gggctgtgtg cacgaacccc ccgttcagcc    9060
cgaccgctgc gccttatccg gtaactatcg tcttgagtcc aacccggtaa gacacgactt    9120
atcgccactg gcagcagcca ctggtaacag gattagcaga gcgaggtatg taggcggtgc    9180
tacagagttc ttgaagtggt ggcctaacta cggctacact agaagaacag tatttggtat    9240
ctgcgctctg ctgaagccag ttaccttcgg aaaaagagtt ggtagctctt gatccggcaa    9300
acaaaccacc gctggtagcg tggtttttt tgtttgcaag cagcagatta cgcgcagaaa    9360
aaaaggatct caagaagatc ctttgatctt ttctacgggg tctgacgctc agtggaacga    9420
aaactcacgt taagggattt tggtcatgag attatcaaaa aggatcttca cctagatcct    9480
tttaaattaa aaatgaagtt ttaaatcaat ctaaagtata tatgagtaaa cttggtctga    9540
cagttaccaa tgcttaatca gtgaggcacc tatctcagcg atctgtctat ttcgttcatc    9600
catagttgcc tgactcctgc aaaccacgtt gtgtctcaaa atctctgatg ttacattgca    9660
caagataaaa atatatcatc atgaacaata aaactgtctg cttacataaa cagtaataca    9720
aggggtgtta tgagccatat tcaacgggaa acgtcttgct cgaggccgcg attaaattcc    9780
aacatggatg ctgatttata tgggtataaa tgggctcgcg ataatgtcgg gcaatcaggt    9840
gcgacaatct atcgattgta tgggaagccc gatgcgccag agttgtttct gaaacatggc    9900
aaaggtagcg ttgccaatga tgttacagat gagatggtca gactaaactg gctgacggaa    9960
tttatgcctc ttccgaccat caagcatttt atccgtactc ctgatgatgc atggttactc    10020
accactgcga tccccgggaa aacagcattc caggtattag aagaatatcc tgattcaggt    10080
gaaaatattg ttgatgcgct ggcagtgttc ctgcgccggt tgcattcgat tcctgtttgt    10140
aattgtcctt ttaacagcga tcgcgtattt cgtctcgctc aggcgcaatc acgaatgaat    10200
aacggtttgg ttgatgcgag tgattttgat gacgagcgta atggctggcc tgttaacaa    10260 gtctggaaag aaatgcataa gcttttgcca ttctcaccgg attcagtcgt cactcatggt    10320
gatttctcac ttgataacct tatttttgac gaggggaaat taataggttg tattgatgtt    10380
ggacgagtcg gaatcgcaga ccgataccag gatcttgcca tcctatggaa ctgcctcggt    10440
```

```
gagtttctc cttcattaca gaaacggctt tttcaaaaat atggtattga taatcctgat      10500
atgaataaat tgcagtttca tttgatgctc gatgagtttt tctaagggcg gcctgccacc    10560 atcccacgc cgaaacaagc gctcatgagc ccgaagtggc gagcccgatc ttccccatcg     10620
gtgatgtcgg cgatataggc gccagcaacc gcacctgtgg cgccggtgat gagggcgcgc    10680
caagtcgacg tccggcagtc                                                10700
```

<210> SEQ ID NO 10
<211> LENGTH: 10700
<212> TYPE: DNA
<213> ORGANISM: Artificial sequence
<220> FEATURE:
<223> OTHER INFORMATION: Synthetic polynucleotide

<400> SEQUENCE: 10

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgctag ctctgggtat ttaagcccga gtgagcacgc     180
agggtctcca ttttgaagcg ggaggttacg cgttcgtcga ctactagtgg gtaccagagc     240
tccctaggtt ctagaaccgg tgacgtctcc catggtgaag cttggatctg aattcggtac     300
ctagttatta atagtaatca attacggggt cattagttca tagcccatat atggagttcc     360
gcgttacata acttacggta aatggcccgc ctggctgacc gcccaacgac ccccgcccat     420
tgacgtcaat aatgacgtat gttcccatag taacgccaat agggactttc cattgacgtc     480
aatgggtgga gtatttacgg taaactgccc acttggcagt acatcaagtg tatcatatgc     540
caagtacgcc ccctattgac gtcaatgacg gtaaatggcc cgcctggcat tatgcccagt     600
acatgacctt atgggacttt cctacttggc agtacatcta cgtattagtc atcgctatta     660
ccatggtcga ggtgagcccc acgttctgct tcactctccc catctccccc cctccccac     720 ccccaatttt gtatttattt atttttaat tattttgtgc agcgatgggg gcggggggggg      780 gggggggcg cgcgccaggc ggggcggggc ggggcgaggg gcggggcggg gcgaggcgga     840
gaggtgcggc ggcagccaat cagagcggcg cgctccgaaa gtttccttt atggcgaggc     900 ggcggcggcg gcggccctat aaaaagcgaa gcgcgcggcg ggcgggagtc gctgcgacgc     960
tgccttcgcc ccgtgccccg ctccgccgcc gcctcgcgcc gcccgcccg gctctgactg    1020 accgcgttac tcccacaggt gagcgggcgg gacggccctt ctcctccggg ctgtaattag    1080
cgcttggttt aatgacggct tgtttctttt cgtgtggctgc gtgaaagcct tgaggggctc    1140
cgggagctag agcctctgct aaccatgttc atgccttctt cttttttccta cagctcctgg    1200 gcaacgtgct ggttattgtg ctgtctcatc atttttggcaa agaattcctc gaagatccga    1260
agggaaagtc ttccacgact gtgggatccg ttcgaagata tcaccggttg agccaccatg    1320
gaattcagca gccccagcag agaggaatgc cccaagcctc tgagccgggt gtcaatcatg    1380
gccggatctc tgacaggact gctgctgctt caggccgtgt cttgggcttc tggcgctaga    1440
ccttgcatcc ccaagagctt cggctacagc agcgtcgtgt gcgtgtgcaa tgccacctac    1500
tgcgacagct cgaccctcc tacctttcct gctctgggca ccttcagcag atacgagagc    1560
accagatccg gcagacggat ggaactgagc atgggaccca tccaggccaa tcacacaggc    1620
actggcctgc tgctgacact gcagcctgag cagaaattcc agaaagtgaa aggcttcggc    1680
ggagccatga cagatgccgc cgctctgaat atcctggctc tgtctccacc agctcagaac    1740
ctgctgctca agagctactt cagcgaggaa ggcatcggct acaacatcat cagagtgccc    1800
```

```
atggccagct gcgacttcag catcaggacc tacacctacg ccgacacacc cgacgatttc    1860
cagctgcaca acttcagcct gcctgaagag gacaccaagc tgaagatccc tctgatccac    1920
agagccctgc agctggcaca aagacccgtg tcactgctgg cctctccatg gacatctccc    1980
acctggctga aaacaaatgg cgccgtgaat ggcaagggca gcctgaaagg ccaacctggc    2040
gacatctacc accagacctg ggccagatac ttcgtgaagt tcctggacgc ctatgccgag    2100
cacaagctgc agttttgggc cgtgacagcc gagaacgaac cttctgctgg actgctgagc    2160
ggctaccct ttcagtgcct gggctttaca cccgagcacc agcgggactt tatcgcccgt    2220
gatctgggac ccacactggc caatagcacc accataatg tgcggctgct gatgctggac    2280
gaccagagac tgcttctgcc ccactgggct aaagtggtgc tgacagatcc tgaggccgcc    2340
aaatacgtgc acggaatcgc cgtgcactgg tatctggact ttctggcccc tgccaaggcc    2400
acactgggag agacacacag actgttcccc aacaccatgc tgttcgccag cgaagcctgt    2460
gtgggcagca gttttggga acagagcgtg cggctcggca gctgggatag aggcatgcag    2520
tacagccaca gcatcatcac caacctgctg taccacgtcg tcggctggac cgactggaat    2580
ctggccctga tcctgaaggc ggccctaac tgggtccgaa acttcgtgga cagccccatc    2640
atcgtggaca tcaccaagga caccttctac aagcagccca tgttctacca cctgggacac    2700
ttcagcaagt tcatccccga gggctctcag cgcgttggac tggtggcttc ccagaagaac    2760
gatctggacg ccgtggctct gatgcaccct gatggatctg ctgtggtggt ggtcctgaac    2820
cgcagcagca agatgtgcc cctgaccatc aaggatcccg ccgtgggatt cctggaaaca    2880
atcagccctg gctactccat ccacacctac ctgtggcgta gacagtgaca attgttaatt    2940
aagtttaaac cctcgaggcc gcaagcttat cgataatcaa cctctggatt acaaaatttg    3000
tgaaagattg actggtattc ttaactatgt tgctcctttt acgctatgtg gatacgctgc    3060
tttaatgcct ttgtatcatg ctattgcttc ccgtatggct ttcattttct cctccttgta    3120
taaatcctgg ttgctgtctc tttatgagga gttgtggccc gttgtcaggc aacgtggcgt    3180
ggtgtgcact gtgtttgctg acgcaacccc cactggttgg ggcattgcca ccacctgtca    3240
gctcctttcc gggactttcg ctttcccct cctattgcc acggcggaac tcatcgccgc    3300
ctgccttgcc cgctgctgga caggggctcg gctgttgggc actgacaatt ccgtggtgtt    3360
gtcggggaaa tcatcgtcct ttccttggct gctcgcctgt gttgccacct ggattctgcg    3420
cgggacgtcc ttctgctacg tccccttcggc cctcaatcca gcggaccttc cttcccgcgg    3480
cctgctgccg gctctgcggc ctcttccgcg tcttcgcctt cgccctcaga cgagtcggat    3540
ctccctttgg gccgcctccc cgcatcgata ccgtcgacta gagctcgctg atcagcctcg    3600
actgtgcctt ctagttgcca gccatctgtt gtttgcccct cccccgtgcc ttccttgacc    3660
ctggaaggtg ccactcccac tgtcctttcc taataaaatg aggaaattgc atcgcattgt    3720
ctgagtaggt gtcattctat tctgggggt ggggtgggc aggacagcaa ggggaggat     3780
tgggaagaca atagcaggca tgctggggag agatccacga taacaaacag cttttttggg    3840
gtgaacatat tgactgaatt ccctgcagga ggaacccta gtgatggagt tggccactcc    3900
ctctctcgcg ctcgctcgc tcactgaggc cgcccgggca aagcccgggc gtcgggcgac    3960
ctttggtcgc ccggcctcag tgagcgagcg agcgcgcaga gagggagtgg ccaagcggcc    4020
gctcgtacgg tctcgaggaa ttcctgcagg ataacttgcc aacctcattc taaaatgtat    4080
atagaagccc aaaagacaat aacaaaaata ttcttgtaga acaaaatggg aagaatgtt     4140
```

```
ccactaaata tcaagattta gagcaaagca tgagatgtgt ggggatagac agtgaggctg    4200
ataaaataga gtagagctca gaaacagacc cattgatata tgtaagtgac ctatgaaaaa    4260
aatatggcat tttacaatgg gaaatgatg gtctttttct tttttagaaa acagggaaa     4320 tatatttata tgtaaaaaat aaaagggaac ccatatgtca taccatacac acaaaaaat    4380 tccagtgaat tataagtcta aatggagaag gcaaaacttt aaatctttta gaaaataata   4440
tagaagcatg cagaccagcc tggccaacat gatgaaaccc tctctactaa taataaaatc   4500
agtagaacta ctcaggacta cttttgagtgg gaagtccttt tctatgaaga cttcttggc   4560 caaaattagg ctctaaatgc aaggagatag tgcatcatgc ctggctgcac ttactgataa   4620
atgatgttat caccatcttt aaccaaatgc acaggaacaa gttatggtac tgatgtgctg   4680
gattgagaag gagctctact tccttgacag gacacatttg tatcaactta aaaaagcaga   4740 ttttttgccag cagaactatt cattcagagg taggaaactt agaatagatg atgtcactga   4800
ttagcatggc ttccccatct ccacagctgc ttcccaccca ggttgccac agttgagttt     4860 gtccagtgct cagggctgcc cactctcagt aagaagcccc acaccagccc ctctccaaat   4920
atgttggctg ttccttccat taaagtgacc ccactttaga gcagcaagtg gatttctgtt   4980
tcttacagtt caggaaggag gagtcagctg tgagaacctg gagcctgaga tgcttctaag   5040
tcccactgct actggggtca gggaagccag actccagcat cagcagtcag gagcactaag   5100
cccttgccaa catcctgttt ctcagagaaa ctgcttccat tataatggtt gtccttttt    5160 aagctatcaa gccaaacaac cagtgtctac cattattctc atcacctgaa gccaagggtt   5220
ctagcaaaag tcaagctgtc ttgtaatggt tgatgtgcct ccagcttctg tcttcagtca   5280
ctccactctt agcctgctct gaatcaactc tgaccacagt tccctggagc ccctgccacc   5340 tgctgccct gccaccttct ccatctgcag tgctgtgcag ccttctgcac tcttgcagag    5400
ctaataggtg gagacttgaa ggaagaggag gaaagtttct cataatagcc ttgctgcaag   5460
ctcaaatggg aggtgggcac tgtgcccagg agccttggag caaaggctgt gcccaacctc   5520
tgactgcatc caggtttggt cttgacagag ataagaagcc ctggcttttg gagccaaaat   5580
ctaggtcaga cttaggcagg attctcaaag tttatcagca gaacatgagg cagaagaccc   5640
tttctgctcc agcttcttca ggctcaacct tcatcagaat agatagaaag agaggctgtg   5700
agggttctta aaacagaagc aaatctgact cagagaataa acaacctcct agtaaactac   5760
agcttagaca gagcatctgg tggtgagtgt gctcagtgtc ctactcaact gtctggtatc   5820
agccctcatg aggacttctc ttcttttccct catagacctc catctctgtt ttccttagcc   5880
tgcagaaatc tggatggcta ttcacagaat gcctgtgctt tcagagttgc attttttctc   5940
tggtattctg gttcaagcat ttgaaggtag gaaaggttct ccaagtgcaa gaaagccagc   6000
cctgagcctc aactgcctgg ctagtgtggt cagtaggatg caaaggctgt tgaatgccac   6060
aaggccaaac tttaacctgt gtaccacaag cctagcagca gaggcagctc tgctcactgg   6120
aactctctgt cttctttctc ctgagccttt tcttttcctg agttttctag ctctcctcaa   6180
ccttacctct gccctaccca ggacaaaccc aagagccact gtttctgtga tgtcctctcc   6240
agccctaatt aggcatcatg acttcagcct gaccttccat gctcagaagc agtgctaatc   6300
cacttcagat gagctgctct atgcaacaca ggcagagcct acaaaccttt gcaccagagc   6360
cctccacata tcagtgtttg ttcatactca cttcaacagc aaatgtgact gctgagatta   6420
agattttaca caagatggtc tgtaatttca cagttagttt tatcccatta ggtatgaaag   6480
aattagcata attccccctta aacatgaatg aatcttagat ttttaataa atagttttgg    6540
```

```
aagtaaagac agagacatca ggagcacaag gaatagcctg agaggacaaa cagaacaaga    6600
aagagtctgg aaatacacag gatgttcttg gcctcctcaa agcaagtgca agcagatagt    6660
accagcagcc ccaggctatc agagcccagt gaagagaagt accatgaaag ccacagctct    6720
aaccaccctg ttccagagtg acagacagtc cccaagacaa gccagcctga gccagagaga    6780
gaactgcaag agaaagtttc taatttaggt tctgttagat tcagacaagt gcaggtcatc    6840
ctctctccac agctactcac ctctccagcc taacaaagcc tgcagtccac actccaaccc    6900
tggtgtctca cctcctagcc tctcccaaca tcctgctctc tgaccatctt ctgcatctct    6960
catctcacca tctcccactg tctacagcct actcttgcaa ctaccatctc attttctgac    7020
atcctgtcta catcttctgc catactctgc catctaccat accacctctt accatctacc    7080
acaccatctt ttatctccat ccctctcaga agcctccaag ctgaatcctg ctttatgtgt    7140
tcatctcagc ccctgcatgg aaagctgacc ccagaggcag aactattccc agagagcttg    7200
gccaagaaaa acaaaactac cagcctggcc aggctcagga gtagtaagct gcagtgtctg    7260
ttgtgttcta gcttcaacag ctgcaggagt tccactctca aatgctccac atttctcaca    7320
tcctcctgat tctggtcact acccatcttc aaagaacaga atatctcaca tcagcatact    7380
gtgaaggact agtcatgggt gcagctgctc agagctgcaa agtcattctg gatggtggag    7440
agcttacaaa catttcatga tgctcccccc gctctgatgg ctggagccca atccctacac    7500
agactcctgc tgtatgtgtt ttcctttcac tctgagccac agccagaggg caggcattca    7560
gtctcctctt caggctgggg ctggggcact gagaactcac ccaacacctt gctctcactc    7620
cttctgcaaa acaagaaaga gctttgtgct gcagtagcca tgaagaatga aaggaaggct    7680
ttaactaaaa aatgtcagag attattttca accccttact gtggatcacc agcaaggagg    7740
aaacacaaca cagagacatt ttttcccctc aaattatcaa aagaatcact gcatttgtta    7800
aagagagcaa ctgaatcagg aagcagagtt ttgaacatat cagaagttag gaatctgcat    7860
cagagacaaa tgcagtcatg gttgtttgct gcataccagc cctaatcatt agaagcctca    7920
tggacttcaa acatcattcc ctctgacaag atgctctagc ctaactccat gagataaaat    7980
aaatctgcct ttcagagcca aagaagagtc caccagcttc ttctcagtgt gaacaagagc    8040
tccagtcagg ttagtcagtc cagtgcagta gaggagacca gtctgcatcc tctaattttc    8100
aaaggcaaga agatttgttt accctggaca ccaggcacaa gtgaggtcac agagctctta    8160
gatatgcagt cctcatgagt gaggagacta aagcgcatgc catcaagact tcagtgtaga    8220
gaaaacctcc aaaaaagcct cctcactact tctggaatag ctcagaggcc gaggcggcct    8280
cggcctctgc ataaataaaa aaaattagtc agccatgggg cggagaatgg gcggaactgg    8340
gcggagttag gggcgggatg ggcggagtta ggggcgggac tatggttgct gactaattga    8400
gatgcatgct ttgcatactt ctgcctgctg gggagcctgg ggactttcca cacctggttg    8460
ctgactaatt gagatgcatg ctttgcatac ttctgcctgc tggggagcct ggggactttc    8520
cacaccctaa ctgacacaca ttccacagct gcattaatga atcggccaac gcgcggggag    8580
aggcggtttg cgtattgggc gctcttccgc ttcctcgctc actgactcgc tgcgctcggt    8640
cgttcggctg cggcgagcgg tatcagctca ctcaaaggcg gtaatacggt tatccacaga    8700
atcaggggat aacgcaggaa agaacatgtg agcaaaaggc cagcaaaagg ccaggaaccg    8760
taaaaaggcc gcgttgctgg cgttttccca taggctccgc ccccctgacg agcatcacaa    8820
aaatcgacgc tcaagtcaga ggtggcgaaa cccgacagga ctataaagat accaggcgtt    8880
```

| | |
|---|---|
| tcccctgga agctccctcg tgcgctctcc tgttccgacc ctgccgctta ccggatacct | 8940 |
| gtccgccttt ctcccttcgg gaagcgtggc gctttctcat agctcacgct gtaggtatct | 9000 |
| cagttcggtg taggtcgttc gctccaagct gggctgtgtg cacgaacccc ccgttcagcc | 9060 |
| cgaccgctgc gccttatccg gtaactatcg tcttgagtcc aacccggtaa gacacgactt | 9120 |
| atcgccactg gcagcagcca ctggtaacag gattagcaga gcgaggtatg taggcggtgc | 9180 |
| tacagagttc ttgaagtggt ggcctaacta cggctacact agaagaacag tatttggtat | 9240 |
| ctgcgctctg ctgaagccag ttaccttcgg aaaaagagtt ggtagctctt gatccggcaa | 9300 |
| acaaaccacc gctggtagcg gtggtttttt tgtttgcaag cagcagatta cgcgcagaaa | 9360 |
| aaaaggatct caagaagatc ctttgatctt ttctacgggg tctgacgctc agtggaacga | 9420 |
| aaactcacgt taagggattt tggtcatgag attatcaaaa aggatcttca cctagatcct | 9480 |
| tttaaattaa aaatgaagtt ttaaatcaat ctaaagtata tatgagtaaa cttggtctga | 9540 |
| cagttaccaa tgcttaatca gtgaggcacc tatctcagcg atctgtctat ttcgttcatc | 9600 |
| catagttgcc tgactcctgc aaaccacgtt gtgtctcaaa atctctgatg ttacattgca | 9660 |
| caagataaaa atatatcatc atgaacaata aaactgtctg cttacataaa cagtaataca | 9720 |
| aggggtgtta tgagccatat tcaacgggaa acgtcttgct cgaggccgcg attaaattcc | 9780 |
| aacatggatg ctgatttata tgggtataaa tgggctcgcg ataatgtcgg gcaatcaggt | 9840 |
| gcgacaatct atcgattgta tgggaagccc gatgcgccag agttgtttct gaaacatggc | 9900 |
| aaaggtagcg ttgccaatga tgttacagat gagatggtca gactaaactg gctgacggaa | 9960 |
| tttatgcctc ttccgaccat caagcatttt atccgtactc ctgatgatgc atggttactc | 10020 |
| accactgcga tccccgggaa aacagcattc caggtattag aagaatatcc tgattcaggt | 10080 |
| gaaaatattg ttgatgcgct ggcagtgttc ctgcgccggt tgcattcgat tcctgtttgt | 10140 |
| aattgtcctt ttaacagcga tcgcgtattt cgtctcgctc aggcgcaatc acgaatgaat | 10200 |
| aacggtttgg ttgatgcgag tgattttgat gacgagcgta atggctggcc tgttgaacaa | 10260 |
| gtctggaaag aaatgcataa gcttttgcca ttctcaccgg attcagtcgt cactcatggt | 10320 |
| gatttctcac ttgataacct tatttttgac gaggggaaat taataggttg tattgatgtt | 10380 |
| ggacgagtcg gaatcgcaga ccgataccag gatcttgcca tcctatggaa ctgcctcggt | 10440 |
| gagttttctc cttcattaca gaaacggctt tttcaaaaat atggtattga taatcctgat | 10500 |
| atgaataaat tgcagtttca tttgatgctc gatgagtttt tctaagggcg gcctgccacc | 10560 |
| atacccacgc cgaaacaagc gctcatgagc ccgaagtggc gagcccgatc ttccccatcg | 10620 |
| gtgatgtcgg cgatataggc gccagcaacc gcacctgtgg cgccggtgat gagggcgcgc | 10680 |
| caagtcgacg tccggcagtc | 10700 |

<210> SEQ ID NO 11
<211> LENGTH: 11188
<212> TYPE: DNA
<213> ORGANISM: Artificial sequence
<220> FEATURE:
<223> OTHER INFORMATION: Synthetic polynucleotide

<400> SEQUENCE: 11

| | |
|---|---|
| ttggccactc cctctctgcg cgctcgctcg ctcactgagg ccgggcgacc aaaggtcgcc | 60 |
| cgacgcccgg gctttgcccg gcggccctca gtgagcgagc gagcgcgcag agagggagtg | 120 |
| gccaactatt agatctgatg gccgcgctag ctctgggtat ttaagcccga gtgagcacgc | 180 |
| agggtctcca ttttgaagcg ggaggttacg cgttcgtcga ctactagtgg gtaccagagc | 240 |

```
gtggtgactg agatgttttc taggaaacac aaaagataca aaaagaaaca cgtggaagga   300
tagccaaaaa gggggggctgc ccccatttcc tgcacccccgc tgcgatggct ggcaccattt   360
ggaagacttc gagatacact gttgagcgca gtaagacaac agtgtatctc gaagtcttcc   420
agatggggcc agccggtcca ctctgtatcc aggccagttc tgcaaggcgt tcgaggacca   480 ccccccctccc ctcgccacca gggtggtctc atacagaact tataagattc caaatccaa   540 agacatttca cgtttatggt gatttcccag aacacatagc gacatgcaaa tattgcaggg   600
cgccactccc ctgtccctca cagccatctt cctgccaggg cgcacgcgcg ctgggtgttc   660
ccgcctagtg acactgggcc cgcgattcct tggagcgggt tgatgacgtc agcgtttccc   720
atggtgaatc cctaggttct agaaccggtg acgtctccca tggtgaagct tggatctgaa   780
ttcggtacct agttattaat agtaatcaat tacggggtca ttagttcata gcccatatat   840
ggagttccgc gttacataac ttacggtaaa tggcccgcct ggctgaccgc ccaacgaccc   900
ccgcccattg acgtcaataa tgacgtatgt tcccatagta acgccaatag ggactttcca   960
ttgacgtcaa tgggtggagt atttacggta aactgcccac ttggcagtac atcaagtgta  1020
tcatatgcca gtacgccccc ctattgacgt caatgacggt aaatggcccg cctggcatta  1080
tgcccagtac atgaccttat gggactttcc tacttggcag tacatctacg tattagtcat  1140
cgctattacc atggtcgagg tgagccccac gttctgcttc actctcccca tctccccccc  1200
ctccccaccc ccaattttgt atttatttat tttttaatta ttttgtgcag cgatggggggc  1260 ggggggggg gggggcgcg cgccaggcgg ggcggggcgg ggcgaggggc ggggcggggc  1320
gaggcggaga ggtgcggcgg cagccaatca gagcggcgcg ctccgaaagt tccttttat   1380 ggcgaggcgg cggcggcggc ggccctataa aaagcgaagc gcgcggcggg cgggagtcgc  1440
tgcgacgctg ccttcgcccc gtgccccgct ccgccgccgc ctcgcgccgc ccgccccggc  1500
tctgactgac cgcgttactc ccacaggtga gcgggcggga cggcccttct cctccgggct  1560
gtaattagcg cttggtttaa tgacggcttg tttcttttct gtggctgcgt gaaagccttg  1620
aggggctccg ggagctagag cctctgctaa ccatgttcat gccttcttct ttttcctaca  1680
gctcctgggc aacgtgctgg ttattgtgct gtctcatcat tttggcaaag aattcctcga  1740
agatccgaag ggaaagtctt ccacgactgt gggatccgtt cgaagatatc accggttgag  1800
ccaccatgga attcagcagc cccagcagag aggaatgccc caagcctctg agccgggtgt  1860
caatcatggc cggatctctg acaggactgc tgctgcttca ggccgtgtct tgggcttctg  1920
gcgctagacc ttgcatcccc aagagcttcg gctacagcag cgtcgtgtgc gtgtgcaatg  1980
ccacctactg cgacagcttc gaccctccta cctttcctgc tctgggcacc ttcagcagat  2040
acgagagcac cagatccggc agacggatgg aactgagcat gggacccatc caggccaatc  2100
acacaggcac tggcctgctg ctgacactgc agcctgagca gaaattccag aaagtgaaag  2160
gcttcggcgg agccatgaca gatgccgccg ctctgaatat cctggctctg tctccaccag  2220
ctcagaacct gctgctcaag agctacttca gcgaggaagg catcggctac aacatcatca  2280
gagtgcccat ggccagctgc gacttcagca tcaggaccta cacctacgcc gacacacccg  2340
acgatttcca gctgcacaac ttcagcctgc ctgaagagga caccaagctg aagatccctc  2400
tgatccacag agccctgcag ctggcacaaa gacccgtgtc actgctggcc tctccatgga  2460
catctcccac ctggctgaaa acaaatgcgc cgtgaatgg caaggcagc ctgaaaggcc  2520 aacctggcga catctaccac cagacctggg ccagatactt cgtgaagttc ctggacgcct  2580
```

```
atgccgagca caagctgcag ttttgggccg tgacagccga gaacgaacct tctgctggac    2640
tgctgagcgg ctaccccttt cagtgcctgg gctttacacc cgagcaccag cgggacttta    2700
tcgcccgtga tctgggaccc acactggcca atagcaccca ccataatgtg cggctgctga    2760
tgctggacga ccagagactg cttctgcccc actgggctaa agtggtgctg acagatcctg    2820
aggccgccaa atacgtgcac ggaatcgccg tgcactggta tctggacttt ctggcccctg    2880
ccaaggccac actgggagag acacacagac tgttccccaa caccatgctg ttcgccagcg    2940
aagcctgtgt gggcagcaag ttttgggaac agagcgtgcg gctcggcagc tgggatagag    3000
gcatgcagta cagccacagc atcatcacca acctgctgta ccacgtcgtc ggctggaccg    3060
actggaatct ggccctgaat cctgaaggcg ccctaactg gtccgaaac ttcgtggaca     3120
gccccatcat cgtggacatc accaaggaca ccttctacaa gcagcccatg ttctaccacc    3180
tgggacactt cagcaagttc atccccgagg ctctcagcg cgttggactg gtggcttccc    3240
agaagaacga tctggacgcc gtggctctga tgcaccctga tggatctgct gtggtggtgg    3300
tcctgaaccg cagcagcaaa gatgtgcccc tgaccatcaa ggatcccgcc gtgggattcc    3360
tggaaacaat cagccctggc tactccatcc acacctacct gtggcgtaga cagtgacaat    3420
tgttaattaa gtttaaaccc tcgaggccgc aagcttatcg ataatcaacc tctgattac    3480
aaaatttgtg aaagattgac tggtattctt aactatgttg ctccttttac gctatgtgga    3540
tacgctgctt aatgcctttt gtatcatgct attgcttccc gtatggcttt cattttctcc    3600
tccttgtata aatcctggtt gctgtctctt tatgaggagt tgtggcccgt tgtcaggcaa    3660
cgtggcgtgg tgtgcactgt gtttgctgac gcaaccccca ctggttgggg cattgccacc    3720
acctgtcagc tcctttccgg gactttcgct ttccccctcc ctattgccac ggcggaactc    3780
atcgccgcct gccttgcccg ctgctggaca ggggctcggc tgttgggcac tgacaattcc    3840
gtggtgttgt cggggaaatc atcgtccttt ccttggctgc tcgcctgtgt tgccacctgg    3900
attctgcgcg gacgtccttc tgctacgtc ccttcggccc tcaatccagc ggaccttcct    3960
tcccgcggcc tgctgccggc tctgcggcct cttccgcgtc ttcgccttcg ccctcagacg    4020
agtcggatct ccctttgggc cgcctccccg catcgatacc gtcgactaga gctcgctgat    4080
cagcctcgac tgtgccttct agttgccagc catctgttgt ttgcccctcc ccgtgccttt    4140
ccttgaccct ggaaggtgcc actcccactg tcctttccta ataaaatgag gaaattgcat    4200
cgcattgtct gagtaggtgt cattctattc tggggggtgg ggtggggcag gacagcaagg    4260
gggaggattg gaagacaat agcaggcatg ctggggagag atccacgata caaacagct     4320
ttttgggg t gaacatattg actgaattcc ctgcaggttg gccactccct ctctgcgcgc     4380
tcgctcgctc actgaggccg cccgggcaaa gcccggcgt cgggcgacct ttggtcgccc     4440
ggcctcagtg agcgagcgag cgcgcagaga gggagtggcc aactccatca ctaggggttc    4500
ctgcggccgc tcgtacggtc tcgaggaatt cctgcaggat aacttgccaa cctcattcta    4560
aaatgtatat agaagcccaa aagacaataa caaaaatatt cttgtagaac aaaatgggaa    4620
agaatgttcc actaaatatc aagatttaga gcaaagcatg agatgtgtgg ggatagacag    4680
tgaggctgat aaaatagagt agagctcaga aacagaccca ttgatatatg taagtgacct    4740
atgaaaaaaa tatggcattt tacaatggga aaatgatggt cttttctttt tttagaaaaa    4800
cagggaaata tatttatatg taaaaaataa aagggaaccc atatgtcata ccatacacac    4860
aaaaaaaattc cagtgaatta taagtctaaa tggagaaggc aaaactttaa atcttttaga    4920
aaataatata gaagcatgca gaccagcctg gccaacatga tgaaccctc tctactaata    4980
```

```
ataaaatcag tagaactact caggactact ttgagtggga agtccttttc tatgaagact   5040
tctttggcca aaattaggct ctaaatgcaa ggagatagtg catcatgcct ggctgcactt   5100
actgataaat gatgttatca ccatctttaa ccaaatgcac aggaacaagt tatggtactg   5160
atgtgctgga ttgagaagga gctctacttc cttgacagga cacatttgta tcaacttaaa   5220
aaagcagatt tttgccagca gaactattca ttcagaggta ggaaacttag aatagatgat   5280
gtcactgatt agcatggctt ccccatctcc acagctgctt cccacccagg ttgcccacag   5340
ttgagtttgt ccagtgctca gggctgccca ctctcagtaa aagcccccac accagcccct   5400
ctccaaatat gttggctgtt ccttccatta aagtgacccc actttagagc agcaagtgga   5460
tttctgtttc ttacagttca ggaaggagga gtcagctgtg agaacctgga gcctgagatg   5520
cttctaagtc ccactgctac tggggtcagg gaagccagac tccagcatca gcagtcagga   5580
gcactaagcc cttgccaaca tcctgtttct cagagaaact gcttccatta taatggttgt   5640 cctttttaa gctatcaagc caaacaacca gtgtctacca ttattctcat cacctgaagc   5700
caagggttct agcaaaagtc aagctgtctt gtaatggttg atgtgcctcc agcttctgtc   5760
ttcagtcact ccactcttag cctgctctga atcaactctg accacagttc cctggagccc   5820
ctgccacctg ctgcccctgc caccttctcc atctgcagtg ctgtgcagcc ttctgcactc   5880
ttgcagagct aataggtgga gacttgaagg aagaggagga aagtttctca taatagcctt   5940
gctgcaagct caaatgggag gtgggcactg tgcccaggag ccttggagca aaggctgtgc   6000
ccaacctctg actgcatcca ggtttggtct tgacagagat aagaagccct ggcttttgga   6060
gccaaaatct aggtcagact taggcaggat tctcaaagtt tatcagcaga acatgaggca   6120
gaagacccct tctgctccag cttcttcagg ctcaaccttc atcagaatag atagaaagag   6180
aggctgtgag ggttcttaaa acagaagcaa atctgactca gagaataaac aacctcctag   6240
taaactacag cttagacaga gcatctggtg gtgagtgtgc tcagtgtcct actcaactgt   6300
ctggtatcag ccctcatgag gacttctctt cttcccctca tagacctcca tctctgtttt   6360
ccttagcctg cagaaatctg gatggctatt cacagaatgc ctgtgctttc agagttgcat   6420 ttttctctg gtattctggt tcaagcattt gaaggtagga aaggttctcc aagtgcaaga   6480
aagccagccc tgagcctcaa ctgcctggct agtgtggtca gtaggatgca aaggctgttg   6540
aatgccacaa ggccaaactt taacctgtgt accacaagcc tagcagcaga ggcagctctg   6600
ctcactggaa ctctctgtct tctttctcct gagccttttc ttttcctgag ttttctagct   6660
ctcctcaacc ttacctctgc cctacccagg acaaacccaa gagccactgt ttctgtgatg   6720
tcctctccag ccctaattag gcatcatgac ttcagcctga ccttccatgc tcagaagcag   6780
tgctaatcca cttcagatga gctgctctat gcaacacagg cagagcctac aaaccttgc    6840 accagagccc tccacatatc agtgtttgtt catactcact tcaacagcaa atgtgactgc   6900
tgagattaag attttacaca agatggtctg taatttcaca gttagtttta tcccattagg   6960
tatgaaagaa ttagcataat tccccttaaa catgaatgaa tcttagattt tttaataaat   7020
agttttggaa gtaaagacag agacatcagg agcacaagga atagcctgag aggacaaaca   7080
gaacaagaaa gagtctggaa atacacagga tgttcttggc ctcctcaaag caagtgcaag   7140
cagatagtac cagcagcccc aggctatcag agcccagtga agagaagtac catgaaagcc   7200
acagctctaa ccaccctgtt ccagagtgac agacagtccc caagacaagc cagcctgagc   7260
cagagagaga actgcaagag aaagtttcta atttaggttc tgttagattc agacaagtgc   7320
```

```
aggtcatcct ctctccacag ctactcacct ctccagccta acaaagcctg cagtccacac    7380
tccaaccctg gtgtctcacc tcctagcctc tcccaacatc ctgctctctg accatcttct    7440
gcatctctca tctcaccatc tcccactgtc tacagcctac tcttgcaact accatctcat    7500
tttctgacat cctgtctaca tcttctgcca tactctgcca tctaccatac cacctcttac    7560
catctaccac accatctttt atctccatcc ctctcagaag cctccaagct gaatcctgct    7620
ttatgtgttc atctcagccc ctgcatggaa agctgacccc agaggcagaa ctattcccag    7680
agagcttggc caagaaaaac aaaactacca gcctggccag gctcaggagt agtaagctgc    7740
agtgtctgtt gtgttctagc ttcaacagct gcaggagttc cactctcaaa tgctccacat    7800
ttctcacatc ctcctgattc tggtcactac ccatcttcaa agaacagaat atctcacatc    7860
agcatactgt gaaggactag tcatgggtgc agctgctcag agctgcaaag tcattctgga    7920
tggtggagag cttacaaaca tttcatgatg ctcccccgc tctgatggct ggagcccaat    7980
ccctacacag actcctgctg tatgtgtttt cctttcactc tgagccacag ccagagggca    8040
ggcattcagt ctcctcttca ggctgggggct ggggcactga gaactcaccc aacaccttgc    8100
tctcactcct tctgcaaaac aagaaagagc tttgtgctgc agtagccatg aagaatgaaa    8160
ggaaggcttt aactaaaaaa tgtcagagat tattttcaac cccttactgt ggatcaccag    8220
caaggaggaa acacaacaca gagacatttt ttcccctcaa attatcaaaa gaatcactgc    8280
atttgttaaa gagagcaact gaatcaggaa gcagagtttt gaacatatca gaagttagga    8340
atctgcatca gagacaaatg cagtcatggt tgtttgctgc ataccagccc taatcattag    8400
aagcctcatg gacttcaaac atcattccct ctgacaagat gctctagcct aactccatga    8460
gataaaataa atctgccttt cagagccaaa gaagagtcca ccagcttctt ctcagtgtga    8520
acaagagctc cagtcaggtt agtcagtcca gtgcagtaga ggagaccagt ctgcatcctc    8580
taattttcaa aggcaagaag atttgtttac cctggacacc aggcacaagt gaggtcacag    8640
agctcttaga tatgcagtcc tcatgagtga ggagactaaa gcgcatgcca tcaagacttc    8700
agtgtagaga aaacctccaa aaaagcctcc tcactacttc tggaatagct cagaggccga    8760
ggcggcctcg gcctctgcat aaataaaaaa aattagtcag ccatggggcg gagaatgggc    8820
ggaactgggc ggagttaggg gcgggatggg cggagttagg ggcgggacta tggttgctga    8880
ctaattgaga tgcatgcttt gcatacttct gcctgctggg gagcctgggg acttccaca    8940 cctggttgct gactaattga gatgcatgct ttgcatactt ctgcctgctg gggagcctgg    9000
ggactttcca caccctaact gacacacatt ccacagctgc attaatgaat cggccaacgc    9060
gcggggagag gcggtttgcg tattgggcgc tcttccgctt cctcgctcac tgactcgctg    9120
cgctcggtcg ttcggctgcg gcgagcggta tcagctcact caaaggcggt aatacggtta    9180
tccacagaat caggggataa cgcaggaaag aacatgtgag caaaaggcca gcaaaaggcc    9240
aggaaccgta aaaaggccgc gttgctggcg ttttttccata ggctccgccc ccctgacgag    9300
catcacaaaa atcgacgctc aagtcagagg tggcgaaacc cgacaggact ataaagatac    9360
caggcgtttc ccctggaag ctccctcgtg cgctctcctg ttccgaccct gccgcttacc    9420
ggatacctgt ccgcctttct cccttcggga agcgtggcgc tttctcatag ctcacgctgt    9480
aggtatctca gttcggtgta ggtcgttcgc tccaagctgg gctgtgtgca cgaaccccc    9540 gttcagcccg accgctgcgc cttatccggt aactatcgtc ttgagtccaa cccggtaaga    9600
cacgacttat cgccactggc agcagccact ggtaacagga ttagcagagc gaggtatgta    9660
ggcggtgcta cagagttctt gaagtggtgg cctaactacg gctacactag aagaacagta    9720
```

```
tttggtatct gcgctctgct gaagccagtt accttcggaa aaagagttgg tagctcttga    9780
tccggcaaac aaaccaccgc tggtagcggt ggttttttg tttgcaagca gcagattacg    9840
cgcagaaaaa aaggatctca agaagatcct ttgatctttt ctacggggtc tgacgctcag    9900
tggaacgaaa actcacgtta agggattttg gtcatgagat tatcaaaaag gatcttcacc    9960
tagatccttt taaattaaaa atgaagtttt aaatcaatct aaagtatata tgagtaaact   10020
tggtctgaca gttaccaatg cttaatcagt gaggcaccta tctcagcgat ctgtctattt   10080
cgttcatcca tagttgcctg actcctgcaa accacgttgt gtctcaaaat ctctgatgtt   10140
acattgcaca agataaaaat atatcatcat gaacaataaa actgtctgct tacataaaca   10200
gtaatacaag gggtgttatg agccatattc aacgggaaac gtcttgctcg aggccgcgat   10260
taaattccaa catggatgct gatttatatg ggtataaatg gctcgcgat aatgtcgggc    10320 aatcaggtgc gacaatctat cgattgtatg ggaagcccga tgcgccagag ttgtttctga   10380
aacatggcaa aggtagcgtt gccaatgatg ttacagatga gatggtcaga ctaaactggc   10440
tgacggaatt tatgcctctt ccgaccatca agcattttat ccgtactcct gatgatgcat   10500
ggttactcac cactgcgatc cccgggaaaa cagcattcca ggtattagaa gaatatcctg   10560
attcaggtga aaatattgtt gatgcgctgg cagtgttcct gcgccggttg cattcgattc   10620
ctgtttgtaa ttgtccttt aacagcgatc gcgtatttcg tctcgctcag gcgcaatcac    10680
gaatgaataa cggtttggtt gatgcgagtg attttgatga cgagcgtaat ggctggcctg   10740
ttgaacaagt ctggaaagaa atgcataagc ttttgccatt ctcaccggat tcagtcgtca   10800
ctcatggtga tttctcactt gataaccttat ttttgacga ggggaaatta ataggttgta   10860
ttgatgttgg acgagtcgga atcgcagacc gataccagga tcttgccatc ctatggaact   10920
gcctcggtga gttttctcct tcattacaga aacggctttt tcaaaaatat ggtattgata   10980
atcctgatat gaataaattg cagtttcatt tgatgctcga tgagtttttc taagggcggc   11040
ctgccaccat acccacgccg aaacaagcgc tcatgagccc gaagtggcga gcccgatctt   11100
ccccatcggt gatgtcggcg atataggcgc cagcaaccgc acctgtggcg ccggtgatga   11160
gggcgcgcca agtcgacgtc cggcagtc                                      11188

<210> SEQ ID NO 12
<211> LENGTH: 11187
<212> TYPE: DNA
<213> ORGANISM: Artificial sequence
<220> FEATURE:
<223> OTHER INFORMATION: Synthetic polynucleotide

<400> SEQUENCE: 12
ctagaaccgg tgacgtctcc catggtgaag cttggatctg aattcggtac ctagttataa      60
tagtaatcaa ttacggggtc attagttcat agcccatata tggagttccg cgttacataa     120
cttacggtaa atggcccgcc tggctgaccg cccaacgacc cccgcccatt gacgtcaata     180
atgacgtatg ttcccatagt aacgccaata gggactttcc attgacgtca atgggtggag     240
tatttacggt aaactgccca cttggcagta catcaagtgt atcatatgcc aagtacgccc     300
cctattgacg tcaatgacgg taaatggccc gcctggcatt atgcccagta catgacctta     360
tgggactttc ctacttggca gtacatctac gtattagtca tcgctattac catggtcgag     420
gtgagcccca cgttctgctt cactctcccc atctcccccc cctccccacc cccaattttg     480
tatttattta ttttttaatt attttgtgca gcgatggggg cggggggggg gggggggcgc     540
```

```
gcgccaggcg gggcggggcg gggcgagggg cggggcgggg cgaggcggag aggtgcggcg    600
gcagccaatc agagcggcgc gctccgaaag tttcctttta tggcgaggcg gcggcggcgg    660
cggccctata aaagcgaag cgcgcggcgg gcgggagtcg ctgcgacgct gccttcgccc     720
cgtgccccgc tccgccgccg cctcgcgccg cccgccccgg ctctgactga ccgcgttact    780
cccacaggtg agcgggcggg acggcccttc tcctccgggc tgtaattagc gcttggttta    840
atgacggctt gtttcttttc tgtggctgcg tgaaagcctt gaggggctcc gggagctaga    900
gcctctgcta accatgttca tgccttcttc ttttttcctac agctcctggg caacgtgctg    960
gttattgtgc tgtctcatca ttttggcaaa gaattcctcg aagatccgaa gggaaagtct   1020
tccacgactg tgggatccgt tcgaagatat caccggttga gccaccatgg aattcagcag   1080
ccccagcaga gaggaatgcc ccaagcctct gagccgggtg tcaatcatgg ccggatctct   1140
gacaggactg ctgctgcttc aggccgtgtc ttgggcttct ggcgctagac cttgcatccc   1200
caagagcttc ggctacagca gcgtcgtgtg cgtgtgcaat gccacctact gcgacagctt   1260
cgaccctcct acctttcctg ctctgggcac cttcagcaga tacgagagca ccagatccgg   1320
cagacggatg gaactgagca tgggacccat ccaggccaat cacacaggca ctggcctgct   1380
gctgacactg cagcctgagc agaaattcca gaaagtgaaa ggcttcggcg gagccatgac   1440
agatgccgcc gctctgaata tcctggctct gtctccacca gctcagaacc tgctgctcaa   1500
gagctacttc agcgaggaag gcatcggcta caacatcatc agagtgccca tggccagctg   1560
cgacttcagc atcaggacct acacctacgc cgacacaccc gacgatttcc agctgcacaa   1620
cttcagcctg cctgaagagg acaccaagct gaagatccct ctgatccaca gagccctgca   1680
gctggcacaa agaccgtgt cactgctggc ctctccatgg acatctccca cctggctgaa   1740
aacaaatggc gccgtgaatg gcaagggcag cctgaaaggc caacctggcg acatctacca   1800
ccagacctgg gccagatact tcgtgaagtt cctggacgcc tatgccgagc acaagctgca   1860
gttttgggcc gtgacagccg agaacgaacc ttctgctgga ctgctgagcg gctacccctt   1920
tcagtgcctg ggctttacac ccgagcacca gcgggacttt atcgcccgtg atctgggacc   1980
cacactggcc aatagcaccc accataatgt gcggctgctg atgctggacg accagagact   2040
gcttctgccc cactgggcta agtggtgct gacagatcct gaggccgcca atacgtgca    2100 cggaatcgcc gtgcactggt atctggactt tctggcccct gccaaggcca cactgggaga   2160
gacacacaga ctgttcccca acaccatgct gttcgccagc gaagcctgtg tgggcagcaa   2220
gttttgggaa cagagcgtgc ggctcggcag ctgggataga ggcatgcagt acagccacag   2280
catcatcacc aacctgctgt accacgtcgt cggctggacc gactggaatc tggcccctga   2340
tcctgaaggc ggccctaact gggtccgaaa cttcgtggac agccccatca tcgtggacat   2400
caccaaggac accttctaca gcagcccat gttctaccac ctgggacact tcagcaagtt   2460
catccccgag ggctctcagc gcgttggact ggtggcttcc cagaagaacg atctggacgc   2520
cgtggctctg atgcaccctg atggatctgc tgtggtggtg gtcctgaacc gcagcagcaa   2580
agatgtgccc ctgaccatca aggatcccgc cgtgggattc ctggaaacaa tcagccctgg   2640
ctactccatc cacacctacc tgtggcgtag acagtgacaa ttgttaatta agtttaaacc   2700
ctcgaggccg caagcttatc gataatcaac ctctggatta caaaatttgt gaaagattga   2760
ctggtattct taactatgtt gctccttta cgctatgtgg atacgctgct ttaatgcctt   2820
tgtatcatgc tattgcttcc cgtatggctt tcattttctc ctccttgtat aaatcctggt   2880
tgctgtctct ttatgaggag ttgtggcccg ttgtcaggca acgtggcgtg gtgtgcactg   2940
```

-continued

```
tgtttgctga cgcaaccccc actggttggg gcattgccac cacctgtcag ctccttcccg      3000
ggactttcgc tttcccctc cctattgcca cggcggaact catcgccgcc tgccttgccc       3060
gctgctggac aggggctcgg ctgttgggca ctgacaattc cgtggtgttg tcggggaaat      3120
catcgtcctt tccttggctg ctcgcctgtg ttgccacctg gattctgcgc gggacgtcct      3180
tctgctacgt cccttcggcc ctcaatccag cggaccttcc ttcccgcggc ctgctgccgg      3240
ctctgcggcc tcttccgcgt cttcgccttc gccctcagac gagtcggatc tcctttggg      3300
ccgcctcccc gcatcgatac cgtcgactag agctcgctga tcagcctcga ctgtgccttc      3360
tagttgccag ccatctgttg tttgcccctc ccccgtgcct tccttgaccc tggaaggtgc      3420
cactcccact gtcctttcct aataaaatga ggaaattgca tcgcattgtc tgagtaggtg      3480
tcattctatt ctgggggtg gggtggggca ggacagcaag ggggaggatt gggaagacaa       3540
tagcaggcat gctggggaga gatccacgat aacaaacagc ttttttgggg tgaacatatt     3600
gactgaattc cctgcaggtt ggccactccc tctctgcgcg ctcgctcgct cactgaggcc     3660
gcccgggcaa agcccgggcg tcgggcgacc tttggtcgcc cggcctcagt gagcgagcga     3720
gcgcgcagag agggagtggc caactccatc actaggggtt cctgcggccg ctcgtacggt    3780
ctcgaggaat tcctgcagga taacttgcca acctcattct aaaatgtata tagaagccca    3840
aaagacaata acaaaaatat tcttgtagaa caaaatggga aagaatgttc cactaaatat    3900
caagatttag agcaaagcat gagatgtgtg gggatagaca gtgaggctga taaaatagag   3960
tagagctcag aaacagaccc attgatatat gtaagtgacc tatgaaaaaa atatggcatt   4020
ttacaatggg aaaatgatgg tctttttctt ttttagaaaa acagggaaat atatttatat   4080
gtaaaaaata aagggaacc catatgtcat accatacaca caaaaaaatt ccagtgaatt    4140
ataagtctaa atggagaagg caaaacttta aatcttttag aaaataatat agaagcatgc   4200
agaccagcct ggccaacatg atgaaaccct ctctactaat aataaaatca gtagaactac   4260
tcaggactac tttgagtggg aagtcctttt ctatgaagac ttctttggcc aaaattaggc   4320
tctaaatgca aggagatagt gcatcatgcc tggctgcact tactgataaa tgatgttatc   4380
accatcttta accaaatgca caggaacaag ttatggtact gatgtgctgg attgagaagg   4440
agctctactt ccttgacagg acacatttgt atcaacttaa aaaagcagat ttttgccagc   4500
agaactattc attcagaggt aggaaactta gaatagatga tgtcactgat tagcatggct   4560
tccccatctc cacagctgct tcccacccag gttgcccaca gttgagtttg tccagtgctc    4620
agggctgccc actctcagta agaagcccca caccagcccc tctccaaata tgttggctgt   4680
tccttccatt aaagtgaccc cactttagag cagcaagtgg atttctgttt cttacagttc   4740
aggaaggagg agtcagctgt gagaacctgg agcctgagat gcttctaagt cccactgcta    4800
ctggggtcag ggaagccaga ctccagcatc agcagtcagg agcactaagc ccttgccaac   4860
atcctgtttc tcagagaaac tgcttccatt ataatggttg tcctttttta agctatcaag    4920
ccaaacaacc agtgtctacc attattctca tcacctgaag ccaagggttc tagcaaaagt   4980
caagctgtct tgtaatggtt gatgtgcctc cagcttctgt cttcagtcac tccactctta   5040
gcctgctctg aatcaactct gaccacagtt ccctggagcc cctgccacct gctgcccctg   5100
ccaccttctc catctgcagt gctgtgcagc cttctgcact cttgcagagc taataggtgg   5160
agacttgaag gaagaggagg aaagtttctc ataatagcct tgctgcaagc tcaaatggga   5220
ggtgggcact gtgcccagga gccttggagc aaaggctgtg cccaacctct gactgcatcc   5280
```

```
aggtttggtc ttgacagaga taagaagccc tggcttttgg agccaaaatc taggtcagac    5340
ttaggcagga ttctcaaagt ttatcagcag aacatgaggc agaagaccct ttctgctcca    5400
gcttcttcag gctcaacctt catcagaata gatagaaaga gaggctgtga gggttcttaa    5460
aacagaagca aatctgactc agagaataaa caacctccta gtaaactaca gcttagacag    5520
agcatctggt ggtgagtgtg ctcagtgtcc tactcaactg tctggtatca gccctcatga    5580
ggacttctct tctttccctc atagacctcc atctctgttt tccttagcct gcagaaatct    5640
ggatggctat tcacagaatg cctgtgcttt cagagttgca ttttttctct ggtattctgg    5700
ttcaagcatt tgaaggtagg aaaggttctc caagtgcaag aaagccagcc ctgagcctca    5760
actgcctggc tagtgtggtc agtaggatgc aaaggctgtt gaatgccaca aggccaaact    5820
ttaacctgtg taccaaagc ctagcagcag aggcagctct gctcactgga actctctgtc    5880
ttctttctcc tgagcctttt cttttcctga gttttctagc tctcctcaac cttacctctg    5940
ccctacccag acaaaccca agagccactg tttctgtgat gtcctctcca gccctaatta    6000
ggcatcatga cttcagcctg accttccatg ctcagaagca gtgctaatcc acttcagatg    6060
agctgctcta tgcaacacag gcagagccta caaacctttg caccagagcc ctccacatat    6120
cagtgtttgt tcatactcac ttcaacagca aatgtgactc ctgagattaa gattttacac    6180
aagatggtct gtaatttcac agttagtttt atcccattag gtatgaaaga attagcataa    6240
ttccccttaa acatgaatga atcttagatt ttttaataaa tagttttgga agtaaagaca    6300
gagacatcag gagcacaagg aatagcctga gaggacaaac agaacaagaa agagtctgga    6360
aatacacagg atgttcttgg cctcctcaaa gcaagtgcaa gcagatagta ccagcagccc    6420
caggctatca gagcccagtg aagagaagta ccatgaaagc cacagctcta accaccctgt    6480
tccagagtga cagacagtcc ccaagacaag ccagcctgag ccagagagag aactgcaaga    6540
gaaagtttct aatttaggtt ctgttagatt cagacaagtg caggtcatcc tctctccaca    6600
gctactcacc tctccagcct aacaaagcct gcagtccaca ctccaaccct ggtgtctcac    6660
ctcctagcct ctcccaacat cctgctctct gaccatcttc tgcatctctc atctcaccat    6720
ctcccactgt ctacagccta ctcttgcaac taccatctca ttttctgaca tcctgtctac    6780
atcttctgcc atactctgcc atctaccata ccacctctta ccatctacca caccatcttt    6840
tatctccatc cctctcagaa gcctccaagc tgaatcctgc tttatgtgtt catctcagcc    6900
cctgcatgga aagctgaccc cagaggcaga actattccca gagagcttgg ccaagaaaaa    6960
caaaactacc agcctggcca ggctcaggag tagtaagctg cagtgtctgt tgtgttctag    7020
cttcaacagc tgcaggagtt ccactctcaa atgctccaca tttctcacat cctcctgatt    7080
ctggtcacta cccatcttca aagaacagaa tatctcacat cagcatactg tgaaggacta    7140
gtcatgggtg cagctgctca gagctgcaaa gtcattctgg atggtggaga gcttacaaac    7200
atttcatgat gctccccccg ctctgatggc tggagcccaa tccctacaca gactcctgct    7260
gtatgtgttt tcctttcact ctgagccaca gccagagggc aggcattcag tctcctcttc    7320
aggctggggc tggggcactg agaactcacc caacaccttg ctctcactcc ttctgcaaaa    7380
caagaaagag ctttgtgctg cagtagccat gaagaatgaa aggaaggctt taactaaaaa    7440
atgtcagaga ttatttttcaa ccccttactg tggatcacca gcaaggagga aacacaacac    7500
agagacattt ttcccctca aattatcaaa agaatcactg catttgttaa agagagcaac    7560
tgaatcagga agcagagttt tgaacatatc agaagttagg aatctgcatc agagacaaat    7620
gcagtcatgg ttgtttgctg cataccagcc ctaatcatta gaagcctcat ggacttcaaa    7680
```

```
catcattccc tctgacaaga tgctctagcc taactccatg agataaaata aatctgcctt    7740
tcagagccaa agaagagtcc accagcttct tctcagtgtg aacaagagct ccagtcaggt    7800
tagtcagtcc agtgcagtag aggagaccag tctgcatcct ctaattttca aaggcaagaa    7860
gatttgttta ccctgacac caggcacaag tgaggtcaca gagctcttag atatgcagtc     7920
ctcatgagtg aggagactaa agcgcatgcc atcaagactt cagtgtagag aaaacctcca    7980
aaaaagcctc ctcactactt ctggaatagc tcagaggccg aggcggcctc ggcctctgca    8040
taaataaaaa aaattagtca gccatggggc ggagaatggg cggaactggg cggagttagg    8100
ggcgggatgg gcggagttag gggcgggact atggttgctg actaattgag atgcatgctt    8160
tgcatacttc tgcctgctgg ggagcctggg gactttccac acctggttgc tgactaattg    8220
agatgcatgc tttgcatact tctgcctgct ggggagcctg ggactttcc acccctaac      8280 tgacacacat tccacagctg cattaatgaa tcggccaacg cgcggggaga ggcggtttgc    8340
gtattgggcg ctcttccgct tcctcgctca ctgactcgct gcgctcggtc gttcggctgc    8400
ggcgagcggt atcagctcac tcaaaggcgg taatacggtt atccacagaa tcaggggata    8460
acgcaggaaa gaacatgtga gcaaaaggcc agcaaaaggc caggaaccgt aaaaaggccg    8520
cgttgctggc gtttttccat aggctccgcc cccctgacga gcatcacaaa aatcgacgct    8580
caagtcagag gtggcgaaac ccgacaggac tataaagata ccaggcgttt ccccctggaa    8640
gctccctcgt gcgctctcct gttccgaccc tgccgcttac cggatacctg tccgcctttc    8700
tcccttcggg aagcgtggcg ctttctcata gctcacgctg taggtatctc agttcggtgt    8760
aggtcgttcg ctccaagctg ggctgtgtgc acgaaccccc cgttcagccc gaccgctgcg    8820
ccttatccgg taactatcgt cttgagtcca acccggtaag acacgactta tcgccactgg    8880
cagcagccac tggtaacagg attagcagag cgaggtatgt aggcggtgct acagagttct    8940
tgaagtggtg gcctaactac ggctacacta agaacagt atttggtatc tgcgctctgc      9000
tgaagccagt taccttcgga aaaagagttg gtagctcttg atccggcaaa caaaccaccg    9060
ctggtagcgg tggtttttt gtttgcaagc agcagattac gcgcagaaaa aaaggatctc     9120
aagaagatcc tttgatcttt tctacggggt ctgacgctca gtggaacgaa aactcacgtt    9180
aagggatttt ggtcatgaga ttatcaaaaa ggatcttcac ctagatcctt ttaaattaaa    9240
aatgaagttt taaatcaatc taaagtatat atgagtaaac ttggtctgac agttaccaat    9300
gcttaatcag tgaggcacct atctcagcga tctgtctatt tcgttcatcc atagttgcct    9360
gactcctgca aaccacgttg tgtctcaaaa tctctgatgt tacattgcac aagataaaaa    9420
tatatcatca tgaacaataa aactgtctgc ttacataaac agtaatacaa ggggtgttat    9480
gagccatatt caacgggaaa cgtcttgctc gaggccgcga ttaaattcca acatggatgc    9540
tgatttatat gggtataaat gggctcgcga taatgtcggg caatcaggtg cgacaatcta    9600
tcgattgtat gggaagcccg atgcgccaga gttgtttctg aaacatggca aaggtagcgt    9660
tgccaatgat gttacagatg agatggtcag actaaactgg ctgacggaat ttatgcctct    9720
tccgaccatc aagcatttta tccgtactcc tgatgatgca tggttactca ccactgcgat    9780 cccccgggaaa acagcattcc aggtattaga agaatatcct gattcaggtg aaaatattgt    9840
tgatgcgctg gcagtgttcc tgcgccggtt gcattcgatt cctgtttgta attgtccttt    9900
taacagcgat cgcgtatttc gtctcgctca ggcgcaatca cgaatgaata cggtttggt     9960 tgatgcgagt gattttgatg acgagcgtaa tggctggcct gttgaacaag tctggaaaga   10020
```

```
aatgcataag cttttgccat tctcaccgga ttcagtcgtc actcatggtg atttctcact    10080
tgataacctt attttgacg aggggaaatt aataggttgt attgatgttg acgagtcgg    10140
```
(Note: line 10140 as printed: `tgataacctt attttgacg aggggaaatt aataggttgt attgatgttg acgagtcgg`)

```
aatgcataag cttttgccat tctcaccgga ttcagtcgtc actcatggtg atttctcact    10080
tgataacctt attttgacg aggggaaatt aataggttgt attgatgttg acgagtcgg    10140
aatcgcagac cgataccagg atcttgccat cctatggaac tgcctcggtg agttttctcc    10200
ttcattacag aaacggcttt ttcaaaaata tggtattgat aatcctgata tgaataaatt    10260
gcagtttcat ttgatgctcg atgagttttt ctaagggcgg cctgccacca tacccacgcc    10320
gaaacaagcg ctcatgagcc cgaagtggcg agcccgatct tccccatcgg tgatgtcggc    10380
gatataggcg ccagcaaccg cacctgtggc gccggtgatg agggcgcgcc aagtcgacgt    10440
ccggcagtct tggccactcc ctctctgcgc gctcgctcgc tcactgaggc cgggcgacca    10500
aaggtcgccc gacgcccggg ctttgcccgg gcggcctcag tgagcgagcg agcgcgcaga    10560
gagggagtgg ccaactccat cactaggggt tcctgctagc tctgggtatt taagcccgag    10620
tgagcacgca gggtctccat tttgaagcgg gaggttacgc gttcgtcgac tactagtggg    10680
taccagagcg tggtgactga gatgttttct aggaaacaca aaagatacaa aaagaacac    10740
gtggaaggat agccaaaaag gggggctgcc cccatttcct gcaccccgct gcgatggctg    10800
gcaccatttg gaagacttcg agatacactg ttgagcgcag taagacaaca gtgtatctcg    10860
aagtcttcca gatggggcca gccggtccac tctgtatcca ggccagttct gcaaggcgtt    10920
cgaggaccac cccctcccc tcgccaccag ggtggtctca tacagaactt ataagattcc    10980
caaatccaaa gacatttcac gtttatggtg atttcccaga acacatagcg acatgcaaat    11040
attgcagggc gccactcccc tgtccctcac agccatcttc ctgccagggc gcacgcgcgc    11100
tgggtgttcc cgcctagtga cactgggccc gcgattcctt ggagcgggtt gatgacgtca    11160
gcgtttccca tggtgaatcc ctaggtt                                       11187
```

<210> SEQ ID NO 13
<211> LENGTH: 10960
<212> TYPE: DNA
<213> ORGANISM: Artificial sequence
<220> FEATURE:
<223> OTHER INFORMATION: Synthetic polynucleotide

<400> SEQUENCE: 13

```
ttggccactc cctctctgcg cgctcgctcg ctcactgagg ccgggcgacc aaaggtcgcc      60
cgacgcccgg gctttgcccg gcggcctca gtgagcgagc gagcgcgcag agagggagtg     120
gccaactcca tcactagggg ttcctgctag ctctgggtat ttaagcccga gtgagcacgc     180
agggtctcca ttttgaagcg ggaggttacg cgttcgtcga ctactagtgg gtaccagagc     240
tccctaggtt ctagaaccgg tgacgtctcc catggtgaag cttggatctg aattcggtac     300
cctagttatt aatagtaatc aattacgggg tcattagttc atagcccata tatggagttc     360
cgcgttacat aacttacggt aaatggcccg cctggctgac cgcccaacga cccccgccca     420
ttgacgtcaa taatgacgta tgttcccata gtaacgccaa tagggacttt ccattgacgt     480
caatgggtgg actatttacg gtaaactgcc cacttggcag tacatcaagt gtatcatatg     540
ccaagtacgc cccctattga cgtcaatgac ggtaaatggc ccgcctggca ttatgcccag     600
tacatgacct tatgggactt tcctacttgg cagtacatct acgtattagt catcgctatt     660
accatggtcg aggtgagccc cacgttctgc ttcactctcc ccatctcccc ccctcccca     720
cccccaattt tgtatttatt tattttttaa ttatttgtg cagcgatggg ggcgggggg     780
gggggggggc gcgcgccagg cggggcgggg cgggcgaggg gcgggcgcgg ggcgaggcgg     840
agaggtgcgg cggcagccaa tcagagcggc gcgctccgaa agtttccttt tatggcgagg     900
```

```
cggcggcggc ggcggcccta taaaaagcga agcgcgcggc gggcgggagt cgctgcgacg     960
ctgccttcgc cccgtgcccc gctccgccgc cgcctcgcgc cgcccgcccc ggctctgact    1020
gaccgcgtta ctcccacagg tgagcgggcg ggacggccct tctcctccgg gctgtaatta    1080
gcgcttggtt taatgacggc ttgtcctggt ggcgagggga gggggtggt cctcgaacgc     1140
cttgcagaac tggcctggat acagagtgga ccggctggcc ccatctggaa gacttcgaga    1200
tacactgttt tcttactgcg ctcaacagtg tatctcgaag tcttccaaat ggtgccagcc    1260
atcgcagcgg ggtgcaggaa atgggggcag cccccctttt tggctatcct tccacgtgtt    1320
cttttttgta tcttttgtgt ttcctagaaa acatctcagt caccacctt tctgtggctgc     1380
gtgaaagcct tgaggggctc cgggagctag agcctctgct aaccatgttc atgccttctt    1440
cttttttccta cagctcctgg gcaacgtgct ggttattgtg ctgtctcatc attttggcaa    1500
agaattcctc gaagatccga agggaaagtc ttccacgact gtgggatccg ttcgaagata    1560
tcaccggttg agccaccatg gaattcagca gccccagcag agaggaatgc ccaagcctc     1620
tgagccgggt gtcaatcatg gccggatctc tgacaggact gctgctgctt caggccgtgt    1680
cttgggcttc tggcgctaga ccttgcatcc ccaagagctt cggctacagc agcgtcgtgt    1740
gcgtgtgcaa tgccacctac tgcgacagct tcgaccctcc tacctttcct gctctgggca    1800
ccttcagcag atacgagagc accagatccg gcagacggat ggaactgagc atgggaccca    1860
tccaggccaa tcacacaggc actggcctgc tgctgacact gcagcctgag cagaaattcc    1920
agaaagtgaa aggcttcggc ggagccatga cagatgccgc cgctctgaat atcctggctc    1980
tgtctccacc agctcagaac ctgctgctca agagctactt cagcgaggaa ggcatcggct    2040
acaacatcat cagagtgccc atggccagct gcgacttcag catcaggacc tacacctacg    2100
ccgacacacc cgacgatttc cagctgcaca acttcagcct gcctgaagag acaccaagc    2160
tgaagatccc tctgatccac agagcccctgc agctggcaca aagacccgtg tcactgctgg    2220
cctctccatg gacatctccc acctggctga aaacaaatgg cgccgtgaat ggcaagggca    2280
gcctgaaagg ccaacctggc gacatctacc accagacctg gccagatac ttcgtgaagt     2340
tcctggacgc ctatgccgag cacaagctgc agttttgggc cgtgacagcc gagaacgaac    2400
cttctgctgg actgctgagc ggctaccccct tcagtgcct gggctttaca cccgagcacc    2460
agcgggactt tatcgcccgt gatctgggac ccacactggc caatagcacc caccataatg    2520
tgcggctgct gatgctggac gaccagagac tgcttctgcc ccactgggct aaagtggtgc    2580
tgacagatcc tgaggccgcc aaatacgtgc acggaatcgc cgtgcactgg tatctggact    2640
ttctggcccc tgccaaggcc acactgggag agacacacag actgttcccc aacaccatgc    2700
tgttcgccag cgaagcctgt gtgggcagca agttttggga acagagcgtg cggctcggca    2760
gctgggatag aggcatgcag tacagccaca gcatcatcac caacctgctg taccacgtcg    2820
tcggctggac cgactggaat ctggccctga atcctgaagg cggccctaac tgggtccgaa    2880
acttcgtgga cagccccatc atcgtggaca tcaccaagga caccttctac aagcagccca    2940
tgttctacca cctgggacac ttcagcaagt tcatccccga gggctctcag cgcgttggac    3000
tggtggcttc ccagaagaac gatctggacg ccgtggctct gatgcaccct gatggatctg    3060
ctgtggtggt ggtcctgaac cgcagcagca agatgtgcc cctgaccatc aaggatcccg    3120
ccgtgggatt cctggaaaca atcagccctg gctactccat ccacacctac ctgtggcgta    3180
gacagtgaca attgttaatt aagtttaaac cctcgaggcc gcaagcttat cgataatcaa    3240
```

```
cctctggatt acaaaatttg tgaaagattg actggtattc ttaactatgt tgctcctttt    3300
acgctatgtg gatacgctgc tttaatgcct ttgtatcatg ctattgcttc ccgtatggct    3360
ttcattttct cctccttgta taaatcctgg ttgctgtctc tttatgagga gttgtggccc    3420
gttgtcaggc aacgtggcgt ggtgtgcact gtgtttgctg acgcaacccc cactggttgg    3480
ggcattgcca ccacctgtca gctcctttcc gggactttcg ctttccccct ccctattgcc    3540
acggcggaac tcatcgccgc ctgccttgcc cgctgctgga caggggctcg gctgttgggc    3600
actgacaatt ccgtggtgtt gtcggggaaa tcatcgtcct ttccttggct gctcgcctgt    3660
gttgccacct ggattctgcg cgggacgtcc ttctgctacg tcccttcggc cctcaatcca    3720
gcggaccttc cttcccgcgg cctgctgccg gctctgcggc ctcttccgcg tcttcgcctt    3780
cgccctcaga cgagtcggat ctccctttgg gccgcctccc cgcatcgata ccgtcgacta    3840
gagctcgctg atcagcctcg actgtgcctt ctagttgcca gccatctgtt gtttgcccct    3900
cccccgtgcc ttccttgacc ctggaaggtg ccactcccac tgtcctttcc taataaaatg    3960
aggaaattgc atcgcattgt ctgagtaggt gtcattctat tctgggggt ggggtggggc    4020
aggacagcaa gggggaggat tgggaagaca atagcaggca tgctggggag agatccacga    4080
taacaaacag cttttttggg gtgaacatat tgactgaatt ccctgcaggt tggccactcc    4140
ctctctgcgc gctcgctcgc tcactgaggc cgcccgggca aagcccgggc gtcgggcgac    4200
ctttggtcgc ccggcctcag tgagcgagcg agcgcgcaga gagggagtgg ccaactccat    4260
cactaggggt tcctgcggcc gctcgtacgg tctcgaggaa ttcctgcagg ataacttgcc    4320
aacctcattc taaaatgtat atagaagccc aaaagacaat aacaaaaata ttcttgtaga    4380
acaaaatggg aaagaatgtt ccactaaata tcaagattta gagcaaagca tgagatgtgt    4440
ggggatagac agtgaggctg ataaaataga gtagagctca gaaacagacc cattgatata    4500
tgtaagtgac ctatgaaaaa aatatggcat tttacaatgg gaaaatgatg gtctttttct    4560
ttttagaaa aacagggaaa tatatttata tgtaaaaaat aaaagggaac ccatatgtca    4620
taccatacac acaaaaaaat tccagtgaat tataagtcta aatggagaag gcaaaacttt    4680
aaatctttta gaaataataa tagaagcatg cagaccagcc tggccaacat gatgaaaccc    4740
tctctactaa taataaaatc agtagaacta ctcaggacta ctttgagtgg gaagtccttt    4800
tctatgaaga cttctttggc caaaattagg ctctaaatgc aaggagatag tgcatcatgc    4860
ctggctgcac ttactgataa atgatgttat caccatcttt aaccaaatgc acaggaacaa    4920
gttatggtac tgatgtgctg gattgagaag gagctctact tccttgacag gacacatttg    4980
tatcaactta aaaaagcaga tttttgccag cagaactatt cattcagagg taggaaactt    5040
agaatagatg atgtcactga ttagcatggc ttccccatct ccacagctgc ttccacccca    5100
ggttgcccac agttgagttt gtccagtgct cagggctgcc cactctcagt aagaagcccc    5160
acaccagccc ctctccaaat atgttggctg ttccttccat taaagtgacc ccactttaga    5220
gcagcaagtg gatttctgtt tcttacagtt caggaaggag gagtcagctg tgagaacctg    5280
gagcctgaga tgcttctaag tcccactgct actggggtca gggaagccag actccagcat    5340
cagcagtcag gagcactaag cccttgccaa catcctgтттт tcagagaaa ctgcttccat    5400
tataatggtt gtcctttttt aagctatcaa gccaaacaac cagtgtctac cattattctc    5460
atcacctgaa gccaagggtt ctagcaaaag tcaagctgtc ttgtaatggt tgatgtgcct    5520
ccagcttctg tcttcagtca ctccactctt agcctgctct gaatcaactc tgaccacagt    5580
tccctggagc cctgccacc tgctgcccct gccaccttct ccatctgcag tgctgtgcag    5640
```

```
ccttctgcac tcttgcagag ctaataggtg gagacttgaa ggaagaggag gaaagtttct   5700
cataatagcc ttgctgcaag ctcaaatggg aggtgggcac tgtgcccagg agccttggag   5760
caaaggctgt gcccaacctc tgactgcatc caggtttggt cttgacagag ataagaagcc   5820
ctggcttttg gagccaaaat ctaggtcaga cttaggcagg attctcaaag tttatcagca   5880
gaacatgagg cagaagaccc tttctgctcc agcttcttca ggctcaacct tcatcagaat   5940
agatagaaag agaggctgtg agggttctta aaacagaagc aaatctgact cagagaataa   6000
acaacctcct agtaaactac agcttagaca gagcatctgg tggtgagtgt gctcagtgtc   6060
ctactcaact gtctggtatc agccctcatg aggacttctc ttctttccct catagacctc   6120
catctctgtt ttccttagcc tgcagaaatc tggatggcta ttcacagaat gcctgtgctt   6180
tcagagttgc atttttctc tggtattctg gttcaagcat ttgaaggtag aaaggttct    6240 ccaagtgcaa gaaagccagc cctgagcctc aactgcctgg ctagtgtggt cagtaggatg   6300
caaaggctgt tgaatgccac aaggccaaac tttaacctgt gtaccacaag cctagcagca   6360
gaggcagctc tgctcactgg aactctctgt cttctttctc ctgagccttt tcttttcctg   6420
agttttctag ctctcctcaa ccttacctct gccctaccca ggacaaaccc aagagccact   6480
gtttctgtga tgtcctctcc agccctaatt aggcatcatg acttcagcct gaccttccat   6540
gctcagaagc agtgctaatc cacttcagat gagctgctct atgcaacaca ggcagagcct   6600
acaaaccttt gcaccagagc cctccacata tcagtgtttg ttcatactca cttcaacagc   6660
aaatgtgact gctgagatta agattttaca caagatggtc tgtaatttca cagttagttt   6720
tatcccatta ggtatgaaag aattagcata attcccctta aacatgaatg aatcttagat   6780 ttttaataa atagttttgg aagtaaagac agagacatca ggagcacaag gaatagcctg    6840
agaggacaaa cagaacaaga aagagtctgg aaatacacag gatgttcttg gcctcctcaa   6900
agcaagtgca agcagatagt accagcagcc ccaggctatc agagcccagt gaagagaagt   6960
accatgaaag ccacagctct aaccaccctg ttccagagtg acagacagtc cccaagacaa   7020
gccagcctga gccagagaga gaactgcaag agaaagtttc taatttaggt tctgttagat   7080
tcagacaagt gcaggtcatc ctctctccac agctactcac ctctccagcc taacaaagcc   7140
tgcagtccac actccaaccc tggtgtctca cctcctagcc tctcccaaca tcctgctctc   7200
tgaccatctt ctgcatctct catctcacca tctcccactg tctacagcct actcttgcaa   7260
ctaccatctc attttctgac atcctgtcta catcttctgc catactctgc catctaccat   7320
accacctctt accatctacc acaccatctt ttatctccat ccctctcaga agcctccaag   7380
ctgaatcctg ctttatgtgt tcatctcagc ccctgcatgg aaagctgacc ccagaggcag   7440
aactattccc agagagcttg gccaagaaaa acaaaactac cagcctggcc aggctcagga   7500
gtagtaagct gcagtgtctg ttgtgttcta gcttcaacag ctgcaggagt tccactctca   7560
aatgctccac atttctcaca tcctcctgat tctggtcact acccatcttc aaagaacaga   7620
atatctcaca tcagcatact gtgaaggact agtcatgggt gcagctgctc agagctgcaa   7680
agtcattctg gatggtggag agcttacaaa catttcatga tgctcccccc gctctgatgg   7740
ctggagccca atccctacac agactcctgc tgtatgtgtt ttccttttcac tctgagccac   7800 agccagaggg caggcattca gtctcctctt caggctgggg ctggggcact gagaactcac   7860
ccaacacctt gctctcactc cttctgcaaa acaagaaaga gctttgtgct gcagtagcca   7920
tgaagaatga aaggaaggct ttaactaaaa aatgtcagag attattttca accccttact   7980
```

```
gtggatcacc agcaaggagg aaacacaaca cagagacatt ttttcccctc aaattatcaa   8040
aagaatcact gcatttgtta aagagagcaa ctgaatcagg aagcagagtt ttgaacatat   8100
cagaagttag gaatctgcat cagagacaaa tgcagtcatg gttgtttgct gcataccagc   8160
cctaatcatt agaagcctca tggacttcaa acatcattcc ctctgacaag atgctctagc   8220
ctaactccat gagataaaat aaatctgcct ttcagagcca aagaagagtc caccagcttc   8280
ttctcagtgt gaacaagagc tccagtcagg ttagtcagtc cagtgcagta gaggagacca   8340
gtctgcatcc tctaattttc aaaggcaaga agatttgttt accctggaca ccaggcacaa   8400
gtgaggtcac agagctctta gatatgcagt cctcatgagt gaggagacta aagcgcatgc   8460
catcaagact tcagtgtaga gaaaacctcc aaaaaagcct cctcactact tctggaatag   8520
ctcagaggcc gaggcggcct cggcctctgc ataaataaaa aaaattagtc agccatgggg   8580
cggagaatgg gcggaactgg gcggagttag gggcgggatg ggcggagtta ggggcgggac   8640
tatggttgct gactaattga gatgcatgct ttgcatactt ctgcctgctg gggagcctgg   8700
ggactttcca cacctggttg ctgactaatt gagatgcatg ctttgcatac ttctgcctgc   8760
tggggagcct ggggactttc cacaccctaa ctgacacaca ttccacagct gcattaatga   8820
atcggccaac gcgcggggag aggcggtttg cgtattgggc gctcttccgc ttcctcgctc   8880
actgactcgc tgcgctcggt cgttcggctg cggcgagcgg tatcagctca ctcaaaggcg   8940
gtaatacggt tatccacaga atcagggat aacgcaggaa agaacatgtg agcaaaaggc   9000
cagcaaaagg ccaggaaccg taaaaaggcc gcgttgctgg cgtttttcca taggctccgc   9060
cccccctgacg agcatcacaa aaatcgacgc tcaagtcaga ggtggcgaaa cccgacagga   9120
ctataaagat accaggcgtt tccccctgga agctccctcg tgcgctctcc tgttccgacc   9180
ctgccgctta ccggatacct gtccgccttt ctcccttcgg gaagcgtggc gctttctcat   9240
agctcacgct gtaggtatct cagttcggtg taggtcgttc gctccaagct gggctgtgtg   9300
cacgaaccc ccgttcagcc cgaccgctgc gccttatccg gtaactatcg tcttgagtcc   9360
aacccggtaa gacacgactt atcgccactg gcagcagcca ctggtaacag gattagcaga   9420
gcgaggtatg taggcggtgc tacagagttc ttgaagtggt ggcctaacta cggctacact   9480
agaagaacag tatttggtat ctgcgctctg ctgaagccag ttaccttcgg aaaaagagtt   9540
ggtagctctt gatccggcaa acaaaccacc gctggtagcg tggttttttt tgtttgcaag   9600
cagcagatta cgcgcagaaa aaaaggatct caagaagatc ctttgatctt ttctacgggg   9660
tctgacgctc agtggaacga aaactcacgt taagggattt tggtcatgag attatcaaaa   9720
aggatcttca cctagatcct tttaaattaa aaatgaagtt ttaaatcaat ctaaagtata   9780
tatgagtaaa cttggtctga cagttaccaa tgcttaatca gtgaggcacc tatctcagcg   9840
atctgtctat ttcgttcatc catagttgcc tgactccctgc aaaccacgtt gtgtctcaaa   9900
atctctgatg ttacattgca caagataaaa atatatcatc atgaacaata aaactgtctg   9960
cttacataaa cagtaataca aggggtgtta tgagccatat tcaacgggaa acgtcttgct  10020
cgaggccgcg attaaattcc aacatggatg ctgatttata tgggtataaa tgggctcgcg  10080
ataatgtcgg gcaatcaggt gcgacaatct atcgattgta tgggaagccc gatgcgccag  10140
agttgtttct gaaacatggc aaaggtagcg ttgccaatga tgttacagat gagatggtca  10200
gactaaactg gctgacggaa tttatgcctc ttccgaccat caagcatttt atccgtactc  10260
ctgatgatgc atggttactc accactgcga tccccgggaa aacagcattc caggtattag  10320
aagaatatcc tgattcaggt gaaaatattg ttgatgcgct ggcagtgttc ctgcgccggt  10380
```

-continued

```
tgcattcgat tcctgtttgt aattgtcctt ttaacagcga tcgcgtattt cgtctcgctc    10440
aggcgcaatc acgaatgaat aacggtttgg ttgatgcgag tgattttgat gacgagcgta    10500
atggctggcc tgttgaacaa gtctggaaag aaatgcataa gcttttgcca ttctcaccgg    10560
attcagtcgt cactcatggt gatttctcac ttgataacct tattttgac gaggggaaat     10620 taataggttg tattgatgtt ggacgagtcg gaatcgcaga ccgataccag gatcttgcca    10680
tcctatggaa ctgcctcggt gagttttctc cttcattaca gaaacggctt ttcaaaaat    10740 atggtattga taatcctgat atgaataaat tgcagtttca tttgatgctc gatgagtttt    10800
tctaagggcg gcctgccacc ataccacgc cgaaacaagc gctcatgagc ccgaagtggc     10860
gagcccgatc ttccccatcg gtgatgtcgg cgatataggc gccagcaacc gcacctgtgg    10920
cgccggtgat gagggcgcgc caagtcgacg tccggcagtc                          10960
```

<210> SEQ ID NO 14
<211> LENGTH: 536
<212> TYPE: PRT
<213> ORGANISM: Homo sapiens

<400> SEQUENCE: 14

```
Met Glu Phe Ser Ser Pro Ser Arg Glu Glu Cys Pro Lys Pro Leu Ser
1               5                   10                  15

Arg Val Ser Ile Met Ala Gly Ser Leu Thr Gly Leu Leu Leu Leu Gln
                20                  25                  30

Ala Val Ser Trp Ala Ser Gly Ala Arg Pro Cys Ile Pro Lys Ser Phe
            35                  40                  45

Gly Tyr Ser Ser Val Val Cys Val Cys Asn Ala Thr Tyr Cys Asp Ser
        50                  55                  60

Phe Asp Pro Pro Thr Phe Pro Ala Leu Gly Thr Phe Ser Arg Tyr Glu
65                  70                  75                  80

Ser Thr Arg Ser Gly Arg Arg Met Glu Leu Ser Met Gly Pro Ile Gln
                85                  90                  95

Ala Asn His Thr Gly Thr Gly Leu Leu Leu Thr Leu Gln Pro Glu Gln
            100                 105                 110

Lys Phe Gln Lys Val Lys Gly Phe Gly Gly Ala Met Thr Asp Ala Ala
        115                 120                 125

Ala Leu Asn Ile Leu Ala Leu Ser Pro Pro Ala Gln Asn Leu Leu Leu
    130                 135                 140

Lys Ser Tyr Phe Ser Glu Glu Gly Ile Gly Tyr Asn Ile Ile Arg Val
145                 150                 155                 160

Pro Met Ala Ser Cys Asp Phe Ser Ile Arg Thr Tyr Thr Tyr Ala Asp
                165                 170                 175

Thr Pro Asp Asp Phe Gln Leu His Asn Phe Ser Leu Pro Glu Glu Asp
            180                 185                 190

Thr Lys Leu Lys Ile Pro Leu Ile His Arg Ala Leu Gln Leu Ala Gln
        195                 200                 205

Arg Pro Val Ser Leu Leu Ala Ser Pro Trp Thr Ser Pro Thr Trp Leu
    210                 215                 220

Lys Thr Asn Gly Ala Val Asn Gly Lys Gly Ser Leu Lys Gly Gln Pro
225                 230                 235                 240

Gly Asp Ile Tyr His Gln Thr Trp Ala Arg Tyr Phe Val Lys Phe Leu
                245                 250                 255

Asp Ala Tyr Ala Glu His Lys Leu Gln Phe Trp Ala Val Thr Ala Glu
            260                 265                 270
```

Asn Glu Pro Ser Ala Gly Leu Leu Ser Gly Tyr Pro Phe Gln Cys Leu
            275                 280                 285

Gly Phe Thr Pro Glu His Gln Arg Asp Phe Ile Ala Arg Asp Leu Gly
            290                 295                 300

Pro Thr Leu Ala Asn Ser Thr His His Asn Val Arg Leu Leu Met Leu
305                 310                 315                 320

Asp Asp Gln Arg Leu Leu Leu Pro His Trp Ala Lys Val Val Leu Thr
            325                 330                 335

Asp Pro Glu Ala Ala Lys Tyr Val His Gly Ile Ala Val His Trp Tyr
            340                 345                 350

Leu Asp Phe Leu Ala Pro Ala Lys Ala Thr Leu Gly Glu Thr His Arg
            355                 360                 365

Leu Phe Pro Asn Thr Met Leu Phe Ala Ser Glu Ala Cys Val Gly Ser
            370                 375                 380

Lys Phe Trp Glu Gln Ser Val Arg Leu Gly Ser Trp Asp Arg Gly Met
385                 390                 395                 400

Gln Tyr Ser His Ser Ile Ile Thr Asn Leu Leu Tyr His Val Val Gly
            405                 410                 415

Trp Thr Asp Trp Asn Leu Ala Leu Asn Pro Glu Gly Gly Pro Asn Trp
            420                 425                 430

Val Arg Asn Phe Val Asp Ser Pro Ile Ile Val Asp Ile Thr Lys Asp
            435                 440                 445

Thr Phe Tyr Lys Gln Pro Met Phe Tyr His Leu Gly His Phe Ser Lys
450                 455                 460

Phe Ile Pro Glu Gly Ser Gln Arg Val Gly Leu Val Ala Ser Gln Lys
465                 470                 475                 480

Asn Asp Leu Asp Ala Val Ala Leu Met His Pro Asp Gly Ser Ala Val
            485                 490                 495

Val Val Val Leu Asn Arg Ser Ser Lys Asp Val Pro Leu Thr Ile Lys
            500                 505                 510

Asp Pro Ala Val Gly Phe Leu Glu Thr Ile Ser Pro Gly Tyr Ser Ile
            515                 520                 525

His Thr Tyr Leu Trp Arg Arg Gln
            530                 535

<210> SEQ ID NO 15
<211> LENGTH: 1608
<212> TYPE: DNA
<213> ORGANISM: Homo sapiens

<400> SEQUENCE: 15
atggaattca gcagccccag cagagaggaa tgccccaagc ctctgagccg ggtgtcaatc      60
atggccggat ctctgacagg actgctgctg cttcaggccg tgtcttgggc ttctggcgct     120
agaccttgca tccccaagag cttcggctac agcagcgtcg tgtgcgtgtg caatgccacc     180
tactgcgaca gcttcgaccc tcctaccttt cctgctctgg gcaccttcag cagatacgag     240
agcaccagat ccggcagacg gatggaactg agcatgggac ccatccaggc caatcacaca     300
ggcactggcc tgctgctgac actgcagcct gagcagaaat ccagaaagt gaaaggcttc     360 ggcggagcca tgacagatgc cgccgctctg aatatcctgg ctctgtctcc accagctcag     420
aacctgctgc tcaagagcta cttcagcgag gaaggcatcg gctacaacat catcagagtg     480
cccatggcca gctgcgactt cagcatcagg acctacacct acgccgacac acccgacgat     540
ttccagctgc acaacttcag cctgcctgaa gaggacacca gctgaagat ccctctgatc     600

```
cacagagccc tgcagctggc acaaagaccc gtgtcactgc tggcctctcc atggacatct    660
cccacctggc tgaaaacaaa tggcgccgtg aatggcaagg cagcctgaa aggccaacct     720
ggcgacatct accaccagac ctgggccaga tacttcgtga agttcctgga cgcctatgcc    780
gagcacaagc tgcagttttg gccgtgaca gccgagaacg aaccttctgc tggactgctg     840
agcggctacc cctttcagtg cctgggcttt acacccgagc accagcggga cttatcgcc    900
cgtgatctgg gacccacact ggccaatagc acccaccata atgtgcggct gctgatgctg    960
gacgaccaga gactgcttct gccccactgg gctaaagtgg tgctgacaga tcctgaggcc   1020
gccaaatacg tgcacggaat cgccgtgcac tggtatctgg actttctggc cctgccaag    1080
gccacactgg gagagacaca cagactgttc cccaacacca tgctgttcgc cagcgaagcc   1140
tgtgtgggca gcaagttttg ggaacagagc gtgcggctcg gcagctggga tagaggcatg   1200
cagtacagcc acagcatcat caccaacctg ctgtaccacg tcgtcggctg gaccgactgg   1260
aatctggccc tgaatcctga aggcggccct aactgggtcc gaaacttcgt ggacagcccc   1320
atcatcgtgg acatcaccaa ggacaccttc tacaagcagc ccatgttcta ccacctggga   1380
cacttcagca agttcatccc cgagggctct cagcgcgttg gactggtggc ttcccagaag   1440
aacgatctgg acgccgtggc tctgatgcac cctgatggat ctgctgtggt ggtggtcctg   1500
aaccgcagca gcaaagatgt gcccctgacc atcaaggatc cgccgtggg attcctggaa    1560
acaatcagcc ctggctactc catccacacc tacctgtggc gtagacag                1608
```

<210> SEQ ID NO 16
<211> LENGTH: 524
<212> TYPE: PRT
<213> ORGANISM: Homo sapiens

<400> SEQUENCE: 16

```
Met Tyr Ala Leu Phe Leu Leu Ala Ser Leu Leu Gly Ala Ala Leu Ala
1               5                   10                  15

Gly Pro Val Leu Gly Leu Lys Glu Cys Thr Arg Gly Ser Ala Val Trp
            20                  25                  30

Cys Gln Asn Val Lys Thr Ala Ser Asp Cys Gly Ala Val Lys His Cys
        35                  40                  45

Leu Gln Thr Val Trp Asn Lys Pro Thr Val Lys Ser Leu Pro Cys Asp
    50                  55                  60

Ile Cys Lys Asp Val Val Thr Ala Ala Gly Asp Met Leu Lys Asp Asn
65                  70                  75                  80

Ala Thr Glu Glu Glu Ile Leu Val Tyr Leu Glu Lys Thr Cys Asp Trp
                85                  90                  95

Leu Pro Lys Pro Asn Met Ser Ala Ser Cys Lys Glu Ile Val Asp Ser
            100                 105                 110

Tyr Leu Pro Val Ile Leu Asp Ile Ile Lys Gly Glu Met Ser Arg Pro
        115                 120                 125

Gly Glu Val Cys Ser Ala Leu Asn Leu Cys Glu Ser Leu Gln Lys His
    130                 135                 140

Leu Ala Glu Leu Asn His Gln Lys Gln Leu Glu Ser Asn Lys Ile Pro
145                 150                 155                 160

Glu Leu Asp Met Thr Glu Val Val Ala Pro Phe Met Ala Asn Ile Pro
                165                 170                 175

Leu Leu Leu Tyr Pro Gln Asp Gly Pro Arg Ser Lys Pro Gln Pro Lys
            180                 185                 190
```

```
Asp Asn Gly Asp Val Cys Gln Asp Cys Ile Gln Met Val Thr Asp Ile
            195                 200                 205

Gln Thr Ala Val Arg Thr Asn Ser Thr Phe Val Gln Ala Leu Val Glu
210                 215                 220

His Val Lys Glu Glu Cys Asp Arg Leu Gly Pro Gly Met Ala Asp Ile
225                 230                 235                 240

Cys Lys Asn Tyr Ile Ser Gln Tyr Ser Glu Ile Ala Ile Gln Met Met
                245                 250                 255

Met His Met Gln Pro Lys Glu Ile Ala Leu Val Gly Phe Cys Asp
            260                 265                 270

Glu Val Lys Glu Met Pro Met Gln Thr Leu Val Pro Ala Lys Val Ala
            275                 280                 285

Ser Lys Asn Val Ile Pro Ala Leu Glu Leu Val Glu Pro Ile Lys Lys
290                 295                 300

His Glu Val Pro Ala Lys Ser Asp Val Tyr Cys Glu Val Cys Glu Phe
305                 310                 315                 320

Leu Val Lys Glu Val Thr Lys Leu Ile Asp Asn Asn Lys Thr Glu Lys
                325                 330                 335

Glu Ile Leu Asp Ala Phe Asp Lys Met Cys Ser Lys Leu Pro Lys Ser
            340                 345                 350

Leu Ser Glu Glu Cys Gln Val Val Asp Thr Tyr Gly Ser Ser Ile
355                 360                 365

Leu Ser Ile Leu Leu Glu Glu Val Ser Pro Glu Leu Val Cys Ser Met
370                 375                 380

Leu His Leu Cys Ser Gly Thr Arg Leu Pro Ala Leu Thr Val His Val
385                 390                 395                 400

Thr Gln Pro Lys Asp Gly Gly Phe Cys Glu Val Cys Lys Lys Leu Val
                405                 410                 415

Gly Tyr Leu Asp Arg Asn Leu Glu Lys Asn Ser Thr Lys Gln Glu Ile
            420                 425                 430

Leu Ala Ala Leu Glu Lys Gly Cys Ser Phe Leu Pro Asp Pro Tyr Gln
435                 440                 445

Lys Gln Cys Asp Gln Phe Val Ala Glu Tyr Glu Pro Val Leu Ile Glu
450                 455                 460

Ile Leu Val Glu Val Met Asp Pro Ser Phe Val Cys Leu Lys Ile Gly
465                 470                 475                 480

Ala Cys Pro Ser Ala His Lys Pro Leu Leu Gly Thr Glu Lys Cys Ile
                485                 490                 495

Trp Gly Pro Ser Tyr Trp Cys Gln Asn Thr Glu Thr Ala Ala Gln Cys
            500                 505                 510

Asn Ala Val Glu His Cys Lys Arg His Val Trp Asn
515                 520

<210> SEQ ID NO 17
<211> LENGTH: 1572
<212> TYPE: DNA
<213> ORGANISM: Homo sapiens

<400> SEQUENCE: 17
atgtacgccc tgttcctgct ggccagcctg ctgggcgccg ccctggccgg ccccgtgctg    60
ggcctgaagg agtgcacccg cggcagcgcc gtgtggtgcc agaacgtgaa gaccgccagc   120
gactgcggcg ccgtgaagca ctgcctgcag accgtgtgga acaagcccac cgtgaagagc   180
ctgccctgcg acatctgcaa ggacgtggtg accgccgccg cgacatgct gaaggacaac   240
```

```
gccaccgagg aggagatcct ggtgtacctg gagaagacct gcgactggct gcccaagccc      300
aacatgagcg ccagctgcaa ggagatcgtg acagctacc tgcccgtgat cctggacatc      360
atcaagggcg agatgagccg ccccggcgag gtgtgcagcg ccctgaacct gtgcgagagc      420
ctgcagaagc acctggccga gctgaaccac cagaagcagc tggagagcaa caagatcccc      480
gagctggaca tgaccgaggt ggtggccccc ttcatggcca acatcccct gctgctgtac       540 ccccaggacg cccccgcag caagcccag cccaaggaca cggcgacgt gtgccaggac         600 tgcatccaga tggtgaccga catccagacc gccgtgcgca ccaacagcac cttcgtgcag      660
gccctggtgg agcacgtgaa ggaggagtgc gaccgcctgg ccccggcat ggccgacatc      720 tgcaagaact acatcagcca gtacagcgag atcgccatcc agatgatgat gcacatgcag     780
cccaaggaga tctgcgccct ggtgggcttc tgcgacgagg tgaaggagat gcccatgcag     840
accctggtgc ccgccaaggt ggccagcaag aacgtgatcc ccgccctgga gctggtggag    900
cccatcaaga agcacgaggt gcccgccaag agcgacgtgt actgcgaggt gtgcgagttc   960
ctggtgaagg aggtgaccaa gctgatcgac aacaacaaga ccgagaagga gatcctggac  1020
gccttcgaca gatgtgcag caagctgccc aagagcctga gcgaggagtg ccaggaggtg   1080
gtggacacct acggcagcag catcctgagc atcctgctgg aggaggtgag ccccgagctg   1140
gtgtgcagca tgctgcacct gtgcagcggc acccgcctgc ccgccctgac cgtgcacgtg   1200
acccagccca aggacggcgg cttctgcgag gtgtgcaaga gctggtggg ctacctggac    1260 cgcaacctgg agaagaacag caccaagcag gagatcctgg ccgccctgga agggctgc    1320 agcttcctgc ccgaccccta ccagaagcag tgcgaccagt tcgtggccga gtacgagccc   1380
gtgctgatcg agatcctggt ggaggtgatg gaccccagct tcgtgtgcct gaagatcggc   1440
gcctgcccca gcgcccacaa gcccctgctg ggcaccgaga agtgcatctg ggcccccagc   1500
tactggtgcc agaacaccga gaccgccgcc cagtgcaacg ccgtggagca ctgcaagcgc   1560
cacgtgtgga ac                                                        1572
```

<210> SEQ ID NO 18
<211> LENGTH: 478
<212> TYPE: PRT
<213> ORGANISM: Homo sapiens

<400> SEQUENCE: 18

```
Met Gly Arg Cys Cys Phe Tyr Thr Ala Gly Thr Leu Ser Leu Leu Leu
1               5                   10                  15

Leu Val Thr Ser Val Thr Leu Leu Val Ala Arg Val Phe Gln Lys Ala
            20                  25                  30

Val Asp Gln Ser Ile Glu Lys Lys Ile Val Leu Arg Asn Gly Thr Glu
        35                  40                  45

Ala Phe Asp Ser Trp Glu Lys Pro Pro Leu Pro Val Tyr Thr Gln Phe
    50                  55                  60

Tyr Phe Phe Asn Val Thr Asn Pro Glu Glu Ile Leu Arg Gly Glu Thr
65                  70                  75                  80

Pro Arg Val Glu Glu Val Gly Pro Tyr Thr Tyr Arg Glu Leu Arg Asn
                85                  90                  95

Lys Ala Asn Ile Gln Phe Gly Asp Asn Gly Thr Thr Ile Ser Ala Val
            100                 105                 110

Ser Asn Lys Ala Tyr Val Phe Glu Arg Asp Gln Ser Val Gly Asp Pro
        115                 120                 125
```

Lys Ile Asp Leu Ile Arg Thr Leu Asn Ile Pro Val Leu Thr Val Ile
130                 135                 140

Glu Trp Ser Gln Val His Phe Leu Arg Glu Ile Glu Ala Met Leu
145                 150                 155                 160

Lys Ala Tyr Gln Gln Lys Leu Phe Val Thr His Thr Val Asp Glu Leu
                165                 170                 175

Leu Trp Gly Tyr Lys Asp Glu Ile Leu Ser Leu Ile His Val Phe Arg
            180                 185                 190

Pro Asp Ile Ser Pro Tyr Phe Gly Leu Phe Tyr Glu Lys Asn Gly Thr
            195                 200                 205

Asn Asp Gly Asp Tyr Val Phe Leu Thr Gly Glu Asp Ser Tyr Leu Asn
210                 215                 220

Phe Thr Lys Ile Val Glu Trp Asn Gly Lys Thr Ser Leu Asp Trp Trp
225                 230                 235                 240

Ile Thr Asp Lys Cys Asn Met Ile Asn Gly Thr Asp Gly Asp Ser Phe
                245                 250                 255

His Pro Leu Ile Thr Lys Asp Glu Val Leu Tyr Val Phe Pro Ser Asp
            260                 265                 270

Phe Cys Arg Ser Val Tyr Ile Thr Phe Ser Asp Tyr Glu Ser Val Gln
        275                 280                 285

Gly Leu Pro Ala Phe Arg Tyr Lys Val Pro Ala Glu Ile Leu Ala Asn
290                 295                 300

Thr Ser Asp Asn Ala Gly Phe Cys Ile Pro Glu Gly Asn Cys Leu Gly
305                 310                 315                 320

Ser Gly Val Leu Asn Val Ser Ile Cys Lys Asn Gly Ala Pro Ile Ile
                325                 330                 335

Met Ser Phe Pro His Phe Tyr Gln Ala Asp Glu Arg Phe Val Ser Ala
            340                 345                 350

Ile Glu Gly Met His Pro Asn Gln Gly Asp His Glu Thr Phe Val Asp
            355                 360                 365

Ile Asn Pro Leu Thr Gly Ile Ile Leu Lys Ala Ala Lys Arg Phe Gln
370                 375                 380

Ile Asn Ile Tyr Val Lys Lys Leu Asp Asp Phe Val Glu Thr Gly Asp
385                 390                 395                 400

Ile Arg Thr Met Val Phe Pro Val Met Tyr Leu Asn Glu Ser Val His
                405                 410                 415

Ile Asp Lys Glu Thr Ala Ser Arg Leu Lys Ser Met Ile Asn Thr Thr
            420                 425                 430

Leu Ile Ile Thr Asn Ile Pro Tyr Ile Ile Met Ala Leu Gly Val Phe
            435                 440                 445

Phe Gly Leu Val Phe Thr Trp Leu Ala Cys Lys Gly Gln Gly Ser Met
        450                 455                 460

Asp Glu Gly Thr Ala Asp Glu Arg Ala Pro Leu Ile Arg Thr
465                 470                 475

<210> SEQ ID NO 19
<211> LENGTH: 1434
<212> TYPE: DNA
<213> ORGANISM: Homo sapiens

<400> SEQUENCE: 19
atgggccgct gctgcttcta caccgccggc accctgagcc tgctgctgct ggtgaccagc    60
gtgaccctgc tggtggcccg cgtgttccag aaggccgtgg accagagcat cgagaagaag   120

-continued

```
atcgtgctgc gcaacggcac cgaggccttc gacagctggg agaagccccc cctgcccgtg    180
tacacccagt tctacttctt caacgtgacc aaccccgagg agatcctgcg cggcgagacc    240
ccccgcgtgg aggaggtggg ccctacacc taccgcgagc tgcgcaacaa ggccaacatc     300
cagttcggcg acaacggcac caccatcagc gccgtgagca caaggccta cgtgttcgag     360 cgcgaccaga gcgtgggcga ccccaagatc gacctgatcc gcaccctgaa catccccgtg   420
ctgaccgtga tcgagtggag ccaggtgcac ttcctgcgcg agatcatcga ggccatgctg    480
aaggcctacc agcagaagct gttcgtgacc cacaccgtgg acgagctgct gtggggctac    540
aaggacgaga tcctgagcct gatccacgtg ttccgccccg acatcagccc ctacttcggc    600
ctgttctacg agaagaacgg caccaacgac ggcgactacg tgttcctgac cggcgaggac    660
agctacctga acttcaccaa gatcgtggag tggaacggca agaccagcct ggactggtgg    720
atcaccgaca agtgcaacat gatcaacggc accgacggcg acagcttcca ccccctgatc    780
accaaggacg aggtgctgta cgtgttcccc agcgacttct gccgcagcgt gtacatcacc    840
ttcagcgact acgagagcgt gcagggcctg cccgccttcc gctacaaggt gcccgccgag    900
atcctggcca acaccagcga caacgccggc ttctgcatcc ccagggcaa ctgcctgggc     960 agcggcgtgc tgaacgtgag catctgcaag aacggcgccc ccatcatcat gagcttcccc   1020
cacttctacc aggccgacga gcgcttcgtg agcgccatcg agggcatgca ccccaaccag   1080
gaggaccacg agaccttcgt ggacatcaac ccctgaccg catcatcct gaaggccgcc    1140 aagcgcttcc agatcaacat ctacgtgaag aagctggacg acttcgtgga gaccggcgac   1200
atccgcacca tggtgttccc cgtgatgtac ctgaacgaga gcgtgcacat cgacaaggag   1260
accgccagcc gcctgaagag catgatcaac accaccctga tcatcaccaa catcccctac   1320
atcatcatgg ccctgggcgt gttcttcggc ctggtgttca cctggctggc ctgcaagggc   1380
cagggcagca tggacgaggg caccgccgac gagcgcgccc ccctgatccg cacc          1434
```

<210> SEQ ID NO 20
<211> LENGTH: 23
<212> TYPE: DNA
<213> ORGANISM: Artificial sequence
<220> FEATURE:
<223> OTHER INFORMATION: Synthetic polynucleotide

<400> SEQUENCE: 20

```
tggaagactt cgagatacac tgt                                              23
```

<210> SEQ ID NO 21
<211> LENGTH: 23
<212> TYPE: DNA
<213> ORGANISM: Artificial sequence
<220> FEATURE:
<223> OTHER INFORMATION: Synthetic polynucleotide

<400> SEQUENCE: 21

```
acagtgtatc tcgaagtctt cca                                              23
```

<210> SEQ ID NO 22
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 22

```
tttagaaata agtggtagtc a                                                21
```

<210> SEQ ID NO 23
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 23
tgactaccac ttatttctaa a                                     21

<210> SEQ ID NO 24
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 24
agggtatcaa gactacgaa                                        19

<210> SEQ ID NO 25
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 25
ttcgtagtct tgataccct                                        19

<210> SEQ ID NO 26
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 26
tattagatct gatggccgc                                        19

<210> SEQ ID NO 27
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 27
ctccatcact aggggttcct                                       20

<210> SEQ ID NO 28
<211> LENGTH: 60
<212> TYPE: DNA
<213> ORGANISM: Artificial sequence
<220> FEATURE:
<223> OTHER INFORMATION: Synthetic polynucleotide

<400> SEQUENCE: 28
agctctgggt atttaagccc gagtgagcac gcagggtctc catttttgaag cgggaggtta    60

<210> SEQ ID NO 29
<211> LENGTH: 145
<212> TYPE: DNA
<213> ORGANISM: Unknown
<220> FEATURE:

<223> OTHER INFORMATION: AAV2 ITR

<400> SEQUENCE: 29

```
aggaacccct agtgatggag ttggccactc cctctctgcg cgctcgctcg ctcactgagg      60
ccgggcgacc aaaggtcgcc cgacgcccgg gctttgcccg gcggcctca gtgagcgagc      120
gagcgcgcag agagggagtg gccaa                                            145
```

<210> SEQ ID NO 30
<211> LENGTH: 927
<212> TYPE: PRT
<213> ORGANISM: Homo sapiens

<400> SEQUENCE: 30

```
Met Gly Thr Gln Asp Pro Gly Asn Met Gly Thr Gly Val Pro Ala Ser
1               5                   10                  15

Glu Gln Ile Ser Cys Ala Lys Glu Asp Pro Gln Val Tyr Cys Pro Glu
            20                  25                  30

Glu Thr Gly Gly Thr Lys Asp Val Gln Val Thr Asp Cys Lys Ser Pro
        35                  40                  45

Glu Asp Ser Arg Pro Pro Lys Glu Thr Asp Cys Cys Asn Pro Glu Asp
    50                  55                  60

Ser Gly Gln Leu Met Val Ser Tyr Glu Gly Lys Ala Met Gly Tyr Gln
65                  70                  75                  80

Val Pro Pro Phe Gly Trp Arg Ile Cys Leu Ala His Glu Phe Thr Glu
                85                  90                  95

Lys Arg Lys Pro Phe Gln Ala Asn Asn Val Ser Leu Ser Asn Met Ile
            100                 105                 110

Lys His Ile Gly Met Gly Leu Arg Tyr Leu Gln Trp Trp Tyr Arg Lys
        115                 120                 125

Thr His Val Glu Lys Lys Thr Pro Phe Ile Asp Met Ile Asn Ser Val
    130                 135                 140

Pro Leu Arg Gln Ile Tyr Gly Cys Pro Leu Gly Gly Ile Gly Gly Gly
145                 150                 155                 160

Thr Ile Thr Arg Gly Trp Arg Gly Gln Phe Cys Arg Trp Gln Leu Asn
                165                 170                 175

Pro Gly Met Tyr Gln His Arg Thr Val Ile Ala Asp Gln Phe Thr Val
            180                 185                 190

Cys Leu Arg Arg Glu Gly Gln Thr Val Tyr Gln Val Leu Ser Leu
        195                 200                 205

Glu Arg Pro Ser Val Leu Arg Ser Trp Asn Trp Gly Leu Cys Gly Tyr
    210                 215                 220

Phe Ala Phe Tyr His Ala Leu Tyr Pro Arg Ala Trp Thr Val Tyr Gln
225                 230                 235                 240

Leu Pro Gly Gln Asn Val Thr Leu Thr Cys Arg Gln Ile Thr Pro Ile
                245                 250                 255

Leu Pro His Asp Tyr Gln Asp Ser Ser Leu Pro Val Gly Val Phe Val
            260                 265                 270

Trp Asp Val Glu Asn Glu Gly Asp Glu Ala Leu Asp Val Ser Ile Met
        275                 280                 285

Phe Ser Met Arg Asn Gly Leu Gly Gly Asp Asp Ala Pro Gly Gly
    290                 295                 300

Leu Trp Asn Glu Pro Phe Cys Leu Glu Arg Ser Gly Glu Thr Val Arg
305                 310                 315                 320
```

```
Gly Leu Leu Leu His His Pro Thr Leu Pro Asn Pro Tyr Thr Met Ala
            325                 330                 335

Val Ala Ala Arg Val Thr Ala Ala Thr Thr Val Thr His Ile Thr Ala
            340                 345                 350

Phe Asp Pro Asp Ser Thr Gly Gln Gln Val Trp Gln Asp Leu Leu Gln
            355                 360                 365

Asp Gly Gln Leu Asp Ser Pro Thr Gly Gln Ser Thr Pro Thr Gln Lys
            370                 375                 380

Gly Val Gly Ile Ala Gly Ala Val Cys Val Ser Ser Lys Leu Arg Pro
385                 390                 395                 400

Arg Gly Gln Cys Arg Leu Glu Phe Ser Leu Ala Trp Asp Met Pro Arg
            405                 410                 415

Ile Met Phe Gly Ala Lys Gly Gln Val His Tyr Arg Arg Tyr Thr Arg
            420                 425                 430

Phe Phe Gly Gln Asp Gly Asp Ala Ala Pro Ala Leu Ser His Tyr Ala
            435                 440                 445

Leu Cys Arg Tyr Ala Glu Trp Glu Arg Ile Ser Ala Trp Gln Ser
            450                 455                 460

Pro Val Leu Asp Asp Arg Ser Leu Pro Ala Trp Tyr Lys Ser Ala Leu
465                 470                 475                 480

Phe Asn Glu Leu Tyr Phe Leu Ala Asp Gly Gly Thr Val Trp Leu Glu
            485                 490                 495

Val Leu Glu Asp Ser Leu Pro Glu Glu Leu Gly Arg Asn Met Cys His
            500                 505                 510

Leu Arg Pro Thr Leu Arg Asp Tyr Gly Arg Phe Gly Tyr Leu Glu Gly
            515                 520                 525

Gln Glu Tyr Arg Met Tyr Asn Thr Tyr Asp Val His Phe Tyr Ala Ser
            530                 535                 540

Phe Ala Leu Ile Met Leu Trp Pro Lys Leu Glu Leu Ser Leu Gln Tyr
545                 550                 555                 560

Asp Met Ala Leu Ala Thr Leu Arg Glu Asp Leu Thr Arg Arg Arg Tyr
            565                 570                 575

Leu Met Ser Gly Val Met Ala Pro Val Lys Arg Arg Asn Val Ile Pro
            580                 585                 590

His Asp Ile Gly Asp Pro Asp Glu Pro Trp Leu Arg Val Asn Ala
            595                 600                 605

Tyr Leu Ile His Asp Thr Ala Asp Trp Lys Asp Leu Asn Leu Lys Phe
            610                 615                 620

Val Leu Gln Val Tyr Arg Asp Tyr Tyr Leu Thr Gly Asp Gln Asn Phe
625                 630                 635                 640

Leu Lys Asp Met Trp Pro Val Cys Leu Ala Val Met Glu Ser Glu Met
            645                 650                 655

Lys Phe Asp Lys Asp His Asp Gly Leu Ile Glu Asn Gly Gly Tyr Ala
            660                 665                 670

Asp Gln Thr Tyr Asp Gly Trp Val Thr Thr Gly Pro Ser Ala Tyr Cys
            675                 680                 685

Gly Gly Leu Trp Leu Ala Ala Val Ala Val Met Val Gln Met Ala Ala
            690                 695                 700

Leu Cys Gly Ala Gln Asp Ile Gln Asp Lys Phe Ser Ser Ile Leu Ser
705                 710                 715                 720

Arg Gly Gln Glu Ala Tyr Glu Arg Leu Leu Trp Asn Gly Arg Tyr Tyr
            725                 730                 735
```

| | | | | | | | | | | | |
|---|---|---|---|---|---|---|---|---|---|---|---|
| Asn | Tyr | Asp | Ser | Ser | Arg | Pro | Gln | Ser | Arg | Ser | Val | Met | Ser | Asp |
| | | | 740 | | | | 745 | | | | 750 | | | |
| Gln | Cys | Ala | Gly | Gln | Trp | Phe | Leu | Lys | Ala | Cys | Gly | Leu | Gly | Glu | Gly |
| | | 755 | | | | | 760 | | | | | 765 | | | |
| Asp | Thr | Glu | Val | Phe | Pro | Thr | Gln | His | Val | Val | Arg | Ala | Leu | Gln | Thr |
| 770 | | | | | | 775 | | | | | 780 | | | | |
| Ile | Phe | Glu | Leu | Asn | Val | Gln | Ala | Phe | Ala | Gly | Gly | Ala | Met | Gly | Ala |
| 785 | | | | | 790 | | | | | 795 | | | | | 800 |
| Val | Asn | Gly | Met | Gln | Pro | His | Gly | Val | Pro | Asp | Lys | Ser | Ser | Val | Gln |
| | | | | 805 | | | | | 810 | | | | | 815 | |
| Ser | Asp | Glu | Val | Trp | Val | Gly | Val | Val | Tyr | Gly | Leu | Ala | Ala | Thr | Met |
| | | | 820 | | | | | 825 | | | | | 830 | | |
| Ile | Gln | Glu | Gly | Leu | Thr | Trp | Glu | Gly | Phe | Gln | Thr | Ala | Glu | Gly | Cys |
| | | | 835 | | | | | 840 | | | | | 845 | | |
| Tyr | Arg | Thr | Val | Trp | Glu | Arg | Leu | Gly | Leu | Ala | Phe | Gln | Thr | Pro | Glu |
| | | 850 | | | | | 855 | | | | | 860 | | | |
| Ala | Tyr | Cys | Gln | Gln | Arg | Val | Phe | Arg | Ser | Leu | Ala | Tyr | Met | Arg | Pro |
| 865 | | | | | 870 | | | | | 875 | | | | | 880 |
| Leu | Ser | Ile | Trp | Ala | Met | Gln | Leu | Ala | Leu | Gln | Gln | Gln | Gln | His | Lys |
| | | | | 885 | | | | | 890 | | | | | 895 | |
| Lys | Ala | Ser | Trp | Pro | Lys | Val | Lys | Gln | Gly | Thr | Gly | Leu | Arg | Thr | Gly |
| | | | | 900 | | | | | 905 | | | | | 910 | |
| Pro | Met | Phe | Gly | Pro | Lys | Glu | Ala | Met | Ala | Asn | Leu | Ser | Pro | Glu | |
| | | | 915 | | | | | 920 | | | | | 925 | | |

<210> SEQ ID NO 31
<211> LENGTH: 2781
<212> TYPE: DNA
<213> ORGANISM: Homo sapiens

<400> SEQUENCE: 31

| | | |
|---|---|---|
| atgggcaccc aggaccccgg caacatgggc accggcgtgc cgccagcga gcagatcagc | 60 |
| tgcgccaagg aggaccccca ggtgtactgc cccgaggaga ccggcggcac caaggacgtg | 120 |
| caggtgaccg actgcaagag ccccgaggac agccgccccc ccaaggagac cgactgctgc | 180 |
| aaccccgagg acagcggcca gctgatggtg agctacgagg caaggccat gggctaccag | 240 |
| gtgccccct cggctggcg catctgcctg gcccacgagt tcaccgagaa gcaagccc | 300 |
| ttccaggcca caacgtgag cctgagcaac atgatcaagc acatcggcat gggcctgcgc | 360 |
| tacctgcagt ggtggtaccg caagacccac gtggagaaga gaccccctt catcgacatg | 420 |
| atcaacagcg tgccctgcg ccagatctac ggctgccccc tgggcggcat cggcggcggc | 480 |
| accatcaccc gcggctggcg cggccagttc tgccgctggc agctgaaccc cggcatgtac | 540 |
| cagcaccgca ccgtgatcgc cgaccagttc accgtgtgcc tgcgccgcga gggccagacc | 600 |
| gtgtaccagc aggtgctgag cctggagcgc ccagcgtgc tgcgcagctg gaactggggc | 660 |
| ctgtgcggct acttcgcctt ctaccacgcc ctgtaccccc gcgcctggac cgtgtaccag | 720 |
| ctgcccggcc agaacgtgac cctgacctgc cgccagatca cccccatcct gccccacgac | 780 |
| taccaggaca gcagcctgcc cgtgggcgtg ttcgtgtggg acgtggagaa cgagggcgac | 840 |
| gaggccctgg acgtgagcat catgttcagc atgcgcaacg gcctgggcgg cggcgacgac | 900 |
| gcccccggcg cctgtggaa cgagcccttc tgcctggagc gcagcggcga ccgtgcgc | 960 |
| ggcctgctgc tgcaccaccc cacccctgccc aaccctaca ccatggccgt ggccgccgc | 1020 |
| gtgaccgccg ccaccaccgt gacccacatc accgccttcg accccgacag caccggccag | 1080 |

```
caggtgtggc aggacctgct gcaggacggc cagctggaca gccccaccgg ccagagcacc    1140
cccacccaga agggcgtggg catcgccggc gccgtgtgcg tgagcagcaa gctgcgcccc    1200
cgcggccagt gccgcctgga gttcagcctg gcctgggaca tgccccgcat catgttcggc    1260
gccaagggcc aggtgcacta ccgccgctac acccgcttct tcggccagga cggcgacgcc    1320
gcccccgccc tgagccacta cgccctgtgc cgctacgccg agtgggagga gcgcatcagc    1380
gcctggcaga gccccgtgct ggacgaccgc agcctgcccg cctggtacaa gagcgccctg    1440
ttcaacgagc tgtacttcct ggccgacggc ggcaccgtgt ggctggaggt gctggaggac    1500
agcctgcccg aggagctggg ccgcaacatg tgccacctgc gccccaccct gcgcgactac    1560
ggccgcttcg gctacctgga gggccaggag taccgcatgt acaacaccta cgacgtgcac    1620
ttctacgcca gcttcgccct gatcatgctg tggcccaagc tggagctgag cctgcagtac    1680
gacatggccc tggccaccct gcgcgaggac ctgacccgcc gccgctacct gatgagcggc    1740
gtgatggccc ccgtgaagcg ccgcaacgtg atccccacg acatcggcga ccccgacgac    1800
gagccctggc tgcgcgtgaa cgcctacctg atccacgaca ccgccgactg aaggacctg    1860 aacctgaagt tcgtgctgca ggtgtaccgc gactactacc tgaccggcga ccagaacttc    1920
ctgaaggaca tgtggcccgt gtgcctggcc gtgatggaga gcgagatgaa gttcgacaag    1980
gaccacgacg gcctgatcga gaacggcggc tacgccgacc agacctacga cggctgggtg    2040
accaccggcc ccagcgccta ctgcggcggc ctgtggctgg ccgccgtggc cgtgatggtg    2100
cagatggccg ccctgtgcgg cgcccaggac atccaggaca gttcagcag catcctgagc    2160 cgcggccagg aggcctacga cgcctgctgt ggaacggcc gctactacaa ctacgacagc    2220
agcagccgcc cccagagccg cagcgtgatg agcgaccagt gcgccggcca gtggttcctg    2280
aaggcctgcg gcctgggcga gggcgacacc gaggtgttcc ccacccagca cgtggtgcgc    2340
gccctgcaga ccatcttcga gctgaacgtg caggccttcg ccggcggcgc catgggcgcc    2400
gtgaacggca tgcagcccca cggcgtgccc gacaagagca gcgtgcagag cgacgaggtg    2460
tgggtgggcg tggtgtacgg cctggccgcc accatgatcc aggagggcct gacctgggag    2520
ggcttccaga ccgccgaggg ctgctaccgc accgtgtggg agcgcctggg cctggccttc    2580 cagaccccg aggcctactg ccagcagcgc gtgttccgca gcctggccta catgcgcccc    2640
ctgagcatct gggccatgca gctggccctg cagcagcagc agcacaagaa ggccagctgg    2700
cccaaggtga gcagggcac cggcctgcgc accggcccca tgttcggccc caaggaggcc    2760
atggccaacc tgagccccga g                                             2781

<210> SEQ ID NO 32
<211> LENGTH: 11264
<212> TYPE: DNA
<213> ORGANISM: Artificial sequence
<220> FEATURE:
<223> OTHER INFORMATION: Synthetic polynucleotide

<400> SEQUENCE: 32
ttggccactc cctctctgcg cgctcgctcg ctcactgagg ccgggcgacc aaaggtcgcc      60
cgacgcccgg gctttgcccg gcggcctca gtgagcgagc gagcgcgcag agagggagtg     120
gccaactcca tcactagggg ttcctgctag ctctgggtat ttaagcccga gtgagcacgc     180
agggtctcca ttttgaagcg ggaggttacg cgttcgtcga ctactagtgg gtaccagagc     240
tccctaggtt ctagaaccgg tgacgtctcc catggtgaag cttggatctg agtaagtcac     300
```

```
tgactgtcta tgcctgggaa agggtgggca ggagatgggg cagtgcagga aaagtggcac    360
tatgaaccct cctggtggcg aggggagggg ggtggtcctc gaacgccttg cagaactggc    420
ctggatacag agtggaccgg ctggccccat ctggaagact tcgagataca ctgttgtctt    480
actgcgctca acagtgtatc tcgaagtctt ccaaatggtg ccagccatcg cagcggggtg    540
caggaaatgg gggcagcccc ccttttttggc tatccttcca cgtgttcttt tttgtatctt    600
ttgtgttttcc tagaaaacat ctcagtcacc accgcagccc taggaatgca tctagacaat    660
tgtactaacc ttcttctctt tcctctcctg acagtccgga aagccaccat gggcacccag    720
gaccccggca acatgggcac cggcgtgccc gccagcgagc agatcagctg cgccaaggag    780
gacccccagg tgtactgccc cgaggagacc ggcggcacca aggacgtgca ggtgaccgac    840
tgcaagagcc ccgaggacag ccgccccccc aaggagaccg actgctgcaa ccccgaggac    900
agcggccagc tgatggtgag ctacgagggc aaggccatgg gctaccaggt gcccccttc    960
ggctggcgca tctgcctggc ccacgagttc accgagaagc gcaagccctt ccaggccaac   1020
aacgtgagcc tgagcaacat gatcaagcac atcggcatgg gcctgcgcta cctgcagtgg   1080
tggtaccgca agacccacgt ggagaagaag acccccttca tcgacatgat caacagcgtg   1140
cccctgcgcc agatctacgg ctgccccctg ggcggcatcg gcggcggcac catcacccgc   1200
ggctggcgcg gccagttctg ccgctggcag ctgaaccccg gcatgtacca gcaccgcacc   1260
gtgatcgccg accagttcac cgtgtgcctg cgccgcgagg ccagaccgt gtaccagcag   1320
gtgctgagcc tggagcgccc cagcgtgctg cgcagctgga actggggcct gtgcggctac   1380
ttcgccttct accacgccct gtaccccgc gcctggaccg tgtaccagct gcccggccag   1440
aacgtgaccc tgacctgccg ccagatcacc cccatcctgc ccacgacta ccaggacagc   1500
agcctgcccg tgggcgtgtt cgtgtgggac gtggagaacg agggcgacga ggccctggac   1560
gtgagcatca tgttcagcat gcgcaacggc ctgggcggcg gcgacgacgc cccccggcggc   1620
ctgtggaacg agcccttctg cctggagcgc agcggcgaga ccgtgcgcgg cctgctgctg   1680
caccacccca ccctgcccaa ccctacacc atggccgtgg ccgcccgcgt gaccgccgcc   1740
accaccgtga cccacatcac cgccttcgac cccgacagca ccggccagca ggtgtggcag   1800
gacctgctgc aggacggcca gctggacagc cccaccggcc agagcacccc cacccagaag   1860
ggcgtgggca tcgccggcgc cgtgtgcgtg agcagcaagc tgcgccccg cggccagtgc   1920
cgcctggagt tcagcctggc ctgggacatg ccccgcatca tgttcggcgc caagggccag   1980
gtgcactacc gccgctacac ccgcttcttc ggccaggacg gcgacgccgc ccccgccctg   2040
agccactacg ccctgtgccg ctacgccgag tgggaggagc gcatcagcgc ctggcagagc   2100
cccgtgctgg acgaccgcag cctgcccgcc tggtacaaga gcgccctgtt caacgagctg   2160
tacttcctgg ccgacggcgg caccgtgtgg ctggaggtgc tggaggacag cctgcccgag   2220
gagctgggcc gcaacatgtg ccacctgcgc cccaccctgc gcgactacgg ccgcttcggc   2280
tacctggagg gccaggagta ccgcatgtac aacacctacg acgtgcactt ctacgccagc   2340
ttcgccctga tcatgctgtg gcccaagctg agctgagcc tgcagtacga catggccctg   2400
gccaccctgc gcgaggacct gaccgccgcc gctacctga tgagcggcgt gatggccccc   2460
gtgaagcgcc gcaacgtgat ccccacgac atcggcgacc ccgacgacga gccctggctg   2520
cgcgtgaacg cctacctgat ccacgacacc gccgactgga aggacctgaa cctgaagttc   2580
gtgctgcagg tgtaccgcga ctactacctg accggcgacc agaacttcct gaaggacatg   2640
tggccccgtgt gcctggccgt gatggagagc gagatgaagt tcgacaagga ccacgacggc   2700
```

```
ctgatcgaga acggcggcta cgccgaccag acctacgacg gctgggtgac caccggcccc    2760
agcgcctact gcggcggcct gtggctggcc gccgtggccg tgatggtgca gatggccgcc    2820
ctgtgcggcg cccaggacat ccaggacaag ttcagcagca tcctgagccg cggccaggag    2880
gcctacgagc gcctgctgtg aacggccgc tactacaact acgacagcag cagccgcccc     2940
cagagccgca gcgtgatgag cgaccagtgc gccggccagt ggttcctgaa ggcctgcggc    3000
ctgggcgagg gcgacaccga ggtgttcccc acccagcacg tggtgcgcgc cctgcagacc    3060
atcttcgagc tgaacgtgca ggccttcgcc ggcggcgcca tgggcgccgt gaacggcatg    3120
cagccccacg gcgtgcccga caagagcagc gtgcagagcg acgaggtgtg ggtgggcgtg    3180
gtgtacggcc tggccgccac catgatccag gagggcctga cctgggaggg cttccagacc    3240
gccgagggct gctaccgcac cgtgtgggag cgcctgggcc tggccttcca gacccccgag    3300
gcctactgcc agcagcgcgt gttccgcagc ctggcctaca tgcgcccccct gagcatctgg    3360
gccatgcagc tggccctgca gcagcagcag cacaagaagg ccagctggcc caaggtgaag    3420
cagggcaccg gcctgcgcac cggccccatg ttcggcccca aggaggccat ggccaacctg    3480
agccccgagt gacaattgtt aattaagttt aaaccctcga ggccgcaagc ttatcgataa    3540
tcaacctctg gattacaaaa tttgtgaaag attgactggt attcttaact atgttgctcc    3600
ttttacgcta tgtggatacg ctgctttaat gcctttgtat catgctattg cttcccgtat    3660
ggctttcatt ttctcctcct tgtataaatc ctggttgctg tctctttatg aggagttgtg    3720
gcccgttgtc aggcaacgtg gcgtggtgtg cactgtgttt gctgacgcaa cccccactgg    3780
ttggggcatt gccaccacct gtcagctcct ttccgggact ttcgctttcc ccctccctat    3840
tgccacggcg gaactcatcg ccgcctgcct tgcccgctgc tggacagggg ctcggctgtt    3900
gggcactgac aattccgtgg tgttgtcggg gaaatcatcg tcctttcctt ggctgctcgc    3960
ctgtgttgcc acctggattc tgcgcgggac gtccttctgc tacgtccctt cggccctcaa    4020
tccagcggac cttccttccc gcggcctgct gccggctctg cggcctcttc cgcgtcttcg    4080
ccttcgccct cagacgagtc ggatctccct ttgggccgcc tccccgcatc gataccgtcg    4140
actagagctc gctgatcagc ctcgactgtg ccttctagtt gccagccatc tgttgtttgc    4200
ccctcccccg tgccttcctt gaccctggaa ggtgccactc ccactgtcct ttcctaataa    4260
aatgaggaaa ttgcatcgca ttgtctgagt aggtgtcatt ctattctggg gggtggggtg    4320
gggcaggaca gcaaggggga ggattgggaa gacaatagca ggcatgctgg ggagagatcc    4380
acgataacaa acagcttttt tggggtgaac atattgactg aattccctgc aggttggcca    4440
ctccctctct gcgcgctcgc tcgctcactg aggccgcccg ggcaaagccc gggcgtcggg    4500
cgacctttgg tcgcccggcc tcagtgagcg agcgagcgcg cagagaggga gtggccaact    4560
ccatcactag gggttcctgc ggccgctcgt acggtctcga ggaattcctg caggataact    4620
tgccaacctc attctaaaat gtatatagaa gcccaaaaga caataacaaa atattcttg     4680
tagaacaaaa tgggaaagaa tgttccacta aatatcaaga tttagagcaa agcatgagat    4740
gtgtggggat agacagtgag gctgataaaa tagagtagag ctcagaaaca gacccattga    4800
tatatgtaag tgacctatga aaaaaatatg gcattttaca atgggaaaat gatggtcttt    4860
ttcttttttta gaaaacagg gaaatatatt tatatgtaaa aataaaagg gaacccatat     4920
gtcataccat acacacaaaa aaattccagt gaattataag tctaaatgga gaaggcaaaa    4980
ctttaaatct tttagaaaat aatatagaag catgcagacc agcctggcca acatgatgaa    5040
```

```
accctctcta ctaataataa aatcagtaga actactcagg actactttga gtgggaagtc    5100
cttttctatg aagacttctt tggccaaaat taggctctaa atgcaaggag atagtgcatc    5160
atgcctggct gcacttactg ataaatgatg ttatcaccat ctttaaccaa atgcacagga    5220
acaagttatg gtactgatgt gctggattga gaaggagctc tacttccttg acaggacaca    5280
tttgtatcaa cttaaaaaag cagattttg ccagcagaac tattcattca gaggtaggaa     5340
acttagaata gatgatgtca ctgattagca tggcttcccc atctccacag ctgcttccca    5400
cccaggttgc ccacagttga gtttgtccag tgctcagggc tgcccactct cagtaagaag    5460
ccccacacca gccctctcc aaatatgttg gctgttcctt ccattaaagt gaccccactt      5520
tagagcagca agtggatttc tgtttcttac agttcaggaa ggaggagtca gctgtgagaa    5580
cctggagcct gagatgcttc taagtccac tgctactggg gtcagggaag ccagactcca     5640
gcatcagcag tcaggagcac taagcccttg ccaacatcct gtttctcaga gaaactgctt    5700
ccattataat ggttgtcctt ttttaagcta tcaagccaaa caaccagtgt ctaccattat    5760
tctcatcacc tgaagccaag ggttctagca aaagtcaagc tgtcttgtaa tggttgatgt    5820
gcctccagct tctgtcttca gtcactccac tcttagcctg ctctgaatca actctgacca    5880
cagttccctg gagcccctgc cacctgctgc ccctgccacc ttctccatct gcagtgctgt    5940
gcagccttct gcactcttgc agagctaata ggtggagact tgaaggaaga ggaggaaagt    6000
ttctcataat agccttgctg caagctcaaa tgggaggtgg gcactgtgcc caggagcctt    6060
ggagcaaagg ctgtgcccaa cctctgactg catccaggtt tggtcttgac agagataaga    6120
agccctggct tttggagcca aaatctaggt cagacttagg caggattctc aaagtttatc    6180
agcagaacat gaggcagaag acccttctg ctccagcttc ttcaggctca accttcatca     6240
gaatagatag aaagagaggc tgtgagggtt cttaaaacag aagcaaatct gactcagaga    6300
ataaacaacc tcctagtaaa ctacagctta gacagagcat ctggtggtga gtgtgctcag    6360
tgtcctactc aactgtctgg tatcagccct catgaggact tctcttcttt ccctcataga    6420
cctccatctc tgttttcctt agcctgcaga atctggatg gctattcaca gaatgcctgt     6480
gctttcagag ttgcattttt tctctggtat tctggttcaa gcatttgaag gtaggaaagg    6540
ttctccaagt gcaagaaagc cagccctgag cctcaactgc ctggctagtg tggtcagtag    6600
gatgcaaagg ctgttgaatg ccacaaggcc aaactttaac ctgtgtacca caagcctagc    6660
agcagaggca gctctgctca ctggaactct ctgtcttctt tctcctgagc cttttctttt    6720
cctgagtttt ctagctctcc tcaaccttac ctctgcccta cccaggacaa acccaagagc    6780
cactgtttct gtgatgtcct ctccagccct aattaggcat catgacttca gcctgaccct    6840
ccatgctcag aagcagtgct aatccacttc agatgagctg ctctatgcaa cacaggcaga    6900
gcctacaaac cttttgcacca gagccctcca catatcagtg tttgttcata ctcacttcaa    6960
cagcaaatgt gactgctgag attaagattt tacacaagat ggtctgtaat ttcacagtta    7020
gttttatccc attaggtatg aaagaattag cataattccc cttaaacatg aatgaatctt    7080
agatttttta ataaatagtt ttggaagtaa agacagagac atcaggagca caaggaatag    7140
cctgagagga caaacagaac aagaaagagt ctggaaatac acaggatgtt cttggcctcc    7200
tcaaagcaag tgcaagcaga tagtaccagc agcccaggc tatcagagcc cagtgaagag     7260
aagtaccatg aaagccacag ctctaaccac cctgttccag agtgacagac agtccccaag    7320
acaagccagc ctgagccaga gagaactg caagagaaag tttctaattt aggttctgtt      7380
agattcagac aagtgcaggt catcctctct ccacagctac tcacctctcc agcctaacaa    7440
```

```
agcctgcagt ccacactcca accctggtgt ctcacctcct agcctctccc aacatcctgc   7500
tctctgacca tcttctgcat ctctcatctc accatctccc actgtctaca gcctactctt   7560
gcaactacca tctcattttc tgacatcctg tctacatctt ctgccatact ctgccatcta   7620
ccataccacc tcttaccatc taccacacca tcttttatct ccatccctct cagaagcctc   7680
caagctgaat cctgctttat gtgttcatct cagcccctgc atggaaagct gaccccagag   7740
gcagaactat tcccagagag cttggccaag aaaaacaaaa ctaccagcct ggccaggctc   7800
aggagtagta agctgcagtg tctgttgtgt tctagcttca acagctgcag gagttccact   7860
ctcaaatgct ccacatttct cacatcctcc tgattctggt cactaccat cttcaaagaa   7920 cagaatatct cacatcagca tactgtgaag gactagtcat gggtgcagct gctcagagct   7980
gcaaagtcat tctggatggt ggagagctta caaacatttc atgatgctcc ccccgctctg   8040
atggctggag cccaatccct acacagactc ctgctgtatg tgttttcctt tcactctgag   8100
ccacagccag agggcaggca ttcagtctcc tcttcaggct ggggctgggg cactgagaac   8160
tcacccaaca ccttgctctc actccttctg caaaacaaga aagagctttg tgctgcagta   8220
gccatgaaga atgaaaggaa ggctttaact aaaaaatgtc agagattatt ttcaacccct   8280
tactgtggat caccagcaag gaggaaacac aacacagaga catttttttcc cctcaaatta   8340 tcaaaagaat cactgcattt gttaaagaga gcaactgaat caggaagcag agttttgaac   8400
atatcagaag ttaggaatct gcatcagaga caaatgcagt catggttgtt tgctgcatac   8460
cagccctaat cattagaagc ctcatggact tcaaacatca ttccctctga caagatgctc   8520
tagcctaact ccatgagata aaataaatct gcctttcaga gccaagaag agtccaccag   8580 cttcttctca gtgtgaacaa gagctccagt caggttagtc agtccagtgc agtagaggag   8640
accagtctgc atcctctaat tttcaaaggc aagaagattt gtttaccctg acaccaggc   8700 acaagtgagg tcacagagct cttagatatg cagtcctcat gagtgaggag actaaagcgc   8760
atgccatcaa gacttcagtg tagagaaaac ctccaaaaaa gcctcctcac tacttctgga   8820
atagctcaga ggccgaggcg gcctcggcct ctgcataaat aaaaaaaatt agtcagccat   8880
ggggcggaga atgggcggaa ctgggcggag ttaggggcgg gatgggcgga gttaggggcg   8940
ggactatggt tgctgactaa ttgagatgca tgctttgcat acttctgcct gctggggagc   9000
ctggggactt tccacacctg gttgctgact aattgagatg catgctttgc atacttctgc   9060
ctgctgggga gcctggggac tttccacacc ctaactgaca cacattccac agctgcatta   9120
atgaatcggc caacgcgcgg ggagaggcgg tttgcgtatt gggcgctctt ccgcttcctc   9180
gctcactgac tcgctgcgct cggtcgttcg gctgcggcga gcggtatcag ctcactcaaa   9240
ggcggtaata cggttatcca cagaatcagg ggataacgca ggaaagaaca tgtgagcaaa   9300
aggccagcaa aaggccagga accgtaaaaa ggccgcgttg ctggcgtttt tccataggct   9360 ccgccccct gacgagcatc acaaaaatcg acgctcaagt cagaggtggc gaaacccgac   9420
aggactataa agataccagg cgtttccccc tggaagctcc ctcgtgcgct ctcctgttcc   9480
gaccctgccg cttaccggat acctgtccgc ctttctccct tcgggaagcg tggcgctttc   9540
tcatagctca cgctgtaggt atctcagttc ggtgtaggtc gttcgctcca agctgggctg   9600
tgtgcacgaa ccccccgttc agcccgaccg ctgcgcctta tccggtaact atcgtcttga   9660
gtccaacccg gtaagacacg acttatcgcc actggcagca gccactggta acaggattag   9720
cagagcgagg tatgtaggcg gtgctacaga gttcttgaag tggtggccta actacggcta   9780
```

| | |
|---|---|
| cactagaaga acagtatttg gtatctgcgc tctgctgaag ccagttacct tcggaaaaag | 9840 |
| agttggtagc tcttgatccg gcaaacaaac caccgctggt agcggtggtt tttttgtttg | 9900 |
| caagcagcag attacgcgca gaaaaaagg atctcaagaa gatcctttga tcttttctac | 9960 |
| ggggtctgac gctcagtgga acgaaaactc acgttaaggg attttggtca tgagattatc | 10020 |
| aaaaggatc ttcacctaga tccttttaaa ttaaaatga agttttaaat caatctaaag | 10080 |
| tatatatgag taaacttggt ctgacagtta ccaatgctta atcagtgagg cacctatctc | 10140 |
| agcgatctgt ctatttcgtt catccatagt tgcctgactc ctgcaaacca cgttgtgtct | 10200 |
| caaaatctct gatgttacat tgcacaagat aaaaatatat catcatgaac aataaaactg | 10260 |
| tctgcttaca taaacagtaa tacaaggggt gttatgagcc atattcaacg ggaaacgtct | 10320 |
| tgctcgaggc cgcgattaaa ttccaacatg gatgctgatt tatatgggta taaatgggct | 10380 |
| cgcgataatg tcgggcaatc aggtgcgaca atctatcgat tgtatgggaa gcccgatgcg | 10440 |
| ccagagttgt ttctgaaaca tggcaaaggt agcgttgcca atgatgttac agatgagatg | 10500 |
| gtcagactaa actggctgac ggaatttatg cctcttccga ccatcaagca ttttatccgt | 10560 |
| actcctgatg atgcatggtt actcaccact gcgatccccg ggaaaacagc attccaggta | 10620 |
| ttagaagaat atcctgattc aggtgaaaat attgttgatg cgctggcagt gttcctgcgc | 10680 |
| cggttgcatt cgattcctgt ttgtaattgt ccttttaaca gcgatcgcgt atttcgtctc | 10740 |
| gctcaggcgc aatcacgaat gaataacggt ttggttgatg cgagtgattt tgatgacgag | 10800 |
| cgtaatggct ggcctgttga caagtctgg aaagaaatgc ataagctttt gccattctca | 10860 |
| ccggattcag tcgtcactca tggtgatttc tcacttgata accttatttt tgacgagggg | 10920 |
| aaattaatag gttgtattga tgttggacga gtcggaatcg cagaccgata ccaggatctt | 10980 |
| gccatcctat ggaactgcct cggtgagttt tctccttcat tacagaaacg ctttttcaa | 11040 |
| aaatatggta ttgataatcc tgatatgaat aaattgcagt ttcatttgat gctcgatgag | 11100 |
| ttttttctaag gcggcctgc caccataccc acgccgaaac aagcgctcat gagcccgaag | 11160 |
| tggcgagccc gatcttcccc atcggtgatg tcggcgatat aggcgccagc aaccgcacct | 11220 |
| gtggcgccgg tgatgagggc gcgccaagtc gacgtccggc agtc | 11264 |

<210> SEQ ID NO 33
<211> LENGTH: 685
<212> TYPE: PRT
<213> ORGANISM: Artificial sequence
<220> FEATURE:
<223> OTHER INFORMATION: Synthetic polypeptide

<400> SEQUENCE: 33

```
Met Ala Glu Trp Leu Leu Ser Ala Ser Trp Gln Arg Arg Ala Lys Ala
1               5                   10                  15

Met Thr Ala Ala Ala Gly Ser Ala Gly Arg Ala Val Pro Leu Leu
            20                  25                  30

Leu Cys Ala Leu Leu Ala Pro Gly Gly Ala Tyr Val Leu Asp Asp Ser
        35                  40                  45

Asp Gly Leu Gly Arg Glu Phe Asp Gly Ile Gly Ala Val Ser Gly Gly
    50                  55                  60

Gly Ala Thr Ser Arg Leu Leu Val Asn Tyr Pro Glu Pro Tyr Arg Ser
65                  70                  75                  80

Gln Ile Leu Asp Tyr Leu Phe Lys Pro Asn Phe Gly Ala Ser Leu His
                85                  90                  95
```

-continued

Ile Leu Lys Val Glu Ile Gly Gly Asp Gly Gln Thr Thr Asp Gly Thr
            100                 105                 110

Glu Pro Ser His Met His Tyr Ala Leu Asp Glu Asn Tyr Phe Arg Gly
            115                 120                 125

Tyr Glu Trp Trp Leu Met Lys Glu Ala Lys Lys Arg Asn Pro Asn Ile
        130                 135                 140

Thr Leu Ile Gly Leu Pro Trp Ser Phe Pro Gly Trp Leu Gly Lys Gly
145                 150                 155                 160

Phe Asp Trp Pro Tyr Val Asn Leu Gln Leu Thr Ala Tyr Tyr Val Val
                165                 170                 175

Thr Trp Ile Val Gly Ala Lys Arg Tyr His Asp Leu Asp Ile Asp Tyr
            180                 185                 190

Ile Gly Ile Trp Asn Glu Arg Ser Tyr Asn Ala Asn Tyr Ile Lys Ile
        195                 200                 205

Leu Arg Lys Met Leu Asn Tyr Gln Gly Leu Gln Arg Val Lys Ile Ile
    210                 215                 220

Ala Ser Asp Asn Leu Trp Glu Ser Ile Ser Ala Ser Met Leu Leu Asp
225                 230                 235                 240

Ala Glu Leu Phe Lys Val Val Asp Val Ile Gly Ala His Tyr Pro Gly
                245                 250                 255

Thr His Ser Ala Lys Asp Ala Lys Leu Thr Gly Lys Lys Leu Trp Ser
            260                 265                 270

Ser Glu Asp Phe Ser Thr Leu Asn Ser Asp Met Gly Ala Gly Cys Trp
        275                 280                 285

Gly Arg Ile Leu Asn Gln Asn Tyr Ile Asn Gly Tyr Met Thr Ser Thr
    290                 295                 300

Ile Ala Trp Asn Leu Val Ala Ser Tyr Tyr Glu Gln Leu Pro Tyr Gly
305                 310                 315                 320

Arg Cys Gly Leu Met Thr Ala Gln Glu Pro Trp Ser Gly His Tyr Val
                325                 330                 335

Val Glu Ser Pro Val Trp Val Ser Ala His Thr Thr Gln Phe Thr Gln
            340                 345                 350

Pro Gly Trp Tyr Tyr Leu Lys Thr Val Gly His Leu Glu Lys Gly Gly
        355                 360                 365

Ser Tyr Val Ala Leu Thr Asp Gly Leu Gly Asn Leu Thr Ile Ile Ile
    370                 375                 380

Glu Thr Met Ser His Lys His Ser Lys Cys Ile Arg Pro Phe Leu Pro
385                 390                 395                 400

Tyr Phe Asn Val Ser Gln Gln Phe Ala Thr Phe Val Leu Lys Gly Ser
                405                 410                 415

Phe Ser Glu Ile Pro Glu Leu Gln Val Trp Tyr Thr Leu Leu Gly Lys
            420                 425                 430

Thr Ser Glu Arg Phe Leu Phe Lys Gln Leu Asp Ser Leu Trp Leu Leu
        435                 440                 445

Asp Ser Asp Gly Ser Phe Thr Leu Ser Leu His Glu Asp Glu Leu Phe
    450                 455                 460

Thr Leu Thr Thr Leu Thr Thr Gly Arg Lys Gly Ser Tyr Pro Leu Pro
465                 470                 475                 480

Pro Lys Ser Gln Pro Phe Pro Ser Thr Tyr Lys Asp Phe Asn Val
                485                 490                 495

Asp Tyr Pro Phe Phe Ser Glu Ala Pro Asn Phe Ala Asp Gln Thr Gly
            500                 505                 510

```
Val Phe Glu Tyr Phe Thr Asn Ile Glu Asp Pro Gly Glu His His Phe
        515                 520                 525

Thr Leu Arg Gln Val Leu Asn Gln Arg Pro Ile Thr Trp Ala Ala Asp
        530                 535                 540

Ala Ser Asn Thr Ile Ser Ile Ile Gly Asp Tyr Asn Trp Thr Asn Leu
545                 550                 555                 560

Thr Ile Lys Cys Asp Val Tyr Ile Glu Thr Pro Asp Thr Gly Gly Val
                565                 570                 575

Phe Ile Ala Gly Arg Val Asn Lys Gly Ile Leu Ile Arg Ser Ala
            580                 585                 590

Arg Gly Ile Phe Phe Trp Ile Phe Ala Asn Gly Ser Tyr Arg Val Thr
        595                 600                 605

Gly Asp Leu Ala Gly Trp Ile Ile Tyr Ala Leu Gly Arg Val Glu Val
        610                 615                 620

Thr Ala Lys Lys Trp Tyr Thr Leu Thr Leu Thr Ile Lys Gly His Phe
625                 630                 635                 640

Thr Ser Gly Met Leu Asn Asp Lys Ser Leu Trp Thr Asp Ile Pro Val
                645                 650                 655

Asn Phe Pro Lys Asn Gly Trp Ala Ala Ile Gly Thr His Ser Phe Glu
            660                 665                 670

Phe Ala Gln Phe Asp Asn Phe Leu Val Glu Ala Thr Arg
        675                 680                 685

<210> SEQ ID NO 34
<211> LENGTH: 2055
<212> TYPE: DNA
<213> ORGANISM: Artificial sequence
<220> FEATURE:
<223> OTHER INFORMATION: Synthetic polynucleotide

<400> SEQUENCE: 34
atggccgagt ggctgctgag cgccagctgg cagcgccgcg ccaaggccat gaccgccgcc        60
gccggcagcg ccggccgcgc cgccgtgccc ctgctgctgt gcgccctgct ggcccccggc       120
ggcgcctacg tgctggacga cagcgacggc ctgggccgcg agttcgacgg catcggcgcc       180
gtgagcggcg gcggcgccac cagccgcctg ctggtgaact ccccgagcc ctaccgcagc        240
cagatcctgg actacctgtt caagcccaac ttcggcgcca gcctgcacat cctgaaggtg       300
gagatcggcg cgacggcca gaccaccgac ggcaccgagc cagccacat gcactacgcc         360
ctggacgaga actacttccg cggctacgag tggtggctga tgaaggaggc caagaagcgc       420
aacccccaaca tcaccctgat cggcctgccc tggagcttcc ccggctggct gggcaagggc      480
ttcgactggc cctacgtgaa cctgcagctg accgcctact acgtggtgac ctggatcgtg      540
ggcgccaagc gctaccacga cctggacatc gactacatcg gcatctggaa cgagcgcagc      600
tacaacgcca actacatcaa gatcctgcgc aagatgctga actaccaggg cctgcagcgc      660
gtgaagatca tcgccagcga caacctgtgg gagagcatca cgccagcat gctgctggac      720
gccgagctgt tcaaggtggt ggacgtgatc ggcgcccact accccggcac ccacagcgcc     780
aaggacgcca agctgaccgg caagaagctg tggagcagcg aggacttcag cacccctgaac     840
agcgacatgg gcgccggctg ctggggccgc atcctgaacc agaactacat caacggctac      900
atgaccagca ccatcgcctg gaacctggtg gccagctact acgagcagct gccctacggc      960
cgctgcggcc tgatgaccgc ccaggagccc tggagcggcc actacgtggt ggagagcccc     1020
gtgtgggtga gcgcccacac cacccagttc acccagcccg gctggtacta cctgaagacc     1080
```

```
gtgggccacc tggagaaggg cggcagctac gtggccctga ccgacggcct gggcaacctg    1140
accatcatca tcgagaccat gagccacaag cacagcaagt gcatccgccc cttcctgccc    1200
tacttcaacg tgagccagca gttcgccacc ttcgtgctga agggcagctt cagcgagatc    1260
cccgagctgc aggtgtggta caccaagctg ggcaagacca gcgagcgctt cctgttcaag    1320
cagctggaca gcctgtggct gctggacagc gacggcagct tcaccctgag cctgcacgag    1380
gacgagctgt tcaccctgac cacccgtacc accggccgca agggcagcta ccccctgccc    1440
cccaagagcc agcccttccc cagcacctac aaggacgact caacgtgga ctacccctc     1500 ttcagcgagg cccccaactt cgccgaccag accggcgtgt cgagtactt caccaacatc    1560 gaggaccccg cgagcacca cttcaccctg cgccaggtgc tgaaccagcg ccccatcacc    1620
tgggccgccg acgccagcaa caccatcagc atcatcggcg actacaactg gaccaacctg    1680
accatcaagt gcgacgtgta catcgagacc cccgacaccg gcggcgtgtt catcgccggc    1740
cgcgtgaaca agggcggcat cctgatccgc agcgcccgcg gcatcttctt ctggatcttc    1800
gccaacggca gctaccgcgt gaccggcgac ctggccggct ggatcatcta cgccctgggc    1860
cgcgtggagg tgaccgccaa gaagtggtac accctgaccc tgaccatcaa gggccacttc    1920
accagcggca tgctgaacga caagagcctg tggaccgaca tccccgtgaa cttccccaag    1980
aacggctggg ccgccatcgg caccacagc ttcgagttcg cccagttcga caacttcctg    2040
gtggaggcca cccgc                                                     2055
```

<210> SEQ ID NO 35
<211> LENGTH: 339
<212> TYPE: PRT
<213> ORGANISM: Artificial sequence
<220> FEATURE:
<223> OTHER INFORMATION: Synthetic polypeptide

<400> SEQUENCE: 35

```
Met Trp Gln Leu Trp Ala Ser Leu Cys Cys Leu Leu Val Leu Ala Asn
1               5                   10                  15

Ala Arg Ser Arg Pro Ser Phe His Pro Leu Ser Asp Glu Leu Val Asn
            20                  25                  30

Tyr Val Asn Lys Arg Asn Thr Thr Trp Gln Ala Gly His Asn Phe Tyr
        35                  40                  45

Asn Val Asp Met Ser Tyr Leu Lys Arg Leu Cys Gly Thr Phe Leu Gly
    50                  55                  60

Gly Pro Lys Pro Pro Gln Arg Val Met Phe Thr Glu Asp Leu Lys Leu
65                  70                  75                  80

Pro Ala Ser Phe Asp Ala Arg Glu Gln Trp Pro Gln Cys Pro Thr Ile
                85                  90                  95

Lys Glu Ile Arg Asp Gln Gly Ser Cys Gly Ser Cys Trp Ala Phe Gly
            100                 105                 110

Ala Val Glu Ala Ile Ser Asp Arg Ile Cys Ile His Thr Asn Ala His
        115                 120                 125

Val Ser Val Glu Val Ser Ala Glu Asp Leu Leu Thr Cys Cys Gly Ser
    130                 135                 140

Met Cys Gly Asp Gly Cys Asn Gly Gly Tyr Pro Ala Glu Ala Trp Asn
145                 150                 155                 160

Phe Trp Thr Arg Lys Gly Leu Val Ser Gly Gly Leu Tyr Glu Ser His
                165                 170                 175

Val Gly Cys Arg Pro Tyr Ser Ile Pro Pro Cys Glu His His Val Asn
            180                 185                 190
```

Gly Ser Arg Pro Pro Cys Thr Gly Glu Gly Asp Thr Pro Lys Cys Ser
            195                 200                 205

Lys Ile Cys Glu Pro Gly Tyr Ser Pro Thr Tyr Lys Gln Asp Lys His
    210                 215                 220

Tyr Gly Tyr Asn Ser Tyr Ser Val Ser Asn Ser Glu Lys Asp Ile Met
225                 230                 235                 240

Ala Glu Ile Tyr Lys Asn Gly Pro Val Glu Gly Ala Phe Ser Val Tyr
                245                 250                 255

Ser Asp Phe Leu Leu Tyr Lys Ser Gly Val Tyr Gln His Val Thr Gly
            260                 265                 270

Glu Met Met Gly Gly His Ala Ile Arg Ile Leu Gly Trp Gly Val Glu
            275                 280                 285

Asn Gly Thr Pro Tyr Trp Leu Val Ala Asn Ser Trp Asn Thr Asp Trp
        290                 295                 300

Gly Asp Asn Gly Phe Phe Lys Ile Leu Arg Gly Gln Asp His Cys Gly
305                 310                 315                 320

Ile Glu Ser Glu Val Val Ala Gly Ile Pro Arg Thr Asp Gln Tyr Trp
                325                 330                 335

Glu Lys Ile

<210> SEQ ID NO 36
<211> LENGTH: 1017
<212> TYPE: DNA
<213> ORGANISM: Artificial sequence
<220> FEATURE:
<223> OTHER INFORMATION: Synthetic polynucleotide

<400> SEQUENCE: 36

```
atgtggcagc tgtgggccag cctgtgctgc ctgctggtgc tggccaacgc ccgcagccgc    60
cccagcttcc accccctgag cgacgagctg gtgaactacg tgaacaagcg caacaccacc   120
tggcaggccg ccacaacttt ctacaacgtg gacatgagct acctgaagcg cctgtgcggc   180
accttcctgg cggccccaa gcccccccag cgcgtgatgt tcaccgagga cctgaagctg   240
cccgccagct cgacgcccg cgagcagtgg ccccagtgcc ccaccatcaa ggagatccgc   300
gaccagggca gctgcggcag ctgctgggcc ttcggcgccg tggaggccat cagcgaccgc   360
atctgcatcc acaccaacgc ccacgtgagc gtggaggtga cgccgaggga cctgctgacc   420
tgctgcggca gcatgtgcgg cgacggctgc aacggcggct accccgccga ggcctggaac   480
ttctggaccc gcaagggcct ggtgagcggc ggcctgtacg agagccacgt gggctgccgc   540
ccctacagca tcccccctg cgagcaccac gtgaacggca gccgcccccc ctgcaccggc   600
gagggcgaca cccccaagtg cagcaagatc tgcgagcccg gctacagccc cacctacaag   660
caggacaagc actacggcta caacagctac agcgtgagca cagcgagaa ggacatcatg   720
gccgagatct acaagaacgg ccccgtggag ggcgccttca gcgtgtacag cgacttcctg   780
ctgtacaaga gcggcgtgta ccagcacgtg accggcgaga tgatgggcgg ccacgccatc   840
cgcatcctgg gctggggcgt ggagaacggc acccctact ggctggtggc caacagctgg   900
aacaccgact ggggcgacaa cggcttcttc aagatcctgc gcggccagga ccactgcggc   960
atcgagagcg aggtggtggc cggcatcccc cgcaccgacc agtactggga gaagatc    1017
```

<210> SEQ ID NO 37
<211> LENGTH: 631
<212> TYPE: PRT
<213> ORGANISM: Artificial sequence
<220> FEATURE:
<223> OTHER INFORMATION: Synthetic polypeptide

<400> SEQUENCE: 37

```
Met Pro Arg Tyr Gly Ala Ser Leu Arg Gln Ser Cys Pro Arg Ser Gly
1               5                   10                  15

Arg Glu Gln Gly Gln Asp Gly Thr Ala Gly Ala Pro Gly Leu Leu Trp
            20                  25                  30

Met Gly Leu Val Leu Ala Leu Ala Leu Ala Leu Ala Leu Ala Leu Ala
        35                  40                  45

Leu Ser Asp Ser Arg Val Leu Trp Ala Pro Ala Glu Ala His Pro Leu
    50                  55                  60

Ser Pro Gln Gly His Pro Ala Arg Leu His Arg Ile Val Pro Arg Leu
65                  70                  75                  80

Arg Asp Val Phe Gly Trp Gly Asn Leu Thr Cys Pro Ile Cys Lys Gly
                85                  90                  95

Leu Phe Thr Ala Ile Asn Leu Gly Leu Lys Lys Glu Pro Asn Val Ala
            100                 105                 110

Arg Val Gly Ser Val Ala Ile Lys Leu Cys Asn Leu Leu Lys Ile Ala
        115                 120                 125

Pro Pro Ala Val Cys Gln Ser Ile Val His Leu Phe Glu Asp Asp Met
    130                 135                 140

Val Glu Val Trp Arg Arg Ser Val Leu Ser Pro Ser Glu Ala Cys Gly
145                 150                 155                 160

Leu Leu Leu Gly Ser Thr Cys Gly His Trp Asp Ile Phe Ser Ser Trp
                165                 170                 175

Asn Ile Ser Leu Pro Thr Val Pro Lys Pro Pro Lys Pro Pro Ser
            180                 185                 190

Pro Pro Ala Pro Gly Ala Pro Val Ser Arg Ile Leu Phe Leu Thr Asp
        195                 200                 205

Leu His Trp Asp His Asp Tyr Leu Glu Gly Thr Asp Pro Asp Cys Ala
    210                 215                 220

Asp Pro Leu Cys Cys Arg Arg Gly Ser Gly Leu Pro Pro Ala Ser Arg
225                 230                 235                 240

Pro Gly Ala Gly Tyr Trp Gly Glu Tyr Ser Lys Cys Asp Leu Pro Leu
                245                 250                 255

Arg Thr Leu Glu Ser Leu Leu Ser Gly Leu Gly Pro Ala Gly Pro Phe
            260                 265                 270

Asp Met Val Tyr Trp Thr Gly Asp Ile Pro Ala His Asp Val Trp His
        275                 280                 285

Gln Thr Arg Gln Asp Gln Leu Arg Ala Leu Thr Thr Val Thr Ala Leu
    290                 295                 300

Val Arg Lys Phe Leu Gly Pro Val Pro Val Tyr Pro Ala Val Gly Asn
305                 310                 315                 320

His Glu Ser Thr Pro Val Asn Ser Phe Pro Pro Phe Ile Glu Gly
                325                 330                 335

Asn His Ser Ser Arg Trp Leu Tyr Glu Ala Met Ala Lys Ala Trp Glu
            340                 345                 350

Pro Trp Leu Pro Ala Glu Ala Leu Arg Thr Leu Arg Ile Gly Gly Phe
        355                 360                 365

Tyr Ala Leu Ser Pro Tyr Pro Gly Leu Arg Leu Ile Ser Leu Asn Met
    370                 375                 380

Asn Phe Cys Ser Arg Glu Asn Phe Trp Leu Leu Ile Asn Ser Thr Asp
385                 390                 395                 400
```

```
Pro Ala Gly Gln Leu Gln Trp Leu Val Gly Glu Leu Gln Ala Ala Glu
                405                 410                 415

Asp Arg Gly Asp Lys Val His Ile Ile Gly His Ile Pro Gly His
            420                 425                 430

Cys Leu Lys Ser Trp Ser Trp Asn Tyr Tyr Arg Ile Val Ala Arg Tyr
            435                 440                 445

Glu Asn Thr Leu Ala Ala Gln Phe Phe Gly His Thr His Val Asp Glu
        450                 455                 460

Phe Glu Val Phe Tyr Asp Glu Thr Leu Ser Arg Pro Leu Ala Val
465                 470                 475                 480

Ala Phe Leu Ala Pro Ser Ala Thr Thr Tyr Ile Gly Leu Asn Pro Gly
                485                 490                 495

Tyr Arg Val Tyr Gln Ile Asp Gly Asn Tyr Ser Gly Ser Ser His Val
            500                 505                 510

Val Leu Asp His Glu Thr Tyr Ile Leu Asn Leu Thr Gln Ala Asn Ile
        515                 520                 525

Pro Gly Ala Ile Pro His Trp Gln Leu Leu Tyr Arg Ala Arg Glu Thr
    530                 535                 540

Tyr Gly Leu Pro Asn Thr Leu Pro Thr Ala Trp His Asn Leu Val Tyr
545                 550                 555                 560

Arg Met Arg Gly Asp Met Gln Leu Phe Gln Thr Phe Trp Phe Leu Tyr
                565                 570                 575

His Lys Gly His Pro Pro Ser Glu Pro Cys Gly Thr Pro Cys Arg Leu
            580                 585                 590

Ala Thr Leu Cys Ala Gln Leu Ser Ala Arg Ala Asp Ser Pro Ala Leu
        595                 600                 605

Cys Arg His Leu Met Pro Asp Gly Ser Leu Pro Glu Ala Gln Ser Leu
    610                 615                 620

Trp Pro Arg Pro Leu Phe Cys
625                 630

<210> SEQ ID NO 38
<211> LENGTH: 1896
<212> TYPE: DNA
<213> ORGANISM: Artificial sequence
<220> FEATURE:
<223> OTHER INFORMATION: Synthetic polynucleotide

<400> SEQUENCE: 38
atgccccgct acggcgccag cctgcgccag agctgccccc gcagcggccg cgagcagggc        60
caggacggca ccgccggcgc ccccggcctg ctgtggatgg gcctggtgct ggccctggcc       120
ctggccctgg ccctggccct ggccctgagc gacagccgcg tgctgtgggc ccccgccgag       180
gcccaccccc tgagccccca gggccacccc gcccgcctgc accgcatcgt gccccgcctg       240
cgcgacgtgt tcggctgggg caacctgacc tgccccatct gcaagggcct gttcaccgcc       300
atcaacctgg gcctgaagaa ggagcccaac gtggcccgcg tgggcagcgt ggccatcaag       360
ctgtgcaacc tgctgaagat cgcccccccc gccgtgtgcc agagcatcgt gcacctgttc       420
gaggacgaca tggtggaggt gtggcgccgc agcgtgctga gcccagcga ggcctgcggc        480 ctgctgctgg gcagcacctg cggccactgg gacatcttca gcagctggaa catcagcctg       540
cccaccgtgc ccaagccccc ccccaagccc ccagccccc cgccccggg cgccccgtg         600 agccgcatcc tgttcctgac cgacctgcac tgggaccacg actacctgga gggcaccgac       660
cccgactgcg ccgacccccct gtgctgccgc cgcggcagcg gcctgccccc cgccagccgc       720
```

| | |
|---|---|
| cccggcgccg gctactgggg cgagtacagc aagtgcgacc tgcccctgcg caccctggag | 780 |
| agcctgctga gcggcctggg ccccgccggc cccttcgaca tggtgtactg gaccggcgac | 840 |
| atccccgccc acgacgtgtg gcaccagacc cgccaggacc agctgcgcgc cctgaccacc | 900 |
| gtgaccgccc tggtgcgcaa gttcctgggc ccgtgccg tgtaccccgc cgtgggcaac | 960 |
| cacgagagca cccccgtgaa cagcttcccc ccccccttca tcgagggcaa ccacagcagc | 1020 |
| cgctggctgt acgaggccat ggccaaggcc tgggagccct ggctgccgc cgaggccctg | 1080 |
| cgcaccctgc gcatcggcgg cttctacgcc ctgagcccct accccggcct cgcctgatc | 1140 |
| agcctgaaca tgaacttctg cagccgcgag aacttctggc tgctgatcaa cagcaccgac | 1200 |
| cccgccggcc agctgcagtg gctggtgggc gagctgcagg ccgccgagga ccgcggcgac | 1260 |
| aaggtgcaca tcatcggcca catcccccc ggccactgcc tgaagagctg gagctggaac | 1320 |
| tactaccgca tcgtggcccg ctacgagaac accctggccg cccagttctt cggccacacc | 1380 |
| cacgtggacg agttcgaggt gttctacgac gaggagaccc tgagccgccc cctggccgtg | 1440 |
| gccttcctgg cccccagcgc caccacctac atcggcctga accccggcta ccgcgtgtac | 1500 |
| cagatcgacg caactacag cggcagcagc cacgtggtgc tggaccacga gacctacatc | 1560 |
| ctgaacctga cccaggccaa catccccggc gccatccccc actggcagct gctgtaccgc | 1620 |
| gcccgcgaga cctacggcct gcccaacacc ctgcccaccg cctggcacaa cctggtgtac | 1680 |
| cgcatgcgcg gcgacatgca gctgttccag accttctggt tcctgtacca caagggccac | 1740 |
| cccccccagcg agccctgcgg caccccctgc cgcctggcca cctgtgcgc ccagctgagc | 1800 |
| gcccgcgccg acagccccgc cctgtgccgc cacctgatgc ccgacggcag cctgcccgag | 1860 |
| gcccagagcc tgtggccccg ccccctgttc tgctaa | 1896 |

<210> SEQ ID NO 39
<211> LENGTH: 11329
<212> TYPE: DNA
<213> ORGANISM: Artificial sequence
<220> FEATURE:
<223> OTHER INFORMATION: Synthetic polynucleotide

<400> SEQUENCE: 39

| | |
|---|---|
| ttggccactc cctctctgcg cgctcgctcg ctcactgagg ccgggcgacc aaaggtcgcc | 60 |
| cgacgcccgg gctttgcccg gcggcctca gtgagcgagc gagcgcgcag agagggagtg | 120 |
| gccaactcca tcactagggg ttcctgctag ctctgggtat ttaagcccga gtgagcacgc | 180 |
| agggtctcca ttttgaagcg ggaggttacg cgttcgtcga ctactagtgg gtaccagagc | 240 |
| tccctaggtt ctagaaccgg tgacgtctcc catggtgaag cttggatctg agggcggagt | 300 |
| tagggcggag ccaatcagcg tgcgccgttc cgaaagttgc cttttatggc tgggcggaga | 360 |
| atgggcggtg aacgccgatg attatataag gacgcgccgg gtgtggcaca gctagttccg | 420 |
| tcgcagccgg gatttgggtc gcggttcttg tttgtggatc cctgtgatcg tcacttggta | 480 |
| agtcactgac tgtctatgcc tgggaagggg tgggcaggag atgggcagt gcaggaaaag | 540 |
| tggcactatg aaccctgcag ccctaggaat gcatctagac aattgtacta accttcttct | 600 |
| cttcctctc ctgacagtcc ggaaagccac catggaattc agcagcccca gcagagagga | 660 |
| atgcccaag cctctgagcc gggtgtcaat catggccgga tctctgacag gactgctgct | 720 |
| gcttcaggcc gtgtcttggg cttctggcgc tagaccttgc atcccaaga gcttcggcta | 780 |
| cagcagcgtc gtgtgcgtgt gcaatgccac ctactgcgac agcttcgacc ctcctacctt | 840 |

```
tcctgctctg ggcaccttca gcagatacga gagcaccaga tccggcagac ggatggaact    900
gagcatggga cccatccagg ccaatcacac aggcactggc ctgctgctga cactgcagcc    960
tgagcagaaa ttccagaaag tgaaaggctt cggcggagcc atgacagatg ccgccgctct   1020
gaatatcctg gctctgtctc caccagctca gaacctgctg ctcaagagct acttcagcga   1080
ggaaggcatc ggctacaaca tcatcagagt gcccatggcc agctgcgact tcagcatcag   1140
gacctacacc tacgccgaca cacccgacga tttccagctg cacaacttca gcctgcctga   1200
agaggacacc aagctgaaga tccctctgat ccacagagcc ctgcagctgg cacaaagacc   1260
cgtgtcactg ctggcctctc catggacatc tcccacctgg ctgaaaacaa atggcgccgt   1320
gaatggcaag ggcagcctga aggccaacct ggcgacatc taccaccaga cctgggccag   1380
atacttcgtg aagttcctgg acgcctatgc cgagcacaag ctgcagtttt gggccgtgac   1440
agccgagaac gaaccttctg ctggactgct gagcggctac ccctttcagt gcctgggctt   1500
tacacccgag caccagcggg actttatcgc ccgtgatctg ggaccacac tggccaatag   1560
cacccaccat aatgtgcggc tgctgatgct ggacgaccag agactgcttc tgccccactg   1620
ggctaaagtg gtgctgacag atcctgaggc cgccaaatac gtgcacggaa tcgccgtgca   1680
ctggtatctg gactttctgg cccctgccaa ggccacactg ggagagacac acagactgtt   1740
ccccaacacc atgctgttcg ccagcgaagc ctgtgtgggc agcaagtttt gggaacagag   1800
cgtgcggctc ggcagctggg atagaggcat gcagtacagc cacagcatca tcaccaacct   1860
gctgtaccac gtcgtcggct ggaccgactg gaatctggcc ctgaatcctg aaggcggccc   1920
taactgggtc cgaaacttcg tggacagccc catcatcgtg gacatcacca aggacacctt   1980
ctacaagcag cccatgttct accacctggg acacttcagc aagttcatcc ccgagggctc   2040
tcagcgcgtt ggactggtgg cttcccagaa gaacgatctg gacgccgtgg ctctgatgca   2100
ccctgatgga tctgctgtgg tggtggtcct gaaccgcagc agcaaagatg tgcccctgac   2160
catcaaggat cccgccgtgg gattcctgga acaatcagc cctggctact ccatccacac   2220
ctacctgtgg cgtagacagg agggcagagg aagtcttctg acatgcggag acgtggaaga   2280
gaatcccggc cctatggccg agtggctgct gagcgccagc tggcagcgcc gcgccaaggc   2340
catgaccgcc gccgccggca gcgccggccg cgccgccgtg cccctgctgc tgtgcgccct   2400
gctggccccc ggcggcgcct acgtgctgga cgacagcgac ggcctgggcc gcgagttcga   2460
cggcatcggc gccgtgagcg gcggcggcgc caccagccgc ctgctggtga actaccccga   2520
gccctaccgc agccagatcc tggactacct gttcaagccc aacttcggcg ccagcctgca   2580
catcctgaag gtggagatcg gcgcgacgg ccagaccacc gacggcaccg agcccagcca   2640
catgcactac gccctggacg agaactactt ccgcggctac gagtggtggc tgatgaagga   2700
ggccaagaag cgcaaccccca acatcaccct gatcggcctg ccctggagct tccccggctg   2760
gctgggcaag ggcttcgact ggcccctacgt gaacctgcag ctgaccgcct actacgtggt   2820
gacctggatc gtgggcgcca gcgctacca cgacctggac atcgactaca tcggcatctg   2880
gaacgagcgc agctacaacg ccaactacat caagatcctg cgcaagatgc tgaactacca   2940
gggcctgcag cgcgtgaaga tcatcgccag cgacaacctg tggagagca tcagcgcagc   3000
catgctgctg gacgccgagc tgttcaaggt ggtggacgtg atcggcgccc actaccccgg   3060
cacccacagc gccaaggacg ccaagctgac cggcaagaag ctgtggagca gcgaggactt   3120
cagcaccctg aacagcgaca tgggcgccgg ctgctgggc gcatcctga accagaacta   3180
catcaacggc tacatgacca gcaccatcgc ctggaacctg gtggccagct actacgagca   3240
```

```
gctgccctac ggccgctgcg gcctgatgac cgcccaggag ccctggagcg gccactacgt   3300
ggtggagagc cccgtgtggg tgagcgccca caccacccag ttcacccagc ccggctggta   3360
ctacctgaag accgtgggcc acctggagaa gggcggcagc tacgtggccc tgaccgacgg   3420
cctgggcaac ctgaccatca tcatcgagac catgagccac aagcacagca agtgcatccg   3480 cccttcctg ccctacttca acgtgagcca gcagttcgcc accttcgtgc tgaagggcag   3540
cttcagcgag atccccgagc tgcaggtgtg gtacaccaag ctgggcaaga ccagcgagcg   3600
cttcctgttc aagcagctgg acagcctgtg gctgctggac agcgacggca gcttcaccct   3660
gagcctgcac gaggacgagc tgttcaccct gaccaccctg accaccggcc gcaagggcag   3720
ctaccccctg ccccccaaga gccagccctt cccagcacc tacaaggacg acttcaacgt   3780
ggactacccc ttcttcagcg aggccccaa cttcgccgac cagaccggcg tgttcgagta   3840
cttcaccaac atcgaggacc ccggcgagca ccacttcacc ctgcgccagg tgctgaacca   3900
gcgccccatc acctgggccg ccgacgcag caacaccatc agcatcatcg gcgactacaa   3960
ctggaccaac ctgaccatca agtgcgacgt gtacatcgag accccgaca ccggcggcgt   4020 gttcatcgcc ggccgcgtga acaagggcgg catcctgatc cgcagcgccc gcggcatctt   4080
cttctggatc ttcgccaacg gcagctaccg cgtgaccggc gacctggccg gctggatcat   4140
ctacgccctg ggccgcgtgg aggtgaccgc caagaagtgg tacaccctga ccctgaccat   4200
caagggccac ttcaccagcg gcatgctgaa cgacaagagc ctgtggaccg acatccccgt   4260
gaacttcccc aagaacggct gggccgccat cggcacccac agcttcgagt tcgcccagtt   4320
cgacaacttc ctggtggagg ccacccgctg acaattgtta attaagttta aaccctcgag   4380
gccgcaagca ataaaatatc tttattttca ttacatctgt gtgttggttt tttgtgtgga   4440
gatccacgat aacaaacagc ttttttgggg tgaacatatt gactgaattc cctgcaggtt   4500
ggccactccc tctctgcgcg ctcgctcgct cactgaggcc gcccgggcaa agcccgggcg   4560
tcgggcgacc tttggtcgcc cggcctcagt gagcgagcga gcgcgcagag agggagtggc   4620
caactccatc actaggggtt cctgcggccg ctcgtacggt ctcgaggaat tcctgcagga   4680
taacttgcca acctcattct aaaatgtata tagaagccca aaagacaata acaaaaatat   4740
tcttgtagaa caaaatggga aagaatgttc cactaaatat caagatttag agcaaagcat   4800
gagatgtgtg gggatagaca gtgaggctga taaaatagag tagagctcag aaacagaccc   4860
attgatatat gtaagtgacc tatgaaaaaa atatggcatt ttacaatggg aaaatgatgg   4920 tcttttttctt ttttagaaaa acaggaaat atatttat gtaaaaaata aagggaacc   4980 catatgtcat accatacaca caaaaaaatt ccagtgaatt ataagtctaa atggagaagg   5040
caaaacttta aatctttag aaaataatat agaagcatgc agaccagcct ggccaacatg   5100
atgaaaccct ctctactaat aataaaatca gtagaactac tcaggactac tttgagtggg   5160
aagtcctttt ctatgaagac ttctttggcc aaaattaggc tctaaatgca aggagatagt   5220
gcatcatgcc tggctgcact tactgataaa tgatgttatc accatcttta accaaatgca   5280
caggaacaag ttatggtact gatgtgctgg attgagaagg agctctactt ccttgacagg   5340
acacatttgt atcaacttaa aaagcagat ttttgccagc agaactattc attcagaggt   5400
aggaaactta gaatagatga tgtcactgat tagcatggct tccccatctc cacagctgct   5460
tcccacccag gttgcccaca gttgagtttg tccagtgctc agggctgccc actctcagta   5520
agaagcccca caccagcccc tctccaaata tgttggctgt tccttccatt aaagtgaccc   5580
```

```
cactttagag cagcaagtgg atttctgttt cttacagttc aggaaggagg agtcagctgt    5640
gagaacctgg agcctgagat gcttctaagt cccactgcta ctggggtcag ggaagccaga    5700
ctccagcatc agcagtcagg agcactaagc ccttgccaac atcctgtttc tcagagaaac    5760
tgcttccatt ataatggttg tccttttta agctatcaag ccaaacaacc agtgtctacc    5820
attattctca tcacctgaag ccaagggttc tagcaaaagt caagctgtct tgtaatggtt    5880
gatgtgcctc cagcttctgt cttcagtcac tccactctta gcctgctctg aatcaactct    5940
gaccacagtt ccctggagcc cctgccacct gctgccctg ccaccttctc catctgcagt     6000
gctgtgcagc cttctgcact cttgcagagc taataggtgg agacttgaag gaagaggagg    6060
aaagtttctc ataatagcct tgctgcaagc tcaaatggga ggtgggcact gtgcccagga    6120
gccttggagc aaaggctgtg cccaacctct gactgcatcc aggtttggtc ttgacagaga    6180
taagaagccc tggcttttgg agccaaaatc taggtcagac ttaggcagga ttctcaaagt    6240
ttatcagcag aacatgaggc agaagaccct ttctgctcca gcttcttcag gctcaacctt    6300
catcagaata gatagaaaga gaggctgtga gggttcttaa aacagaagca aatctgactc    6360
agagaataaa caacctccta gtaaactaca gcttagacag agcatctggt ggtgagtgtg    6420
ctcagtgtcc tactcaactg tctggtatca gccctcatga ggacttctct tctttccctc    6480
atagacctcc atctctgttt tccttagcct gcagaaatct ggatggctat tcacagaatg    6540
cctgtgcttt cagagttgca ttttttctct ggtattctgg ttcaagcatt tgaaggtagg    6600
aaaggttctc caagtgcaag aaagccagcc ctgagcctca actgcctggc tagtgtggtc    6660
agtaggatgc aaaggctgtt gaatgccaca aggccaaact ttaacctgtg taccacaagc    6720
ctagcagcag aggcagctct gctcactgga actctctgtc ttctttctcc tgagccttt     6780 cttttcctga gttttctagc tctcctcaac cttacctctg ccctacccag acaaacccca    6840
agagccactg tttctgtgat gtcctctcca gccctaatta ggcatcatga cttcagcctg    6900
accttccatg ctcagaagca gtgctaatcc acttcagatg agctgctcta tgcaacacag    6960
gcagagccta caaaccttg caccagagcc ctccacatat cagtgtttgt tcatactcac     7020
ttcaacagca aatgtgactg ctgagattaa gattttacac aagatggtct gtaatttcac    7080
agttagtttt atcccattag gtatgaaaga attagcataa ttccccttaa acatgaatga    7140
atcttagatt ttttaataaa tagttttgga agtaaagaca gagacatcag gagcacaagg    7200
aatagcctga gaggacaaac agaacaagaa agagtctgga aatacacagg atgttcttgg    7260
cctcctcaaa gcaagtgcaa gcagatagta ccagcagccc caggctatca gagcccagtg    7320
aagagaagta ccatgaaagc cacagctcta accaccctgt tccagagtga cagacagtcc    7380
ccaagacaag ccagcctgag ccagagagag aactgcaaga gaaagtttct aatttaggtt    7440
ctgttagatt cagacaagtg caggtcatcc tctctccaca gctactcacc tctccagcct    7500
aacaaagcct gcagtccaca ctccaaccct ggtgtctcac ctcctagcct ctcccaacat    7560
cctgctctct gaccatcttc tgcatctctc atctcaccat ctcccactgt ctacagccta    7620
ctcttgcaac taccatctca ttttctgaca tcctgtctac atcttctgcc atactctgcc    7680
atctaccata ccacctctta ccatctacca ccatctttt tatctccatc cctctcagaa     7740
gcctccaagc tgaatcctgc tttatgtgtt catctcagcc cctgcatgga aagctgaccc    7800
cagaggcaga actattccca gagagcttgg ccaagaaaaa caaaactacc agcctggcca    7860
ggctcaggag tagtaagctg cagtgtctgt tgtgttctag cttcaacagc tgcaggagtt    7920
ccactctcaa atgctccaca tttctcacat cctcctgatt ctggtcacta cccatcttca    7980
```

-continued

```
aagaacagaa tatctcacat cagcatactg tgaaggacta gtcatgggtg cagctgctca    8040
gagctgcaaa gtcattctgg atggtggaga gcttacaaac atttcatgat gctcccccg     8100
ctctgatggc tggagcccaa tccctacaca gactcctgct gtatgtgttt tcctttcact    8160
ctgagccaca gccagagggc aggcattcag tctcctcttc aggctgggc tggggcactg     8220
agaactcacc caacaccttg ctctcactcc ttctgcaaaa caagaagag ctttgtgctg     8280
cagtagccat gaagaatgaa aggaaggctt aactaaaaa atgtcagaga ttattttcaa     8340
cccttactg tggatcacca gcaaggagga aacacaacac agagacattt tttcccctca     8400
aattatcaaa agaatcactg catttgttaa agagagcaac tgaatcagga agcagagttt    8460
tgaacatatc agaagttagg aatctgcatc agagacaaat gcagtcatgg ttgtttgctg    8520
cataccagcc ctaatcatta gaagcctcat ggacttcaaa catcattccc tctgacaaga    8580
tgctctagcc taactccatg agataaaata atctgccttt tcagagccaa agaagagtcc    8640
accagcttct tctcagtgtg aacaagagct ccagtcaggt tagtcagtcc agtgcagtag    8700
aggagaccag tctgcatcct ctaattttca aaggcaagaa gatttgttta ccctggacac    8760
caggcacaag tgaggtcaca gagctcttag atatgcagtc ctcatgagtg aggagactaa    8820
agcgcatgcc atcaagactt cagtgtagag aaaacctcca aaaagcctc ctcactactt     8880
ctggaatagc tcagaggccg aggcggcctc ggcctctgca taaataaaaa aaattagtca    8940
gccatggggc ggagaatggg cggaactggg cggagttagg ggcgggatgg gcggagttag    9000
gggcgggact atggttgctg actaattgag atgcatgctt tgcatacttc tgcctgctgg    9060
ggagcctggg gactttccac acctggttgc tgactaattg agatgcatgc tttgcatact    9120
tctgcctgct ggggagcctg gggactttcc acaccctaac tgacacacat tccacagctg    9180
cattaatgaa tcggccaacg cgcggggaga ggcggtttgc gtattgggcg ctcttccgct    9240
tcctcgctca ctgactcgct gcgctcggtc gttcggctgc ggcgagcggt atcagctcac    9300
tcaaaggcgg taatacggtt atccacagaa tcagggata acgcaggaaa gaacatgtga     9360
gcaaaaggcc agcaaaaggc caggaaccgt aaaaaggccg cgttgctggc gtttttccat    9420
aggctccgcc cccctgacga gcatcacaaa aatcgacgct caagtcagag gtggcgaaac    9480
ccgacaggac tataaagata caggcgttt ccccctggaa gctccctcgt gcgctctcct     9540
gttccgaccc tgccgcttac cggatacctg tccgcctttc tcccttcggg aagcgtggcg    9600
ctttctcata gctcacgctg taggtatctc agttcggtgt aggtcgttcg ctccaagctg    9660
ggctgtgtgc acgaaccccc cgttcagccc gaccgctgcg ccttatccgg taactatcgt    9720
cttgagtcca acccggtaag acacgactta tcgccactgg cagcagccac tggtaacagg    9780
attagcagag cgaggtatgt aggcggtgct acagagttct tgaagtggtg gcctaactac    9840
ggctacacta gaagaacagt atttggtatc tgcgctctgc tgaagccagt taccttcgga    9900
aaaagagttg gtagctcttg atccggcaaa caaaccaccg ctggtagcgg tggtttttt    9960
gtttgcaagc agcagattac gcgcagaaaa aaaggatctc aagaagatcc tttgatcttt   10020
tctacgggt ctgacgctca gtggaacgaa aactcacgtt aagggatttt ggtcatgaga    10080
ttatcaaaaa ggatcttcac ctagatcctt ttaaattaaa aatgaagttt taaatcaatc   10140
taaagtatat atgagtaaac ttggtctgac agttaccaat gcttaatcag tgaggcacct   10200
atctcagcga tctgtctatt tcgttcatcc atagttgcct gactccgtgca aaccacgttg   10260
tgtctcaaaa tctctgatgt tacattgcac aagataaaaa tatatcatca tgaacaataa   10320
```

```
aactgtctgc ttacataaac agtaatacaa ggggtgttat gagccatatt caacgggaaa    10380
cgtcttgctc gaggccgcga ttaaattcca acatggatgc tgatttatat gggtataaat    10440
gggctcgcga taatgtcggg caatcaggtg cgacaatcta tcgattgtat gggaagcccg    10500
atgcgccaga gttgtttctg aaacatggca aaggtagcgt tgccaatgat gttacagatg    10560
agatggtcag actaaactgg ctgacggaat ttatgcctct tccgaccatc aagcatttta    10620
tccgtactcc tgatgatgca tggttactca ccactgcgat ccccgggaaa acagcattcc    10680
aggtattaga agaatatcct gattcaggtg aaaatattgt tgatgcgctg gcagtgttcc    10740
tgcgccggtt gcattcgatt cctgtttgta attgtccttt taacagcgat cgcgtatttc    10800
gtctcgctca ggcgcaatca cgaatgaata cggtttggt tgatgcgagt gattttgatg    10860
acgagcgtaa tggctggcct gttgaacaag tctggaaaga atgcataag cttttgccat    10920 tctcaccgga ttcagtcgtc actcatggtg atttctcact tgataacctt attttgacg    10980 agggggaaatt aataggttgt attgatgttg gacgagtcgg aatcgcagac cgataccagg    11040
atcttgccat cctatggaac tgcctcggtg agttttctcc ttcattacag aaacggcttt    11100
ttcaaaaata tggtattgat aatcctgata tgaataaatt gcagtttcat ttgatgctcg    11160
atgagttttt ctaagggcgg cctgccacca tacccacgcc gaaacaagcg ctcatgagcc    11220
cgaagtggcg agcccgatct tccccatcgg tgatgtcggc gatataggcg ccagcaaccg    11280
cacctgtggc gccggtgatg agggcgcgcc aagtcgacgt ccggcagtc                11329
```

<210> SEQ ID NO 40
<211> LENGTH: 11776
<212> TYPE: DNA
<213> ORGANISM: Artificial sequence
<220> FEATURE:
<223> OTHER INFORMATION: Synthetic polynucleotide

<400> SEQUENCE: 40

```
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctgctag ctctgggtat ttaagcccga gtgagcacgc     180
agggtctcca ttttgaagcg ggaggttacg cgttcgtcga ctactagtgg gtaccagagc     240
tccctaggtt ctagaaccgg tgacgtctcc catggtgaag cttggatctg agggcggagt     300
tagggcggag ccaatcagcg tgcgccgttc cgaaagttgc cttttatggc tgggcggaga     360
atgggcggtg aacgccgatg attatataag gacgcgccgg gtgtggcaca gctagttccg     420
tcgcagccgg gatttgggtc gcggttcttg tttgtggatc cctgtgatcg tcacttggta     480
agtcactgac tgtctatgcc tgggaaaggg tgggcaggag atgggcagt gcaggaaaag     540 tggcactatg aaccctgcag ccctaggaat gcatctagac aattgtacta accttcttct     600
ctttcctctc ctgacagtcc ggaaagccac catggccgag tggctgctga gcgccagctg     660
gcagcgccgc gccaaggcca tgaccgccgc cgccggcagc gccggccgcg ccgccgtgcc     720
cctgctgctg tgcgccctgc tggcccccgg cggcgcctac gtgctggacg acagcgacgg     780
cctgggccgc gagttcgacg gcatcggcgc cgtgagcggc ggcggcgcca ccagccgcct     840
gctggtgaac taccccgagc cctaccgcag ccagatcctg gactacctgt tcaagcccaa     900
cttcggcgcc agcctgcaca tcctgaaggt ggagatcggc ggcgacgcc agaccaccga     960 cggcaccgag cccagccaca tgcactacgc cctggacgaa aactacttcc gcggctacga    1020
gtggtggctg atgaaggagg ccaagaagcg caacccccaac atcaccctga tcggcctgcc    1080
```

```
ctggagcttc cccggctggc tgggcaaggg cttcgactgg ccctacgtga acctgcagct    1140
gaccgcctac tacgtggtga cctggatcgt gggcgccaag cgctaccacg acctggacat    1200
cgactacatc ggcatctgga acgagcgcag ctacaacgcc aactacatca agatcctgcg    1260
caagatgctg aactaccagg gcctgcagcg cgtgaagatc atcgccagcg acaacctgtg    1320
ggagagcatc agcgccagca tgctgctgga cgccgagctg ttcaaggtgg tggacgtgat    1380
cggcgcccac taccccggca cccacagcgc caaggacgcc aagctgaccg gcaagaagct    1440
gtggagcagc gaggacttca gcaccctgaa cagcgacatg ggcgccggct gctggggccg    1500
catcctgaac cagaactaca tcaacggcta catgaccagc accatcgcct ggaacctggt    1560
ggccagctac tacgagcagc tgccctacgg ccgctgcggc ctgatgaccg cccaggagcc    1620
ctggagcggc cactacgtgg tggagagccc cgtgtgggtg agcgcccaca ccacccagtt    1680
cacccagccc ggctggtact acctgaagac cgtgggccac ctggagaagg gcggcagcta    1740
cgtggccctg accgacgcc tgggcaacct gaccatcatc atcgagacca tgagccacaa    1800
gcacagcaag tgcatccgcc ccttcctgcc ctacttcaac gtgagccagc agttcgccac    1860
cttcgtgctg aagggcagct tcagcgagat ccccgagctg caggtgtggt acaccaagct    1920
gggcaagacc agcgagcgct tcctgttcaa gcagctggac agcctgtggc tgctggacag    1980
cgacggcagc ttcaccctga gctgcacga ggacgagctg ttcaccctga ccaccctgac    2040
caccggccgc aagggcagct accccctgcc ccccaagagc cagcccttcc ccagcaccta    2100
caaggacgac ttcaacgtgg actacccctt cttcagcgag ccccaact cgccgacca    2160 gaccggcgtg ttcgagtact tcaccaacat cgaggacccc ggcgagcacc acttcaccct    2220
gcgccaggtg ctgaaccagc gccccatcac ctgggccgcc gacgccagca acaccatcag    2280
catcatcggc gactacaact ggaccaacct gaccatcaag tgcgacgtgt acatcgagac    2340
ccccgacacc ggcggcgtgt catcgccgg ccgcgtgaac aagggcggca tcctgatccg    2400
cagcgcccgc ggcatcttct tctggatctt cgccaacggc agctaccgcg tgaccggcga    2460
cctggccggc tggatcatct acgccctggg ccgcgtggag gtgaccgcca agaagtggta    2520
caccctgacc ctgaccatca agggccactt caccagcggc atgctgaacg acaagagcct    2580
gtggaccgac atccccgtga acttccccaa gaacggctgg ccgccatcg cacccacag    2640 cttcgagttc gcccagttcg acaacttcct ggtggaggcc acccgctgat gtgccgaa    2700 ccgccgaact cagaggccgg ccccagaaaa cccgagcgag taggggcgg cgcgcaggag    2760 ggaggagaac tggggcgcg ggaggctggt gggtgtgggg ggtggagatg tagaagatgt    2820
gacgccgcgg cccggcgggt gccagattag cggacgcggt gcccgcggtt gcaacgggat    2880
cccgggcgct gcagcttggg aggcggctct cccaggcgg cgtccgcgga cacccatc    2940 cgtgaacccc aggtcccggg ccgccggctc gccgcgcacc agggccggc ggacagaaga    3000 gcggccgagc ggctcgaggc tggggaccg cgggcgcggc cgcgcgctgc cgggcggag    3060 gctgggggc cggggccggg gccgtgcccc ggagcgggtc ggaggccggg gccggggccg    3120
ggggacggcg gctccccgcg cggctccagc ggctcgggga tcccggccgg gccccgcagg    3180
gaccatgatg gaattcagca gccccagcag agaggaatgc cccaagcctc tgagccgggt    3240
gtcaatcatg gccggatctc tgacaggact gctgctgctt caggccgtgt cttgggcttc    3300
tggcgctaga ccttgcatcc ccaagagctt cggctacagc agcgtcgtgt gcgtgtgcaa    3360
tgccacctac tgcgacagct tcgaccctcc tacctttcct gctctgggca ccttcagcag    3420
```

```
atacgagagc accagatccg gcagacggat ggaactgagc atgggaccca tccaggccaa    3480
tcacacaggc actggcctgc tgctgacact gcagcctgag cagaaattcc agaaagtgaa    3540
aggcttcggc ggagccatga cagatgccgc cgctctgaat atcctggctc tgtctccacc    3600
agctcagaac ctgctgctca agagctactt cagcgaggaa ggcatcggct acaacatcat    3660
cagagtgccc atggccagct gcgacttcag catcaggacc tacacctacg ccgacacacc    3720
cgacgatttc cagctgcaca acttcagcct gcctgaagag gacaccaagc tgaagatccc    3780
tctgatccac agagccctgc agctggcaca aagacccgtg tcactgctgg cctctccatg    3840
gacatctccc acctggctga aaacaaatgg cgccgtgaat ggcaagggca gcctgaaagg    3900
ccaacctggc gacatctacc accagacctg ggccagatac ttcgtgaagt tcctggacgc    3960
ctatgccgag cacaagctgc agttttgggc cgtgacagcc gagaacgaac cttctgctgg    4020
actgctgagc ggctacccct ttcagtgcct gggctttaca cccgagcacc agcgggactt    4080
tatcgcccgt gatctgggac ccacactggc caatagcacc caccataatg tgcggctgct    4140
gatgctggac gaccagagac tgcttctgcc ccactgggct aaagtggtgc tgacagatcc    4200
tgaggccgcc aaatacgtgc acggaatcgc cgtgcactgg tatctggact ttctggcccc    4260
tgccaaggcc acactgggag agacacacag actgttcccc aacaccatgc tgttcgccag    4320
cgaagcctgt gtgggcagca gttttgggga acagagcgtg cggctcggca gctgggatag    4380
aggcatgcag tacagccaca gcatcatcac caacctgctg taccacgtcg tcggctggac    4440
cgactggaat ctggccctga tcctgaagg cggccctaac tgggtccgaa acttcgtgga    4500
cagccccatc atcgtggaca tcaccaagga caccttctac aagcagccca tgttctacca    4560
cctgggacac ttcagcaagt tcatccccga gggctctcag cgcgttggac tggtggcttc    4620
ccagaagaac gatctggacg ccgtggctct gatgcaccct gatggatctg ctgtggtggt    4680
ggtcctgaac cgcagcagca agatgtgcc cctgaccatc aaggatcccg ccgtgggatt    4740
cctggaaaca atcagccctg ctactccat ccacacctac ctgtggcgta cagtgaca    4800 attgttaatt aagtttaaac cctcgaggcc gcaagcaata aaatatcttt attttcatta    4860
catctgtgtg ttggttttttt gtgtggagat ccacgataac aaacagcttt ttgggggtga    4920
acatattgac tgaattccct gcaggttggc cactccctct ctgcgcgctc gctcgctcac    4980
tgaggccgcc cggcaaagc ccgggcgtcg ggcgaccttt ggtcgcccgg cctcagtgag    5040
cgagcgagcg cgcagagagg gagtggccaa ctccatcact aggggttcct gcggccgctc    5100
gtacggtctc gaggaattcc tgcaggataa cttgccaacc tcattctaaa atgtatatag    5160
aagcccaaaa gacaataaca aaaatattct tgtagaacaa aatgggaaag aatgttccac    5220
taaatatcaa gatttagagc aaagcatgag atgtgtgggg atagacagtg aggctgataa    5280
aatagagtag agctcagaaa cagacccatt gatatatgta agtgacctat gaaaaaaata    5340 tggcattta caatgggaaa atgatggtct ttttcttttt tagaaaaaca gggaaatata    5400
tttatatgta aaaataaaa gggaacccat atgtcatacc atacacacaa aaaaattcca    5460
gtgaattata agtctaaatg gagaaggcaa aactttaaat cttttagaaa ataatataga    5520
agcatgcaga ccagcctggc caacatgatg aaaccctctc tactaataat aaaatcagta    5580
gaactactca ggactacttt gagtgggaag tccttttcta tgaagacttc tttggccaaa    5640
attaggctct aaatgcaagg agatagtgca tcatgcctgg ctgcacttac tgataaatga    5700
tgttatcacc atctttaacc aaatgcacag gaacaagtta tggtactgat gtgctggatt    5760
gagaaggagc tctacttcct tgacaggaca catttgtatc aacttaaaaa agcagatttt    5820
```

```
tgccagcaga actattcatt cagaggtagg aaacttagaa tagatgatgt cactgattag    5880
catggcttcc ccatctccac agctgcttcc cacccaggtt gcccacagtt gagtttgtcc    5940
agtgctcagg gctgcccact ctcagtaaga agccccacac cagcccctct ccaaatatgt    6000
tggctgttcc ttccattaaa gtgacccac tttagagcag caagtggatt tctgtttctt     6060
acagttcagg aaggaggagt cagctgtgag aacctggagc ctgagatgct tctaagtccc    6120
actgctactg gggtcaggga agccagactc cagcatcagc agtcaggagc actaagccct    6180
tgccaacatc ctgtttctca gagaaactgc ttccattata atggttgtcc ttttttaagc    6240
tatcaagcca aacaaccagt gtctaccatt attctcatca cctgaagcca agggttctag    6300
caaaagtcaa gctgtcttgt aatggttgat gtgcctccag cttctgtctt cagtcactcc    6360
actcttagcc tgctctgaat caactctgac cacagttccc tggagcccct gccacctgct    6420 gccctgcca ccttctccat ctgcagtgct gtgcagcctt ctgcactctt gcagagctaa     6480
taggtggaga cttgaaggaa gaggaggaaa gtttctcata atagccttgc tgcaagctca    6540
aatgggaggt gggcactgtg cccaggagcc ttggagcaaa ggctgtgccc aacctctgac    6600
tgcatccagg tttggtcttg acagagataa gaagccctgg cttttggagc caaaatctag    6660
gtcagactta ggcaggattc tcaaagttta tcagcagaac atgaggcaga agaccctttc    6720
tgctccagct tcttcaggct caaccttcat cagaatagat agaaagagag ctgtgaggg    6780 ttcttaaaac agaagcaaat ctgactcaga gaataaacaa cctcctagta aactacagct    6840
tagacagagc atcggtggt gagtgtgctc agtgtcctac tcaactgtct ggtatcagcc     6900
ctcatgagga cttctcttct ttccctcata gacctccatc tctgttttcc ttagcctgca    6960
gaaatctgga tggctattca cagaatgcct gtgctttcag agttgcattt tttctctggt    7020
attctggttc aagcatttga aggtaggaaa ggttctccaa gtgcaagaaa gccagccctg    7080
agcctcaact gcctggctag tgtggtcagt aggatgcaaa ggctgttgaa tgccacaagg    7140
ccaaacttta acctgtgtac cacaagccta gcagcagagg cagctctgct cactggaact    7200
ctctgtcttc tttctcctga gccttttctt ttcctgagtt ttctagctct cctcaacctt    7260
acctctgccc tacccaggac aaacccaaga gccactgttt ctgtgatgtc ctctccagcc    7320
ctaattaggc atcatgactt cagcctgacc ttccatgctc agaagcagtg ctaatccact    7380
tcagatgagc tgctctatgc aacacaggca gagcctacaa ccttgcac cagagccctc      7440 cacatatcag tgtttgttca tactcacttc aacagcaaat gtgactgctg agattaagat    7500
tttacacaag atggtctgta atttcacagt tagttttatc ccattaggta tgaaagaatt    7560
agcataattc cccttaaaca tgaatgaatc ttagattttt taataaatag ttttggaagt    7620
aaagacagag acatcaggag cacaggaat agcctgagag gacaaacaga acaagaaaga     7680
gtctggaaat acacaggatg ttcttggcct cctcaaagca agtgcaagca gatagtacca    7740
gcagccccag gctatcagag cccagtgaag agaagtacca tgaaagccac agctctaacc    7800
accctgttcc agagtgacag acagtcccca agacaagcca gcctgagcca gagagagaac    7860
tgcaagagaa agtttctaat ttaggttctg ttagattcag acaagtgcag gtcatcctct    7920
ctccacagct actcacctct ccagcctaac aaagcctgca gtccacactc caaccctggt    7980
gtctcacctc ctagcctctc ccaacatcct gctctctgac catcttctgc atctctcatc    8040
tcaccatctc ccactgtcta cagcctactc ttgcaactac catctcattt tctgacatcc    8100
tgtctacatc ttctgccata ctctgccatc taccatacca cctcttacca tctaccacac    8160
```

```
catcttttat ctccatccct ctcagaagcc tccaagctga atcctgcttt atgtgttcat    8220
ctcagcccct gcatggaaag ctgacccag  aggcagaact attcccagag agcttggcca    8280
agaaaaacaa aactaccagc ctggccaggc tcaggagtag taagctgcag tgtctgttgt    8340
gttctagctt caacagctgc aggagttcca ctctcaaatg ctccacattt ctcacatcct    8400
cctgattctg gtcactaccc atcttcaaag aacagaatat ctcacatcag catactgtga    8460
aggactagtc atgggtgcag ctgctcagag ctgcaaagtc attctggatg gtggagagct    8520
tacaaacatt tcatgatgct cccccgctc  tgatggctgg agcccaatcc ctacacagac    8580
tcctgctgta tgtgttttcc tttcactctg agccacagcc agagggcagg cattcagtct    8640
cctcttcagg ctggggctgg ggcactgaga actcacccaa caccttgctc tcactccttc    8700
tgcaaaacaa gaaagagctt tgtgctgcag tagccatgaa gaatgaaagg aaggctttaa    8760
ctaaaaaatg tcagagatta ttttcaaccc cttactgtgg atcaccagca aggaggaaac    8820
acaacacaga gacatttttt cccctcaaat tatcaaaaga atcactgcat ttgttaaaga    8880
gagcaactga atcaggaagc agagttttga acatatcaga agttaggaat ctgcatcaga    8940
gacaaatgca gtcatggttg tttgctgcat accagcccta atcattagaa gcctcatgga    9000
cttcaaacat cattccctct gacaagatgc tctagcctaa ctccatgaga taaataaat    9060 ctgcctttca gagccaaaga agagtccacc agcttcttct cagtgtgaac aagagctcca    9120
gtcaggttag tcagtccagt gcagtagagg agaccagtct gcatcctcta attttcaaag    9180
gcaagaagat ttgtttaccc tggacaccag gcacaagtga ggtcacagag ctcttagata    9240
tgcagtcctc atgagtgagg agactaaagc gcatgccatc aagacttcag tgtagagaaa    9300
acctccaaaa aagcctcctc actacttctg gaatagctca gaggccgagg cggcctcggc    9360
ctctgcataa ataaaaaaa  ttagtcagcc atggggcgga gaatgggcgg aactgggcgg    9420
agttaggggc gggatgggcg gagttagggg cgggactatg gttgctgact aattgagatg    9480 catgcttgc  atacttctgc ctgctgggga gcctggggac tttccacacc tggttgctga    9540
ctaattgaga tgcatgcttt gcatacttct gcctgctggg gagcctgggg actttccaca    9600
ccctaactga cacacattcc acagctgcat taatgaatcg gccaacgcgc ggggagaggc    9660
ggtttgcgta ttgggcgctc ttccgcttcc tcgctcactg actcgctgcg ctcggtcgtt    9720
cggctgcggc gagcggtatc agctcactca aaggcggtaa tacggttatc cacagaatca    9780
ggggataacg caggaaagaa catgtgagca aaaggccagc aaaaggccag gaaccgtaaa    9840
aaggccgcgt tgctggcgtt tttccatagg ctccgccccc ctgacgagca tcacaaaaat    9900
cgacgctcaa gtcagaggtg gcgaaacccg acaggactat aaagatacca ggcgtttccc    9960
cctggaagct ccctcgtgcg ctctcctgtt ccgaccctgc cgcttaccgg atacctgtcc   10020
gcctttctcc cttcgggaag cgtggcgctt tctcatagct cacgctgtag gtatctcagt   10080
tcggtgtagg tcgttcgctc caagctgggc tgtgtgcacg aaccccccgt tcagcccgac   10140
cgctgcgcct tatccggtaa ctatcgtctt gagtccaacc cggtaagaca cgacttatcg   10200
ccactggcag cagccactgg taacaggatt agcagagcga ggtatgtagg cggtgctaca   10260
gagttcttga agtggtggcc taactacggc tacactagaa gaacagtatt tggtatctgc   10320
gctctgctga agccagttac cttcggaaaa agagttggta gctcttgatc cggcaaacaa   10380
accaccgctg gtagcggtgg tttttttgtt tgcaagcagc agattacgcg cagaaaaaaa   10440
ggatctcaag aagatccttt gatcttttct acggggtctg acgctcagtg gaacgaaaac   10500
tcacgttaag ggattttggt catgagatta tcaaaaagga tcttcaccta gatccttta    10560
```

| | | |
|---|---|---|
| aattaaaaat gaagttttaa atcaatctaa agtatatatg agtaaacttg gtctgacagt | 10620 |
| taccaatgct taatcagtga ggcacctatc tcagcgatct gtctatttcg ttcatccata | 10680 |
| gttgcctgac tcctgcaaac cacgttgtgt ctcaaaatct ctgatgttac attgcacaag | 10740 |
| ataaaaatat atcatcatga acaataaaac tgtctgctta cataaacagt aatacaaggg | 10800 |
| gtgttatgag ccatattcaa cgggaaacgt cttgctcgag gccgcgatta aattccaaca | 10860 |
| tggatgctga tttatatggg tataaatggg ctcgcgataa tgtcgggcaa tcaggtgcga | 10920 |
| caatctatcg attgtatggg aagcccgatg cgccagagtt gtttctgaaa catggcaaag | 10980 |
| gtagcgttgc caatgatgtt acagatgaga tggtcagact aaactggctg acggaattta | 11040 |
| tgcctcttcc gaccatcaag cattttatcc gtactcctga tgatgcatgg ttactcacca | 11100 |
| ctgcgatccc cgggaaaaca gcattccagg tattagaaga atatcctgat tcaggtgaaa | 11160 |
| atattgttga tgcgctggca gtgttcctgc gccggttgca ttcgattcct gtttgtaatt | 11220 |
| gtccttttaa cagcgatcgc gtatttcgtc tcgctcaggc gcaatcacga atgaataacg | 11280 |
| gtttggttga tgcgagtgat tttgatgacg agcgtaatgg ctggcctgtt gaacaagtct | 11340 |
| ggaaagaaat gcataagctt ttgccattct caccggattc agtcgtcact catggtgatt | 11400 |
| tctcacttga taaccttatt tttgacgagg ggaaattaat aggttgtatt gatgttggac | 11460 |
| gagtcggaat cgcagaccga taccaggatc ttgccatcct atggaactgc ctcggtgagt | 11520 |
| tttctccttc attacagaaa cggctttttc aaaaatatgg tattgataat cctgatatga | 11580 |
| ataaattgca gtttcatttg atgctcgatg agttttttcta agggcggcct gccaccatac | 11640 |
| ccacgccgaa acaagcgctc atgagcccga gtggcgagc ccgatcttcc ccatcggtga | 11700 |
| tgtcggcgat ataggcgcca gcaaccgcac ctgtggcgcc ggtgatgagg gcgcgccaag | 11760 |
| tcgacgtccg gcagtc | 11776 |

<210> SEQ ID NO 41
<211> LENGTH: 11348
<212> TYPE: DNA
<213> ORGANISM: Artificial sequence
<220> FEATURE:
<223> OTHER INFORMATION: Synthetic polynucleotide

<400> SEQUENCE: 41

| | | |
|---|---|---|
| ttggccactc cctctctgcg cgctcgctcg ctcactgagg ccgggcgacc aaaggtcgcc | 60 |
| cgacgcccgg gctttgcccg gcggcctca gtgagcgagc gagcgcgcag agagggagtg | 120 |
| gccaactcca tcactagggg ttcctgctag ctctgggtat ttaagcccga gtgagcacgc | 180 |
| agggtctcca ttttgaagcg ggaggttacg cgttcgtcga ctactagtgg gtaccagagc | 240 |
| tccctaggtt ctagaaccgg tgacgtctcc catggtgaag cttggatctg agggcggagt | 300 |
| tagggcggag ccaatcagcg tgcgccgttc cgaaagttgc cttttatggc tgggcggaga | 360 |
| atgggcggtg aacgccgatg attatataag gacgcgccgg gtgtggcaca gctagttccg | 420 |
| tcgcagccgg gatttgggtc gcggttcttg tttgtggatc cctgtgatcg tcacttggta | 480 |
| agtcactgac tgtctatgcc tgggaaaggg tgggcaggag atgggcagt gcaggaaaag | 540 |
| tggcactatg aaccctcctg gtggcgaggg gagggggtg gtcctcgaac gccttgcaga | 600 |
| actggcctgg atacagagtg gaccggctgg ccccatctgg aagacttcga gatacactgt | 660 |
| tgtcttactg cgctcaacag tgtatctcga agtcttccaa atggtgccag ccatcgcagc | 720 |
| ggggtgcagg aaatgggggc agccccccctt tttggctatc cttccacgtg ttcttttttg | 780 |

```
tatcttttgt gtttcctaga aaacatctca gtcaccaccg cagccctagg aatgcatcta    840
gacaattgta ctaaccttct tctctttcct ctcctgacag tccggaaagc caccatgtgg    900
cagctgtggg ccagcctgtg ctgcctgctg gtgctggcca acgcccgcag ccgccccagc    960
ttccaccccc tgagcgacga gctggtgaac tacgtgaaca gcgcaacac cacctggcag    1020 gccggccaca acttctacaa cgtggacatg agctacctga agcgcctgtg cggcaccttc    1080
ctgggcggcc caagccccc ccagcgcgtg atgttcaccg aggacctgaa gctgcccgcc    1140
agcttcgacg cccgcgagca gtggccccag tgccccacca tcaaggagat ccgcgaccag    1200
ggcagctgcg gcagctgctg ggccttcggc gccgtggagg ccatcagcga ccgcatctgc    1260
atccacacca acgcccacgt gagcgtggag gtgagcgccg aggacctgct gacctgctgc    1320
ggcagcatgt gcggcgacgg ctgcaacggc ggctacccccg ccgaggcctg gaacttctgg    1380
acccgcaagg gcctggtgag cggcggcctg tacgagagcc acgtgggctg ccgcccctac    1440
agcatccccc cctgcgagca ccacgtgaac ggcagccgcc cccctgcac cggcgagggc    1500 gacaccccca gtgcagcaa gatctgcgag cccggctaca gccccaccta caagcaggac    1560
aagcactacg gctacaacag ctacagcgtg agcaacagcg agaaggacat catggccgag    1620
atctacaaga acggccccgt ggagggcgcc ttcagcgtgt acagcgactt cctgctgtac    1680
aagagcggcg tgtaccagca cgtgaccggc gagatgatgg gcggccacgc catccgcatc    1740
ctgggctggg gcgtggagaa cggcaccccc tactggctgg tggccaacag ctggaacacc    1800
gactggggcg acaacggctt cttcaagatc ctgcgcggcc aggaccactg cggcatcgag    1860
agcgaggtgg tggccggcat ccccgcaccc gaccagtact gggagaagat cgagggcaga    1920
ggaagtcttc tgacatgcgg agacgtggaa gagaatcccg gccctatgga attcagcagc    1980
cccagcagag aggaatgccc caagcctctg agcgggtgt caatcatggc cggatctctg    2040
acaggactgc tgctgcttca ggccgtgtct tgggcttctg gcgctagacc ttgcatcccc    2100
aagagcttcg gctacagcag cgtcgtgtgc gtgtgcaatg ccacctactg cgacagcttc    2160
gaccctccta ccttccctgc tctgggcacc ttcagcagat acgagagcac cagatccggc    2220
agacggatga aactgagcat gggacccatc caggccaatc acacaggcac tggcctgctg    2280
ctgacactgc agcctgagca gaaattccag aaagtgaaag gcttcggcgg agccatgaca    2340
gatgccgccg ctctgaatat cctggctctg tctccaccag ctcagaacct gctgctcaag    2400
agctacttca gcgaggaagg catcggctac aacatcatca gagtgcccat ggccagctgc    2460
gacttcagca tcaggaccta cacctacgcc gacacaccg acgatttcca gctgcacaac    2520
ttcagcctgc tgaagaggga caccaagctg aagatccctc tgatccacag agccctgcag    2580
ctggcacaaa gacccgtgtc actgctggcc tctccatgga catctcccac ctggctgaaa    2640
acaaatggcg ccgtgaatgg caagggcagc ctgaaaggcc aacctggcga catctaccac    2700
cagacctggg ccagatactt cgtgaagttc ctggacgcct atgccgagca caagctgcag    2760
ttttgggccg tgacagccga gaacgaacct tctgctggac tgctgagcgg ctaccccttt    2820
cagtgcctgg gctttacacc cgagcaccag cgggacttta tcgcccgtga tctgggaccc    2880
acactggcca atagcaccca ccataatgtg cggctgctga tgctggacga ccagagactg    2940
cttctgcccc actgggctaa agtggtgctg acagatcctg aggccgccaa atacgtgcac    3000
ggaatcgccg tgcactggta tctggacttt ctggcccctg ccaaggccac actgggagag    3060
acacacagac tgttccccaa caccatgctg ttcgccagca agcctgtgt gggcagcaag    3120 ttttgggaac agagcgtgcg gctcggcagc tgggatagag gcatgcagta cagccacagc    3180
```

```
atcatcacca acctgctgta ccacgtcgtc ggctggaccg actggaatct ggccctgaat    3240
cctgaaggcg gccctaactg ggtccgaaac ttcgtggaca gccccatcat cgtggacatc    3300
accaaggaca ccttctacaa gcagcccatg ttctaccacc tgggacactt cagcaagttc    3360
atccccgagg gctctcagcg cgttggactg gtggcttccc agaagaacga tctggacgcc    3420
gtggctctga tgcaccctga tggatctgct gtggtggtgg tcctgaaccg cagcagcaaa    3480
gatgtgcccc tgaccatcaa ggatcccgcc gtgggattcc tggaaacaat cagccctggc    3540
tactccatcc acacctacct gtggcgtaga cagtgacaat tgttaattaa gtttaaaccc    3600
tcgaggccgc aagcttatcg ataatcaacc tctggattac aaaatttgtg aaagattgac    3660
tggtattctt aactatgttg ctccttttac gctatgtgga tacgctgctt taatgccttt    3720
gtatcatgct attgcttccc gtatggcttt cattttctcc tccttgtata atcctggtt     3780 gctgtctctt tatgaggagt tgtggcccgt tgtcaggcaa cgtggcgtgg tgtgcactgt    3840
gtttgctgac gcaaccccca ctggttgggg cattgccacc acctgtcagc tcctttccgg    3900
gactttcgct ttccccctcc ctattgccac ggcggaactc atcgccgcct gccttgcccg    3960
ctgctggaca gggctcggc tgtgggcac tgacaattcc gtggtgttgt cggggaaatc       4020
atcgtccttt ccttggctgc tcgcctgtgt tgccacctgg attctgcgcg ggacgtcctt    4080
ctgctacgtc ccttcggccc tcaatccagc ggaccttcct tcccgcggcc tgctgccggc    4140
tctgcggcct cttccgcgtc ttcgccttcg ccctcagacg agtcggatct ccctttgggc    4200
cgcctccccg catcgatacc gtcgactaga gctcgctgat cagcctcgac tgtgccttct    4260
agttgccagc catctgttgt ttgcccctcc cccgtgcctt ccttgaccct ggaaggtgcc    4320
actcccactg tccttttccta ataaaatgag gaaattgcat cgcattgtct gagtaggtgt    4380
cattctattc tggggggtgg ggtggggcag gacagcaagg gggaggattg ggaagacaat    4440
agcaggcatg ctggggagag atccacgata acaaacagct ttttggggt gaacatattg       4500 actgaattcc ctgcaggttg gccactccct ctctgcgcgc tcgctcgctc actgaggccg    4560
cccgggcaaa gcccgggcgt cgggcgacct ttggtcgccc ggcctcagtg agcgagcgag    4620
cgcgcagaga gggagtggcc aactccatca ctaggggttc ctgcggccgc tcgtacggtc    4680
tcgaggaatt cctgcaggat aacttgccaa cctcattcta aaatgtatat agaagcccaa    4740
aagacaataa caaaaatatt cttgtagaac aaaatgggaa agaatgttcc actaaatatc    4800
aagatttaga gcaaagcatg agatgtgtgg ggatagacag tgaggctgat aaaatagagt    4860
agagctcaga aacagaccca ttgatatatg taagtgacct atgaaaaaaa tatggcattt    4920
tacaatggga aaatgatggt ctttttcttt tttagaaaaa cagggaaata tatttatatg    4980
taaaaaataa aagggaaccc atatgtcata ccatacacac aaaaaaattc cagtgaatta    5040
taagtctaaa tggagaaggc aaaacttta atctttaga aataatata gaagcatgca         5100 gaccagcctg gccaacatga tgaaaccctc tctactaata ataaaatcag tagaactact    5160
caggactact ttgagtggga agtccttttc tatgaagact tctttggcca aaattaggct    5220
ctaaatgcaa ggagatagtg catcatgcct ggctgcactt actgataaat gatgttatca    5280
ccatctttaa ccaaatgcac aggaacaagt tatggtactg atgtgctgga ttgagaagga    5340
gctctacttc cttgacagga cacatttgta tcaacttaaa aaagcagatt tttgccagca    5400
gaactattca ttcagaggta ggaaacttag aatagatgat gtcactgatt agcatggctt    5460
ccccatctcc acagctgctt cccacccagg ttgcccacag ttgagtttgt ccagtgctca    5520
```

```
gggctgccca ctctcagtaa gaagccccac accagcccct ctccaaatat gttggctgtt      5580
ccttccatta aagtgacccc actttagagc agcaagtgga tttctgtttc ttacagttca      5640
ggaaggagga gtcagctgtg agaacctgga gcctgagatg cttctaagtc ccactgctac      5700
tggggtcagg gaagccagac tccagcatca gcagtcagga gcactaagcc cttgccaaca      5760
tcctgtttct cagagaaact gcttccatta taatggttgt cctttttaa gctatcaagc       5820 caaacaacca gtgtctacca ttattctcat cacctgaagc caagggttct agcaaaagtc      5880
aagctgtctt gtaatggttg atgtgcctcc agcttctgtc ttcagtcact ccactcttag      5940
cctgctctga tcaactctg accacagttc cctggagccc ctgccacctg ctgcccctgc        6000
caccttctcc atctgcagtg ctgtgcagcc ttctgcactc ttgcagagct aataggtgga      6060
gacttgaagg aagaggagga aagtttctca taatagcctt gctgcaagct caaatgggag      6120
gtgggcactg tgcccaggag ccttggagca aaggctgtgc ccaacctctg actgcatcca      6180
ggtttggtct tgacagagat aagaagccct ggcttttgga gccaaaatct aggtcagact      6240
taggcaggat tctcaaagtt tatcagcaga acatgaggca gaagacccct tctgctccag      6300
cttcttcagg ctcaaccttc atcagaatag atagaaagag aggctgtgag ggttcttaaa      6360
acagaagcaa atctgactca gagaataaac aacctcctag taaactacag cttagacaga      6420
gcatctggtg gtgagtgtgc tcagtgtcct actcaactgt ctggtatcag ccctcatgag      6480
gacttctctt ctttccctca tagacctcca tctctgtttt ccttagcctg cagaaatctg      6540
gatggctatt cacagaatgc ctgtgctttc agagttgcat ttttctctg gtattctggt       6600 tcaagcattt gaaggtagga aaggttctcc aagtgcaaga aagccagccc tgagcctcaa      6660
ctgcctggct agtgtggtca gtaggatgca aaggctgttg aatgccacaa ggccaaactt      6720
taacctgtgt accacaagcc tagcagcaga ggcagctctg ctcactggaa ctctctgtct      6780
tctttctcct gagcctttc ttttcctgag ttttctagct ctcctcaacc ttacctctgc        6840
cctacccagg acaaacccaa gagccactgt ttctgtgatg tcctctccag ccctaattag      6900
gcatcatgac ttcagcctga ccttccatgc tcagaagcag tgctaatcca cttcagatga      6960
gctgctctat gcaacacagg cagagcctac aaacctttgc accagagccc tccacatatc      7020
agtgtttgtt catactcact tcaacagcaa atgtgactgc tgagattaag attttacaca     7080
agatggtctg taatttcaca gttagtttta tcccattagg tatgaaagaa ttagcataat      7140
tccccttaaa catgaatgaa tcttagattt tttaataaat agttttggaa gtaaagacag     7200
agacatcagg agcacaagga atagcctgag aggacaaaca gaacaagaaa gagtctggaa      7260
atacacagga tgttcttggc ctcctcaaag caagtgcaag cagatagtac cagcagcccc      7320
aggctatcag agcccagtga agagaagtac catgaaagcc acagctctaa ccaccctgtt      7380
ccagagtgac agacagtccc caagacaagc cagcctgagc cagagagaga actgcaagag     7440
aaagtttcta atttaggttc tgttagattc agacaagtgc aggtcatcct ctctccacag     7500
ctactcacct ctccagccta acaaagcctg cagtccacac tccaaccctg gtgtctcacc      7560
tcctagcctc tcccaacatc ctgctctctg accatcttct gcatctctca tctcaccatc     7620
tcccactgtc tacagcctac tcttgcaact accatctcat tttctgacat cctgtctaca      7680
tcttctgcca tactctgcca tctaccatac cacctcttac catctaccac accatctttt      7740
atctccatcc ctctcagaag cctccaagct gaatcctgct ttatgtgttc atctcagccc      7800
ctgcatggaa agctgacccc agaggcagaa ctattcccag agagcttggc caagaaaaac      7860
aaaactacca gcctggccag gctcaggagt agtaagctgc agtgtctgtt gtgttctagc      7920
```

```
ttcaacagct gcaggagttc cactctcaaa tgctccacat ttctcacatc ctcctgattc   7980
tggtcactac ccatcttcaa agaacagaat atctcacatc agcatactgt gaaggactag   8040
tcatgggtgc agctgctcag agctgcaaag tcattctgga tggtggagag cttacaaaca   8100
tttcatgatg ctcccccgc tctgatggct ggagcccaat ccctacacag actcctgctg    8160
tatgtgtttt cctttcactc tgagccacag ccagagggca ggcattcagt ctcctcttca   8220
ggctggggct ggggcactga gaactcaccc aacaccttgc tctcactcct tctgcaaaac   8280
aagaaagagc tttgtgctgc agtagccatg aagaatgaaa ggaaggcttt aactaaaaaa   8340
tgtcagagat tattttcaac cccttactgt ggatcaccag caaggaggaa acacaacaca   8400
gagacatttt ttcccctcaa attatcaaaa gaatcactgc atttgttaaa gagagcaact   8460
gaatcaggaa gcagagtttt gaacatatca gaagttagga atctgcatca gagacaaatg   8520
cagtcatggt tgtttgctgc ataccagccc taatcattag aagcctcatg gacttcaaac   8580
atcattccct ctgacaagat gctctagcct aactccatga gataaaataa atctgccttt   8640
cagagccaaa gaagagtcca ccagcttctt ctcagtgtga acaagagctc cagtcaggtt   8700
agtcagtcca gtgcagtaga ggagaccagt ctgcatcctc taattttcaa aggcaagaag   8760
atttgtttac cctggacacc aggcacaagt gaggtcacag agctcttaga tatgcagtcc   8820
tcatgagtga ggagactaaa gcgcatgcca tcaagacttc agtgtagaga aaacctccaa   8880
aaaagcctcc tcactacttc tggaatagct cagaggccga ggcggcctcg gcctctgcat   8940
aaataaaaaa aattagtcag ccatggggcg gagaatgggc ggaactgggc ggagttaggg   9000
gcgggatggg cggagttagg ggcgggacta tggttgctga ctaattgaga tgcatgcttt   9060
gcatacttct gcctgctggg gagcctgggg actttccaca cctggttgct gactaattga   9120
gatgcatgct ttgcatactt ctgcctgctg gggagcctgg ggactttcca caccctaact   9180
gacacacatt ccacagctgc attaatgaat cggccaacgc gcggggagag gcggtttgcg   9240
tattgggcgc tcttccgctt cctcgctcac tgactcgctg cgctcggtcg ttcggctgcg   9300
gcgagcggta tcagctcact caaaggcggt aatacggtta ccacagaat cagggqataa    9360
cgcaggaaag aacatgtgag caaaaggcca gcaaaaggcc aggaaccgta aaaaggccgc   9420
gttgctggcg ttttccata ggctccgccc ccctgacgag catcacaaaa atcgacgctc     9480
aagtcagagg tggcgaaacc cgacaggact ataaagatac caggcgtttc ccctggaag    9540
ctcctcgtg cgctctcctg ttccgaccct gccgcttacc ggatacctgt ccgcctttct     9600
cccttcggga agcgtggcgc tttctcatag ctcacgctgt aggtatctca gttcggtgta   9660
ggtcgttcgc tccaagctgg gctgtgtgca cgaaccccc gttcagcccg accgctgcgc    9720
cttatccggt aactatcgtc ttgagtccaa cccggtaaga cacgacttat cgccactggc   9780
agcagccact ggtaacagga ttagcagagc gaggtatgta ggcggtgcta cagagttctt   9840
gaagtggtgg cctaactacg gctacactag aagaacagta tttggtatct gcgctctgct   9900
gaagccagtt accttcggaa aaagagttgg tagctcttga tccggcaaac aaaccaccgc   9960
tggtagcggt ggtttttttg tttgcaagca gcagattacg cgcagaaaaa aaggatctca  10020
agaagatcct ttgatctttt ctacgggtc tgacgctcag tggaacgaaa actcacgtta   10080
agggattttg gtcatgagat tatcaaaaag gatcttcacc tagatccttt taaattaaaa  10140
atgaagtttt aaatcaatct aaagtatata tgagtaaact tggtctgaca gttaccaatg  10200
cttaatcagt gaggcaccta tctcagcgat ctgtctattt cgttcatcca tagttgcctg  10260
```

```
actcctgcaa accacgttgt gtctcaaaat ctctgatgtt acattgcaca agataaaaat    10320
atatcatcat gaacaataaa actgtctgct tacataaaca gtaatacaag gggtgttatg    10380
agccatattc aacgggaaac gtcttgctcg aggccgcgat taaattccaa catggatgct    10440
gatttatatg ggtataaatg ggctcgcgat aatgtcgggc aatcaggtgc gacaatctat    10500
cgattgtatg ggaagcccga tgcgccagag ttgtttctga acatggcaa aggtagcgtt    10560 gccaatgatg ttacagatga gatggtcaga ctaaactggc tgacggaatt tatgcctctt    10620
ccgaccatca agcattttat ccgtactcct gatgatgcat ggttactcac cactgcgatc    10680
cccgggaaaa cagcattcca ggtattagaa gaatatcctg attcaggtga aaatattgtt    10740
gatgcgctgg cagtgttcct gcgccggttg cattcgattc ctgtttgtaa ttgtccttt    10800 aacagcgatc gcgtatttcg tctcgctcag gcgcaatcac gaatgaataa cggtttggtt    10860
gatgcgagtg attttgatga cgagcgtaat ggctggcctg ttgaacaagt ctggaaagaa    10920
atgcataagc ttttgccatt ctcaccggat tcagtcgtca ctcatggtga tttctcactt    10980 gataaccta ttttttgacga ggggaaatta ataggttgta ttgatgttgg acgagtcgga    11040
atcgcagacc gataccagga tcttgccatc ctatggaact gcctcggtga gttttctcct    11100
tcattacaga aacggctttt tcaaaaatat ggtattgata atcctgatat gaataaattg    11160
cagtttcatt tgatgctcga tgagtttttc taagggcggc ctgccaccat acccacgccg    11220
aaacaagcgc tcatgagccc gaagtggcga gcccgatctt ccccatcggt gatgtcggcg    11280
atataggcgc cagcaaccgc acctgtggcg ccggtgatga gggcgcgcca agtcgacgtc    11340
cggcagtc                                                            11348
```

<210> SEQ ID NO 42
<211> LENGTH: 11433
<212> TYPE: DNA
<213> ORGANISM: Artificial sequence
<220> FEATURE:
<223> OTHER INFORMATION: Synthetic polynucleotide

<400> SEQUENCE: 42

```
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctgctag ctctgggtat ttaagcccga gtgagcacgc     180
agggtctcca ttttgaagcg ggaggttacg cgttcgtcga ctactagtgg gtaccagagc     240
tccctaggtt ctagaaccgg tgacgtctcc catggtgaag cttggatctg agggcggagt    300
tagggcggag ccaatcagcg tgcgccgttc cgaaagttgc ctttatggc tgggcggaga     360 atgggcggtg aacgccgatg attatataag gacgcgccgg gtgtggcaca gctagttccg    420
tcgcagccgg gattgggtc gcggttcttg tttgtggatc cctgtgatcg tcacttggta     480
agtcactgac tgtctatgcc tgggaaaggg tgggcaggag atggggcagt gcaggaaaag    540
tggcactatg aaccctcctg gtggcgaggg gaggggggtg gtcctcgaac gccttgcaga    600
actggcctgg atacagagtg gaccggctgg ccccatctgg aagacttcga gatacactgt    660
tgtcttactg cgctcaacag tgtatctcga agtcttccaa atggtgccag ccatcgcagc    720
ggggtgcagg aaatgggggc agccccccctt tttggctatc cttccacgtg ttcttttttg    780
tatcttttgt gtttcctaga aaacatctca gtcaccaccg cagccctagg aatgcatcta    840
gacaattgta ctaaccttct tctctttcct ctcctgacag tccggaaagc caccatggaa    900
ttcagcagcc ccagcagaga ggaatgcccc aagcctctga gccgggtgtc aatcatggcc    960
```

-continued

```
ggatctctga caggactgct gctgcttcag gccgtgtctt gggcttctgg cgctagacct    1020
tgcatcccca agagcttcgg ctacagcagc gtcgtgtgcg tgtgcaatgc cacctactgc    1080
gacagcttcg accctcctac ctttcctgct ctgggcacct tcagcagata cgagagcacc    1140
agatccggca gacggatgga actgagcatg ggacccatcc aggccaatca cacaggcact    1200
ggcctgctgc tgacactgca gcctgagcag aaattccaga agtgaaaggc ttcggcgga    1260
gccatgacag atgccgccgc tctgaatatc ctggctctgt ctccaccagc tcagaacctg    1320
ctgctcaaga gctacttcag cgaggaaggc atcggctaca acatcatcag agtgcccatg    1380
gccagctgcg acttcagcat caggacctac acctacgccg acacacccga cgatttccag    1440
ctgcacaact tcagcctgcc tgaagaggac accaagctga agatccctct gatccacaga    1500
gccctgcagc tggcacaaag acccgtgtca ctgctggcct ctccatggac atctcccacc    1560
tggctgaaaa caaatggcgc cgtgaatggc aagggcagcc tgaaaggcca acctggcgac    1620
atctaccacc agacctgggc cagatacttc gtgaagttcc tggacgccta tgccgagcac    1680
aagctgcagt tttgggccgt gacagccgag aacgaaacct tctgctggact gctgagcggc    1740
taccccttc agtgcctggg ctttacaccc gagcaccagc gggactttat cgcccgtgat    1800
ctgggaccca cactggccaa tagcacccac cataatgtgc ggctgctgat gctggacgac    1860
cagagactgc ttctgcccca ctgggctaaa gtggtgctga cagatcctga ggccgccaaa    1920
tacgtgcacg aatcgccgt gcactggtat ctggactttc tggcccctgc caaggccaca    1980
ctgggagaga cacacagact gttccccaac accatgctgt tcgccagcga agcctgtgtg    2040
ggcagcaagt tttgggaaca gagcgtgcgg ctcggcagct gggatagagg catgcagtac    2100
agccacagca tcatcaccaa cctgctgtac cacgtcgtcg gctggaccga ctggaatctg    2160
gccctgaatc ctgaaggcgg ccctaactgg gtccgaaact tcgtggacag ccccatcatc    2220
gtggacatca ccaaggacac cttctacaag cagcccatgt tctaccacct gggacacttc    2280
agcaagttca tccccgaggg ctctcagcgc gttggactgg tggcttccca gaagaacgat    2340
ctggacgccg tggctctgat gcaccctgat ggatctgctg tggtggtggt cctgaaccgc    2400
agcagcaaag atgtgcccct gaccatcaag gatcccgccg tgggattcct ggaaacaatc    2460
agccctggct actccatcca cacctacctg tggcgtagac aggagggcag aggaagtctt    2520
ctgacatgcg agacgtggaa agagaatccc ggccctatgc cccgctacgg cgccagcctg    2580
cgccagagct gcccccgcag cggccgcgag cagggccagg acggcaccgc cggcgccccc    2640
ggcctgctgt ggatgggcct ggtgctggcc ctggccctgg ccctggccct ggccctggcc    2700
ctgagcgaca gccgcgtgct gtgggccccc gccgaggccc accccctgag cccccagggc    2760
caccccgccc gcctgcaccg catcgtgccc cgcctgcgcg acgtgttcgg ctggggcaac    2820
ctgacctgcc ccatctgcaa gggcctgttc accgccatca acctgggcct gaagaaggag    2880
cccaacgtgg cccgcgtggg cagcgtggcc atcaagctgt gcaacctgct gaagatcgcc    2940
cccccgccg tgtgccagag catcgtgcac ctgttcgagg acgacatggt ggaggtgtgg    3000
cgccgcagcg tgctgagccc cagcgaggcc tgcggcctgc tgctgggcag cacctgcggc    3060
cactgggaca tcttcagcag ctggaacatc agcctgccca ccgtgcccaa gcccccccc    3120
aagcccccca gcccccccgc cccccggcgcc ccgtgagcc gcatcctgtt cctgaccgac    3180
ctgcactggg accacgacta cctggagggc accgaccccg actgcgccga ccccctgtgc    3240
tgccgccgcg gcagcggcct gccccccgcc agccgccccg cgccggcta ctggggcgag    3300
```

```
tacagcaagt gcgacctgcc cctgcgcacc ctggagagcc tgctgagcgg cctgggcccc    3360
gccggcccct cgacatggt gtactggacc ggcgacatcc ccgcccacga cgtgtggcac    3420
cagacccgcc aggaccagct gcgcgccctg accaccgtga ccgccctggt gcgcaagttc    3480
ctgggccccg tgcccgtgta ccccgccgtg ggcaaccacg agagcacccc cgtgaacagc    3540
ttcccccccc ccttcatcga gggcaaccac agcagccgct ggctgtacga ggccatggcc    3600
aaggcctggg agccctggct gccgccgag gccctgcgca ccctgcgcat cggcggcttc    3660
tacgccctga ccccctaccc cggcctgcgc ctgatcagcc tgaacatgaa cttctgcagc    3720
cgcgagaact tctggctgct gatcaacagc accgaccccg ccggccagct gcagtggctg    3780
gtgggcgagc tgcaggccgc cgaggaccgc ggcgacaagg tgcacatcat cggccacatc    3840
ccccccggcc actgcctgaa gagctggagc tggaactact accgcatcgt ggcccgctac    3900
gagaacaccc tggccgccca gttcttcggc cacacccacg tggacgagtt cgaggtgttc    3960
tacgacgagg agaccctgag ccgcccctg gccgtggcct tcctggcccc cagcgccacc    4020
acctacatcg gcctgaaccc cggctaccgc gtgtaccaga tcgacggcaa ctacagcggc    4080
agcagccacg tggtgctgga ccacgagacc tacatcctga acctgaccca ggccaacatc    4140
cccgcgcca tcccccactg gcagctgctg taccgcgccc gcgagaccta cggcctgccc    4200
aacaccctgc ccaccgcctg gcacaacctg gtgtaccgca tgcgcggcga catgcagctg    4260
ttccagacct tctggttcct gtaccacaag ggccaccccc ccagcgagcc ctgcggcacc    4320
ccctgccgcc tggccaccct gtgcgcccag ctgagcgccc gcgccgacag ccccgccctg    4380
tgccgccacc tgatgcccga cggcagcctg cccgaggccc agagcctgtg gccccgcccc    4440
ctgttctgct aatgacaatt gttaattaag tttaaccct cgaggccgca agcaataaaa    4500
tatctttatt ttcattacat ctgtgtgttg gttttttgtg tggagatcca cgataacaaa    4560
cagcttttt ggggtgaaca tattgactga attccctgca ggttggccac tccctctctg    4620
cgcgctcgct cgctcactga ggccgccgg gcaaagcccg ggcgtcgggc gacctttggt    4680
cgcccggcct cagtgagcga gcgagcgcgc agagagggag tggccaactc catcactagg    4740
ggttcctgcg gccgctcgta cggtctcgag gaattcctgc aggataactt gccaacctca    4800
ttctaaaatg tatatagaag cccaaaagac aataacaaaa atattcttgt agaacaaaat    4860
gggaaagaat gttccactaa atatcaagat ttagagcaaa gcatgagatg tgtggggata    4920
gacagtgagg ctgataaaat agagtagagc tcagaaacag acccattgat atatgtaagt    4980
gacctatgaa aaaatatgg cattttacaa tgggaaatg atggtctttt tcttttttag    5040
aaaaacaggg aaatatattt atatgtaaaa aataaagggg aacccatatg tcataccata    5100
cacacaaaaa aattccagtg aattataagt ctaaatggag aaggcaaaac tttaaatctt    5160
ttagaaaata atatagaagc atgcagacca gcctggccaa catgatgaaa ccctctctac    5220
taataataaa atcagtagaa ctactcagga ctactttgag tgggaagtcc ttttctatga    5280
agacttcttt ggccaaaatt aggctctaaa tgcaaggaga tagtgcatca tgcctggctg    5340
cacttactga taaatgatgt tatcaccatc tttaaccaaa tgcacaggaa caagttatgg    5400
tactgatgtg ctggattgag aaggagctct acttccttga caggacacat ttgtatcaac    5460
ttaaaaagc agattttgc cagcagaact attcattcag aggtaggaaa cttagaatag    5520
atgatgtcac tgattagcat ggcttcccca tctccacagc tgcttccac ccaggttgcc    5580
cacagttgag tttgtccagt gctcagggct gcccactctc agtaagaagc cccacaccag    5640
cccctctcca aatatgttgg ctgttccttc cattaaagtg accccacttt agagcagcaa    5700
```

-continued

```
gtggatttct gtttcttaca gttcaggaag gaggagtcag ctgtgagaac ctggagcctg    5760
agatgcttct aagtcccact gctactgggg tcagggaagc cagactccag catcagcagt    5820
caggagcact aagcccttgc caacatcctg tttctcagag aaactgcttc cattataatg    5880
gttgtccttt tttaagctat caagccaaac aaccagtgtc taccattatt ctcatcacct    5940
gaagccaagg gttctagcaa aagtcaagct gtcttgtaat ggttgatgtg cctccagctt    6000
ctgtcttcag tcactccact cttagcctgc tctgaatcaa ctctgaccac agttccctgg    6060
agcccctgcc acctgctgcc cctgccacct tctccatctg cagtgctgtg cagccttctg    6120
cactcttgca gagctaatag gtggagactt gaaggaagag gaggaaagtt tctcataata    6180
gccttgctgc aagctcaaat gggaggtggg cactgtgccc aggagccttg agcaaaggc    6240 tgtgcccaac ctctgactgc atccaggttt ggtcttgaca gagataagaa gccctggctt    6300
ttggagccaa aatctaggtc agacttaggc aggattctca agtttatca gcagaacatg    6360 aggcagaaga ccctttctgc tccagcttct tcaggctcaa ccttcatcag aatagataga    6420
aagagaggct gtgagggttc ttaaaacaga agcaaatctg actcagagaa taaacaacct    6480
cctagtaaac tacagcttag acagagcatc tggtggtgag tgtgctcagt gtcctactca    6540
actgtctggt atcagccctc atgaggactt ctcttctttc cctcatagac ctccatctct    6600
gttttcctta gcctgcagaa atctggatgg ctattcacag aatgcctgtg ctttcagagt    6660 tgcattttt ctctggtatt ctggttcaag catttgaagg taggaaaggt tctccaagtg    6720
caagaaagcc agccctgagc ctcaactgcc tggctagtgt ggtcagtagg atgcaaaggc    6780
tgttgaatgc cacaaggcca aactttaacc tgtgtaccac aagcctagca gcagaggcag    6840
ctctgctcac tggaactctc tgtcttcttt ctcctgagcc tttctttc ctgagttttc    6900 tagctctcct caaccttacc tctgccctac ccaggacaaa cccaagagcc actgtttctg    6960
tgatgtcctc tccagcccta attaggcatc atgacttcag cctgaccttc catgctcaga    7020
agcagtgcta atccacttca gatgagctgc tctatgcaac acaggcagag cctacaaacc    7080
tttgcaccag agccctccac atatcagtgt ttgttcatac tcacttcaac agcaaatgtg    7140
actgctgaga ttaagatttt acacaagatg gtctgtaatt tcacagttag ttttatccca    7200
ttaggtatga aagaattagc ataattcccc ttaaacatga atgaatctta gattttttaa    7260
taaatagttt tggaagtaaa gacagagaca tcaggagcac aaggaatagc ctgagaggac    7320
aaacagaaca agaaagagtc tggaaataca caggatgttc ttggcctcct caaagcaagt    7380
gcaagcagat agtaccagca gccccaggct atcagagccc agtgaagaga agtaccatga    7440
aagccacagc tctaaccacc ctgttccaga gtgacagaca gtccccaaga caagccagcc    7500
tgagccagag agagaactgc aagagaaagt ttctaattta ggttctgtta gattcagaca    7560
agtgcaggtc atcctctctc cacagctact cacctctcca gcctaacaaa gcctgcagtc    7620
cacactccaa ccctggtgtc tcacctccta gcctctccca acatcctgct ctctgaccat    7680
cttctgcatc tctcatctca ccatctccca ctgtctacag cctactcttg caactaccat    7740 ctcatttct gacatcctgt ctacatcttc tgccatactc tgccatctac ataccacct    7800 cttaccatct accacaccat ctttatctc catccctctc agaagcctcc aagctgaatc    7860
ctgctttatg tgttcatctc agcccctgca tggaaagctg accccagagg cagaactatt    7920
cccagagagc ttggccaaga aaacaaaac taccagcctg gccaggctca ggagtagtaa    7980
gctgcagtgt ctgttgtgtt ctagcttcaa cagctgcagg agttccactc tcaaatgctc    8040
```

```
cacatttctc acatcctcct gattctggtc actacccatc ttcaaagaac agaatatctc   8100
acatcagcat actgtgaagg actagtcatg ggtgcagctg ctcagagctg caaagtcatt   8160
ctggatggtg gagagcttac aaacatttca tgatgctccc cccgctctga tggctggagc   8220
ccaatcccta cacagactcc tgctgtatgt gttttccttt cactctgagc acagccaga   8280 gggcaggcat tcagtctcct cttcaggctg gggctggggc actgagaact cacccaacac   8340
cttgctctca ctccttctgc aaaacaagaa agagctttgt gctgcagtag ccatgaagaa   8400
tgaaaggaag gctttaacta aaaaatgtca gagattattt tcaaccccctt actgtggatc   8460 accagcaagg aggaaacaca acacagagac atttttccc ctcaaattat caaaagaatc   8520
actgcatttg ttaaagagag caactgaatc aggaagcaga gttttgaaca tatcagaagt   8580
taggaatctg catcagagac aaatgcagtc atggttgttt gctgcatacc agccctaatc   8640
attagaagcc tcatggactt caaacatcat tccctctgac aagatgctct agcctaactc   8700
catgagataa aataaatctg cctttcagag ccaaagaaga gtccaccagc ttcttctcag   8760
tgtgaacaag agctccagtc aggttagtca gtccagtgca gtagaggaga ccagtctgca   8820
tcctctaatt ttcaaaggca agaagatttg tttaccctgg acaccaggca caagtgaggt   8880
cacagagctc ttagatatgc agtcctcatg agtgaggaga ctaaagcgca tgccatcaag   8940
acttcagtgt agagaaaacc tccaaaaaag cctcctcact acttctggaa tagctcagag   9000
gccgaggcgg cctcggcctc tgcataaata aaaaaaatta gtcagccatg gggcggagaa   9060
tgggcggaac tgggcggagt taggggcggg atgggcggag ttaggggcgg gactatggtt   9120
gctgactaat tgagatgcat gctttgcata cttctgcctg ctggggagcc tggggactt   9180 ccacacctgg ttgctgacta attgagatgc atgctttgca tacttctgcc tgctggggag   9240
cctggggact ttccacaccc taactgacac acattccaca gctgcattaa tgaatcggcc   9300
aacgcgcggg gagaggcggt ttgcgtattg ggcgctcttc cgcttcctcg ctcactgact   9360
cgctgcgctc ggtcgttcgg ctgcggcgag cggtatcagc tcactcaaag gcggtaatac   9420
ggttatccac agaatcaggg gataacgcag gaaagaacat gtgagcaaaa ggccagcaaa   9480
aggccaggaa ccgtaaaaag gccgcgttgc tggcgttttt ccataggctc cgcccccctg   9540
acgagcatca caaaaatcga cgctcaagtc agaggtggcg aaacccgaca ggactataaa   9600
gataccaggc gtttccccct ggaagctccc tcgtgcgctc tcctgttccg accctgccgc   9660
ttaccggata cctgtccgcc tttctccctt cgggaagcgt ggcgctttct catagctcac   9720
gctgtaggta tctcagttcg gtgtaggtcg ttcgctccaa gctgggctgt gtgcacgaac   9780
cccccgttca gcccgaccgc tgcgccttat ccggtaacta tcgtcttgag tccaacccgg   9840
taagacacga cttatcgcca ctggcagcag ccactggtaa caggattagc agagcgaggt   9900
atgtaggcgg tgctacagag ttcttgaagt ggtggcctaa ctacggctac actagaagaa   9960
cagtatttgg tatctgcgct ctgctgaagc cagttacctt cggaaaaaga gttggtagct   10020
cttgatccgg caaacaaacc accgctggta gcggtggttt ttttgtttgc aagcagcaga   10080
ttacgcgcag aaaaaaagga tctcaagaag atccttttgat cttttctacg gggtctgacg   10140
ctcagtggaa cgaaaactca cgttaaggga ttttggtcat gagattatca aaaggatct   10200 tcacctagat ccttttaaat taaaaatgaa gttttaaatc aatctaaagt atatatgagt   10260
aaacttggtc tgacagttac caatgcttaa tcagtgaggc acctatctca gcgatctgtc   10320
tatttcgttc atccatagtt gcctgactcc tgcaaaccac gttgtgtctc aaaatctctg   10380
atgttacatt gcacaagata aaaatatatc atcatgaaca ataaaactgt ctgcttacat   10440
```

```
aaacagtaat acaaggggtg ttatgagcca tattcaacgg gaaacgtctt gctcgaggcc     10500
gcgattaaat tccaacatgg atgctgattt atatgggtat aaatgggctc gcgataatgt     10560
cgggcaatca ggtgcgacaa tctatcgatt gtatgggaag cccgatgcgc cagagttgtt     10620
tctgaaacat ggcaaaggta gcgttgccaa tgatgttaca gatgagatgg tcagactaaa     10680
ctggctgacg gaatttatgc ctcttccgac catcaagcat tttatccgta ctcctgatga     10740
tgcatggtta ctcaccactg cgatcccggg aaaacagca ttccaggtat tagaagaata     10800
tcctgattca ggtgaaaata ttgttgatgc gctggcagtg ttcctgcgcc ggttgcattc     10860
gattcctgtt tgtaattgtc cttttaacag cgatcgcgta tttcgtctcg ctcaggcgca     10920
atcacgaatg aataacggtt tggttgatgc gagtgatttt gatgacgagc gtaatggctg     10980
gcctgttgaa caagtctgga aagaaatgca taagcttttg ccattctcac cggattcagt     11040
cgtcactcat ggtgatttct cacttgataa ccttattttt gacgagggga aattaatagg     11100
ttgtattgat gttggacgag tcggaatcgc agaccgatac caggatcttg ccatcctatg     11160
gaactgcctc ggtgagtttt ctccttcatt acagaaacgg cttttcaaa aatatggtat     11220 tgataatcct gatatgaata aattgcagtt tcatttgatg ctcgatgagt ttttctaagg     11280
gcggcctgcc accataccca cgccgaaaca agcgctcatg agcccgaagt ggcgagcccg     11340
atcttcccca tcggtgatgt cggcgatata ggcgccagca accgcacctg tggcgccggt     11400
gatgagggcg cgccaagtcg acgtccggca gtc                                  11433

<210> SEQ ID NO 43
<211> LENGTH: 11776
<212> TYPE: DNA
<213> ORGANISM: Artificial sequence
<220> FEATURE:
<223> OTHER INFORMATION: Synthetic polynucleotide

<400> SEQUENCE: 43
ttggccactc cctctctgcg cgctcgctcg ctcactgagg ccgggcgacc aaaggtcgcc         60
cgacgcccgg gctttgcccg ggcggcctca gtgagcgagc gagcgcgcag agagggagtg        120
gccaactcca tcactagggg ttcctgctag ctctgggtat ttaagcccga gtgagcacgc        180
agggtctcca ttttgaagcg ggaggttacg cgttcgtcga ctactagtgg gtaccagagc        240
tccctaggtt ctagaaccgg tgacgtctcc catggtgaag cttggatctg agggcggagt        300
tagggcggag ccaatcagcg tgcgccgttc cgaaagttgc cttttatggc tgggcggaga        360
atgggcggtg aacgccgatg attatataag gacgcgccgg gtgtggcaca gctagttccg        420
tcgcagccgg gatttgggtc gcggttcttg tttgtggatc cctgtgatcg tcacttggta        480
agtcactgac tgtctatgcc tgggaaaggg tgggcaggag atgggcagt gcaggaaaag        540 tggcactatg aaccctgcag ccctaggaat gcatctagac aattgtacta accttcttct        600 cttttcctctc ctgacagtcc ggaaagccac catggccgag tggctgctga gcgccagctg        660
gcagcgccgc gccaaggcca tgaccgccgc cgccggcagc gccggccgcg ccgccgtgcc        720
cctgctgctg tgcgccctgc tggccccgg cggcgcctac gtgctggacg acagcgacgg        780
cctgggccgc gagttcgacg gcatcggcgc cgtgagcggc ggcggcgcca ccagccgcct        840
gctggtgaac taccccgagc cctaccgcag ccagatcctg gactacctgt tcaagcccaa        900
cttcggcgcc agcctgcaca tcctgaaggt ggagatcggc ggcgacgcc agaccaccga        960 cggcaccgag cccagccaca tgcactacgc cctggacgag aactacttcc gcggctacga       1020
```

```
gtggtggctg atgaaggagg ccaagaagcg caaccccaac atcaccctga tcggcctgcc    1080
ctggagcttc cccggctggc tgggcaaggg cttcgactgg ccctacgtga acctgcagct    1140
gaccgcctac tacgtggtga cctggatcgt gggcgccaag cgctaccacg acctggacat    1200
cgactacatc ggcatctgga acgagcgcag ctacaacgcc aactacatca agatcctgcg    1260
caagatgctg aactaccagg gcctgcagcg cgtgaagatc atcgccagcg acaacctgtg    1320
ggagagcatc agcgccagca tgctgctgga cgccgagctg ttcaaggtgg tggacgtgat    1380
cggcgcccac taccccggca cccacagcgc caaggacgcc aagctgaccg gcaagaagct    1440
gtggagcagc gaggacttca gcaccctgaa cagcgacatg ggcgccggct gctggggccg    1500
catcctgaac cagaactaca tcaacggcta catgaccagc accatcgcct ggaacctggt    1560
ggccagctac tacgagcagc tgccctacgg ccgctgcggc ctgatgaccg cccaggagcc    1620
ctggagcggc cactacgtgg tggagagccc cgtgtgggtg agcgcccaca ccacccagtt    1680
cacccagccc ggctggtact acctgaagac cgtgggccac ctggagaagg gcggcagcta    1740
cgtggccctg accgacggcc tgggcaacct gaccatcatc atcgagacca tgagccacaa    1800
gcacagcaag tgcatccgcc ccttcctgcc ctacttcaac gtgagccagc agttcgccac    1860
cttcgtgctg aagggcagct tcagcgagat ccccgagctg caggtgtggt acaccaagct    1920
gggcaagacc agcgagcgct tcctgttcaa gcagctggac agcctgtggc tgctggacag    1980
cgacggcagc ttcaccctga gcctgcacga ggacgagctg ttcaccctga ccaccctgac    2040
caccggccgc aagggcagct accccctgcc ccccaagagc cagcccttcc ccagcaccta    2100
caaggacgac ttcaacgtgg actacccctt cttcagcgag gccccaact tcgccgacca    2160 gaccggcgtg ttcgagtact tcaccaacat cgaggacccc ggcgagcacc acttcaccct    2220
gcgccaggtg ctgaaccagc gccccatcac ctgggccgcc gacgccagca acaccatcag    2280
catcatcggc gactacaact ggaccaacct gaccatcaag tgcgacgtgt acatcgagac    2340
ccccgacacc ggcggcgtgt catcgccgg ccgcgtgaac aagggcggca tcctgatccg    2400
cagcgcccgc ggcatcttct tctggatctt cgccaacggc agctaccgcg tgaccggcga    2460
cctggccggc tggatcatct acgccctggg ccgcgtggag gtgaccgcca agaagtggta    2520
caccctgacc ctgaccatca agggccactt caccagcggc atgctgaacg acaagagcct    2580
gtggaccgac atccccgtga acttccccaa gaacggctgg ccgccatcg gcacccacag    2640 cttcgagttc gcccagttcg acaacttcct ggtggaggcc acccgctgat gtggccgaa    2700 ccgccgaact cagaggccgg ccccagaaaa cccgagcgag tagggggcgg cgcgcaggag    2760
ggaggagaac tggggcgcg ggaggctggt gggtgtgggg ggtggagatg tagaagatgt    2820
gacgccgcgg cccggcgggt gccagattag cggacgcgt gcccgcgtt caacgggat    2880 cccgggcgct gcagcttggg aggcggctct ccccaggcgg cgtccgcgga gacacccatc    2940
cgtgaacccc aggtccgggg ccgccggctc gccgcgcacc aggggccggc ggacagaaga    3000
gcggccgagc ggctcgaggc tggggaccg cgggcgcgg cgcgcgctgc cgggcggag    3060 gctggggggc cggggccggg gccgtgcccc ggagcgggtc ggaggccggg gccggggccg    3120
ggggacggcg gctcccgcg cggctccagc ggctcgggga tccggccgg ccccgcagg    3180 gaccatgatg gaattcagca gccccagcag agaggaatgc cccaagcctc tgagccgggt    3240
gtcaatcatg gccggatctc tgacaggact gctgctgctt caggccgtgt cttgggcttc    3300
tggcgctaga ccttgcatcc ccaagagctt cggctacagc agcgtcgtgt gcgtgtgcaa    3360
tgccacctac tgcgacagct tcgaccctcc tacctttcct gctctgggca ccttcagcag    3420
```

```
atacgagagc accagatccg gcagacggat ggaactgagc atgggaccca tccaggccaa   3480
tcacacaggc actggcctgc tgctgacact gcagcctgag cagaaattcc agaaagtgaa   3540
aggcttcggc ggagccatga cagatgccgc cgctctgaat atcctggctc tgtctccacc   3600
agctcagaac ctgctgctca agagctactt cagcgaggaa ggcatcggct acaacatcat   3660
cagagtgccc atggccagct gcgacttcag catcaggacc tacacctacg ccgacacacc   3720
cgacgatttc cagctgcaca acttcagcct gcctgaagag gacaccaagc tgaagatccc   3780
tctgatccac agagccctgc agctggcaca agacccgtg tcactgctgg cctctccatg   3840
gacatctccc acctggctga aaacaaatgg cgccgtgaat ggcaagggca gcctgaaagg   3900
ccaacctggc gacatctacc accagacctg gccagatac ttcgtgaagt tcctggacgc   3960
ctatgccgag cacaagctgc agttttgggc cgtgacagcc gagaacgaac cttctgctgg   4020
actgctgagc ggctacccct ttcagtgcct gggctttaca cccgagcacc agcgggactt   4080
tatcgcccgt gatctgggac ccacactggc caatagcacc caccataatg tgcggctgct   4140
gatgctggac gaccagagac tgcttctgcc ccactgggct aaagtggtgc tgacagatcc   4200
tgaggccgcc aaatacgtgc acggaatcgc cgtgcactgg tatctggact ttctggcccc   4260
tgccaaggcc acactgggag agacacacag actgttcccc aacaccatgc tgttcgccag   4320
cgaagcctgt gtgggcagca gttttggga acagagcgtg cggctcggca gctgggatag   4380
aggcatgcag tacagccaca gcatcatcac caacctgctg taccacgtcg tcggctggac   4440
cgactggaat ctggccctga tcctgaagg cggccctaac tgggtccgaa acttcgtgga   4500
cagccccatc atcgtggaca tcaccaagga caccttctac aagcagccca tgttctacca   4560
cctgggacac ttcagcaagt tcatccccga gggctctcag cgcgttggac tggtggcttc   4620
ccagaagaac gatctggacg ccgtggctct gatgcaccct gatggatctg ctgtggtggt   4680
ggtcctgaac cgcagcagca agatgtgcc cctgaccatc aaggatcccg ccgtgggatt   4740
cctgaaaaca atcagccctg ctactccat ccacacctac ctgtggcgta cagagtgaca   4800
attgttaatt aagtttaaac cctcgaggcc gcaagcaata aaatatcttt attttcatta   4860
catctgtgtg ttggtttttt gtgtggagat ccacgataac aaacagcttt tttggggtga   4920
acatattgac tgaattccct gcaggttggc cactccctct ctgcgcgctc gctcgctcac   4980
tgaggccgcc cgggcaaagc ccgggcgtcg ggcgaccttt ggtcgcccgg cctcagtgag   5040
cgagcgagcg cgcagagagg gagtggccaa ctccatcact aggggttcct gcggccgctc   5100
gtacggtctc gaggaattcc tgcaggataa cttgccaacc tcattctaaa atgtatatag   5160
aagcccaaaa gacaataaca aaaatattct tgtagaacaa atgggaaag aatgttccac   5220 taaatatcaa gatttagagc aaagcatgag atgtgtgggg atagacagtg aggctgataa   5280
aatagagtag agctcagaaa cagacccatt gatatatgta agtgacctat gaaaaaaata   5340 tggcattttta caatgggaaa atgatggtct ttttcttttt tagaaaaaca gggaaatata   5400
tttatatgta aaaaataaaa gggaacccat atgtcatacc atacacacaa aaaaattcca   5460
gtgaattata agtctaaatg gagaaggcaa aactttaaat ctttttagaaa ataatataga   5520 agcatgcaga ccagcctggc caacatgatg aaaccctctc tactaataat aaaatcagta   5580
gaactactca ggactacttt gagtgggaag tccttttcta tgaagacttc tttggccaaa   5640
attaggctct aaatgcaagg agatagtgca tcatgcctgg ctgcacttac tgataaatga   5700
tgttatcacc atctttaacc aaatgcacag gaacaagtta tggtactgat gtgctggatt   5760
```

```
gagaaggagc tctacttcct tgacaggaca catttgtatc aacttaaaaa agcagatttt    5820
tgccagcaga actattcatt cagaggtagg aaacttagaa tagatgatgt cactgattag    5880
catggcttcc ccatctccac agctgcttcc cacccaggtt gcccacagtt gagtttgtcc    5940
agtgctcagg gctgcccact ctcagtaaga agccccacac cagcccctct ccaaatatgt    6000
tggctgttcc ttccattaaa gtgacccccac tttagagcag caagtggatt tctgtttctt    6060
acagttcagg aaggaggagt cagctgtgag aacctggagc ctgagatgct tctaagtccc    6120
actgctactg gggtcaggga agccagactc cagcatcagc agtcaggagc actaagccct    6180
tgccaacatc ctgtttctca gagaaactgc ttccattata atggttgtcc tttttttaagc   6240 tatcaagcca aacaaccagt gtctaccatt attctcatca cctgaagcca agggttctag    6300
caaaagtcaa gctgtcttgt aatggttgat gtgcctccag cttctgtctt cagtcactcc    6360
actcttagcc tgctctgaat caactctgac cacagttccc tggagcccct gccacctgct    6420 gccccctgcca ccttctccat ctgcagtgct gtgcagcctt ctgcactctt gcagagctaa   6480
taggtggaga cttgaaggaa gaggaggaaa gtttctcata atagccttgc tgcaagctca    6540
aatgggaggt gggcactgtg cccaggagcc ttggagcaaa ggctgtgccc aacctctgac    6600
tgcatccagg tttggtcttg acagagataa gaagccctgg cttttggagc caaaatctag    6660
gtcagactta ggcaggattc tcaaagttta tcagcagaac atgaggcaga agacccttttc   6720 tgctccagct tcttcaggct caaccttcat cagaatagat agaaagagag gctgtgaggg    6780
ttcttaaaac agaagcaaat ctgactcaga gaataaacaa cctcctagta aactacagct    6840
tagacagagc atctggtggt gagtgtgctc agtgtcctac tcaactgtct ggtatcagcc    6900
ctcatgagga cttctcttct ttccctcata gacctccatc tctgttttcc ttagcctgca    6960
gaaatctgga tggctattca cagaatgcct gtgctttcag agttgcattt tttctctggt    7020
attctggttc aagcatttga aggtaggaaa ggttctccaa gtgcaagaaa gccagccctg    7080
agcctcaact gcctggctag tgtggtcagt aggatgcaaa ggctgttgaa tgccacaagg    7140
ccaaacttta acctgtgtac cacaagccta gcagcagagg cagctctgct cactggaact    7200
ctctgtcttc tttctcctga gccttttctt ttcctgagtt ttctagctct cctcaacctt    7260
acctctgccc tacccaggac aaacccaaga gccactgttt ctgtgatgtc ctctccagcc    7320
ctaattaggc atcatgactt cagcctgacc ttccatgctc agaagcagtg ctaatccact    7380
tcagatgagc tgctctatgc aacacaggca gagcctacaa acctttgcac cagagccctc    7440
cacatatcag tgtttgttca tactcacttc aacagcaaat gtgactgctg agattaagat    7500
tttacacaag atggtctgta atttcacagt tagtttttatc ccattaggta tgaaagaatt    7560
agcataattc cccttaaaca tgaatgaatc ttagattttt taataaatag ttttggaagt    7620
aaagacagag acatcaggag cacaaggaat agcctgagag gacaaacaga acaagaaaga    7680
gtctggaaat acacaggatg ttcttggcct cctcaaagca agtgcaagca gatagtacca    7740
gcagccccag gctatcagag cccagtgaag agaagtacca tgaaagccac agctctaacc    7800
accctgttcc agagtgacag acagtcccca agacaagcca gcctgagcca gagagagaac    7860
tgcaagagaa agtttctaat ttaggttctg ttagattcag acaagtgcag gtcatcctct    7920
ctccacagct actcacctct ccagcctaac aaagcctgca gtccacactc caaccctggt    7980
gtctcacctc ctagcctctc ccaacatcct gctctctgac catcttctgc atctctcatc    8040
tcaccatctc ccactgtcta cagcctactc ttgcaactac catctcattt tctgacatct    8100
tgtctacatc ttctgccata ctctgccatc taccatacca cctcttacca tctaccacac    8160
```

```
catcttttat ctccatccct ctcagaagcc tccaagctga atcctgcttt atgtgttcat   8220
ctcagcccct gcatggaaag ctgacccag  aggcagaact attcccagag agcttggcca   8280
agaaaaacaa aactaccagc ctggccaggc tcaggagtag taagctgcag tgtctgttgt   8340
gttctagctt caacagctgc aggagttcca ctctcaaatg ctccacattt ctcacatcct   8400
cctgattctg gtcactaccc atcttcaaag aacagaatat ctcacatcag catactgtga   8460
aggactagtc atgggtgcag ctgctcagag ctgcaaagtc attctggatg gtggagagct   8520
tacaaacatt tcatgatgct ccccccgctc tgatggctgg agcccaatcc ctacacagac   8580
tcctgctgta tgtgttttcc tttcactctg agccacagcc agagggcagg cattcagtct   8640
cctcttcagg ctggggctgg ggcactgaga actcacccaa caccttgctc tcactccttc   8700
tgcaaaacaa gaaagagctt tgtgctgcag tagccatgaa gaatgaaagg aaggctttaa   8760
ctaaaaaatg tcagagatta ttttcaaccc cttactgtgg atcaccagca aggaggaaac   8820
acaacacaga gacatttttt cccctcaaat tatcaaaaga atcactgcat ttgttaaaga   8880
gagcaactga atcaggaagc agagttttga acatatcaga agttaggaat ctgcatcaga   8940
gacaaatgca gtcatggttg tttgctgcat accagcccta atcattagaa gcctcatgga   9000
cttcaaacat cattccctct gacaagatgc tctagcctaa ctccatgaga taaaataaat   9060
ctgcctttca gagccaaaga agagtccacc agcttcttct cagtgtgaac aagagctcca   9120
gtcaggttag tcagtccagt gcagtagagg agaccagtct gcatcctcta attttcaaag   9180
gcaagaagat ttgtttaccc tggacaccag gcacaagtga ggtcacagag ctcttagata   9240
tgcagtcctc atgagtgagg agactaaagc gcatgccatc aagacttcag tgtagagaaa   9300
acctccaaaa aagcctcctc actacttctg gaatagctca gaggccgagg cggcctcggc   9360
ctctgcataa ataaaaaaaa ttagtcagcc atggggcgga gaatgggcgg aactgggcgg   9420
agttaggggc gggatggggcg gagttagggg cgggactatg gttgctgact aattgagatg   9480
catgctttgc atacttctgc ctgctgggga gcctgggac  tttccacacc tggttgctga   9540
ctaattgaga tgcatgcttt gcatacttct gcctgctggg gagcctgggg actttccaca   9600
ccctaactga cacacattcc acagctgcat taatgaatcg gccaacgcgc ggggagaggc   9660
ggtttgcgta ttgggcgctc ttccgcttcc tcgctcactg actcgctgcg ctcggtcgtt   9720
cggctgcggc gagcggtatc agctcactca aaggcggtaa tacggttatc cacagaatca   9780
ggggataacg caggaaagaa catgtgagca aaaggccagc aaaaggccag gaaccgtaaa   9840
aaggccgcgt tgctggcgtt tttccatagg ctccgccccc ctgacgagca tcacaaaaat   9900
cgacgctcaa gtcagaggtg gcgaaacccg acaggactat aaagatacca ggcgtttccc   9960
cctggaagct ccctcgtgcg ctctcctgtt ccgaccctgc cgcttaccgg atacctgtcc  10020
gcctttctcc cttcgggaag cgtggcgctt tctcatagct cacgctgtag gtatctcagt  10080
tcggtgtagg tcgttcgctc caagctgggc tgtgtgcacg aaccccccgt tcagcccgac  10140
cgctgcgcct tatccggtaa ctatcgtctt gagtccaacc cggtaagaca cgacttatcg  10200
ccactggcag cagccactgg taacaggatt agcagagcga ggtatgtagg cggtgctaca  10260
gagttcttga agtggtggcc taactacggc tacactagaa gaacagtatt tggtatctgc  10320
gctctgctga agccagttac cttcggaaaa agagttggta gctcttgatc cggcaaacaa  10380
accaccgctg gtagcggtgg tttttttgtt tgcaagcagc agattacgcg cagaaaaaaa  10440
ggatctcaag aagatccttt gatcttttct acggggtctg acgctcagtg gaacgaaaac  10500
```

| | |
|---|---|
| tcacgttaag ggattttggt catgagatta tcaaaaagga tcttcaccta gatccttta | 10560 |
| aattaaaaat gaagttttaa atcaatctaa agtatatatg agtaaacttg gtctgacagt | 10620 |
| taccaatgct taatcagtga ggcacctatc tcagcgatct gtctatttcg ttcatccata | 10680 |
| gttgcctgac tcctgcaaac cacgttgtgt ctcaaaatct ctgatgttac attgcacaag | 10740 |
| ataaaaatat atcatcatga acaataaaac tgtctgctta cataaacagt aatacaaggg | 10800 |
| gtgttatgag ccatattcaa cgggaaacgt cttgctcgag gccgcgatta aattccaaca | 10860 |
| tggatgctga tttatatggg tataaatggg ctcgcgataa tgtcgggcaa tcaggtgcga | 10920 |
| caatctatcg attgtatggg aagcccgatg cgccagagtt gtttctgaaa catggcaaag | 10980 |
| gtagcgttgc caatgatgtt acagatgaga tggtcagact aaactggctg acggaattta | 11040 |
| tgcctcttcc gaccatcaag catttttatcc gtactcctga tgatgcatgg ttactcacca | 11100 |
| ctgcgatccc cgggaaaaca gcattccagg tattagaaga atatcctgat tcaggtgaaa | 11160 |
| atattgttga tgcgctggca gtgttcctgc gccggttgca ttcgattcct gtttgtaatt | 11220 |
| gtcctttaa cagcgatcgc gtatttcgtc tcgctcaggc gcaatcacga atgaataacg | 11280 |
| gtttggttga tgcgagtgat tttgatgacg agcgtaatgg ctggcctgtt gaacaagtct | 11340 |
| ggaaagaaat gcataagctt ttgccattct caccggattc agtcgtcact catggtgatt | 11400 |
| tctcacttga taaccttatt tttgacgagg ggaaattaat aggttgtatt gatgttggac | 11460 |
| gagtcggaat cgcagaccga taccaggatc ttgccatcct atggaactgc ctcggtgagt | 11520 |
| tttctccttc attacagaaa cggctttttc aaaaatatgg tattgataat cctgatatga | 11580 |
| ataaattgca gtttcatttg atgctcgatg agttttttcta agggcggcct gccaccatac | 11640 |
| ccacgccgaa acaagcgctc atgagcccga agtggcgagc ccgatcttcc ccatcggtga | 11700 |
| tgtcggcgat ataggcgcca gcaaccgcac ctgtggcgcc ggtgatgagg gcgcgccaag | 11760 |
| tcgacgtccg gcagtc | 11776 |

<210> SEQ ID NO 44
<211> LENGTH: 11064
<212> TYPE: DNA
<213> ORGANISM: Artificial sequence
<220> FEATURE:
<223> OTHER INFORMATION: Synthetic polynucleotide

<400> SEQUENCE: 44

| | |
|---|---|
| ttggccactc cctctctgcg cgctcgctcg ctcactgagg ccgggcgacc aaaggtcgcc | 60 |
| cgacgcccgg gctttgcccg gcggcctca gtgagcgagc gagcgcgcag agagggagtg | 120 |
| gccaactcca tcactagggg ttcctgctag ctctgggtat ttaagcccga gtgagcacgc | 180 |
| agggtctcca ttttgaagcg ggaggttacg cgttcgtcga ctactagtgg gtaccagagc | 240 |
| tccctaggtt ctagaaccgg tgacgtctcc catggtgaag cttggatctg agggcggagt | 300 |
| tagggcggag ccaatcagcg tgcgccgttc cgaaagttgc cttttatggc tgggcggaga | 360 |
| atgggcggtg aacgccgatg attatataag gacgcgccgg gtgtggcaca gctagttccg | 420 |
| tcgcagccgg gatttgggtc gcggttcttg tttgtggatc cctgtgatcg tcacttggta | 480 |
| agtcactgac tgtctatgcc tgggaaaggg tgggcaggag atgggcagt gcaggaaaag | 540 |
| tggcactatg aaccctgcag ccctaggaat gcatctagac aattgtacta accttcttct | 600 |
| ctttcctctc ctgacagtcc ggaaagccac catggaattc agcagcccca gcagagagga | 660 |
| atgccccaag cctctgagcc gggtgtcaat catggccgga tctctgacag gactgctgct | 720 |
| gcttcaggcc gtgtcttggg cttctggcgc tagaccttgc atccccaaga gcttcggcta | 780 |

```
cagcagcgtc gtgtgcgtgt gcaatgccac ctactgcgac agcttcgacc ctcctacctt      840
tcctgctctg ggcaccttca gcagatacga gagcaccaga tccggcagac ggatggaact      900
gagcatggga cccatccagg ccaatcacac aggcactggc ctgctgctga cactgcagcc      960
tgagcagaaa ttccagaaag tgaaaggctt cggcggagcc atgacagatg ccgccgctct     1020
gaatatcctg ctctgtctc caccagctca gaacctgctg ctcaagagct acttcagcga      1080
ggaaggcatc ggctacaaca tcatcagagt gcccatggcc agctgcgact cagcatcag      1140
gacctacacc tacgccgaca cacccgacga tttccagctg cacaacttca gcctgcctga     1200
agaggacacc aagctgaaga tccctctgat ccacagagcc ctgcagctgg cacaaagacc     1260
cgtgtcactg ctggcctctc catggacatc tcccacctgg ctgaaaacaa atggcgccgt     1320
gaatggcaag gcagcctga aaggccaacc tggcgacatc taccaccaga cctgggccag      1380
atacttcgtg aagttcctgg acgcctatgc cgagcacaag ctgcagtttt gggccgtgac     1440
agccgagaac gaaccttctg ctggactgct gagcggctac ccctttcagt gcctgggctt     1500
tacacccgag caccagcggg actttatcgc ccgtgatctg ggacccacac tggccaatag     1560
cacccaccat aatgtgcggc tgctgatgct ggacgaccag agactgcttc tgccccactg     1620
ggctaaagtg gtgctgacag atcctgaggc cgccaaatac gtgcacggaa tcgccgtgca     1680
ctggtatctg gactttctgg cccctgccaa ggccacactg ggagagacac acagactgtt     1740
ccccaacacc atgctgttcg ccagcgaagc ctgtgtgggc agcaagtttt gggaacagag     1800
cgtgcggctc ggcagctggg atagaggcat gcagtacagc cacagcatca tcaccaacct     1860
gctgtaccac gtcgtcggct ggaccgactg gaatctggcc ctgaatcctg aaggcggccc     1920
taactgggtc cgaaacttcg tggacagccc catcatcgtg gacatcacca aggacacctt     1980
ctacaagcag cccatgttct accacctggg acacttcagc aagttcatcc ccgagggctc     2040
tcagcgcgtt ggactggtgg cttcccagaa gaacgatctg gacgccgtgg ctctgatgca     2100
ccctgatgga tctgctgtgg tggtggtcct gaaccgcagc agcaaagatg tgccctgac     2160
catcaaggat cccgccgtgg gattcctgga acaatcagc cctggctact ccatccacac      2220
ctacctgtgg cgtagacagt gacaattgtt aattaagttt aaaccctcga ggccgcaagc     2280
cgcatcgata ccgtcgacta gagctcgctg atcagcctcg actgtgcctt ctagttgcca     2340
gccatctgtt gtttgcccct cccccgtgcc ttccttgacc ctggaaggtg ccactcccac     2400
tgtcctttcc taataaaatg aggaaattgc atcgcattgt ctgagtaggt gtcattctat     2460
tctggggggt gggtgggggc aggacagcaa ggggaggat tggaagaca atagcaggca       2520
tgctggggag agatccacga taacaaacag cttttttggg ggcggagt tagggcggag       2580
ccaatcagcg tgcgccgttc cgaaagttgc cttttatggc tgggcggaga atgggcggtg     2640
aacgccgatg attatataag gacgcgccgg gtgtggcaca gctagttccg tcgcagccgg     2700
gatttgggtc gcggttcttg tttgtggatc cctgtgatcg tcacttggta agtcactgac     2760
tgtctatgcc tgggaaaggg tgggcaggag atggggcagt gcaggaaaag tggcactatg     2820
aaccctgcag ccctaggaat gcatctagac aattgtacta accttcttct ctttcctctc     2880
ctgacagtcc ggaaagccac catgtggcag ctgtgggcca gctgtgctg cctgctggtg     2940
ctggccaacg cccgcagccg ccccagcttc acccccctga gcgacgagct ggtgaactac     3000
gtgaacaagc gcaacaccac ctggcaggcc ggccacaact tctacaacgt ggacatgagc     3060
tacctgaagc gcctgtgcgg caccttcctg ggcggcccca gcccccccca gcgcgtgatg     3120
```

-continued

```
ttcaccgagg acctgaagct gcccgccagc ttcgacgccc gcgagcagtg gccccagtgc      3180
cccaccatca aggagatccg cgaccagggc agctgcggca gctgctgggc cttcggcgcc      3240
gtggaggcca tcagcgaccg catctgcatc cacaccaacg cccacgtgag cgtggaggtg      3300
agcgccgagg acctgctgac ctgctgcggc agcatgtgcg cgacggctg caacggcggc       3360 taccccgccg aggcctggaa cttctggacc cgcaagggcc tggtgagcgg cggcctgtac      3420
gagagccacg tgggctgccg cccctacagc atccccccct gcgagcacca cgtgaacggc      3480
agccgccccc cctgcaccgg cgagggcgac accccaagt gcagcaagat ctgcgagccc       3540
ggctacagcc ccacctacaa gcaggacaag cactacggct acaacagcta cagcgtgagc      3600
aacagcgaga aggacatcat ggccgagatc tacaagaacg gccccgtgga gggcgccttc      3660
agcgtgtaca cgcgacttcct gctgtacaag agcggcgtgt accagcacgt gaccggcgag     3720
atgatgggcg ccacgccat ccgcatcctg ggctggggcg tggagaacgg cacccctac        3780 tggctggtgg ccaacagctg gaacaccgac tggggcgaca cggcttctt caagatcctg       3840 cgcggccagg accactgcgg catcgagagc gaggtggtgg ccggcatccc ccgcaccgac      3900
cagtactggg agaagatctg acccagggga ctcagcggcc gctcgagtct agagggcccg      3960
tttaaacccg ctgatcagcc tcgaagacat gataagatac attgatgagt ttggacaaac      4020
cacaacaaga atgcagtgaa aaaaatgctt tatttgtgaa atttgtgatg ctattgcttt      4080
atttgtaacc attataagct gcaataaaca agttaacaac aacaattgca ttcattttat      4140
gtttcaggtt cagggggaga tgtgggaggt tttttaaagc aagtaaaacc tctacaaatg      4200
tggtatgaac atattgactg aattccctgc aggttggcca ctccctctct gcgcgctcgc      4260
tcgctcactg aggccgcccg ggcaaagccc gggcgtcggg cgacctttgg tcgcccggcc      4320
tcagtgagcg agcgagcgcg cagagaggga gtggccaact ccatcactag ggttcctgc       4380 ggccgctcgt acggtctcga ggaattcctg caggataact tgccaacctc attctaaaat      4440
gtatatagaa gcccaaaaga caataacaaa aatattcttg tagaacaaaa tgggaaagaa      4500
tgttccacta aatatcaaga tttagagcaa agcatgagat gtgtggggat agacagtgag      4560
gctgataaaa tagagtagag ctcagaaaca gacccattga tatatgtaag tgacctatga      4620
aaaaaatatg gcattttaca atgggaaaat gatggtcttt ttcttttta gaaaacagg        4680 gaaatatatt tatatgtaaa aaataaaagg gaacccatat gtcataccat acacacaaaa      4740
aaattccagt gaattataag tctaaatgga gaaggcaaaa cttttaaatct tttagaaaat     4800 aatatagaag catgcagacc agcctggcca acatgatgaa accctctcta ctaataataa      4860
aatcagtaga actactcagg actactttga gtgggaagtc cttttctatg aagacttctt      4920
tggccaaaat taggctctaa atgcaaggag atagtgcatc atgcctggct gcacttactg      4980
ataaatgatg ttatcaccat ctttaaccaa atgcacagga acaagttatg gtactgatgt      5040
gctggattga gaaggagctc tacttccttg acaggacaca tttgtatcaa cttaaaaaag      5100 cagattttg ccagcagaac tattcattca gaggtaggaa acttagaata gatgatgtca      5160
ctgattagca tggcttcccc atctccacag ctgcttccca cccaggttgc ccacagttga      5220
gtttgtccag tgctcaggc tgcccactct cagtaagaag ccccacacca gcccctctcc       5280
aaatatgttg gctgttcctt ccattaaagt gaccccactt tagagcagca agtggatttc      5340
tgtttcttac agttcaggaa ggaggagtca gctgtgagaa cctggagcct gagatgcttc      5400 taagtccac tgctactggg gtcagggaag ccagactcca gcatcagcag tcaggagcac       5460
taagcccttg ccaacatcct gtttctcaga gaaactgctt ccattataat ggttgtcctt      5520
```

-continued

```
ttttaagcta tcaagccaaa caaccagtgt ctaccattat tctcatcacc tgaagccaag   5580
ggttctagca aaagtcaagc tgtcttgtaa tggttgatgt gcctccagct tctgtcttca   5640
gtcactccac tcttagcctg ctctgaatca actctgacca cagttccctg gagcccctgc   5700
cacctgctgc ccctgccacc ttctccatct gcagtgctgt gcagccttct gcactcttgc   5760
agagctaata ggtggagact tgaaggaaga ggaggaaagt ttctcataat agccttgctg   5820
caagctcaaa tgggaggtgg gcactgtgcc caggagcctt ggagcaaagg ctgtgcccaa   5880
cctctgactg catccaggtt tggtcttgac agagataaga agccctggct tttggagcca   5940
aaatctaggt cagacttagg caggattctc aaagtttatc agcagaacat gaggcagaag   6000
accctttctg ctccagcttc ttcaggctca accttcatca gaatagatag aaagagaggc   6060
tgtgagggtt cttaaaacag aagcaaatct gactcagaga ataaacaacc tcctagtaaa   6120
ctacagctta gacagagcat ctggtggtga gtgtgctcag tgtcctactc aactgtctgg   6180
tatcagccct catgaggact tctcttcttt ccctcataga cctccatctc tgttttcctt   6240
agcctgcaga atctggatg gctattcaca gaatgcctgt gctttcagag ttgcattttt   6300
tctctggtat tctggttcaa gcatttgaag gtaggaaagg ttctccaagt gcaagaaagc   6360
cagccctgag cctcaactgc ctggctagtg tggtcagtag gatgcaaagg ctgttgaatg   6420
ccacaaggcc aaactttaac ctgtgtacca caagcctagc agcagaggca gctctgctca   6480
ctggaactct ctgtcttctt tctcctgagc cttttctttt cctgagtttt ctagctctcc   6540
tcaaccttac ctctgcccta cccaggacaa acccaagagc cactgtttct gtgatgtcct   6600
ctccagccct aattaggcat catgacttca gcctgaccct ccatgctcag aagcagtgct   6660
aatccacttc agatgagctg ctctatgcaa cacaggcaga gcctacaaac ctttgcacca   6720
gagccctcca catatcagtg tttgttcata ctcacttcaa cagcaaatgt gactgctgag   6780
attaagattt tacacaagat ggtctgtaat ttcacagtta gttttatccc attaggtatg   6840
aaagaattag cataattccc cttaaacatg aatgaatctt agatttttta ataaatagtt   6900
ttggaagtaa agacagagac atcaggagca caaggaatag cctgagagga caaacagaac   6960
aagaaagagt ctggaaatac acaggatgtt cttggcctcc tcaaagcaag tgcaagcaga   7020
tagtaccagc agccccaggc tatcagagcc cagtgaagag aagtaccatg aaagccacag   7080
ctctaaccac cctgttccag agtgacagac agtccccaag acaagccagc ctgagccaga   7140
gagagaactg caagagaaag tttctaattt aggttctgtt agattcagac aagtgcaggt   7200
catcctctct ccacagctac tcacctctcc agcctaacaa agcctgcagt ccacactcca   7260
accctggtgt ctcacctcct agcctctccc aacatcctgc tctctgacca tcttctgcat   7320
ctctcatctc accatctccc actgtctaca gcctactctt gcaactacca tctcattttc   7380
tgacatcctg tctacatctt ctgccatact ctgccatcta ccataccacc tcttaccatc   7440
taccacacca tcttttatct ccatccctct cagaagcctc caagctgaat cctgctttat   7500
gtgttcatct cagcccctgc atggaaagct gaccccagag gcagaactat tcccagagag   7560
cttggccaag aaaaacaaaa ctaccagcct ggccaggctc aggagtagta agctgcagtg   7620
tctgttgtgt tctagcttca acagctgcag gagttccact ctcaaatgct ccacatttct   7680
cacatcctcc tgattctggt cactacccat cttcaaagaa cagaatatct cacatcagca   7740
tactgtgaag gactagtcat gggtgcagct gctcagagct gcaaagtcat tctgatggt   7800 ggagagctta caaacatttc atgatgctcc ccccgctctg atggctggag cccaatccct   7860
```

```
acacagactc ctgctgtatg tgttttcctt tcactctgag ccacagccag agggcaggca    7920
ttcagtctcc tcttcaggct ggggctgggg cactgagaac tcacccaaca ccttgctctc    7980
actccttctg caaaacaaga aagagctttg tgctgcagta gccatgaaga atgaaaggaa    8040
ggctttaact aaaaaatgtc agagattatt ttcaacccct tactgtggat caccagcaag    8100
gaggaaacac aacacagaga cattttttcc cctcaaatta tcaaaagaat cactgcattt    8160
gttaaagaga gcaactgaat caggaagcag agttttgaac atatcagaag ttaggaatct    8220
gcatcagaga caaatgcagt catggttgtt tgctgcatac cagccctaat cattagaagc    8280
ctcatggact caaacatca ttccctctga caagatgctc tagcctaact ccatgagata    8340
aaataaatct gcctttcaga gccaaagaag agtccaccag cttcttctca gtgtgaacaa    8400
gagctccagt caggttagtc agtccagtgc agtagaggag accagtctgc atcctctaat    8460
tttcaaaggc aagaagattt gtttaccctg gacaccaggc acaagtgagg tcacagagct    8520
cttagatatg cagtcctcat gagtgaggag actaaagcgc atgccatcaa gacttcagtg    8580
tagagaaaac ctccaaaaaa gcctcctcac tacttctgga atagctcaga ggccgaggcg    8640
gcctcggcct ctgcataaat aaaaaaaatt agtcagccat ggggcggaga atgggcggaa    8700
ctgggcggag ttaggggcgg gatgggcgga gttaggggcg ggactatggt tgctgactaa    8760
ttgagatgca tgctttgcat acttctgcct gctgggagc ctgggactt ccacacctg    8820
gttgctgact aattgagatg catgctttgc atacttctgc ctgctgggga gcctgggac    8880
tttccacacc ctaactgaca cacattccac agctgcatta atgaatcggc caacgcgcgg    8940
ggagaggcgg tttgcgtatt gggcgctctt ccgcttcctc gctcactgac tcgctgcgct    9000
cggtcgttcg gctgcggcga gcggtatcag ctcactcaaa ggcggtaata cggttatcca    9060
cagaatcagg ggataacgca ggaaagaaca tgtgagcaaa aggccagcaa aaggccagga    9120
accgtaaaaa ggccgcgttg ctggcgtttt tccataggct ccgcccccct gacgagcatc    9180
acaaaaatcg acgctcaagt cagaggtggc gaaacccgac aggactataa agataccagg    9240
cgtttccccc tggaagctcc ctcgtgcgct ctcctgttcc gaccctgccg cttaccggat    9300
acctgtccgc ctttctccct tcgggaagcg tggcgctttc tcatagctca cgctgtaggt    9360
atctcagttc ggtgtaggtc gttcgctcca agctgggctg tgtgcacgaa ccccccgttc    9420
agcccgaccg ctgcgcctta tccggtaact atcgtcttga gtccaacccg gtaagacacg    9480
acttatcgcc actggcagca gccactggta acaggattag cagagcgagg tatgtaggcg    9540
gtgctacaga gttcttgaag tggtggccta actacggcta cactagaaga acagtatttg    9600
gtatctgcgc tctgctgaag ccagttacct tcggaaaaag agttggtagc tcttgatccg    9660
gcaaacaaac caccgctggt agcggtggtt tttttgtttg caagcagcag attacgcgca    9720
gaaaaaaagg atctcaagaa gatcctttga tcttttctac ggggtctgac gctcagtgga    9780
acgaaaactc acgttaaggg attttggtca tgagattatc aaaaaggatc ttcacctaga    9840
tccttttaaa ttaaaaatga agttttaaat caatctaaag tatatatgag taaacttggt    9900
ctgacagtta ccaatgctta atcagtgagg cacctatctc agcgatctgt ctatttcgtt    9960
catccatagt tgcctgactc ctgcaaacca cgttgtgtct caaaatctct gatgttacat    10020
tgcacaagat aaaaatatat catcatgaac aataaaactg tctgcttaca taaacagtaa    10080
tacaagtgggt gttatgagcc atattcaacg ggaaacgtct tgctcgaggc cgcgattaaa    10140
ttccaacatg gatgctgatt tatatgggta taaatgggct cgcgataatg tcgggcaatc    10200
aggtgcgaca atctatcgat tgtatgggaa gcccgatgcg ccagagttgt ttctgaaaca    10260
```

```
tggcaaaggt agcgttgcca atgatgttac agatgagatg gtcagactaa actggctgac   10320
ggaatttatg cctcttccga ccatcaagca ttttatccgt actcctgatg atgcatggtt   10380
actcaccact gcgatcccg ggaaaacagc attccaggta ttagaagaat atcctgattc    10440
aggtgaaaat attgttgatg cgctggcagt gttcctgcgc cggttgcatt cgattcctgt   10500
ttgtaattgt ccttttaaca gcgatcgcgt atttcgtctc gctcaggcgc aatcacgaat   10560
gaataacggt ttggttgatg cgagtgattt tgatgacgag cgtaatggct ggcctgttga   10620
acaagtctgg aaagaaatgc ataagctttt gccattctca ccggattcag tcgtcactca   10680
tggtgatttc tcacttgata accttatttt tgacgagggg aaattaatag gttgtattga   10740
tgttggacga gtcggaatcg cagaccgata ccaggatctt gccatcctat ggaactgcct   10800
cggtgagttt tctccttcat tacagaaacg gcttttttcaa aaatatggta ttgataatcc   10860
tgatatgaat aaattgcagt ttcatttgat gctcgatgag ttttttctaag gcggcctgc    10920 caccataccc acgccgaaac aagcgctcat gagcccgaag tggcgagccc gatcttcccc   10980
atcggtgatg tcggcgatat aggcgccagc aaccgcacct gtggcgccgg tgatgagggc   11040
gcgccaagtc gacgtccggc agtc                                          11064
```

<210> SEQ ID NO 45
<211> LENGTH: 250
<212> TYPE: PRT
<213> ORGANISM: Artificial sequence
<220> FEATURE:
<223> OTHER INFORMATION: Synthetic polypeptide

<400> SEQUENCE: 45

```
Met Glu Lys Gly Pro Val Arg Ala Pro Ala Glu Lys Pro Arg Gly Ala
1               5                   10                  15

Arg Cys Ser Asn Gly Phe Pro Glu Arg Asp Pro Pro Arg Pro Gly Pro
            20                  25                  30

Ser Arg Pro Ala Glu Lys Pro Arg Pro Glu Ala Lys Ser Ala Gln
        35                  40                  45

Pro Ala Asp Gly Trp Lys Gly Glu Arg Pro Arg Ser Glu Glu Asp Asn
    50                  55                  60

Glu Leu Asn Leu Pro Asn Leu Ala Ala Ala Tyr Ser Ser Ile Leu Ser
65                  70                  75                  80

Ser Leu Gly Glu Asn Pro Gln Arg Gln Gly Leu Leu Lys Thr Pro Trp
                85                  90                  95

Arg Ala Ala Ser Ala Met Gln Phe Phe Thr Lys Gly Tyr Gln Glu Thr
            100                 105                 110

Ile Ser Asp Val Leu Asn Asp Ala Ile Phe Asp Glu Asp His Asp Glu
        115                 120                 125

Met Val Ile Val Lys Asp Ile Asp Met Phe Ser Met Cys Glu His His
    130                 135                 140

Leu Val Pro Phe Val Gly Lys Val His Ile Gly Tyr Leu Pro Asn Lys
145                 150                 155                 160

Gln Val Leu Gly Leu Ser Lys Leu Ala Arg Ile Val Glu Ile Tyr Ser
                165                 170                 175

Arg Arg Leu Gln Val Gln Glu Arg Leu Thr Lys Gln Ile Ala Val Ala
            180                 185                 190

Ile Thr Glu Ala Leu Arg Pro Ala Gly Val Gly Val Val Val Glu Ala
        195                 200                 205
```

Thr His Met Cys Met Val Met Arg Gly Val Gln Lys Met Asn Ser Lys
    210                 215                 220

Thr Val Thr Ser Thr Met Leu Gly Val Phe Arg Glu Asp Pro Lys Thr
225                 230                 235                 240

Arg Glu Glu Phe Leu Thr Leu Ile Arg Ser
            245                 250

<210> SEQ ID NO 46
<211> LENGTH: 750
<212> TYPE: DNA
<213> ORGANISM: Artificial sequence
<220> FEATURE:
<223> OTHER INFORMATION: Synthetic polynucleotide

<400> SEQUENCE: 46

| | | | | | |
|---|---|---|---|---|---|
| atggagaagg | ccccgtgcg | cgcccccgcc | gagaagcccc | gcggcgcccg | ctgcagcaac | 60 |
| ggcttccccg | agcgcgaccc | ccccgcccc | ggccccagcc | gccccgccga | aagcccccc | 120 |
| cgccccgagg | ccaagagcgc | ccagcccgcc | gacggctgga | agggcgagcg | ccccccgcagc | 180 |
| gaggaggaca | cgagctgaa | cctgcccaac | ctggccgccg | cctacagcag | catcctgagc | 240 |
| agcctgggcg | agaaccccca | gcgccagggc | ctgctgaaga | cccctggcg | cgccgccagc | 300 |
| gccatgcagt | tcttcaccaa | gggctaccag | gagaccatca | gcgacgtgct | gaacgacgcc | 360 |
| atcttcgacg | aggaccacga | cgagatggtg | atcgtgaagg | acatcgacat | gttcagcatg | 420 |
| tgcgagcacc | acctggtgcc | cttcgtgggc | aaggtgcaca | tcggctacct | gcccaacaag | 480 |
| caggtgctgg | gcctgagcaa | gctggcccgc | atcgtggaga | tctacagccg | ccgcctgcag | 540 |
| gtgcaggagc | gcctgaccaa | gcagatcgcc | gtggccatca | ccgaggccct | cgccccgcc | 600 |
| ggcgtgggcg | tggtggtgga | ggccacccac | atgtgcatgg | tgatgcgcgg | cgtgcagaag | 660 |
| atgaacagca | agaccgtgac | cagcaccatg | ctgggcgtgt | tccgcgagga | ccccaagacc | 720 |
| cgcgaggagt | tcctgaccct | gatccgcagc | | | | 750 |

<210> SEQ ID NO 47
<211> LENGTH: 203
<212> TYPE: PRT
<213> ORGANISM: Artificial sequence
<220> FEATURE:
<223> OTHER INFORMATION: Synthetic polypeptide

<400> SEQUENCE: 47

Met Gly Ser Arg Asp His Leu Phe Lys Val Leu Val Val Gly Asp Ala
1               5                   10                  15

Ala Val Gly Lys Thr Ser Leu Val Gln Arg Tyr Ser Gln Asp Ser Phe
                20                  25                  30

Ser Lys His Tyr Lys Ser Thr Val Gly Val Asp Phe Ala Leu Lys Val
            35                  40                  45

Leu Gln Trp Ser Asp Tyr Glu Ile Val Arg Leu Gln Leu Trp Asp Ile
    50                  55                  60

Ala Gly Gln Glu Arg Phe Thr Ser Met Thr Arg Leu Tyr Tyr Arg Asp
65                  70                  75                  80

Ala Ser Ala Cys Val Ile Met Phe Asp Val Thr Asn Ala Thr Thr Phe
                85                  90                  95

Ser Asn Ser Gln Arg Trp Lys Gln Asp Leu Asp Ser Lys Leu Thr Leu
            100                 105                 110

Pro Asn Gly Glu Pro Val Pro Cys Leu Leu Leu Ala Asn Lys Cys Asp
        115                 120                 125

Leu Ser Pro Trp Ala Val Ser Arg Asp Gln Ile Asp Arg Phe Ser Lys
            130                 135                 140

Glu Asn Gly Phe Thr Gly Trp Thr Glu Thr Ser Val Lys Glu Asn Lys
145                 150                 155                 160

Asn Ile Asn Glu Ala Met Arg Val Leu Ile Glu Lys Met Met Arg Asn
                165                 170                 175

Ser Thr Glu Asp Ile Met Ser Leu Ser Thr Gln Gly Asp Tyr Ile Asn
                180                 185                 190

Leu Gln Thr Lys Ser Ser Ser Trp Ser Cys Cys
            195                 200

<210> SEQ ID NO 48
<211> LENGTH: 609
<212> TYPE: DNA
<213> ORGANISM: Artificial sequence
<220> FEATURE:
<223> OTHER INFORMATION: Synthetic polynucleotide

<400> SEQUENCE: 48
atgggcagcc gcgaccacct gttcaaggtg ctggtggtgg gcgacgccgc cgtgggcaag      60
accagcctgg tgcagcgcta cagccaggac agcttcagca agcactacaa gagcaccgtg     120
ggcgtggact tcgccctgaa ggtgctgcag tggagcgact acgagatcgt cgcctgcag      180
ctgtgggaca tcgccggcca ggagcgcttc accagcatga cccgcctgta ctaccgcgac     240
gccagcgcct gcgtgatcat gttcgacgtg accaacgcca ccaccttcag caacagccag     300
cgctggaagc aggacctgga cagcaagctg accctgccca cggcgagcc cgtgccctgc      360
ctgctgctgg ccaacaagtg cgacctgagc ccctgggccg tgagccgcga ccagatcgac     420
cgcttcagca aggagaacgg cttcaccggc tggaccgaga ccagcgtgaa ggagaacaag     480
aacatcaacg aggccatgcg cgtgctgatc gagaagatga tgcgcaacag caccgaggac     540
atcatgagcc tgagcaccca gggcgactac atcaacctgc agaccaagag cagcagctgg     600
agctgctgc                                                              609

<210> SEQ ID NO 49
<211> LENGTH: 796
<212> TYPE: PRT
<213> ORGANISM: Artificial sequence
<220> FEATURE:
<223> OTHER INFORMATION: Synthetic polypeptide

<400> SEQUENCE: 49

Met Pro Thr Thr Gln Gln Ser Pro Gln Asp Glu Gln Glu Lys Leu Leu
1               5                   10                  15

Asp Glu Ala Ile Gln Ala Val Lys Val Gln Ser Phe Gln Met Lys Arg
                20                  25                  30

Cys Leu Asp Lys Asn Lys Leu Met Asp Ala Leu Lys His Ala Ser Asn
            35                  40                  45

Met Leu Gly Glu Leu Arg Thr Ser Met Leu Ser Pro Lys Ser Tyr Tyr
        50                  55                  60

Glu Leu Tyr Met Ala Ile Ser Asp Glu Leu His Tyr Leu Glu Val Tyr
65                  70                  75                  80

Leu Thr Asp Glu Phe Ala Lys Gly Arg Lys Val Ala Asp Leu Tyr Glu
                85                  90                  95

Leu Val Gln Tyr Ala Gly Asn Ile Ile Pro Arg Leu Tyr Leu Leu Ile
                100                 105                 110

```
Thr Val Gly Val Val Tyr Val Lys Ser Phe Pro Gln Ser Arg Lys Asp
            115                 120                 125

Ile Leu Lys Asp Leu Val Glu Met Cys Arg Gly Val Gln His Pro Leu
    130                 135                 140

Arg Gly Leu Phe Leu Arg Asn Tyr Leu Leu Gln Cys Thr Arg Asn Ile
145                 150                 155                 160

Leu Pro Asp Glu Gly Glu Pro Thr Asp Glu Thr Thr Gly Asp Ile
                165                 170                 175

Ser Asp Ser Met Asp Phe Val Leu Leu Asn Phe Ala Glu Met Asn Lys
            180                 185                 190

Leu Trp Val Arg Met Gln His Gln Gly His Ser Arg Asp Arg Glu Lys
    195                 200                 205

Arg Glu Arg Glu Arg Gln Glu Leu Arg Ile Leu Val Gly Thr Asn Leu
210                 215                 220

Val Arg Leu Ser Gln Leu Glu Gly Val Asn Val Glu Arg Tyr Lys Gln
225                 230                 235                 240

Ile Val Leu Thr Gly Ile Leu Glu Gln Val Val Asn Cys Arg Asp Ala
                245                 250                 255

Leu Ala Gln Glu Tyr Leu Met Glu Cys Ile Ile Gln Val Phe Pro Asp
            260                 265                 270

Glu Phe His Leu Gln Thr Leu Asn Pro Phe Leu Arg Ala Cys Ala Glu
            275                 280                 285

Leu His Gln Asn Val Asn Val Lys Asn Ile Ile Ala Leu Ile Asp
            290                 295                 300

Arg Leu Ala Leu Phe Ala His Arg Glu Asp Gly Pro Gly Ile Pro Ala
305                 310                 315                 320

Asp Ile Lys Leu Phe Asp Ile Phe Ser Gln Gln Val Ala Thr Val Ile
                325                 330                 335

Gln Ser Arg Gln Asp Met Pro Ser Glu Asp Val Val Ser Leu Gln Val
            340                 345                 350

Ser Leu Ile Asn Leu Ala Met Lys Cys Tyr Pro Asp Arg Val Asp Tyr
            355                 360                 365

Val Asp Lys Val Leu Glu Thr Thr Val Glu Ile Phe Asn Lys Leu Asn
            370                 375                 380

Leu Glu His Ile Ala Thr Ser Ser Ala Val Ser Lys Glu Leu Thr Arg
385                 390                 395                 400

Leu Leu Lys Ile Pro Val Asp Thr Tyr Asn Asn Ile Leu Thr Val Leu
                405                 410                 415

Lys Leu Lys His Phe His Pro Leu Phe Glu Tyr Phe Asp Tyr Glu Ser
            420                 425                 430

Arg Lys Ser Met Ser Cys Tyr Val Leu Ser Asn Val Leu Asp Tyr Asn
            435                 440                 445

Thr Glu Ile Val Ser Gln Asp Gln Val Asp Ser Ile Met Asn Leu Val
            450                 455                 460

Ser Thr Leu Ile Gln Asp Gln Pro Asp Gln Pro Val Glu Asp Pro Asp
465                 470                 475                 480

Pro Glu Asp Phe Ala Asp Glu Gln Ser Leu Val Gly Arg Phe Ile His
                485                 490                 495

Leu Leu Arg Ser Glu Asp Pro Asp Gln Gln Tyr Leu Ile Leu Asn Thr
            500                 505                 510

Ala Arg Lys His Phe Gly Ala Gly Gly Asn Gln Arg Ile Arg Phe Thr
            515                 520                 525
```

```
Leu Pro Pro Leu Val Phe Ala Ala Tyr Gln Leu Ala Phe Arg Tyr Lys
    530                 535                 540

Glu Asn Ser Lys Val Asp Asp Lys Trp Glu Lys Cys Gln Lys Ile
545                 550                 555                 560

Phe Ser Phe Ala His Gln Thr Ile Ser Ala Leu Ile Lys Ala Glu Leu
                565                 570                 575

Ala Glu Leu Pro Leu Arg Leu Phe Leu Gln Gly Ala Leu Ala Ala Gly
                580                 585                 590

Glu Ile Gly Phe Glu Asn His Glu Thr Val Ala Tyr Glu Phe Met Ser
                595                 600                 605

Gln Ala Phe Ser Leu Tyr Glu Asp Glu Ile Ser Asp Ser Lys Ala Gln
            610                 615                 620

Leu Ala Ala Ile Thr Leu Ile Ile Gly Thr Phe Glu Arg Met Lys Cys
625                 630                 635                 640

Phe Ser Glu Glu Asn His Glu Pro Leu Arg Thr Gln Cys Ala Leu Ala
                645                 650                 655

Ala Ser Lys Leu Leu Lys Lys Pro Asp Gln Gly Arg Ala Val Ser Thr
                660                 665                 670

Cys Ala His Leu Phe Trp Ser Gly Arg Asn Thr Asp Lys Asn Gly Glu
                675                 680                 685

Glu Leu His Gly Gly Lys Arg Val Met Glu Cys Leu Lys Lys Ala Leu
            690                 695                 700

Lys Ile Ala Asn Gln Cys Met Asp Pro Ser Leu Gln Val Gln Leu Phe
705                 710                 715                 720

Ile Glu Ile Leu Asn Arg Tyr Ile Tyr Phe Tyr Glu Lys Glu Asn Asp
                725                 730                 735

Ala Val Thr Ile Gln Val Leu Asn Gln Leu Ile Gln Lys Ile Arg Glu
                740                 745                 750

Asp Leu Pro Asn Leu Glu Ser Ser Glu Glu Thr Glu Gln Ile Asn Lys
            755                 760                 765

His Phe His Asn Thr Leu Glu His Leu Arg Leu Arg Arg Glu Ser Pro
770                 775                 780

Glu Ser Glu Gly Pro Ile Tyr Glu Gly Leu Ile Leu
            785                 790                 795

<210> SEQ ID NO 50
<211> LENGTH: 2388
<212> TYPE: DNA
<213> ORGANISM: Artificial sequence
<220> FEATURE:
<223> OTHER INFORMATION: Synthetic polynucleotide

<400> SEQUENCE: 50
atgcccacca cccagcagag cccccaggac gagcaggaga agctgctgga cgaggccatc     60
caggccgtga aggtgcagag cttccagatg aagcgctgcc tggacaagaa caagctgatg    120
gacgccctga agcacgccag caacatgctg ggcgagctgc gcaccagcat gctgagcccc    180
aagagctact acgagctgta catggccatc agcgacgagc tgcactacct ggaggtgtac    240
ctgaccgacg agttcgccaa gggccgcaag gtggccgacc tgtacgagct ggtgcagtac    300
gccggcaaca tcatcccccg cctgtacctg ctgatcaccg tgggcgtggt gtacgtgaag    360
agcttccccc agagccgcaa ggacatcctg aaggacctgg tggagatgtg ccgcggcgtg    420
cagcaccccc tgcgcggcct gttcctgcgc aactacctgc tgcagtgcac cgcaacatc     480 ctgcccgacg agggcgagcc caccgacgag gagaccaccg gcgacatcag cgacagcatg    540
```

```
gacttcgtgc tgctgaactt cgccgagatg aacaagctgt gggtgcgcat gcagcaccag    600
ggccacagcc gcgaccgcga gaagcgcgag cgcgagcgcc aggagctgcg catcctggtg    660
ggcaccaacc tggtgcgcct gagccagctg gagggcgtga acgtggagcg ctacaagcag    720
atcgtgctga ccggcatcct ggagcaggtg gtgaactgcc gcgacgccct ggcccaggag    780
tacctgatgg agtgcatcat ccaggtgttc cccgacgagt tccacctgca gaccctgaac    840
cccttcctgc gcgcctgcgc cgagctgcac cagaacgtga acgtgaagaa catcatcatc    900
gccctgatcg accgcctggc cctgttcgcc caccgcgagg acggcccgg catccccgcc     960 gacatcaagc tgttcgacat cttcagccag caggtggcca ccgtgatcca gagccgccag    1020
gacatgccca gcgaggacgt ggtgagcctg caggtgagcc tgatcaacct ggccatgaag    1080
tgctaccccg accgcgtgga ctacgtggac aaggtgctgg agaccaccgt ggagatcttc    1140
aacaagctga acctggagca catcgccacc agcagcgccg tgagcaagga gctgacccgc    1200
ctgctgaaga tccccgtgga cacctacaac aacatcctga ccgtgctgaa gctgaagcac    1260
ttccaccccc tgttcgagta cttcgactac gagagccgca agagcatgag ctgctacgtg    1320
ctgagcaacg tgctggacta caacaccgag atcgtgagcc aggaccaggt ggacagcatc    1380
atgaacctgg tgagcaccct gatccaggac cagcccgacc agcccgtgga ggaccccgac    1440
cccgaggact cgccgacga gcagagcctg gtgggccgct tcatccacct gctgcgcagc    1500
gaggaccccg accagcagta cctgatcctg aacaccgccc gcaagcactt cggcgccggc    1560
ggcaaccagc gcatccgctt caccctgccc cccctggtgt cgccgccta ccagctggcc    1620 ttccgctaca aggagaacag caaggtggac gacaagtggg agaagaagtg ccagaagatc    1680
ttcagcttcg cccaccagac catcagcgcc ctgatcaagg ccgagctggc cgagctgccc    1740
ctgcgcctgt tcctgcaggg cgccctggcc gccggcgaga tcggcttcga gaaccacgag    1800
accgtggcct acgagttcat gagccaggcc ttcagcctgt acgaggacga gatcagcgac    1860
agcaaggccc agctggccgc catcaccctg atcatcggca ccttcgagcg catgaagtgc    1920
ttcagcgagg agaaccacga gccccctgcgc acccagtgcg ccctggccgc cagcaagctg    1980
ctgaagaagc ccgaccaggg ccgcgccgtg agcacctgcg cccacctgtt ctggagcggc    2040
cgcaacaccg acaagaacgg cgaggagctg cacggcggca agcgcgtgat ggagtgcctg    2100
aagaaggccc tgaagatcgc caaccagtgc atggacccca gcctgcaggt gcagctgttc    2160
atcgagatcc tgaaccgcta catctacttc tacgagaagg agaacgacgc cgtgaccatc    2220
caggtgctga accagctgat ccagaagatc cgcgaggacc tgcccaacct ggagagcagc    2280
gaggagaccg agcagatcaa caagcacttc cacaacaccc tggagcacct gcgcctgcgc    2340
cgcgagagcc ccgagagcga gggccccatc tacgagggcc tgatcctg               2388
```

<210> SEQ ID NO 51
<211> LENGTH: 11081
<212> TYPE: DNA
<213> ORGANISM: Artificial sequence
<220> FEATURE:
<223> OTHER INFORMATION: Synthetic polynucleotide

<400> SEQUENCE: 51

```
ttggccactc cctctctgcg cgctcgctcg ctcactgagg ccgggcgacc aaaggtcgcc     60
cgacgcccgg gctttgcccg gcggcctca gtgagcgagc gagcgcgcag agagggagtg    120
gccaactcca tcactagggg ttcctgctag ctctgggtat ttaagcccga gtgagcacgc    180
```

```
agggtctcca tttttgaagcg ggaggttacg cgttcgtcga ctactagtgg gtaccagagc    240
tccctaggtt ctagaaccgg tgacgtctcc catggtgaag cttggatctg agggcggagt    300
tagggcggag ccaatcagcg tgcgccgttc cgaaagttgc cttttatggc tgggcggaga    360
atgggcggtg aacgccgatg attatataag gacgcgccgg gtgtggcaca gctagttccg    420
tcgcagccgg gatttgggtc gcggttcttg tttgtggatc cctgtgatcg tcacttggta    480
agtcactgac tgtctatgcc tgggaaaggg tgggcaggag atgggcagt gcaggaaaag    540 tggcactatg aaccctcctg gtggcgaggg gaggggggtg gtcctcgaac gccttgcaga    600
actggcctgg atacagagtg gaccggctgg ccccatctgg aagacttcga gatacactgt    660
tgtcttactg cgctcaacag tgtatctcga agtcttccaa atggtgccag ccatcgcagc    720
ggggtgcagg aaatggggc agccccccctt tttggctatc cttccacgtg ttctttttg    780 tatcttttgt gtttcctaga aaacatctca gtcaccaccg cagccctagg aatgcatcta    840
gacaattgta ctaaccttct tctctttcct ctcctgacag tccggaaagc caccatggaa    900
ttcagcagcc ccagcagaga ggaatgcccc aagcctctga gccgggtgtc aatcatggcc    960
ggatctctga caggactgct gctgcttcag gccgtgtctt gggcttctgg cgctagacct    1020
tgcatcccca gagcttcgg ctacagcagc gtcgtgtgcg tgtgcaatgc cacctactgc    1080
gacagcttcg accctcctac ctttcctgct ctgggcacct tcagcagata cgagagcacc    1140
agatccggca gacggatgga actgagcatg ggacccatcc aggccaatca cacaggcact    1200
ggcctgctgc tgacactgca gcctgagcag aaattccaga agtgaaagg cttcggcgga    1260 gccatgacag atgccgccgc tctgaatatc ctggctctgt ctccaccagc tcagaacctg    1320
ctgctcaaga gctacttcag cgaggaaggc atcggctaca acatcatcag agtgcccatg    1380
gccagctgcg acttcagcat caggacctac acctacgccg acacacccga cgatttccag    1440
ctgcacaact tcagcctgcc tgaagaggac accaagctga agatccctct gatccacaga    1500
gccctgcagc tggcacaaag acccgtgtca ctgctggcct ctccatggac atctcccacc    1560
tggctgaaaa caaatggcgc cgtgaatggc aagggcagcc tgaaaggcca acctggcgac    1620
atctaccacc agacctgggc cagatacttc gtgaagttcc tggacgccta tgccgagcac    1680
aagctgcagt tttgggccgt gacagccgag aacgaacctt ctgctggact gctgagcggc    1740
tacccctttc agtgcctggg ctttacaccc gagcaccagc gggactttat cgcccgtgat    1800 ctgggacccca cactggccaa tagcacccac cataatgtgc ggctgctgat gctggacgac    1860
cagagactgc ttctgcccca ctgggctaaa gtggtgctga cagatcctga ggccgccaaa    1920
tacgtgcacg gaatcgccgt gcactggtat ctggactttc tggcccctgc caaggccaca    1980
ctgggagaga cacacagact gttccccaac accatgctgt cgccagcga agcctgtgtg    2040 ggcagcaagt tttgggaaca gagcgtgcgg ctcggcagct gggatagagg catgcagtac    2100
agccacagca tcatccaccaa cctgctgtac cacgtcgtcg gctggaccga ctggaatctg    2160
gccctgaatc ctgaaggcgg ccctaactgg gtccgaaact tcgtggacag ccccatcatc    2220
gtggacatca ccaaggacac cttctacaag cagcccatgt ctaccacct gggacacttc    2280 agcaagttca tccccgaggg ctctcagcgc gttggactgg tggcttccca gaagaacgat    2340
ctggacgccg tggctctgat gcaccctgat ggatctgctg tggtggtggt cctgaaccgc    2400
agcagcaaag atgtgcccct gaccatcaag gatcccgccg tgggattcct ggaaacaatc    2460
agccctggct actccatcca cacctacctg tggcgtagac aggagggcag aggaagtctt    2520
ctgacatgcg gagacgtgga agagaatccc ggccctatgg agaagggccc cgtgcgcgcc    2580
```

```
cccgccgaga agccccgcgg cgcccgctgc agcaacggct tccccgagcg cgacccccc     2640
cgccccggcc ccagccgccc cgccgagaag ccccccccgcc ccgaggccaa gagcgcccag   2700
cccgccgacg gctggaaggg cgagcgcccc cgcagcgagg aggacaacga gctgaacctg   2760
cccaacctgg ccgccgccta cagcagcatc ctgagcagcc tgggcgagaa cccccagcgc   2820
cagggcctgc tgaagacccc ctggcgcgcc gccagcgcca tgcagttctt caccaagggc   2880
taccaggaga ccatcagcga cgtgctgaac gacgccatct tcgacgagga ccacgacgag   2940
atggtgatcg tgaaggacat cgacatgttc agcatgtgcg agcaccacct ggtgcccttc   3000
gtgggcaagg tgcacatcgg ctacctgccc aacaagcagg tgctgggcct gagcaagctg   3060
gcccgcatcg tggagatcta cagccgccgc ctgcaggtgc aggagcgcct gaccaagcag   3120
atcgccgtgg ccatcaccga ggccctgcgc ccgccggcg tgggcgtggt ggtggaggcc   3180
acccacatgt gcatggtgat gcgcggcgtg cagaagatga acagcaagac cgtgaccagc   3240
accatgctgg gcgtgttccg cgaggacccc aagacccgcg aggagttcct gaccctgatc   3300
cgcagctgac aattgttaat taagtttaaa ccctcgaggc cgcaagctta tcgataatca   3360
acctctggat tacaaaattt gtgaaagatt gactggtatt cttaactatg ttgctccttt   3420
tacgctatgt ggatacgctg ctttaatgcc tttgtatcat gctattgctt cccgtatggc   3480
tttcattttc tcctccttgt ataaatcctg gttgctgtct ctttatgagg agttgtggcc   3540
cgttgtcagg caacgtggcg tggtgtgcac tgtgtttgct gacgcaaccc ccactggttg   3600
gggcattgcc accacctgtc agctcctttc cgggactttc gctttccccc tccctattgc   3660
cacggcggaa ctcatcgccg cctgccttgc ccgctgctgg acaggggctc ggctgttggg   3720
cactgacaat tccgtggtgt tgtcggggaa atcatcgtcc tttccttggc tgctcgcctg   3780
tgttgccacc tggattctgc gcgggacgtc cttctgctac gtcccttcgg ccctcaatcc   3840
agcggacctt ccttcccgcg gcctgctgcc ggctctgcgg cctcttccgc gtcttcgcct   3900
tcgccctcag acgagtcgga tctccctttg ggccgcctcc ccgcatcgat accgtcgact   3960
agagctcgct gatcagcctc gactgtgcct tctagttgcc agccatctgt tgtttgcccc   4020
tcccccgtgc cttccttgac cctggaaggt gccactccca ctgtccttc ctaataaaat   4080
gaggaaattg catcgcattg tctgagtagg tgtcattcta ttctgggggg tggggtgggg   4140
caggacagca agggggagga ttgggaagac aatagcaggc atgctgggga gagatccacg   4200
ataacaaaca gcttttttgg ggtgaacata ttgactgaat tccctgcagg ttggccactc   4260
cctctctgcg cgctcgctcg ctcactgagg ccgcccgggc aaagcccggg cgtcgggcga   4320
cctttggtcg cccggcctca gtgagcgagc gagcgcgcag agagggagtg gccaactcca   4380
tcactagggg ttcctgcggc cgctcgtacg gtctcgagga attcctgcag gataacttgc   4440
caacctcatt ctaaaatgta tatagaagcc caaaagacaa taacaaaaat attcttgtag   4500
aacaaaatgg gaaagaatgt tccactaaat atcaagattt agagcaaagc atgagatgtg   4560
tggggataga cagtgaggct gataaaatag agtagagctc agaaacagac ccattgatat   4620
atgtaagtga cctatgaaaa aaatatggca ttttacaatg ggaaaatgat ggtcttttc    4680
ttttttagaa aaacagggaa atatatttat atgtaaaaaa taaagggaa cccatatgtc    4740
ataccataca cacaaaaaaa ttccagtgaa ttataagtct aaatggagaa ggcaaaactt   4800
taaatctttt agaaataat atagaagcat gcagaccagc ctggccaaca tgatgaaacc   4860
ctctctacta ataataaaat cagtagaact actcaggact actttgagtg ggaagtcctt   4920
```

```
ttctatgaag acttctttgg ccaaaattag gctctaaatg caaggagata gtgcatcatg    4980
cctggctgca cttactgata aatgatgtta tcaccatctt taaccaaatg cacaggaaca    5040
agttatggta ctgatgtgct ggattgagaa ggagctctac ttccttgaca ggacacattt    5100
gtatcaactt aaaaaagcag attttttgcca gcagaactat tcattcagag gtaggaaact    5160
tagaatagat gatgtcactg attagcatgg cttccccatc tccacagctg cttcccaccc    5220
aggttgccca cagttgagtt tgtccagtgc tcagggctgc ccactctcag taagaagccc    5280
cacaccagcc cctctccaaa tatgttggct gttccttcca ttaaagtgac cccactttag    5340
agcagcaagt ggatttctgt ttcttacagt tcaggaagga ggagtcagct gtgagaacct    5400
ggagcctgag atgcttctaa gtcccactgc tactggggtc agggaagcca gactccagca    5460
tcagcagtca ggagcactaa gcccttgcca acatcctgtt tctcagagaa actgcttcca    5520
ttataatggt tgtccttttt taagctatca agccaaacaa ccagtgtcta ccattattct    5580
catcacctga agccaagggt tctagcaaaa gtcaagctgt cttgtaatgg ttgatgtgcc    5640
tccagcttct gtcttcagtc actccactct tagcctgctc tgaatcaact ctgaccacag    5700
ttccctggag cccctgccac ctgctgcccc tgccaccttc tccatctgca gtgctgtgca    5760
gccttctgca ctcttgcaga gctaataggt ggagacttga aggaagagga ggaaagtttc    5820
tcataatagc cttgctgcaa gctcaaatgg gaggtgggca ctgtgcccag gagccttgga    5880
gcaaaggctg tgcccaacct ctgactgcat ccaggtttgg tcttgacaga gataagaagc    5940
cctggctttt ggagccaaaa tctaggtcag acttaggcag gattctcaaa gtttatcagc    6000
agaacatgag gcagaagacc ctttctgctc cagcttcttc aggctcaacc ttcatcagaa    6060
tagatagaaa gagaggctgt gagggttctt aaaacagaag caaatctgac tcagagaata    6120
aacaacctcc tagtaaacta cagcttagac agagcatctg gtggtgagtg tgctcagtgt    6180
cctactcaac tgtctggtat cagccctcat gaggacttct cttctttccc tcatagacct    6240
ccatctctgt tttccttagc ctgcagaaat ctggatggca ttcacagaaa tgcctgtgct    6300
ttcagagttg catttttttct ctggtattct ggttcaagca tttgaaggta ggaaaggttc    6360
tccaagtgca agaaagccag ccctgagcct caactgcctg gctagtgtgg tcagtaggat    6420
gcaaaggctg ttgaatgcca caaggccaaa ctttaacctg tgtaccacaa gcctagcagc    6480
agaggcagct ctgctcactg gaactctctg tcttctttct cctgagcctt tcttttcct    6540 gagttttcta gctctcctca accttacctc tgccctaccc aggacaaacc caagagccac    6600
tgtttctgtg atgtcctctc cagccctaat taggcatcat gacttcagcc tgaccttcca    6660
tgctcagaag cagtgctaat ccacttcaga tgagctgctc tatgcaacac aggcagagcc    6720
tacaaacctt tgcaccagag ccctccacat atcagtgttt gttcatactc acttcaacag    6780
caaatgtgac tgctgagatt aagattttac acaagatggt ctgtaatttc acagttagtt    6840
ttatcccatt aggtatgaaa gaattagcat aattccccct aaacatgaat gaatcttaga    6900 tttttaata aatagtttg gaagtaaaga cagagacatc aggagcacaa ggaatagcct    6960
gagaggacaa acagaacaag aaagagtctg gaaatacaca ggatgttctt ggcctcctca    7020
aagcaagtgc aagcagatag taccagcagc cccaggctat cagagcccag tgaagagaag    7080
taccatgaaa gccacagctc taaccaccct gttccagagt gacagacagt ccccaagaca    7140
agccagcctg agccagagag agaactgcaa gagaaagtttt ctaatttagg ttctgttaga    7200
ttcagacaag tgcaggtcat cctctctcca cagctactca cctctccagc ctaacaaagc    7260
ctgcagtcca cactccaacc ctggtgtctc acctcctagc ctctcccaac atcctgctct    7320
```

```
ctgaccatct tctgcatctc tcatctcacc atctcccact gtctacagcc tactcttgca    7380
actaccatct cattttctga catcctgtct acatcttctg ccatactctg ccatctacca    7440
taccacctct taccatctac cacaccatct tttatctcca tccctctcag aagcctccaa    7500
gctgaatcct gctttatgtg ttcatctcag cccctgcatg gaaagctgac cccagaggca    7560
gaactattcc cagagagctt ggccaagaaa aacaaaacta ccagcctggc caggctcagg    7620
agtagtaagc tgcagtgtct gttgtgttct agcttcaaca gctgcaggag ttccactctc    7680
aaatgctcca catttctcac atcctcctga ttctggtcac tacccatctt caaagaacag    7740
aatatctcac atcagcatac tgtgaaggac tagtcatggg tgcagctgct cagagctgca    7800
aagtcattct ggatggtgga gagcttacaa acatttcatg atgctccccc cgctctgatg    7860
gctggagccc aatccctaca cagactcctg ctgtatgtgt tttcctttca ctctgagcca    7920
cagccagagg gcaggcattc agtctcctct tcaggctggg gctggggcac tgagaactca    7980
cccaacacct tgctctcact ccttctgcaa aacaagaaag agctttgtgc tgcagtagcc    8040
atgaagaatg aaaggaaggc tttaactaaa aaatgtcaga gattattttc aacccttac    8100 tgtggatcac cagcaaggag gaaacacaac acagagacat ttttccccct caaattatca    8160
aaagaatcac tgcatttgtt aaagagagca actgaatcag gaagcagagt tttgaacata    8220
tcagaagtta ggaatctgca tcagagacaa atgcagtcat ggttgtttgc tgcataccag    8280
ccctaatcat tagaagcctc atggacttca aacatcattc cctctgacaa gatgctctag    8340
cctaactcca tgagataaaa taaatctgcc tttcagagcc aaagaagagt ccaccagctt    8400
cttctcagtg tgaacaagag ctccagtcag gttagtcagt ccagtgcagt agaggagacc    8460
agtctgcatc ctctaatttt caaaggcaag aagatttgtt taccctggac accaggcaca    8520
agtgaggtca cagagctctt agatatgcag tcctcatgag tgaggagact aaagcgcatg    8580
ccatcaagac ttcagtgtag agaaaacctc caaaaaagcc tcctcactac ttctggaata    8640
gctcagaggc cgaggcggcc tcggcctctg cataaataaa aaaaattagt cagccatggg    8700
gcggagaatg ggcggaactg ggcggagtta ggggcgggat gggcggagtt aggggcggga    8760
ctatggttgc tgactaattg agatgcatgc tttgcatact tctgcctgct ggggagcctg    8820
gggactttcc acacctggtt gctgactaat tgagatgcat gctttgcata cttctgcctg    8880
ctggggagcc tggggacttt ccacacccta actgacacac attccacagc tgcattaatg    8940
aatcggccaa cgcgcgggga gaggcggttt gcgtattggg cgctcttccg cttcctcgct    9000
cactgactcg ctgcgctcgg tcgttcggct gcggcgagcg gtatcagctc actcaaaggc    9060
ggtaatacgg ttatccacag aatcagggga taacgcagga agaacatgt gagcaaaagg     9120 ccagcaaaag gccaggaacc gtaaaaaggc cgcgttgctg gcgttttcc ataggctccg     9180 ccccccctgac gagcatcaca aaaatcgacg ctcaagtcag aggtggcgaa acccgacagg    9240
actataaaga taccaggcgt ttccccctgg aagctccctc gtgcgctctc ctgttccgac    9300
cctgccgctt accggatacc tgtccgcctt tctcccttcg ggaagcgtgg cgctttctca    9360
tagctcacgc tgtaggtatc tcagttcggt gtaggtcgtt cgctccaagc tgggctgtgt    9420
gcacgaaccc cccgttcagc ccgaccgctg cgccttatcc ggtaactatc gtcttgagtc    9480
caacccggta agacacgact tatcgccact ggcagcagcc actggtaaca ggattagcag    9540
agcgaggtat gtaggcggtg ctacagagtt cttgaagtgg tggcctaact acggctacac    9600
tagaagaaca gtatttggta tctgcgctct gctgaagcca gttaccttcg gaaaaagagt    9660
```

```
tggtagctct tgatccggca aacaaaccac cgctggtagc ggtggttttt ttgtttgcaa     9720
gcagcagatt acgcgcagaa aaaaggatc tcaagaagat cctttgatct tttctacggg       9780
gtctgacgct cagtggaacg aaaactcacg ttaagggatt ttggtcatga gattatcaaa     9840
aaggatcttc acctagatcc ttttaaatta aaatgaagt tttaaatcaa tctaaagtat       9900
atatgagtaa acttggtctg acagttacca atgcttaatc agtgaggcac ctatctcagc     9960
gatctgtcta tttcgttcat ccatagttgc ctgactcctg caaaccacgt tgtgtctcaa     10020
aatctctgat gttacattgc acaagataaa aatatatcat catgaacaat aaaactgtct    10080
gcttacataa acagtaatac aagggtgtt atgagccata ttcaacggga aacgtcttgc     10140
tcgaggccgc gattaaattc caacatggat gctgatttat atgggtataa atgggctcgc    10200
gataatgtcg ggcaatcagg tgcgacaatc tatcgattgt atgggaagcc cgatgcgcca    10260
gagttgtttc tgaaacatgg caaaggtagc gttgccaatg atgttacaga tgagatggtc    10320
agactaaact ggctgacgga atttatgcct cttccgacca tcaagcattt tatccgtact    10380
cctgatgatg catggttact caccactgcg atccccggga aaacagcatt ccaggtatta    10440
gaagaatatc ctgattcagg tgaaaatatt gttgatgcgc tggcagtgtt cctgcgccgg    10500
ttgcattcga ttcctgtttg taattgtcct tttaacagcg atcgcgtatt tcgtctcgct    10560
caggcgcaat cacgaatgaa taacggtttg gttgatgcga gtgattttga tgacgagcgt    10620
aatggctggc ctgttgaaca gtctggaaa gaaatgcata agcttttgcc attctcaccg    10680
gattcagtcg tcactcatgg tgatttctca cttgataacc ttatttttga cgaggggaaa    10740
ttaataggtt gtattgatgt tggacgagtc ggaatcgcag accgatacca ggatcttgcc    10800
atcctatgga actgcctcgg tgagttttct ccttcattac agaaacggct ttttcaaaaa    10860
tatggtattg ataatcctga tatgaataaa ttgcagtttc atttgatgct cgatgagttt    10920
ttctaagggc ggcctgccac catacccacg ccgaaacaag cgctcatgag cccgaagtgg    10980
cgagcccgat cttccccatc ggtgatgtcg gcgatatagg cgccagcaac cgcacctgtg    11040
gcgccggtga tgagggcgcg ccaagtcgac gtccggcagt c                        11081
```

<210> SEQ ID NO 52
<211> LENGTH: 10940
<212> TYPE: DNA
<213> ORGANISM: Artificial sequence
<220> FEATURE:
<223> OTHER INFORMATION: Synthetic polynucleotide

<400> SEQUENCE: 52

```
ttggccactc cctctctgcg cgctcgctcg ctcactgagg ccgggcgacc aaaggtcgcc       60
cgacgcccgg gctttgcccg gcggcctca gtgagcgagc gagcgcgcag agagggagtg       120
gccaactcca tcactagggg ttcctgctag ctctgggtat ttaagcccga gtgagcacgc      180
agggtctcca ttttgaagcg ggaggttacg cgttcgtcga ctactagtgg gtaccagagc     240
tccctaggtt ctagaaccgg tgacgtctcc catggtgaag cttggatctg agggcggagt    300
tagggcggag ccaatcagcg tgcgccgttc cgaaagttgc ctttttatggc tgggcggaga    360 atgggcggtg aacgccgatg attatataag gacgcgccgg gtgtggcaca gctagttccg    420
tcgcagccgg gatttgggtc gcggttcttg tttgtggatc cctgtgatcg tcacttggta    480
agtcactgac tgtctatgcc tgggaaaggg tgggcaggag atgggcagt gcaggaaaag    540 tggcactatg aaccctcctg gtggcgaggg gagggggtg tcctcgaac gccttgcaga    600 actggcctgg atacagagtg gaccggctgg ccccatctgg aagacttcga gatacactgt   660
```

```
tgtcttactg cgctcaacag tgtatctcga agtcttccaa atggtgccag ccatcgcagc    720
ggggtgcagg aaatgggggc agcccccctt tttggctatc cttccacgtg ttctttttg    780
tatcttttgt gtttcctaga aaacatctca gtcaccaccg cagccctagg aatgcatcta    840
gacaattgta ctaaccttct tctctttcct ctcctgacag tccggaaagc caccatgggc    900
agccgcgacc acctgttcaa ggtgctggtg gtgggcgacg ccgccgtggg caagaccagc    960
ctggtgcagc gctacagcca ggacagcttc agcaagcact acaagagcac cgtgggcgtg   1020
gacttcgccc tgaaggtgct gcagtggagc gactacgaga tcgtgcgcct gcagctgtgg   1080
gacatcgccg gccaggagcg cttcaccagc atgacccgcc tgtactaccg cgacgccagc   1140
gcctgcgtga tcatgttcga cgtgaccaac gccaccacct tcagcaacag ccagcgctgg   1200
aagcaggacc tggacagcaa gctgacccctg cccaacggcg agcccgtgcc ctgcctgctg   1260
ctggccaaca agtgcgacct gagcccctgg gccgtgagcc gcgaccagat cgaccgcttc   1320
agcaaggaga acggcttcac cggctggacc gagaccagct gaaggagaa caagaacatc   1380
aacgaggcca tgcgcgtgct gatcgagaag atgatgcgca acagcaccga ggacatcatg   1440
agcctgagca cccagggcga ctacatcaac ctgcagacca gagcagcag ctggagctgc   1500
tgcgagggca gaggaagtct tctgacatgc ggagacgtgg aagagaatcc cggccctatg   1560
gaattcagca gccccagcag agaggaatgc cccaagcctc tgagccgggt gtcaatcatg   1620
gccggatctc tgacaggact gctgctgctt caggccgtgt cttggcttc tggcgctaga   1680
ccttgcatcc ccaagagctt cggctacagc agcgtcgtgt gcgtgtgcaa tgccacctac   1740
tgcgacagct tcgaccctcc tacctttcct gctctgggca ccttcagcag atacgagagc   1800
accagatccg gcagacggat ggaactgagc atgggaccca tccaggccaa tcacacaggc   1860
actggcctgc tgctgacact gcagcctgag cagaaattcc agaaagtgaa aggcttcggc   1920
ggagccatga cagatgccgc cgctctgaat atcctggctc tgtctccacc agctcagaac   1980
ctgctgctca gagctacttt cagcgaggaa ggcatcggct acaacatcat cagagtgccc   2040
atggccagct gcgacttcag catcaggacc tacacctacg ccgacacacc cgacgattc   2100
cagctgcaca acttcagcct gcctgaagag gacaccaagc tgaagatccc tctgatccac   2160
agagccctgc agctggcaca aagacccgtg tcactgctgg cctctccatg gacatctccc   2220
acctggctga aaacaaatgg cgccgtgaat ggcaagggca gcctgaaagg ccaacctggc   2280
gacatctacc accagacctg gccagatac ttcgtgaagt tcctggacgc ctatgccgag   2340
cacaagctgc agttttgggc cgtgacagcc gagaacgaac cttctgctgg actgctgagc   2400
ggctaccct ttcagtgcct gggctttaca cccgagcacc agcgggactt tatcgcccgt   2460
gatctgggac ccacactggc caatagcacc accataatg tgcggctgct gatgctggac   2520
gaccagagac tgcttctgcc ccactgggct aaagtggtgc tgacagatcc tgaggccgcc   2580
aaatacgtgc acggaatcgc cgtgcactgg tatctggact tctggcccc tgccaaggcc   2640
acactgggag agacacacag actgttcccc aacaccatgc tgttcgccag cgaagcctgt   2700
gtgggcagca gttttggga acagagcgtg cggctcggca gctgggatag aggcatgcag   2760
tacagccaca gcatcatcac caacctgctg taccacgtcg tcggctggac cgactggaat   2820
ctggccctga atcctgaagg cggccctaac tgggtccgaa acttcgtgga cagccccatc   2880
atcgtggaca tcaccaagga caccttctac aagcagccca tgttctacca cctgggacac   2940
ttcagcaagt tcatccccga gggctctcag cgcgttggac tggtggcttc ccagaagaac   3000
```

```
gatctggacg ccgtggctct gatgcaccct gatggatctg ctgtggtggt ggtcctgaac    3060
cgcagcagca aagatgtgcc cctgaccatc aaggatcccg ccgtgggatt cctggaaaca    3120
atcagccctg gctactccat ccacacctac ctgtggcgta gacagtgaca attgttaatt    3180
aagtttaaac cctcgaggcc gcaagcttat cgataatcaa cctctggatt acaaaatttg    3240
tgaaagattg actggtattc ttaactatgt tgctcctttt acgctatgtg gatacgctgc    3300
tttaatgcct ttgtatcatg ctattgcttc ccgtatggct ttcattttct cctccttgta    3360
taaatcctgg ttgctgtctc tttatgagga gttgtggccc gttgtcaggc aacgtggcgt    3420
ggtgtgcact gtgtttgctg acgcaacccc cactggttgg ggcattgcca ccacctgtca    3480
gctccttccc gggactttcg ctttccccct cccattgccc acggcggaac tcatcgccgc    3540
ctgccttgcc cgctgctgga caggggctcg gctgttgggc actgacaatt ccgtggtgtt    3600
gtcggggaaa tcatcgtcct tccttggct gctcgcctgt gttgccacct ggattctgcg    3660
cgggacgtcc ttctgctacg tcccttcggc cctcaatcca gcggaccttc cttcccgcgg    3720
cctgctgccg gctctgcggc ctcttccgcg tcttcgcctt cgccctcaga cgagtcggat    3780
ctccctttgg gccgcctccc cgcatcgata ccgtcgacta gagctcgctg atcagcctcg    3840
actgtgcctt ctagttgcca gccatctgtt gtttgccccct ccccgtgcc ttccttgacc    3900 ctggaaggtg ccactcccac tgtcctttcc taataaaatg aggaaattgc atcgcattgt    3960
ctgagtaggt gtcattctat tctggggggt ggggtgggc aggacagcaa ggggaggat    4020 tgggaagaca atagcaggca tgctgggag agatccacga taacaaacag ctttttgg    4080 gtgaacatat tgactgaatt ccctgcaggt tggccactcc ctctctgcgc gctcgctcgc    4140
tcactgaggc cgcccgggca agcccgggc gtcgggcgac cttggtcgc ccggcctcag    4200 tgagcgagcg agcgcgcaga gagggagtgg ccaactccat cactagggt tcctgcggcc    4260 gctcgtacgg tctcgaggaa ttcctgcagg ataacttgcc aacctcattc taaaatgtat    4320
atagaagccc aaaagacaat aacaaaaata ttcttgtaga acaaaatggg aaagaatgtt    4380
ccactaaata tcaagattta gagcaaagca tgagatgtgt ggggatagac agtgaggctg    4440
ataaaataga gtagagctca gaaacagacc cattgatata tgtaagtgac ctatgaaaaa    4500
aatatggcat tttacaatgg gaaaatgatg gtctttttct tttttagaaa acagggaaa    4560 tatatttata tgtaaaaaat aaagggaac ccatatgtca taccatacac acaaaaaaat    4620
tccagtgaat tataagtcta aatggagaag gcaaaacttt aaatctttta gaaaataata    4680
tagaagcatg cagaccagcc tggccaacat gatgaaaccc tctctactaa taataaaatc    4740
agtagaacta ctcaggacta cttttgagtgg gaagtccttt tctatgaaga cttctttggc    4800
caaaattagg ctctaaatgc aaggagatag tgcatcatgc ctggctgcac ttactgataa    4860
atgatgttat caccatcttt aaccaaatgc acaggaacaa gttatggtac tgatgtgctg    4920
gattgagaag gagctctact tccttgacag gacacatttg tatcaactta aaaaagcaga    4980 ttttttgccag cagaactatt cattcagagg taggaaactt agaatagatg atgtcactga    5040
ttagcatggc ttccccatct ccacagctgc ttcccaccca ggttgcccac agttgagttt    5100
gtccagtgct cagggctgcc cactctcagt aagaagcccc acaccagccc ctctccaaat    5160
atgttggctg ttccttccat taaagtgacc ccactttaga gcagcaagtg gatttctgtt    5220
tcttacagtt caggaaggag gagtcagctg tgaaacctg gagcctgaga tgcttctaag    5280
tcccactgct actggggtca gggaagccag actccagcat cagcagtcag gagcactaag    5340
cccttgccaa catcctgttt ctcagagaaa ctgcttccat tataatggtt gtccttttt    5400
```

| | |
|---|---|
| aagctatcaa gccaaacaac cagtgtctac cattattctc atcacctgaa gccaagggtt | 5460 |
| ctagcaaaag tcaagctgtc ttgtaatggt tgatgtgcct ccagcttctg tcttcagtca | 5520 |
| ctccactctt agcctgctct gaatcaactc tgaccacagt tccctggagc ccctgccacc | 5580 |
| tgctgcccct gccaccttct ccatctgcag tgctgtgcag ccttctgcac tcttgcagag | 5640 |
| ctaataggtg gagacttgaa ggaagaggag gaaagtttct cataatagcc ttgctgcaag | 5700 |
| ctcaaatggg aggtgggcac tgtgcccagg agccttggag caaaggctgt gcccaacctc | 5760 |
| tgactgcatc caggtttggt cttgacagag ataagaagcc ctggcttttg gagccaaaat | 5820 |
| ctaggtcaga cttaggcagg attctcaaag tttatcagca gaacatgagg cagaagaccc | 5880 |
| tttctgctcc agcttcttca ggctcaacct tcatcagaat agatagaaag agaggctgtg | 5940 |
| agggttctta aaacagaagc aaatctgact cagagaataa acaacctcct agtaaactac | 6000 |
| agcttagaca gagcatctgg tggtgagtgt gctcagtgtc ctactcaact gtctggtatc | 6060 |
| agccctcatg aggacttctc ttctttccct catagacctc catctctgtt ttccttagcc | 6120 |
| tgcagaaatc tggatggcta ttcacagaat gcctgtgctt tcagagttgc atttttctc | 6180 |
| tggtattctg gttcaagcat ttgaaggtag gaaaggttct ccaagtgcaa gaaagccagc | 6240 |
| cctgagcctc aactgcctgg ctagtgtggt cagtaggatg caaaggctgt tgaatgccac | 6300 |
| aaggccaaac tttaacctgt gtaccacaag cctagcagca gaggcagctc tgctcactgg | 6360 |
| aactctctgt cttctttctc ctgagccttt tcttttcctg agttttctag ctctcctcaa | 6420 |
| ccttacctct gccctaccca ggacaaaccc aagagccact gtttctgtga tgtcctctcc | 6480 |
| agccctaatt aggcatcatg acttcagcct gaccttccat gctcagaagc agtgctaatc | 6540 |
| cacttcagat gagctgctct atgcaacaca ggcagagcct acaaaccttt gcaccagagc | 6600 |
| cctccacata tcagtgtttg ttcatactca cttcaacagc aaatgtgact gctgagatta | 6660 |
| agattttaca caagatggtc tgtaatttca cagttagttt tatcccatta ggtatgaaag | 6720 |
| aattagcata attcccctta aacatgaatg aatcttagat ttttaataa atagttttgg | 6780 |
| aagtaaagac agagacatca ggagcacaag gaatagcctg agaggacaaa cagaacaaga | 6840 |
| aagagtctgg aaatacacag gatgttcttg gcctcctcaa agcaagtgca agcagatagt | 6900 |
| accagcagcc ccaggctatc agagcccagt gaagagaagt accatgaaag ccacagctct | 6960 |
| aaccaccctg ttccagagtg acagacagtc cccaagacaa gccagcctga gccagagaga | 7020 |
| gaactgcaag agaaagtttc taatttaggt tctgttagat tcagacaagt gcaggtcatc | 7080 |
| ctctctccac agctactcac ctctccagcc taacaaagcc tgcagtccac actccaaccc | 7140 |
| tggtgtctca cctcctagcc tctcccaaca tcctgctctc tgaccatctt ctgcatctct | 7200 |
| catctcacca tctcccactg tctacagcct actcttgcaa ctaccatctc attttctgac | 7260 |
| atcctgtcta catcttctgc catactctgc catctaccat accacctctt accatctacc | 7320 |
| acaccatctt ttatctccat ccctctcaga agcctccaag ctgaatcctg ctttatgtgt | 7380 |
| tcatctcagc ccctgcatgg aaagctgacc ccagaggcag aactattccc agagagcttg | 7440 |
| gccaagaaaa acaaaactac cagcctggcc aggctcagga gtagtaagct gcagtgtctg | 7500 |
| ttgtgttcta gcttcaacag ctgcaggagt tccactctca aatgctccac atttctcaca | 7560 |
| tcctcctgat tctggtcact acccatcttc aaagaacaga atatctcaca tcagcatact | 7620 |
| gtgaaggact agtcatgggt gcagctgctc agagctgcaa agtcattctg gatggtggag | 7680 |
| agcttacaaa catttcatga tgctcccccc gctctgatgg ctggagccca atccctacac | 7740 |

```
agactcctgc tgtatgtgtt ttcctttcac tctgagccac agccagaggg caggcattca    7800
gtctcctctt caggctgggg ctggggcact gagaactcac ccaacacctt gctctcactc    7860
cttctgcaaa acaagaaaga gctttgtgct gcagtagcca tgaagaatga aaggaaggct    7920
ttaactaaaa aatgtcagag attattttca accccttact gtggatcacc agcaaggagg    7980
aaacacaaca cagagacatt ttttcccctc aaattatcaa aagaatcact gcatttgtta    8040
aagagagcaa ctgaatcagg aagcagagtt ttgaacatat cagaagttag gaatctgcat    8100
cagagacaaa tgcagtcatg gttgtttgct gcataccagc cctaatcatt agaagcctca    8160
tggacttcaa acatcattcc ctctgacaag atgctctagc ctaactccat gagataaaat    8220
aaatctgcct ttcagagcca aagaagagtc caccagcttc ttctcagtgt gaacaagagc    8280
tccagtcagg ttagtcagtc cagtgcagta gaggagacca gtctgcatcc tctaattttc    8340
aaaggcaaga agatttgttt accctggaca ccaggcacaa gtgaggtcac agagctctta    8400
gatatgcagt cctcatgagt gaggagacta aagcgcatgc catcaagact tcagtgtaga    8460
gaaaacctcc aaaaaagcct cctcactact tctggaatag ctcagaggcc gaggcggcct    8520
cggcctctgc ataaataaaa aaaattagtc agccatgggg cggagaatgg gcggaactgg    8580
gcggagttag gggcgggatg ggcggagtta ggggcgggac tatggttgct gactaattga    8640
gatgcatgct ttgcatactt ctgcctgctg gggagcctgg ggactttcca cacctggttg    8700
ctgactaatt gagatgcatg cttttgcatac ttctgcctgc tggggagcct ggggactttc    8760
cacaccctaa ctgacacaca ttccacagct gcattaatga atcggccaac gcgcggggag    8820
aggcggtttg cgtattgggc gctcttccgc ttcctcgctc actgactcgc tgcgctcggt    8880
cgttcggctg cggcgagcgg tatcagctca ctcaaaggcg gtaatacggt tatccacaga    8940 atcagggggat aacgcaggaa agaacatgtg agcaaaaggc cagcaaaagg ccaggaaccg    9000
taaaaaggcc gcgttgctgg cgttttttcca taggctccgc cccctgacg agcatcacaa    9060 aaatcgacgc tcaagtcaga ggtggcgaaa cccgacagga ctataaagat accaggcgtt    9120 tcccccctgga agctccctcg tgcgctctcc tgttccgacc ctgccgctta ccggatacct    9180
gtccgccttt ctcccttcgg gaagcgtggc gctttctcat agctcacgct gtaggtatct    9240
cagttcggtg taggtcgttc gctccaagct gggctgtgtg cacgaacccc ccgttcagcc    9300
cgaccgctgc gccttatccg gtaactatcg tcttgagtcc aacccggtaa gacacgactt    9360
atcgccactg gcagcagcca ctggtaacag gattagcaga gcgaggtatg taggcggtgc    9420
tacagagttc ttgaagtggt ggcctaacta cggctacact agaagaacag tatttggtat    9480
ctgcgctctg ctgaagccag ttaccttcgg aaaaagagtt ggtagctctt gatccggcaa    9540
acaaaccacc gctggtagcg tggttttttt tgtttgcaag cagcagatta cgcgcagaaa    9600
aaaaggatct caagaagatc ctttgatctt ttctacgggg tctgacgctc agtggaacga    9660
aaactcacgt taagggattt tggtcatgag attatcaaaa aggatcttca cctagatcct    9720
tttaaattaa aaatgaagtt ttaaatcaat ctaaagtata tatgagtaaa cttggtctga    9780
cagttaccaa tgcttaatca gtgaggcacc tatctcagcg atctgtctat ttcgttcatc    9840
catagttgcc tgactcctgc aaaccacgtt gtgtctcaaa atctctgatg ttacattgca    9900
caagataaaa atatatcatc atgaacaata aaactgtctg cttacataaa cagtaataca    9960
aggggtgtta tgagccatat tcaacgggaa acgtcttgct cgaggccgcg attaaattcc   10020
aacatggatg ctgatttata tgggtataaa tgggctcgcg ataatgtcgg gcaatcaggt   10080
gcgacaatct atcgattgta tgggaagccc gatgcgccag agttgtttct gaaacatggc   10140
```

```
aaaggtagcg ttgccaatga tgttacagat gagatggtca gactaaactg gctgacggaa    10200
tttatgcctc ttccgaccat caagcatttt atccgtactc ctgatgatgc atggttactc    10260
accactgcga tccccgggaa aacagcattc caggtattag aagaatatcc tgattcaggt    10320
gaaaatattg ttgatgcgct ggcagtgttc ctgcgccggt tgcattcgat tcctgtttgt    10380
aattgtcctt ttaacagcga tcgcgtattt cgtctcgctc aggcgcaatc acgaatgaat    10440
aacggtttgg ttgatgcgag tgattttgat gacgagcgta atggctggcc tgttgaacaa    10500
gtctggaaag aaatgcataa gcttttgcca ttctcaccgg attcagtcgt cactcatggt    10560
gatttctcac ttgataacct tattttgac gagggaaat taataggttg tattgatgtt    10620
ggacgagtcg gaatcgcaga ccgataccag gatcttgcca tcctatggaa ctgcctcggt    10680
gagttttctc cttcattaca gaaacggctt tttcaaaaat atggtattga taatcctgat    10740
atgaataaat tgcagtttca tttgatgctc gatgagtttt tctaagggcg gcctgccacc    10800
atacccacgc cgaaacaagc gctcatgagc ccgaagtggc gagcccgatc ttccccatcg    10860
gtgatgtcgg cgataaggc gccagcaacc gcacctgtgg cgccggtgat gagggcgcgc    10920
caagtcgacg tccggcagtc                                                10940

<210> SEQ ID NO 53
<211> LENGTH: 10934
<212> TYPE: DNA
<213> ORGANISM: Artificial sequence
<220> FEATURE:
<223> OTHER INFORMATION: Synthetic polynucleotide

<400> SEQUENCE: 53
ttggccactc cctctctgcg cgctcgctcg ctcactgagg ccgggcgacc aaaggtcgcc      60
cgacgcccgg gctttgcccg gcggcctca gtgagcgagc gagcgcgcag agagggagtg     120
gccaactcca tcactagggg ttcctgctag ctctgggtat ttaagcccga gtgagcacgc     180
agggtctcca ttttgaagcg ggaggttacg cgttcgtcga ctactagtgg gtaccagagc     240
tccctaggtt ctagaaccgg tgacgtctcc catggtgaag cttggatctg agggcggagt     300
tagggcggag ccaatcagcg tgcgccgttc cgaaagttgc cttttatggc tgggcggaga     360
atgggcggtg aacgccgatg attatataag gacgcgccgg gtgtggcaca gctagttccg     420
tcgcagccgg gatttgggtc gcggttcttg tttgtggatc cctgtgatcg tcacttggta     480
agtcactgac tgtctatgcc tgggaaaggg tgggcaggag atgggcagt gcaggaaaag     540 tggcactatg aaccctcctg gtggcgaggg gagggggtg gtcctcgaac gccttgcaga     600
actggcctgg atacagagtg gaccggctgg ccccatctgg aagacttcga gatacactgt     660
tgtcttactg cgctcaacag tgtatctcga agtcttccaa atggtgccag ccatcgcagc     720
ggggtgcagg aaatggggc agccccctt tttggctatc cttccacgtg ttcttttttg     780
tatcttttgt gtttcctaga aaacatctca gtcaccaccg cagccctagg aatgcatcta     840
gacaattgta ctaaccttct ctctttcct ctcctgacag tccggaaagc caccatggaa     900
ttcagcagcc ccagcagaga ggaatgcccc aagcctctga gccgggtgtc aatcatggcc     960
ggatctctga caggactgct gctgcttcag gccgtgtctt gggcttctgg cgctagacct    1020
tgcatcccca gagcttcgg ctacagcagc gtcgtgtgcg tgtgcaatgc cacctactgc    1080
gacagcttcg accctcctac ctttcctgct ctgggcacct tcagcagata cgagagcacc    1140
agatccggca gacggatgga actgagcatg ggacccatcc aggccaatca cacaggcact    1200
```

```
ggcctgctgc tgacactgca gcctgagcag aaattccaga aagtgaaagg cttcggcgga    1260
gccatgacag atgccgccgc tctgaatatc ctggctctgt ctccaccagc tcagaacctg    1320
ctgctcaaga gctacttcag cgaggaaggc atcggctaca acatcatcag agtgcccatg    1380
gccagctgcg acttcagcat caggacctac acctacgccg acacacccga cgatttccag    1440
ctgcacaact tcagcctgcc tgaagaggac accaagctga agatccctct gatccacaga    1500
gccctgcagc tggcacaaag acccgtgtca ctgctggcct ctccatggac atctcccacc    1560
tggctgaaaa caaatggcgc cgtgaatggc aagggcagcc tgaaaggcca acctggcgac    1620
atctaccacc agacctgggc cagatacttc gtgaagttcc tggacgccta tgccgagcac    1680
aagctgcagt tttgggccgt gacagccgag aacgaaccct ctgctggact gctgagcggc    1740
taccccttct cagtgcctgg gctttacaccc gagcaccagc gggactttat cgcccgtgat    1800
ctgggaccca cactggccaa tagcacccac cataatgtgc ggctgctgat gctggacgac    1860
cagagactgc ttctgcccca ctgggctaaa gtggtgctga cagatcctga ggccgccaaa    1920
tacgtgcacg gaatcgccgt gcactggtat ctggactttc tggcccctgc caaggccaca    1980
ctgggagaga cacacagact gttcccccaac accatgctgt cgccagcga agcctgtgtg    2040 ggcagcaagt tttgggaaca gagcgtgcgg ctcggcagct gggatagagg catgcagtac    2100
agccacagca tcatcaccaa cctgctgtac cacgtcgtcg gctggaccga ctggaatctg    2160
gccctgaatc ctgaaggcgg ccctaactgg gtccgaaact cgtggacag ccccatcatc    2220 gtggacatca ccaaggacac cttctacaag cagcccatgt ctaccacct gggacacttc    2280 agcaagttca tccccgaggg ctctcagcgc gttggactgg tggcttccca gaagaacgat    2340
ctggacgccg tggctctgat gcaccctgat ggatctgctg tggtggtggt cctgaaccgc    2400
agcagcaaag atgtgcccct gaccatcaag gatcccgccg tgggattcct ggaaacaatc    2460
agccctggct actccatcca cacctacctg tggcgtagac agtgattgtg ccgaaccgc    2520 cgaactcaga ggccggcccc agaaaacccg agcgagtagg gggcggcgcg caggagggag    2580
gagaactggg ggcgcgggag gctggtgggt gtggggggtg gagatgtaga agatgtgacg    2640
ccgcggcccg cgggtgcca gattagcgga cgccggtgccc gcggttgcaa cgggatcccg    2700
ggcgctgcag cttgggaggc ggctctcccc aggcggcgtc cgcggagaca cccatccgtg    2760
aaccccaggt cccgggccgc cggctcgccg cgcaccaggg gccggcggac agaagagcgg    2820
ccgagcggct cgaggctggg ggaccgcggg cgcggccgcg cgctgccggg cgggaggctg    2880
gggggccggg gccggggccg tgccccggag cgggtcggag gccggggccg gggcggggg    2940 acggcggctc cccgcgcggc tccagcggct cggggatccc ggccgggccc cgcagggacc    3000
atgatggaga agggccccgt gcgcgccccc gccgagaagc ccgcggcgc ccgctgcagc    3060 aacggcttcc ccgagcgcga ccccccccgc cccggcccca gccgcccgc cgagaagccc    3120 ccccgccccg aggccaagag cgcccagccc gccgacggct ggaagggcga gcgccccgc    3180 agcgaggagg acaacgagct gaacctgccc aacctggccg ccgcctacag cagcatcctg    3240
agcagcctgg gcgagaaccc ccagcgccag ggcctgctga agacccctg gcgcgccgcc    3300 agcgccatga gagttcttcac caagggctac caggagacca tcagcgacgt gctgaacgac    3360
gccatcttcg acgaggacca cgacgagatg gtgatcgtga aggacatcga catgttcagc    3420
atgtgcgagc accacctggt gcccttcgtg ggcaaggtgc acatcggcta cctgcccaac    3480
aagcaggtgc tgggcctgag caagctgacc cgcatcgtgg agatctacag ccgccgcctg    3540
caggtgcagg agcgcctgac caagcagatc gccgtggcca tcaccgaggc cctgcgcccc    3600
```

-continued

```
gccggcgtgg gcgtggtggt ggaggccacc cacatgtgca tggtgatgcg cggcgtgcag      3660
aagatgaaca gcaagaccgt gaccagcacc atgctgggcg tgttccgcga ggaccccaag      3720
acccgcgagg agttcctgac cctgatccgc agctgacaat tgttaattaa gtttaaaccc      3780
tcgaggccgc aagccgcatc gataccgtcg actagagctc gctgatcagc ctcgactgtg      3840
ccttctagtt gccagccatc tgttgtttgc ccctcccccg tgccttcctt gaccctggaa      3900
ggtgccactc ccactgtcct ttcctaataa aatgaggaaa ttgcatcgca ttgtctgagt      3960
aggtgtcatt ctattctggg gggtggggtg gggcaggaca gcaaggggga ggattgggaa      4020
gacaatagca ggcatgctgg ggagagatcc acgataacaa acagcttttt tggggtgaac      4080
atattgactg aattccctgc aggttggcca ctccctctct gcgcgctcgc tcgctcactg      4140
aggccgcccg ggcaaagccc gggcgtcggg cgacctttgg tcgcccggcc tcagtgagcg      4200
agcgagcgcg cagagaggga gtggccaact ccatcactag gggttcctgc ggccgctcgt      4260
acggtctcga ggaattcctg caggataact tgccaacctc attctaaaat gtatatagaa      4320
gcccaaaaga caataacaaa atattcttg tagaacaaaa tgggaaagaa tgttccacta      4380
aatatcaaga tttagagcaa agcatgagat gtgtggggat agacagtgag gctgataaaa      4440
tagagtagag ctcagaaaca gacccattga tatatgtaag tgacctatga aaaaaatatg      4500
gcattttaca atgggaaaat gatggtcttt ttctttttta gaaaacagg gaaatatatt      4560 tatatgtaaa aaataaaagg gaacccatat gtcataccat acacacaaaa aaattccagt      4620
gaattataag tctaaatgga gaaggcaaaa ctttaaatct tttagaaaat aatatagaag      4680
catgcagacc agcctggcca acatgatgaa accctctcta ctaataataa aatcagtaga      4740
actactcagg actactttga gtgggaagtc cttttctatg aagacttctt tggccaaaat      4800
taggctctaa atgcaaggag atagtgcatc atgcctggct gcacttactg ataaatgatg      4860
ttatcaccat cttttaaccaa atgcacagga acaagttatg gtactgatgt gctggattga      4920
gaaggagctc tacttccttg acaggacaca tttgtatcaa cttaaaaaag cagattttg       4980 ccagcagaac tattcattca gaggtaggaa acttagaata gatgatgtca ctgattagca      5040
tggcttcccc atctccacag ctgcttccca cccaggttgc ccacagttga gtttgtccag      5100
tgctcagggc tgcccactct cagtaagaag ccccacacca gcccctctcc aaatatgttg      5160
gctgttcctt ccattaaagt gaccccactt tagagcagca agtggatttc tgtttcttac      5220
agttcaggaa ggaggagtca gctgtgagaa cctggagcct gagatgcttc taagtcccac      5280
tgctactggg gtcagggaag ccagactcca gcatcagcag tcaggagcac taagcccttg      5340
ccaacatcct gtttctcaga gaaactgctt ccattataat ggttgtcctt ttttaagcta      5400
tcaagccaaa caaccagtgt ctaccattat tctcatcacc tgaagccaag ggttctagca      5460
aaagtcaagc tgtcttgtaa tggttgatgt gcctccagct tctgtcttca gtcactccac      5520
tcttagcctg ctctgaatca actctgacca cagttccctg gagcccctgc acctgctgc       5580 ccctgccacc ttctccatct gcagtgctgt gcagccttct gcactcttgc agagctaata      5640
ggtggagact tgaaggaaga ggaggaaagt ttctcataat agccttgctg caagctcaaa      5700
tgggaggtgg gcactgtgcc caggagcctt ggagcaaagg ctgtgcccaa cctctgactg      5760
catccaggtt tggtcttgac agagataaga agccctggct tttggagcca aaatctaggt      5820
cagacttagg caggattctc aaagtttatc agcagaacat gaggcagaag acccttctg      5880 ctccagcttc ttcaggctca accttcatca gaatagatag aaagagaggc tgtgagggtt      5940
```

```
cttaaaacag aagcaaatct gactcagaga ataaacaacc tcctagtaaa ctacagctta    6000
gacagagcat ctggtggtga gtgtgctcag tgtcctactc aactgtctgg tatcagccct    6060
catgaggact tctcttcttt ccctcataga cctccatctc tgttttcctt agcctgcaga    6120
aatctggatg gctattcaca gaatgcctgt gctttcagag ttgcattttt tctctggtat    6180
tctggttcaa gcatttgaag gtaggaaagg ttctccaagt gcaagaaagc cagccctgag    6240
cctcaactgc ctggctagtg tggtcagtag gatgcaaagg ctgttgaatg ccacaaggcc    6300
aaactttaac ctgtgtacca caagcctagc agcagaggca gctctgctca ctggaactct    6360
ctgtcttctt tctcctgagc cttttctttt cctgagtttt ctagctctcc tcaaccttac    6420
ctctgcccta cccaggacaa acccaagagc cactgtttct gtgatgtcct ctccagccct    6480
aattaggcat catgacttca gcctgaccct ccatgctcag aagcagtgct aatccacttc    6540
agatgagctg ctctatgcaa cacaggcaga gcctacaaac ctttgcacca gagccctcca    6600
catatcagtg tttgttcata ctcacttcaa cagcaaatgt gactgctgag attaagattt    6660
tacacaagat ggtctgtaat ttcacagtta gttttatccc attaggtatg aaagaattag    6720
cataattccc cttaaacatg aatgaatctt agatttttta ataaatagtt ttggaagtaa    6780
agacagagac atcaggagca caaggaatag cctgagagga caaacagaac aagaaagagt    6840
ctggaaatac acaggatgtt cttggcctcc tcaaagcaag tgcaagcaga tagtaccagc    6900
agccccaggc tatcagagcc cagtgaagag aagtaccatg aaagccacag ctctaaccac    6960
cctgttccag agtgacagac agtccccaag acaagccagc ctgagccaga gagagaactg    7020
caagagaaag tttctaattt aggttctgtt agattcagac aagtgcaggt catcctctct    7080
ccacagctac tcacctctcc agcctaacaa agcctgcagt ccacactcca accctggtgt    7140
ctcacctcct agcctctccc aacatcctgc tctctgacca tcttctgcat ctctcatctc    7200
accatctccc actgtctaca gcctactctt gcaactacca tctcattttc tgacatcctg    7260
tctacatctt ctgccatact ctgccatcta ccataccacc tcttaccatc taccacacca    7320
tcttttatct ccatccctct cagaagcctc caagctgaat cctgctttat gtgttcatct    7380
cagcccctgc atggaaagct gaccccagag gcagaactat tcccagagag cttggccaag    7440
aaaaacaaaa ctaccagcct ggccaggctc aggagtagta agctgcagtg tctgttgtgt    7500
tctagcttca acagctgcag gagttccact ctcaaatgct ccacatttct cacatcctcc    7560
tgattctggt cactacccat cttcaaagaa cagaatatct cacatcagca tactgtgaag    7620
gactagtcat gggtgcagct gctcagagct gcaaagtcat tctggatggt ggagagctta    7680
caaacatttc atgatgctcc ccccgctctg atggctggag cccaatccct acacagactc    7740
ctgctgtatg tgttttcctt tcactctgag ccacagccag agggcaggca ttcagtctcc    7800
tcttcaggct ggggctgggg cactgagaac tcacccaaca ccttgctctc actccttctg    7860
caaaacaaga aagagctttg tgctgcagta gccatgaaga atgaaaggaa ggctttaact    7920
aaaaaatgtc agagattatt ttcaaccccc tactgtggat caccagcaag gaggaaacac    7980
aacacagaga cattttttcc cctcaaatta tcaaagaat cactgcattt gttaaagaga    8040
gcaactgaat caggaagcag agttttgaac atatcagaag ttaggaatct gcatcagaga    8100
caaatgcagt catggttgtt tgctgcatac cagccctaat cattagaagc ctcatggact    8160
tcaaacatca ttccctctga caagatgctc tagcctaact ccatgagata aaataaatct    8220
gcctttcaga gccaaagaag agtccaccag cttcttctca gtgtgaacaa gagctccagt    8280
caggttagtc agtccagtgc agtagaggag accagtctgc atcctctaat tttcaaaggc    8340
```

```
aagaagattt gtttaccctg gacaccaggc acaagtgagg tcacagagct cttagatatg    8400
cagtcctcat gagtgaggag actaaagcgc atgccatcaa gacttcagtg tagagaaaac    8460
ctccaaaaaa gcctcctcac tacttctgga atagctcaga ggccgaggcg gcctcggcct    8520
ctgcataaat aaaaaaaatt agtcagccat ggggcggaga atgggcggaa ctgggcggag    8580
ttaggggcgg gatgggcgga gttaggggcg ggactatggt tgctgactaa ttgagatgca    8640
tgctttgcat acttctgcct gctggggagc ctggggactt ccacacctg gttgctgact     8700 aattgagatg catgctttgc atacttctgc ctgctgggga gcctgggac tttccacacc     8760 ctaactgaca cacattccac agctgcatta atgaatcggc caacgcgcgg ggagaggcgg    8820
tttgcgtatt gggcgctctt ccgcttcctc gctcactgac tcgctgcgct cggtcgttcg    8880
gctgcggcga gcggtatcag ctcactcaaa ggcggtaata cggttatcca cagaatcagg    8940
ggataacgca ggaaagaaca tgtgagcaaa aggccagcaa aaggccagga accgtaaaaa    9000
ggccgcgttg ctggcgtttt tccataggct ccgcccccct gacgagcatc acaaaaatcg    9060
acgctcaagt cagaggtggc gaaacccgac aggactataa agataccagg cgtttccccc    9120
tggaagctcc ctcgtgcgct ctcctgttcc gaccctgccg cttaccggat acctgtccgc    9180
ctttctccct tcgggaagcg tggcgctttc tcatagctca cgctgtaggt atctcagttc    9240
ggtgtaggtc gttcgctcca agctgggctg tgtgcacgaa ccccccgttc agcccgaccg    9300
ctgcgcctta tccggtaact atcgtcttga gtccaacccg gtaagacacg acttatcgcc    9360
actggcagca gccactggta acaggattag cagagcgagg tatgtaggcg gtgctacaga    9420
gttcttgaag tggtggccta actacggcta cactagaaga acagtatttg gtatctgcgc    9480
tctgctgaag ccagttacct tcggaaaaag agttggtagc tcttgatccg gcaaacaaac    9540
caccgctggt agcggtggtt tttttgtttg caagcagcag attacgcgca gaaaaaaagg    9600
atctcaagaa gatcctttga tcttttctac ggggtctgac gctcagtgga acgaaaactc    9660
acgttaaggg attttggtca tgagattatc aaaaaggatc ttcacctaga tccttttaaa    9720
ttaaaaatga agttttaaat caatctaaag tatatatgag taaacttggt ctgacagtta    9780
ccaatgctta atcagtgagg cacctatctc agcgatctgt ctatttcgtt catccatagt    9840
tgcctgactc ctgcaaacca cgttgtgtct caaaatctct gatgttacat gcacaagat     9900 aaaaatatat catcatgaac aataaaactg tctgcttaca taaacagtaa tacaaggggt    9960
gttatgagcc atattcaacg ggaaacgtct gctcgaggc cgcgattaaa ttccaacatg      10020
gatgctgatt tatatgggta taaatgggct cgcgataatg tcgggcaatc aggtgcgaca    10080
atctatcgat tgtatgggaa gcccgatgcg ccagagttgt ttctgaaaca tggcaaaggt    10140
agcgttgcca atgatgttac agatgagatg gtcagactaa actggctgac ggaatttatg    10200
cctcttccga ccatcaagca ttttatccgt actcctgatg atgcatggtt actcaccact    10260 gcgatcccg ggaaaacagc attccaggta ttagaagaat atcctgattc aggtgaaaat      10320
attgttgatg cgctggcagt gttcctgcgc cggttgcatt cgattcctgt ttgtaattgt    10380
ccttttaaca cgatcgcgt atttcgtctc gctcaggcgc aatcacgaat gaataacggt      10440
ttggttgatg cgagtgattt tgatgacgag cgtaatggct ggcctgttga caagtctgg     10500 aaagaaatgc ataagctttt gccattctca ccggattcag tcgtcactca tggtgatttc    10560
tcacttgata accttatttt tgacgagggg aaattaatag gttgtattga tgttggacga    10620
gtcggaatcg cagaccgata ccaggatctt gccatcctat ggaactgcct cggtgagttt    10680
```

| | |
|---|---:|
| tctccttcat tacagaaacg gctttttcaa aaatatggta ttgataatcc tgatatgaat | 10740 |
| aaattgcagt ttcatttgat gctcgatgag tttttctaag ggcggcctgc caccataccc | 10800 |
| acgccgaaac aagcgctcat gagcccgaag tggcgagccc gatcttcccc atcggtgatg | 10860 |
| tcggcgatat aggcgccagc aaccgcacct gtggcgccgg tgatgagggc gcgccaagtc | 10920 |
| gacgtccggc agtc | 10934 |

<210> SEQ ID NO 54
<211> LENGTH: 11138
<212> TYPE: DNA
<213> ORGANISM: Artificial sequence
<220> FEATURE:
<223> OTHER INFORMATION: Synthetic polynucleotide

<400> SEQUENCE: 54

| | |
|---|---:|
| ttggccactc cctctctgcg cgctcgctcg ctcactgagg ccgggcgacc aaaggtcgcc | 60 |
| cgacgcccgg gctttgcccg ggcggcctca gtgagcgagc gagcgcgcag agagggagtg | 120 |
| gccaactcca tcactagggg ttcctgctag ctctgggtat ttaagcccga gtgagcacgc | 180 |
| agggtctcca ttttgaagcg ggaggttacg cgttcgtcga ctactagtgg gtaccagagc | 240 |
| tccctaggtt ctagaaccgg tgacgtctcc catggtgaag cttggatctg agtaagtcac | 300 |
| tgactgtcta tgcctgggaa agggtgggca ggagatgggg cagtgcagga aaagtggcac | 360 |
| tatgaaccct cctggtggcg aggggagggg ggtggtcctc gaacgccttg cagaactggc | 420 |
| ctggatacag agtggaccgg ctggccccat ctggaagact tcgagataca ctgttgtctt | 480 |
| actgcgctca acagtgtatc tcgaagtctt ccaaatggtg ccagccatcg cagcggggtg | 540 |
| caggaaatgg gggcagcccc ccttttttggc tatccttcca cgtgttcttt tttgtatctt | 600 |
| ttgtgtttcc tagaaaacat ctcagtcacc accgtgatat cacaaggtcc cagggctggg | 660 |
| gtcagaaatt ctctcccgag ggaatgaagc cacaggagcc aagagcagga ggaccaaggc | 720 |
| cctggcgaag gccgtggcct cgttcaagta aaagatccta gtacagtgca ggtcccaatg | 780 |
| tgtactagga tcttttactt gaacggggac gccggcatcc gggctcagga cccccctctc | 840 |
| tgccagaggc accaacacca gagttcacaa atcagtctcc tgcccttgtc atgtagcaaa | 900 |
| gcagccctag gaatgcatct agacaattgt actaaccttc ttctcttttcc tctcctgaca | 960 |
| gtccggaaag ccaccatgcc caccacccag cagagccccc aggacgagca ggagaagctg | 1020 |
| ctggacgagg ccatccaggc cgtgaaggtg cagagcttcc agatgaagcg ctgcctggac | 1080 |
| aagaacaagc tgatggacgc cctgaagcac gccagcaaca tgctgggcga gctgcgcacc | 1140 |
| agcatgctga gccccaagag ctactacgag ctgtacatgg ccatcagcga cgagctgcac | 1200 |
| tacctggagg tgtacctgac cgacgagttc gccaagggcc gcaaggtggc cgacctgtac | 1260 |
| gagctggtgc agtacgccgg caacatcatc ccccgcctgt acctgctgat caccgtgggc | 1320 |
| gtggtgtacg tgaagagctt cccccagagc cgcaaggaca tcctgaagga cctggtggag | 1380 |
| atgtgccgcg gcgtgcagca ccccctgcgc ggcctgttcc tgcgcaacta cctgctgcag | 1440 |
| tgcacccgca acatcctgcc cgacgagggc gagcccaccg acgaggagac caccggcgac | 1500 |
| atcagcgaca gcatggactt cgtgctgctg aacttcgccg agatgaacaa gctgtgggtg | 1560 |
| cgcatgcagc accagggcca cagccgcgac cgcgagaagc gcgagcgcga cgccaggag | 1620 |
| ctgcgcatcc tggtgggcac caacctggtg cgcctgagcc agctggaggg cgtgaacgtg | 1680 |
| gagcgctaca gcagatcgt gctgaccggc atcctggagc aggtggtgaa ctgccgcgac | 1740 |
| gccctggccc aggagtacct gatggagtgc atcatccagg tgttccccga cgagttccac | 1800 |

```
ctgcagaccc tgaacccctt cctgcgcgcc tgcgccgagc tgcaccagaa cgtgaacgtg   1860
aagaacatca tcatcgccct gatcgaccgc ctggccctgt cgcccaccg cgaggacggc    1920
cccggcatcc ccgccgacat caagctgttc gacatcttca gccagcaggt ggccaccgtg   1980
atccagagcc gccaggacat gcccagcgag gacgtggtga gcctgcaggt gagcctgatc   2040
aacctggcca tgaagtgcta ccccgaccgc gtggactacg tggacaaggt gctggagacc   2100
accgtggaga tcttcaacaa gctgaacctg agcacatcg ccaccagcag cgccgtgagc    2160
aaggagctga cccgcctgct gaagatcccc gtggacacct acaacaacat cctgaccgtg   2220
ctgaagctga agcacttcca ccccctgttc gagtacttcg actacgagag ccgcaagagc   2280
atgagctgct acgtgctgag caacgtgctg gactacaaca ccgagatcgt gagccaggac   2340
caggtggaca gcatcatgaa cctggtgagc accctgatcc aggaccagcc cgaccagccc   2400
gtggaggacc ccgaccccga ggacttcgcc gacgagcaga gcctggtggg ccgcttcatc   2460
cacctgctgc gcagcgagga ccccgaccag cagtacctga tcctgaacac cgcccgcaag   2520
cacttcggcg ccggcggcaa ccagcgcatc cgcttcaccc tgcccccct ggtgttcgcc    2580
gcctaccagc tggccttccg ctacaaggag aacagcaagg tggacgacaa gtgggagaag   2640
aagtgccaga agatcttcag cttcgcccac cagaccatca gcgccctgat caaggccgag   2700
ctggccgagc tgccctgcg cctgttcctg cagggcgccc tggccgccgg cgagatcggc    2760
ttcgagaacc acgagaccgt ggcctacgag ttcatgagcc aggccttcag cctgtacgag   2820
gacgagatca gcgacagcaa ggcccagctg gccgccatca ccctgatcat cggcaccttc   2880
gagcgcatga agtgcttcag cgaggagaac cacgagcccc tgcgcaccca gtgcgccctg   2940
gccgccagca gctgctgaa gaagcccgac cagggccgcg ccgtgagcac ctgcgcccac    3000
ctgttctgga gcggccgcaa caccgacaag aacggcgagg agctgcacgg cggcaagcgc   3060
gtgatggagt gcctgaagaa ggccctgaag atcgccaacc agtgcatgga ccccagcctg   3120
caggtgcagc tgttcatcga gatcctgaac cgctacatct acttctacga aggagaac     3180
gacgccgtga ccatccaggt gctgaaccag ctgatccaga gatccgcga ggacctgccc    3240
aacctggaga gcagcgagga gaccgagcag atcaacaagc acttccacaa cacctggag    3300
cacctgcgcc tgcgccgcga gagccccgag agcgagggcc catctacga gggcctgatc    3360
ctgtgacaat tgttaattaa gtttaaaccc tcgaggccgc aagcttatcg ataatcaacc   3420
tctggattac aaaatttgtg aaagattgac tggtattctt aactatgttg ctccttttac   3480
gctatgtgga tacgctgctt taatgccttt gtatcatgct attgcttccc gtatggcttt   3540
cattttctcc tccttgtata atcctggtt gctgtctctt tatgaggagt tgtggcccgt    3600
tgtcaggcaa cgtggcgtgg tgtgcactgt gtttgctgac gcaaccccca ctggttgggg   3660
cattgccacc acctgtcagc tcctttccgg gactttcgct ttccccctcc ctattgccac   3720
ggcggaactc atcgccgcct gccttgcccg ctgctggaca ggggctcggc tgttgggcac   3780
tgacaattcc gtggtgttgt cggggaaatc atcgtccttt ccttggctgc tcgcctgtgt   3840
tgccacctgg attctgcgcg gacgtcctt ctgctacgtc ccttcggccc tcaatccagc    3900
ggaccttcct tcccgcggcc tgctgccggc tctgcggcct cttccgcgtc ttcgccttcg   3960
ccctcagacg agtcggatct ccctttgggc cgcctcccg catcgatacc gtcgactaga   4020
gctcgctgat cagcctcgac tgtgccttct agttgccagc catctgttgt ttgcccctcc   4080
cccgtgcctt ccttgaccct ggaaggtgcc actcccactg tcctttccta ataaaatgag   4140
```

```
gaaattgcat cgcattgtct gagtaggtgt cattctattc tggggggtgg ggtggggcag    4200
gacagcaagg gggaggattg ggaagacaat agcaggcatg ctggggagag atccacgata    4260
acaaacagct ttttgggggt gaacatattg actgaattcc ctgcaggttg gccactccct    4320
ctctgcgcgc tcgctcgctc actgaggccg cccgggcaaa gcccgggcgt cgggcgacct    4380
ttggtcgccc ggcctcagtg agcgagcgag cgcgcagaga gggagtggcc aactccatca    4440
ctaggggttc ctgcggccgc tcgtacggtc tcgaggaatt cctgcaggat aacttgccaa    4500
cctcattcta aaatgtatat agaagcccaa aagacaataa caaaaatatt cttgtagaac    4560
aaaatgggaa agaatgttcc actaaatatc aagatttaga gcaaagcatg agatgtgtgg    4620
ggatagacag tgaggctgat aaaatagagt agagctcaga aacagaccca ttgatatatg    4680
taagtgacct atgaaaaaaa tatggcattt tacaatggga aaatgatggt ctttttcttt    4740
tttagaaaaa cagggaaata tatttatatg taaaaaataa aagggaaccc atatgtcata    4800
ccatacacac aaaaaaattc cagtgaatta taagtctaaa tggagaaggc aaaacttaa     4860
atcttttaga aaataatata gaagcatgca gaccagcctg gccaacatga tgaaaccctc    4920
tctactaata ataaaatcag tagaactact caggactact ttgagtggga agtccttttc    4980
tatgaagact tctttggcca aaattaggct ctaaatgcaa ggagatagtg catcatgcct    5040
ggctgcactt actgataaat gatgttatca ccatctttaa ccaaatgcac aggaacaagt    5100
tatggtactg atgtgctgga ttgagaagga gctctacttc cttgacagga cacatttgta    5160
tcaacttaaa aaagcagatt tttgccagca gaactattca ttcagaggta ggaaacttag    5220
aatagatgat gtcactgatt agcatggctt ccccatctcc acagctgctt cccacccagg    5280
ttgcccacag ttgagtttgt ccagtgctca gggctgccca ctctcagtaa gaagccccac    5340
accagccct  ctccaaatat gttggctgtt ccttccatta aagtgacccc actttagagc    5400
agcaagtgga tttctgtttc ttacagttca ggaaggagga gtcagctgtg agaacctgga    5460
gcctgagatg cttctaagtc ccactgctac tggggtcagg gaagccagac tccagcatca    5520
gcagtcagga gcactaagcc cttgccaaca tcctgtttct cagagaaact gcttccatta    5580
taatggttgt cctttttaa  gctatcaagc caaacaacca gtgtctacca ttattctcat    5640
cacctgaagc caagggttct agcaaaagtc aagctgtctt gtaatggttg atgtgcctcc    5700
agcttctgtc ttcagtcact ccactcttag cctgctctga atcaactctg accacagttc    5760
cctggagccc ctgccacctg ctgcccctgc caccttctcc atctgcagtg ctgtgcagcc    5820
ttctgcactc ttgcagagct aataggtgga gacttgaagg aagaggagga aagtttctca    5880
taatagcctt gctgcaagct caaatgggag gtgggcactg tgcccaggag ccttggagca    5940
aaggctgtgc ccaacctctg actgcatcca ggtttggtct tgacagagat aagaagccct    6000
ggcttttgga gccaaaatct aggtcagact taggcaggat tctcaaagtt tatcagcaga    6060
acatgaggca gaagacccctt tctgctccag cttcttcagg ctcaaccttc atcagaatag    6120
atagaaagag aggctgtgag ggttcttaaa acagaagcaa atctgactca gagaataaac    6180
aacctcctag taaactacag cttagacaga gcatctggtg gtgagtgtgc tcagtgtcct    6240
actcaactgt ctggtatcag ccctcatgag gacttctctt ctttccctca tagacctcca    6300
tctctgtttt ccttagcctg cagaaatctg gatggctatt cacagaatgc ctgtgctttc    6360
agagttgcat tttttctctg gtattctggt tcaagcattt gaaggtagga aaggttctcc    6420
aagtgcaaga aagccagccc tgagcctcaa ctgcctggct agtgtggtca gtaggatgca    6480
aaggctgttg aatgccacaa ggccaaactt taacctgtgt accacaagcc tagcagcaga    6540
```

```
ggcagctctg ctcactggaa ctctctgtct tctttctcct gagccttttc ttttcctgag    6600
ttttctagct ctcctcaacc ttacctctgc cctacccagg acaaacccaa gagccactgt    6660
ttctgtgatg tcctctccag ccctaattag gcatcatgac ttcagcctga ccttccatgc    6720
tcagaagcag tgctaatcca cttcagatga gctgctctat gcaacacagg cagagcctac    6780
aaacctttgc accagagccc tccacatatc agtgtttgtt catactcact caacagcaa     6840
atgtgactgc tgagattaag attttacaca agatggtctg taatttcaca gttagtttta    6900
tcccattagg tatgaaagaa ttagcataat tccccttaaa catgaatgaa tcttagattt    6960
tttaataaat agttttggaa gtaaagacag agacatcagg agcacaagga atagcctgag    7020
aggacaaaca gaacaagaaa gagtctggaa atacacagga tgttcttggc ctcctcaaag    7080
caagtgcaag cagatagtac cagcagcccc aggctatcag agcccagtga agagaagtac    7140
catgaaagcc acagctctaa ccaccctgtt ccagagtgac agacagtccc caagacaagc    7200
cagcctgagc cagagagaga actgcaagag aaagtttcta atttaggttc tgttagattc    7260
agacaagtgc aggtcatcct ctctccacag ctactcacct ctccagccta acaaagcctg    7320
cagtccacac tccaaccctg gtgtctcacc tcctagcctc tcccaacatc ctgctctctg    7380
accatcttct gcatctctca tctcaccatc tcccactgtc tacagcctac tcttgcaact    7440
accatctcat tttctgacat cctgtctaca tcttctgcca tactctgcca tctaccatac    7500
cacctcttac catctaccac accatctttt atctccatcc ctctcagaag cctccaagct    7560
gaatcctgct ttatgtgttc atctcagccc ctgcatggaa agctgacccc agaggcagaa    7620
ctattcccag agagcttggc caagaaaaac aaaactacca gcctggccag gctcaggagt    7680
agtaagctgc agtgtctgtt gtgttctagc ttcaacagct gcaggagttc cactctcaaa    7740
tgctccacat ttctcacatc ctcctgattc tggtcactac ccatcttcaa agaacagaat    7800
atctcacatc agcatactgt gaaggactag tcatgggtgc agctgctcag agctgcaaag    7860
tcattctgga tggtggagag cttacaaaca tttcatgatg ctccccccgc tctgatggct    7920
ggagcccaat ccctacacag actcctgctg tatgtgtttt cctttcactc tgagccacag    7980
ccagagggca ggcattcagt ctcctcttca ggctgggggct ggggcactga gaactcaccc    8040
aacaccttgc tctcactcct tctgcaaaac aagaaagagc tttgtgctgc agtagccatg    8100
aagaatgaaa ggaaggcttt aactaaaaaa tgtcagagat tattttcaac cccttactgt    8160
ggatcaccag caaggaggaa acacaacaca gagacatttt ttcccctcaa attatcaaaa    8220
gaatcactgc atttgttaaa gagagcaact gaatcaggaa gcagagtttt gaacatatca    8280
gaagttagga atctgcatca gagacaaatg cagtcatggt tgtttgctgc ataccagccc    8340
taatcattag aagcctcatg gacttcaaac atcattccct ctgacaagat gctctagcct    8400
aactccatga gataaaataa atctgccttt cagagccaaa gaagagtcca ccagcttctt    8460
ctcagtgtga acaagagctc cagtcaggtt agtcagtcca gtgcagtaga ggagaccagt    8520
ctgcatcctc taattttcaa aggcaagaag atttgtttac cctggacacc aggcacaagt    8580
gaggtcacag agctcttaga tatgcagtcc tcatgagtga ggagactaaa gcgcatgcca    8640
tcaagacttc agtgtagaga aaacctccaa aaaagcctcc tcactacttc tggaatagct    8700
cagaggccga ggcggcctcg gcctctgcat aaataaaaaa aattagtcag ccatggggcg    8760
gagaatgggc ggaactgggc ggagttaggg gcgggatggg cggagttagg ggcgggacta    8820
tggttgctga ctaattgaga tgcatgcttt gcatacttct gcctgctggg gagcctgggg    8880
```

-continued

```
actttccaca cctggttgct gactaattga gatgcatgct ttgcatactt ctgcctgctg    8940
gggagcctgg ggactttcca caccctaact gacacacatt ccacagctgc attaatgaat    9000
cggccaacgc gcggggagag gcggtttgcg tattgggcgc tcttccgctt cctcgctcac    9060
tgactcgctg cgctcggtcg ttcggctgcg gcgagcggta tcagctcact caaaggcggt    9120
aatacggtta tccacagaat cagggggataa cgcaggaaag aacatgtgag caaaaggcca    9180
gcaaaaggcc aggaaccgta aaaaggccgc gttgctggcg ttttttccata ggctccgccc    9240 ccctgacgag catcacaaaa atcgacgctc aagtcagagg tggcgaaacc cgacaggact    9300
ataaagatac caggcgtttc ccctggaag ctccctcgtg cgctctcctg ttccgaccct    9360
gccgcttacc ggatacctgt ccgcctttct cccttcggga agcgtggcgc tttctcatag    9420
ctcacgctgt aggtatctca gttcggtgta ggtcgttcgc tccaagctgg gctgtgtgca    9480 cgaaccccc gttcagcccg accgctgcgc cttatccggt aactatcgtc ttgagtccaa    9540
cccggtaaga cacgacttat cgccactggc agcagccact ggtaacagga ttagcagagc    9600
gaggtatgta ggcggtgcta cagagttctt gaagtggtgg cctaactacg gctacactag    9660
aagaacagta tttggtatct gcgctctgct gaagccagtt accttcggaa aaagagttgg    9720
tagctcttga tccggcaaac aaaccaccgc tggtagcggt ggttttttg tttgcaagca    9780 gcagattacg cgcagaaaaa aaggatctca agaagatcct ttgatctttt ctacggggtc    9840
tgacgctcag tggaacgaaa actcacgtta agggattttg gtcatgagat tatcaaaaag    9900
gatcttcacc tagatccttt taaattaaaa atgaagttt aaatcaatct aaagtatata    9960
tgagtaaact tggtctgaca gttaccaatg cttaatcagt gaggcaccta tctcagcgat   10020
ctgtctattt cgttcatcca tagttgcctg actcctgcaa accacgttgt gtctcaaaat   10080
ctctgatgtt acattgcaca agataaaaat atatcatcat gaacaataaa actgtctgct   10140
tacataaaca gtaatacaag gggtgttatg agccatattc aacgggaaac gtcttgctcg   10200
aggccgcgat taaattccaa catggatgct gatttatatg ggtataaatg gctcgcgat   10260 aatgtcgggc aatcaggtgc gacaatctat cgattgtatg ggaagcccga tgcgccagag   10320
ttgtttctga aacatggcaa aggtagcgtt gccaatgatg ttacagatga gatggtcaga   10380
ctaaactggc tgacggaatt tatgcctctt ccgaccatca agcattttat ccgtactcct   10440
gatgatgcat ggttactcac cactgcgatc cccgggaaaa cagcattcca ggtattagaa   10500
gaatatcctg attcaggtga aaatattgtt gatgcgctgg cagtgttcct gcgccggttg   10560
cattcgattc ctgtttgtaa ttgtcctttt aacagcgatc gcgtatttcg tctcgctcag   10620
gcgcaatcac gaatgaataa cggtttggtt gatgcgagtg attttgatga cgagcgtaat   10680
ggctggcctg ttgaacaagt ctggaaagaa atgcataagc ttttgccatt ctcaccggat   10740
tcagtcgtca ctcatggtga tttctcactt gataaccta tttttgacga ggggaaatta   10800
ataggttgta ttgatgttgg acgagtcgga atcgcagacc gataccagga tcttgccatc   10860
ctatggaact gcctcggtga gttttctcct tcattacaga aacggctttt tcaaaaatat   10920
ggtattgata atcctgatat gaataaattg cagtttcatt tgatgctcga tgagttttc   10980 taagggcggc ctgccaccat acccacgccg aaacaagcgc tcatgagccc gaagtggcga   11040
gcccgatctt ccccatcggt gatgtcggcg atataggcgc cagcaaccgc acctgtggcg   11100
ccggtgatga gggcgcgcca agtcgacgtc cggcagtc                           11138
```

<210> SEQ ID NO 55
<211> LENGTH: 242

```
<212> TYPE: PRT
<213> ORGANISM: Artificial sequence
<220> FEATURE:
<223> OTHER INFORMATION: Synthetic polypeptide

<400> SEQUENCE: 55

Met Pro Arg Gly Phe Thr Trp Leu Arg Tyr Leu Gly Ile Phe Leu Gly
1               5                   10                  15

Val Ala Leu Gly Asn Glu Pro Leu Glu Met Trp Pro Leu Thr Gln Asn
            20                  25                  30

Glu Glu Cys Thr Val Thr Gly Phe Leu Arg Asp Lys Leu Gln Tyr Arg
        35                  40                  45

Ser Arg Leu Gln Tyr Met Lys His Tyr Phe Pro Ile Asn Tyr Lys Ile
    50                  55                  60

Ser Val Pro Tyr Glu Gly Val Phe Arg Ile Ala Asn Val Thr Arg Leu
65                  70                  75                  80

Gln Arg Ala Gln Val Ser Glu Arg Glu Leu Arg Tyr Leu Trp Val Leu
                85                  90                  95

Val Ser Leu Ser Ala Thr Glu Ser Val Gln Asp Val Leu Leu Glu Gly
            100                 105                 110

His Pro Ser Trp Lys Tyr Leu Gln Glu Val Glu Thr Leu Leu Leu Asn
        115                 120                 125

Val Gln Gln Gly Leu Thr Asp Val Glu Val Ser Pro Lys Val Glu Ser
    130                 135                 140

Val Leu Ser Leu Leu Asn Ala Pro Gly Pro Asn Leu Lys Leu Val Arg
145                 150                 155                 160

Pro Lys Ala Leu Leu Asp Asn Cys Phe Arg Val Met Glu Leu Leu Tyr
                165                 170                 175

Cys Ser Cys Cys Lys Gln Ser Ser Val Leu Asn Trp Gln Asp Cys Glu
            180                 185                 190

Val Pro Ser Pro Gln Ser Cys Ser Pro Glu Pro Ser Leu Gln Tyr Ala
        195                 200                 205

Ala Thr Gln Leu Tyr Pro Pro Pro Trp Ser Pro Ser Ser Pro Pro
    210                 215                 220

His Ser Thr Gly Ser Val Arg Pro Val Arg Ala Gln Gly Glu Gly Leu
225                 230                 235                 240

Leu Pro

<210> SEQ ID NO 56
<211> LENGTH: 729
<212> TYPE: DNA
<213> ORGANISM: Artificial sequence
<220> FEATURE:
<223> OTHER INFORMATION: Synthetic polynucleotide

<400> SEQUENCE: 56
atgccccgcg gcttcacctg gctgcgctac ctgggcatct tcctgggcgt ggccctgggc      60
aacgagcccc tggagatgtg gcccctgacc cagaacgagg agtgcaccgt gaccggcttc     120
ctgcgcgaca agctgcagta ccgcagccgc ctgcagtaca tgaagcacta cttccccatc     180
aactacaaga tcagcgtgcc ctacgagggc gtgttccgca tcgccaacgt gacccgcctg     240
cagcgcgccc aggtgagcga gcgcgagctg cgctacctgt gggtgctggt gagcctgagc     300
gccaccgaga gcgtgcagga cgtgctgctg gagggccacc ccagctggaa gtacctgcag     360
gaggtggaga ccctgctgct gaacgtgcag cagggcctga ccgacgtgga ggtgagcccc     420
aaggtggaga gcgtgctgag cctgctgaac gcccccggcc ccaacctgaa gctggtgcgc     480
```

```
cccaaggccc tgctggacaa ctgcttccgc gtgatggagc tgctgtactg cagctgctgc      540
aagcagagca gcgtgctgaa ctggcaggac tgcgaggtgc ccagccccca gagctgcagc      600
cccgagccca gcctgcagta cgccgccacc cagctgtacc cccccccccc ctggagcccc      660
agcagccccc cccacagcac cggcagcgtg cgccccgtgc gcgcccaggg cgagggcctg      720
ctgccctaa                                                              729
```

<210> SEQ ID NO 57
<211> LENGTH: 230
<212> TYPE: PRT
<213> ORGANISM: Artificial sequence
<220> FEATURE:
<223> OTHER INFORMATION: Synthetic polypeptide

<400> SEQUENCE: 57

```
Met Glu Pro Leu Arg Leu Leu Ile Leu Leu Phe Val Thr Glu Leu Ser
1               5                   10                  15

Gly Ala His Asn Thr Thr Val Phe Gln Gly Val Ala Gly Gln Ser Leu
            20                  25                  30

Gln Val Ser Cys Pro Tyr Asp Ser Met Lys His Trp Gly Arg Arg Lys
        35                  40                  45

Ala Trp Cys Arg Gln Leu Gly Glu Lys Gly Pro Cys Gln Arg Val Val
    50                  55                  60

Ser Thr His Asn Leu Trp Leu Leu Ser Phe Leu Arg Arg Trp Asn Gly
65                  70                  75                  80

Ser Thr Ala Ile Thr Asp Asp Thr Leu Gly Gly Thr Leu Thr Ile Thr
                85                  90                  95

Leu Arg Asn Leu Gln Pro His Asp Ala Gly Leu Tyr Gln Cys Gln Ser
            100                 105                 110

Leu His Gly Ser Glu Ala Asp Thr Leu Arg Lys Val Leu Val Glu Val
        115                 120                 125

Leu Ala Asp Pro Leu Asp His Arg Asp Ala Gly Asp Leu Trp Phe Pro
    130                 135                 140

Gly Glu Ser Glu Ser Phe Glu Asp Ala His Val Glu His Ser Ile Ser
145                 150                 155                 160

Arg Ser Leu Leu Glu Gly Glu Ile Pro Phe Pro Pro Thr Ser Ile Leu
                165                 170                 175

Leu Leu Leu Ala Cys Ile Phe Leu Ile Lys Ile Leu Ala Ala Ser Ala
            180                 185                 190

Leu Trp Ala Ala Ala Trp His Gly Gln Lys Pro Gly Thr His Pro Pro
        195                 200                 205

Ser Glu Leu Asp Cys Gly His Asp Pro Gly Tyr Gln Leu Gln Thr Leu
    210                 215                 220

Pro Gly Leu Arg Asp Thr
225                 230
```

<210> SEQ ID NO 58
<211> LENGTH: 690
<212> TYPE: DNA
<213> ORGANISM: Artificial sequence
<220> FEATURE:
<223> OTHER INFORMATION: Synthetic polynucleotide

<400> SEQUENCE: 58

```
atggagcccc tgcgcctgct gatcctgctg ttcgtgaccg agctgagcgg cgcccacaac      60
accaccgtgt tccagggcgt ggccggccag agcctgcagg tgagctgccc ctacgacagc     120
```

```
atgaagcact ggggccgccg caaggcctgg tgccgccagc tgggcgagaa gggccCctgc      180
cagcgcgtgg tgagcaccca caacctgtgg ctgctgagct tcctgcgccg ctggaacggc      240
agcaccgcca tcaccgacga caccctgggc ggcaccctga ccatcaccct gcgcaacctg      300
cagccccacg acgccggcct gtaccagtgc cagagcctgc acggcagcga ggccgacacc      360
ctgcgcaagg tgctggtgga ggtgctggcc gaccccctgg accaccgcga cgccggcgac      420
ctgtggttcc ccggcgagag cgagagcttc gaggacgccc acgtggagca cagcatcagc      480
cgcagcctgc tggagggcga gatccccttc ccccccacca gcatcctgct gctgctggcc      540
tgcatcttcc tgatcaagat cctggccgcc agcgccctgt gggccgccgc ctggcacggc      600
cagaagcccg gcacccaccc ccccagcgag ctggactgcg ccacgaccc cggctaccag      660 ctgcagaccc tgcccggcct gcgcgacacc                                       690

<210> SEQ ID NO 59
<211> LENGTH: 11060
<212> TYPE: DNA
<213> ORGANISM: Artificial sequence
<220> FEATURE:
<223> OTHER INFORMATION: Synthetic polynucleotide

<400> SEQUENCE: 59
ttggccactc cctctctgcg cgctcgctcg ctcactgagg ccgggcgacc aaaggtcgcc       60
cgacgcccgg gctttgcccg gcggcctca gtgagcgagc gagcgcgcag agagggagtg      120
gccaactcca tcactagggg ttcctgctag ctctgggtat ttaagcccga gtgagcacgc      180
agggtctcca ttttgaagcg ggaggttacg cgttcgtcga ctactagtgg gtaccagagc      240
tccctaggtt ctagaaccgg tgacgtctcc catggtgaag cttggatctg agggcggagt      300
tagggcggag ccaatcagcg tgcgccgttc cgaaagttgc cttttatggc tgggcggaga      360
atgggcggtg aacgccgatg attatataag gacgcgccgg gtgtggcaca gctagttccg      420
tcgcagccgg gatttgggtc gcggttcttg tttgtggatc cctgtgatcg tcacttggta      480
agtcactgac tgtctatgcc tgggaaaggg tgggcaggag atgggcagt gcaggaaaag      540 tggcactatg aaccctcctg gtggcgaggg aggggggtg gtcctcgaac gccttgcaga      600
actggcctgg atacagagtg gaccggctgg ccccatctgg aagacttcga gatacactgt      660
tgtcttactg cgctcaacag tgtatctcga agtcttccaa atggtgccag ccatcgcagc      720
ggggtgcagg aaatgggggc agcccccctt tttggctatc cttccacgtg ttctttttg      780 tatcttttgt gtttcctaga aaacatctca gtcaccaccg cagccctagg aatgcatcta      840
gacaattgta ctaaccttct tctctttcct ctcctgacag tccggaaagc caccatggaa      900
ttcagcagcc ccagcagaga ggaatgcccc aagcctctga gccgggtgtc aatcatggcc      960
ggatctctga caggactgct gctgcttcag gccgtgtctt gggcttctgg cgctagacct     1020
tgcatcccca agagcttcgg ctacagcagc gtcgtgtgcg tgtgcaatgc cacctactgc     1080
gacagcttcg accctcctac ctttcctgct ctgggcacct tcagcagata cgagagcacc     1140
agatccggca cggatgga actgagcatg gacccatcc aggccaatca cacaggcact     1200
ggcctgctgc tgacactgca gcctgagcag aaattccaga agtgaaagg cttcggcgga     1260 gccatgacag atgccgccgc tctgaatatc ctggctctgt ctccaccagc tcagaacctg     1320
ctgctcaaga gctacttcag cgaggaaggc atcggctaca acatcatcag agtgcccatg     1380
gccagctgcg acttcagcat caggacctac acctacgccg acacacccga cgatttccag     1440
```

```
ctgcacaact tcagcctgcc tgaagaggac accaagctga agatccctct gatccacaga    1500
gccctgcagt ggcacaaag acccgtgtca ctgctggcct ctccatggac atctcccacc    1560
tggctgaaaa caaatggcgc cgtgaatggc aagggcagcc tgaaaggcca acctggcgac    1620
atctaccacc agacctgggc cagatacttc gtgaagttcc tggacgccta tgccgagcac    1680
aagctgcagt tttgggccgt gacagccgag aacgaaccct ctgctggact gctgagcggc    1740 taccccttc agtgcctggg ctttacaccc gagcaccagc gggactttat cgccgtgat     1800 ctgggaccca cactggccaa tagcacccac cataatgtgc ggctgctgat gctggacgac    1860
cagagactgc ttctgcccca ctgggctaaa gtggtgctga cagatcctga ggccgccaaa    1920
tacgtgcacg gaatcgccgt gcactggtat ctggactttc tggcccctgc caaggccaca    1980
ctgggagaga cacacagact gttccccaac accatgctgt tcgccagcga agcctgtgtg    2040
ggcagcaagt tttgggaaca gagcgtgcgg ctcggcagct gggatagagg catgcagtac    2100
agccacagca tcatcaccaa cctgctgtac cacgtcgtcg gctggaccga ctggaatctg    2160
gccctgaatc ctgaaggcgg ccctaactgg gtccgaaact cgtggacag ccccatcatc    2220 gtggacatca ccaaggacac cttctacaag cagcccatgt tctaccacct gggacacttc    2280
agcaagttca tccccgaggg ctctcagcgc gttggactgg tggcttccca gaagaacgat    2340
ctggacgccg tggctctgat gcaccctgat ggatctgctg tggtggtggt cctgaaccgc    2400
agcagcaaag atgtgcccct gaccatcaag gatcccgccg tgggattcct ggaaacaatc    2460
agccctggct actccatcca cacctacctg tggcgtagac aggagggcag aggaagtctt    2520
ctgacatgcg gagacgtgga agagaatccc ggccctatgc cccgcggctt cacctggctg    2580
cgctacctgg gcatcttcct gggcgtggcc ctgggcaacg agcccctgga gatgtggccc    2640
ctgacccaga acgaggagtg caccgtgacc ggcttcctgc gcgacaagct gcagtaccgc    2700
agccgcctgc agtacatgaa gcactacttc cccatcaact acaagatcag cgtgccctac    2760
gagggcgtgt ccgcatcgc caacgtgacc cgcctgcagc gcgcccaggt gagcgagcgc    2820
gagctgcgct acctgtgggt gctggtgagc ctgagcgcca ccgagagcgt gcaggacgtg    2880
ctgctggagg gccaccccag ctggaagtac ctgcaggagg tggagaccct gctgctgaac    2940
gtgcagcagg gcctgaccga cgtggaggtg agccccaagg tggagagcgt gctgagcctg    3000
ctgaacgccc ccgcccccaa cctgaagctg gtgcgcccca aggccctgct ggacaactgc    3060
ttccgcgtga tggagctgct gtactgcagc tgctgcaagc agagcagcgt gctgaactgg    3120
caggactgcg aggtgcccag cccccagagc tgcagcccg agcccagcct gcagtacgcc    3180
gccacccagc tgtaccccc ccccccctgg agcccagca gccccccca cagcaccggc    3240 agcgtgcgcc ccgtgcgcgc ccagggcgag ggcctgctgc ctaatgaca attgttaatt    3300 aagtttaaac cctcgaggcc gcaagcttat cgataatcaa cctctggatt acaaaatttg    3360
tgaaagattg actggtattc ttaactatgt tgctcctttt acgctatgtg gatacgctgc    3420
tttaatgcct ttgtatcatg ctattgcttc ccgtatggct ttcattttct cctccttgta    3480
taaatcctgg ttgctgtctc tttatgagga gttgtggccc gttgtcaggc aacgtggcgt    3540
ggtgtgcact gtgtttgctg acgcaacccc cactggttgg ggcattgcca ccacctgtca    3600
gctcctttcc gggactttcg ctttccccct ccctattgcc acggcggaac tcatcgccgc    3660
ctgccttgcc cgctgctgga caggggctcg gctgttgggc actgacaatt ccgtggtgtt    3720
gtcggggaaa tcatcgtcct ttccttggct gctcgcctgt gttgccacct ggattctgcg    3780
cgggacgtcc ttctgctacg tccccttcggc cctcaatcca gcggaccttc cttcccgcgg    3840
```

```
cctgctgccg gctctgcggc ctcttccgcg tcttcgcctt cgccctcaga cgagtcggat    3900
ctccctttgg gccgcctccc cgcatcgata ccgtcgacta gagctcgctg atcagcctcg    3960
actgtgcctt ctagttgcca gccatctgtt gtttgcccct cccccgtgcc ttccttgacc    4020
ctggaaggtg ccactcccac tgtcctttcc taataaaatg aggaaattgc atcgcattgt    4080
ctgagtaggt gtcattctat tctgggggt ggggtggggc aggacagcaa ggggaggat     4140 tgggaagaca atagcaggca tgctggggag agatccacga taacaaacag cttttttggg    4200
gtgaacatat tgactgaatt ccctgcaggt tggccactcc ctctctgcgc gctcgctcgc    4260
tcactgaggc cgcccgggca agcccgggc gtcgggcgac ctttggtcgc ccggcctcag     4320
tgagcgagcg agcgcgcaga gagggagtgg ccaactccat cactaggggt tcctgcggcc    4380
gctcgtacgg tctcgaggaa ttcctgcagg ataacttgcc aacctcattc taaaatgtat    4440
atagaagccc aaaagacaat aacaaaaata ttcttgtaga acaaatggg aagaatgtt     4500 ccactaaata tcaagattta gagcaaagca tgagatgtgt ggggatagac agtgaggctg    4560
ataaaataga gtagagctca gaaacagacc cattgatata tgtaagtgac ctatgaaaaa    4620 aatatgcat tttacaatgg gaaaatgatg gtcttttttct tttttagaaa aacagggaaa    4680
tatatttata tgtaaaaaat aaagggaac ccatatgtca taccatacac acaaaaaaat    4740
tccagtgaat tataagtcta aatggagaag gcaaaacttt aaatcttta gaaataata     4800 tagaagcatg cagaccagcc tggccaacat gatgaaaccc tctctactaa taataaaatc    4860
agtagaacta ctcaggacta cttttgagtgg gaagtccttt tctatgaaga cttcttggc    4920 caaaattagg ctctaaatgc aaggagatag tgcatcatgc ctggctgcac ttactgataa    4980
atgatgttat caccatcttt aaccaaatgc acaggaacaa gttatggtac tgatgtgctg    5040
gattgagaag gagctctact tccttgacag gacacatttg tatcaactta aaaagcaga    5100 ttttttgccag cagaactatt cattcagagg taggaaactt agaatagatg atgtcactga    5160
ttagcatggc ttccccatct ccacagctgc ttcccaccca ggttgcccac agttgagttt    5220
gtccagtgct cagggctgcc cactctcagt aagaagcccc acaccagccc ctctccaaat    5280
atgttggctg ttccttccat taaagtgacc ccactttaga gcagcaagtg gatttctgtt    5340
tcttacagtt caggaaggag gagtcagctg tgagaacctg gagcctgaga tgcttctaag    5400
tcccactgct actggggtca gggaagccag actccagcat cagcagtcag gagcactaag    5460
cccttgccaa catcctgttt ctcagagaaa ctgcttccat tataatggtt gtccttttt     5520 aagctatcaa gccaaacaac cagtgtctac cattattctc atcacctgaa gccaagggtt    5580
ctagcaaaag tcaagctgtc ttgtaatggt tgatgtgcct ccagcttctg tcttcagtca    5640
ctccactctt agcctgctct gaatcaactc tgaccacagt tccctggagc cctgccacc    5700 tgctgcccct gccaccttct ccatctgcag tgctgtgcag ccttctgcac tcttgcagag    5760
ctaataggtg gagacttgaa ggaagaggag gaaagtttct cataatagcc ttgctgcaag    5820
ctcaaatggg aggtgggcac tgtgcccagg agccttggag caaaggctgt gcccaacctc    5880
tgactgcatc caggttttggt cttgacagag ataagaagcc ctggcttttg gagccaaaat    5940
ctaggtcaga cttaggcagg attctcaaag tttatcagca gaacatgagg cagaagaccc    6000
tttctgctcc agcttcttca ggctcaacct tcatcagaat agatagaaag agaggctgtg    6060
agggttctta aacagaagc aaatctgact cagagaataa acaacctcct agtaaactac      6120
agcttagaca gagcatctgg tggtgagtgt gctcagtgtc ctactcaact gtctggtatc    6180
```

```
agccctcatg aggacttctc ttctttccct catagacctc catctctgtt ttccttagcc    6240
tgcagaaatc tggatggcta ttcacagaat gcctgtgctt tcagagttgc attttttctc    6300
tggtattctg gttcaagcat ttgaaggtag gaaaggttct ccaagtgcaa gaaagccagc    6360
cctgagcctc aactgcctgg ctagtgtggt cagtaggatg caaaggctgt tgaatgccac    6420
aaggccaaac tttaacctgt gtaccacaag cctagcagca gaggcagctc tgctcactgg    6480
aactctctgt cttcttttctc ctgagccttt tcttttcctg agttttctag ctctcctcaa    6540
ccttacctct gccctaccca ggacaaaccc aagagccact gtttctgtga tgtcctctcc    6600
agccctaatt aggcatcatg acttcagcct gaccttccat gctcagaagc agtgctaatc    6660
cacttcagat gagctgctct atgcaacaca ggcagagcct acaaaccttt gcaccagagc    6720
cctccacata tcagtgtttg ttcatactca cttcaacagc aaatgtgact gctgagatta    6780
agattttaca caagatggtc tgtaatttca cagttagttt tatcccatta ggtatgaaag    6840
aattagcata attcccctta aacatgaatg aatcttagat tttttaataa atagttttgg    6900
aagtaaagac agagacatca ggagcacaag gaatagcctg agaggacaaa cagaacaaga    6960
aagagtctgg aaatacacag gatgttcttg gcctcctcaa agcaagtgca agcagatagt    7020
accagcagcc ccaggctatc agagcccagt gaagagaagt accatgaaag ccacagctct    7080
aaccaccctg ttccagagtg acagacagtc cccaagacaa gccagcctga gccagagaga    7140
gaactgcaag agaaagtttc taatttaggt tctgttagat tcagacaagt gcaggtcatc    7200
ctctctccac agctactcac ctctccagcc taacaaagcc tgcagtccac actccaaccc    7260
tggtgtctca cctcctagcc tctcccaaca tcctgctctc tgaccatctt ctgcatctct    7320
catctcacca tctcccactg tctacagcct actcttgcaa ctaccatctc attttctgac    7380
atcctgtcta catcttctgc catactctgc catctaccat accacctctt accatctacc    7440
acaccatctt ttatctccat ccctctcaga agcctccaag ctgaatcctg ctttatgtgt    7500
tcatctcagc ccctgcatgg aaagctgacc ccagaggcag aactattccc agagagcttg    7560
gccaagaaaa acaaaactac cagcctggcc aggctcagga gtagtaagct gcagtgtctg    7620
ttgtgttcta gcttcaacag ctgcaggagt tccactctca aatgctccac atttctcaca    7680
tcctcctgat tctggtcact acccatcttc aaagaacaga atatctcaca tcagcatact    7740
gtgaaggact agtcatgggt gcagctgctc agagctgcaa agtcattctg gatggtggag    7800
agcttacaaa catttcatga tgctcccccc gctctgatgg ctggagccca atccctacac    7860
agactcctgc tgtatgtgtt ttcctttcac tctgagccac agccagaggg caggcattca    7920
gtctcctctt caggctgggg ctgggcact gagaactcac ccaacacctt gctctcactc    7980
cttctgcaaa acaagaaaga ctttgtgct gcagtagcca tgaagaatga aggaaggct    8040 ttaactaaaa aatgtcagag attattttca accccttact gtggatcacc agcaaggagg    8100
aaacacaaca cagagacatt ttttcccctc aaattatcaa aagaatcact gcatttgtta    8160
aagagagcaa ctgaatcagg aagcagagtt ttgaacatat cagaagttag gaatctgcat    8220
cagagacaaa tgcagtcatg gttgtttgct gcataccagc cctaatcatt agaagcctca    8280
tggacttcaa acatcattcc ctctgacaag atgctctagc ctaactccat gagataaaat    8340
aaatctgcct ttcagagcca aagaagagtc caccagcttc ttctcagtgt gaacaagagc    8400
tccagtcagg ttagtcagtc cagtgcagta gaggagacca gtctgcatcc tctaattttc    8460
aaaggcaaga agatttgttt accctggaca ccaggcacaa gtgaggtcac agagctctta    8520
gatatgcagt cctcatgagt gaggagacta aagcgcatgc catcaagact tcagtgtaga    8580
```

```
gaaaacctcc aaaaaagcct cctcactact tctggaatag ctcagaggcc gaggcggcct   8640
cggcctctgc ataaataaaa aaaattagtc agccatgggg cggagaatgg gcggaactgg   8700
gcggagttag gggcgggatg ggcggagtta ggggcgggac tatggttgct gactaattga   8760
gatgcatgct ttgcatactt ctgcctgctg gggagcctgg ggactttcca cacctggttg   8820
ctgactaatt gagatgcatg ctttgcatac ttctgcctgc tggggagcct ggggactttc   8880
cacaccctaa ctgacacaca ttccacagct gcattaatga atcggccaac gcgcggggag   8940
aggcggtttg cgtattgggc gctcttccgc ttcctcgctc actgactcgc tgcgctcggt   9000
cgttcggctg cggcgagcgg tatcagctca ctcaaaggcg gtaatacggt tatccacaga   9060
atcaggggat aacgcaggaa agaacatgtg agcaaaaggc cagcaaaagg ccaggaaccg   9120
taaaaaggcc gcgttgctgg cgttttccca taggctccgc cccccctgacg agcatcacaa   9180 aaatcgacgc tcaagtcaga ggtggcgaaa cccgacagga ctataaagat accaggcgtt   9240
tccccctgga agctccctcg tgcgctctcc tgttccgacc ctgccgctta ccggatacct   9300
gtccgccttt ctcccttcgg gaagcgtggc gctttctcat agctcacgct gtaggtatct   9360
cagttcggtg taggtcgttc gctccaagct gggctgtgtg cacgaaccc ccgttcagcc   9420 cgaccgctgc gccttatccg gtaactatcg tcttgagtcc aacccggtaa gacacgactt   9480
atcgccactg gcagcagcca ctggtaacag gattagcaga gcgaggtatg taggcggtgc   9540
tacagagttc ttgaagtggt ggcctaacta cggctacact agaagaacag tatttggtat   9600
ctgcgctctg ctgaagccag ttaccttcgg aaaaagagtt ggtagctctt gatccggcaa   9660
acaaaccacc gctggtagcg gtggtttttt tgtttgcaag cagcagatta cgcgcagaaa   9720
aaaaggatct caagaagatc ctttgatctt ttctacgggg tctgacgctc agtggaacga   9780
aaactcacgt taagggattt tggtcatgag attatcaaaa aggatcttca cctagatcct   9840
tttaaattaa aaatgaagtt ttaaatcaat ctaaagtata tatgagtaaa cttggtctga   9900
cagttaccaa tgcttaatca gtgaggcacc tatctcagcg atctgtctat ttcgttcatc   9960
catagttgcc tgactcctgc aaaccacgtt gtgtctcaaa atctctgatg ttacattgca   10020
caagataaaa atatatcatc atgaacaata aaactgtctg cttacataaa cagtaataca   10080
aggggtgtta tgagccatat tcaacgggaa acgtcttgct cgaggccgcg attaaattcc   10140
aacatggatg ctgatttata tgggtataaa tgggctcgcg ataatgtcgg gcaatcaggt   10200
gcgacaatct atcgattgta tgggaagccc gatgcgccag agttgtttct gaaacatggc   10260
aaaggtagcg ttgccaatga tgttacagat gagatggtca gactaaactg gctgacggaa   10320
tttatgcctc ttccgaccat caagcatttt atccgtactc ctgatgatgc atggttactc   10380
accactgcga tccccgggaa aacagcattc caggtattag aagaatatcc tgattcaggt   10440
gaaaatattg ttgatgcgct ggcagtgttc ctgcgccggt tgcattcgat tcctgtttgt   10500
aattgtcctt ttaacagcga tcgcgtattt cgtctcgctc aggcgcaatc acgaatgaat   10560
aacggtttgg ttgatgcgag tgattttgat gacgagcgta atggctggcc tgttgaacaa   10620
gtctggaaag aaatgcataa gcttttgcca ttctcaccgg attcagtcgt cactcatggt   10680
gatttctcac ttgataacct tatttttgac gaggggaaat taataggttg tattgatgtt   10740
ggacgagtcg gaatcgcaga ccgataccag gatcttgcca tcctatggaa ctgcctcggt   10800
gagttttctc cttcattaca gaaacggctt tttcaaaaat atggtattga taatcctgat   10860
atgaataaat tgcagtttca tttgatgctc gatgagtttt tctaagggcg gcctgccacc   10920
```

```
ataccacgc cgaaacaagc gctcatgagc ccgaagtggc gagcccgatc ttccccatcg   10980
gtgatgtcgg cgatataggc gccagcaacc gcacctgtgg cgccggtgat gagggcgcgc   11040
caagtcgacg tccggcagtc                                              11060
```

<210> SEQ ID NO 60
<211> LENGTH: 10913
<212> TYPE: DNA
<213> ORGANISM: Artificial sequence
<220> FEATURE:
<223> OTHER INFORMATION: Synthetic polynucleotide

<400> SEQUENCE: 60

```
ttggccactc cctctctgcg cgctcgctcg ctcactgagg ccgggcgacc aaaggtcgcc     60
cgacgcccgg gctttgcccg ggcggcctca gtgagcgagc gagcgcgcag agagggagtg    120
gccaactcca tcactagggg ttcctgctag ctctgggtat ttaagcccga gtgagcacgc    180
agggtctcca tttttgaagcg ggaggttacg cgttcgtcga ctactagtgg gtaccagagc   240
tccctaggtt ctagaaccgg tgacgtctcc catggtgaag cttggatctg agggcggagt    300
tagggcggag ccaatcagcg tgcgccgttc cgaaagttgc cttttatggc tgggcggaga    360
atgggcggtg aacgccgatg attatataag gacgcgccgg gtgtggcaca gctagttccg    420
tcgcagccgg gatttgggtc gcggttcttg tttgtggatc cctgtgatcg tcacttggta    480
agtcactgac tgtctatgcc tgggaaaggg tgggcaggag atgggggcagt gcaggaaaag   540 tggcactatg aaccctcctg gtggcgaggg gagggggggtg gtcctcgaac gccttgcaga    600
actggcctgg atacagagtg gaccggctgg ccccatctgg aagacttcga gatacactgt    660
tgtcttactg cgctcaacag tgtatctcga agtcttccaa atggtgccag ccatcgcagc    720
ggggtgcagg aaatggggc agccccccctt tttggctatc cttccacgtg ttcttttttg    780
tatcttttgt gtttcctaga aaacatctca gtcaccaccg cagccctagg aatgcatcta    840
gacaattgta ctaaccttct tctctttcct ctcctgacag tccggaaagc caccatggaa    900
ttcagcagcc ccagcagaga ggaatgcccc aagcctctga gccgggtgtc aatcatggcc    960
ggatctctga caggactgct gctgcttcag gccgtgtctt gggcttctgg cgctagacct   1020
tgcatcccca agagcttcgg ctacagcagc gtcgtgtgcg tgtgcaatgc cacctactgc   1080
gacagcttcg accctcctac ctttcctgct ctgggcacct tcagcagata cgagagcacc   1140
agatccggca gacggatgga actgagcatg gacccatcc aggccaatca cacaggcact   1200
ggcctgctgc tgacactgca gcctgagcag aaattccaga agtgaaaggg cttcggcgga   1260
gccatgacag atgccgccgc tctgaatatc ctggctctgt ctccaccagc tcagaacctg   1320
ctgctcaaga gctacttcag cgaggaaggc atcggctaca acatcatcag agtgcccatg   1380
gccagctgcg acttcagcat caggacctac acctacgccg acacacccga cgatttccag   1440
ctgcacaact tcagcctgcc tgaagaggac accaagctga gatccctct gatccacaga   1500 gccctgcagc tggcacaaag acccgtgtca ctgctggcct ctcccatggac atctcccacc   1560 tggctgaaaa caaatggcgc cgtgaatggc aagggcagcc tgaaaggcca acctggcgac   1620
atctaccacc agacctgggc cagatacttc gtgaagttcc tggacgccta tgccgagcac   1680
aagctgcagt tttgggccgt gacagccgag aacgaacctt ctgctggact gctgagcggc   1740
tacccctttc agtgcctggg ctttacaccc gagcaccagc gggactttat cgcccgtgat   1800
ctgggaccca cactgccaa tagcacccac cataatgtgc ggctgctgat gctgacgac   1860 cagagactgc ttctgccca ctgggctaaa gtggtgctga cagatcctga ggccgccaaa   1920
```

```
tacgtgcacg gaatcgccgt gcactggtat ctggactttc tggcccctgc caaggccaca    1980
ctgggagaga cacacagact gttccccaac accatgctgt tcgccagcga agcctgtgtg    2040
ggcagcaagt tttgggaaca gagcgtgcgg ctcggcagct gggatagagg catgcagtac    2100
agccacagca tcatcaccaa cctgctgtac cacgtcgtcg gctggaccga ctggaatctg    2160
gccctgaatc ctgaaggcgg ccctaactgg gtccgaaact tcgtggacag ccccatcatc    2220
gtggacatca ccaaggacac cttctacaag cagcccatgt tctaccacct gggacacttc    2280
agcaagttca tccccgaggg ctctcagcgc gttggactgg tggcttccca gaagaacgat    2340
ctggacgccg tggctctgat gcaccctgat ggatctgctg tggtggtggt cctgaaccgc    2400
agcagcaaag atgtgcccct gaccatcaag gatcccgccg tgggattcct ggaaacaatc    2460
agccctggct actccatcca cacctacctg tggcgtagac agtgattgtg ccgaaccgc     2520 cgaactcaga ggccggcccc agaaaacccg agcgagtagg gggcggcgcg caggagggag    2580
gagaactggg ggcgcgggag gctggtgggt gtgggggtg gagatgtaga agatgtgacg     2640
ccgcggcccg gcgggtgcca gattagcgga cgcggtgccc gcggttgcaa cgggatcccg    2700
ggcgctgcag cttgggaggc ggctctcccc aggcggcgtc cgcggagaca cccatccgtg    2760
aaccccaggt cccgggccgc cggctcgccg cgcaccaggg gccggcggac agaagagcgg    2820
ccgagcggct cgaggctggg ggaccgcggg cgcggccgcg cgctgccggg cgggaggctg    2880
gggggccggg gccggggccg tgccccggag cgggtcggag gccggggccg ggccggggg    2940 acggcggctc cccgcgcggc tccagcggct cggggatccc ggccgggccc cgcagggacc    3000
atgatgcccc gcggcttcac ctggctgcgc tacctgggca tcttcctggg cgtggccctg    3060
ggcaacgagc ccctggagat gtggcccctg acccagaacg aggagtgcac cgtgaccggc    3120
ttcctgcgcg acaagctgca gtaccgcagc cgcctgcagt acatgaagca ctacttcccc    3180
atcaactaca gatcagcgt gccctacgag ggcgtgttcc gcatcgccaa cgtgacccgc    3240
ctgcagcgcg cccaggtgag cgagcgcgag ctgcgctacc tgtgggtgct ggtgagcctg    3300
agcgccaccg agagcgtgca ggacgtgctg ctggagggcc accccagctg gaagtacctg    3360
caggaggtgg agaccctgct gctgaacgtg cagcagggcc tgaccgacgt ggaggtgagc    3420
cccaaggtgg agagcgtgct gagcctgctg aacgcccccg gccccaacct gaagctggtg    3480
cgccccaagg ccctgctgga caactgcttc cgcgtgatgg agctgctgta ctgcagctgc    3540
tgcaagcaga gcagcgtgct gaactggcag gactgcgagg tgcccagccc ccagagctgc    3600
agccccgagc ccagcctgca gtacgccgcc acccagctgt acccccccccc ccctggagc    3660 cccagcagcc ccccccacag caccggcagc gtgcgccccg tgcgcgccca gggcgagggc    3720
ctgctgccct aatgacaatt gttaattaag tttaaaccct cgaggccgca agccgcatcg    3780
ataccgtcga ctagagctcg ctgatcagcc tcgactgtgc cttctagttg ccagccatct    3840
gttgtttgcc cctcccccgt gccttccttg accctggaag gtgccactcc cactgtcctt    3900
tcctaataaa atgaggaaat tgcatcgcat tgtctgagta ggtgtcattc tattctgggg    3960
ggtggggtgg ggcaggacag caaggggag gattgggaag acaatagcag gcatgctggg    4020
gagagatcca cgataacaaa cagctttttt ggggtgaaca tattgactga attccctgca    4080
ggttggccac tccctctctg cgcgctcgct cgctcactga ggccgcccgg gcaaagcccg    4140
ggcgtcgggc gacctttggt cgcccggcct cagtgagcga gcgagcgcgc agagagggag    4200
tggccaactc catcactagg ggttcctgcg gccgctcgta cggtctcgag gaattcctgc    4260
```

```
aggataactt gccaacctca ttctaaaatg tatatagaag cccaaaagac aataacaaaa    4320
atattcttgt agaacaaaat gggaaagaat gttccactaa atatcaagat ttagagcaaa    4380
gcatgagatg tgtggggata gacagtgagg ctgataaaat agagtagagc tcagaaacag    4440
acccattgat atatgtaagt gacctatgaa aaaaatatgg cattttacaa tgggaaaatg    4500
atggtctttt tcttttttag aaaaacaggg aaatatattt atatgtaaaa aataaaaggg    4560
aacccatatg tcataccata cacacaaaaa aattccagtg aattataagt ctaaatggag    4620
aaggcaaaac tttaaatctt ttagaaaata atatagaagc atgcagacca gcctggccaa    4680
catgatgaaa ccctctctac taataataaa atcagtagaa ctactcagga ctactttgag    4740
tgggaagtcc ttttctatga agacttcttt ggccaaaatt aggctctaaa tgcaaggaga    4800
tagtgcatca tgcctggctg cacttactga taaatgatgt tatcaccatc tttaaccaaa    4860
tgcacaggaa caagttatgg tactgatgtg ctggattgag aaggagctct acttccttga    4920
caggacacat ttgtatcaac ttaaaaaagc agatttttgc cagcagaact attcattcag    4980
aggtaggaaa cttagaatag atgatgtcac tgattagcat ggcttcccca tctccacagc    5040
tgcttcccac ccaggttgcc cacagttgag tttgtccagt gctcagggct gcccactctc    5100
agtaagaagc cccacaccag cccctctcca aatatgttgg ctgttccttc cattaaagtg    5160
accccacttt agagcagcaa gtggatttct gtttcttaca gttcaggaag gaggagtcag    5220
ctgtgagaac ctggagcctg agatgcttct aagtcccact gctactgggg tcagggaagc    5280
cagactccag catcagcagt caggagcact aagcccttgc caacatcctg tttctcagag    5340
aaactgcttc cattataatg gttgtccttt tttaagctat caagccaaac aaccagtgtc    5400
taccattatt ctcatcacct gaagccaagg gttctagcaa aagtcaagct gtcttgtaat    5460
ggttgatgtg cctccagctt ctgtcttcag tcactccact cttagcctgc tctgaatcaa    5520
ctctgaccac agttccctgg agccctgcc acctgctgcc cctgccacct tctccatctg    5580
cagtgctgtg cagccttctg cactcttgca gagctaatag gtggagactt gaaggaagag    5640
gaggaaagtt tctcataata gccttgctgc aagctcaaat gggaggtggg cactgtgccc    5700
aggagccttg gagcaaaggc tgtgcccaac ctctgactgc atccaggttt ggtcttgaca    5760
gagataagaa gccctggctt ttggagccaa atctaggtc agacttaggc aggattctca    5820
aagtttatca gcagaacatg aggcagaaga ccctttctgc tccagcttct tcaggctcaa    5880
ccttcatcag aatagataga aagagaggct gtgagggttc ttaaaacaga agcaaatctg    5940
actcagagaa taaacaacct cctagtaaac tacagcttag acagagcatc tggtggtgag    6000
tgtgctcagt gtcctactca actgtctggt atcagccctc atgaggactt ctcttctttc    6060
cctcatagac ctccatctct gttttcctta gcctgcagaa atctggatgg ctattcacag    6120
aatgcctgtg ctttcagagt tgcatttttt ctctggtatt ctggttcaag catttgaagg    6180
taggaaaggt tctccaagtg caagaaagcc agccctgagc ctcaactgcc tggctagtgt    6240
ggtcagtagg atgcaaaggc tgttgaatgc cacaaggcca aactttaacc tgtgtaccac    6300
aagcctagca gcagaggcag ctctgctcac tggaactctc tgtcttcttt ctcctgagcc    6360
ttttcttttc ctgagttttc tagctctcct caaccttacc tctgccctac ccaggacaaa    6420
cccaagagcc actgtttctg tgatgtcctc tccagcccta attaggcatc atgacttcag    6480
cctgaccttc catgctcaga agcagtgcta atccacttca gatgagctgc tctatgcaac    6540
acaggcagag cctacaaacc tttgcaccag agccctccac atatcagtgt tgttcatac    6600 tcacttcaac agcaaatgtg actgctgaga ttaagatttt acacaagatg gtctgtaatt    6660
```

```
tcacagttag ttttatccca ttaggtatga aagaattagc ataattcccc ttaaacatga     6720
atgaatctta gattttttaa taaatagttt tggaagtaaa gacagagaca tcaggagcac     6780
aaggaatagc ctgagaggac aaacagaaca agaaagagtc tggaaataca caggatgttc     6840
ttggcctcct caaagcaagt gcaagcagat agtaccagca gccccaggct atcagagccc     6900
agtgaagaga agtaccatga aagccacagc tctaaccacc ctgttccaga gtgacagaca     6960
gtccccaaga caagccagcc tgagccagag agagaactgc aagagaaagt ttctaattta     7020
ggttctgtta gattcagaca agtgcaggtc atcctctctc cacagctact cacctctcca     7080
gcctaacaaa gcctgcagtc cacactccaa ccctggtgtc tcacctccta gcctctccca     7140
acatcctgct ctctgaccat cttctgcatc tctcatctca ccatctccca ctgtctacag     7200
cctactcttg caactaccat ctcattttct gacatcctgt ctacatcttc tgccatactc     7260
tgccatctac cataccacct cttaccatct accacaccat cttttatctc catccctctc     7320
agaagcctcc aagctgaatc ctgctttatg tgttcatctc agccctgca tggaaagctg      7380 accccagagg cagaactatt cccagagagc ttggccaaga aaacaaaac taccagcctg      7440 gccaggctca ggagtagtaa gctgcagtgt ctgttgtgtt ctagcttcaa cagctgcagg     7500
agttccactc tcaaatgctc cacatttctc acatcctcct gattctggtc actacccatc     7560
ttcaaagaac agaatatctc acatcagcat actgtgaagg actagtcatg ggtgcagctg     7620
ctcagagctg caaagtcatt ctggatggtg gagagcttac aaacatttca tgatgctccc     7680
cccgctctga tggctggagc ccaatcccta cacagactcc tgctgtatgt gttttccttt     7740
cactctgagc cacagccaga gggcaggcat tcagtctcct cttcaggctg gggctggggc     7800
actgagaact cacccaacac cttgctctca ctccttctgc aaaacaagaa agagctttgt     7860
gctgcagtag ccatgaagaa tgaaaggaag gctttaacta aaaaatgtca gagattattt     7920 tcaaccccctt actgtggatc accagcaagg aggaaacaca acacagagac atttttccc     7980 ctcaaattat caaaagaatc actgcatttg ttaaagagag caactgaatc aggaagcaga    8040
gttttgaaca tatcagaagt taggaatctg catcagagac aaatgcagtc atggttgttt     8100
gctgcatacc agccctaatc attagaagcc tcatggactt caaacatcat tccctctgac     8160
aagatgctct agcctaactc catgagataa aataaatctg cctttcagag ccaaagaaga     8220
gtccaccagc ttcttctcag tgtgaacaag agctccagtc aggttagtca gtccagtgca     8280
gtagaggaga ccagtctgca tcctctaatt ttcaaaggca agaagatttg tttaccctgg     8340
acaccaggca caagtgaggt cacagagctc ttagatatgc agtcctcatg agtgaggaga     8400
ctaaagcgca tgccatcaag acttcagtgt agagaaaacc tccaaaaaag cctcctcact     8460
acttctggaa tagctcagag gccgaggcgg cctcggcctc tgcataaata aaaaaaatta     8520
gtcagccatg gggcggagaa tgggcggaac tgggcggagt tagggggcggg atgggcggag     8580 ttaggggcgg gactatggtt gctgactaat tgagatgcat gctttgcata cttctgcctg     8640
ctggggagcc tggggacttt ccacacctgg ttgctgacta attgagatgc atgctttgca     8700
tacttctgcc tgctggggag cctggggact ttccacaccc taactgacac acattccaca     8760
gctgcattaa tgaatcggcc aacgcgcggg gagaggcggt ttgcgtattg ggcgctcttc     8820
cgcttcctcg ctcactgact cgctgcgctc ggtcgttcgg ctgcggcgag cggtatcagc     8880
tcactcaaag gcggtaatac ggttatccac agaatcaggg gataacgcag gaaagaacat     8940
gtgagcaaaa ggccagcaaa aggccaggaa ccgtaaaaag gccgcgttgc tggcgttttt     9000
```

| | | | | | |
|---|---|---|---|---|---|
| ccataggctc | cgccccctg | acgagcatca | caaaaatcga | cgctcaagtc | agaggtggcg | 9060 |
| aaacccgaca | ggactataaa | gataccaggc | gtttccccct | ggaagctccc | tcgtgcgctc | 9120 |
| tcctgttccg | accctgccgc | ttaccggata | cctgtccgcc | tttctccctt | cgggaagcgt | 9180 |
| ggcgctttct | catagctcac | gctgtaggta | tctcagttcg | gtgtaggtcg | ttcgctccaa | 9240 |
| gctgggctgt | gtgcacgaac | cccccgttca | gcccgaccgc | tgcgccttat | ccggtaacta | 9300 |
| tcgtcttgag | tccaacccgg | taagacacga | cttatcgcca | ctggcagcag | ccactggtaa | 9360 |
| caggattagc | agagcgaggt | atgtaggcgg | tgctacagag | ttcttgaagt | ggtggcctaa | 9420 |
| ctacggctac | actagaagaa | cagtatttgg | tatctgcgct | ctgctgaagc | cagttacctt | 9480 |
| cggaaaaaga | gttggtagct | cttgatccgg | caaacaaacc | accgctggta | gcggtggttt | 9540 |
| ttttgtttgc | aagcagcaga | ttacgcgcag | aaaaaaagga | tctcaagaag | atcctttgat | 9600 |
| cttttctacg | gggtctgacg | ctcagtggaa | cgaaaactca | cgttaaggga | ttttggtcat | 9660 |
| gagattatca | aaaaggatct | tcacctagat | ccttttaaat | taaaaatgaa | gttttaaatc | 9720 |
| aatctaaagt | atatatgagt | aaacttggtc | tgacagttac | caatgcttaa | tcagtgaggc | 9780 |
| acctatctca | gcgatctgtc | tatttcgttc | atccatagtt | gcctgactcc | tgcaaaccac | 9840 |
| gttgtgtctc | aaaatctctg | atgttacatt | gcacaagata | aaaatatatc | atcatgaaca | 9900 |
| ataaaactgt | ctgcttacat | aaacagtaat | acaaggggtg | ttatgagcca | tattcaacgg | 9960 |
| gaaacgtctt | gctcgaggcc | gcgattaaat | tccaacatgg | atgctgattt | atatgggtat | 10020 |
| aaatgggctc | gcgataatgt | cgggcaatca | ggtgcgacaa | tctatcgatt | gtatgggaag | 10080 |
| cccgatgcgc | cagagttgtt | tctgaaacat | ggcaaaggta | gcgttgccaa | tgatgttaca | 10140 |
| gatgagatgg | tcagactaaa | ctggctgacg | gaatttatgc | ctcttccgac | catcaagcat | 10200 |
| tttatccgta | ctcctgatga | tgcatggtta | ctcaccactg | cgatccccgg | gaaaacagca | 10260 |
| ttccaggtat | tagaagaata | tcctgattca | ggtgaaaata | ttgttgatgc | gctggcagtg | 10320 |
| ttcctgcgcc | ggttgcattc | gattcctgtt | tgtaattgtc | cttttaacag | cgatcgcgta | 10380 |
| tttcgtctcg | ctcaggcgca | atcacgaatg | aataacggtt | tggttgatgc | gagtgatttt | 10440 |
| gatgacgagc | gtaatggctg | gcctgttgaa | caagtctgga | aagaaatgca | taagcttttg | 10500 |
| ccattctcac | cggattcagt | cgtcactcat | ggtgatttct | cacttgataa | ccttattttt | 10560 |
| gacgagggga | aattaatagg | ttgtattgat | gttggacgag | tcggaatcgc | agaccgatac | 10620 |
| caggatcttg | ccatcctatg | gaactgcctc | ggtgagtttt | ctccttcatt | acagaaacgg | 10680 |
| ctttttcaaa | aatatggtat | tgataatcct | gatatgaata | aattgcagtt | tcatttgatg | 10740 |
| ctcgatgagt | ttttctaagg | gcggcctgcc | accatacccc | gccgaaaca | agcgctcatg | 10800 |
| agcccgaagt | ggcgagcccg | atcttcccca | tcggtgatgt | cggcgatata | ggcgccagca | 10860 |
| accgcacctg | tggcgccggt | gatgagggcg | cgccaagtcg | acgtccggca | gtc | 10913 |

<210> SEQ ID NO 61
<211> LENGTH: 11209
<212> TYPE: DNA
<213> ORGANISM: Artificial sequence
<220> FEATURE:
<223> OTHER INFORMATION: Synthetic polynucleotide

<400> SEQUENCE: 61

| | | | | | |
|---|---|---|---|---|---|
| ttggccactc | cctctctgcg | cgctcgctcg | ctcactgagg | ccgggcgacc | aaaggtcgcc | 60 |
| cgacgcccgg | gctttgcccg | ggcggcctca | gtgagcgagc | gagcgcgcag | agagggagtg | 120 |
| gccaactcca | tcactagggg | ttcctgctag | ctctgggtat | ttaagcccga | gtgagcacgc | 180 |

-continued

```
agggtctcca ttttgaagcg ggaggttacg cgttcgtcga ctactagtgg gtaccagagc      240
tccctaggtt ctagaaccgg tgacgtctcc catggtgaag cttggatctg agggcggagt      300
tagggcggag ccaatcagcg tgcgccgttc cgaaagttgc cttttatggc tgggcggaga      360
atgggcggtg aacgccgatg attatataag gacgcgccgg gtgtggcaca gctagttccg      420
tcgcagccgg gatttgggtc gcggttcttg tttgtggatc cctgtgatcg tcacttggta      480
agtcactgac tgtctatgcc tgggaaaggg tgggcaggag atggggcagt gcaggaaaag      540
tggcactatg aaccctgcag ccctaggaat gcatctagac aattgtacta accttcttct      600 cttcctctc ctgacagtcc ggaaagccac catggaattc agcagcccca gcagagagga       660 atgcccaag cctctgagcc gggtgtcaat catggccgga tctctgacag gactgctgct       720
gcttcaggcc gtgtcttggg cttctggcgc tagaccttgc atcccaaga gcttcggcta       780 cagcagcgtc gtgtgcgtgt gcaatgccac ctactgcgac agcttcgacc ctcctacctt      840
tcctgctctg gcaccttca gcagatacga gagcaccaga tccggcagac ggatggaact       900
gagcatggga cccatccagg ccaatcacac aggcactggc ctgctgctga cactgcagcc      960
tgagcagaaa ttccagaaag tgaaaggctt cggcggagcc atgacagatg ccgccgctct      1020
gaatatcctg gctctgtctc caccagctca gaacctgctg ctcaagagct acttcagcga      1080
ggaaggcatc ggctacaaca tcatcagagt gcccatggcc agctgcgact tcagcatcag      1140
gacctacacc tacgccgaca cacccgacga tttccagctg cacaacttca gcctgcctga      1200
agaggacacc aagctgaaga tccctctgat ccacagagcc ctgcagctgg cacaaagacc      1260
cgtgtcactg ctggcctctc catggacatc tcccacctgg ctgaaaacaa atggcgccgt      1320
gaatggcaag gcagcctga aaggccaacc tggcgacatc taccaccaga cctgggccag      1380
atacttcgtg aagttcctgg acgcctatgc cgagcacaag ctgcagtttt gggccgtgac      1440
agccgagaac gaaccttctg ctggactgct gagcggctac ccctttcagt gcctgggctt      1500
tacacccgag caccagcggg actttatcgc ccgtgatctg ggacccacac tggccaatag      1560
cacccaccat aatgtgcggc tgctgatgct ggacgaccag agactgcttc tgccccactg      1620
ggctaaagtg gtgctgacag atcctgaggc cgccaaatac gtgcacggaa tcgccgtgca      1680
ctggtatctg gactttctgg cccctgccaa ggccacactg ggagagacac acagactgtt      1740
ccccaacacc atgctgttcg ccagcgaagc ctgtgtgggc agcaagtttt gggaacagag      1800
cgtgcggctc ggcagctggg atagaggcat gcagtacagc cacagcatca tcaccaacct      1860
gctgtaccac gtcgtcggct ggaccgactg gaatctggcc ctgaatcctg aaggcggccc      1920
taactgggtc cgaaacttcg tggacagccc catcatcgtg gacatcacca aggacacctt      1980
ctacaagcag cccatgttct accacctggg acacttcagc aagttcatcc ccgagggctc      2040
tcagcgcgtt ggactggtgg cttcccagaa gaacgatctg gacgccgtgg ctctgatgca      2100
ccctgatgga tctgctgtgg tggtggtcct gaaccgcagc agcaaagatg tgcccctgac      2160
catcaaggat cccgccgtgg gattcctgga acaatcagc cctggctact ccatccacac       2220
ctacctgtgg cgtagacagt gacaattgtt aattaagttt aaaccctcga ggccgcaagc      2280
cgcatcgata ccgtcgacta gagctcgctg atcagcctcg actgtgcctt ctagttgcca      2340
gccatctgtt gtttgcccct ccccgtgcc ttccttgacc ctggaaggtg ccactcccac       2400
tgtcctttcc taataaaatg aggaaattgc atcgcattgt ctgagtaggt gtcattctat      2460
tctggggggt ggggtggggc aggacagcaa ggggaggat tggaagaca atagcaggca       2520
```

```
tgctggggag agatccacga taacaaacag cttttttggg ggatatcaaa ctgcctgttt      2580
gggcttctca tttcttacct cccct tccct ctcccacctg ctactgggtg catctctgct     2640
ccccccttcc ccagcagatg gttacctttg ggctgttgct ttcttgtcac catctgagtt     2700
ctcagacgct ggaaagccat gttctcggct ctgtgaatga caatgctgac tggagtgctg     2760
cccctctgta aagggctggg tgtggatggt cacaagcccc tcacatgcct cagccaagag     2820
gaagtagtac aggggtcagc ccagaggtcc aggggaaagg agtggaaacc gatttcccca     2880
ccaagggagg ggcctgtacc tcagctgttc ccatagctta cttgccacaa ctgccaagca     2940
agtttcgctg agtttgacac atggatccct gtggatcaac tgccctagga ctccgtttgc     3000
acccatgtga cactgttgac tttgccctga cgaagcaggg ccaacagtcc cctaacttaa     3060
ttacaaaaac taatgactaa gagagaggtg gctagagctg aggcccctga gtcaggctgt     3120
gggtgggatc atctccagta caggaagtga gactttcatt tcctccttc caagagaggg     3180 ctgagggagc agggttgagc aactggtgca gacagcctag ctggactttg ggtgaggcgg     3240
ttcagccata tcgaattctg ctggggctac tggcaggtaa ggaggaagga ggctgagggg     3300
agggggcccc tgggagggag cctgccctgg gttgctaacc atctcctctc tgccaaaagt     3360
ccggaaagcc accatggagc ccctgcgcct gctgatcctg ctgttcgtga ccagctgag     3420 cggcgcccac aacaccaccg tgttccaggg cgtggccggc cagagcctgc aggtgagctg     3480
cccctacgac agcatgaagc actggggccg ccgcaaggcc tggtgccgcc agctgggcga     3540
gaagggcccc tgccagcgcg tggtgagcac ccacaacctg tggctgctga gcttcctgcg     3600
ccgctggaac ggcagcaccg ccatcaccga cgacaccctg ggcggcaccc tgaccatcac     3660
cctgcgcaac ctgcagcccc acgacgccgg cctgtaccag tgccagagcc tgcacggcag     3720
cgaggccgac accctgcgca aggtgctggt ggaggtgctg gccgaccccc tggaccaccg     3780
cgacgccggc gacctgtggt tccccggcga gagcgagagc ttcgaggacg cccacgtgga     3840
gcacagcatc agccgcagcc tgctggaggg cgagatcccc ttccccccca ccagcatcct     3900
gctgctgctg gcctgcatct tcctgatcaa gatcctggcc gccagcgccc tgtgggccgc     3960
cgcctggcac ggccagaagc ccggcaccca ccccccaagc gagctggact gcggccacga     4020
ccccggctac cagctgcaga ccctgcccgg cctgcgcgac acctgaccca ggggactcag     4080
cggccgctcg agtctagagg gcccgtttaa acccgctgat cagcctcgaa gacatgataa     4140
gatacattga tgagtttgga caaccacaa caagaatgca gtgaaaaaa tgctttattt     4200 gtgaaatttg tgatgctatt gctttatttg taaccattat aagctgcaat aaacaagtta     4260
acaacaacaa ttgcattcat tttatgtttc aggttcaggg ggagatgtgg gaggtttttt     4320
aaagcaagta aaacctctac aaatgtggta tgaacatatt gactgaattc cctgcaggtt     4380
ggccactccc tctctgcgcg ctcgctcgct cactgaggcc gcccgggcaa agcccgggcg     4440
tcgggcgacc tttggtcgcc cggcctcagt gagcgagcga gcgcgcagag agggagtggc     4500
caactccatc actaggggtt cctgcggccg ctcgtacggt ctcgaggaat tcctgcagga     4560
taacttgcca acctcattct aaaatgtata tagaagccca aagacaata acaaaaatat     4620 tcttgtagaa caaatggga aagaatgttc cactaaatat caagattag agcaaagcat     4680 gagatgtgtg gggatagaca gtgaggctga taaaatagag tagagctcag aaacagaccc     4740
attgatatat gtaagtgacc tatgaaaaaa atatggcatt ttacaatggg aaaatgatgg     4800 tcttttttctt ttttagaaaa acaggaaat atatttatg gtaaaaaata aagggaacc      4860 catatgtcat accatacaca caaaaaaatt ccagtgaatt ataagtctaa atggagaagg     4920
```

```
caaaacttta aatctttag aaaataatat agaagcatgc agaccagcct ggccaacatg    4980
atgaaaccct ctctactaat aataaaatca gtagaactac tcaggactac tttgagtggg    5040
aagtcctttt ctatgaagac ttctttggcc aaaattaggc tctaaatgca aggagatagt    5100
gcatcatgcc tggctgcact tactgataaa tgatgttatc accatcttta accaaatgca    5160
caggaacaag ttatggtact gatgtgctgg attgagaagg agctctactt ccttgacagg    5220
acacatttgt atcaacttaa aaaagcagat ttttgccagc agaactattc attcagaggt    5280
aggaaactta gaatagatga tgtcactgat tagcatggct tccccatctc cacagctgct    5340
tcccacccag gttgcccaca gttgagtttg tccagtgctc agggctgccc actctcagta    5400
agaagcccca caccagcccc tctccaaata tgttggctgt tccttccatt aaagtgaccc    5460
cactttagag cagcaagtgg atttctgttt cttacagttc aggaaggagg agtcagctgt    5520
gagaacctgg agcctgagat gcttctaagt cccactgcta ctggggtcag ggaagccaga    5580
ctccagcatc agcagtcagg agcactaagc ccttgccaac atcctgtttc tcagagaaac    5640
tgcttccatt ataatggttg tcctttttta agctatcaag ccaaacaacc agtgtctacc    5700
attattctca tcacctgaag ccaagggttc tagcaaaagt caagctgtct tgtaatggtt    5760
gatgtgcctc cagcttctgt cttcagtcac tccactctta gcctgctctg aatcaactct    5820
gaccacagtt ccctggagcc cctgccacct gctgccctg ccaccttctc catctgcagt    5880
gctgtgcagc cttctgcact cttgcagagc taataggtgg agacttgaag aagaggagg    5940 aaagtttctc ataatagcct tgctgcaagc tcaaatggga ggtgggcact gtgcccagga    6000
gccttggagc aaaggctgtg cccaacctct gactgcatcc aggtttggtc ttgacagaga    6060
taagaagccc tggcttttgg agccaaaatc taggtcagac ttaggcagga ttctcaaagt    6120
ttatcagcag aacatgaggc agaagaccct ttctgctcca gcttcttcag gctcaacctt    6180
catcagaata gatagaaaga gaggctgtga gggttcttaa aacagaagca aatctgactc    6240
agagaataaa caacctccta gtaaactaca gcttagacag agcatctggt ggtgagtgtg    6300
ctcagtgtcc tactcaactg tctggtatca gccctcatga ggacttctct tctttccctc    6360
atagacctcc atctctgttt tccttagcct gcagaaatct ggatggctat tcacagaatg    6420
cctgtgcttt cagagttgca ttttttctct ggtattctgg ttcaagcatt tgaaggtagg    6480
aaaggttctc caagtgcaag aaagccagcc ctgagcctca actgcctggc tagtgtggtc    6540
agtaggatgc aaaggctgtt gaatgccaca aggccaaact ttaacctgtg taccacaagc    6600
ctagcagcag aggcagctct gctcactgga actctctgtc ttctttctcc tgagcctttt    6660
cttttcctga gtttctagc tctcctcaac cttacctctg ccctacccag gacaaaccca    6720
agagccactg tttctgtgat gtcctctcca gccctaatta ggcatcatga cttcagcctg    6780
accttccatg ctcagaagca gtgctaatcc acttcagatg agctgctcta tgcaacacag    6840
gcagagccta caaacctttg caccagagcc ctccacatat cagtgtttgt tcatactcac    6900
ttcaacagca aatgtgactg ctgagattaa gattttacac aagatggtct gtaatttcac    6960
agttagtttt atcccattag gtatgaaaga attagcataa ttccccttaa acatgaatga    7020
atcttagatt ttttaataaa tagttttgga agtaaagaca gagacatcag gagcacaagg    7080
aatagcctga gaggacaaac agaacaagaa agagtctgga aatacacagg atgttcttgg    7140
cctcctcaaa gcaagtgcaa gcagatagta ccagcagccc caggctatca gagcccagtg    7200
aagagaagta ccatgaaagc cacagctcta accaccctgt tccagagtga cagacagtcc    7260
```

-continued

```
ccaagacaag ccagcctgag ccagagagag aactgcaaga gaaagtttct aatttaggtt      7320
ctgttagatt cagacaagtg caggtcatcc tctctccaca gctactcacc tctccagcct      7380
aacaaagcct gcagtccaca ctccaaccct ggtgtctcac ctcctagcct ctcccaacat      7440
cctgctctct gaccatcttc tgcatctctc atctcaccat ctcccactgt ctacagccta      7500
ctcttgcaac taccatctca ttttctgaca tcctgtctac atcttctgcc atactctgcc      7560
atctaccata ccacctctta ccatctacca caccatcttt tatctccatc cctctcagaa      7620
gcctccaagc tgaatcctgc tttatgtgtt catctcagcc cctgcatgga aagctgaccc      7680
cagaggcaga actattccca gagagcttgg ccaagaaaaa caaaactacc agcctggcca      7740
ggctcaggag tagtaagctg cagtgtctgt tgtgttctag cttcaacagc tgcaggagtt      7800
ccactctcaa atgctccaca tttctcacat cctcctgatt ctggtcacta cccatcttca      7860
aagaacagaa tatctcacat cagcatactg tgaaggacta gtcatgggtg cagctgctca      7920
gagctgcaaa gtcattctgg atggtggaga gcttacaaac atttcatgat gctccccccg      7980
ctctgatggc tggagcccaa tccctacaca gactcctgct gtatgtgttt cctttcact       8040 ctgagccaca gccagagggc aggcattcag tctcctcttc aggctggggc tggggcactg      8100
agaactcacc caacaccttg ctctcactcc ttctgcaaaa caagaaagag ctttgtgctg      8160
cagtagccat gaagaatgaa aggaaggctt taactaaaaa atgtcagaga ttattttcaa      8220
ccccttactg tggatcacca gcaaggagga acacaacac agagacattt tttcccctca       8280
aattatcaaa agaatcactg catttgttaa agagagcaac tgaatcagga agcagagttt      8340
tgaacatatc agaagttagg aatctgcatc agagacaaat gcagtcatgg ttgtttgctg      8400
cataccagcc ctaatcatta gaagcctcat ggacttcaaa catcattccc tctgacaaga      8460
tgctctagcc taactccatg agataaaata aatctgcctt tcagagccaa agaagagtcc      8520
accagcttct tctcagtgtg aacaagagct ccagtcaggt tagtcagtcc agtgcagtag      8580
aggagaccag tctgcatcct ctaattttca aaggcaagaa gatttgttta ccctggacac      8640
caggcacaag tgaggtcaca gagctcttag atatgcagtc ctcatgagtg aggagactaa      8700
agcgcatgcc atcaagactt cagtgtagag aaaacctcca aaaagcctc ctcactactt       8760 ctggaatagc tcagaggccg aggcggcctc ggcctctgca taaataaaaa aaattagtca      8820
gccatggggc ggagaatggg cggaactggg cggagttagg ggcgggatgg gcggagttag      8880
gggcgggact atggttgctg actaattgag atgcatgctt tgcatacttc tgcctgctgg      8940
ggagcctggg gactttccac acctggttgc tgactaattg agatgcatgc tttgcatact      9000
tctgcctgct ggggagcctg gggactttcc acaccctaac tgacacacat tccacagctg      9060
cattaatgaa tcggccaacg cgcggggaga ggcggtttgc gtattgggcg ctcttccgct      9120
tcctcgctca ctgactcgct gcgctcggtc gttcggctgc ggcgagcggt atcagctcac      9180
tcaaaggcgg taatacggtt atccacagaa tcagggata acgcaggaaa gaacatgtga       9240
gcaaaaggcc agcaaaaggc caggaaccgt aaaaaggccg cgttgctggc gtttttccat      9300
aggctccgcc cccctgacga gcatcacaaa aatcgacgct caagtcagag gtggcgaaac      9360
ccgacaggac tataaagata ccaggcgttt ccccctggaa gctccctcgt gcgctctcct      9420
gttccgaccc tgccgcttac cggatacctg tccgcctttc tcccttcggg aagcgtggcg      9480
ctttctcata gctcacgctg taggtatctc agttcggtgt aggtcgttcg ctccaagctg      9540
ggctgtgtgc acgaaccccc cgttcagccc gaccgctgcg ccttatccgg taactatcgt      9600
cttgagtcca acccggtaag acacgactta tcgccactgg cagcagccac tggtaacagg      9660
```

```
attagcagag cgaggtatgt aggcggtgct acagagttct tgaagtggtg gcctaactac    9720
ggctacacta gaagaacagt atttggtatc tgcgctctgc tgaagccagt taccttcgga    9780
aaaagagttg gtagctcttg atccggcaaa caaaccaccg ctggtagcgg tggttttttt    9840
gtttgcaagc agcagattac gcgcagaaaa aaggatctc aagaagatcc tttgatcttt    9900
tctacggggt ctgacgctca gtggaacgaa aactcacgtt aagggatttt ggtcatgaga    9960
ttatcaaaaa ggatcttcac ctagatcctt taaattaaa aatgaagttt taaatcaatc    10020
taaagtatat atgagtaaac ttggtctgac agttaccaat gcttaatcag tgaggcacct    10080
atctcagcga tctgtctatt tcgttcatcc atagttgcct gactcctgca aaccacgttg    10140
tgtctcaaaa tctctgatgt tacattgcac aagataaaaa tatatcatca tgaacaataa    10200
aactgtctgc ttacataaac agtaatacaa ggggtgttat gagccatatt caacgggaaa    10260
cgtcttgctc gaggccgcga ttaaattcca acatggatgc tgatttatat gggtataaat    10320
gggctcgcga taatgtcggg caatcaggtg cgacaatcta tcgattgtat gggaagcccg    10380
atgcgccaga gttgtttctg aaacatggca aaggtagcgt tgccaatgat gttacagatg    10440
agatggtcag actaaactgg ctgacggaat ttatgcctct tccgaccatc aagcatttta    10500
tccgtactcc tgatgatgca tggttactca ccactgcgat ccccgggaaa acagcattcc    10560
aggtattaga agaatatcct gattcaggtg aaaatattgt tgatgcgctg gcagtgttcc    10620
tgcgccggtt gcattcgatt cctgtttgta attgtccttt taacagcgat cgcgtatttc    10680
gtctcgctca ggcgcaatca cgaatgaata acggtttggt tgatgcgagt gattttgatg    10740
acgagcgtaa tggctggcct gttgaacaag tctggaaaga aatgcataag cttttgccat    10800
tctcaccgga ttcagtcgtc actcatggtg atttctcact tgataacctt attttttgacg    10860 aggggaaatt aataggttgt attgatgttg gacgagtcgg aatcgcagac cgataccagg    10920
atcttgccat cctatggaac tgcctcggtg agttttctcc ttcattacag aaacggcttt    10980
ttcaaaaata tggtattgat aatcctgata tgaataaatt gcagtttcat ttgatgctcg    11040
atgagttttt ctaagggcgg cctgccacca tacccacgcc gaaacaagcg ctcatgagcc    11100
cgaagtggcg agcccgatct tccccatcgg tgatgtcggc gatataggcg ccagcaaccg    11160
cacctgtggc gccggtgatg agggcgcgcc aagtcgacgt ccggcagtc             11209
```

<210> SEQ ID NO 62
<211> LENGTH: 11459
<212> TYPE: DNA
<213> ORGANISM: Artificial sequence
<220> FEATURE:
<223> OTHER INFORMATION: Synthetic polynucleotide

<400> SEQUENCE: 62

```
ttggccactc cctctctgcg cgctcgctcg ctcactgagg ccgggcgacc aaaggtcgcc     60
cgacgcccgg gctttgcccg gcggcctca gtgagcgagc gagcgcgcag agagggagtg    120
gccaactcca tcactagggg ttcctgctag ctctgggtat ttaagcccga gtgagcacgc    180
agggtctcca ttttgaagcg ggaggttacg cgttcgtcga ctactagtgg gtaccagagc    240
tccctaggtt ctagaaccgg tgacgtctcc catggtgaag cttggatctg aattcggtac    300
cctagttatt aatagtaatc aattacgggg tcattagttc atagcccata tatggagttc    360
cgcgttacat aacttacggt aaatggcccg cctggctgac cgcccaacga ccccgcccc    420 ttgacgtcaa taatgacgta tgttcccata gtaacgccaa tagggacttt ccattgacgt    480
```

```
caatgggtgg actatttacg gtaaactgcc cacttggcag tacatcaagt gtatcatatg    540
ccaagtacgc cccctattga cgtcaatgac ggtaaatggc ccgcctggca ttatgcccag    600
tacatgacct tatgggactt tcctacttgg cagtacatct acgtattagt catcgctatt    660
accatggtcg aggtgagccc cacgttctgc ttcactctcc ccatctcccc ccctccccca    720 ccccaattt tgtatttatt tatttttaa ttatttgtg cagcgatggg ggcggggggg    780
gggggggggc gcgcgccagg cggggcgggg cggggcgagg ggcggggcgg ggcgaggcgg    840
agaggtgcgg cggcagccaa tcagagcggc gcgctccgaa agtttccttt tatggcgagg    900
cggcggcggc ggcggcccta taaaaagcga agcgcgcggc gggcgggagt cgctgcgacg    960
ctgccttcgc cccgtgcccc gctccgccgc cgcctcgcgc cgcccgcccc ggctctgact   1020
gaccgcgtta ctcccacagg tgagcgggcg ggacggccct tctcctccgg gctgtaatta   1080
gcgcttggtt taatgacggc ttgttttctg tggctgcgtg aaagccttga ggggctccgg   1140
gagctagagc ctctgctaac catgttcatg ccttcttctt tttcctacag ctcctgggca   1200
acgtgctggt tattgtgctg tctcatcatt ttggcaaaga attcctcgaa gatccgaagg   1260
gaaagtcttc cacgactgtg ggatccgttc gaagatatca ccggttgagc caccatggaa   1320
ttcagcagcc ccagcagaga ggaatgcccc aagcctctga gccgggtgtc aatcatggcc   1380
ggatctctga caggactgct gctgcttcag gccgtgtctt gggcttctgg cgctagacct   1440
tgcatcccca gagcttcgg ctacagcagc gtcgtgtgcg tgtgcaatgc cacctactgc   1500
gacagcttcg accctcctac ctttcctgct ctgggcacct tcagcagata cgagagcacc   1560
agatccggca gacggatgga actgagcatg ggacccatcc aggccaatca cacaggcact   1620
ggcctgctgc tgacactgca gcctgagcag aaattccaga agtgaaagg cttcggcgga   1680 gccatgacag atgccgccgc tctgaatatc ctggctctgt ctccaccagc tcagaacctg   1740
ctgctcaaga gctacttcag cgaggaaggc atcggctaca acatcatcag agtgcccatg   1800
gccagctgcg acttcagcat caggacctac acctacgccg acacacccga cgatttccag   1860
ctgcacaact tcagcctgcc tgaagaggac accaagctga agatccctct gatccacaga   1920
gccctgcagc tggcacaaag acccgtgtca ctgctggcct ctccatggac atctcccacc   1980
tggctgaaaa caaatggcgc cgtgaatggc aagggcagcc tgaaaggcca acctggcgac   2040
atctaccacc agacctgggc cagatacttc gtgaagttcc tggacgccta tgccgagcac   2100
aagctgcagt tttgggccgt gacagccgag aacgaacctt ctgctggact gctgagcggc   2160
tacccctttc agtgcctggg ctttacaccc gagcaccagc gggactttat cgcccgtgat   2220
ctgggaccca cactggccaa tagcacccac cataatgtgc ggctgctgat gctggacgac   2280
cagagactgc ttctgcccca ctgggctaaa gtggtgctga cagatcctga ggccgccaaa   2340
tacgtgcacg gaatcgccgt gcactggtat ctggactttc tggcccctgc caaggccaca   2400
ctgggagaga cacacagact gttccccaac accatgctgt cgccagcga agcctgtgtg   2460 ggcagcaagt tttgggaaca gagcgtgcgg ctcggcagct gggatagagg catgcagtac   2520
agccacagca tcatcaccaa cctgctgtac cacgtcgtcg gctggaccga ctggaatctg   2580
gccctgaatc ctgaaggcgg ccctaactgg gtccgaaact cgtggacag ccccatcatc   2640 gtggacatca ccaaggacac cttctacaag cagcccatgt tctaccacct gggacacttc   2700
agcaagttca tccccgaggg ctctcagcgc gttggactgg tggcttccca gaagaacgat   2760
ctggacgccg tggctctgat gcaccctgat ggatctgctg tggtggtggt cctgaaccgc   2820
agcagcaaag atgtgcccct gaccatcaag gatccgccg tgggattcct ggaaacaatc   2880
```

```
agccctggct actccatcca cacctacctg tggcgtagac agtgacaatt gttaattaag    2940
tttaaaccct cgaggccgca agccgcatcg ataccgtcga ctagagctcg ctgatcagcc    3000
tcgactgtgc cttctagttg ccagccatct gttgtttgcc cctcccccgt gccttccttg    3060
accctggaag gtgccactcc cactgtcctt tcctaataaa atgaggaaat tgcatcgcat    3120
tgtctgagta ggtgtcattc tattctgggg ggtggggtgg ggcaggacag caaggggag    3180
gattgggaag acaatagcag gcatgctggg gagagatcca cgataacaaa cagcttttt    3240
ggggggggcgg agttagggcg gagccaatca gcgtgcgccg ttccgaaagt tgccttttat    3300
ggctgggcgg agaatgggcg gtgaacgccg atgattatat aaggacgcgc cgggtgtggc    3360
acagctagtt ccgtcgcagc cgggatttgg gtcgcggttc ttgtttgtgg atccctgtga    3420
tcgtcacttg gtaagtcact gactgtctat gcctgggaaa gggtgggcag gagatggggc    3480
agtgcaggaa aagtggcact atgaaccctg cagccctagg aatgcatcta gacaattgta    3540
ctaaccttct tctctttcct ctcctgacag tccggaaagc caccatgccc cgcggcttca    3600
cctggctgcg ctacctgggc atcttcctgg gcgtggccct gggcaacgag cccctggaga    3660
tgtggcccct gacccagaac gaggagtgca ccgtgaccgg cttcctgcgc gacaagctgc    3720
agtaccgcag ccgcctgcag tacatgaagc actacttccc catcaactac aagatcagcg    3780
tgccctacga gggcgtgttc cgcatcgcca acgtgacccg cctgcagcgc gccaggtga    3840
gcgagcgcga gctgcgctac ctgtgggtgc tggtgagcct gagcgccacc gagagcgtgc    3900
aggacgtgct gctggagggc caccccagct ggaagtacct gcaggaggtg gagaccctgc    3960
tgctgaacgt gcagcagggc ctgaccgacg tggaggtgag cccaaggtg gagagcgtgc    4020
tgagcctgct gaacgcccc ggccccaacc tgaagctggt gcgccccaag gccctgctgg    4080
acaactgctt ccgcgtgatg gagctgctgt actgcagctg ctgcaagcag agcagcgtgc    4140
tgaactggca ggactgcgag gtgcccagcc ccagagctg cagccccgag ccagcctgc    4200
agtacgccgc cacccagctg tacccccccc cccctggag ccccagcagc cccccccaca    4260
gcaccggcag cgtgcgcccc gtgcgcgcc agggcgaggg cctgctgccc taatgaccca    4320
ggggactcag cggccgctcg agtctagagg gcccgtttaa acccgctgat cagcctcgaa    4380
gacatgataa gatacattga tgagtttgga caaaccacaa caagaatgca gtgaaaaaaa    4440
tgctttatt gtgaaatttg tgatgctatt gctttatttg taaccattat aagctgcaat    4500
aaacaagtta acaacaacaa ttgcattcat tttatgtttc aggttcaggg ggagatgtgg    4560
gaggtttttt aaagcaagta aaacctctac aaatgtggta tgaacatatt gactgaattc    4620
cctgcaggtt ggccactccc tctctgcgcg ctcgctcgct cactgaggcc gcccgggcaa    4680
agcccgggcg tcgggcgacc tttggtcgcc cggcctcagt gagcgagcga gcgcgcagag    4740
agggagtggc caactccatc actaggggtt cctgcggccg ctcgtacggt ctcgaggaat    4800
tcctgcagga taacttgcca acctcattct aaaatgtata tagaagccca aaagacaata    4860
acaaaaatat tcttgtagaa caaatggga agaatgttc cactaaatat caagatttag    4920
agcaaagcat gagatgtgtg gggatagaca gtgaggctga taaaatagag tagagctcag    4980
aaacagaccc attgatatat gtaagtgacc tatgaaaaaa atatggcatt ttacaatggg    5040
aaaatgatgg tctttttctt tttagaaaa acagggaaat atatttatat gtaaaaaata    5100
aaagggaacc catatgtcat accatacaca caaaaaaatt ccagtgaatt ataagtctaa    5160
atggagaagg caaaacttta aatctttag aaaataatat agaagcatgc agaccagcct    5220
```

```
ggccaacatg atgaaaccct ctctactaat aataaaatca gtagaactac tcaggactac    5280
tttgagtggg aagtccttt  ctatgaagac ttctttggcc aaaattaggc tctaaatgca    5340
aggagatagt gcatcatgcc tggctgcact tactgataaa tgatgttatc accatcttta    5400
accaaatgca caggaacaag ttatggtact gatgtgctgg attgagaagg agctctactt    5460
ccttgacagg acacatttgt atcaacttaa aaaagcagat ttttgccagc agaactattc    5520
attcagaggt aggaaactta gaatagatga tgtcactgat tagcatggct tccccatctc    5580
cacagctgct tcccacccag gttgcccaca gttgagtttg tccagtgctc agggctgccc    5640
actctcagta agaagcccca caccagcccc tctccaaata tgttggctgt tccttccatt    5700
aaagtgaccc cactttagag cagcaagtgg atttctgttt cttacagttc aggaaggagg    5760
agtcagctgt gagaacctgg agcctgagat gcttctaagt cccactgcta ctggggtcag    5820
ggaagccaga ctccagcatc agcagtcagg agcactaagc ccttgccaac atcctgtttc    5880
tcagagaaac tgcttccatt ataatggttg tccttttta  agctatcaag ccaaacaacc    5940
agtgtctacc attattctca tcacctgaag ccaagggttc tagcaaaagt caagctgtct    6000
tgtaatggtt gatgtgcctc cagcttctgt cttcagtcac tccactctta gcctgctctg    6060
aatcaactct gaccacagtt ccctggagcc cctgccacct gctgccctg  ccaccttctc    6120 catctgcagt gctgtgcagc cttctgcact cttgcagagc taataggtgg agacttgaag    6180
gaagaggagg aaagtttctc ataatagcct tgctgcaagc tcaaatggga ggtgggcact    6240
gtgcccagga gccttggagc aaaggctgtg cccaacctct gactgcatcc aggtttggtc    6300
ttgacagaga taagaagccc tggcttttgg agccaaaatc taggtcagac ttaggcagga    6360
ttctcaaagt ttatcagcag aacatgaggc agaagaccct ttctgctcca gcttcttcag    6420
gctcaacctt catcagaata gatagaaaga gaggctgtga gggttcttaa aacagaagca    6480
aatctgactc agagaataaa caacctccta gtaaactaca gcttagacag agcatctggt    6540
ggtgagtgtg ctcagtgtcc tactcaactg tctggtatca gccctcatga ggacttctct    6600
tctttccctc atagacctcc atctctgttt tccttagcct gcagaaatct ggatggctat    6660
tcacagaatg cctgtgcttt cagagttgca tttttttctct ggtattctgg ttcaagcatt    6720
tgaaggtagg aaaggttctc caagtgcaag aaagccagcc ctgagcctca actgcctggc    6780
tagtgtggtc agtaggatgc aaaggctgtt gaatgccaca aggccaaact ttaacctgtg    6840
taccacaagc ctagcagcag aggcagctct gctcactgga actctctgtc ttctttctcc    6900
tgagcctttt cttttcctga gttttctagc tctcctcaac cttacctctg ccctacccag    6960
gacaaaccca agagccactg tttctgtgat gtcctctcca gccctaatta ggcatcatga    7020
cttcagcctg accttccatg ctcagaagca gtgctaatcc acttcagatg agctgctcta    7080
tgcaacacag gcagagccta caaacctttg caccagagcc ctccacatat cagtgtttgt    7140
tcatactcac ttcaacagca aatgtgactg ctgagattaa gattttacac aagatggtct    7200
gtaatttcac agttagtttt atcccattag gtatgaaaga attagcataa ttccccttaa    7260
acatgaatga atcttagatt ttttaataaa tagttttgga agtaaagaca gagacatcag    7320
gagcacaagg aatagcctga gaggacaaac agaacaagaa agagtctgga aatacacagg    7380
atgttcttgg cctcctcaaa gcaagtgcaa gcagatagta ccagcagccc caggctatca    7440
gagcccagtg aagagaagta ccatgaaagc cacagctcta accaccctgt tccagagtga    7500
cagacagtcc ccaagacaag ccagcctgag ccagagagag aactgcaaga gaaagtttct    7560
aatttaggtt ctgttagatt cagacaagtg caggtcatcc tctctccaca gctactcacc    7620
```

```
tctccagcct aacaaagcct gcagtccaca ctccaaccct ggtgtctcac ctcctagcct    7680
ctcccaacat cctgctctct gaccatcttc tgcatctctc atctcaccat ctcccactgt    7740
ctacagccta ctcttgcaac taccatctca ttttctgaca tcctgtctac atcttctgcc    7800
atactctgcc atctaccata ccacctctta ccatctacca caccatcttt tatctccatc    7860
cctctcagaa gcctccaagc tgaatcctgc tttatgtgtt catctcagcc cctgcatgga    7920
aagctgaccc cagaggcaga actattccca gagagcttgg ccaagaaaaa caaaactacc    7980
agcctggcca ggctcaggag tagtaagctg cagtgtctgt tgtgttctag cttcaacagc    8040
tgcaggagtt ccactctcaa atgctccaca tttctcacat cctcctgatt ctggtcacta    8100
cccatcttca aagaacagaa tatctcacat cagcatactg tgaaggacta gtcatgggtg    8160
cagctgctca gagctgcaaa gtcattctgg atggtggaga gcttacaaac atttcatgat    8220
gctcccccccg ctctgatggc tggagcccaa tccctacaca gactcctgct gtatgtgttt    8280
tcctttcact ctgagccaca gccagagggc aggcattcag tctcctcttc aggctggggc    8340
tggggcactg agaactcacc caacaccttg ctctcactcc ttctgcaaaa caagaaagag    8400
ctttgtgctg cagtagccat gaagaatgaa aggaaggctt taactaaaaa atgtcagaga    8460
ttattttcaa ccccttactg tggatcacca gcaaggagga aacacaacac agagacattt    8520
tttcccctca aattatcaaa agaatcactg catttgttaa agagagcaac tgaatcagga    8580
agcagagttt tgaacatatc agaagttagg aatctgcatc agagacaaat gcagtcatgg    8640
ttgtttgctg cataccagcc ctaatcatta gaagcctcat ggacttcaaa catcattccc    8700
tctgacaaga tgctctagcc taactccatg agataaaata aatctgcctt tcagagccaa    8760
agaagagtcc accagcttct tctcagtgtg aacaagagct ccagtcaggt tagtcagtcc    8820
agtgcagtag aggagaccag tctgcatcct ctaattttca aaggcaagaa gatttgttta    8880
ccctggacac caggcacaag tgaggtcaca gagctcttag atatgcagtc ctcatgagtg    8940
aggagactaa agcgcatgcc atcaagactt cagtgtagag aaaacctcca aaaagcctc    9000
ctcactactt ctggaatagc tcagaggccg aggcggcctc ggcctctgca taaataaaaa    9060
aaattagtca gccatggggc ggagaatggg cggaactggg cggagttagg ggcgggatgg    9120
gcggagttag gggcgggact atggttgctg actaattgag atgcatgctt tgcatacttc    9180
tgcctgctgg ggagcctggg gactttccac acctggttgc tgactaattg agatgcatgc    9240
tttgcatact tctgcctgct ggggagcctg gggactttcc acaccctaac tgacacacat    9300
tccacagctg cattaatgaa tcggccaacg cgcggggaga ggcggtttgc gtattgggcg    9360
ctcttccgct cctcgctcac tgactcgct gcgctcggtc gttcggctgc ggcgagcggt    9420
atcagctcac tcaaaggcgg taatacggtt atccacagaa tcaggggata acgcaggaaa    9480
gaacatgtga gcaaaaggcc agcaaaaggc caggaaccgt aaaaaggccg cgttgctggc    9540
gttttccat aggctccgcc ccctgacga gcatcacaaa atcgacgct caagtcagag    9600
gtggcgaaac ccgacaggac tataaagata ccaggcgttt ccccctggaa gctccctcgt    9660
gcgctctcct gttccgaccc tgccgcttac cggatacctg tccgcctttc tcccttcggg    9720
aagcgtggcg ctttctcata gctcacgctg taggtatctc agttcggtgt aggtcgttcg    9780
ctccaagctg ggctgtgtgc acgaaccccc cgttcagccc gaccgctgcg ccttatccgg    9840
taactatcgt cttgagtcca acccggtaag acacgactta tcgccactgg cagcagccac    9900
tggtaacagg attagcagag cgaggtatgt aggcggtgct acagagttct tgaagtggtg    9960
```

```
gcctaactac ggctacacta aagaacagt atttggtatc tgcgctctgc tgaagccagt    10020
taccttcgga aaaagagttg gtagctcttg atccggcaaa caaaccaccg ctggtagcgg    10080 tggtttttt gtttgcaagc agcagattac gcgcagaaaa aaaggatctc aagaagatcc    10140
tttgatcttt tctacggggt ctgacgctca gtggaacgaa aactcacgtt aagggatttt    10200
ggtcatgaga ttatcaaaaa ggatcttcac ctagatcctt ttaaattaaa aatgaagttt    10260
taaatcaatc taaagtatat atgagtaaac ttggtctgac agttaccaat gcttaatcag    10320
tgaggcacct atctcagcga tctgtctatt tcgttcatcc atagttgcct gactcctgca    10380
aaccacgttg tgtctcaaaa tctctgatgt tacattgcac aagataaaaa tatatcatca    10440
tgaacaataa aactgtctgc ttacataaac agtaatacaa ggggtgttat gagccatatt    10500
caacgggaaa cgtcttgctc gaggccgcga ttaaattcca acatggatgc tgatttatat    10560
gggtataaat gggctcgcga taatgtcggg caatcaggtg cgacaatcta tcgattgtat    10620
gggaagcccg atgcgccaga gttgtttctg aaacatggca aaggtagcgt tgccaatgat    10680
gttacagatg agatggtcag actaaactgg ctgacggaat ttatgcctct tccgaccatc    10740
aagcatttta tccgtactcc tgatgatgca tggttactca ccactgcgat ccccgggaaa    10800
acagcattcc aggtattaga gaatatcct gattcaggtg aaaatattgt tgatgcgctg    10860
gcagtgttcc tgcgccggtt gcattcgatt cctgtttgta attgtccttt aacagcgat    10920 cgcgtatttc gtctcgctca ggcgcaatca cgaatgaata cggtttggt tgatgcgagt    10980 gattttgatg acgagcgtaa tggctggcct gttgaacaag tctggaaaga atgcataag    11040 cttttgccat tctcaccgga ttcagtcgtc actcatggtg attttctcact tgataacctt    11100 attttgacg aggggaaatt aataggttgt attgatgttg gacgagtcgg aatcgcagac    11160
cgataccagg atcttgccat cctatggaac tgcctcggtg agttttctcc ttcattacag    11220
aaacggcttt tcaaaaaata tggtattgat aatcctgata tgaataaatt gcagtttcat    11280
ttgatgctcg atgagttttt ctaagggcgg cctgccacca tacccacgcc gaaacaagcg    11340
ctcatgagcc cgaagtggcg agcccgatct tccccatcgg tgatgtcggc gatataggcg    11400
ccagcaaccg cacctgtggc gccggtgatg agggcgcgcc aagtcgacgt ccggcagtc    11459
```

<210> SEQ ID NO 63
<211> LENGTH: 274
<212> TYPE: PRT
<213> ORGANISM: Artificial sequence
<220> FEATURE:
<223> OTHER INFORMATION: Synthetic polypeptide

<400> SEQUENCE: 63

```
Met Gly Lys Ser Leu Ser His Leu Pro Leu His Ser Ser Lys Glu Asp
1               5                   10                  15

Ala Tyr Asp Gly Val Thr Ser Glu Asn Met Arg Asn Gly Leu Val Asn
            20                  25                  30

Ser Glu Val His Asn Glu Asp Gly Arg Asn Gly Asp Val Ser Gln Phe
        35                  40                  45

Pro Tyr Val Glu Phe Thr Gly Arg Asp Ser Val Thr Cys Pro Thr Cys
    50                  55                  60

Gln Gly Thr Gly Arg Ile Pro Arg Gly Gln Glu Asn Gln Leu Val Ala
65                  70                  75                  80

Leu Ile Pro Tyr Ser Asp Gln Arg Leu Arg Pro Arg Arg Thr Lys Leu
                85                  90                  95
```

```
Tyr Val Met Ala Ser Val Phe Val Cys Leu Leu Ser Gly Leu Ala
                100                 105                 110
Val Phe Phe Leu Phe Pro Arg Ser Ile Asp Val Lys Tyr Ile Gly Val
            115                 120                 125
Lys Ser Ala Tyr Val Ser Tyr Asp Val Gln Lys Arg Thr Ile Tyr Leu
        130                 135                 140
Asn Ile Thr Asn Thr Leu Asn Ile Thr Asn Asn Tyr Tyr Ser Val
145                 150                 155                 160
Glu Val Glu Asn Ile Thr Ala Gln Val Gln Phe Ser Lys Thr Val Ile
                165                 170                 175
Gly Lys Ala Arg Leu Asn Asn Ile Thr Ile Gly Pro Leu Asp Met
            180                 185                 190
Lys Gln Ile Asp Tyr Thr Val Pro Thr Val Ile Ala Glu Glu Met Ser
        195                 200                 205
Tyr Met Tyr Asp Phe Cys Thr Leu Ile Ser Ile Lys Val His Asn Ile
    210                 215                 220
Val Leu Met Met Gln Val Thr Val Thr Thr Tyr Phe Gly His Ser
225                 230                 235                 240
Glu Gln Ile Ser Gln Glu Arg Tyr Gln Tyr Val Asp Cys Gly Arg Asn
                245                 250                 255
Thr Thr Tyr Gln Leu Gly Gln Ser Glu Tyr Leu Asn Val Leu Gln Pro
            260                 265                 270
Gln Gln

<210> SEQ ID NO 64
<211> LENGTH: 825
<212> TYPE: DNA
<213> ORGANISM: Artificial sequence
<220> FEATURE:
<223> OTHER INFORMATION: Synthetic polynucleotide

<400> SEQUENCE: 64
atgggcaaga gcctgagcca cctgcccctg cacagcagca aggaggacgc ctacgacggc      60
gtgaccagcg agaacatgcg caacggcctg gtgaacagcg aggtgcacaa cgaggacggc     120
cgcaacggcg acgtgagcca gttcccctac gtggagttca ccggccgcga cagcgtgacc     180
tgccccacct gccagggcac cggccgcatc ccccgcggcc aggagaacca gctggtggcc     240
ctgatcccct acagcgacca gcgcctgcgc ccccgccgca ccaagctgta cgtgatggcc     300
agcgtgttcg tgtgcctgct gctgagcggc ctggccgtgt tcttcctgtt cccccgcagc     360
atcgacgtga agtacatcgg cgtgaagagc gcctacgtga gctacgacgt gcagaagcgc     420
accatctacc tgaacatcac caacaccctg aacatcacca acaacaacta ctacagcgtg     480
gaggtggaga acatcaccgc ccaggtgcag ttcagcaaga ccgtgatcgg caaggcccgc     540
ctgaacaaca tcaccatcat cggccccctg gacatgaagc agatcgacta caccgtgccc     600
accgtgatcg ccgaggagat gagctacatg tacgacttct gcaccctgat cagcatcaag     660
gtgcacaaca tcgtgctgat gatgcaggtg accgtgacca ccacctactt cggccacagc     720
gagcagatca gccaggagcg ctaccagtac gtggactgcg gccgcaacac cacctaccag     780
ctgggccaga gcgagtacct gaacgtgctg cagccccagc agtaa                     825

<210> SEQ ID NO 65
<211> LENGTH: 267
<212> TYPE: DNA
<213> ORGANISM: Artificial sequence
```

```
<220> FEATURE:
<223> OTHER INFORMATION: Synthetic polynucleotide

<400> SEQUENCE: 65
gtgatatcac aaggtcccag ggctggggtc agaaattctc tcccgaggga atgaagccac      60
aggagccaag agcaggagga ccaaggccct ggcgaaggcc gtggcctcgt tcaagtaaaa     120
gatcctagta cagtgcaggt cccaatgtgt actaggatct tttacttgaa cggggacgcc     180
ggcatccggg ctcaggaccc ccctctctgc cagaggcacc aacaccagag ttcacaaatc     240
agtctcctgc cctttgcatg tagcaaa                                         267

<210> SEQ ID NO 66
<211> LENGTH: 267
<212> TYPE: DNA
<213> ORGANISM: Artificial sequence
<220> FEATURE:
<223> OTHER INFORMATION: Synthetic polynucleotide

<400> SEQUENCE: 66
tttgctacat gcaaagggca ggagactgat tgtgaactc tggtgttggt gcctctggca       60 gagaggggg tcctgagccc ggatgccggc gtccccgttc aagtaaaaga tcctagtaca      120
cattgggacc tgcactgtac taggatcttt tacttgaacg aggccacggc cttcgccagg     180
gccttggtcc tcctgctctt ggctcctgtg gcttcattcc ctcgggagag aatttctgac     240
cccagccctg ggaccttgtg atatcac                                         267

<210> SEQ ID NO 67
<211> LENGTH: 593
<212> TYPE: PRT
<213> ORGANISM: Artificial sequence
<220> FEATURE:
<223> OTHER INFORMATION: Synthetic polypeptide

<400> SEQUENCE: 67

Met Trp Thr Leu Val Ser Trp Val Ala Leu Thr Ala Gly Leu Val Ala
1               5                   10                  15

Gly Thr Arg Cys Pro Asp Gly Gln Phe Cys Pro Val Ala Cys Cys Leu
            20                  25                  30

Asp Pro Gly Gly Ala Ser Tyr Ser Cys Cys Arg Pro Leu Leu Asp Lys
        35                  40                  45

Trp Pro Thr Thr Leu Ser Arg His Leu Gly Gly Pro Cys Gln Val Asp
    50                  55                  60

Ala His Cys Ser Ala Gly His Ser Cys Ile Phe Thr Val Ser Gly Thr
65                  70                  75                  80

Ser Ser Cys Cys Pro Phe Pro Glu Ala Val Ala Cys Gly Asp Gly His
            85                  90                  95

His Cys Cys Pro Arg Gly Phe His Cys Ser Ala Asp Gly Arg Ser Cys
        100                 105                 110

Phe Gln Arg Ser Gly Asn Asn Ser Val Gly Ala Ile Gln Cys Pro Asp
    115                 120                 125

Ser Gln Phe Glu Cys Pro Asp Phe Ser Thr Cys Val Met Val Asp
    130                 135                 140

Gly Ser Trp Gly Cys Cys Pro Met Pro Gln Ala Ser Cys Cys Glu Asp
145                 150                 155                 160

Arg Val His Cys Cys Pro His Gly Ala Phe Cys Asp Leu Val His Thr
            165                 170                 175
```

```
Arg Cys Ile Thr Pro Thr Gly Thr His Pro Leu Ala Lys Lys Leu Pro
            180                 185                 190

Ala Gln Arg Thr Asn Arg Ala Val Ala Leu Ser Ser Ser Val Met Cys
            195                 200                 205

Pro Asp Ala Arg Ser Arg Cys Pro Asp Gly Ser Thr Cys Cys Glu Leu
            210                 215                 220

Pro Ser Gly Lys Tyr Gly Cys Cys Pro Met Pro Asn Ala Thr Cys Cys
225                 230                 235                 240

Ser Asp His Leu His Cys Cys Pro Gln Asp Thr Val Cys Asp Leu Ile
                245                 250                 255

Gln Ser Lys Cys Leu Ser Lys Glu Asn Ala Thr Thr Asp Leu Leu Thr
            260                 265                 270

Lys Leu Pro Ala His Thr Val Gly Asp Val Lys Cys Asp Met Glu Val
            275                 280                 285

Ser Cys Pro Asp Gly Tyr Thr Cys Cys Arg Leu Gln Ser Gly Ala Trp
            290                 295                 300

Gly Cys Cys Pro Phe Thr Gln Ala Val Cys Cys Glu Asp His Ile His
305                 310                 315                 320

Cys Cys Pro Ala Gly Phe Thr Cys Asp Thr Gln Lys Gly Thr Cys Glu
                325                 330                 335

Gln Gly Pro His Gln Val Pro Trp Met Glu Lys Ala Pro Ala His Leu
            340                 345                 350

Ser Leu Pro Asp Pro Gln Ala Leu Lys Arg Asp Val Pro Cys Asp Asn
            355                 360                 365

Val Ser Ser Cys Pro Ser Ser Asp Thr Cys Cys Gln Leu Thr Ser Gly
            370                 375                 380

Glu Trp Gly Cys Cys Pro Ile Pro Glu Ala Val Cys Cys Ser Asp His
385                 390                 395                 400

Gln His Cys Cys Pro Gln Gly Tyr Thr Cys Val Ala Glu Gly Gln Cys
                405                 410                 415

Gln Arg Gly Ser Glu Ile Val Ala Gly Leu Glu Lys Met Pro Ala Arg
            420                 425                 430

Arg Ala Ser Leu Ser His Pro Arg Asp Ile Gly Cys Asp Gln His Thr
            435                 440                 445

Ser Cys Pro Val Gly Gln Thr Cys Cys Pro Ser Leu Gly Gly Ser Trp
            450                 455                 460

Ala Cys Cys Gln Leu Pro His Ala Val Cys Cys Glu Asp Arg Gln His
465                 470                 475                 480

Cys Cys Pro Ala Gly Tyr Thr Cys Asn Val Lys Ala Arg Ser Cys Glu
                485                 490                 495

Lys Glu Val Val Ser Ala Gln Pro Ala Thr Phe Leu Ala Arg Ser Pro
            500                 505                 510

His Val Gly Val Lys Asp Val Glu Cys Gly Glu Gly His Phe Cys His
            515                 520                 525

Asp Asn Gln Thr Cys Cys Arg Asp Asn Arg Gln Gly Trp Ala Cys Cys
            530                 535                 540

Pro Tyr Arg Gln Gly Val Cys Cys Ala Asp Arg Arg His Cys Cys Pro
545                 550                 555                 560

Ala Gly Phe Arg Cys Ala Ala Arg Gly Thr Lys Cys Leu Arg Arg Glu
                565                 570                 575
```

Ala Pro Arg Trp Asp Ala Pro Leu Arg Asp Pro Ala Leu Arg Gln Leu
        580                 585                 590

Leu

<210> SEQ ID NO 68
<211> LENGTH: 1779
<212> TYPE: DNA
<213> ORGANISM: Artificial sequence
<220> FEATURE:
<223> OTHER INFORMATION: Synthetic polynucleotide

<400> SEQUENCE: 68

| | |
|---|---|
| atgtggaccc tggtgagctg ggtggccctg accgccggcc tggtggccgg cacccgctgc | 60 |
| cccgacggcc agttctgccc cgtggcctgc tgcctggacc ccggcggcgc cagctacagc | 120 |
| tgctgccgcc ccctgctgga caagtggccc accaccctga ccgccacct gggcggcccc | 180 |
| tgccaggtgg acgccactg cagcgccggc cacagctgca tcttcaccgt gagcggcacc | 240 |
| agcagctgct gccccttccc cgaggccgtg gcctgcggcg acggcaccac tgctgcccc | 300 |
| cgcggcttcc actgcagcgc cgacggccgc agctgcttcc agcgcagcgg caacaacagc | 360 |
| gtgggcgcca tccagtgccc cgacagccag ttcgagtgcc ccgacttcag cacctgctgc | 420 |
| gtgatggtgg acggcagctg ggctgctgc cccatgcccc aggccagctg ctgcgaggac | 480 |
| cgcgtgcact gctgccccca cggcgccttc tgcgacctgg tgcacacccg ctgcatcacc | 540 |
| cccaccggca cccaccccct ggccaagaag ctgcccgccc agcgcaccaa ccgcgccgtg | 600 |
| gccctgagca gcagcgtgat gtgccccgac gcccgcagcc gctgccccga cggcagcacc | 660 |
| tgctgcgagc tgcccagcgg caagtacggc tgctgcccca tgcccaacgc cacctgctgc | 720 |
| agcgaccacc tgcactgctg ccccccaggac accgtgtgcg acctgatcca gagcaagtgc | 780 |
| ctgagcaagg agaacgccac caccgacctg ctgaccaagc tgcccgccca ccgtgggc | 840 |
| gacgtgaagt gcgacatgga ggtgagctgc cccgacggct acacctgctg ccgcctgcag | 900 |
| agcggcgcct ggggctgctg ccccttcacc caggccgtgt gctgcgagga ccacatccac | 960 |
| tgctgccccg ccggcttcac ctgcgacacc cagaagggca cctgcgagca gggccccac | 1020 |
| caggtgccct ggatggagaa ggccccgcc cacctgagcc tgcccgaccc ccaggccctg | 1080 |
| aagcgcgacg tgccctgcga caacgtgagc agctgcccca gcagcgacac ctgctgccag | 1140 |
| ctgaccagcg gcgagtgggg ctgctgcccc atccccgagg ccgtgtgctg cagcgaccac | 1200 |
| cagcactgct gccccaggg ctacacctgc gtggccgagg ccagtgcca gcgcggcagc | 1260 |
| gagatcgtgg ccggcctgga agatgcccc gcccgccgcg ccagcctgag ccaccccgc | 1320 |
| gacatcggct gcgaccagca caccagctgc cccgtgggcc agacctgctg ccccagcctg | 1380 |
| ggcggcagct gggcctgctg ccagctgccc cacgccgtgt gctgcgagga ccgccagcac | 1440 |
| tgctgccccg ccggctacac ctgcaacgtg aaggcccgca gctgcgagaa ggaggtggtg | 1500 |
| agcgcccagc ccgccaccct tctggcccgc agccccacg tgggcgtgaa ggacgtggag | 1560 |
| tgcggcgagg gccacttctg ccacgacaac cagacctgct gccgcgacaa ccgccagggc | 1620 |
| tgggcctgct gcccctaccg ccagggcgtg tgctgcgccg accgccgcca ctgctgcccc | 1680 |
| gccggcttcc gctgcgccgc ccgcggcacc aagtgcctgc gccgcgaggc ccccgctgg | 1740 |
| gacgccccc tgcgcgaccc cgccctgcgc cagctgctg | 1779 |

<210> SEQ ID NO 69
<211> LENGTH: 10871

```
<212> TYPE: DNA
<213> ORGANISM: Artificial sequence
<220> FEATURE:
<223> OTHER INFORMATION: Synthetic polynucleotide

<400> SEQUENCE: 69
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctgctag ctctgggtat ttaagcccga gtgagcacgc     180
agggtctcca ttttgaagcg ggaggttacg cgttcgtcga ctactagtgg gtaccagagc     240
tccctaggtt ctagaaccgg tgacgtctcc catggtgaag cttggatctg aattcggtac     300
ctagttatta atagtaatca attacgggt cattagttca tagcccatat atggagttcc      360
gcgttacata acttacggta atggcccgc ctggctgacc gcccaacgac ccccgcccat      420
tgacgtcaat aatgacgtat gttcccatag taacgccaat agggactttc cattgacgtc     480
aatgggtgga gtatttacgg taaactgccc acttggcagt acatcaagtg tatcatatgc     540
caagtacgcc ccctattgac gtcaatgacg gtaaatggcc cgcctggcat tatgcccagt     600
acatgacctt atgggacttt cctacttggc agtacatcta cgtattagtc atcgctatta     660
ccatggtcga ggtgagcccc acgttctgct tcactctccc catctccccc cctccccac     720
ccccaatttt gtatttattt attttttaat tatttgtgc agcgatgggg gcggggggg      780
ggggggggcg cgcgccaggc ggggcggggc ggggcgaggg gcggggcggg gcgaggcgga     840
gaggtgcggc ggcagccaat cagagcgcg cgctccgaaa gtttccttt atggcgaggc      900
ggcggcggcg gcggccctat aaaaagcgaa gcgcgcggcg ggcgggagtc gctgcgacgc     960
tgccttcgcc ccgtgccccg ctccgccgcc gcctcgcgcc gcccgccccg gctctgactg    1020
accgcgttac tcccacaggt gagcgggcgg gacggccctt ctcctccggg ctgtaattag    1080
cgcttggttt aatgacggct tgtttctttt ctgtggctgc gtgaaagcct tgaggggctc    1140
cgggagctag agcctctgct aaccatgttc atgccttctt ctttttccta cagctcctgg    1200
gcaacgtgct ggttattgtg ctgtctcatc attttggcaa agaattcctc gaagatccga    1260
agggaaagtc ttccacgact gtgggatccg ttcgaagata tcaccggttg agccaccatg    1320
tggaccctgg tgagctgggt ggccctgacc gccggcctgg tggccggcac ccgctgcccc    1380
gacggccagt tctgccccgt ggcctgctgc ctggaccccg cgcgccag ctacagctgc     1440
tgccgccccc tgctggacaa gtggccacc accctgagcc gccacctggg cggcccctgc    1500
caggtggacg cccactgcag cgccggccac agctgcatct tcaccgtgag cggcaccagc    1560
agctgctgcc ccttccccga ggccgtggcc tgcggcgacg ccaccactg ctgcccccgc    1620
ggcttccact gcagcgccga cggccgcagc tgcttccagc gcagcggcaa caacagcgtg    1680
ggcgccatcc agtgccccga cagccagttc gagtgccccg acttcagcac ctgctgcgtg    1740
atggtggacg gcagctgggg ctgctgcccc atgccccagg ccagctgctg cgaggaccgc    1800
gtgcactgct gccccccacgg cgccttctgc gacctggtgc acacccgctg catcacccc     1860
accggcaccc accccctggc caagaagctg cccgcccagc gcaccaaccg cgccgtggcc    1920
ctgagcagca gcgtgatgtg ccccgacgcc gcagccgct gccccgacgg cagcacctgc    1980
tgcgagctgc ccagcggcaa gtacggctgc tgccccatgc caacgccac ctgctgcagc    2040
gaccacctgc actgctgccc ccaggacacc gtgtgcgacc tgatccagag caagtgcctg    2100
agcaaggaga acgccaccac cgacctgctg accaagctgc ccgcccacac cgtgggcgac    2160
```

```
gtgaagtgcg acatggaggt gagctgcccc gacggctaca cctgctgccg cctgcagagc      2220
ggcgcctggg gctgctgccc cttcacccag gccgtgtgct gcgaggacca catccactgc      2280
tgccccgccg gcttcacctg cgacacccag aagggcacct gcgagcaggg cccccaccag      2340
gtgccctgga tggagaaggc ccccgcccac ctgagcctgc ccgaccccca ggccctgaag      2400
cgcgacgtgc cctgcgacaa cgtgagcagc tgccccagca gcgacacctg ctgccagctg      2460
accagcggcg agtggggctg ctgccccatc cccgaggccg tgtgctgcag cgaccaccag      2520
cactgctgcc cccagggcta cacctgcgtg gccgagggcc agtgccagcg cggcagcgag      2580
atcgtggccg gcctggagaa gatgcccgcc cgccgcgcca gcctgagcca ccccccgcgac     2640 atcggctgcg accagcacac cagctgcccc gtgggccaga cctgctgccc cagcctgggc      2700
ggcagctggg cctgctgcca gctgcccccac gccgtgtgct gcgaggaccg ccagcactgc     2760
tgccccgccg gctacacctg caacgtgaag gcccgcagct gcgagaagga ggtggtgagc      2820
gcccagcccg ccaccttcct ggcccgcagc cccacgtgg gcgtgaagga cgtggagtgc       2880
ggcgagggcc acttctgcca cgacaaccag acctgctgcc gcgacaaccg ccagggctgg      2940
gcctgctgcc cctaccgcca gggcgtgtgc tgcgccgacc gccgccactg ctgccccgcc      3000
ggcttccgct gcgccgcccg cggcaccaag tgcctgcgcc gcgaggcccc ccgctgggac      3060 gccccctgc gcgaccccgc cctgcgccag ctgctgtgac aattgttaat taagtttaaa       3120
ccctcgaggc cgcaagctta tcgataatca acctctggat tacaaaattt gtgaaagatt      3180
gactggtatt cttaactatg ttgctccttt tacgctatgt ggatacgctg ctttaatgcc      3240
tttgtatcat gctattgctt cccgtatggc tttcattttc tcctccttgt ataaatcctg      3300
gttgctgtct ctttatgagg agttgtggcc cgttgtcagg caacgtggcg tggtgtgcac      3360
tgtgtttgct gacgcaaccc ccactggttg gggcattgcc accacctgtc agctcctttc      3420
cgggactttc gctttccccc tccctattgc cacggcggaa ctcatcgccg cctgccttgc      3480
ccgctgctgg acaggggctc ggctgttggg cactgacaat tccgtggtgt tgtcggggaa      3540
atcatcgtcc tttccttggc tgctcgcctg tgttgccacc tggattctgc gcgggacgtc      3600
cttctgctac gtcccttcgg ccctcaatcc agcggacctt ccttcccgcg gcctgctgcc      3660
ggctctgcgg cctcttccgc gtcttcgcct tcgccctcag acgagtcgga tctccctttg      3720
ggccgcctcc ccgcatcgat accgtcgact agagctcgct gatcagcctc gactgtgcct      3780
tctagttgcc agccatctgt tgtttgcccc tccccgtgc cttccttgac cctggaaggt       3840
gccactccca ctgtcctttc ctaataaaat gaggaaattg catcgcattg tctgagtagg      3900
tgtcattcta ttctgggggg tggggtgggg caggacagca agggggagga ttgggaagac      3960
aatagcaggc atgctgggga gagatccacg ataacaaaca gctttttggg ggtgaacata      4020
ttgactgaat tccctgcagg ttggccactc cctctctgcg cgctcgctcg ctcactgagg      4080
ccgcccgggc aaagcccggg cgtcgggcga cctttggtcg cccggcctca gtgagcgagc      4140
gagcgcgcag agagggagtg gccaactcca tcactagggg ttcctgcggc cgctcgtacg      4200
gtctcgagga attcctgcag gataacttgc caacctcatt ctaaaatgta tatagaagcc      4260
caaaagacaa taacaaaaat attcttgtag aacaaaatgg aaagaatgt tccactaaat       4320 atcaagattt agagcaaagc atgagatgtg tggggataga cagtgaggct gataaaatag      4380
agtagagctc agaaacagac ccattgatat atgtaagtga cctatgaaaa aaatatggca      4440
ttttacaatg ggaaatgat ggtctttttc ttttttagaa aaacagggaa atatatttat       4500
atgtaaaaaa taaagggaa cccatatgtc ataccataca cacaaaaaaa ttccagtgaa      4560
```

```
ttataagtct aaatggagaa ggcaaaactt taaatctttt agaaaataat atagaagcat      4620
gcagaccagc ctggccaaca tgatgaaacc ctctctacta ataataaaat cagtagaact      4680
actcaggact actttgagtg ggaagtcctt ttctatgaag acttctttgg ccaaaattag      4740
gctctaaatg caaggagata gtgcatcatg cctggctgca cttactgata aatgatgtta      4800
tcaccatctt taaccaaatg cacaggaaca agttatggta ctgatgtgct ggattgagaa      4860
ggagctctac ttccttgaca ggacacattt gtatcaactt aaaaaagcag attttttgcca     4920 gcagaactat tcattcagag gtaggaaact tagaatagat gatgtcactg attagcatgg      4980
cttccccatc tccacagctg cttcccaccc aggttgccca cagttgagtt tgtccagtgc      5040
tcagggctgc ccactctcag taagaagccc cacaccagcc cctctccaaa tatgttggct      5100
gttccttcca ttaaagtgac cccactttag agcagcaagt ggatttctgt ttcttacagt      5160
tcaggaagga ggagtcagct gtgagaacct ggagcctgag atgcttctaa gtcccactgc      5220
tactggggtc agggaagcca gactccagca tcagcagtca ggagcactaa gcccttgcca      5280
acatcctgtt tctcagagaa actgcttcca ttataatggt tgtccttttt taagctatca      5340
agccaaacaa ccagtgtcta ccattattct catcacctga agccaagggt tctagcaaaa      5400
gtcaagctgt cttgtaatgg ttgatgtgcc tccagcttct gtcttcagtc actccactct      5460
tagcctgctc tgaatcaact ctgaccacag ttccctggag cccctgccac ctgctgcccc      5520
tgccaccttc tccatctgca gtgctgtgca gccttctgca ctcttgcaga gctaataggt      5580
ggagacttga aggaagagga ggaaagtttc tcataatagc cttgctgcaa gctcaaatgg      5640
gaggtgggca ctgtgcccag gagccttgga gcaaaggctg tgcccaacct ctgactgcat      5700
ccaggtttgg tcttgacaga gataagaagc cctggctttt ggagccaaaa tctaggtcag      5760
acttaggcag gattctcaaa gtttatcagc agaacatgag gcagaagacc ctttctgctc      5820
cagcttcttc aggctcaacc ttcatcagaa tagatagaaa gagaggctgt gagggttctt      5880
aaaacagaag caaatctgac tcagagaata aacaacctcc tagtaaacta cagcttagac      5940
agagcatctg gtggtgagtg tgctcagtgt cctactcaac tgtctggtat cagccctcat      6000
gaggacttct cttctttccc tcatagacct ccatctctgt tttccttagc ctgcagaaat      6060
ctggatggct attcacagaa tgcctgtgct ttcagagttg cattttttct ctggtattct      6120
ggttcaagca tttgaaggta ggaaaggttc tccaagtgca agaaagccag ccctgagcct      6180
caactgcctg gctagtgtgg tcagtaggat gcaaaggctg ttgaatgcca caaggccaaa      6240
cttaaacctg tgtaccacaa gcctagcagc agaggcagct ctgctcactg gaactctctg      6300
tcttctttct cctgagcctt ttcttttcct gagttttcta gctctcctca accttacctc      6360
tgccctaccc aggacaaacc caagagccac tgtttctgtg atgtcctctc cagcccctaat     6420 taggcatcat gacttcagcc tgaccttcca tgctcagaag cagtgctaat ccacttcaga      6480
tgagctgctc tatgcaacac aggcagagcc tacaaacctt tgcaccagag ccctccacat      6540
atcagtgttt gttcatactc acttcaacag caaatgtgac tgctgagatt aagattttac      6600
acaagatggt ctgtaatttc acagttagtt ttatcccatt aggtatgaaa gaattagcat      6660
aattcccctt aaacatgaat gaatcttaga tttttttaata aatagttttg gaagtaaaga      6720
cagagacatc aggagcacaa ggaatagcct gagaggacaa acagaacaag aaagagtctg      6780
gaaatacaca ggatgttctt ggcctcctca aagcaagtgc aagcagatag taccagcagc      6840
cccaggctat cagagcccag tgaagagaag taccatgaaa gccacagctc taaccaccct      6900
```

| | |
|---|---|
| gttccagagt gacagacagt ccccaagaca agccagcctg agccagagag agaactgcaa | 6960 |
| gagaaagttt ctaatttagg ttctgttaga ttcagacaag tgcaggtcat cctctctcca | 7020 |
| cagctactca cctctccagc ctaacaaagc ctgcagtcca cactccaacc ctggtgtctc | 7080 |
| acctcctagc ctctcccaac atcctgctct ctgaccatct tctgcatctc tcatctcacc | 7140 |
| atctcccact gtctacagcc tactcttgca actaccatct cattttctga catcctgtct | 7200 |
| acatcttctg ccatactctg ccatctacca taccacctct taccatctac cacaccatct | 7260 |
| tttatctcca tccctctcag aagcctccaa gctgaatcct gctttatgtg ttcatctcag | 7320 |
| cccctgcatg gaaagctgac cccagaggca gaactattcc cagagagctt ggccaagaaa | 7380 |
| aacaaaacta ccagcctggc caggctcagg agtagtaagc tgcagtgtct gttgtgttct | 7440 |
| agcttcaaca gctgcaggag ttccactctc aaatgctcca catttctcac atcctcctga | 7500 |
| ttctggtcac tacccatctt caaagaacag aatatctcac atcagcatac tgtgaaggac | 7560 |
| tagtcatggg tgcagctgct cagagctgca aagtcattct ggatggtgga gagcttacaa | 7620 |
| acatttcatg atgctccccc cgctctgatg gctggagccc aatccctaca cagactcctg | 7680 |
| ctgtatgtgt tttcctttca ctctgagcca cagccagagg gcaggcattc agtctcctct | 7740 |
| tcaggctggg gctggggcac tgagaactca cccaacacct tgctctcact ccttctgcaa | 7800 |
| aacaagaaag agctttgtgc tgcagtagcc atgaagaatg aaaggaaggc tttaactaaa | 7860 |
| aaatgtcaga gattattttc aacccttac tgtggatcac cagcaaggag gaaacacaac | 7920 |
| acagagacat ttttcccct caaattatca aaagaatcac tgcatttgtt aaagagagca | 7980 |
| actgaatcag gaagcagagt tttgaacata tcagaagtta ggaatctgca tcagagacaa | 8040 |
| atgcagtcat ggttgtttgc tgcataccag ccctaatcat tagaagcctc atggacttca | 8100 |
| aacatcattc cctctgacaa gatgctctag cctaactcca tgagataaaa taaatctgcc | 8160 |
| tttcagagcc aaagaagagt ccaccagctt cttctcagtg tgaacaagag ctccagtcag | 8220 |
| gttagtcagt ccagtgcagt agaggagacc agtctgcatc ctctaatttt caaaggcaag | 8280 |
| aagatttgtt taccctggac accaggcaca agtgaggtca cagagctctt agatatgcag | 8340 |
| tcctcatgag tgaggagact aaagcgcatg ccatcaagac ttcagtgtag agaaaacctc | 8400 |
| caaaaagcc tcctcactac ttctggaata gctcagaggc cgaggcggcc tcggcctctg | 8460 |
| cataaataaa aaaattagt cagccatggg gcggagaatg ggcggaactg ggcggagtta | 8520 |
| ggggcgggat gggcggagtt aggggcggga ctatggttgc tgactaattg agatgcatgc | 8580 |
| tttgcatact tctgcctgct ggggagcctg gggactttcc acacctggtt gctgactaat | 8640 |
| tgagatgcat gctttgcata cttctgcctg ctggggagcc tggggacttt ccacacccta | 8700 |
| actgacacac attccacagc tgcattaatg aatcggccaa cgcgcgggga gaggcggttt | 8760 |
| gcgtattggg cgctcttccg cttcctcgct cactgactcg ctgcgctcgg tcgttcggct | 8820 |
| gcggcgagcg gtatcagctc actcaaaggc ggtaatacgg ttatccacag aatcagggga | 8880 |
| taacgcagga aagaacatgt gagcaaaagg ccagcaaaag gccaggaacc gtaaaaaggc | 8940 |
| cgcgttgctg gcgtttttcc ataggctccg ccccctgac gagcatcaca aaaatcgacg | 9000 |
| ctcaagtcag aggtggcgaa acccgacagg actataaaga taccaggcgt ttccccctgg | 9060 |
| aagctccctc gtgcgctctc ctgttccgac cctgccgctt accggatacc tgtccgcctt | 9120 |
| tctcccttcg ggaagcgtgg cgctttctca tagctcacgc tgtaggtatc tcagttcggt | 9180 |
| gtaggtcgtt cgctccaagc tgggctgtgt gcacgaaccc cccgttcagc ccgaccgctg | 9240 |
| cgccttatcc ggtaactatc gtcttgagtc aacccggta agacacgact tatcgccact | 9300 |

```
ggcagcagcc actggtaaca ggattagcag agcgaggtat gtaggcggtg ctacagagtt   9360
cttgaagtgg tggcctaact acggctacac tagaagaaca gtatttggta tctgcgctct   9420
gctgaagcca gttaccttcg gaaaagagt tggtagctct tgatccggca aacaaaccac    9480
cgctggtagc ggtggttttt ttgtttgcaa gcagcagatt acgcgcagaa aaaaggatc    9540 tcaagaagat cctttgatct tttctacggg gtctgacgct cagtggaacg aaaactcacg   9600
ttaagggatt ttggtcatga gattatcaaa aaggatcttc acctagatcc ttttaaatta   9660
aaaatgaagt tttaaatcaa tctaaagtat atatgagtaa acttggtctg acagttacca   9720
atgcttaatc agtgaggcac ctatctcagc gatctgtcta tttcgttcat ccatagttgc   9780
ctgactcctg caaccacgt tgtgtctcaa aatctctgat gttacattgc acaagataaa    9840
aatatatcat catgaacaat aaaactgtct gcttacataa acagtaatac aagggggtgtt  9900 atgagccata ttcaacggga aacgtcttgc tcgaggccgc gattaaattc caacatggat   9960
gctgatttat atgggtataa atgggctcgc gataatgtcg ggcaatcagg tgcgacaatc  10020
tatcgattgt atgggaagcc cgatgcgcca gagttgtttc tgaaacatgg caaaggtagc  10080
gttgccaatg atgttacaga tgagatggtc agactaaact ggctgacgga atttatgcct  10140
cttccgacca tcaagcattt tatccgtact cctgatgatg catggttact caccactgcg  10200
atccccggga aaacagcatt ccaggtatta gaagaatatc ctgattcagg tgaaaatatt  10260
gttgatgcgc tggcagtgtt cctgcgccgg ttgcattcga ttcctgtttg taattgtcct  10320
tttaacagcg atcgcgtatt tcgtctcgct caggcgcaat cacgaatgaa taacggtttg  10380
gttgatgcga gtgattttga tgacgagcgt aatggctggc ctgttgaaca agtctggaaa  10440
gaaatgcata agcttttgcc attctcaccg gattcagtcg tcactcatgg tgatttctca  10500
cttgataacc ttatttttga cgaggggaaa ttaataggtt gtattgatgt tggacgagtc  10560
ggaatcgcag accgatacca ggatcttgcc atcctatgga actgcctcgg tgagttttct  10620
ccttcattac agaaacggct ttttcaaaaa tatggtattg ataatcctga tatgaataaa  10680
ttgcagtttc atttgatgct cgatgagttt ttctaagggc ggcctgccac catacccacg  10740
ccgaaacaag cgctcatgag cccgaagtgg cgagcccgat cttccccatc ggtgatgtcg  10800
gcgatatagg cgccagcaac cgcacctgtg gcgccggtga tgagggcgcg ccaagtcgac  10860
gtccggcagt c                                                        10871
```

<210> SEQ ID NO 70
<211> LENGTH: 4151
<212> TYPE: DNA
<213> ORGANISM: Artificial sequence
<220> FEATURE:
<223> OTHER INFORMATION: Synthetic polynucleotide

<400> SEQUENCE: 70

```
gggaggttac gcgttcgtcg actactagtg ggtaccagag cgggcggagt tagggcggag     60
ccaatcagcg tgcgccgttc cgaaagttgc ctttttatggc tgggcggaga atgggcggtg   120
aacgccgatg attatataag gacgcgccgg gtgtggcaca gctagttccg tcgcagccgg    180
gatttgggtc gcggttcttg tttgtggatc cctgtgatcg tcacttggta agtcactgac    240
tgtctatgcc tgggaaaggg tgggcaggag atggggcagt gcaggaaaag tggcactatg    300
aaccctgcag ccctaggaat gcatctagac aattgtacta accttcttct ctttcctctc    360
ctgacagtcc ggaaagccac catgtacgcc ctgttcctgc tggccagcct gctgggcgcc    420
```

```
gccctggccg gccccgtgct gggcctgaag gagtgcaccc gcggcagcgc cgtgtggtgc    480
cagaacgtga agaccgccag cgactgcggc gccgtgaagc actgcctgca gaccgtgtgg    540
aacaagccca ccgtgaagag cctgccctgc gacatctgca aggacgtggt gaccgccgcc    600
ggcgacatgc tgaaggacaa cgccaccgag gaggagatcc tggtgtacct ggagaagacc    660
tgcgactggc tgcccaagcc caacatgagc gccagctgca aggagatcgt ggacagctac    720
ctgcccgtga tcctggacat catcaagggc gagatgagcc gccccggcga ggtgtgcagc    780
gccctgaacc tgtgcgagag cctgcagaag cacctggccg agctgaacca ccagaagcag    840
ctggagagca caagatccc cgagctggac atgaccgagg tggtggcccc cttcatggcc    900
aacatccccc tgctgctgta cccccaggac ggcccccgca gcaagcccca gcccaaggac    960
aacggcgacg tgtgccagga ctgcatccag atggtgaccg acatccagac cgccgtgcgc   1020
accaacagca ccttcgtgca ggccctggtg agcacgtga aggaggagtg cgaccgcctg   1080
ggccccggca tggccgacat ctgcaagaac tacatcagcc agtacagcga gatcgccatc   1140
cagatgatga tgcacatgca gcccaaggag atctgcgccc tggtgggctt ctgcgacgag   1200
gtgaaggaga tgcccatgca gaccctggtg cccgccaagg tggccagcaa gaacgtgatc   1260
cccgccctgg agctggtgga gcccatcaag aagcacgagg tgcccgccaa gagcgacgtg   1320
tactgcgagg tgtgcgagtt cctggtgaag gaggtgacca agctgatcga caacaacaag   1380
accgagaagg agatcctgga cgccttcgac aagatgtgca gcaagctgcc caagagcctg   1440
agcgaggagt gccaggaggt ggtggacacc tacggcagca gcatcctgag catcctgctg   1500
gaggaggtga gccccgagct ggtgtgcagc atgctgcacc tgtgcagcgg cacccgcctg   1560
cccgccctga ccgtgcacgt gacccagccc aaggacggcg gcttctgcga ggtgtgcaag   1620
aagctggtgg gctacctgga ccgcaacctg gagaagaaca gcaccaagca ggagatcctg   1680
gccgccctgg agaagggctg cagcttcctg cccgaccct accagaagca gtgcgaccag   1740
ttcgtggccg agtacgagcc cgtgctgatc gagatcctgg tggaggtgat ggaccccagc   1800
ttcgtgtgcc tgaagatcgg cgcctgcccc agcgcccaca gcccctgct gggcaccgag   1860
aagtgcatct ggggccccag ctactggtgc cagaacaccg agaccgccgc ccagtgcaac   1920
gccgtggagc actgcaagcg ccacgtgtgg aacagaagaa agagaggaag tggagagggc   1980
agaggaagtc ttctgacatg cggagacgtg aagagaatc ccggccctat gtggaccctg   2040
gtgagctggg tggccctgac cgccggcctg gtggccggca ccgctgccc cgacggccag   2100
ttctgccccg tggcctgctg cctggacccc ggcggcgcca gctacagctg ctgccgcccc   2160
ctgctggaca agtggcccac caccctgagc cgccacctgg gcggcccctg ccaggtggac   2220
gcccactgca gcgccggcca cagctgcatc ttcaccgtga gcggcaccag cagctgctgc   2280
cccttccccg aggccgtggc ctgcggcgac ggccaccact gctgccccg cggcttccac   2340
tgcagcgccg acggccgcag ctgcttccag cgcagcggca caacagcgt gggcgccatc   2400
cagtgccccg acagccagtt cgagtgcccc gacttcagca cctgctgcgt gatggtggac   2460
ggcagctggg gctgctgccc catgcccag gccagctgct gcgaggaccg cgtgcactgc   2520
tgcccccacg gcgccttctg cgacctggtg cacacccgct gcatcacccc caccggcacc   2580
caccccctgg ccaagaagct gcccgcccag cgcaccaacc gcgccgtggc cctgagcagc   2640
agcgtgatgt gccccgacgc ccgcagccgc tgccccgacg gcagcacctg ctgcgagctg   2700
cccagcggca agtacggctg ctgccccatg cccaacgcca cctgctgcag cgaccacctg   2760
cactgctgcc cccaggacac cgtgtgcgac ctgatccaga gcaagtgcct gagcaaggag   2820
```

-continued

```
aacgccacca ccgacctgct gaccaagctg cccgcccaca ccgtgggcga cgtgaagtgc   2880
gacatggagg tgagctgccc cgacggctac acctgctgcc gcctgcagag cggcgcctgg   2940
ggctgctgcc ccttcaccca ggccgtgtgc tgcgaggacc acatccactg ctgccccgcc   3000
ggcttcacct gcgacaccca gaagggcacc tgcgagcagg cccccacca ggtgccctgg    3060 atggagaagg cccccgccca cctgagcctg cccgaccccc aggccctgaa gcgcgacgtg   3120
ccctgcgaca cgtgagcag ctgccccagc agcgacacct gctgccagct gaccagcggc    3180
gagtggggct gctgccccat ccccgaggcc gtgtgctgca gcgaccacca gcactgctgc   3240
ccccagggct acacctgcgt ggccgagggc cagtgccagc gcggcagcga gatcgtggcc   3300
ggcctggaga agatgcccgc ccgccgcgcc agcctgagcc accccgcga catcggctgc    3360 gaccagcaca ccagctgccc cgtgggccag acctgctgcc ccagcctggg cggcagctgg   3420
gcctgctgcc agctgcccca cgccgtgtgc tgcgaggacc gccagcactg ctgccccgcc   3480
ggctacacct gcaacgtgaa ggcccgcagc tgcgagaagg aggtggtgag cgcccagccc   3540
gccaccttcc tggcccgcag cccccacgtg ggcgtgaagg acgtggagtg cggcgagggc   3600
cacttctgcc acgacaacca gacctgctgc gcgacaacc gccagggctg ggcctgctgc    3660
ccctaccgcc agggcgtgtg ctgcgccgac cgccgccact gctgccccgc cggcttccgc   3720
tgcgccgccc gcggcaccaa gtgcctgcgc gcgcaggccc ccgctgggga cgccccctg    3780 cgcgaccccg ccctgcgcca gctgctgtga caattgttaa ttaagtttaa accctcgagg   3840
ccgcaagcaa taaatatct ttatttcat tacatctgtg tgttggtttt ttgtgtgaca     3900
attgttaatt aagtttaaac gttcgaggcc gcaagcgaga tccacgataa caaacagctt   3960
ttttggggtg aacatattga ctgaattccc tgcaggttgg ccactccctc tctgcgcgct   4020
cgctcgctca ctgaggccgc ccgggcaaag cccgggcgtc gggcgacctt tggtcgcccg   4080
gcctcagtga gcgagcgagc gcgcagagag ggagtggcca actccatcac taggggttcc   4140
tgcggccgct c                                                       4151
```

<210> SEQ ID NO 71
<211> LENGTH: 23
<212> TYPE: DNA
<213> ORGANISM: Artificial sequence
<220> FEATURE:
<223> OTHER INFORMATION: Synthetic polynucleotide

<400> SEQUENCE: 71
aagagggtgt tctctatgta ggc                                            23

<210> SEQ ID NO 72
<211> LENGTH: 22
<212> TYPE: DNA
<213> ORGANISM: Artificial sequence
<220> FEATURE:
<223> OTHER INFORMATION: Synthetic polynucleotide

<400> SEQUENCE: 72
gctcctccaa catttgtcac tt                                             22

<210> SEQ ID NO 73
<211> LENGTH: 23
<212> TYPE: DNA
<213> ORGANISM: Artificial sequence
<220> FEATURE:
<223> OTHER INFORMATION: Synthetic polynucleotide

```
<400> SEQUENCE: 73
acacagtacc taccgttata gca                                              23

<210> SEQ ID NO 74
<211> LENGTH: 23
<212> TYPE: DNA
<213> ORGANISM: Artificial sequence
<220> FEATURE:
<223> OTHER INFORMATION: Synthetic polynucleotide

<400> SEQUENCE: 74
tgttgtcaca gtaacttgca tca                                              23

<210> SEQ ID NO 75
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 75
ctgggctaca ctgagcacc                                                   19

<210> SEQ ID NO 76
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 76
aagtggtcgt tgagggcaat g                                                21

<210> SEQ ID NO 77
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 77
tattagatct gatggccgcg                                                  20

<210> SEQ ID NO 78
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 78
tccatcacta ggggttcctg                                                  20
```

GENE THERAPIES FOR LYSOSOMAL DISORDERS

RELATED APPLICATIONS

This Application is a continuation under 35 U.S.C. § 120 of U.S. application Ser. No. 16/753,322, filed Apr. 2, 2020, which is a national stage filing under 35 U.S.C. § 371 of international PCT application, PCT/US2018/054227, filed Oct. 3, 2018, which claims priority under 35 U.S.C. § 119(e) of the filing date of U.S. Provisional Application Ser. No. 62/567,296, filed Oct. 3, 2017, entitled "GENE THERAPIES FOR LYSOSOMAL DISORDERS", 62/567,311, filed Oct. 3, 2017, entitled "GENE THERAPIES FOR LYSOSOMAL DISORDERS", 62/567,319, filed Oct. 3, 2017, entitled "GENE THERAPIES FOR LYSOSOMAL DISORDERS", 62/567,301, filed Oct. 3, 2018, entitled "GENE THERAPIES FOR LYSOSOMAL DISORDERS", and 62/567,310, filed Oct. 3, 2017, entitled "GENE THERAPIES FOR LYSOSOMAL DISORDERS", the entire contents of each application which are incorporated herein by reference.

BACKGROUND

Gaucher disease is a rare inborn error of glycosphingolipid metabolism due to deficiency of lysosomal acid β-glucocerebrosidase (Gcase, "GBA"). Patients suffer from non-CNS symptoms and findings including hepatosplenomegly, bone marrow insufficiency leading to pancytopenia, lung disorders and fibrosis, and bone defects. In addition, a significant number of patients suffer from neurological manifestations, including defective saccadic eye movements and gaze, seizures, cognitive deficits, developmental delay, and movement disorders including Parkinson's disease.

Several therapeutics exist that address the peripheral disease and the principal clinical manifestations in hematopoietic bone marrow and viscera, including enzyme replacement therapies as described below, chaperone-like small molecule drugs that bind to defective Gcase and improve stability, and substrate reduction therapy that block the production of substrate that accumulate in Gaucher disease leading to symptoms and findings. However, other aspects of Gaucher disease (particularly those affecting the skeleton and brain) appear refractory to treatment.

SUMMARY

In addition to Gaucher disease patients (who possess mutations in both chromosomal alleles of GBA1 gene), patients with mutations in only one allele of GBA1 are at highly increased risk of Parkinson's disease (PD). The severity of PD symptoms—which include gait difficulty, a tremor at rest, rigidity, and often depression, sleep difficulties, and cognitive decline—correlate with the degree of enzyme activity reduction. Thus, Gaucher disease patients have the most severe course, whereas patient with a single mild mutation in GBA1 typically have a more benign course. Mutation carriers are also at high risk of other PD-related disorders, including Lewy Body Dementia, characterized by executive dysfunction, psychosis, and a PD-like movement disorder, and multi-system atrophy, with characteristic motor and cognitive impairments. No therapies exist that alter the inexorable course of these disorders.

Deficits in enzymes such as Gcase (e.g., the gene product of GBA1 gene), as well as common variants in many genes implicated in lysosome function or trafficking of macromolecules to the lysosome (e.g., Lysosomal Membrane Protein 1 (LIMP), also referred to as SCARB2), have been associated with increased PD risk. The disclosure is based, in part, on expression constructs (e.g., vectors) encoding one or more PD-associated genes, for example Gcase, GBA2, prosaposin, progranulin, LIMP2, GALC, CTSB, SMPD1, GCH1, RAB7, VPS35, IL-34, TREM2, TMEM106B, or a combination of any of the foregoing (or portions thereof). In some embodiments, combinations of gene products described herein act together (e.g., synergistically) to reduce one or more signs and symptoms of PD when expressed in a subject.

Accordingly, in some aspects, the disclosure provides an isolated nucleic acid comprising an expression construct encoding a Gcase (e.g., the gene product of GBA1 gene). In some embodiments, the isolated nucleic acid comprises a Gcase-encoding sequence that has been codon optimized (e.g., codon optimized for expression in mammalian cells, for example human cells). In some embodiments, the nucleic acid sequence encoding the Gcase encodes a protein comprising an amino acid sequence as set forth in SEQ ID NO: 14 (e.g., as set forth in NCBI Reference Sequence NP_000148.2). In some embodiments, the isolated nucleic acid comprises the sequence set forth in SEQ ID NO: 15. In some embodiments the expression construct comprises adeno-associated virus (AAV) inverted terminal repeats (ITRs), for example AAV ITRs flanking the nucleic acid sequence encoding the Gcase protein.

In some aspects, the disclosure provides an isolated nucleic acid comprising an expression construct encoding Prosaposin (e.g., the gene product of PSAP gene). In some embodiments, the isolated nucleic acid comprises a prosaposin-encoding sequence that has been codon optimized (e.g., codon optimized for expression in mammalian cells, for example human cells). In some embodiments, the nucleic acid sequence encoding the prosaposin encodes a protein comprising an amino acid sequence as set forth in SEQ ID NO: 16 (e.g., as set forth in NCBI Reference Sequence NP_002769.1). In some embodiments, the isolated nucleic acid comprises the sequence set forth in SEQ ID NO: 17. In some embodiments the expression construct comprises adeno-associated virus (AAV) inverted terminal repeats (ITRs), for example AAV ITRs flanking the nucleic acid sequence encoding the prosaposin protein.

In some aspects, the disclosure provides an isolated nucleic acid comprising an expression construct encoding LIMP2/SCARB2 (e.g., the gene product of SCARB2 gene). In some embodiments, the isolated nucleic acid comprises a SCARB2-encoding sequence that has been codon optimized (e.g., codon optimized for expression in mammalian cells, for example human cells). In some embodiments, the nucleic acid sequence encoding the LIMP2/SCARB2 encodes a protein comprising an amino acid sequence as set forth in SEQ ID NO: 18 (e.g., as set forth in NCBI Reference Sequence NP_005497.1). In some embodiments, the isolated nucleic acid comprises the sequence set forth in SEQ ID NO: 29. In some embodiments the expression construct comprises adeno-associated virus (AAV) inverted terminal repeats (ITRs), for example AAV ITRs flanking the nucleic acid sequence encoding the SCARB2 protein.

In some aspects, the disclosure provides an isolated nucleic acid comprising an expression construct encoding GBA2 protein (e.g., the gene product of GBA2 gene). In some embodiments, the isolated nucleic acid comprises a GBA2-encoding sequence that has been codon optimized (e.g., codon optimized for expression in mammalian cells, for example human cells). In some embodiments, the nucleic acid sequence encoding the GBA2 encodes a protein comprising an amino acid sequence as set forth in SEQ ID NO: 30 (e.g., as set forth in NCBI Reference Sequence NP_065995.1). In some embodiments, the isolated nucleic acid comprises the sequence set forth in SEQ ID NO: 31. In some embodiments the expression construct comprises adeno-associated virus (AAV) inverted terminal repeats (ITRs), for example AAV ITRs flanking the nucleic acid sequence encoding the GBA2 protein.

In some aspects, the disclosure provides an isolated nucleic acid comprising an expression construct encoding GALC protein (e.g., the gene product of GALC gene). In some embodiments, the isolated nucleic acid comprises a GALC-encoding sequence that has been codon optimized (e.g., codon optimized for expression in mammalian cells, for example human cells). In some embodiments, the nucleic acid sequence encoding the GALC encodes a protein comprising an amino acid sequence as set forth in SEQ ID NO: 33 (e.g., as set forth in NCBI Reference Sequence NP_000144.2). In some embodiments, the isolated nucleic acid comprises the sequence set forth in SEQ ID NO: 34. In some embodiments the expression construct comprises adeno-associated virus (AAV) inverted terminal repeats (ITRs), for example AAV ITRs flanking the nucleic acid sequence encoding the GALC protein.

In some aspects, the disclosure provides an isolated nucleic acid comprising an expression construct encoding CTSB protein (e.g., the gene product of CTSB gene). In some embodiments, the isolated nucleic acid comprises a CTSB-encoding sequence that has been codon optimized (e.g., codon optimized for expression in mammalian cells, for example human cells). In some embodiments, the nucleic acid sequence encoding the CTSB encodes a protein comprising an amino acid sequence as set forth in SEQ ID NO: 35 (e.g., as set forth in NCBI Reference Sequence NP_001899.1). In some embodiments, the isolated nucleic acid comprises the sequence set forth in SEQ ID NO: 36. In some embodiments the expression construct comprises adeno-associated virus (AAV) inverted terminal repeats (ITRs), for example AAV ITRs flanking the nucleic acid sequence encoding the CTSB protein.

In some aspects, the disclosure provides an isolated nucleic acid comprising an expression construct encoding SMPD1 protein (e.g., the gene product of SMPD1 gene). In some embodiments, the isolated nucleic acid comprises a SMPD1-encoding sequence that has been codon optimized (e.g., codon optimized for expression in mammalian cells, for example human cells). In some embodiments, the nucleic acid sequence encoding the SMPD1 encodes a protein comprising an amino acid sequence as set forth in SEQ ID NO: 37 (e.g., as set forth in NCBI Reference Sequence NP_000534.3). In some embodiments, the isolated nucleic acid comprises the sequence set forth in SEQ ID NO: 38. In some embodiments the expression construct comprises adeno-associated virus (AAV) inverted terminal repeats (ITRs), for example AAV ITRs flanking the nucleic acid sequence encoding the SMPD1 protein.

In some aspects, the disclosure provides an isolated nucleic acid comprising an expression construct encoding GCH1 protein (e.g., the gene product of GCH1 gene). In some embodiments, the isolated nucleic acid comprises a GCH1-encoding sequence that has been codon optimized (e.g., codon optimized for expression in mammalian cells, for example human cells). In some embodiments, the nucleic acid sequence encoding the GCH1 encodes a protein comprising an amino acid sequence as set forth in SEQ ID NO: 45 (e.g., as set forth in NCBI Reference Sequence NP_000534.3). In some embodiments, the isolated nucleic acid comprises the sequence set forth in SEQ ID NO: 46. In some embodiments the expression construct comprises adeno-associated virus (AAV) inverted terminal repeats (ITRs), for example AAV ITRs flanking the nucleic acid sequence encoding the GCH1 protein.

In some aspects, the disclosure provides an isolated nucleic acid comprising an expression construct encoding RAB7L protein (e.g., the gene product of RAB7L gene). In some embodiments, the isolated nucleic acid comprises a RAB7L-encoding sequence that has been codon optimized (e.g., codon optimized for expression in mammalian cells, for example human cells). In some embodiments, the nucleic acid sequence encoding the RAB7L encodes a protein comprising an amino acid sequence as set forth in SEQ ID NO: 47 (e.g., as set forth in NCBI Reference Sequence NP_003920.1). In some embodiments, the isolated nucleic acid comprises the sequence set forth in SEQ ID NO: 48. In some embodiments the expression construct comprises adeno-associated virus (AAV) inverted terminal repeats (ITRs), for example AAV ITRs flanking the nucleic acid sequence encoding the RAB7L protein.

In some aspects, the disclosure provides an isolated nucleic acid comprising an expression construct encoding VPS35 protein (e.g., the gene product of VPS35 gene). In some embodiments, the isolated nucleic acid comprises a VPS35-encoding sequence that has been codon optimized (e.g., codon optimized for expression in mammalian cells, for example human cells). In some embodiments, the nucleic acid sequence encoding the VPS35 encodes a protein comprising an amino acid sequence as set forth in SEQ ID NO: 49 (e.g., as set forth in NCBI Reference Sequence NP_060676.2). In some embodiments, the isolated nucleic acid comprises the sequence set forth in SEQ ID NO: 50. In some embodiments the expression construct comprises adeno-associated virus (AAV) inverted terminal repeats (ITRs), for example AAV ITRs flanking the nucleic acid sequence encoding the VPS35 protein.

In some aspects, the disclosure provides an isolated nucleic acid comprising an expression construct encoding IL-34 protein (e.g., the gene product of IL34 gene). In some embodiments, the isolated nucleic acid comprises a IL-34-encoding sequence that has been codon optimized (e.g., codon optimized for expression in mammalian cells, for example human cells). In some embodiments, the nucleic acid sequence encoding the IL-34 encodes a protein comprising an amino acid sequence as set forth in SEQ ID NO: 55 (e.g., as set forth in NCBI Reference Sequence NP_689669.2). In some embodiments, the isolated nucleic acid comprises the sequence set forth in SEQ ID NO: 56. In some embodiments the expression construct comprises adeno-associated virus (AAV) inverted terminal repeats (ITRs), for example AAV ITRs flanking the nucleic acid sequence encoding the IL34 protein.

In some aspects, the disclosure provides an isolated nucleic acid comprising an expression construct encoding TREM2 protein (e.g., the gene product of TREM gene). In some embodiments, the isolated nucleic acid comprises a TREM2-encoding sequence that has been codon optimized (e.g., codon optimized for expression in mammalian cells, for example human cells). In some embodiments, the nucleic acid sequence encoding the TREM2 encodes a protein comprising an amino acid sequence as set forth in SEQ ID NO: 57 (e.g., as set forth in NCBI Reference Sequence NP 061838.1). In some embodiments, the isolated nucleic acid comprises the sequence set forth in SEQ ID NO: 58. In some embodiments the expression construct comprises adeno-associated virus (AAV) inverted terminal repeats (ITRs), for example AAV ITRs flanking the nucleic acid sequence encoding the TREM2 protein.

In some aspects, the disclosure provides an isolated nucleic acid comprising an expression construct encoding TMEM106B protein (e.g., the gene product of TMEM106B gene). In some embodiments, the isolated nucleic acid comprises a TMEM106B-encoding sequence that has been codon optimized (e.g., codon optimized for expression in mammalian cells, for example human cells). In some embodiments, the nucleic acid sequence encoding the TMEM106B encodes a protein comprising an amino acid sequence as set forth in SEQ ID NO: 63 (e.g., as set forth in NCBI Reference Sequence NP_060844.2). In some embodiments, the isolated nucleic acid comprises the sequence set forth in SEQ ID NO: 64. In some embodiments the expression construct comprises adeno-associated virus (AAV) inverted terminal repeats (ITRs), for example AAV ITRs flanking the nucleic acid sequence encoding the TMEM106B protein.

In some aspects, the disclosure provides an isolated nucleic acid comprising an expression construct encoding progranulin (e.g., the gene product of PGRN gene). In some embodiments, the isolated nucleic acid comprises a prosaposin-encoding sequence that has been codon optimized (e.g., codon optimized for expression in mammalian cells, for example human cells). In some embodiments, the nucleic acid sequence encoding the progranulin (PRGN) encodes a protein comprising an amino acid sequence as set forth in SEQ ID NO: 67 (e.g., as set forth in NCBI Reference Sequence NP_002078.1). In some embodiments, the isolated nucleic acid comprises the sequence set forth in SEQ ID NO: 68. In some embodiments the expression construct comprises adeno-associated virus (AAV) inverted terminal repeats (ITRs), for example AAV ITRs flanking the nucleic acid sequence encoding the prosaposin protein.

In some aspects, the disclosure provides an isolated nucleic acid comprising an expression construct encoding a first gene product and a second gene product, wherein each gene product independently is selected from the gene products, or portions thereof, set forth in Table 1.

In some embodiments, a first gene product or a second gene product is a Gcase protein, or a portion thereof. In some embodiments, a first gene product is a Gcase protein and a second gene product is selected from GBA2, prosaposin, progranulin, LIMP2, GALC, CTSB, SMPD1, GCH1, RAB7, VPS35, IL-34, TREM2, and TMEM106B.

In some embodiments, an expression construct further encodes an interfering nucleic acid (e.g., shRNA, miRNA, dsRNA, etc.). In some embodiments, an interfering nucleic acid inhibits expression of α-Synuclein (α-Synuclein). In some embodiments, an interfering nucleic acid that targets α-Synuclein comprises a sequence set forth in any one of SEQ ID NOs: 20-25. In some embodiments, an interfering nucleic acid that targets α-Synuclein binds to (e.g., hybridizes with) a sequence set forth in any one of SEQ ID NO: 20-25.

In some embodiments, an interfering nucleic acid inhibits expression of TMEM106B. In some embodiments, an interfering nucleic acid that targets TMEM106B comprises a sequence set forth in SEQ ID NO: 64 or 65. In some embodiments, an interfering nucleic acid that targets TMEM106B binds to (e.g., hybridizes with) a sequence set forth in SEQ ID NO: 64 or 65.

In some embodiments, an expression construct further comprises one or more promoters. In some embodiments, a promoter is a chicken-beta actin (CBA) promoter, a CAG promoter, a CD68 promoter, or a JeT promoter. In some embodiments, a promoter is a RNA pol II promoter (e.g., or an RNA pol III promoter (e.g., U6, etc.).

In some embodiments, an expression construct further comprises an internal ribosomal entry site (IRES). In some embodiments, an IRES is located between a first gene product and a second gene product.

In some embodiments, an expression construct further comprises a self-cleaving peptide coding sequence. In some embodiments, a self-cleaving peptide is a T2A peptide.

In some embodiments, an expression construct comprises two adeno-associated virus (AAV) inverted terminal repeat (ITR) sequences. In some embodiments, ITR sequences flank a first gene product and a second gene product (e.g., are arranged as follows from 5'-end to 3'-end: ITR-first gene product-second gene product-ITR). In some embodiments, one of the ITR sequences of an isolated nucleic acid lacks a functional terminal resolution site (trs). For example, in some embodiments, one of the ITRs is a ΔITR.

The disclosure relates, in some aspects, to rAAV vectors comprising an ITR having a modified "D" region (e.g., a D sequence that is modified relative to wild-type AAV2 ITR, SEQ ID NO: 29). In some embodiments, the ITR having the modified D region is the 5' ITR of the rAAV vector. In some embodiments, a modified "D" region comprises an "S" sequence, for example as set forth in SEQ ID NO: 26. In some embodiments, the ITR having the modified "D" region is the 3' ITR of the rAAV vector. In some embodiments, a modified "D" region comprises a 3'ITR in which the "D" region is positioned at the 3' end of the ITR (e.g., on the outside or terminal end of the ITR relative to the transgene insert of the vector). In some embodiments, a modified "D" region comprises a sequence as set forth in SEQ ID NO: 26 or 27.

In some embodiments, an isolated nucleic acid (e.g., an rAAV vector) comprises a TRY region. In some embodiments, a TRY region comprises the sequence set forth in SEQ ID NO: 28.

In some embodiments, an isolated nucleic acid described by the disclosure comprises or consists of, or encodes a peptide having, the sequence set forth in any one of SEQ ID NOs: 1-78.

In some aspects, the disclosure provides a vector comprising an isolated nucleic acid as described by the disclosure. In some embodiments, a vector is a plasmid, or a viral vector. In some embodiments, a viral vector is a recombinant AAV (rAAV) vector or a Baculovirus vector. In some embodiments, an rAAV vector is single-stranded (e.g., single-stranded DNA).

In some aspects, the disclosure provides a host cell comprising an isolated nucleic acid as described by the disclosure or a vector as described by the disclosure.

In some aspects, the disclosure provides a recombinant adeno-associated virus (rAAV) comprising a capsid protein and an isolated nucleic acid or a vector as described by the disclosure.

In some embodiments, a capsid protein is capable of crossing the blood-brain barrier, for example an AAV9 capsid protein or an AAVrh.10 capsid protein. In some embodiments, an rAAV transduces neuronal cells and non-neuronal cells of the central nervous system (CNS).

In some aspects, the disclosure provides a method for treating a subject having or suspected of having Parkinson's disease, the method comprising administering to the subject a composition (e.g., a composition comprising an isolated nucleic acid or a vector or a rAAV) as described by the disclosure.

In some embodiments, administration comprises direct injection to the CNS of a subject. In some embodiments, direct injection is intracerebral injection, intraparenchymal injection, intrathecal injection, intra-cisterna manga injection, or any combination thereof. In some embodiments, direct injection to the CNS of a subject comprises convection enhanced delivery (CED).

In some embodiments, administration comprises peripheral injection. In some embodiments, peripheral injection is intravenous injection.

BRIEF DESCRIPTION OF THE DRAWINGS

FIG. 36A shows data for overexpression of TREM2. FIG. 36B shows data for overexpression of GBA1 from the same construct.

DETAILED DESCRIPTION

Figure 1:
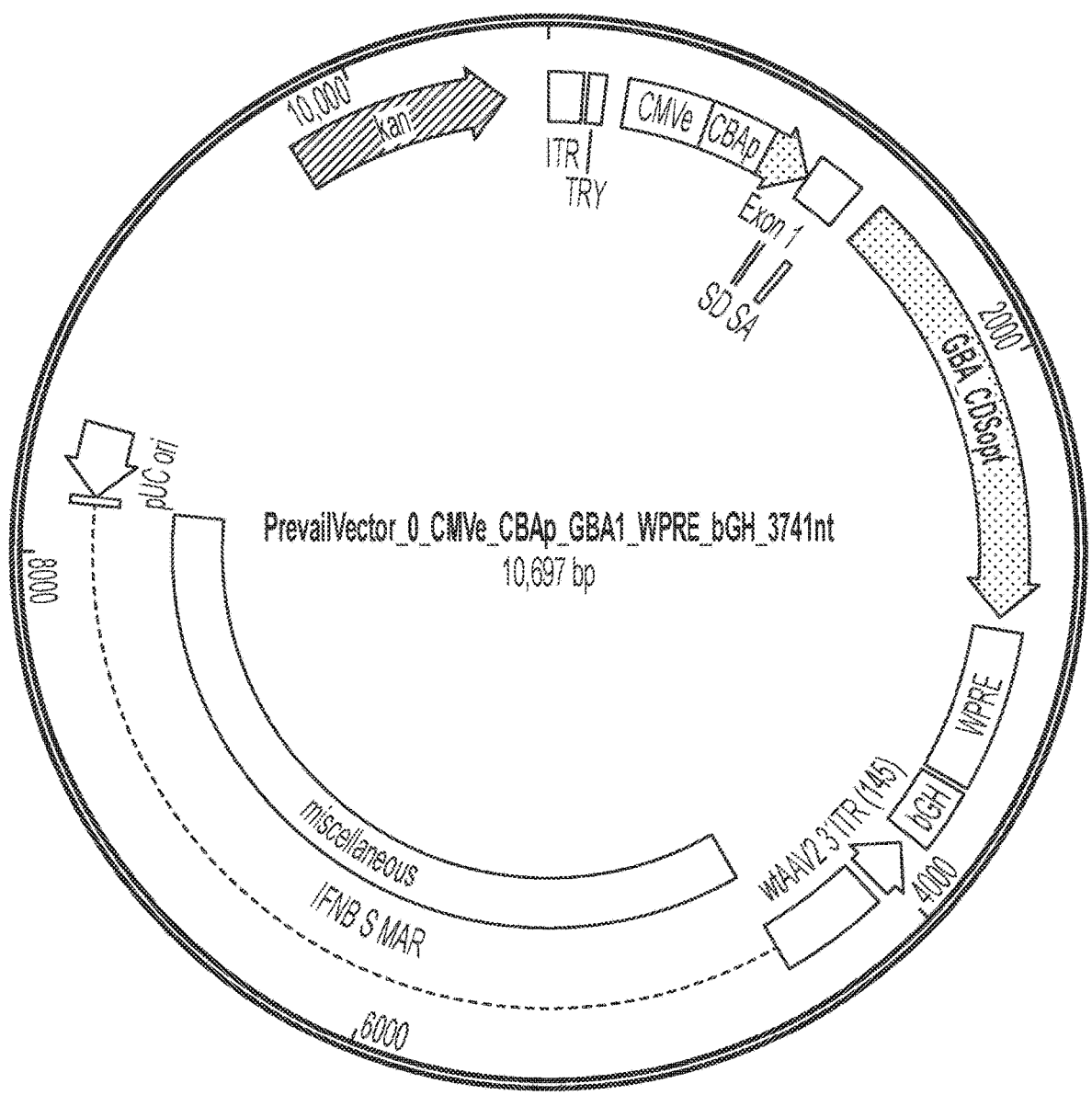
FIG. 1 is a schematic depicting one embodiment of a vector comprising an expression construct encoding Gcase (e.g., GBA1 or a portion thereof).
Figure 2:
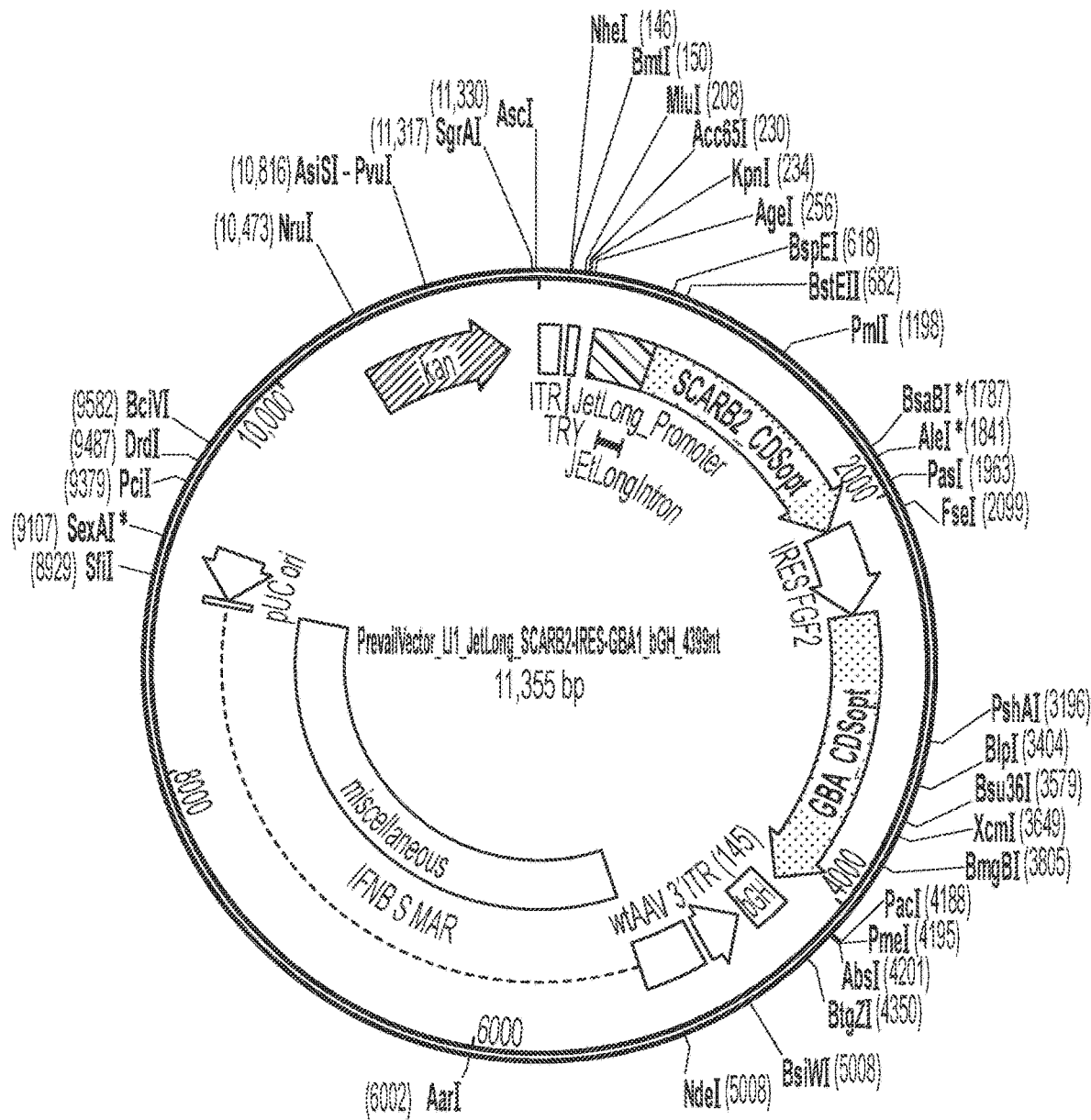
FIG. 2 is a schematic depicting one embodiment of a vector comprising an expression construct encoding Gcase (e.g., GBA1 or a portion thereof) and LIMP2 (SCARB2) or a portion thereof. The coding sequences of Gcase and LIMP2 are separated by an internal ribosomal entry site (IRES).
Figure 3:
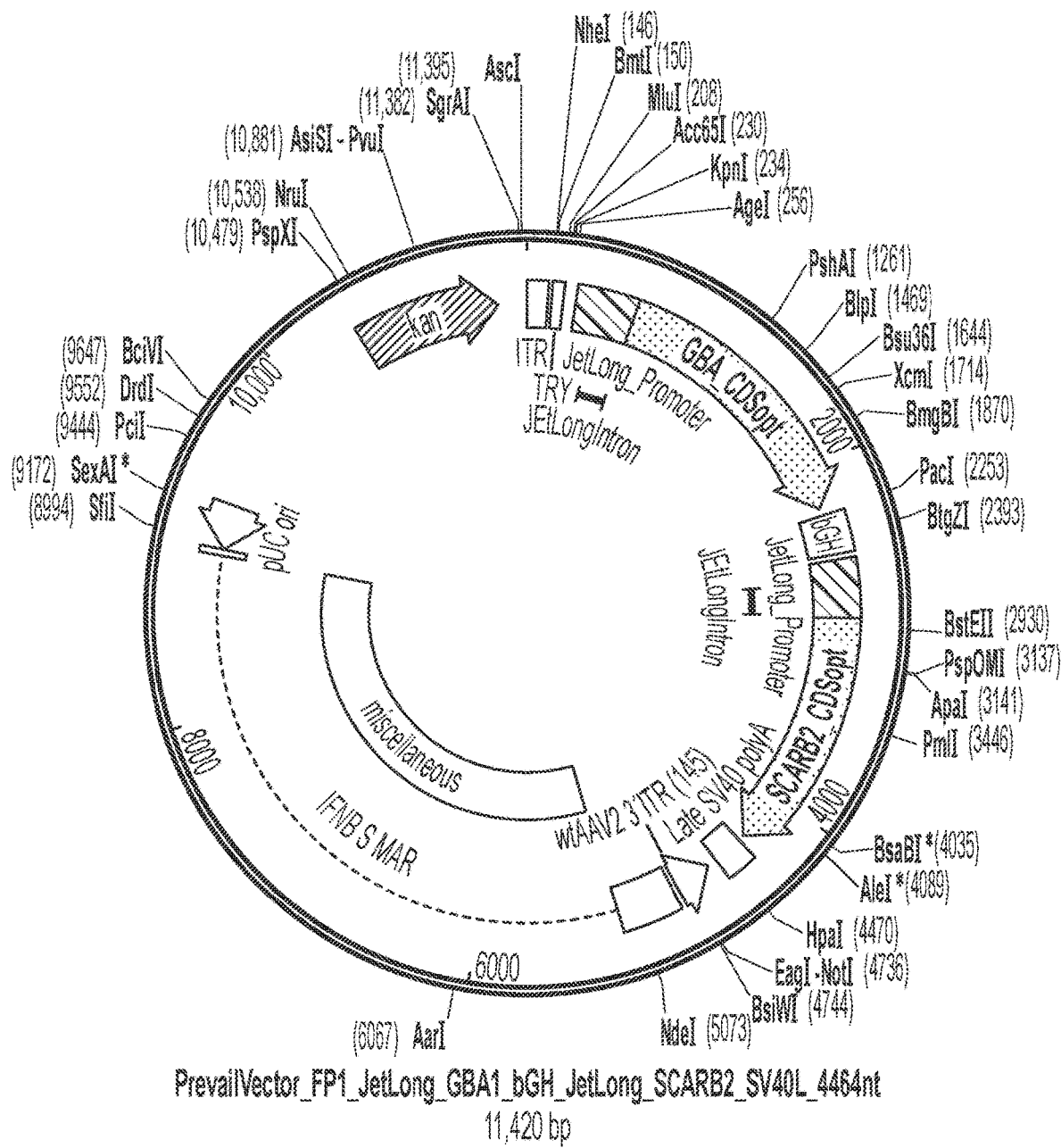
FIG. 3 is a schematic depicting one embodiment of a vector comprising an expression construct encoding Gcase (e.g., GBA1 or a portion thereof) and LIMP2 (SCARB2) or a portion thereof. Expression of the coding sequences of Gcase and LIMP2 are each driven by a separate promoter.
Figure 4:
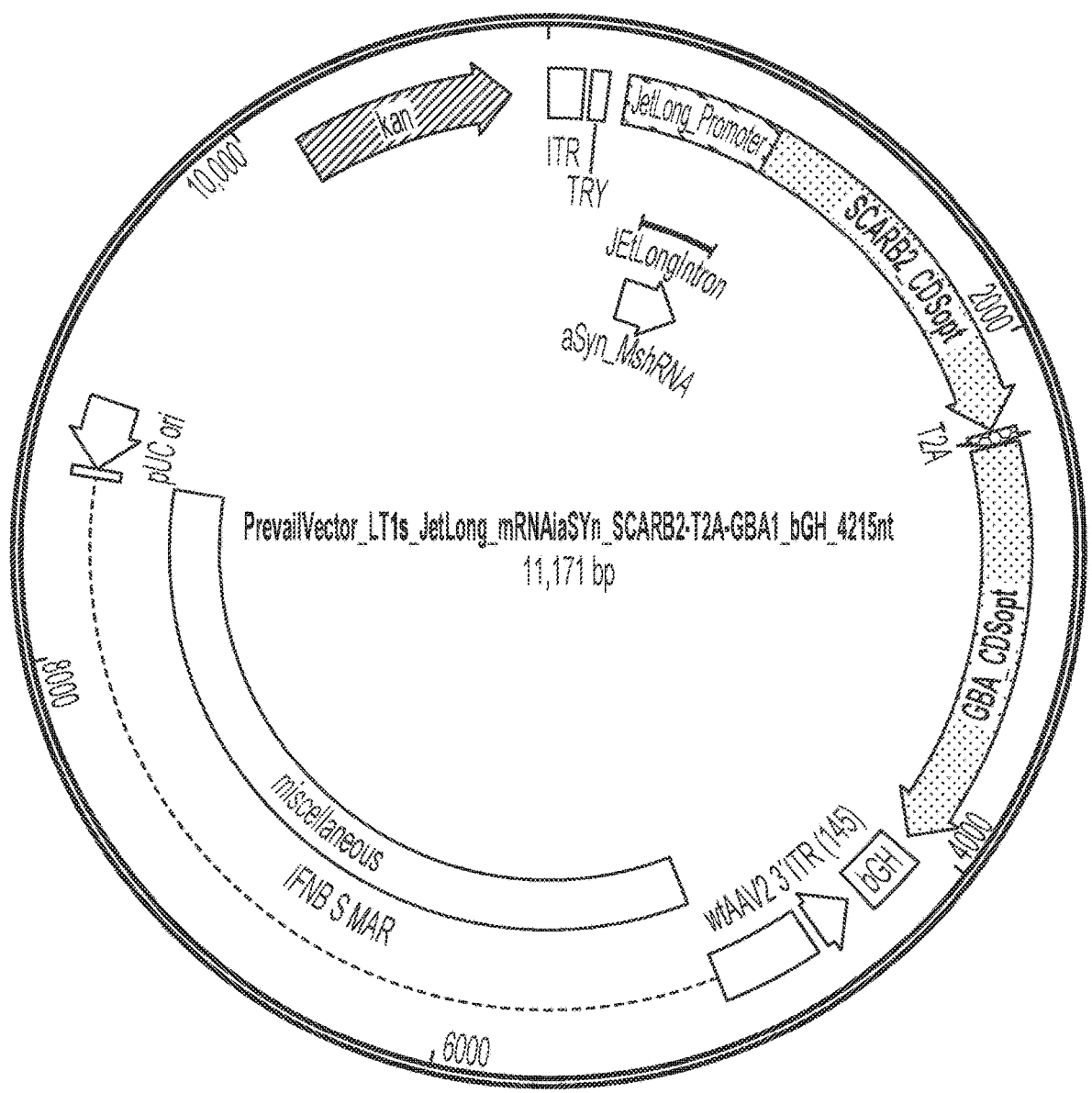
FIG. 4 is a schematic depicting one embodiment of a vector comprising an expression construct encoding Gcase (e.g., GBA1 or a portion thereof), LIMP2 (SCARB2) or a portion thereof, and an interfering RNA for α-Syn.
Figure 5:
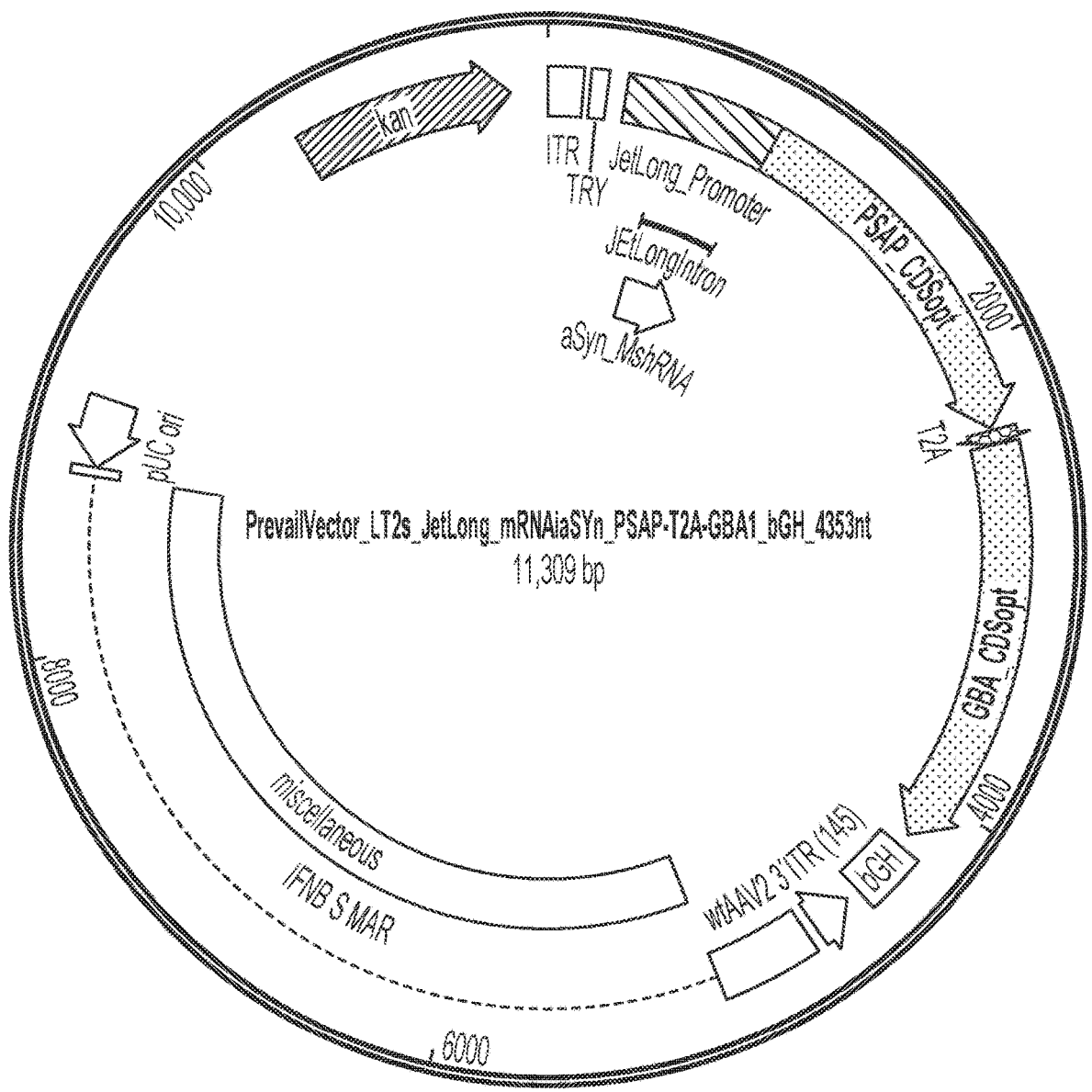
FIG. 5 is a schematic depicting one embodiment of a vector comprising an expression construct encoding Gcase (e.g., GBA1 or a portion thereof), Prosaposin (e.g., PSAP or a portion thereof), and an interfering RNA for α-Syn.
Figure 6:
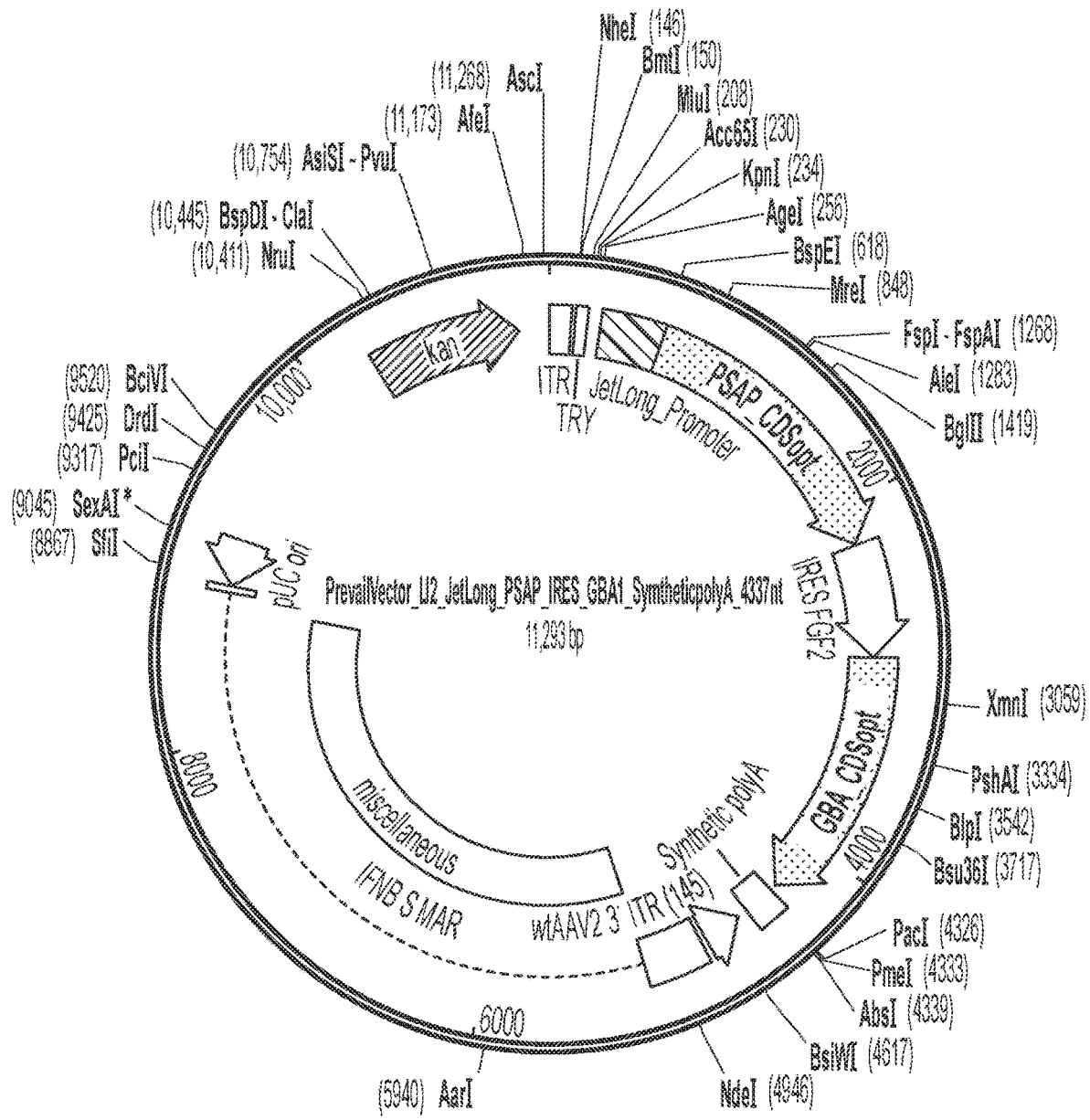
FIG. 6 is a schematic depicting one embodiment of a vector comprising an expression construct encoding Gcase (e.g., GBA1 or a portion thereof) and Prosaposin (e.g., PSAP or a portion thereof). The coding sequences of Gcase and Prosaposin are separated by an internal ribosomal entry site (IRES).

The disclosure is based, in part, on compositions and methods for expression of combinations of PD-associated gene products in a subject. A gene product can be a protein, a fragment (e.g., portion) of a protein, an interfering nucleic acid that inhibits a PD-associated gene, etc. In some embodiments, a gene product is a protein or a protein fragment encoded by a PD-associated gene. In some embodiments, a gene product is an interfering nucleic acid (e.g., shRNA, siRNA, miRNA, amiRNA, etc.) that inhibits a PD-associated gene.

A PD-associated gene refers to a gene encoding a gene product that is genetically, biochemically or functionally associated with PD. For example, individuals having mutations in the GBA1 gene (which encodes the protein Gcase), have been observed to be have an increased risk of developing PD compared to individuals that do not have a mutation in GBA1. In another example, PD is associated with accumulation of protein aggregates comprising α-Synuclein (t-Syn) protein; accordingly, SCNA (which encodes α-Syn) is a PD-associated gene. In some embodiments, an expression cassette described herein encodes a wild-type or non-mutant form of a PD-associated gene (or coding sequence thereof). Examples of PD-associated genes are listed in Table 1.

TABLE 1

Examples of PD-associated genes

| Name | Gene | Function | NCBI Accession No. |
| --- | --- | --- | --- |
| Lysosome membrane protein 2 | SCARB2/ LIMP2 | lysosomal receptor for glucosylceramidase (GBA targeting) | NP_005497.1 (Isoform 1), NP_001191184.1 (Isoform 2) |
| Prosaposin | PSAP | precursor for saposins A, B, C, and D, which localize to the lysosomal compartment and facilitate the catabolism of glycosphingolipids with short oligosaccharide groups | AAH01503.1, AAH07612.1, AAH04275.1, AAA60303.1 |
| beta-Glucocerebrosidase | GBA1 | cleaves the beta-glucosidic linkage of glucocerebroside | NP_001005742.1 (Isoform 1), NP_001165282.1 (Isoform 2), NP_001165283.1 (Isoform 3) |
| Non-lysosomal Glucosylceramidase | GBA2 | catalyzes the conversion of glucosylceramide to free glucose and ceramide | NP_065995.1 (Isoform 1), NP_001317589.1 (Isoform 2) |
| Galactosylceramidase | GALC | removes galactose from ceramide derivatives | EAW81359.1 (Isoform CRA_a), EAW81360.1 (Isoform CRA_b), EAW81362.1 (Isoform CRA_c) |

TABLE 1-continued

Examples of PD-associated genes

| Name | Gene | Function | NCBI Accession No. |
|---|---|---|---|
| Sphingomyelin phosphodiesterase 1 | SMPD1 | converts sphingomyelin to ceramide | EAW68726.1 (Isoform CRA_a), EAW68727.1 (Isoform CRA_b), EAW68728.1 (Isoform CRA_c), EAW68729.1 (Isoform CRA_d) |
| Cathepsin B | CTSB | thiol protease believed to participate in intracellular degradation and turnover of proteins; also implicated in tumor invasion and metastasis | AAC37547.1, AAH95408.1, AAH10240.1 |
| RAB7, member RAS oncogene family-like 1 | RAB7L1 | regulates vesicular transport | AAH02585.1 |
| Vacuolar protein sorting-associated protein 35 | VPS35 | component of retromer cargo-selective complex | NP_060676.2 |
| GTP cyclohydrolase 1 | GCH1 | responsible for hydrolysis of guanosine triphosphate to form 7.8-dihydroneopterin triphosphate | AAH25415.1 |
| Interleukin 34 | IL34 | increases growth or survival of monocytes; elicits activity by binding the Colony stimulating factor 1 receptor | AAH29804.1 |
| Triggering receptor expressed on myeloid cells 2 | TREM2 | forms a receptor signaling complex with the TYRO protein tyrosine kinase binding protein; functions in immune response and may be involved in chronic inflammation | AAF69824.1 |
| Progranulin | PGRN | plays a role in development, inflammation, cell proliferation and protein homeostasis | NP_002087.1 |

Isolated Nucleic Acids and Vectors

An isolated nucleic acid may be DNA or RNA. The disclosure provides, in some aspects, an isolated nucleic acids (e.g., rAAV vectors) comprising an expression construct encoding one or more PD-associated genes, for example a Gcase (e.g., the gene product of GBA1 gene) or a portion thereof. Gcase, also referred to as β-glucocerebrosidase or GBA, refers to a lysosomal protein that cleaves the beta-glucosidic linkage of the chemical glucocerebroside, an intermediate in glycolipid metabolism. In humans, Gcase is encoded by the GBA1 gene, located on chromosome 1. In some embodiments, GBA1 encodes a peptide that is represented by NCBI Reference Sequence NCBI Reference Sequence NP_000148.2 (SEQ ID NO: 14). In some embodiments, an isolated nucleic acid comprises a Gcase-encoding sequence that has been codon optimized (e.g., codon optimized for expression in mammalian cells, for example human cells), such as the sequence set forth in SEQ ID NO: 15.

In some aspects, the disclosure provides an isolated nucleic acid comprising an expression construct encoding Prosaposin (e.g., the gene product of PSAP gene). Prosaposin is a precursor glycoprotein for sphingolipid activator proteins (saposins) A, B, C, and D, which facilitate the catabolism of glycosphingolipids with short oligosaccharide groups. In humans, the PSAP gene is located on chromosome 10. In some embodiments, PSAP encodes a peptide that is represented by NCBI Reference Sequence NP_002769.1 (e.g., SEQ ID NO: 16). In some embodiments, an isolated nucleic acid comprises a prosaposin-encoding sequence that has been codon optimized (e.g., codon optimized for expression in mammalian cells, for example human cells), such as the sequence set forth in SEQ ID NO: 17.

Aspects of the disclosure relate to an isolated nucleic acid comprising an expression construct encoding LIMP2/SCARB2 (e.g., the gene product of SCARB2 gene). SCARB2 refers to a membrane protein that regulates lysosomal and endosomal transport within a cell. In humans, SCARB2 gene is located on chromosome 4. In some embodiments, the SCARB2 gene encodes a peptide that is represented by NCBI Reference Sequence NP_005497.1 (SEQ ID NO: 18). In some embodiments, an isolated nucleic acid comprises the sequence set forth in SEQ ID NO: 19. In some embodiments the isolated nucleic acid comprises a SCARB2-encoding sequence that has been codon optimized.

Aspects of the disclosure relate to an isolated nucleic acid comprising an expression construct encoding GBA2 protein (e.g., the gene product of GBA2 gene). GBA2 protein refers to non-lysosomal glucosylceramidase. In humans, GBA2 gene is located on chromosome 9. In some embodiments, the GBA2 gene encodes a peptide that is represented by NCBI Reference Sequence NP_065995.1 (SEQ ID NO: 30). In some embodiments, an isolated nucleic acid comprises the sequence set forth in SEQ ID NO: 31. In some embodiments the isolated nucleic acid comprises a GBA2-encoding sequence that has been codon optimized.

Aspects of the disclosure relate to an isolated nucleic acid comprising an expression construct encoding GALC protein (e.g., the gene product of GALC gene). GALC protein refers to galactosylceramidase (or galactocerebrosidase), which is an enzyme that hydrolyzes galactose ester bonds of galactocerebroside, galactosylsphingosine, lactosylceramide, and monogalactosyldiglyceride. In humans, GALC gene is located on chromosome 14. In some embodiments, the GALC gene encodes a peptide that is represented by NCBI Reference Sequence NP_000144.2 (SEQ ID NO: 33). In some embodiments, an isolated nucleic acid comprises the sequence set forth in SEQ ID NO: 34. In some embodiments the isolated nucleic acid comprises a GALC-encoding sequence that has been codon optimized.

Aspects of the disclosure relate to an isolated nucleic acid comprising an expression construct encoding CTSB protein (e.g., the gene product of CTSB gene). CTSB protein refers to cathepsin B, which is a lysosomal cysteine protease that plays an important role in intracellular proteolysis. In humans, CTSB gene is located on chromosome 8. In some embodiments, the CTSB gene encodes a peptide that is represented by NCBI Reference Sequence NP_001899.1 (SEQ ID NO: 35). In some embodiments, an isolated nucleic acid comprises the sequence set forth in SEQ ID NO: 36. In some embodiments the isolated nucleic acid comprises a CTSB-encoding sequence that has been codon optimized.

Aspects of the disclosure relate to an isolated nucleic acid comprising an expression construct encoding SMPD1 protein (e.g., the gene product of SMPD1 gene). SMPD1 protein refers to sphingomyelin phosphodiesterase 1, which is a hydrolase enzyme that is involved in sphingolipid metabolism. In humans, SMPD1 gene is located on chromosome 11. In some embodiments, the SMPD1 gene encodes a peptide that is represented by NCBI Reference Sequence NP_000534.3 (SEQ ID NO: 37). In some embodiments, an isolated nucleic acid comprises the sequence set forth in SEQ ID NO: 38. In some embodiments the isolated nucleic acid comprises a SMPD1-encoding sequence that has been codon optimized.

Aspects of the disclosure relate to an isolated nucleic acid comprising an expression construct encoding GCH1 protein (e.g., the gene product of GCH1 gene). GCH1 protein refers to GTP cyclohydrolase I, which is a hydrolase enzyme that is part of the folate and biopterin biosynthesis pathways. In humans, GCH1 gene is located on chromosome 14. In some embodiments, the GCH1 gene encodes a peptide that is represented by NCBI Reference Sequence NP_000152.1 (SEQ ID NO: 45). In some embodiments, an isolated nucleic acid comprises the sequence set forth in SEQ ID NO: 46. In some embodiments the isolated nucleic acid comprises a GCH1-encoding sequence that has been codon optimized.

Aspects of the disclosure relate to an isolated nucleic acid comprising an expression construct encoding RAB7L protein (e.g., the gene product of RAB7L gene). RAB7L protein refers to RAB7, member RAS oncogene family-like 1, which is a GTP binding protein. In humans, RAB7L gene is located on chromosome 1. In some embodiments, the RAB7L gene encodes a peptide that is represented by NCBI Reference Sequence NP_003920.1 (SEQ ID NO: 47). In some embodiments, an isolated nucleic acid comprises the sequence set forth in SEQ ID NO: 48. In some embodiments the isolated nucleic acid comprises a RAB7L-encoding sequence that has been codon optimized.

Aspects of the disclosure relate to an isolated nucleic acid comprising an expression construct encoding VPS35 protein (e.g., the gene product of VPS35 gene). VPS35 protein refers to vacuolar protein sorting-associated protein 35, which is part of a protein complex involved in retrograde transport of proteins from endosomes to the trans-Golgi network. In humans, VPS35 gene is located on chromosome 16. In some embodiments, the VPS35 gene encodes a peptide that is represented by NCBI Reference Sequence NP_060676.2 (SEQ ID NO: 49). In some embodiments, an isolated nucleic acid comprises the sequence set forth in SEQ ID NO: 50. In some embodiments the isolated nucleic acid comprises a VPS35-encoding sequence that has been codon optimized.

Aspects of the disclosure relate to an isolated nucleic acid comprising an expression construct encoding IL-34 protein (e.g., the gene product of IL34 gene). IL-34 protein refers to interleukin 34, which is a cytokine that increases growth and survival of monocytes. In humans, IL34 gene is located on chromosome 16. In some embodiments, the IL34 gene encodes a peptide that is represented by NCBI Reference Sequence NP_689669.2 (SEQ ID NO: 55). In some embodiments, an isolated nucleic acid comprises the sequence set forth in SEQ ID NO: 56. In some embodiments the isolated nucleic acid comprises a IL-34-encoding sequence that has been codon optimized.

Aspects of the disclosure relate to an isolated nucleic acid comprising an expression construct encoding TREM2 protein (e.g., the gene product of TREM2 gene). TREM2 protein refers to triggering receptor expressed on myeloid cells 2, which is an immunoglobulin superfamily receptor found on myeloid cells. In humans, TREM2 gene is located on chromosome 6. In some embodiments, the TREM2 gene encodes a peptide that is represented by NCBI Reference Sequence NP_061838.1 (SEQ ID NO: 57). In some embodiments, the isolated nucleic acid comprises the sequence set forth in SEQ ID NO: 58. In some embodiments an isolated nucleic acid comprises a TREM2-encoding sequence that has been codon optimized.

Aspects of the disclosure relate to an isolated nucleic acid comprising an expression construct encoding TMEM106B protein (e.g., the gene product of TMEM106B gene). TMEM106B protein refers to transmembrane protein 106B, which is a protein involved in dendrite morphogenesis and regulation of lysosomal trafficking. In humans, TMEM106B gene is located on chromosome 7. In some embodiments, the TMEM106B gene encodes a peptide that is represented by NCBI Reference Sequence NP_060844.2 (SEQ ID NO: 62). In some embodiments, an isolated nucleic acid comprises the sequence set forth in SEQ ID NO: 63. In some embodiments the isolated nucleic acid comprises a TMEM106B-encoding sequence that has been codon optimized.

Aspects of the disclosure relate to an isolated nucleic acid comprising an expression construct encoding progranulin protein (e.g., the gene product of PRGN gene). PGRN protein refers to progranulin, which is a protein involved in development, inflammation, cell proliferation and protein homeostasis. In humans, PGRN gene is located on chromosome 17. In some embodiments, the PGRN gene encodes a peptide that is represented by NCBI Reference Sequence NP_002078.1 (SEQ ID NO: 66). In some embodiments, an isolated nucleic acid comprises the sequence set forth in SEQ ID NO: 67. In some embodiments the isolated nucleic acid comprises a PGRN-encoding sequence that has been codon optimized.

In some aspects, the disclosure provides an isolated nucleic acid comprising an expression construct encoding a first gene product and a second gene product, wherein each gene product independently is selected from the gene products, or portions thereof, set forth in Table 1.

In some embodiments, a gene product is encoded by a coding portion (e.g., a cDNA) of a naturally occurring gene. In some embodiments, a first gene product is a protein (or a fragment thereof) encoded by the GBA1 gene. In some embodiments, a gene product is a protein (or a fragment thereof) encoded by another gene listed in Table 1, for example the SCARB2/LIMP2 gene or the PSAP gene. However, the skilled artisan recognizes that the order of expression of a first gene product (e.g., Gcase) and a second gene product (e.g., LIMP2, etc.) can generally be reversed (e.g., LIMP2 is the first gene product and Gcase is the second gene product). In some embodiments, a gene product is a fragment (e.g., portion) of a gene listed in Table 1. A protein fragment may comprise about 50%, about 60%, about 70%, about 80% about 90% or about 99% of a protein encoded by the genes listed in Table 1. In some embodiments, a protein fragment comprises between 50% and 99.9% (e.g., any value between 50% and 99.9%) of a protein encoded by a gene listed in Table 1.

In some embodiments, an expression construct is monocistronic (e.g., the expression construct encodes a single fusion protein comprising a first gene product and a second gene product). In some embodiments, an expression construct is polycistronic (e.g., the expression construct encodes two distinct gene products, for example two different proteins or protein fragments).

A polycistronic expression vector may comprise a one or more (e.g., 1, 2, 3, 4, 5, or more) promoters. Any suitable promoter can be used, for example, a constitutive promoter, an inducible promoter, an endogenous promoter, a tissue-specific promoter (e.g., a CNS-specific promoter), etc. In some embodiments, a promoter is a chicken beta-actin promoter (CBA promoter), a CAG promoter (for example as described by Alexopoulou et al. (2008) *BMC Cell Biol.* 9:2; doi: 10.1186/1471-2121-9-2), a CD68 promoter, or a JeT promoter (for example as described by Tornøe et al. (2002) *Gene* 297(1-2):21-32). In some embodiments, a promoter is operably-linked to a nucleic acid sequence encoding a first gene product, a second gene product, or a first gene product and a second gene product. In some embodiments, an expression cassette comprises one or more additional regulatory sequences, including but not limited to transcription factor binding sequences, intron splice sites, poly(A) addition sites, enhancer sequences, repressor binding sites, or any combination of the foregoing.

In some embodiments, a nucleic acid sequence encoding a first gene product and a nucleic acid sequence encoding a second gene product are separated by a nucleic acid sequence encoding an internal ribosomal entry site (IRES). Examples of IRES sites are described, for example, by Mokrejs et al. (2006) *Nucleic Acids Res.* 34(Database issue): D125-30. In some embodiments, a nucleic acid sequence encoding a first gene product and a nucleic acid sequence encoding a second gene product are separated by a nucleic acid sequence encoding a self-cleaving peptide. Examples of self-cleaving peptides include but are not limited to T2A, P2A, E2A, F2A, BmCPV 2A, and BmIFV 2A, and those described by Liu et al. (2017) *Sci Rep.* 7: 2193. In some embodiments, the self-cleaving peptide is a T2A peptide.

Pathologically, disorders such as PD and Gaucher disease are associated with accumulation of protein aggregates composed largely of α-Synuclein (α-Syn) protein. Accordingly, in some embodiments, isolated nucleic acids described herein comprise an inhibitory nucleic acid that reduces or prevents expression of α-Syn protein. A sequence encoding an inhibitory nucleic acid may be placed in an untranslated region (e.g., intron, 5'UTR, 3'UTR, etc.) of the expression vector.

In some embodiments, an inhibitory nucleic acid is positioned in an intron of an expression construct, for example in an intron upstream of the sequence encoding a first gene product. An inhibitory nucleic acid can be a double stranded RNA (dsRNA), siRNA, micro RNA (miRNA), artificial miRNA (amiRNA), or an RNA aptamer. Generally, an inhibitory nucleic acid binds to (e.g., hybridizes with) between about 6 and about 30 (e.g., any integer between 6 and 30, inclusive) contiguous nucleotides of a target RNA (e.g., mRNA). In some embodiments, the inhibitory nucleic acid molecule is an miRNA or an amiRNA, for example an miRNA that targets SNCA (the gene encoding α-Syn protein) or TMEM106B (e.g. the gene encoding TMEM106B protein). In some embodiments, the miRNA does not comprise any mismatches with the region of SNCA mRNA to which it hybridizes (e.g., the miRNA is "perfected"). In some embodiments, the inhibitory nucleic acid is an shRNA (e.g., an shRNA targeting SNCA or TMEM106B). In some embodiments, an inhibitory nucleic acid is an artificial miRNA (amiRNA) that includes a miR-155 scaffold and a SCNA or TMEM106B targeting sequence.

An isolated nucleic acid as described herein may exist on its own, or as part of a vector. Generally, a vector can be a plasmid, cosmid, phagemid, bacterial artificial chromosome (BAC), or a viral vector (e.g., adenoviral vector, adeno-associated virus (AAV) vector, retroviral vector, baculoviral vector, etc.). In some embodiments, the vector is a plasmid (e.g., a plasmid comprising an isolated nucleic acid as described herein). In some embodiments, an rAAV vector is single-stranded (e.g., single-stranded DNA). In some embodiments, the vector is a recombinant AAV (rAAV) vector. In some embodiments, a vector is a Baculovirus vector (e.g., an *Autographa californica* nuclear polyhedrosis (AcNPV) vector).

Typically an rAAV vector (e.g., rAAV genome) comprises a transgene (e.g., an expression construct comprising one or more of each of the following: promoter, intron, enhancer sequence, protein coding sequence, inhibitory RNA coding sequence, polyA tail sequence, etc.) flanked by two AAV inverted terminal repeat (ITR) sequences. In some embodiments the transgene of an rAAV vector comprises an isolated nucleic acid as described by the disclosure. In some embodiments, each of the two ITR sequences of an rAAV vector is a full-length ITR (e.g., approximately 145 bp in length, and containing functional Rep binding site (RBS) and terminal resolution site (trs)). In some embodiments, one of the ITRs of an rAAV vector is truncated (e.g., shortened or not full-length). In some embodiments, a truncated ITR lacks a functional terminal resolution site (trs) and is used for production of self-complementary AAV vectors (scAAV vectors). In some embodiments, a truncated ITR is a ΔITR, for example as described by McCarty et al. (2003) *Gene Ther.* 10(26):2112-8.

Figure 20:
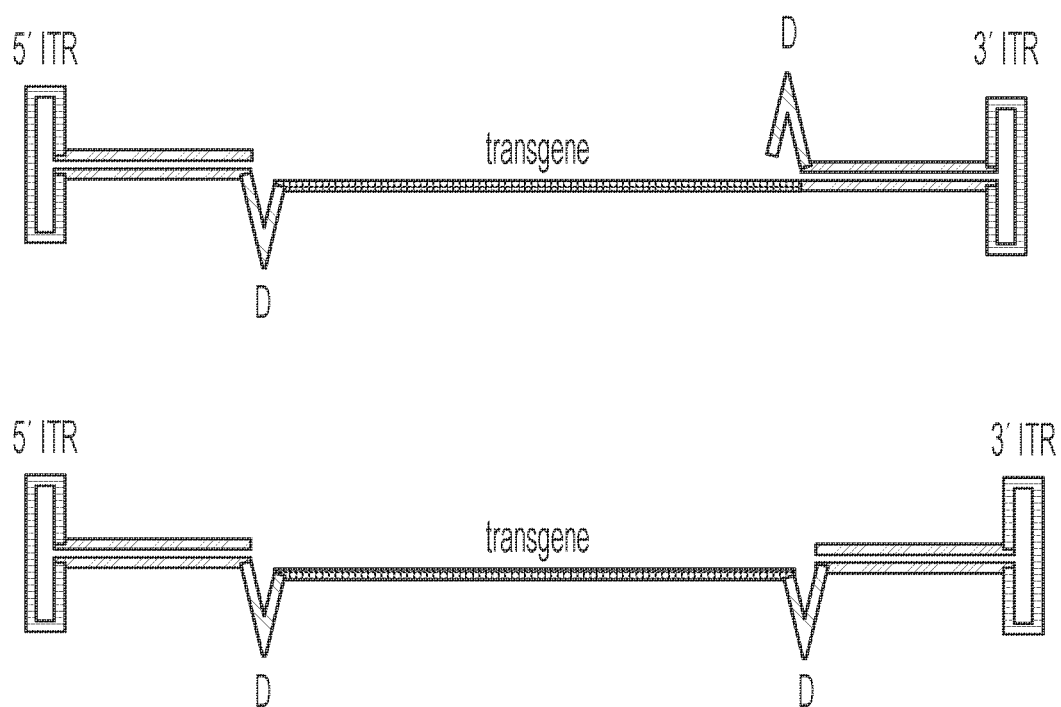
FIG. 20 is a schematic depicting an rAAV vectors comprising a "D" region located on the "outside" of the ITR (e.g., proximal to the terminus of the ITR relative to the transgene insert or expression construct) (top) and a wild-type rAAV vectors having ITRs on the "inside" of the vector (e.g., proximal to the transgene insert of the vector).
Figure 21:
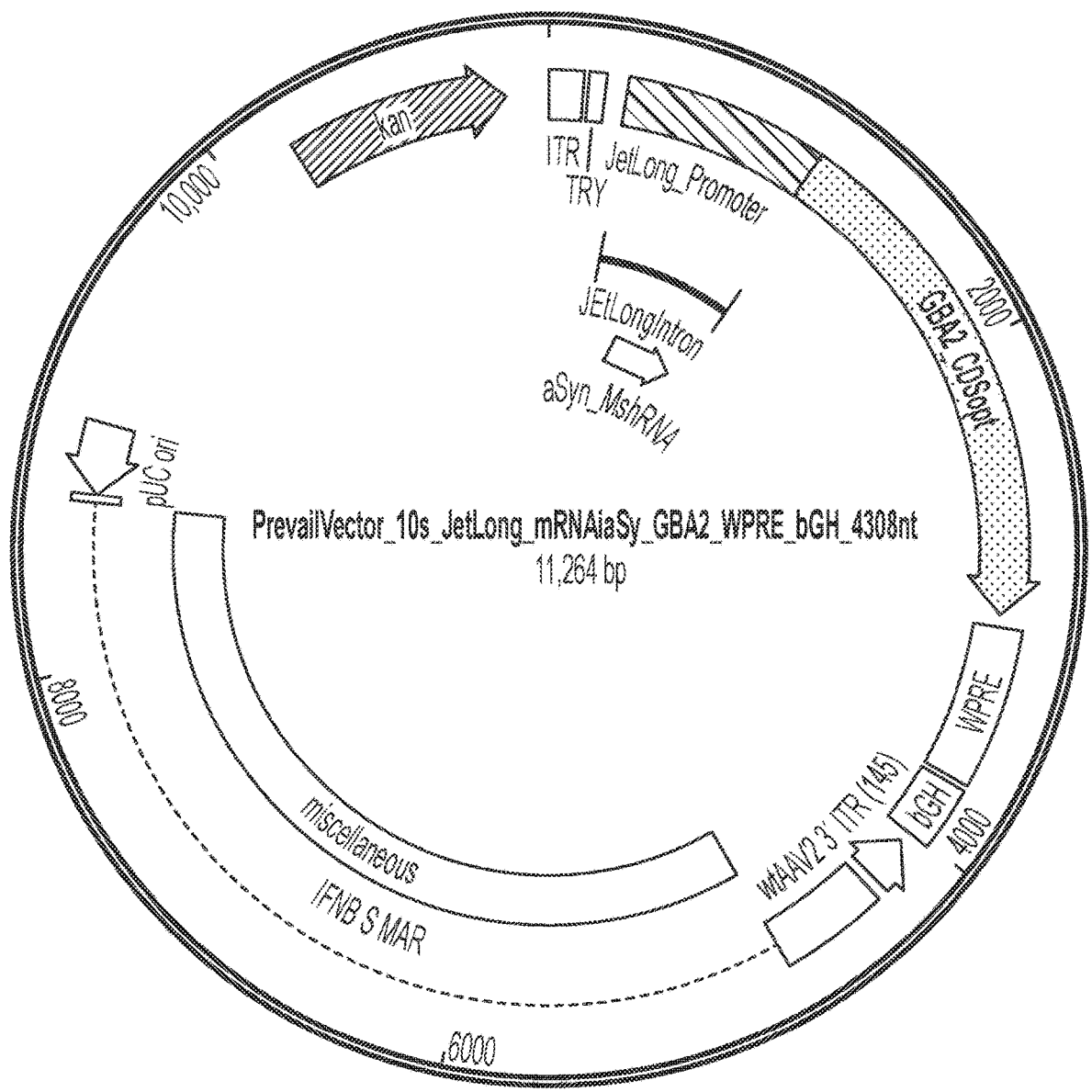
FIG. 21 a schematic depicting one embodiment of a vector comprising an expression construct encoding GBA2 or a portion thereof, and an interfering RNA for α-Syn.
Figure 22:
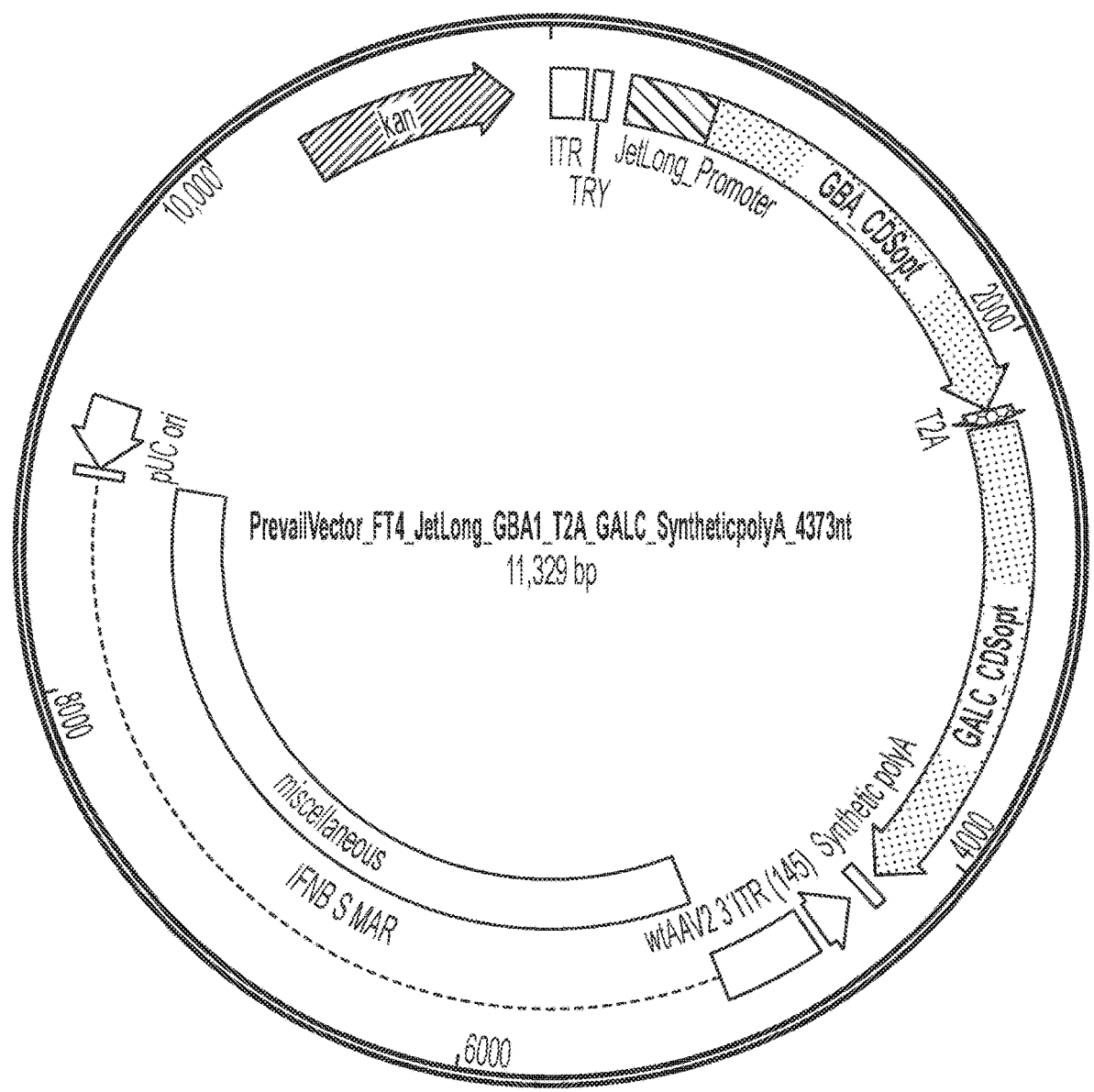
FIG. 22 is a schematic depicting one embodiment of a vector comprising an expression construct encoding Gcase (e.g., GBA1 or a portion thereof) and Galactosylceramidase (e.g., GALC or a portion thereof). Expression of the coding sequences of Gcase and Galactosylceramidase are separated by a T2A self-cleaving peptide sequence.
Figure 23:
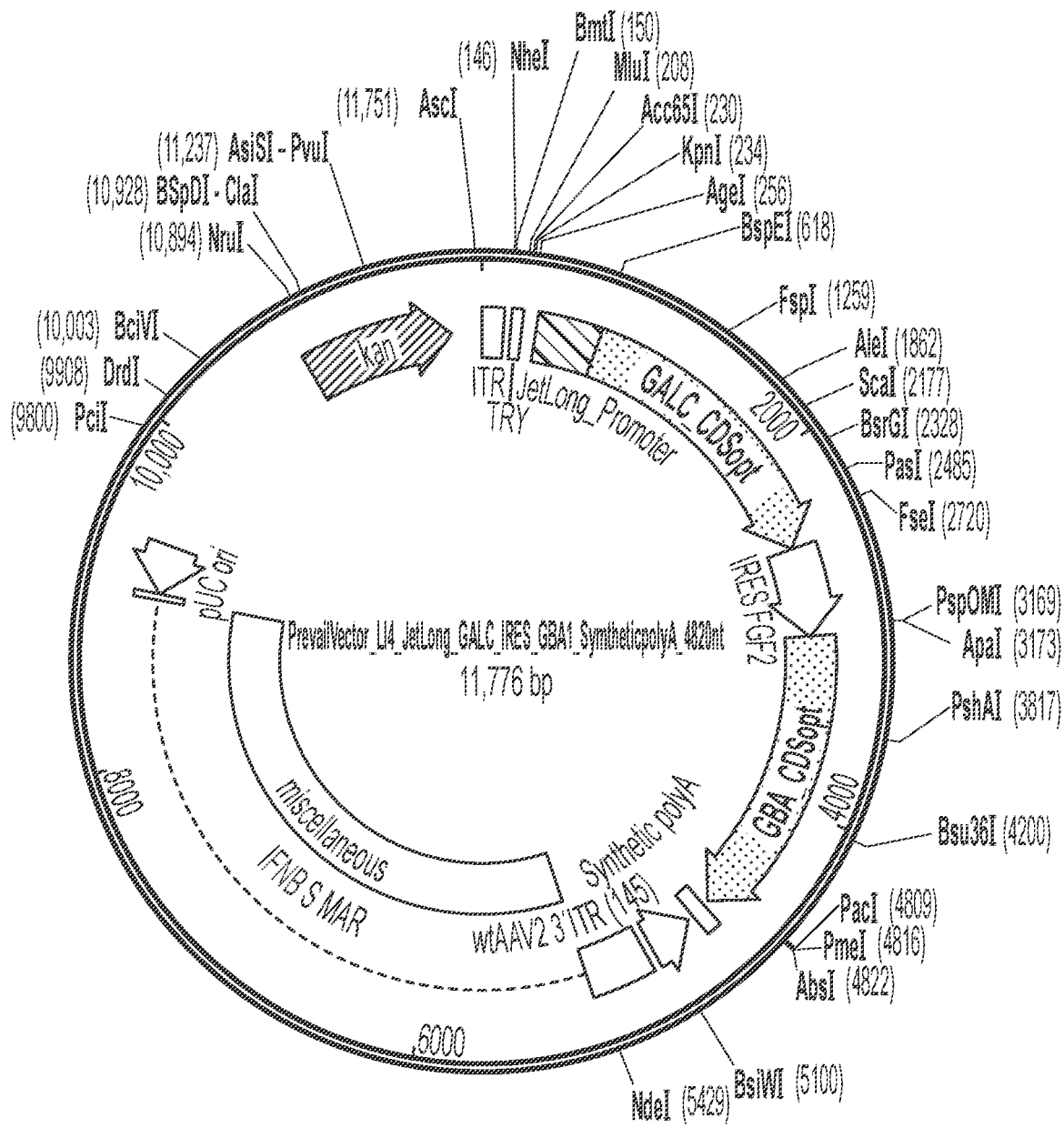
FIG. 23 is a schematic depicting one embodiment of a vector comprising an expression construct encoding Gcase (e.g., GBA1 or a portion thereof) and Galactosylceramidase (e.g., GALC or a portion thereof). Expression of the coding sequences of Gcase and Galactosylceramidase are separated by a T2A self-cleaving peptide sequence.
Figure 24:
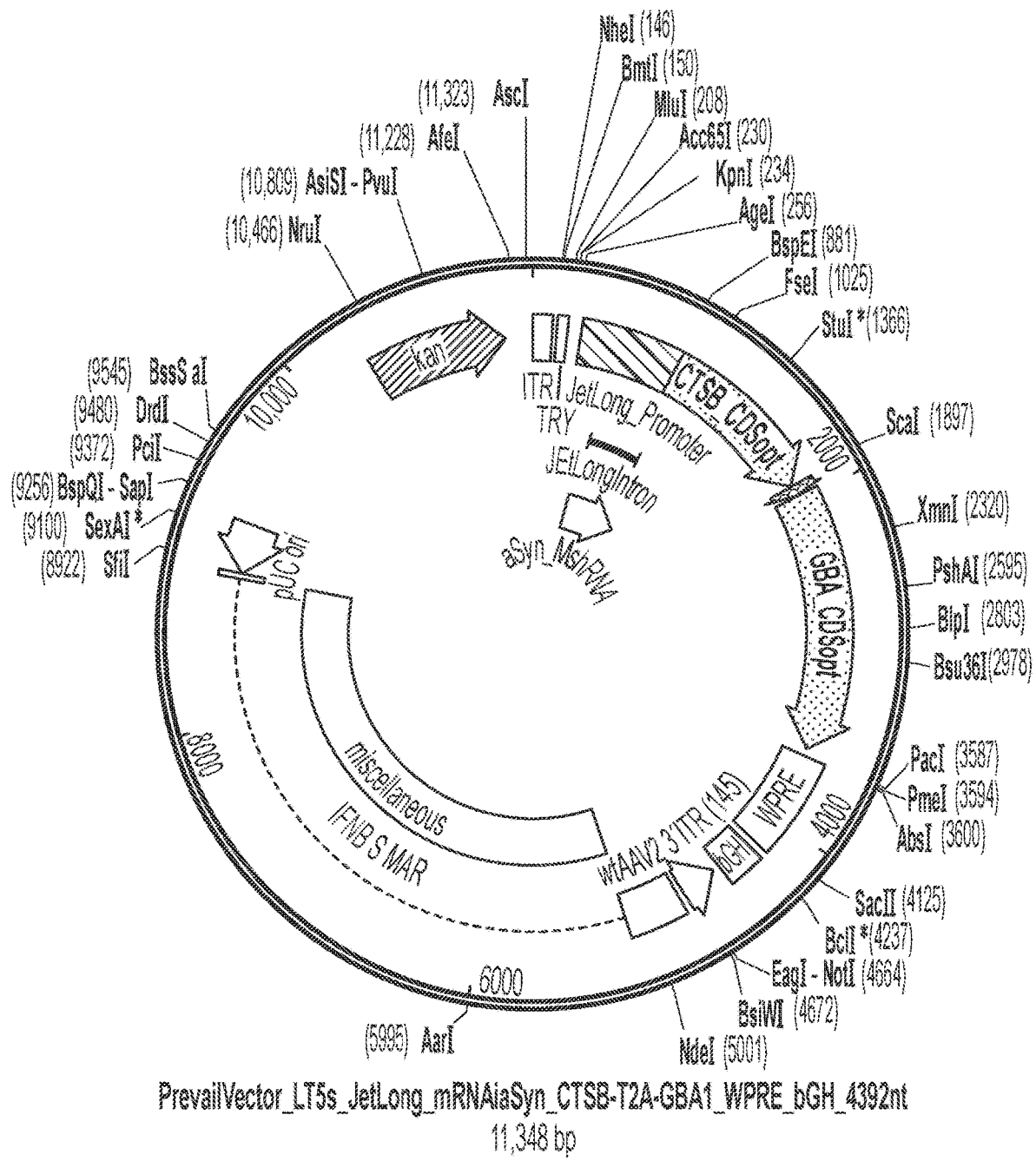
FIG. 24 is a schematic depicting one embodiment of a vector comprising an expression construct encoding Gcase (e.g., GBA1 or a portion thereof), Cathepsin B (e.g., CTSB or a portion thereof), and an interfering RNA for α-Syn. Expression of the coding sequences of Gcase and Cathepsin B are separated by a T2A self-cleaving peptide sequence.
Figure 25:
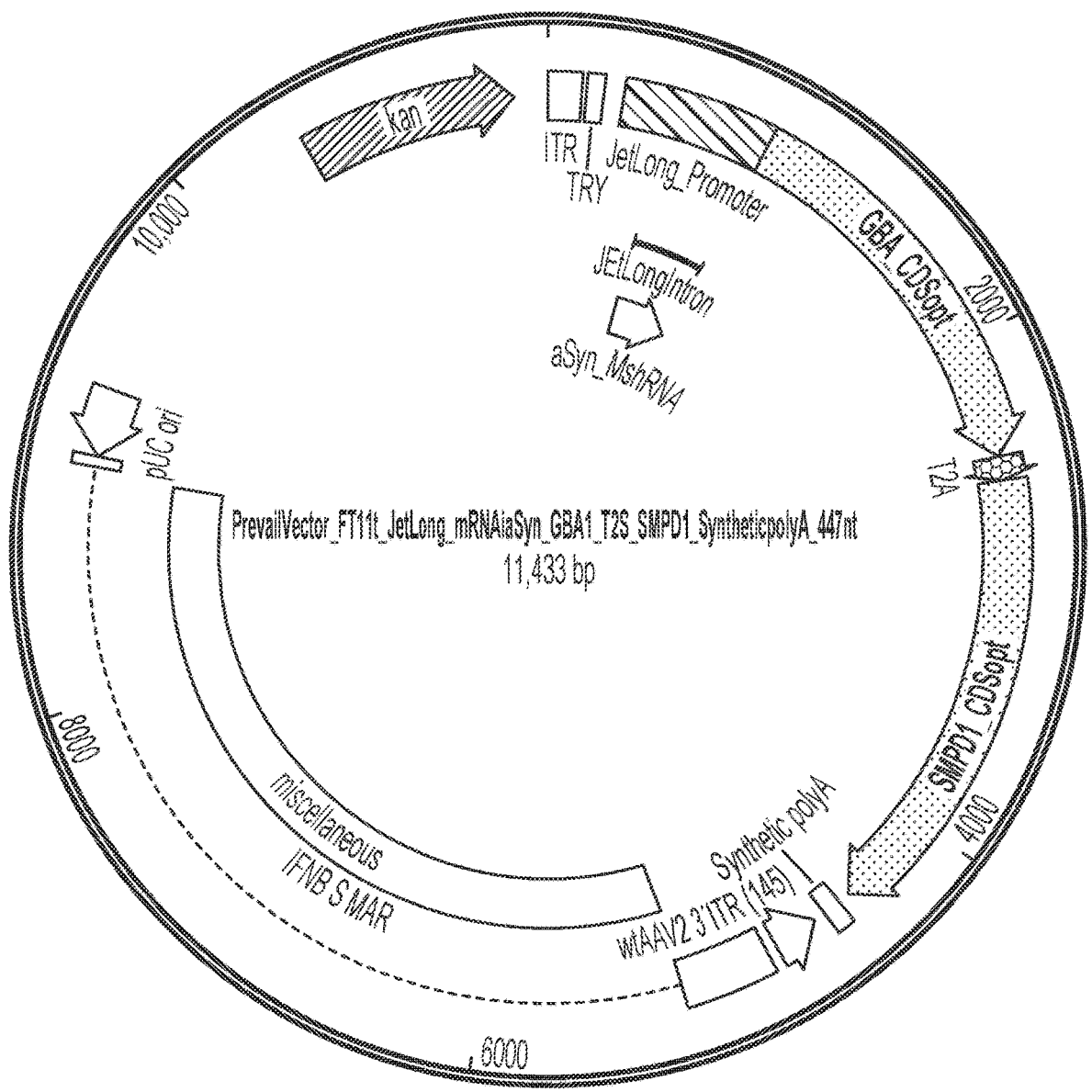
FIG. 25 is a schematic depicting one embodiment of a vector comprising an expression construct encoding Gcase (e.g., GBA1 or a portion thereof), Sphingomyelin phosphodiesterase 1 (e.g., SMPD1 a portion thereof, and an interfering RNA for α-Syn.
Figure 26:
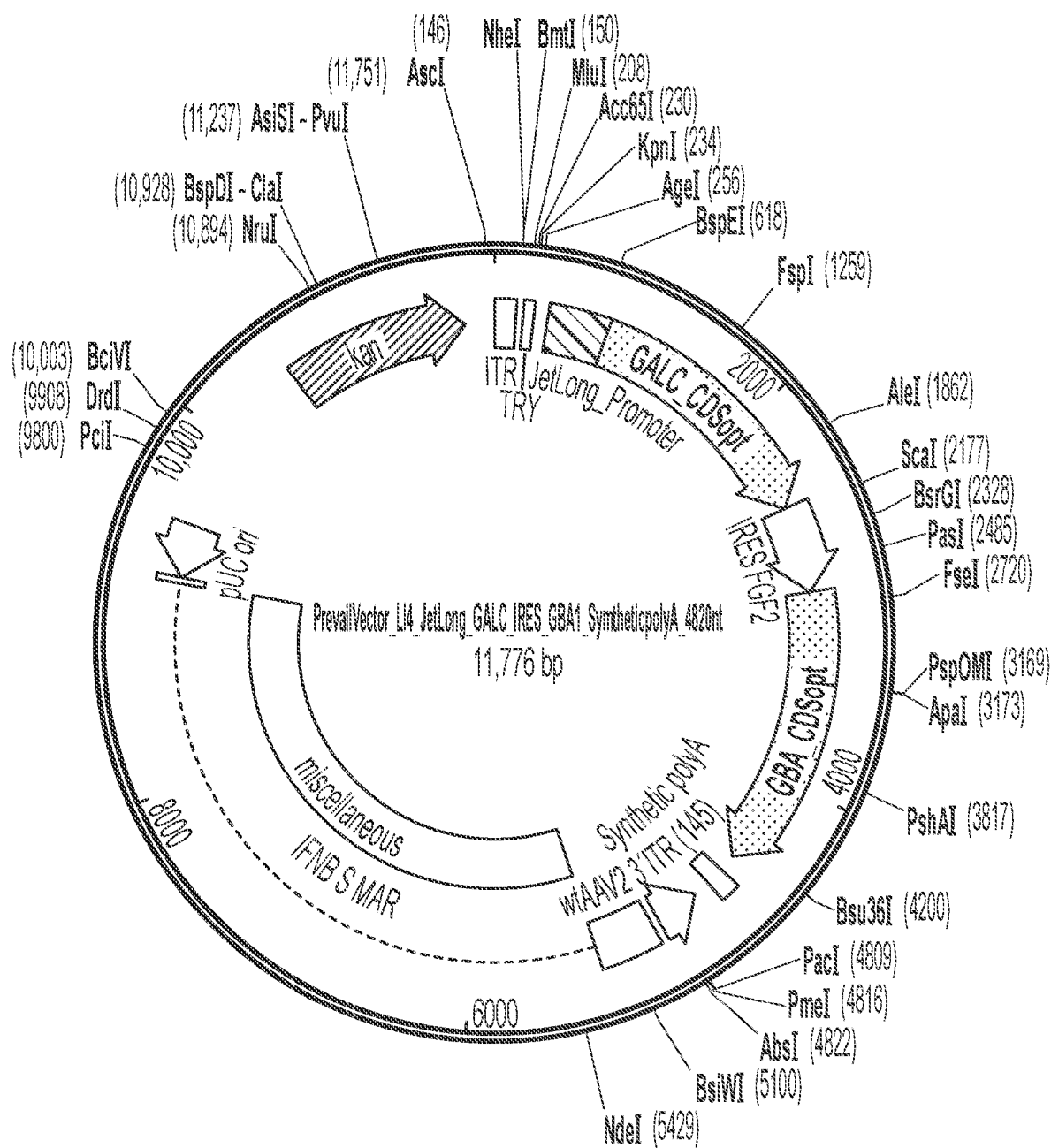
FIG. 26 is a schematic depicting one embodiment of a vector comprising an expression construct encoding Gcase (e.g., GBA1 or a portion thereof) and Galactosylceramidase (e.g., GALC or a portion thereof). The coding sequences of Gcase and Galactosylceramidase are separated by an internal ribosomal entry site (IRES).
Figure 27:
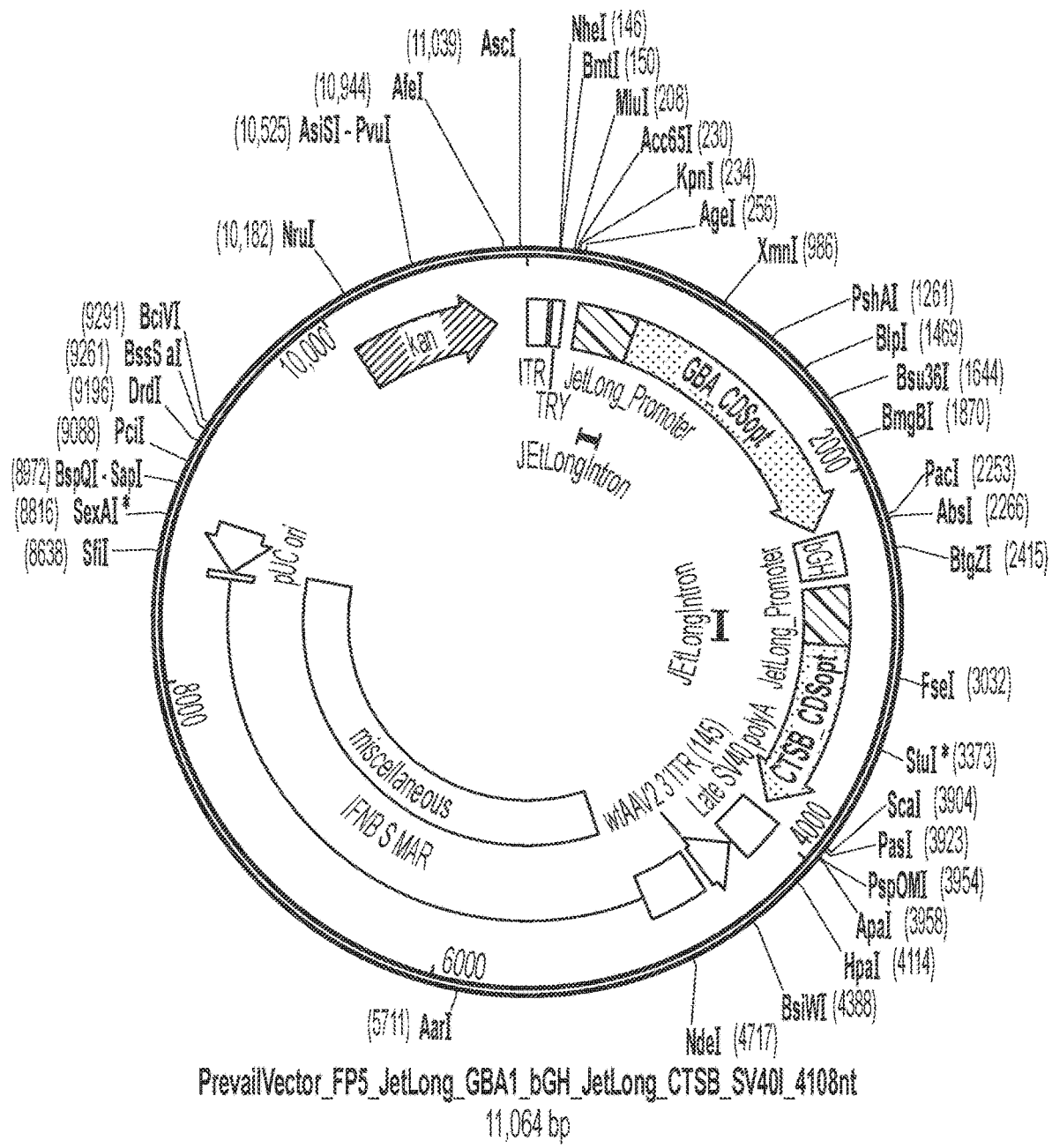
FIG. 27 is a schematic depicting one embodiment of a vector comprising an expression construct encoding Gcase (e.g., GBA1 or a portion thereof) and Cathepsin B (e.g., CTSB or a portion thereof). Expression of the coding sequences of Gcase and Cathepsin B are each driven by a separate promoter.
Figure 28:
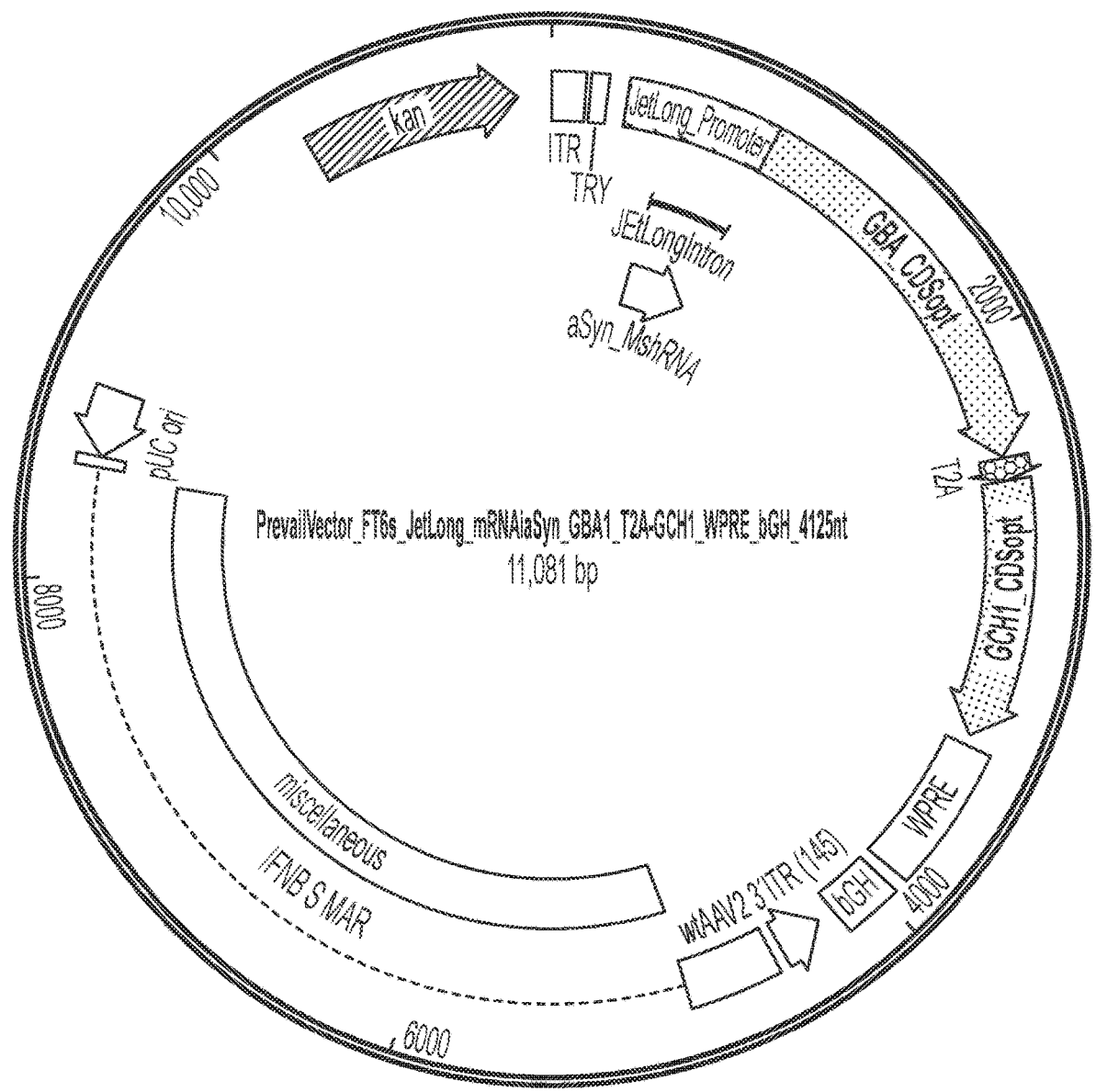
FIG. 28 is a schematic depicting one embodiment of a vector comprising an expression construct encoding Gcase (e.g., GBA1 or a portion thereof), GCH1 (e.g., GCH1 or a portion thereof), and an interfering RNA for α-Syn. The coding sequences of Gcase and GCH1 are separated by an T2A self-cleaving peptide sequence
Figure 29:
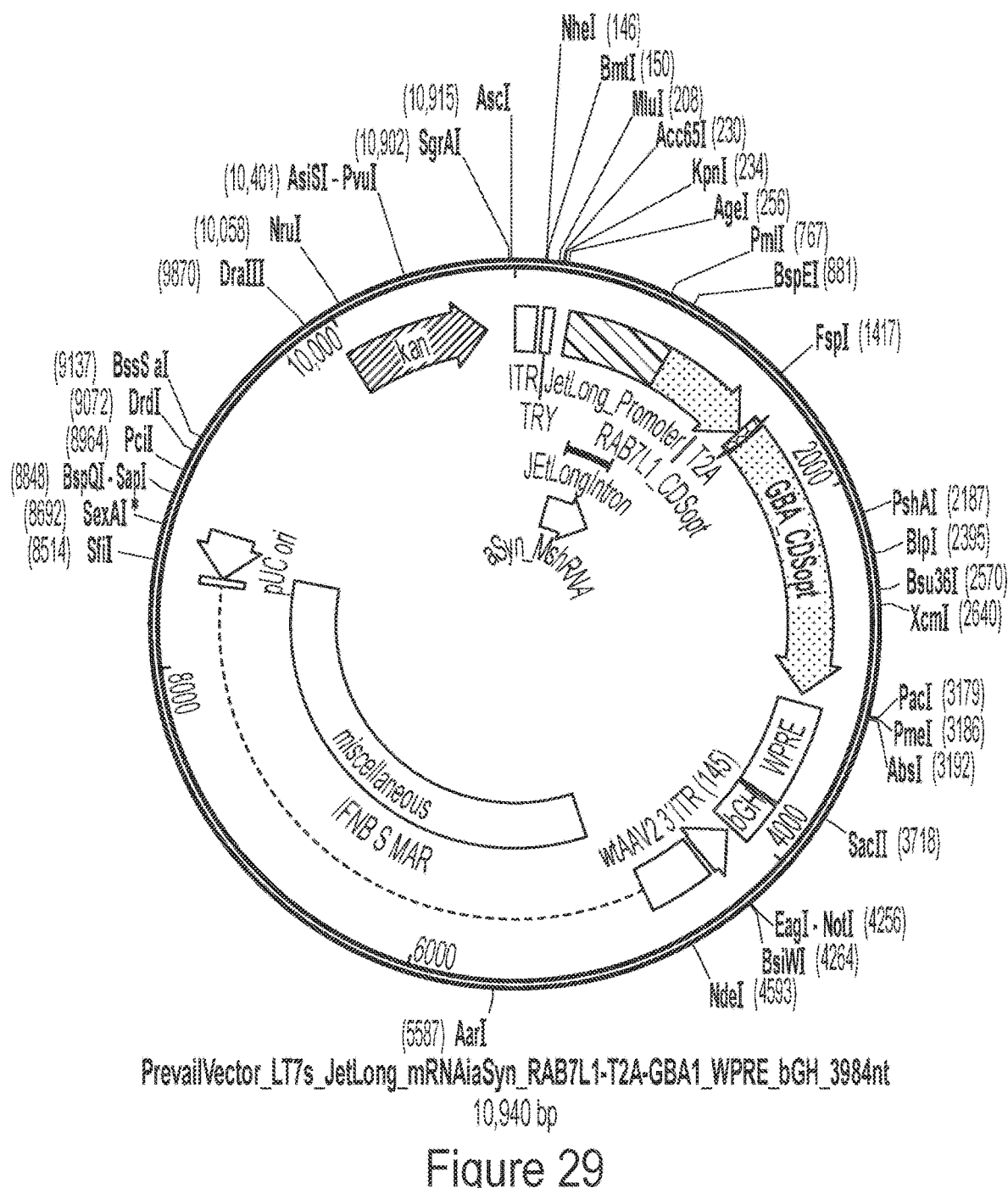
FIG. 29 is a schematic depicting one embodiment of a vector comprising an expression construct encoding Gcase (e.g., GBA1 or a portion thereof), RAB7L1 (e.g., RAB7L1 or a portion thereof), and an interfering RNA for α-Syn. The coding sequences of Gcase and RAB7L1 are separated by an T2A self-cleaving peptide sequence.
Figure 30:
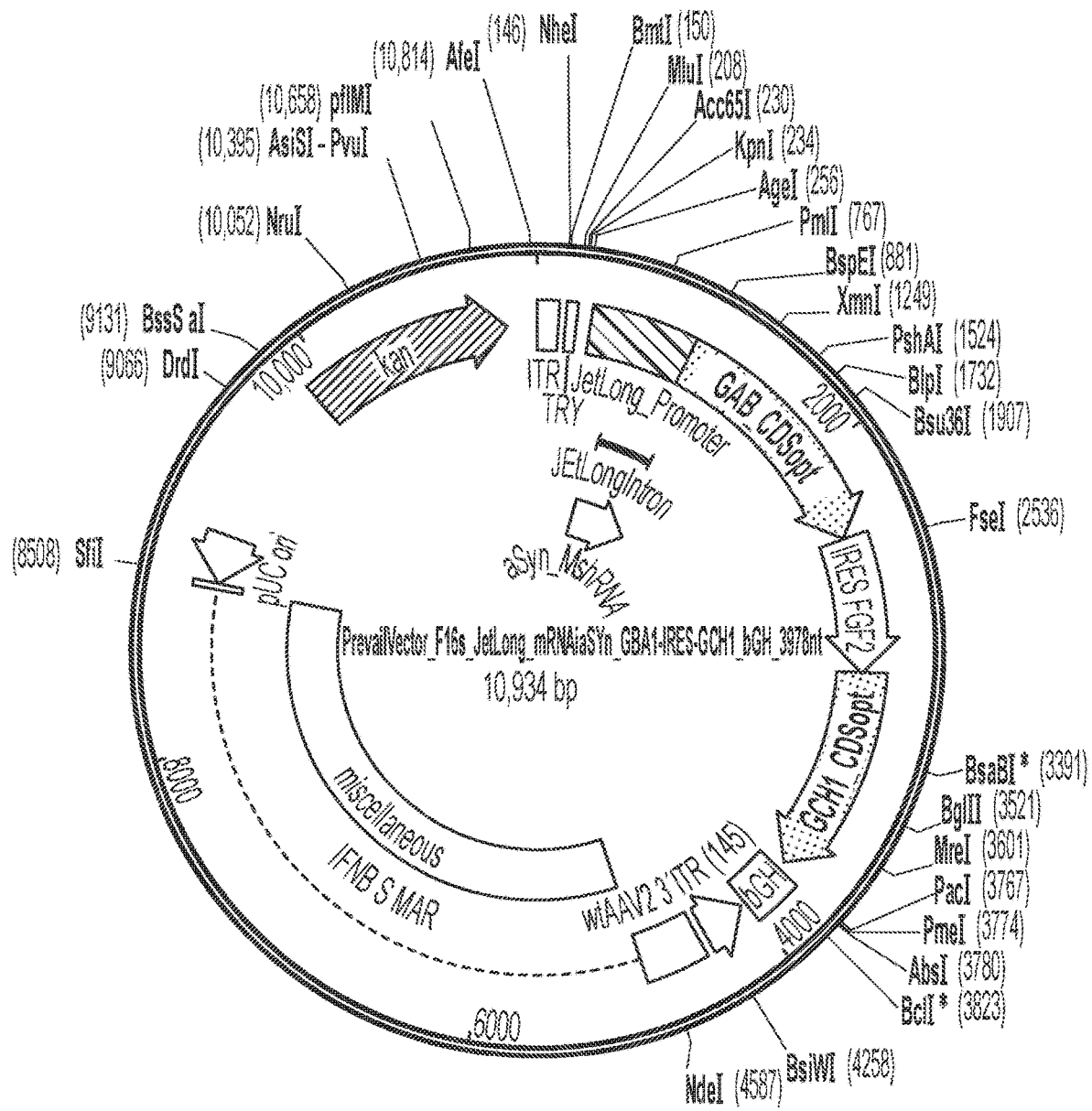
FIG. 30 is a schematic depicting one embodiment of a vector comprising an expression construct encoding Gcase (e.g., GBA1 or a portion thereof), GCH1 (e.g., GCH1 or a portion thereof), and an interfering RNA for α-Syn. Expression of the coding sequences of Gcase and GCH1 are an internal ribosomal entry site (IRES).
Figure 31:
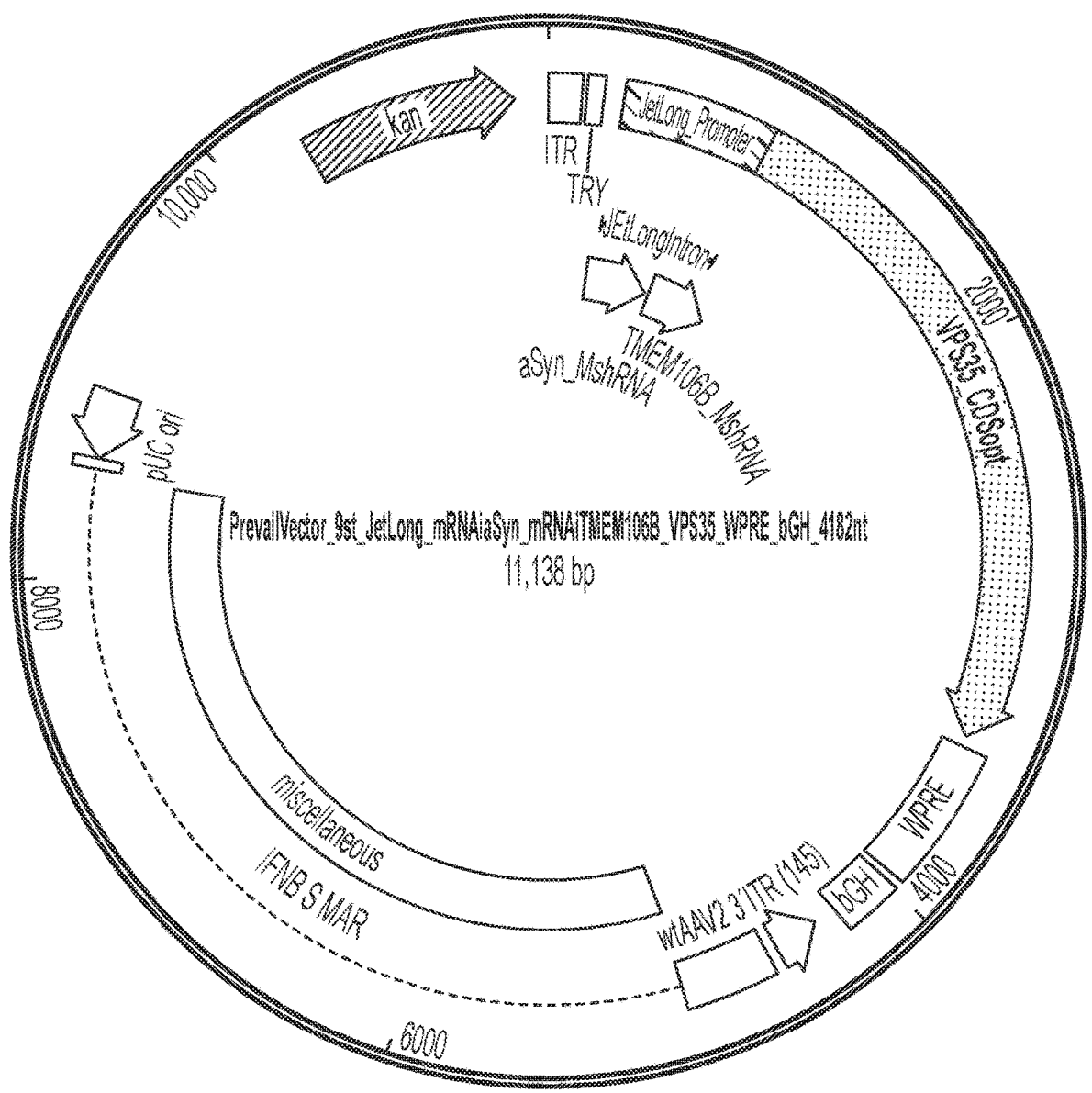
FIG. 31 is a schematic depicting one embodiment of a vector comprising an expression construct encoding VPS35 (e.g., VPS35 or a portion thereof) and interfering RNAs for α-Syn and TMEM106B.
Figure 32:
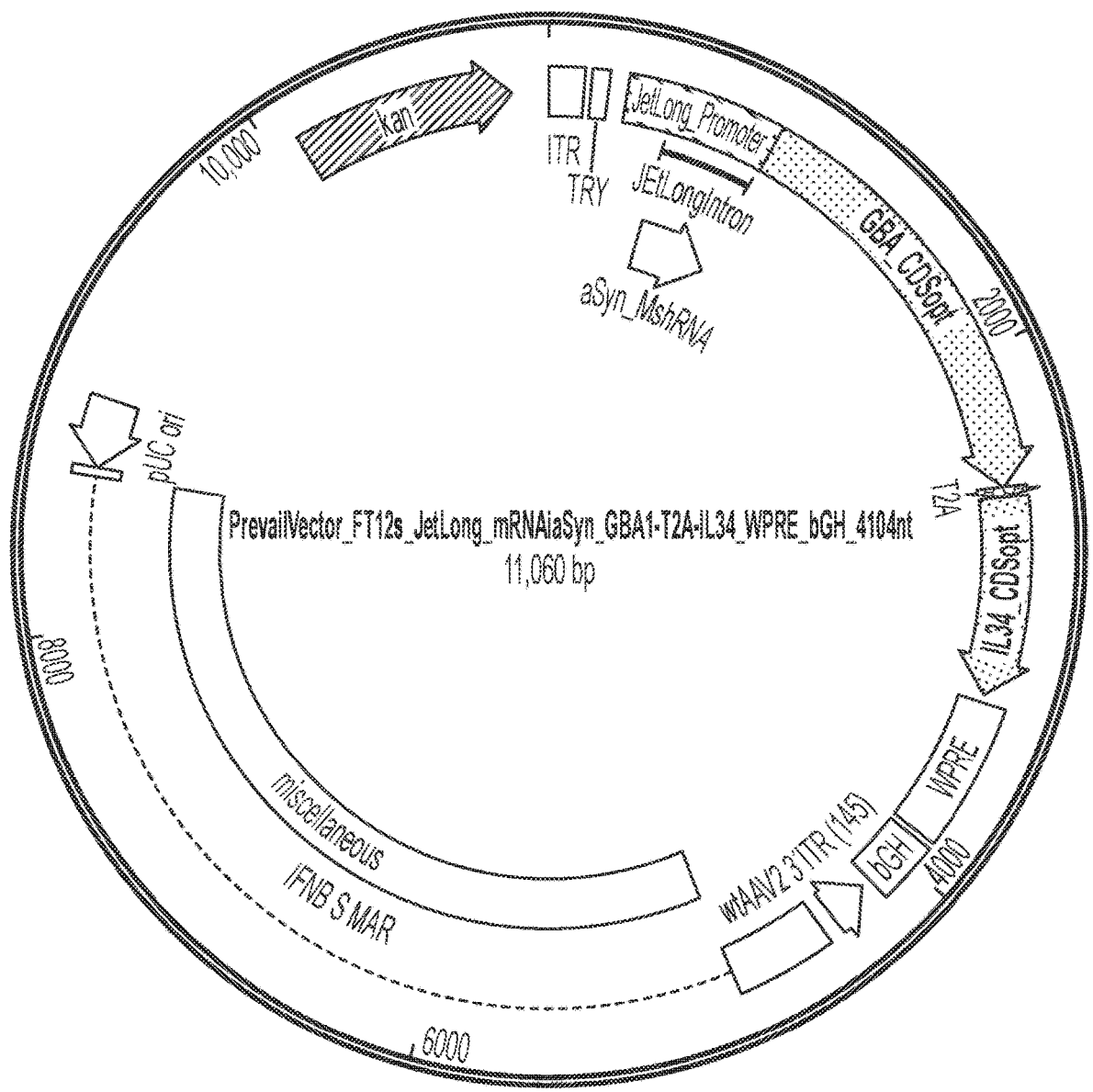
FIG. 32 is a schematic depicting one embodiment of a vector comprising an expression construct encoding Gcase (e.g., GBA1 or a portion thereof), IL-34 (e.g., IL34 or a portion thereof), and an interfering RNA for α-Syn. The coding sequences of Gcase and IL-34 are separated by T2A self-cleaving peptide sequence.
Figure 33:
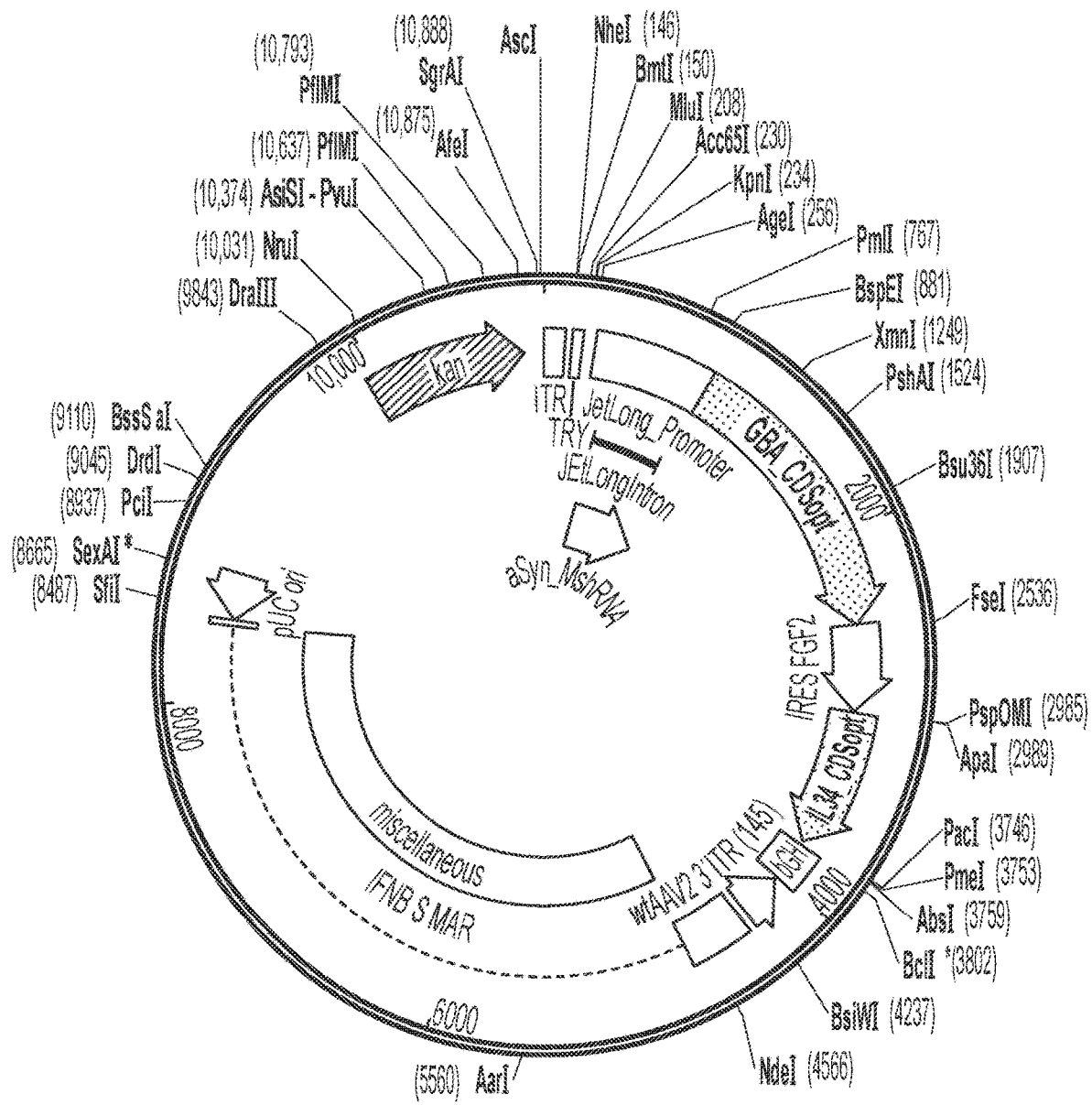
FIG. 33 is a schematic depicting one embodiment of a vector comprising an expression construct encoding Gcase (e.g., GBA1 or a portion thereof) and IL-34 (e.g., IL34 or a portion thereof). The coding sequences of Gcase and IL-34 are separated by an internal ribosomal entry site (IRES).
Figure 34:
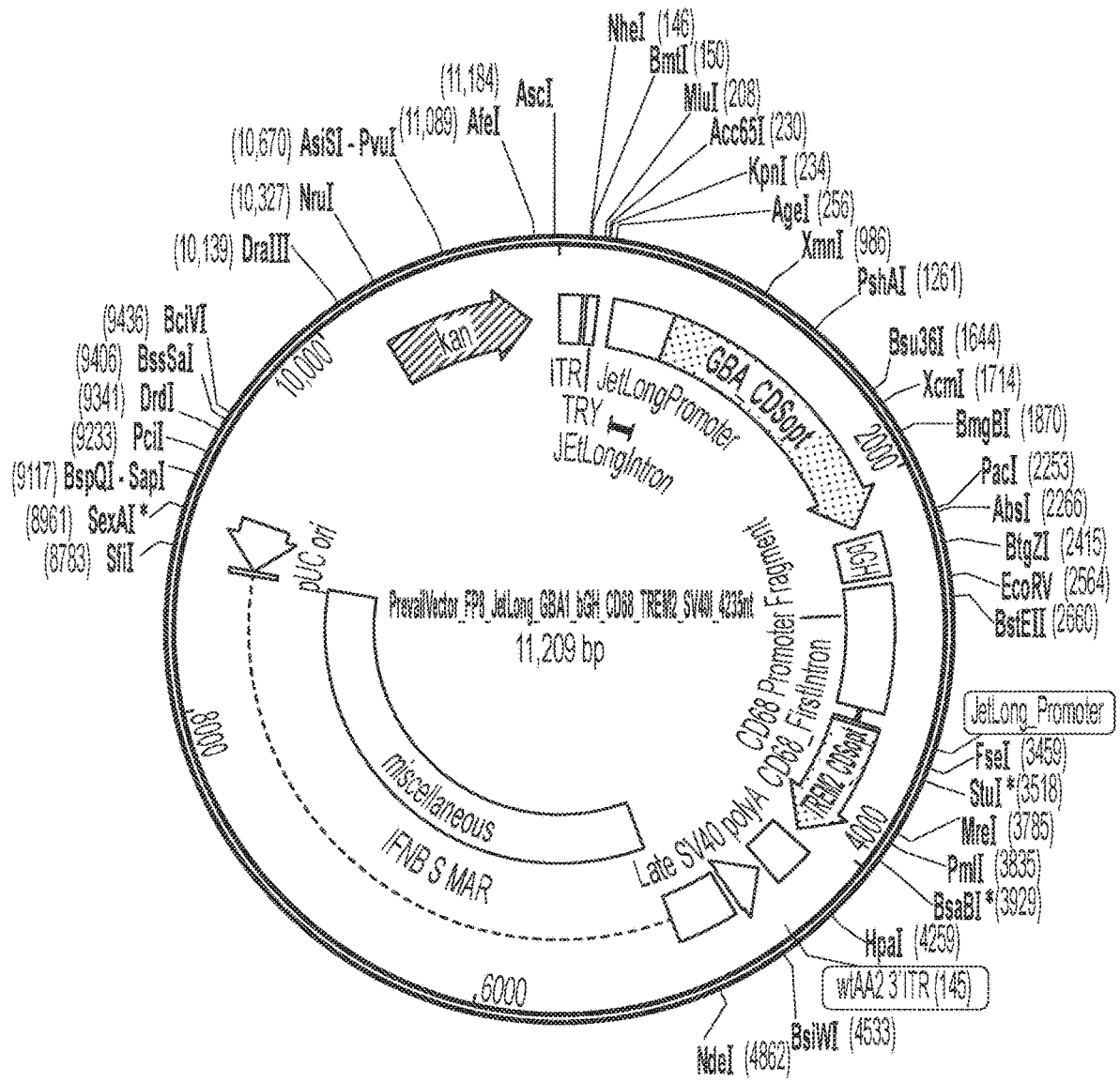
FIG. 34 is a schematic depicting one embodiment of a vector comprising an expression construct encoding Gcase (e.g., GBA1 or a portion thereof) and TREM2 (e.g., TREM2 or a portion thereof). Expression of the coding sequences of Gcase and TREM2 are each driven by a separate promoter.
Figure 35:
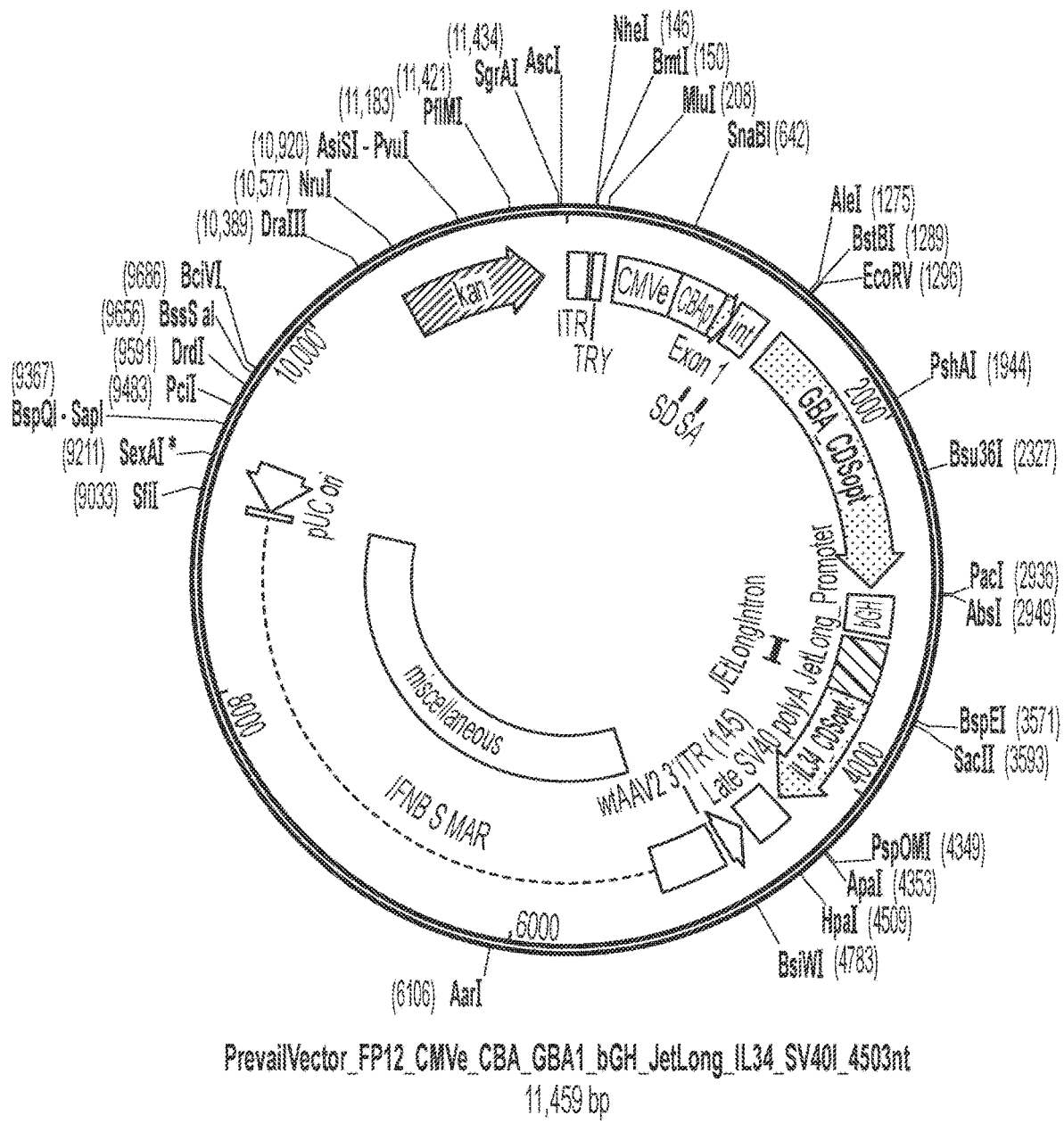
FIG. 35 is a schematic depicting one embodiment of a vector comprising an expression construct encoding Gcase (e.g., GBA1 or a portion thereof) and IL-34 (e.g., IL34 or a portion thereof). Expression of the coding sequences of Gcase and IL-34 are each driven by a separate promoter.

Aspects of the disclosure relate to isolated nucleic acids (e.g., rAAV vectors) comprising an ITR having one or more modifications (e.g., nucleic acid additions, deletions, substitutions, etc.) relative to a wild-type AAV ITR, for example relative to wild-type AAV2 ITR (e.g., SEQ ID NO: 29). The structure of wild-type AAV2 ITR is shown in FIG. 20. Generally, a wild-type ITR comprises a 125 nucleotide region that self-anneals to form a palindromic double-stranded T-shaped, hairpin structure consisting of two cross arms (formed by sequences referred to as B/B' and C/C', respectively), a longer stem region (formed by sequences A/A'), and a single-stranded terminal region referred to as the "D" region (FIG. 20). Generally, the "D" region of an ITR is positioned between the stem region formed by the A/A' sequences and the insert containing the transgene of the rAAV vector (e.g., positioned on the "inside" of the ITR relative to the terminus of the ITR or proximal to the transgene insert or expression construct of the rAAV vector). In some embodiments, a "D" region comprises the sequence set forth in SEQ ID NO: 27. The "D" region has been observed to play an important role in encapsidation of rAAV vectors by capsid proteins, for example as disclosed by Ling et al. (2015) *J Mol Genet Med* 9(3).

The disclosure is based, in part, on the surprising discovery that rAAV vectors comprising a "D" region located on the "outside" of the ITR (e.g., proximal to the terminus of the ITR relative to the transgene insert or expression construct) are efficiently encapsidated by AAV capsid proteins than rAAV vectors having ITRs with unmodified (e.g., wild-type) ITRs In some embodiments, rAAV vectors having a modified "D" sequence (e.g., a "D" sequence in the "outside" position) have reduced toxicity relative to rAAV vectors having wild-type ITR sequences.

In some embodiments, a modified "D" sequence comprises at least one nucleotide substitution relative to a wild-type "D" sequence (e.g., SEQ ID NO: 27). A modified "D" sequence may have at least 1, 2, 3, 4, 5, 6, 7, 8, 9, 10, or more than 10 nucleotide substitutions relative to a wild-type "D" sequence (e.g., SEQ ID NO: 27). In some embodiments, a modified "D" sequence comprises at least 10, 11, 12, 13, 14, 15, 16, 17, 18, or 19 nucleic acid substitutions relative to a wild-type "D" sequence (e.g., SEQ ID NO: 27). In some embodiments, a modified "D" sequence is between about 10% and about 99% (e.g., 10%, 15%, 20%, 25%, 30%, 40%, 45%, 50%, 55%, 60%, 65%, 70%, 75%, 80%, 85%, 90%, 95%, or 99%) identical to a wild-type "D" sequence (e.g., SEQ ID NO: 27). In some embodiments, a modified "D" sequence comprises the sequence set forth in SEQ ID NO: 26, also referred to as an "S" sequence as described in Wang et al. (1995) *J Mol Biol* 250(5):573-80.

An isolated nucleic acid or rAAV vector as described by the disclosure may further comprise a "TRY" sequence, for example as set forth in SEQ ID NO: 28 or as described by Francois, et al. 2005. The Cellular TATA Binding Protein Is Required for Rep-Dependent Replication of a Minimal Adeno-Associated Virus Type 2 p5 Element. J Virol. In some embodiments, a TRY sequence is positioned between an ITR (e.g. a 5' ITR) and an expression construct (e.g. a transgene-encoding insert) of an isolated nucleic acid or rAAV vector.

In some aspects, the disclosure relates to Baculovirus vectors comprising an isolated nucleic acid or rAAV vector as described by the disclosure. In some embodiments, the Baculovirus vector is an *Autographa californica* nuclear polyhedrosis (AcNPV) vector, for example as described by Urabe et al. (2002) *Hum Gene Ther* 13(16):1935-43 and Smith et al. (2009) *Mol Ther* 17(11):1888-1896.

In some aspects, the disclosure provides a host cell comprising an isolated nucleic acid or vector as described herein. A host cell can be a prokaryotic cell or a eukaryotic cell. For example, a host cell can be a mammalian cell, bacterial cell, yeast cell, insect cell, etc. In some embodiments, a host cell is a mammalian cell, for example a HEK293T cell. In some embodiments, a host cell is a bacterial cell, for example an *E. coli* cell.

rAAVs

In some aspects, the disclosure relates to recombinant AAVs (rAAVs) comprising a transgene that encodes a nucleic acid as described herein (e.g., an rAAV vector as described herein). The term "rAAVs" generally refers to viral particles comprising an rAAV vector encapsidated by one or more AAV capsid proteins. An rAAV described by the disclosure may comprise a capsid protein having a serotype selected from AAV1, AAV2, AAV3, AAV4, AAV5, AAV6, AAV7, AAV8, AAV9, and AAV10. In some embodiments, an rAAV comprises a capsid protein from a non-human host, for example a rhesus AAV capsid protein such as AAVrh.10, AAVrh.39, etc. In some embodiments, an rAAV described by the disclosure comprises a capsid protein that is a variant of a wild-type capsid protein, such as a capsid protein variant that includes at least 1, 2, 3, 4, 5, 6, 7, 8, 9, 10, or more than 10 (e.g., 15, 20 25, 50, 100, etc.) amino acid substitutions (e.g., mutations) relative to the wild-type AAV capsid protein from which it is derived.

In some embodiments, rAAVs described by the disclosure readily spread through the CNS, particularly when introduced into the CSF space or directly into the brain parenchyma. Accordingly, in some embodiments, rAAVs described by the disclosure comprise a capsid protein that is capable of crossing the blood-brain barrier (BBB). For example, in some embodiments, an rAAV comprises a capsid protein having an AAV9 or AAVrh.10 serotype. Production of rAAVs is described, for example, by Samulski et al. (1989) *J Virol.* 63(9):3822-8 and Wright (2009) *Hum Gene Ther.* 20(7): 698-706.

In some embodiments, an rAAV as described by the disclosure (e.g., comprising a recombinant rAAV genome encapsidated by AAV capsid proteins to form an rAAV capsid particle) is produced in a Baculovirus vector expression system (BEVS). Production of rAAVs using BEVS are described, for example by Urabe et al. (2002) Hum Gene Ther 13(16):1935-43, Smith et al. (2009) Mol Ther 17(11): 1888-1896, U.S. Pat. Nos. 8,945,918, 9,879,282, and International PCT Publication WO 2017/184879. However, an rAAV can be produced using any suitable method (e.g., using recombinant rep and cap genes).

Pharmaceutical Compositions

In some aspects, the disclosure provides pharmaceutical compositions comprising an isolated nucleic acid or rAAV as described herein and a pharmaceutically acceptable carrier. As used herein, the term "pharmaceutically acceptable" refers to a material, such as a carrier or diluent, which does not abrogate the biological activity or properties of the compound, and is relatively non-toxic, e.g., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

Compositions (e.g., pharmaceutical compositions) provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

Methods

The disclosure is based, in part, on compositions for expression of combinations of PD-associated gene products in a subject that act together (e.g., synergistically) to treat Parkinson's disease. As used herein "treat" or "treating" refers to (a) preventing or delaying onset of Parkinson's disease; (b) reducing severity of Parkinson's disease; (c) reducing or preventing development of symptoms characteristic of Parkinson's disease; (d) and/or preventing worsening of symptoms characteristic of Parkinson's disease. Symptoms of Parkinson's disease include, for example, motor dysfunction (e.g., shaking, rigidity, slowness of movement, difficulty with walking), cognitive dysfunction (e.g., dementia, depression, anxiety), emotional and behavioral dysfunction.

Accordingly, in some aspects, the disclosure provides a method for treating a subject having or suspected of having Parkinson's disease, the method comprising administering to the subject a composition (e.g., a composition comprising an isolated nucleic acid or a vector or a rAAV) as described by the disclosure.

In some embodiments, a composition is administered directly to the CNS of the subject, for example by direct injection into the brain and/or spinal cord of the subject. Examples of CNS-direct administration modalities include but are not limited to intracerebral injection, intraventricular injection, intracisternal injection, intraparenchymal injection, intrathecal injection, and any combination of the foregoing. In some embodiments, direct injection into the CNS of a subject results in transgene expression (e.g., expression of the first gene product, second gene product, and if applicable, third gene product) in the midbrain, striatum and/or cerebral cortex of the subject. In some embodiments, direct injection into the CNS results in transgene expression (e.g., expression of the first gene product, second gene product, and if applicable, third gene product) in the spinal cord and/or CSF of the subject.

In some embodiments, direct injection to the CNS of a subject comprises convection enhanced delivery (CED). Convection enhanced delivery is a therapeutic strategy that involves surgical exposure of the brain and placement of a small-diameter catheter directly into a target area of the brain, followed by infusion of a therapeutic agent (e.g., a composition or rAAV as described herein) directly to the brain of the subject. CED is described, for example by Debinski et al. (2009) *Expert Rev Neurother.* 9(10):1519-27.

In some embodiments, a composition is administered peripherally to a subject, for example by peripheral injection. Examples of peripheral injection include subcutaneous injection, intravenous injection, intra-arterial injection, intraperitoneal injection, or any combination of the foregoing. In some embodiments, the peripheral injection is intra-arterial injection, for example injection into the carotid artery of a subject.

In some embodiments, a composition (e.g., a composition comprising an isolated nucleic acid or a vector or a rAAV) as described by the disclosure is administered both peripherally and directly to the CNS of a subject. For example, in some embodiments, a subject is administered a composition by intra-arterial injection (e.g., injection into the carotid artery) and by intraparenchymal injection (e.g., intraparenchymal injection by CED). In some embodiments, the direct injection to the CNS and the peripheral injection are simultaneous (e.g., happen at the same time). In some embodiments, the direct injection occurs prior (e.g., between 1 minute and 1 week, or more before) to the peripheral injection. In some embodiments, the direct injection occurs after (e.g., between 1 minute and 1 week, or more after) the peripheral injection.

The amount of composition (e.g., a composition comprising an isolated nucleic acid or a vector or a rAAV) as described by the disclosure administered to a subject will vary depending on the administration method. For example, in some embodiments, a rAAV as described herein is administered to a subject at a titer between about $10^9$ Genome copies (GC)/kg and about $10^{14}$ GC/kg (e.g., about $10^9$ GC/kg, about $10^{10}$ GC/kg, about $10^{11}$ GC/kg, about $10^{12}$ GC/kg, about $10^{12}$ GC/kg, or about $10^{14}$ GC/kg). In some embodiments, a subject is administered a high titer (e.g., $>10^{12}$ Genome Copies GC/kg of an rAAV) by injection to the CSF space, or by intraparenchymal injection.

A composition (e.g., a composition comprising an isolated nucleic acid or a vector or a rAAV) as described by the disclosure can be administered to a subject once or multiple times (e.g., 2, 3, 4, 5, 6, 7, 8, 9, 10, 20, or more) times. In some embodiments, a composition is administered to a subject continuously (e.g., chronically), for example via an infusion pump.

EXAMPLES

Example 1: rAAV Vectors

AAV vectors are generated using cells, such as HEK293 cells for triple-plasmid transfection. The ITR sequences flank an expression construct comprising a promoter/enhancer element for each transgene of interest, a 3' polyA signal, and posttranslational signals such as the WPRE element. Multiple gene products can be expressed simultaneously such as GBA1 and LIMP2 and/or Prosaposin, by fusion of the protein sequences; or using a 2A peptide linker, such as T2A or P2A, which leads 2 peptide fragments with added amino acids due to prevention of the creation of a peptide bond; or using an IRES element; or by expression with 2 separate expression cassettes. The presence of a short intronic sequence that is efficiently spliced, upstream of the expressed gene, can improve expression levels. shRNAs and other regulatory RNAs can potentially be included within these sequences. Examples of expression constructs described by the disclosure are shown in FIGS. 1-8 and 21-35, and in Table 2 below.

TABLE 2

| Name | Promoter 1 | shRNA | CDS1 | PolyA1 | Bicistronic element | Promoter 2 | CDS2 | PolyA2 | Length between ITRs |
|---|---|---|---|---|---|---|---|---|---|
| CMVe_CBAp_GBA1_WPRE_bGH | CBA | | GBA1 | WPRE-bGH | | | | | 3741 |
| LT1s_JetLong_mRNAi aSYn_SCARB2-T2A-GBA1_bGH | JetLong | aSyn | SCARB2 | bGH | T2A | | GBA1 | | 4215 |
| LI1_JetLong_SCARB2-IRES-GBA1_bGH | JetLong | | SCARB2 | bGH | IRES | | GBA1 | | 4399 |
| FP1JetLong_GBA1_bGH_JetLong_SCARB2_SV40L | JetLong | | GBA1 | bGH | | JetLong | SCARB2 | SV40L | 4464 |
| PrevailVector_LT2s_JetLong_mRNAiaSYn_PSAP-T2A-GBA1_bGH_4353nt | JetLong | aSyn | PSAP | bGH | T2A | — | GBA1 | — | 4353 |
| PrevailVector LI2 JetLong_PSAP_TRES_GBA1_SyntheticpolyA_4337nt | JetLong | — | PSAP | Synthetic pA | IRES | — | GBA1 | — | 4337 |
| PrevailVector_10s_JetLong_mRNAiaSy_GBA2_WPRE_bGH_4308nt | JetLong | aSyn | GBA2 | WPRE_bGH | — | — | — | — | 4308 |
| PrevailVector_FT4_JetLong_GBA1_T2A_GALC_SyntheticpolyA_4373nt | JetLong | — | GBA1 | Synthetic pA | T2A | — | GALC | — | 4373 |
| PrevailVector_LT4_JetLong_GALC_T2A_GBA1_SyntheticpolyA_4373nt | JetLong | — | GALC | Synthetic pA | T2A | — | GBA1 | — | 4373 |
| PrevailVector_LT5s_JetLong_mRNAiaSyn_CTSB-T2A-GBA1_WPRE_bGH_4392nt | JetLong | aSyn | CTSB | WPRE_bGH | T2A | — | GBA1 | — | 4392 |
| PrevailVector_FT11t_JetLong_mRNAiaSyn_GBA1_T2S_SMPD1_SyntheticpolyA_4477nt | JetLong | aSyn | GBA1 | Synthetic pA | T2A | — | SMPD1 | — | 4477 |
| PrevailVector_LI4_JetLong_GALC_IRES_GBA1_SyntheticpolyA_4820nt | JetLong | — | GALC | Synthetic pA | IRES | — | GBA1 | — | 4820 |
| Prevail Vector_FP5_JetLong_GBA1_bGH_JetLong_CTSB_SV40l_4108nt | JetLong | — | GBA1 | bGH | — | JetLong | CTSB | SV40L | 4108 |
| PrevailVector_FT6s_JetLong_mRNAiaSyn_GBA1-T2A-GCH1_WPRE_bGH_4125nt | JetLong | aSyn | GBA1 | WPRE_bGH | T2A | — | GCH1 | — | 4125 |
| PrevailVector_LT7s_JetLong_mRNAiaSyn_RAB7L1-T2A-GBA1_WPRE_bGH_3984nt | JetLong | aSyn | RAB7L1 | WPRE_bGH | T2A | — | GBA1 | — | 3984 |
| PrevailVector_FI6s_JetLong_mRNAiaSYn_GBA1-IRES-GCH1_bGH_3978nt | JetLong | aSyn | GBA1 | bGH | IRES | — | GCH1 | — | 3978 |
| PrevailVector_9st_JetLong_mRNAiaSyn_mRNAi TMEM106B_VPS35_WPRE_bGH_4182nt | JetLong | aSyn & TMEM 106B | VPS35 | WPRE_bGH | — | — | — | — | 4182 |
| PrevailVector_FT12s_JetLong_mRNAiaSyn_GBA1-T2A-IL34_WPRE_bGH_4104nt | JetLong | aSyn | GBA1 | WPRE_bGH | T2A | — | IL34 | — | 4104 |
| PrevailVector_FI12s_JetLong_mRNAiaSYn_GBA1-IRES-IL34_bGH_3957nt | JetLong | aSyn | GBA1 | bGH | IRES | — | IL34 | — | 3957 |
| PrevailVector_FP8_JetLong_GBA1_bGH_CD68_TREM2_SV40l_4253nt | JetLong | — | GBA1 | bGH | — | CD68 | TREM2 | SV40L | 4253 |
| PrevailVector_FP12_CMVe_CBA_GBA1_bGH_JetLong_IL34_SV40l_4503nt | CBA | | GBA1 | bGH | | JetLong | IL34 | SV40L | 4503 |

Example 2: Cell Based Assays of Viral Transduction into GBA-Deficient Cells

Cells deficient in GBA1 are obtained, for example as fibroblasts from GD patients, monocytes, or hES cells, or patient-derived induced pluripotent stem cells (iPSCs). These cells accumulate substrates such as glucosylceramide and glucosylsphingosine (G1cCer and G1cSph). Treatment of wild-type or mutant cultured cell lines with Gcase inhibitors, such as CBE, is also be used to obtain GBA deficient cells.

Using such cell models, lysosomal defects are quantified in terms of accumulation of protein aggregates, such as of α-Synuclein with an antibody for this protein or phospho-αSyn, followed by imaging using fluorescent microscopy. Imaging for lysosomal abnormalities by ICC for protein markers such as LAMP1, LAMP2, LIMP1, LIMP2, or using dyes such as Lysotracker, or by uptake through the endocytic compartment of fluorescent dextran or other markers is also performed. Imaging for autophagy marker accumulation due to defective fusion with the lysosome, such as for LC3, can also be performed. Western blotting and/or ELISA is used to quantify abnormal accumulation of these markers. Also, the accumulation of glycolipid substrates and products of GBA1 is measured using standard approaches.

Therapeutic endpoints (e.g., reduction of PD-associated pathology) are measured in the context of expression of transduction of the AAV vectors, to confirm and quantify activity and function. Gcase can is also quantified using protein ELISA measures, or by standard Gcase activity assays.

Example 3: In Vivo Assays Using Mutant Mice

This example describes in vivo assays of AAV vectors using mutant mice. In vivo studies of AAV vectors as above in mutant mice are performed using assays described, for example, by Liou et al. (2006) *J. Biol. Chem.* 281(7): 4242-4253, Sun et al. (2005) *J. Lipid Res.* 46:2102-2113, and Farfel-Becker et al. (2011) *Dis. Model Mech.* 4(6):746-752.

The intrathecal or intraventricular delivery of vehicle control and AAV vectors (e.g., at a dose of $2 \times 10^{11}$ vg/mouse) are performed using concentrated AAV stocks, for example at an injection volume between 5-10 µL. Intraparenchymal delivery by convection enhanced delivery is performed.

Treatment is initiated either before onset of symptoms, or subsequent to onset. Endpoints measured are the accumulation of substrate in the CNS and CSF, accumulation of Gcase enzyme by ELISA and of enzyme activity, motor and cognitive endpoints, lysosomal dysfunction, and accumulation of α-Synuclein monomers, protofibrils or fibrils.

Example 4: Chemical Models of Disease

This example describes in vivo assays of AAV vectors using a chemically-induced mouse model of Gaucher disease (e.g., the CBE mouse model). In vivo studies of these AAV vectors are performed in a chemically-induced mouse model of Gaucher disease, for example as described by Vardi et al. (2016) *J Pathol.* 239(4):496-509.

Intrathecal or intraventricular delivery of vehicle control and AAV vectors (e.g., at a dose of $2 \times 10^{11}$ vg/mouse) are performed using concentrated AAV stocks, for example with injection volume between 5-10 µL. Intraparenchymal delivery by convection enhanced delivery is performed. Peripheral delivery is achieved by tail vein injection.

Treatment is initiated either before onset of symptoms, or subsequent to onset. Endpoints measured are the accumulation of substrate in the CNS and CSF, accumulation of Gcase enzyme by ELISA and of enzyme activity, motor and cognitive endpoints, lysosomal dysfunction, and accumulation of α-Synuclein monomers, protofibrils or fibrils.

Example 5: Clinical Trials in PD, LBD, Gaucher Disease Patients

In some embodiments, patients having certain forms of Gaucher disease (e.g., GD1) have an increased risk of developing Parkinson's disease (PD) or Lewy body dementia (LBD). This Example describes clinical trials to assess the safety and efficacy of rAAVs as described by the disclosure, in patients having Gaucher disease, PD and/or LBD.

Clinical trials of such vectors for treatment of Gaucher disease, PD and/or LBD are performed using a study design similar to that described in Grabowski et al. (1995) *Ann. Intern. Med.* 122(1):33-39.

Example 6: Treatment of Peripheral Disease

In some embodiments, patients having certain forms of Gaucher disease exhibit symptoms of peripheral neuropathy, for example as described in Biegstraaten et al. (2010) *Brain* 133(10):2909-2919.

This example describes in vivo assays of AAV vectors as described herein for treatment of peripheral neuropathy associated with Gaucher disease (e.g., Type 1 Gaucher disease). Briefly, Type 1 Gaucher disease patients identified as having signs or symptoms of peripheral neuropathy are administered a rAAV as described by the disclosure. In some embodiments, the peripheral neuropathic signs and symptoms of the subject are monitored, for example using methods described in Biegstraaten et al., after administration of the rAAV.

Levels of transduced gene products as described by the disclosure present in patients (e.g., in serum of a patient, in peripheral tissue (e.g., liver tissue, spleen tissue, etc.)) of a patient are assayed, for example by Western blot analysis, enzymatic functional assays, or imaging studies.

Example 7: Treatment of CNS Forms

This example describes in vivo assays of rAAVs as described herein for treatment of CNS forms of Gaucher disease. Briefly, Gaucher disease patients identified as having a CNS form of Gaucher disease (e.g., Type 2 or Type 3 Gaucher disease) are administered a rAAV as described by the disclosure. Levels of transduced gene products as described by the disclosure present in the CNS of patients (e.g., in serum of the CNS of a patient, in cerebrospinal fluid (CSF) of a patient, or in CNS tissue of a patient) are assayed, for example by Western blot analysis, enzymatic functional assays, or imaging studies.

Example 8: Gene Therapy of Parkinson's Disease in Subjects Having Mutations in GBA1

This example describes administration of a recombinant adeno-associated virus (rAAV) encoding GBA1 to a subject having Parkinson's disease characterized by a mutation in GBA1 gene.

The rAAV-GBA1 vector insert contains the CBA promoter element (CBA), consisting of four parts: the CMV enhancer (CMVe), CBA promoter (CBAp), Exon 1, and intron (int) to constitutively express the codon optimized coding sequence (CDS) of human GBA1 (maroon). The 3' region also contains a Woodchuck hepatitis virus Posttranscriptional Regulatory Element (WPRE) posttranscriptional regulatory element followed by a bovine Growth Hormone polyA signal (bGH polyA) tail. The flanking ITRs allow for the correct packaging of the intervening sequences. Two variants of the 5' ITR sequence (FIG. 7, inset box, bottom sequence) were evaluated; these variants have several nucleotide differences within the 20-nucleotide "D" region of the ITR, which is believed to impact the efficiency of packaging and expression. The rAAV-GBA1 vector product contains the "D" domain nucleotide sequence shown in FIG. 7 (inset box, top sequence). A variant vector harbors a mutant "D" domain (termed an "S" domain herein, with the nucleotide changes shown by shading), performed similarly in preclinical studies. The backbone contains the gene to confer resistance to kanamycin as well as a stuffer sequence to prevent reverse packaging. A schematic depicting a rAAV-GBA1 vector is shown in FIG. 8. The rAAV-GBA1 vector is packaged into an rAAV using AAV9 serotype capsid proteins.

rAAV-GBA1 is administered to a subject as a single dose via a fluoroscopy guided sub-occipital injection into the cisterna magna (intracisternal magna; ICM). One embodiment of a rAAV-GBA1 dosing regimen study is as follows:

A single dose of rAAV-GBA1 is administered to patients (N=12) at one of two dose levels (3e13 vg (low dose); 1e14 vg (high dose), etc.) which are determined based on the results of nonclinical pharmacology and toxicology studies.

Initial studies were conducted in a chemical mouse model involving daily delivery of conduritol-b-epoxide (CBE), an inhibitor of GCase to assess the efficacy and safety of the rAAV-GBA1 vector and a rAAV-GBA1 S-variant construct (as described further below). Additionally, initial studies were performed in a genetic mouse model, which carries a homozygous GBA1 mutation and is partially deficient in saposins (4L/PS-NA). Additional dose-ranging studies in mice and nonhuman primates (NHPs) are conducted to further evaluate vector safety and efficacy.

Figure 7:
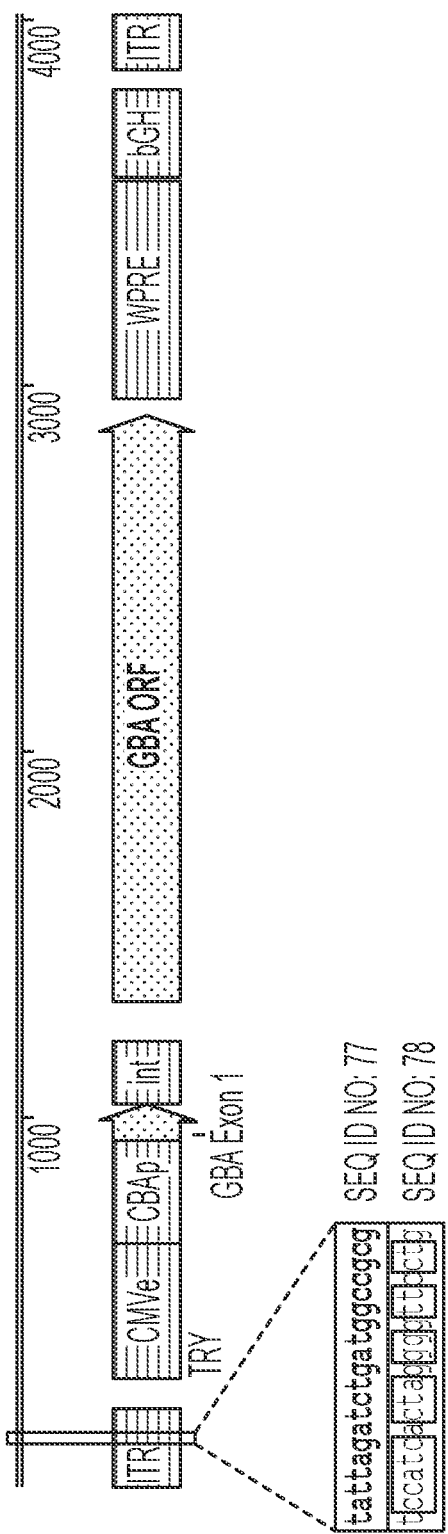
FIG. 7 is a schematic depicting one embodiment of a vector comprising an expression construct encoding a Gcase (e.g., GBA1 or a portion thereof). In this embodiment, the vector comprises a CBA promoter element (CBA), consisting of four parts: the CMV enhancer (CMVe), CBA promoter (CBAp), Exon 1, and intron (int) to constitutively express the codon optimized coding sequence of human GBA1. The 3' region also contains a WPRE regulatory element followed by a bGH polyA tail. Three transcriptional regulatory activation sites are included at the 5' end of the promoter region: TATA, RBS, and YY1. The flanking ITRs allow for the correct packaging of the intervening sequences. Two variants of the 5' ITR sequence (inset box) were evaluated; these have several nucleotide differences within the 20-nucleotide "D" region of wild-type AAV2 ITR. In some embodiments, an rAAV vector contains the "D" domain nucleotide sequence shown on the top line. In some embodiments, a rAAV vector comprises a mutant "D" domain (e.g., an "S" domain, with the nucleotide changes shown on the bottom line).
Figure 8:
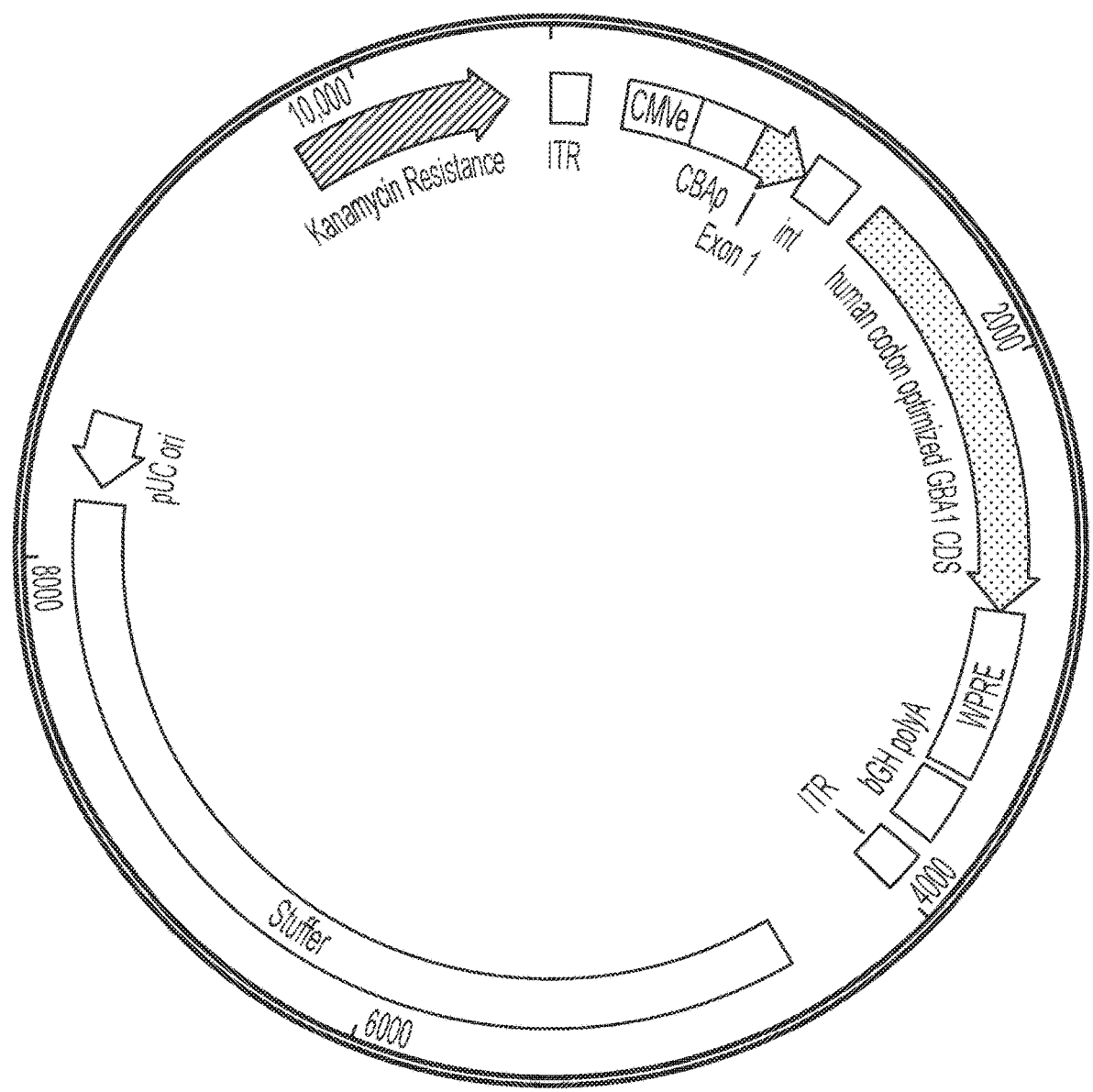
FIG. 8 is a schematic depicting one embodiment of the vector described in FIG. 6

Two slightly different versions of the 5' inverted terminal repeat (ITR) in the AAV backbone were tested to assess manufacturability and transgene expression (FIG. 7). The 20 bp "D" domain within the 145 bp 5' ITR is thought to be necessary for optimal viral vector production, but mutations within the "D" domain have also been reported to increase transgene expression in some cases. Thus, in addition to the viral vector rAAV-GBA1, which harbors an intact "D" domain, a second vector form with a mutant D domain (termed an "S" domain herein) was also evaluated. Both rAAV-GBA1 and the variant express the same transgene. While both vectors produced virus that was efficacious in vivo as detailed below, rAAV-GBA1, which contains a wild-type "D" domain, was selected for further development.

Figure 9:
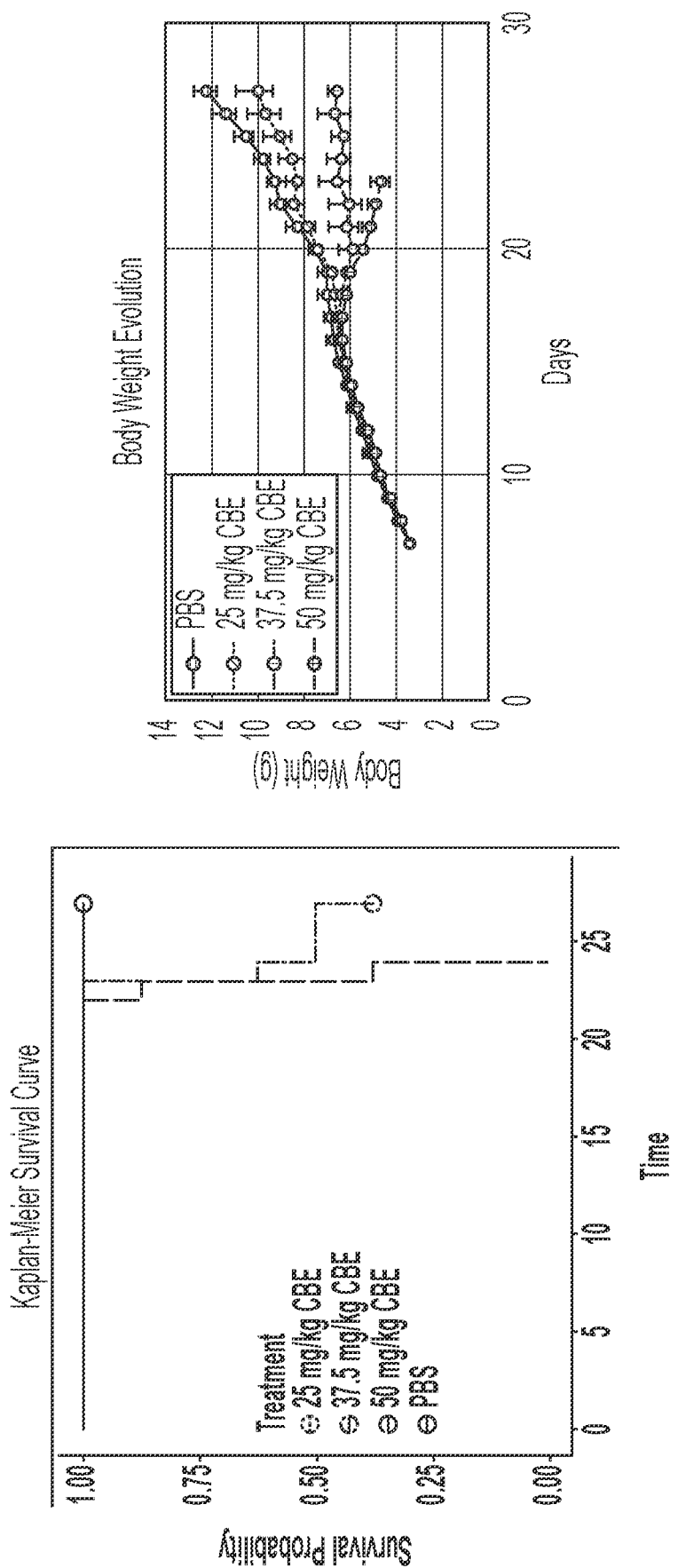
FIG. 9 shows representative data for delivery of an rAAV comprising a transgene encoding a Gcase (e.g., GBA1 or a portion thereof) in a CBE mouse model of Parkinson's disease. Daily IP delivery of PBS vehicle, 25 mg/kg CBE, 37.5 mg/kg CBE, or 50 mg/kg CBE (left to right) initiated at P8. Survival (top left) was checked two times a day and weight (top right) was checked daily. All groups started with n=8. Behavior was assessed by total distance traveled in Open Field (bottom left) at P23 and latency to fall on Rotarod (bottom middle) at P24. Levels of the GCase substrates were analyzed in the cortex of mice in the PBS and 25 mg/kg CBE treatment groups both with (Day 3) and without (Day 1) CBE withdrawal. Aggregate GluSph and GalSph levels (bottom right) are shown as pmol per mg wet weight of the tissue. Means are presented. Error bars are SEM. *$p<0.05$; $p<0.01$; *$p<0.001$, nominal p-values for treatment groups by linear regression.
Figure 9:
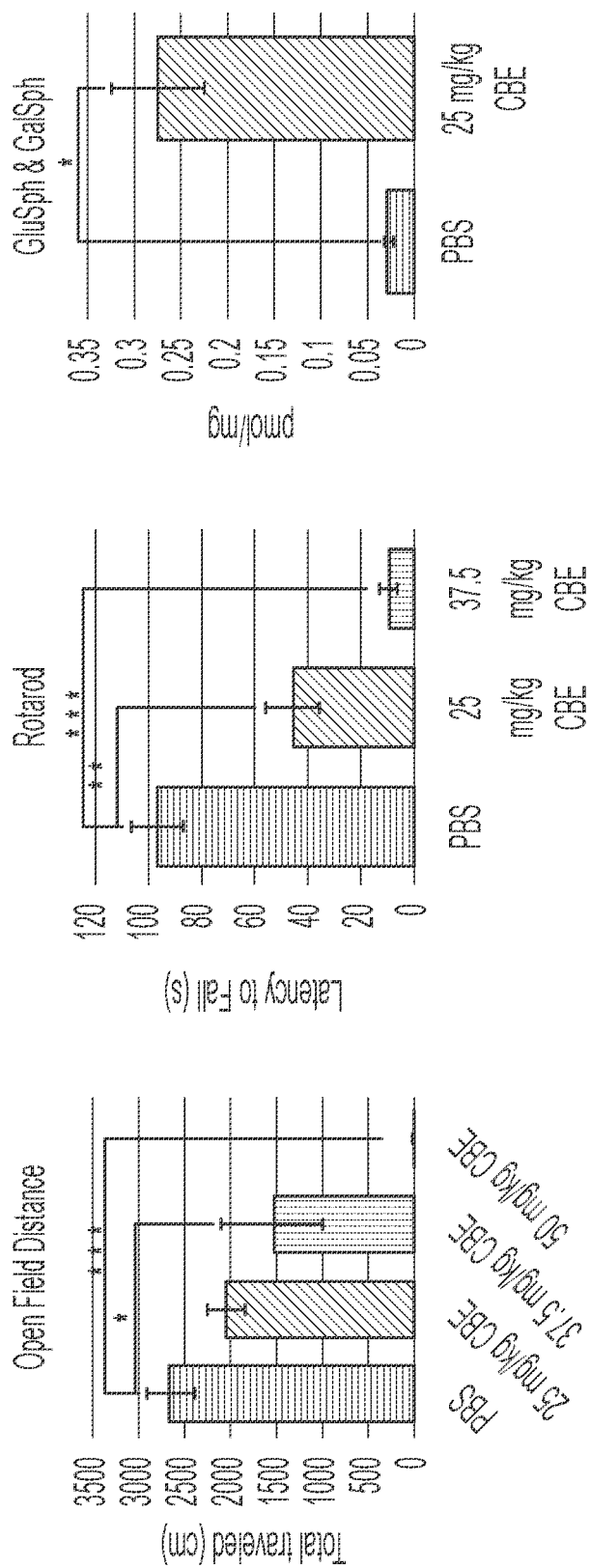

To establish the CBE model of GCase deficiency, juvenile mice were dosed with CBE, a specific inhibitor of GCase. Mice were given CBE by IP injection daily, starting at postnatal day 8 (P8). Three different CBE doses (25 mg/kg, 37.5 mg/kg, 50 mg/kg) and PBS were tested to establish a model that exhibits a behavioral phenotype (FIG. 9). Higher doses of CBE led to lethality in a dose-dependent manner. All mice treated with 50 mg/kg CBE died by P23, and 5 of the 8 mice treated with 37.5 mg/kg CBE died by P27. There was no lethality in mice treated with 25 mg/kg CBE. Whereas CBE-injected mice showed no general motor deficits in the open field assay (traveling the same distance and at the same velocity as mice given PBS), CBE-treated mice exhibited a motor coordination and balance deficit as measured by the rotarod assay.

Mice surviving to the end of the study were sacrificed on the day after their last CBE dose (P27, "Day 1") or after three days of CBE withdrawal (P29, "Day 3"). Lipid analysis was performed on the cortex of mice given 25 mg/kg CBE to evaluate the accumulation of GCase substrates in both the Day 1 and Day 3 cohorts. GluSph and GalSph levels (measured in aggregate in this example) were significantly accumulated in the CBE-treated mice compared to PBS-treated controls, consistent with GCase insufficiency.

Figure 10:
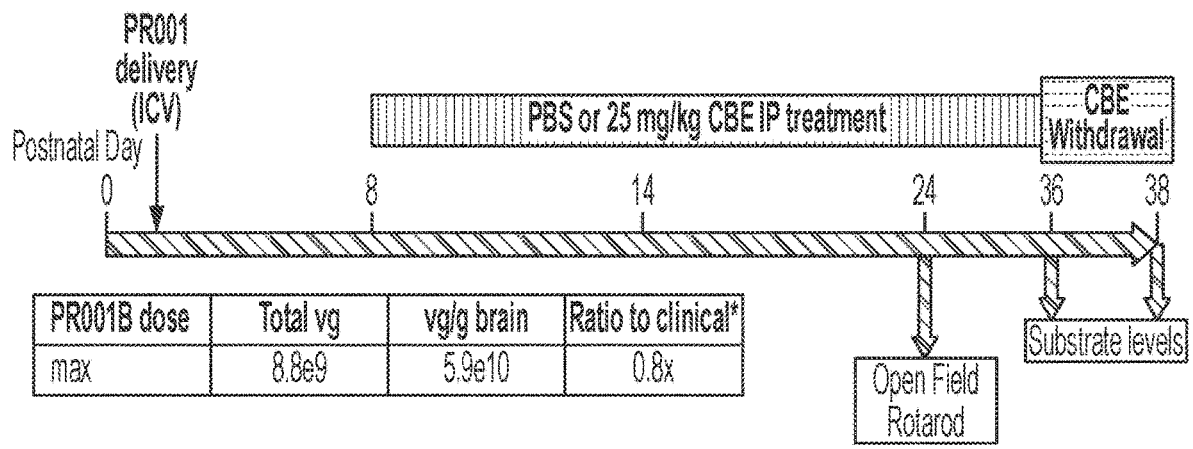
FIG. 10 is a schematic depicting one embodiment of a study design for maximal rAAV dose in a CBE mouse model. Briefly, rAAV was delivered by ICV injection at P3, and daily CBE treatment was initiated at P8. Behavior was assessed in the Open Field and Rotarod assays at P24-25 and substrate levels were measured at P36 and P38.

Based on the study described above, the 25 mg/kg CBE dose was selected since it produced behavioral deficits without impacting survival. To achieve widespread GBA1 distribution throughout the brain and transgene expression during CBE treatment, rAAV-GBA1 or excipient was delivered by intracerebroventricular (ICV) injection at postnatal day 3 (P3) followed by daily IP CBE or PBS treatment initiated at P8 (FIG. 10).

Figure 11:
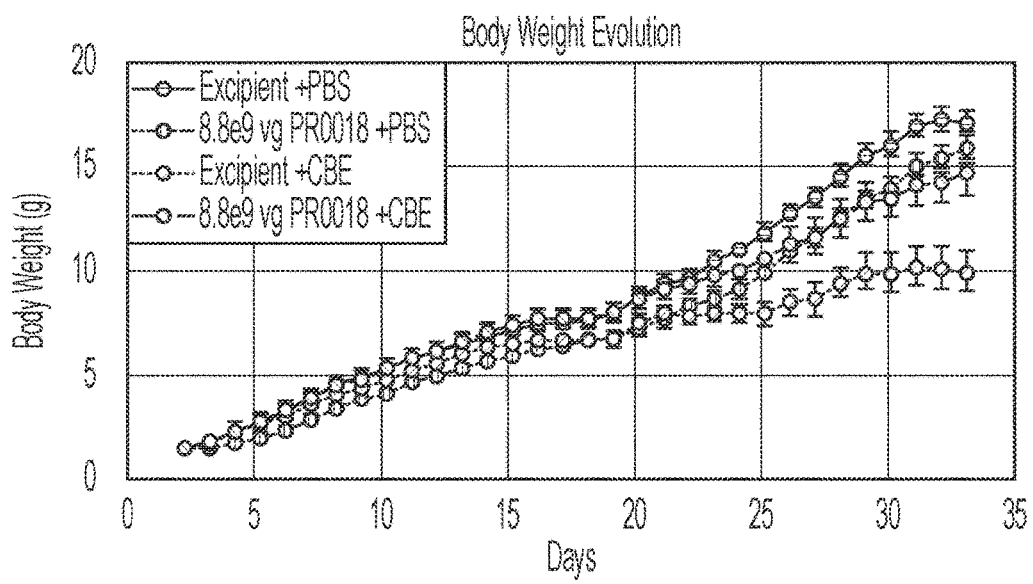
FIG. 11 shows representative data for in-life assessment of maximal rAAV dose in a CBE mouse model. At P3, mice were treated with either excipient or 8.8e9 vg rAAV-GBA1 via ICV delivery. Daily IP delivery of either PBS or 25 mg/kg CBE was initiated at P8. At the end of the study, half the mice were sacrificed one day after their last CBE dose at P36 (Day 1) while the remaining half went through 3 days of CBE withdrawal before sacrifice at P38 (Day3). All treatment groups (excipient+PBS n=8, rAAV-GBA1+PBS n=7, excipient+CBE n=8, and variant+CBE n=9) were weighed daily (top left), and the weight at P36 was analyzed (top right). Behavior was assessed by total distance traveled in Open Field at P23 (bottom left) and latency to fall on Rotarod at P24 (bottom right), evaluated for each animal as the median across 3 trials. Due to lethality, n=7 for the excipient+CBE group for the behavioral assays, while n=8 for all other groups. Means across animals are presented. Error bars are SEM. *$p<0.05$; ***$p<0.001$, nominal p-values for treatment groups by linear regression in the CBE-treated animals.
Figure 11:
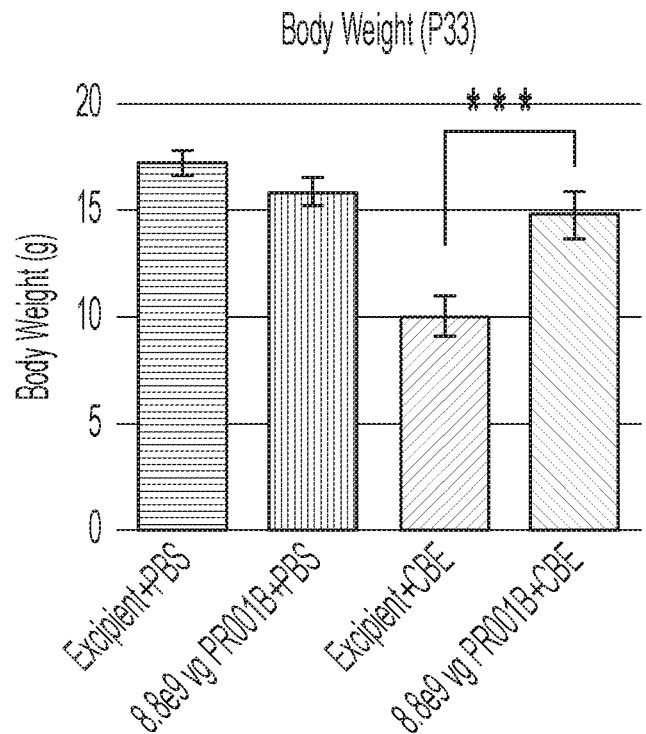
Figure 11:
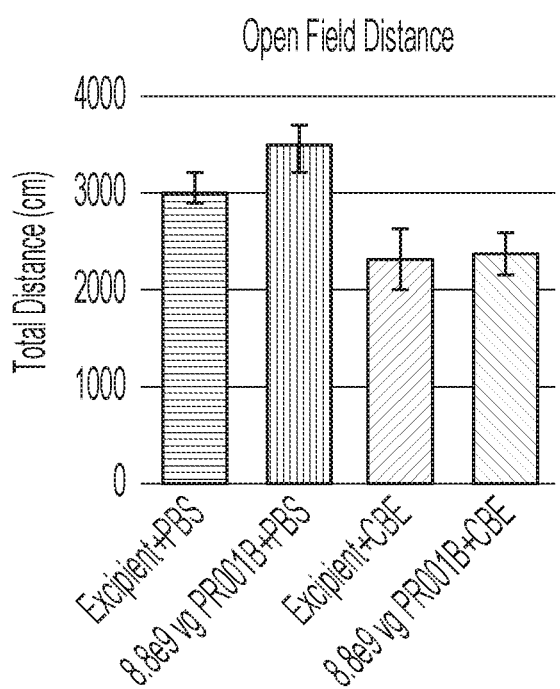
Figure 11:
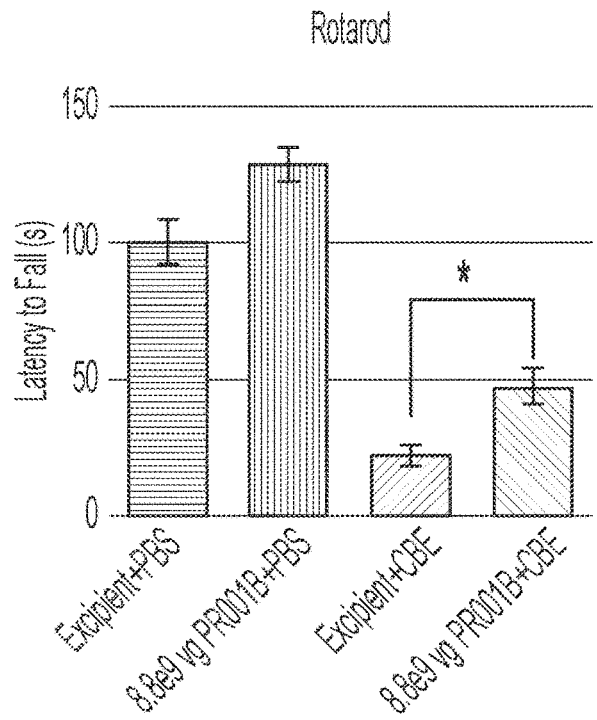

CBE-treated mice that received rAAV-GBA1 performed statistically significantly better on the rotarod than those that received excipient (FIG. 11). Mice in the variant treatment group did not differ from excipient treated mice in terms of other behavioral measures, such as the total distance traveled during testing (FIG. 11).

Figure 12:
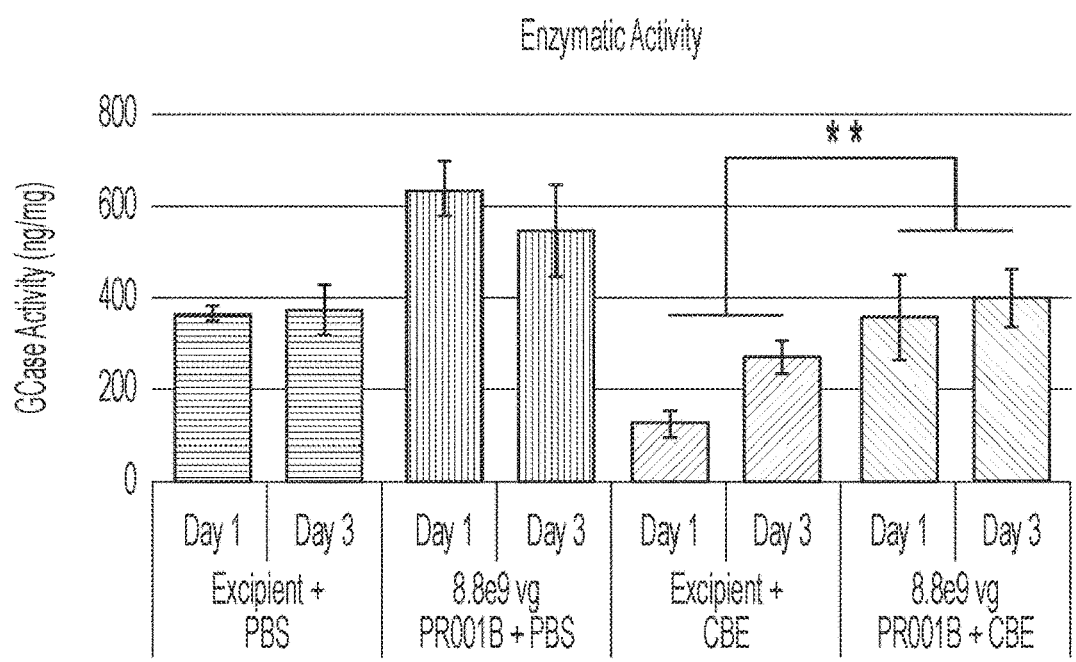
FIG. 12 shows representative data for biochemical assessment of maximal rAAV dose in a CBE mouse model. The cortex of all treatment groups (excipient+PBS n=8, variant+PBS n=7, excipient+CBE n=7, and variant+CBE n=9) was used to measure GCase activity (top left), GluSph levels (top right), GluCer levels (bottom left), and vector genomes (bottom right) in the groups before (Day 1) or after (Day 3) CBE withdrawal. Biodistribution is shown as vector genomes per 1 Vg of genomic DNA. Means are presented. Error bars are SEM. (*)$p<0.1$; $p<0.01$; *$p<0.001$, nominal p-values for treatment groups by linear regression in the CBE-treated animals, with collection days and gender corrected for as covariates.
Figure 12:
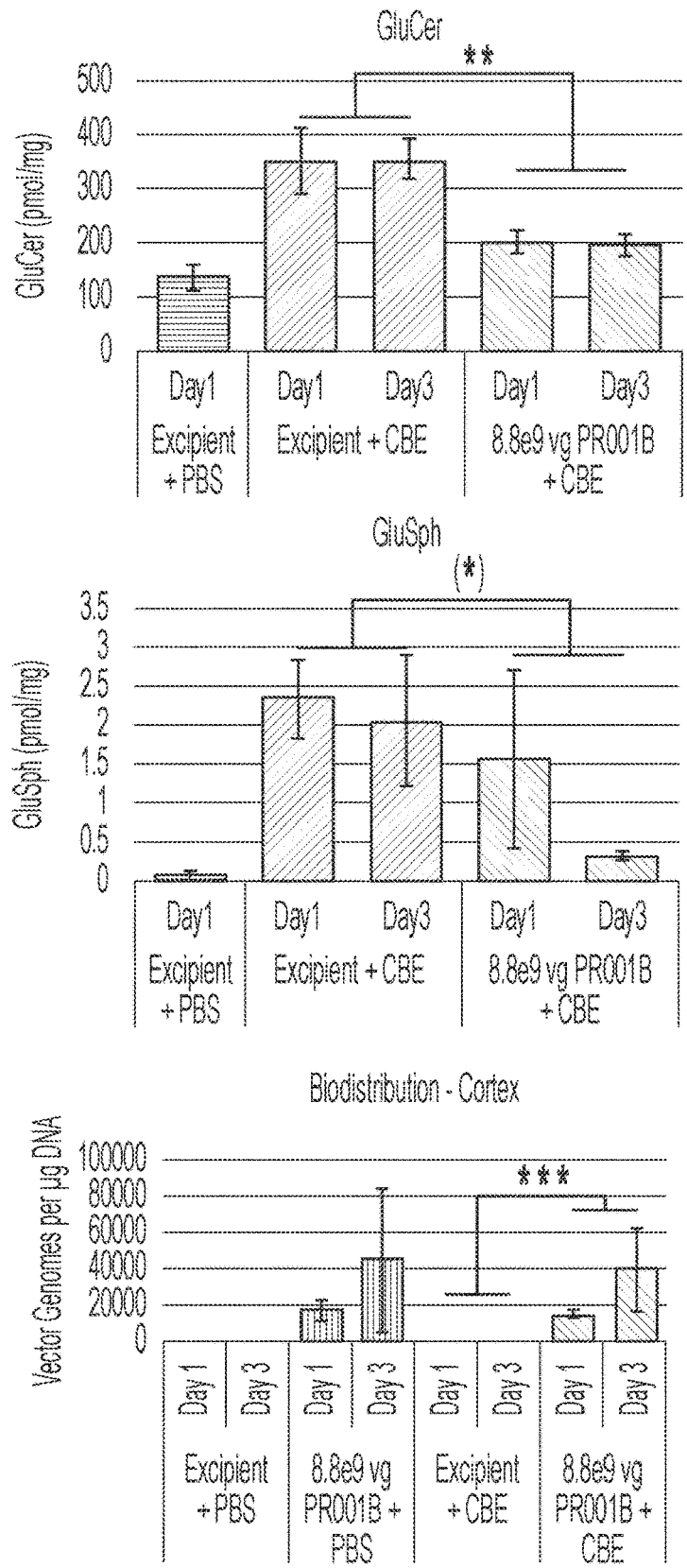

At the completion of the in-life study, half of the mice were sacrificed the day after the last CBE dose (P36, "Day 1") or after three days of CBE withdrawal (P38, "Day 3") for biochemical analysis (FIG. 12). Using a fluorometric enzyme assay performed in biological triplicate, GCase activity was assessed in the cortex. GCase activity was increased in mice that were treated with rAAV-GBA1, while CBE treatment reduced GCase activity. Additionally, mice that received both CBE and rAAV-GBA1 had GCase activity levels that were similar to the PBS-treated group, indicating that delivery of rAAV-GBA1 is able to overcome the inhibition of GCase activity induced by CBE treatment. Lipid analysis was performed on the motor cortex of the mice to examine levels of the substrates GluCer and GluSph. Both lipids accumulated in the brains of mice given CBE, and rAAV-GBA1 treatment significantly reduced substrate accumulation.

Figure 13:
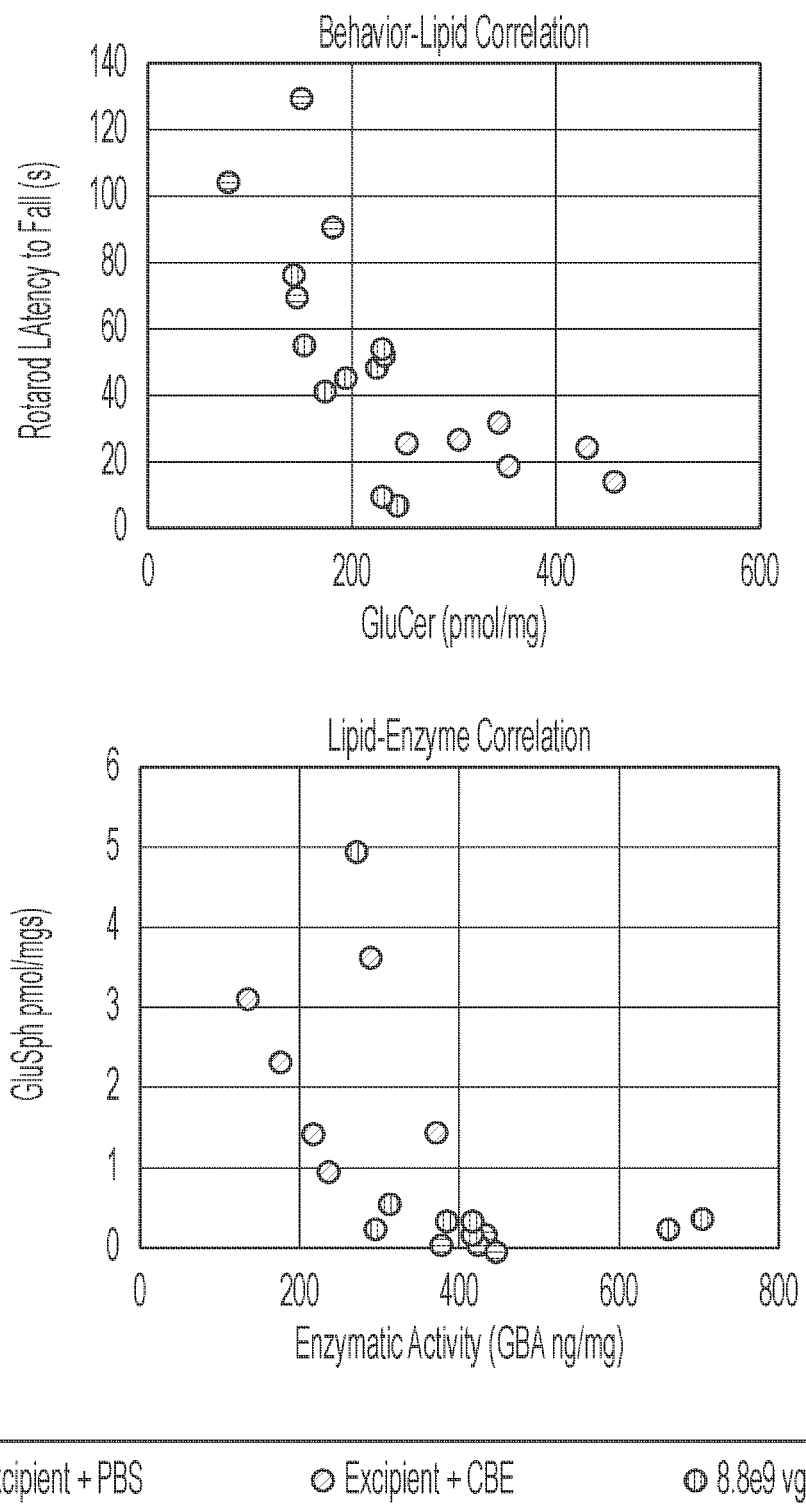
FIG. 13 shows representative data for behavioral and biochemical correlations in a CBE mouse model after administration of excipient+PBS, excipient+CBE, and variant+CBE treatment groups. Across treatment groups, performance on Rotarod was negatively correlated with GluCer accumulation (A, $p=0.0012$ by linear regression), and GluSph accumulation was negatively correlated with increased GCase activity (B, $p=0.0086$ by linear regression).
Figure 14:
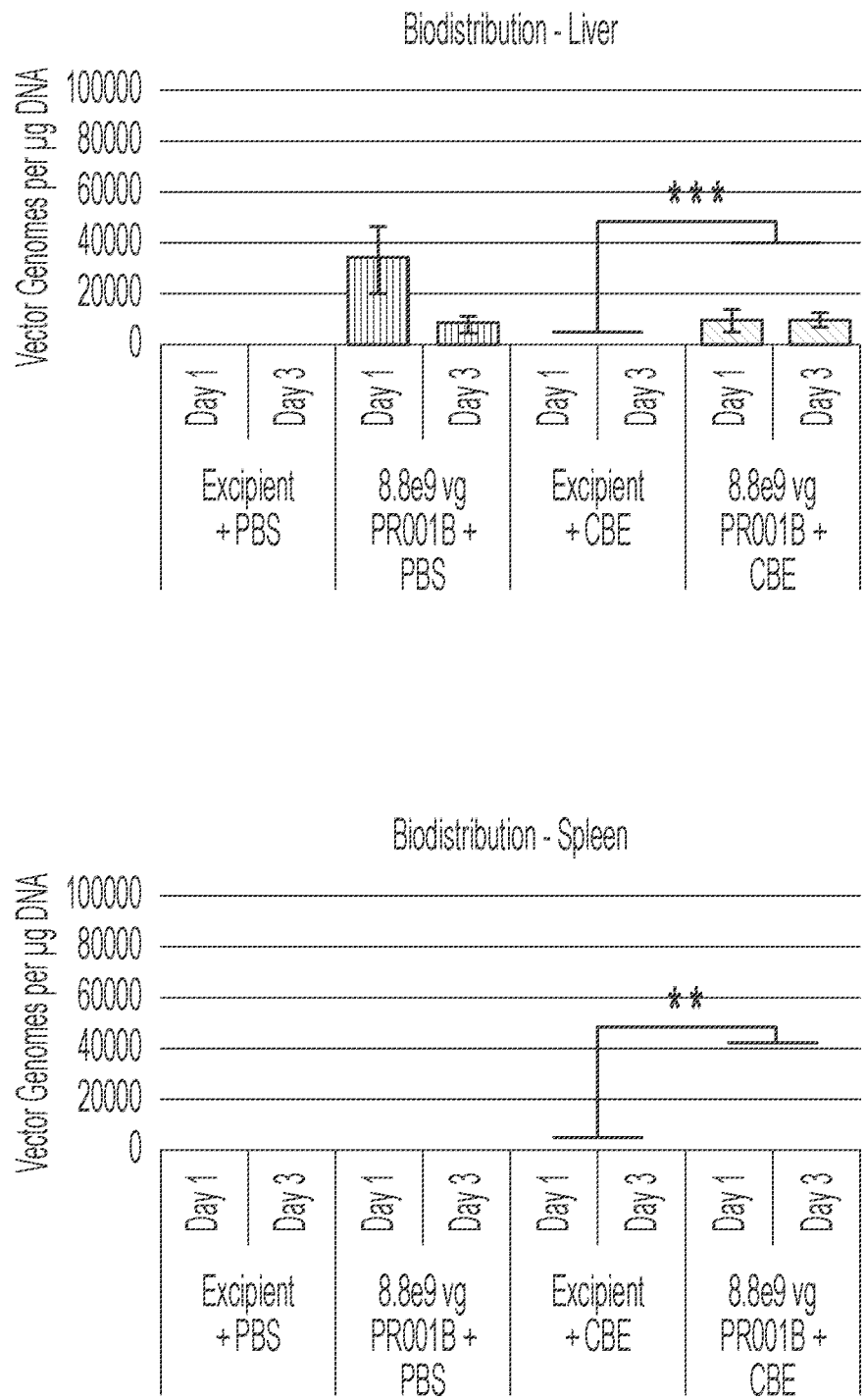
FIG. 14 shows representative data for biodistribution of variant in a CBE mouse model. Presence of vector genomes was assessed in the liver, spleen, kidney, and gonads for all treatment groups (excipient+PBS n=8, variant+PBS n=7, excipient+CBE n=7, and variant+CBE n=9). Biodistribution is shown as vector genomes per 1 μg of genomic DNA. Vector genome presence was quantified by quantitative PCR using a vector reference standard curve; genomic DNA concentration was evaluated by A260 optical density measurement. Means are presented. Error bars are SEM. *p<0.05; p<0.01; *p<0.001, nominal p-values for treatment groups by linear regression in the CBE-treated animals, with collection days and gender corrected for as covariates.
Figure 14:
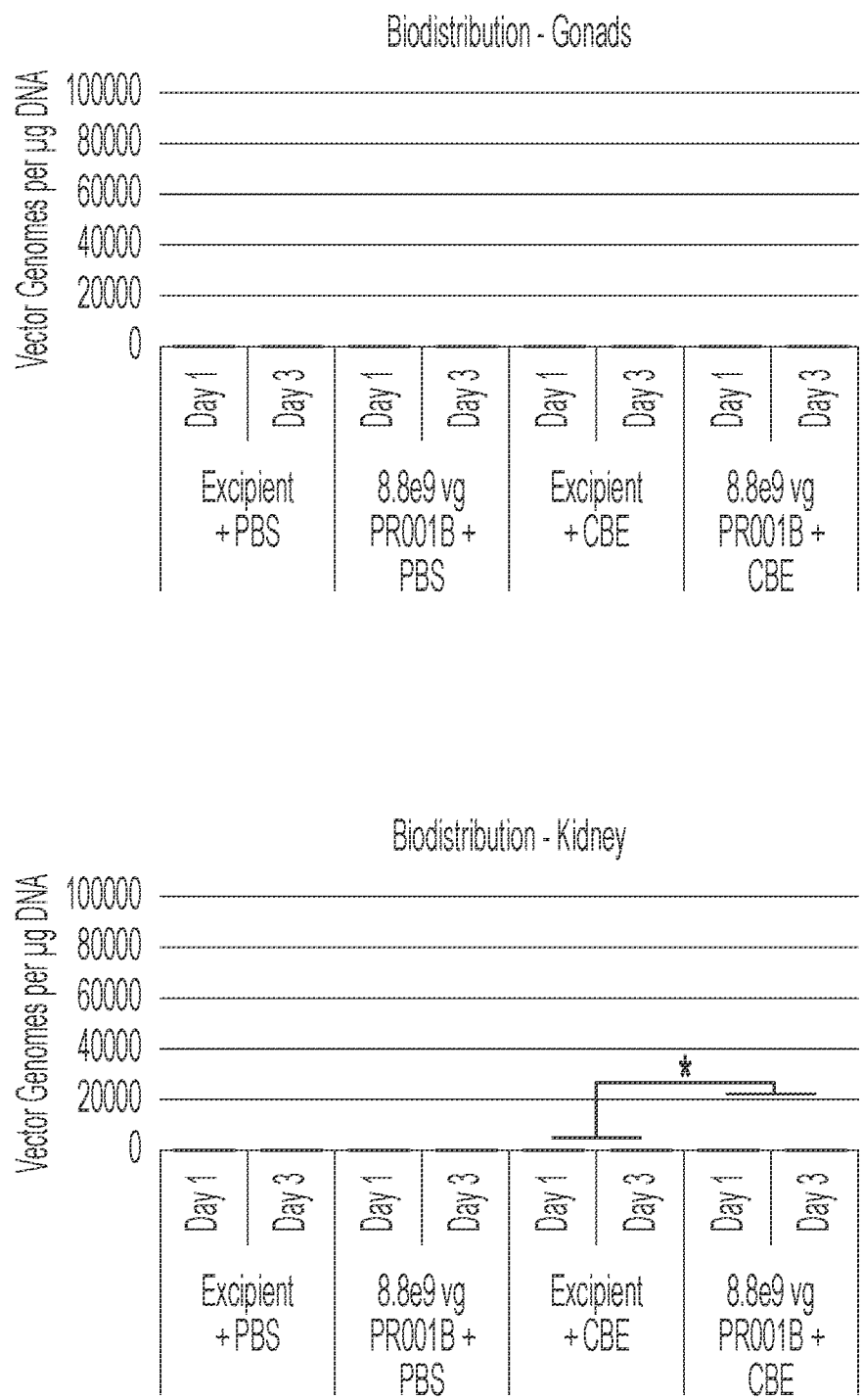

Lipid levels were negatively correlated with both GCase activity and performance on the Rotarod across treatment groups. The increased GCasc activity after rAAV-GBA1 administration was associated with substrate reduction and enhanced motor function (FIG. 13). As shown in FIG. 14, preliminary biodistribution was assessed by vector genome presence, as measured by qPCR (with >100 vector genomes per 1 μg genomic DNA defined as positive). Mice that received rAAV-GBA1, both with and without CBE, were positive for rAAV-GBA1 vector genomes in the cortex, indicating that ICV delivery results in rAAV-GBA1 delivery to the cortex. Additionally, vector genomes were detected in the liver, few in spleen, and none in the heart, kidney or gonads. For all measures, there was no statistically significant difference between the Day 1 and Day 3 groups.

A larger study in the CBE model further explored efficacious doses of rAAV-GBA1 in the CBE model. Using the 25 mg/kg CBE dose model, excipient or rAAV-GBA1 was delivered via ICV at P3, and daily IP PBS or CBE treatment initiated at P8. Given the similarity between the groups with and without CBE withdrawal observed in the previous studies, all mice were sacrificed one day after the final CBE dose (P38-40). The effect of three different rAAV-GBA1 doses was assessed, resulting in the following five groups, with 10 mice (5M/5F) per group:

Excipient ICV+PBS IP
Excipient ICV+25 mg/kg CBE IP
3.2e9 vg (2.13e10 vg/g brain) rAAV-GBA1 ICV+25 mg/kg CBE IP
1.0e10 vg (6.67e10 vg/g brain) rAAV-GBA1 ICV+25 mg/kg CBE IP
3.2e10 vg (2.13e11 vg/g brain) rAAV-GBA1 ICV+25 mg/kg CBE IP.

Figure 15:
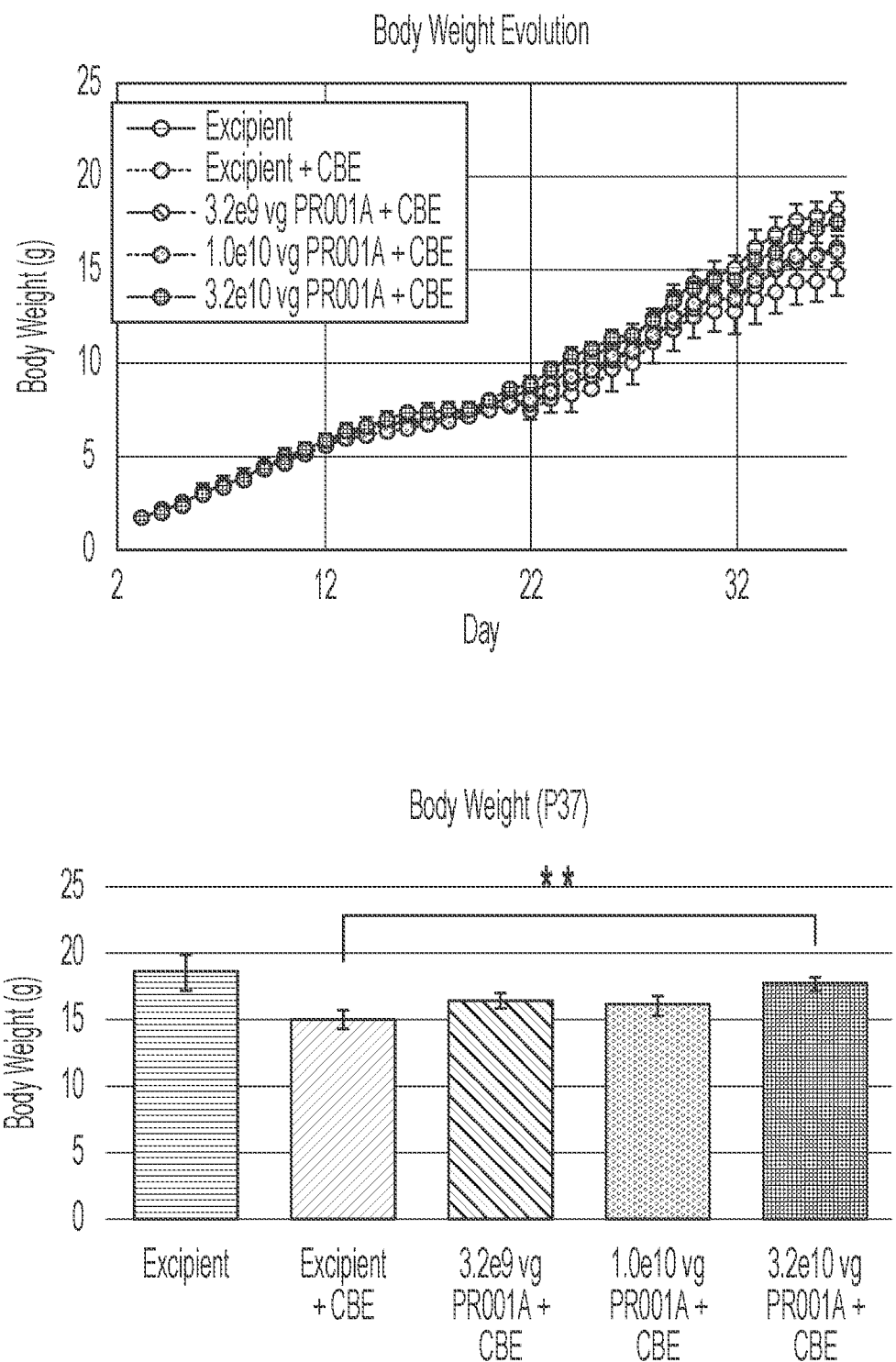
FIG. 15 shows representative data for in-life assessment of rAAV dose ranging in a CBE mouse model. Mice received excipient or one of three different doses of rAAV-GBA1 by ICV delivery at P3: 3.2e9 vg, 1.0e10vg, or 3.2e10 vg. At P8, daily IP treatment of 25 mg/kg CBE was initiated. Mice that received excipient and CBE or excipient and PBS served as controls. All treatment groups started with n=10 (5M/5F) per group. All mice were sacrificed one day after their final CBE dose (P38-P40). All treatment groups were weighed daily, and their weight was analyzed at P36. Motor performance was assessed by latency to fall on Rotarod at P24 and latency to traverse the Tapered Beam at P30. Due to early lethality, the number of mice participating in the behavioral assays was: excipient+PBS n=10, excipient+CBE n=9, and 3.2e9 vg rAAV-GBA1+CBE n=6, 1.0e10 vg rAAV-GBA1+CBE n=10, 3.2e10 vg rAAV-GBA1+CBE n=7. Means are presented. Error bars are SEM; * p<0.05; **p<0.01 for nominal p-values by linear regression in the CBE-treated groups, with gender corrected for as a covariate.
Figure 15:
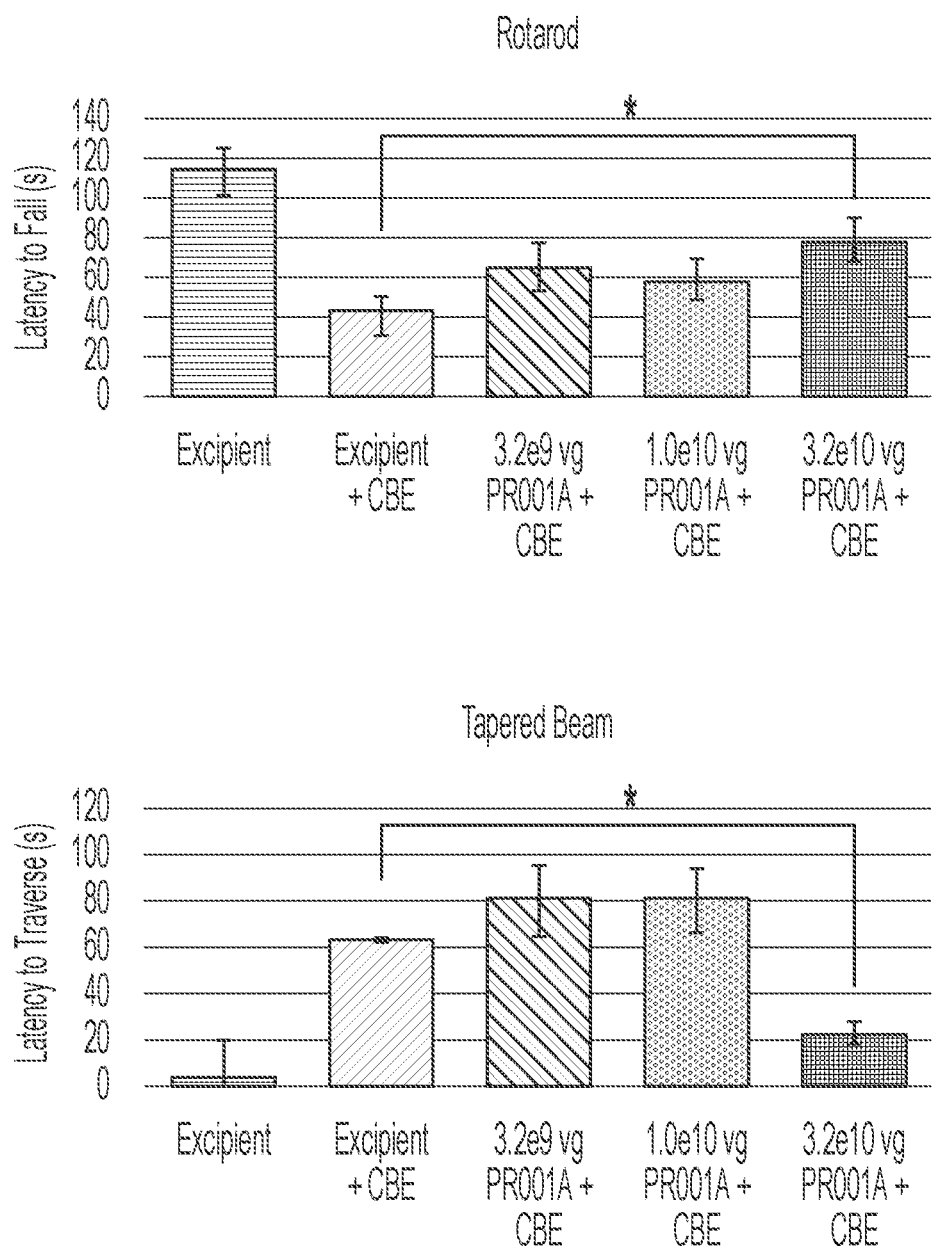

The highest dose of rAAV-GBA1 rescued the CBE treatment-related failure to gain weight at P37. Additionally, this dose resulted in a statistically significant increase in performance on the rotarod and tapered beam compared to the Excipient+CBE treated group (FIG. 15). Lethality was observed in several groups, including both excipient-treated and rAAV-GBA1-treated groups (Excipient+PBS: 0; Excipient+25 mg/kg CBE: 1; 3.2e9 vg rAAV-GBA1+25 mg/kg CBE: 4; 1.0c10 vg rAAV-GBA1+25 mg/kg CBE: 0; 3.2e10 vg rAAV-GBA1+25 mg/kg CBE: 3).

Figure 16:
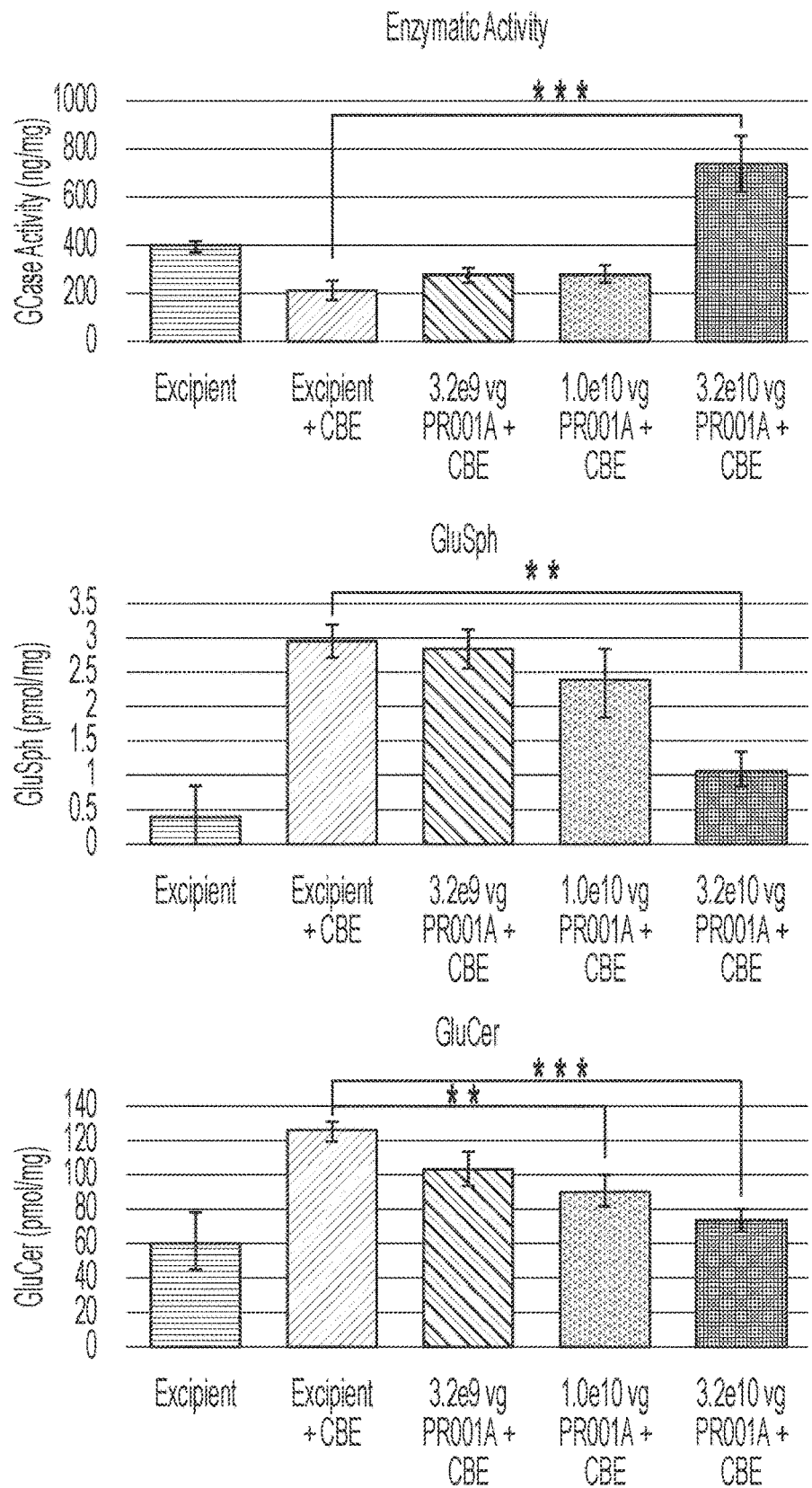
FIG. 16 shows representative data for biochemical assessment of rAAV dose ranging in a CBE mouse model. The cortex of all treatment groups (excipient+PBS n=10, excipient+CBE n=9, and 3.2e9 vg rAAV-GBA1+CBE n=6, 1.0e10 vg rAAV-GBA1+CBE n=10, 3.2e10 vg rAAV-GBA1+CBE n=7) was used to measure GCase activity, GluSph levels, GluCer levels, and vector genomes. GCase activity is shown as ng of GCase per mg of total protein. GluSph and GluCer levels are shown as pmol per mg wet weight of the tissue. Biodistribution is shown as vector genomes per 1 µg of genomic DNA. Vector genome presence was quantified by quantitative PCR using a vector reference standard curve; genomic DNA concentration was evaluated by A260 optical density measurement. Vector genome presence was also measured in the liver (E). Means are presented. Error bars are SEM. p<0.01; *p<0.001 for nominal p-values by linear regression in the CBE-treated groups, with gender corrected for as a covariate.
Figure 16:
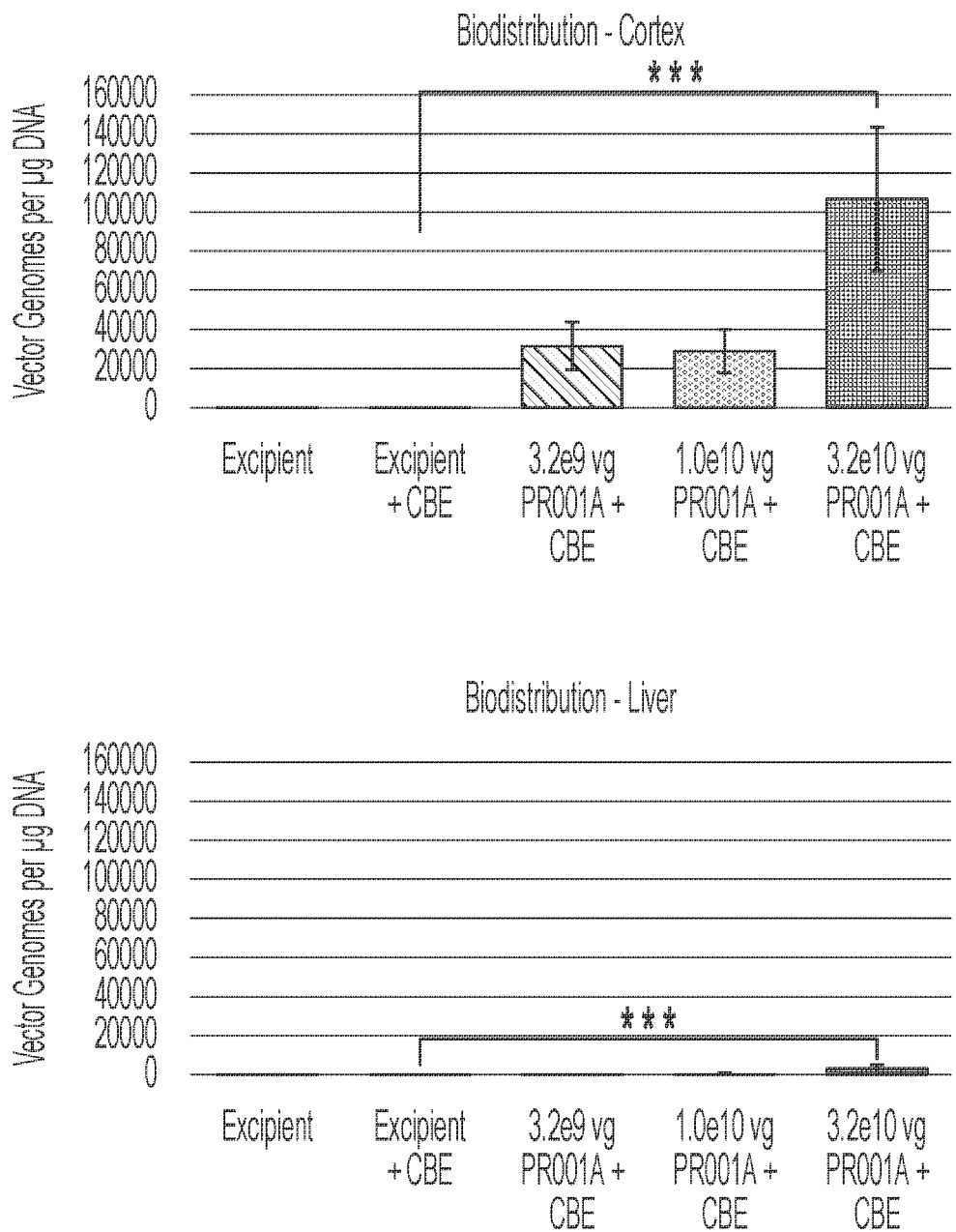

At the completion of the in-life study, mice were sacrificed for biochemical analysis (FIG. 16). GCase activity in the cortex was assessed in biological triplicates by a fluorometric assay. CBE-treated mice showed reduced GCase activity whereas mice that received a high rAAV-GBA1 dose showed a statistically significant increase in GCase activity compared to CBE treatment. CBE-treated mice also had accumulation of GluCer and GluSph, both of which were rescued by administering a high dose of rAAV-GBA1.

Figure 17:
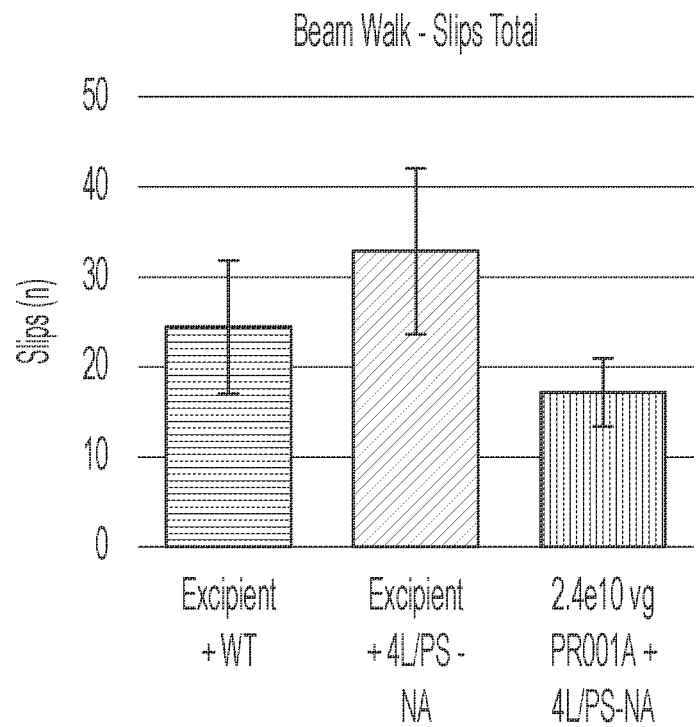
FIG. 17 shows representative data for tapered beam analysis in maximal dose rAAV-GBA1 in a genetic mouse model. Motor performance of the treatment groups (WT+excipient, n=5), 4L/PS-NA+excipient (n=6), and 4L/PS-NA+rAAV-GBA1 (n=5)) was assayed by Beam Walk 4 weeks post rAAV-GBA1 administration. The total slips and active time are shown as total over 5 trials on different beams. Speed and slips per speed are shown as the average over 5 trials on different beams. Means are presented. Error bars are SEM.
Figure 17:
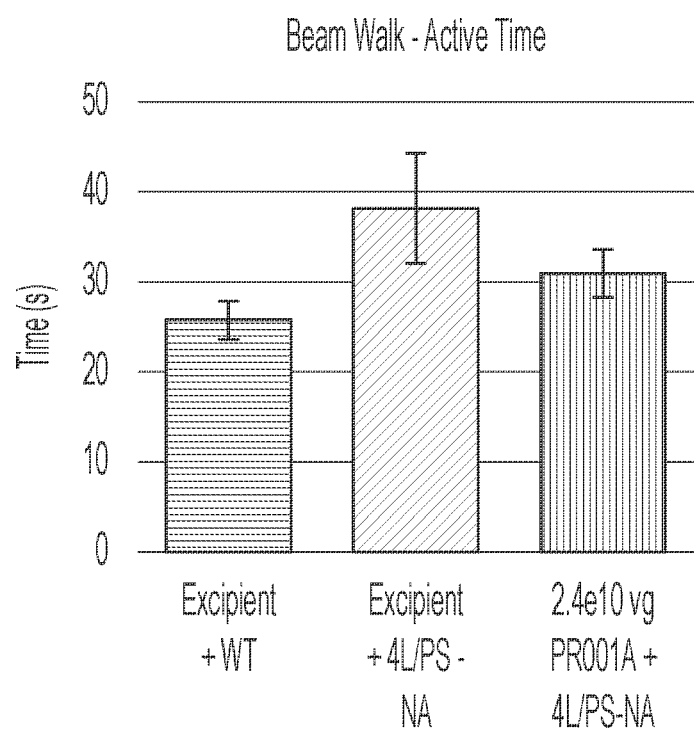
Figure 17:
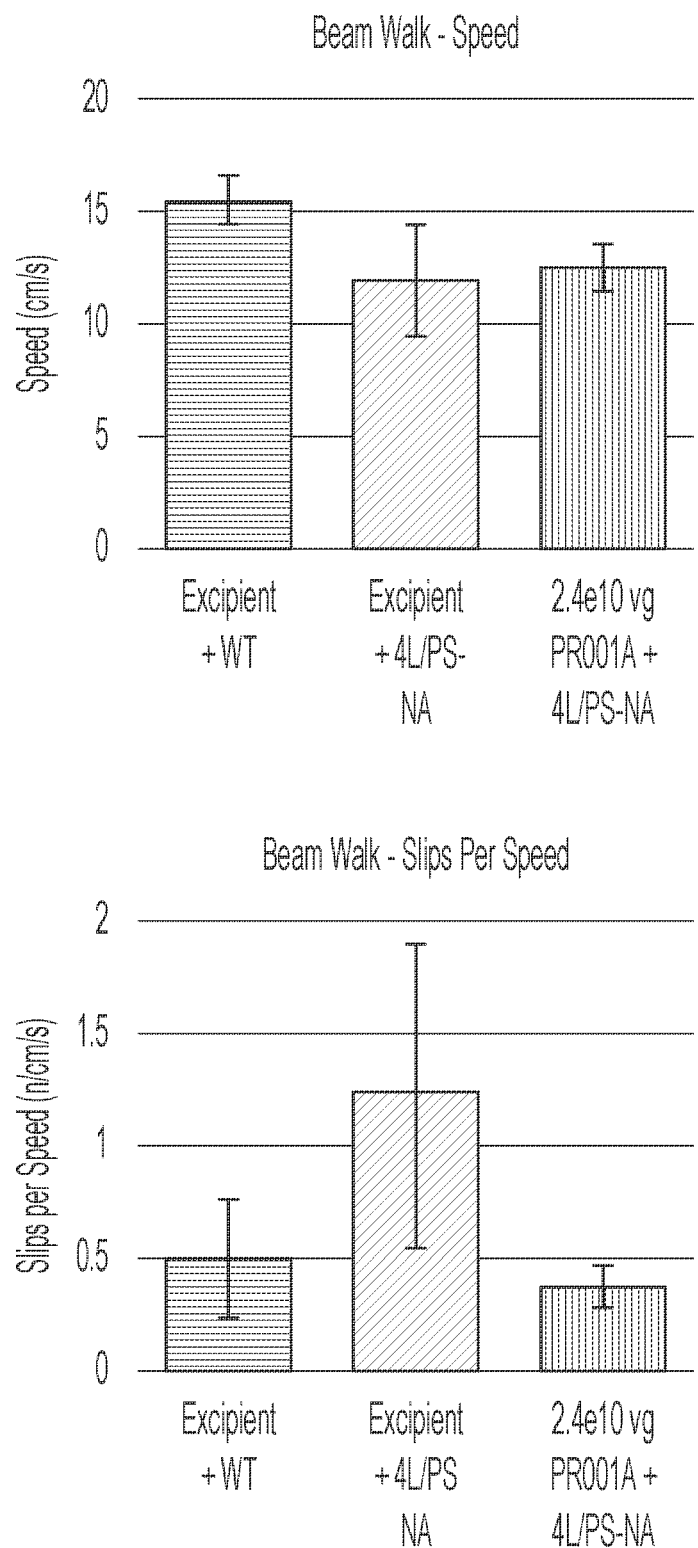

In addition to the established chemical CBE model, rAAV-GBA1 is also evaluated in the 4L/PS-NA genetic model, which is homozygous for the V394L GD mutation in Gba1 and is also partially deficient in saposins, which affect GCase localization and activity. These mice exhibit motor strength, coordination, and balance deficits, as evidenced by their performance in the beam walk, rotarod, and wire hang assays. Typically the lifespan of these mice is less than 22 weeks. In an initial study, 3 μl of maximal titer virus was delivered by ICV at P23, with a final dose of 2.4e10 vg (6.0e10 vg/g brain). With 6 mice per group, the treatment groups were:
  WT+Excipient ICV
  4L/PS-NA+Excipient ICV
  4L/PS-NA+2.4e10 vg (6.0e10 vg/g brain) rAAV-GBA1 ICV Motor performance by the beam walk test was assessed 4 weeks post—rAAV-GBA1 delivery. The group of mutant mice that received rAAV-GBA1 showed a trend towards fewer total slips and fewer slips per speed when compared to mutant mice treated with excipient, restoring motor function to near WT levels (FIG. 17). Since the motor phenotypes become more severe as these mice age, their performance on this and other behavioral tests is assessed at later time points. At the completion of the in-life study, lipid levels, GCase activity, and biodistribution are assessed in these mice.

Additional lower doses of rAAV-GBA1 are currently being tested using the CBE model, corresponding to 0.03×, 0.1×, and 1× the proposed phase 1 high clinical dose. Each group includes 10 mice (5M/5F) per group:
  Excipient ICV
  Excipient ICV+25 mg/kg CBE IP
  3.2e8 vg (2.13e9 vg/g brain) rAAV-GBA1 ICV+25 mg/kg CBE IP
  1.0c9 vg (6.67c9 vg/g brain) rAAV-GBA1 ICV+25 mg/kg CBE IP
  1.0e10 vg (6.67e10 vg/g brain) rAAV-GBA1 ICV+25 mg/kg CBE IP.

In addition to motor phenotypes, lipid levels and GCase activity are assessed in the cortex. Time course of treatments and analyses are also performed.

A larger dose ranging study was initiated to evaluate efficacy and safety data. 10 4L/PS-NA mice (5M/5F per group) were injected with 10 al of rAAV-GBA1. Using an allometric brain weight calculation, the doses correlate to 0.15×, 1.5×, 4.4×, and 14.5× the proposed phase 1 high clinical dose. The injection groups consist of:
  WT+Excipient ICV
  4L/PS-NA+Excipient ICV
  4L/PS-NA+4.3e9 vg (1.1e10 vg/g brain) rAAV-GBA1 ICV
  4L/PS-NA+4.3e10 vg (1.1e11 vg/g/brain) rAAV-GBA1 ICV
  4L/PS-NA+1.3e11 vg (3.2e111 vg/g brain) rAAV-GBA1 ICV
  4L/PS-NA+4.3e11 vg (1.1e12 vg/g brain) rAAV-GBA1 ICV.

A summary of nonclinical studies in the CBE model are shown in Table 3 below.

TABLE 3

Summary of Results in CBE Mouse Model

| Test Material | Study Number | Dose Cohort | Behavioral Changes | | | | | BD | |
|---|---|---|---|---|---|---|---|---|---|
| | | | Tapered Rotarod | Open Beam | Field | Lipids | Enzyme | Brain | Liver |
| rAAV-GBA1 | PRV-2018-005 Dose-ranging rAAV-GBA1 in CBE Model | 3.2e9 vg (2.13e10 vg/g brain) | NS | NS | NS | NS | NS | + | − |
| | | 1.10e10 vg (6.67e10 vg/g brain) | T | NS | NS | T/S | NS | + | + |
| | | 2.3e10 vg (2.13e11 vg/g brain) | S | S | NS | S | S | + | + |
| Variant | PRV-2018-005 Dose-ranging Variant in CBE Model | 8.8e9 vg (5.9e10 vg/g brain) | S | N/A | NS | S | S | + | + |

Note
that positive biodistribution is defined as >100 vg/1 μg genomic DNA.
Abbreviations: BD = biodistribution; NS = nonsignificant; T = trend; S =s ignificant; N/A = not applicable; + = positive; − = negative.

Figure 18:
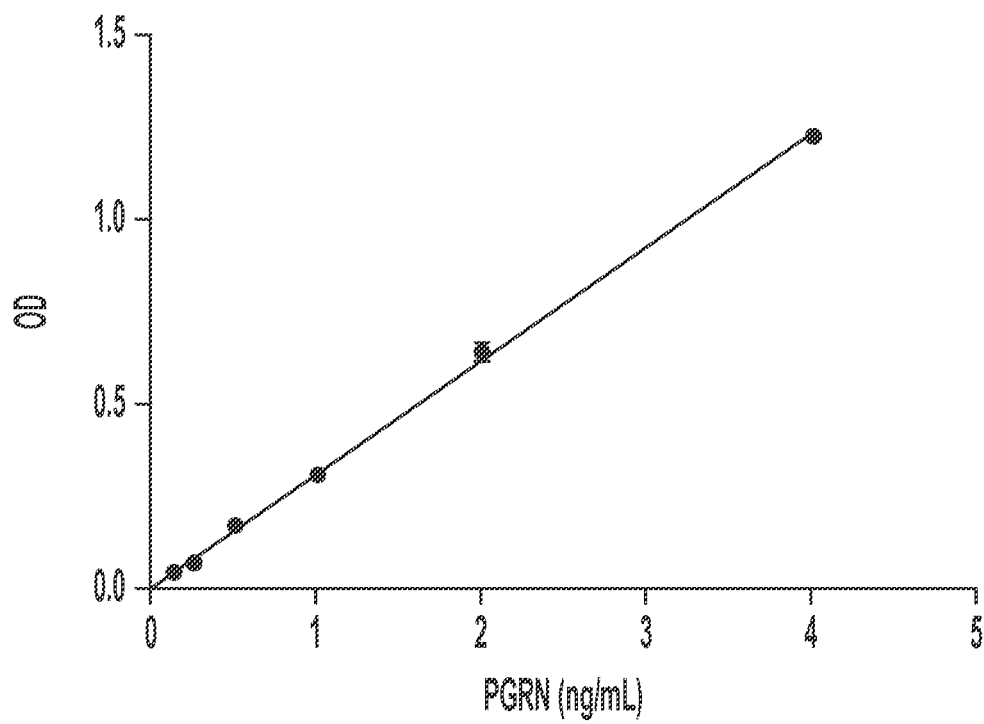
FIG. 18 shows representative data for in vitro expression of rAAV constructs encoding progranulin (PGRN) protein. The left panel shows a standard curve of progranulin (PGRN) ELISA assay. The bottom panel shows a dose-response of PGRN expression measured by ELISA assay in cell lysates of HEK293T cells transduced with rAAV. MOI=multiplicity of infection (vector genomes per cell).
Figure 18:
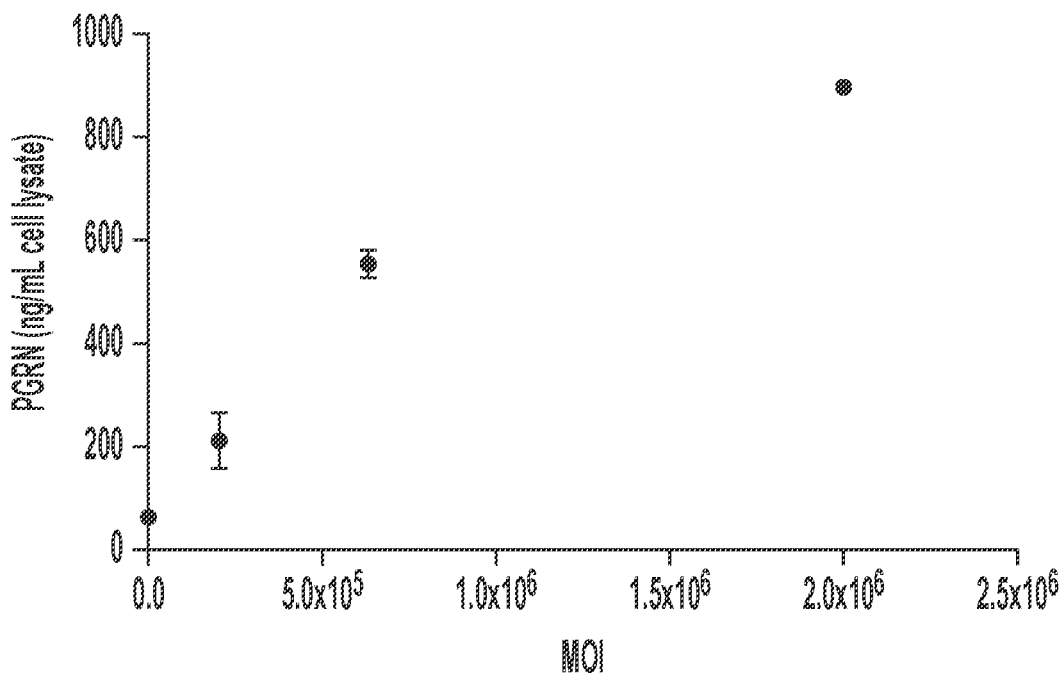

Example 9: In Vitro Analysis of rAA V Vectors rAAV constructs were tested in vitro and in vivo. FIG. 18 shows representative data for in vitro expression of rAAV constructs encoding progranulin (PGRN) protein. The left panel shows a standard curve of progranulin (PGRN) ELISA assay. The bottom panel shows a dose-response of PGRN expression measured by ELISA assay in cell lysates of HEK293T cells transduced with rAAV. MOI=multiplicity of infection (vector genomes per cell).

Figure 19:
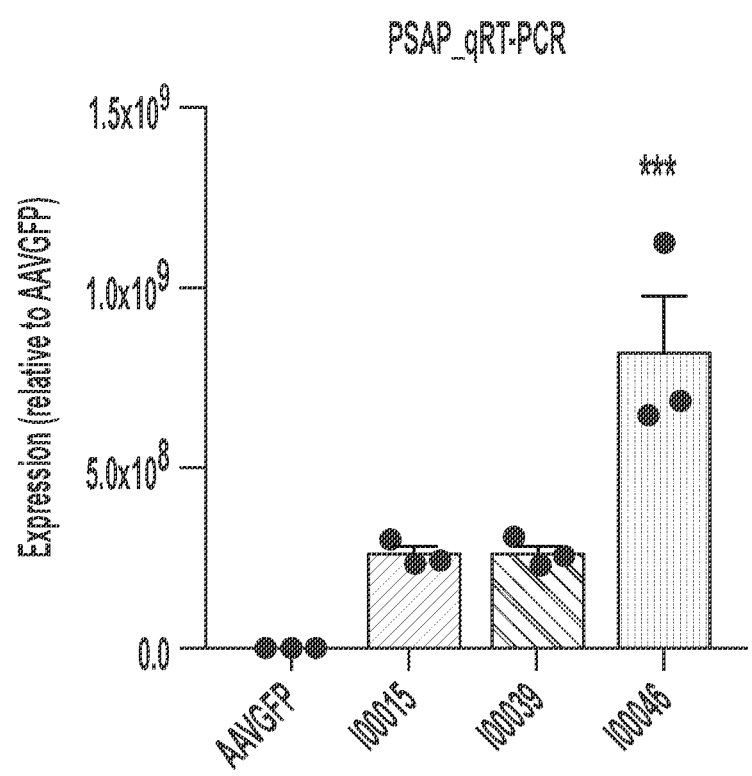
FIG. 19 shows representative data for in vitro expression of rAAV constructs encoding GBA1 in combination with Prosaposin (PSAP), SCARB2, and/or one or more inhibitory nucleic acids. Data indicate transfection of HEK293 cells with each construct resulted in overexpression of the transgenes of interest relative to mock transfected cells.
Figure 19:
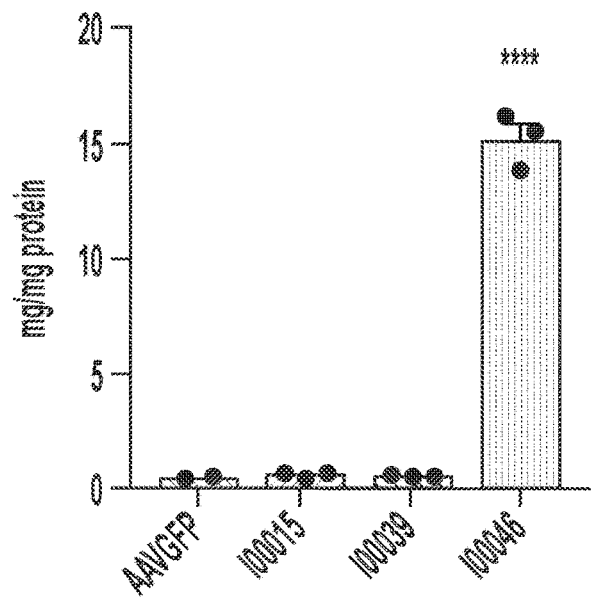
Figure 19:
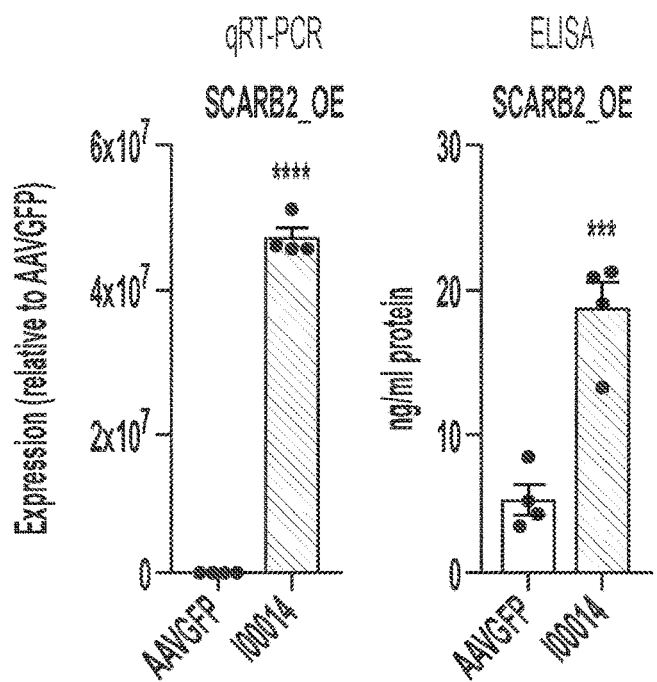
Figure 19:
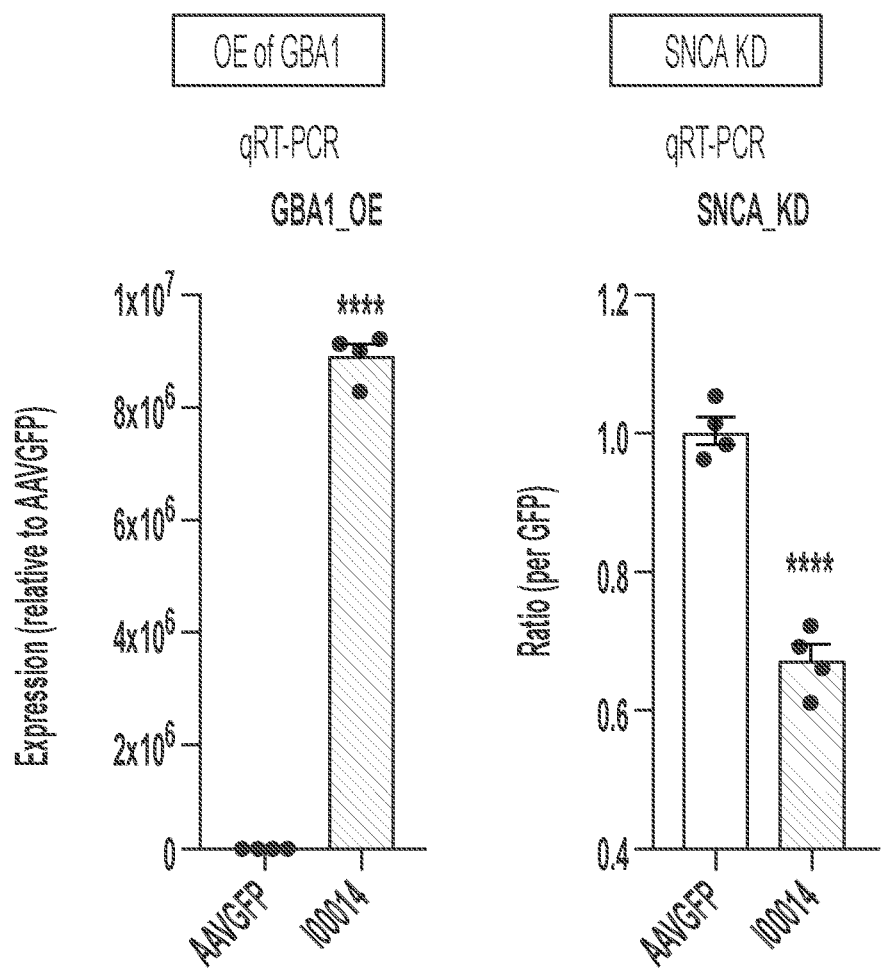

A pilot study was performed to assess in vitro activity of rAAV vectors encoding Prosaposin (PSAP) and SCARB2, alone or in combination with GBA1 and/or one or more inhibitory RNAs. One construct encoding PSAP and progranulin (PGRN) was also tested. Vectors tested include those shown in Table 4. "Opt" refers to a nucleic acid sequence codon optimized for expression in mammalian cells (e.g., human cells). FIG. 19 shows representative data indicating that transfection of HEK293 cells with each of the constructs resulted in overexpression of the corresponding gene product compared to mock transfected cells.

Figure 36A:
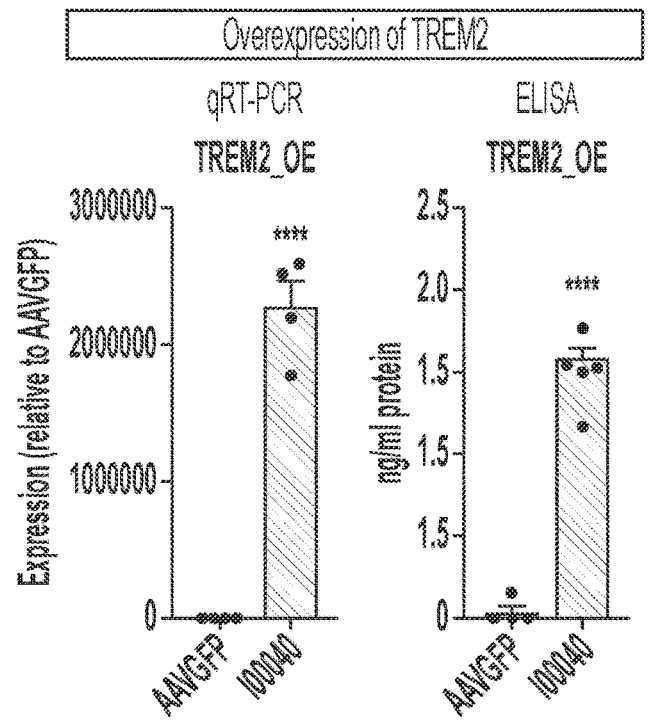
FIGS. 36A-36B show representative data for overexpression of TREM2 and GBA1 in HEK293 cells relative to control transduced cells, as measured by qPCR and ELISA.
Figure 36B:
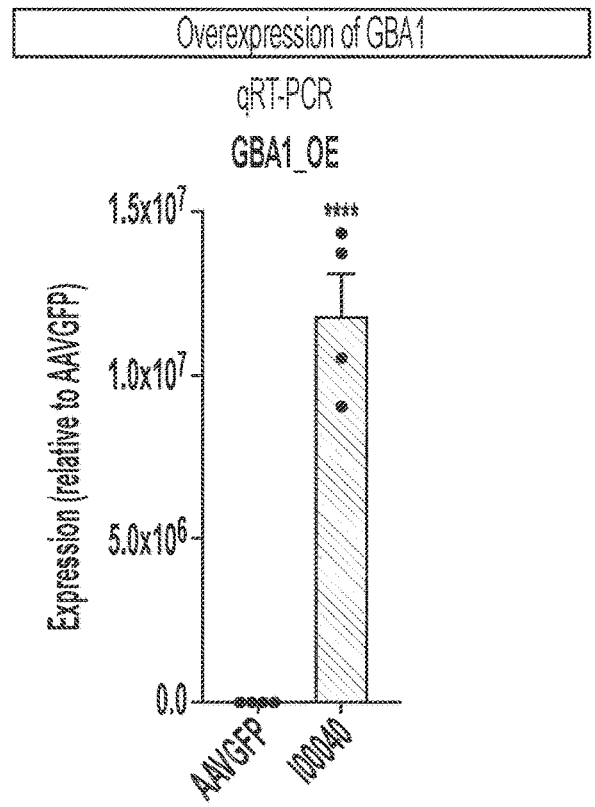

A pilot study was performed to assess in vitro activity of rAAV vectors encoding TREM2, alone or in combination with one or more inhibitory RNAs. Vectors tested include those shown in Table 4. "Opt" refers to a nucleic acid sequence codon optimized for expression in mammalian cells (e.g., human cells). FIGS. 36A-36B show representative data indicating that transfection of HEK293 cells with each of the constructs resulted in overexpression of the corresponding gene product compared to mock transfected cells.

TABLE 4

| ID | Promoter | Inhibitory RNA | Promoter | Transgene |
|---|---|---|---|---|
| I00015 | JL_intronic | SCNA | JetLong | Opt-PSAP_GBA1 |
| I00039 | — | — | JetLong | Opt-PSAP-GRN |
| I00046 | — | — | CBA | Opt-PSAP |
| I00014 | JetLong | SCNA | JetLong | Opt-SCARB2_GBA1 |
| I00040 | | | JL, CD68 | opt-GBA1, TREM2 |

Example 10: Testing of SCNA and TMEM106B shRNA Constructs

HEK293 Cells

Human embryonic kidney 293 cell line (HEK293) were used in this study (#85120602, Sigma-Aldrich). HEK293 cells were maintained in culture media (D-MEM [#11995065, Thermo Fisher Scientific] supplemented with 10% fetal bovine serum [FBS] [#10082147, Thermo Fisher Scientific]) containing 100 units/ml penicillin and 100 µg/ml streptomycin (#15140122, Thermo Fisher Scientific).

Plasmid Transfection

Plasmid transfection was performed using Lipofectamine 2000 transfection reagent (#11668019, Thermo Fisher Scientific) according to the manufacture's instruction. Briefly, HEK293 cells (#12022001, Sigma-Aldrich) were plated at the density of $3 \times 10^5$ cells/ml in culture media without antibiotics. On the following day, the plasmid and Lipofectamine 2000 reagent were combined in Opti-MEM solution (#31985062, Thermo Fisher Scientific). After 5 minutes, the mixtures were added into the HEK293 culture. After 72 hours, the cells were harvested for RNA or protein extraction, or subjected to the imaging analyses. For imaging analyses, the plates were pre-coated with 0.01% poly-L-Lysine solution (P8920, Sigma-Aldrich) before the plating of cells.

Gene Expression Analysis by Quantitative Real-Time PCR (qRT-PCR)

Relative gene expression levels were determined by quantitative real-time PCR (qRT-PCR) using Power SYBR Green Cells-to-CT Kit (#4402955, Thermo Fisher Scientific) according to the manufacturer's instruction. The candidate plasmids were transiently transfected into HEK293 cells plated on 48-well plates ($7.5 \times 10^4$ cells/well) using Lipofectamine 2000 transfection reagent (0.5 µg plasmid and 1.5 µl reagent in 50 µl Opti-MEM solution). After 72 hours, RNA was extracted from the cells and used for reverse transcription to synthesize cDNA according to the manufacturer's instruction. For quantitative PCR analysis, 2~5 µl of cDNA products were amplified in duplicates using gene specific primer pairs (250 nM final concentration) with Power SYBR Green PCR Master Mix (#4367659, Thermo Fisher Scientific). The primer sequences for SNCA, TMEM106B, and GAPDH genes were: 5'-AAG AGG GTG TTC TCT ATG TAG GC-3' (SEQ ID NO: 71), 5'-GCT CCT CCA ACA TTT GTC ACT T-3' (SEQ ID NO: 72) for SNCA, 5'-ACA CAG TAC CTA CCG TTA TAG CA-3' (SEQ ID NO: 73), 5'-TGT TGT CAC AGT AAC TTG CAT CA-3' (SEQ ID NO: 74) for TMEM106B, and 5'-CTG GGC TAC ACT GAG CAC C-3' (SEQ ID NO: 75), 5'-AAG TGG TCG TTG AGG GCA ATG-3' (SEQ ID NO: 76) for GAPDH. Quantitative PCR was performed in a QuantStudio 3 Real-Time PCR system (Thermo Fisher Scientific). Expression levels were normalized by the housekeeping gene GAPDH and calculated using the comparative CT method.

Fluorescence Imaging Analysis

EGFP reporter plasmids, which contain 3'-UTR of human SNCA gene at downstream of EGFP coding region, were used for the validation of SNCA and TMEM106B knockdown plasmids. EGFP reporter plasmids and candidate knockdown plasmids were simultaneously transfected into HEK293 cells plated on poly-L-Lysine coated 96-well plates ($3.0 \times 10^4$ cells/well) using Lipofectamine 2000 transfection reagent (0.04 µg reporter plasmid, 0.06 µg knockdown plasmid and 0.3 µl reagent in 10 µl Opti-MEM solution). After 72 hours, the fluorescent intensities of EGFP signal were measured at excitation 488 nm/emission 512 nm using Varioskan LUX multimode reader (Thermo Fisher Scientific). Cells were fixed with 4% PFA at RT for 10 minutes, and incubated with D-PBS containing 40 µg/ml 7-aminoactinomycin D (7-AAD) for 30 min at RT. After washing with D-PBS, the fluorescent intensities of 7-AAD signal were measured at excitation 546 nm/emission 647 nm using Varioskan reader to quantify cell number. Normalized EGFP signal per 7-AAD signal levels were compared with the control knockdown samples.

Enzyme-Linked Immunosorbent Assay (ELISA)

α-Synuclein reporter plasmids, which contain 3'-UTR of human SNCA gene or TMEM106B gene downstream of SNCA coding region, were used for the validation of knockdown plasmids at the protein level. Levels of α-synuclein protein were determined by ELISA (#KHB0061, Thermo Fisher Scientific) using the lysates extracted from HEK293 cells. The candidate plasmids were transiently transfected into HEK293 cells plated on 48-well plates ($7.5 \times 10^4$ cells/well) using Lipofectamine 2000 transfection reagent (0.1 µg reporter plasmid, 0.15 µg knockdown plasmid and 0.75 µl reagent in 25 µl Opti-MEM solution). After 72 hours, cells were lysed in radioimmunoprecipitation assay (RIPA) buffer (#89900, Thermo Fisher Scientific) supplemented with protease inhibitor cocktail (#P8340, Sigma-Aldrich), and sonicated for a few seconds. After incubation on ice for 30 min, the lysates were centrifuged at 20,000×g at 4° C. for 15 min, and the supernatant was collected. Protein levels were quantified. Plates were read in a Varioskan plate reader at 450 nm, and concentrations were calculated using SoftMax Pro 5 software. Measured protein concentrations were normalized to total protein concentration determined with a bicinchoninic acid assay (#23225, Thermo Fisher Scientific).

Figure 37:
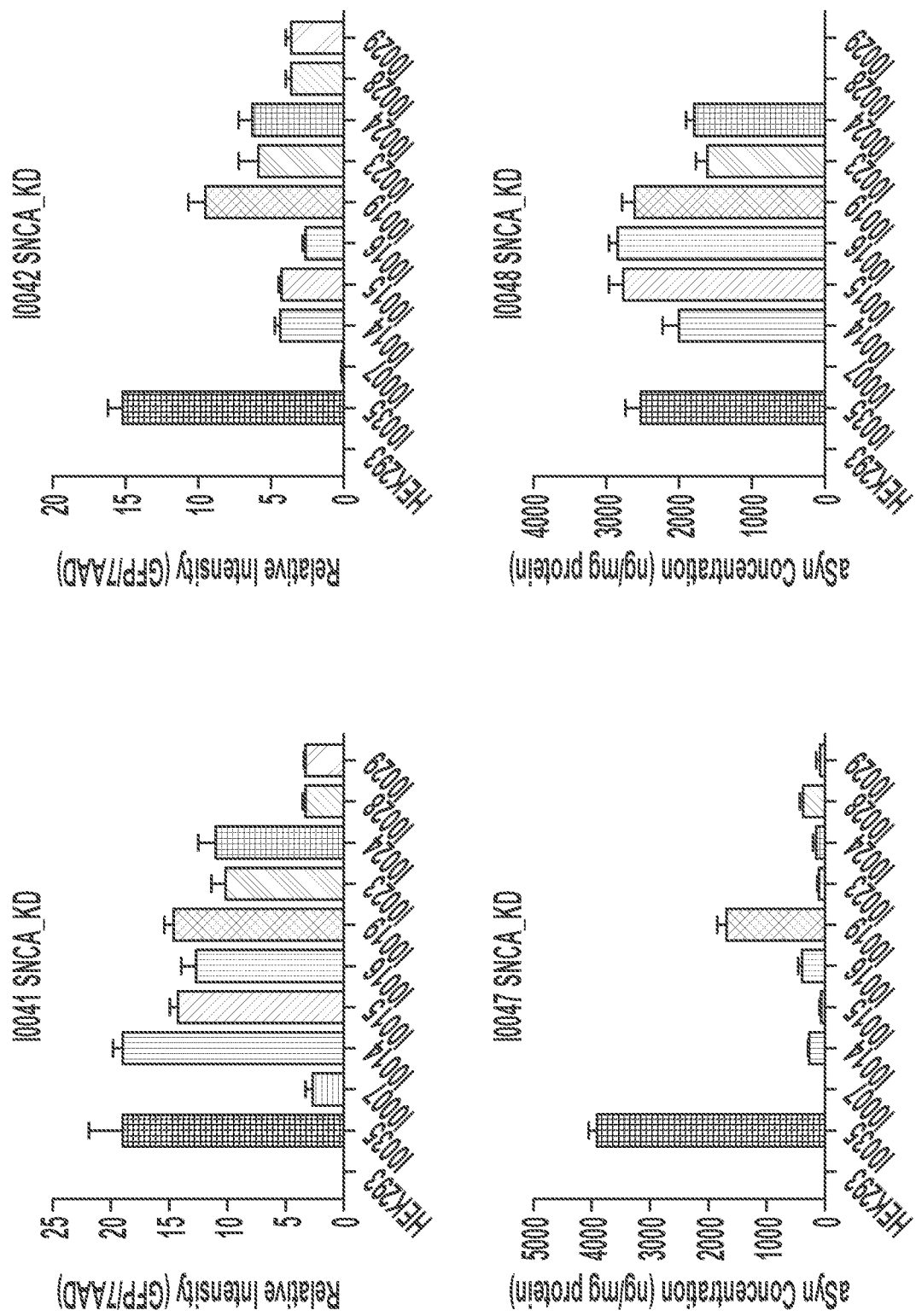
FIG. 37 shows representative data indicating successful silencing of SCNA in vitro by GFP reporter assay (top) and α-Syn assay (bottom).
Figure 38:
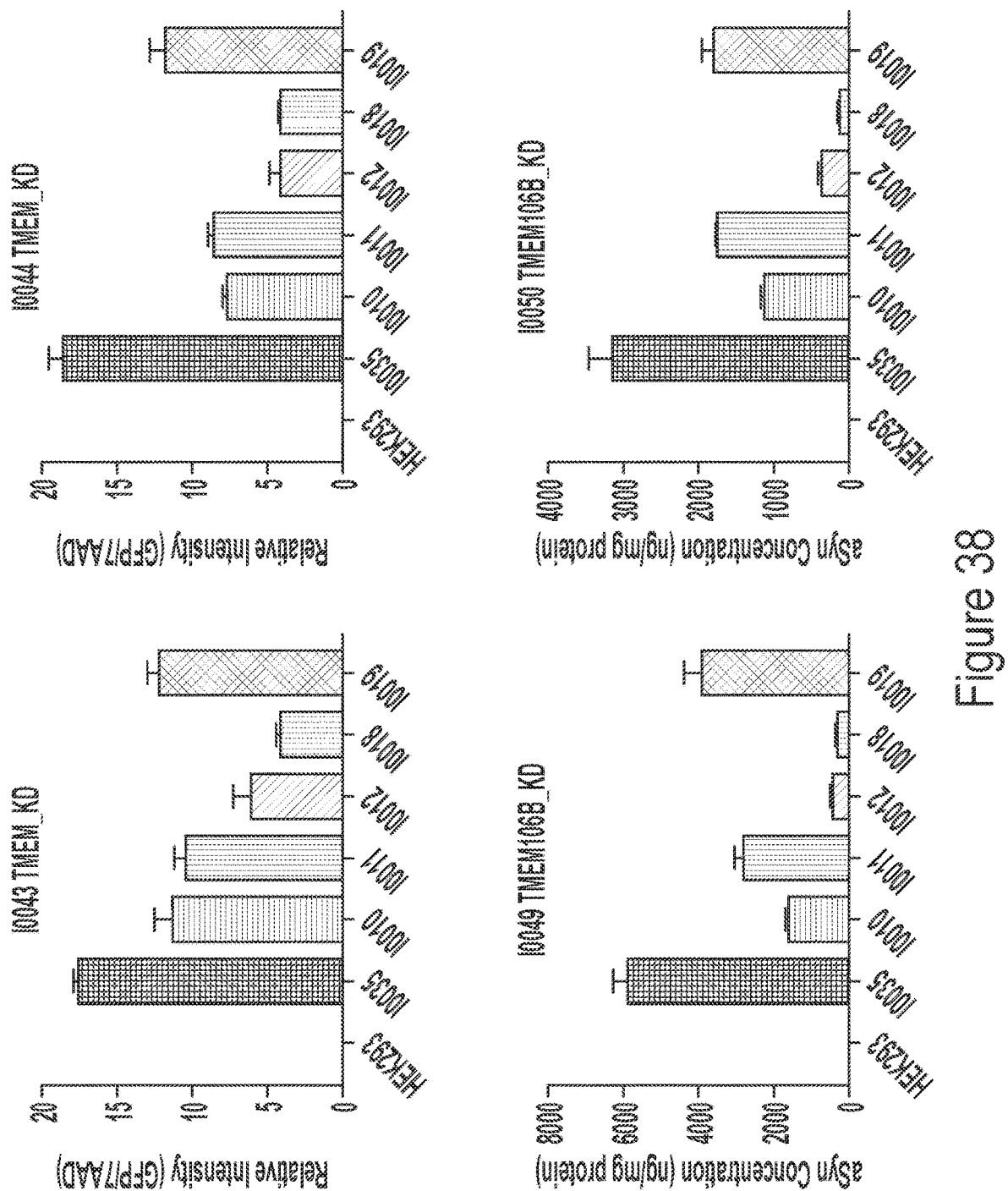
FIG. 38 shows representative data indicating successful silencing of TMEM106B in vitro by GFP reporter assay (top) and α-Syn assay (bottom).

FIG. 37 and Table 5 show representative data indicating successful silencing of SCNA in vitro by GFP reporter assay (top) and α-Syn assay (bottom). FIG. 38 and Table 6 show representative data indicating successful silencing of TMEM106B in vitro by GFP reporter assay (top) and α-Syn assay (bottom).

TABLE 5

| ID | Promoter | Knockdown | Promoter | Overexpress |
| --- | --- | --- | --- | --- |
| I00007 | CMV_intronic | SNCA_mi | CMV | opt-GBA1 |
| I00008 | H1 | SNCA_sh | CMV | opt-GBA1 |
| I00009 | H1 | SNCA_Pubsh4 | CMV | opt-GBA1 |
| I00014 | JL_intronic | SNCA_mi | JetLong | opt-SCARB2_GBA |
| I00015 | JL_intronic | SNCA_mi | JetLong | opt-PSAP_GBA |
| I00016 | JL_intronic | SNCA_mi | JetLong | opt-CTSB_GBA |
| I00019 | JL_intronic | SNCA_TMEM_mi | JetLong | opt-VPS35 |
| I00023 | JL_intronic | SNCA_mi | JetLong | opt-GBA1_IL34 |
| I00024 | JL_intronic | SNCA_mi | JetLong | opt-GBA2 |
| I00028 | intronic | SNCA_Broadsh | CMV | opt-GBA1 |
| I00029 | intronic | SNCA_Pubsh4 | CMV | opt-GBA1 |

TABLE 6

| ID | Promoter | Knockdown | Promoter | Overexpress |
| --- | --- | --- | --- | --- |
| I00010 | H1 | TMEM_Pubsh | CMV | opt-GRN |
| I00011 | JL_intronic | TMEM_mi | JetLong | opt-GBA1_GRN |
| I00012 | H1 | TMEM_sh | CMV | opt-GRN |
| I00019 | JL_intronic | SNCA_TMEM_mi | JetLong | opt-VPS35 |

Example 11: ITR "D" Sequence Placement and Cell Transduction

Figure 40:
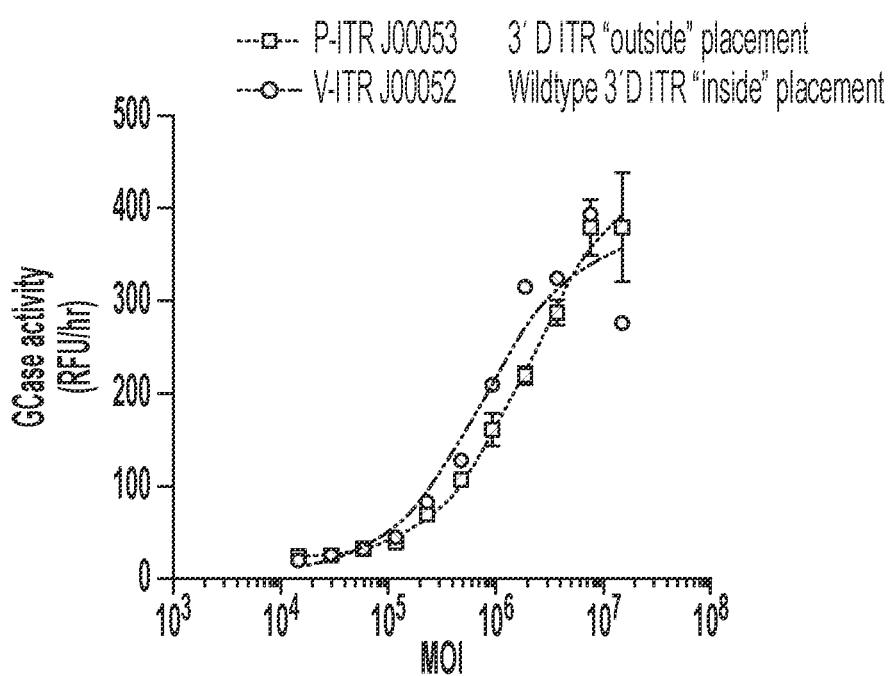
FIG. 40 shows data for transduction of HEK293 cells using rAAVs having ITRs with wild-type (circles) or alternative (e.g., "outside"; squares) placement of the "D" sequence. The rAAVs having ITRs placed on the "outside" were able to transduce cells as efficiently as rAAVs having wild-type ITRs.

The effect of placement of ITR "D" sequence on cell transduction of rAAV vectors was investigated. HEK293 cells were transduced with Gcase-encoding rAAVs having 1) wild-type ITRs (e.g., "D" sequences proximal to the transgene insert and distal to the terminus of the ITR) or 2) ITRs with the "D" sequence located on the "outside" of the vector (e.g., "D" sequence located proximal to the terminus of the ITR and distal to the transgene insert), as shown in FIG. 20. Surprisingly, data indicate that rAAVs having the "D" sequence located in the "outside" position retain the ability to be packaged and transduce cells efficiently (FIG. 40).

Example 12: In Vitro Testing of Progranulin rAAVs

Figure 39:
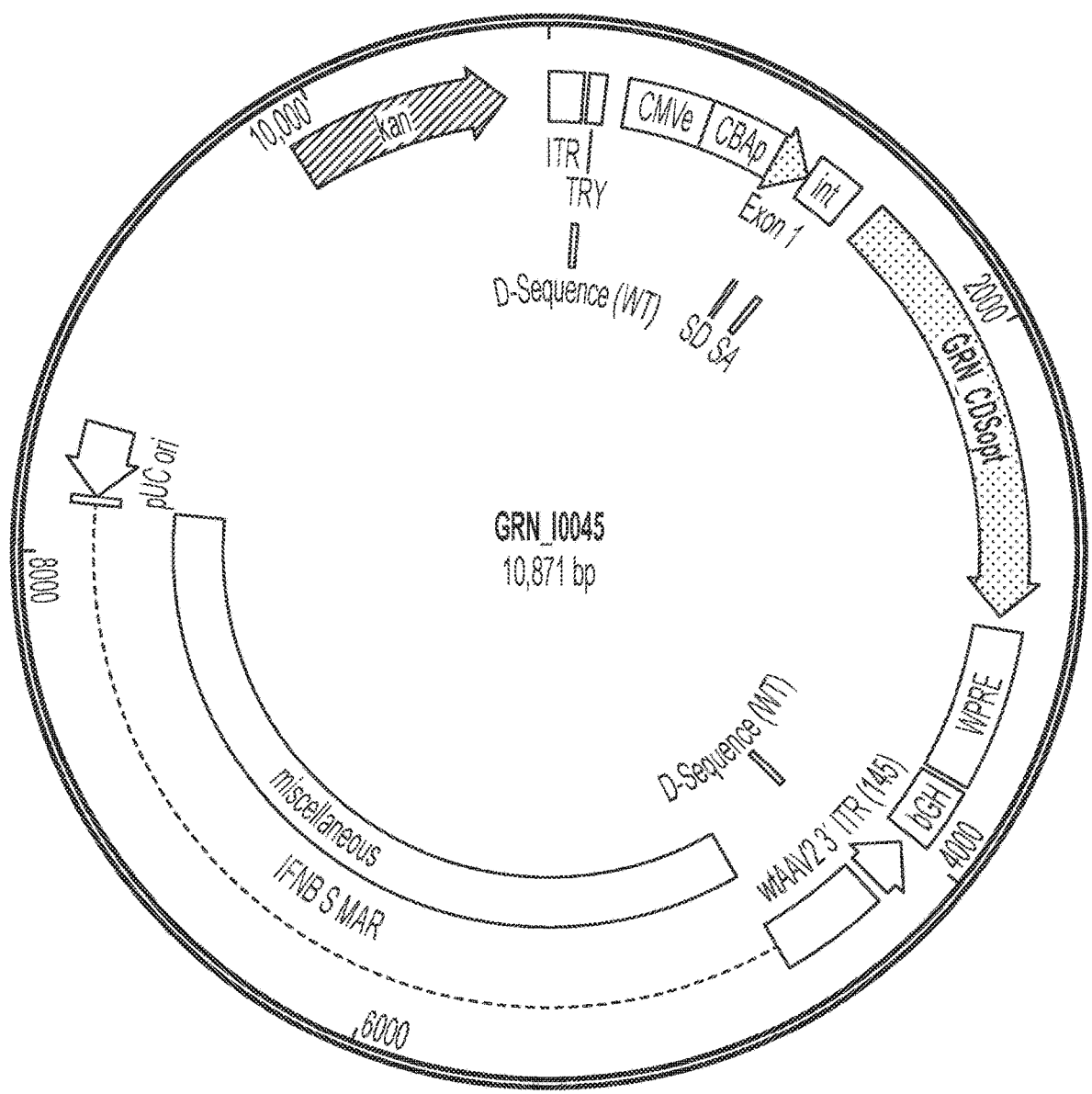
FIG. 39 is a schematic depicting one embodiments of a vector comprising an expression construct encoding PGRN.

FIG. 39 is a schematic depicting one embodiments of a vector comprising an expression construct encoding PGRN. Progranulin is overexpressed in the CNS of rodents deficient in GRN, either heterozygous or homozygous for GRN deletion, by injection of an rAAV vector encoding PGRN (e.g., codon-optimized PGRN), either by intraparenchymal or intrathecal injection such as into the cisterna magna.

Mice are injected at 2 months or 6 months of age, and aged to 6 months or 12 months and analyzed for one or more of the following: expression level of GRN at the RNA and protein levels, behavioral assays (e.g., improved movement), survival assays (e.g., improved survival), microglia and inflammatory markers, gliosis, neuronal loss, Lipofuscinosis, and/or Lysosomal marker accumulation rescue, such as LAMP1. Assays on PGRN-deficient mice are described, for example by Arrant et al. (2017) *Brain* 140: 1477-1465; Arrant et al. (2018) *J. Neuroscience* 38(9):2341-2358; and Amado et al. (2018) doi:https://doi.org/10.1101/30869; the entire contents of which are incorporated herein by reference.

EQUIVALENTS

This application incorporates by reference the contents of the following documents in their entirety: the International PCT Application referred to by filed Oct. 3, 2018; International PCT Application referred to by filed Oct. 3, 2018; Provisional Application Ser. No. 62/567,296, filed Oct. 3, 2017, entitled "GENE THERAPIES FOR LYSOSOMAL DISORDERS"; 62/567,311, filed Oct. 3, 2017, entitled "GENE THERAPIES FOR LYSOSOMAL DISORDERS"; 62/567,319, filed Oct. 3, 2017, entitled "GENE THERAPIES FOR LYSOSOMAL DISORDERS"; 62/567,301, filed Oct. 3, 2018, entitled "GENE THERAPIES FOR LYSOSOMAL DISORDERS"; 62/567,310, filed Oct. 3, 2017, entitled "GENE THERAPIES FOR LYSOSOMAL DISORDERS"; 62/567,303, filed Oct. 3, 2017, entitled "GENE THERAPIES FOR LYSOSOMAL DISORDERS"; and 62/567,305, filed Oct. 3, 2017, entitled "GENE THERAPIES FOR LYSOSOMAL DISORDERS".

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

It should also be understood that, unless clearly indicated to the contrary, in any methods claimed herein that include more than one step or act, the order of the steps or acts of the method is not necessarily limited to the order in which the steps or acts of the method are recited.

SEQUENCES

In some embodiments, an expression cassette encoding one or more gene products (e.g., a first, second and/or third gene product) comprises or consists of (or encodes a peptide having) a sequence set forth in any one of SEQ ID NOs: 1-78. In some embodiments, a gene product is encoded by a portion (e.g., fragment) of any one of SEQ ID NOs: 1-78.

What is claimed is:

1. An isolated nucleic acid comprising
   (i) an expression construct comprising a transgene encoding a prosaposin (PSAP) protein, wherein the PSAP protein is encoded by the nucleic acid sequence in SEQ ID NO: 17; and
   (ii) two adeno-associated virus (AAV) inverted terminal repeat (ITR) sequences flanking the expression construct.

2. The isolated nucleic acid of claim 1, wherein the transgene is operably linked to a promoter.

3. The isolated nucleic acid of claim 2, wherein the promoter comprises a chicken beta-actin (CBA) promoter.

4. The isolated nucleic acid of claim 1, wherein the ITRs are AAV2 ITRs.

5. A Baculovirus vector comprising the isolated nucleic acid of claim 1.

6. A cell comprising:
   (i) a first vector encoding one or more adeno-associated virus (AAV) rep protein and/or one or more AAV virus cap protein; and
   (ii) a second vector comprising the isolated nucleic acid of claim 1.

7. The cell of claim 6, wherein the first vector is a plasmid and the second vector is a plasmid.

8. The cell of claim 6, wherein the first vector is a Baculovirus vector and the second vector is a Baculovirus vector.

9. A recombinant adeno-associated virus (rAAV) vector comprising a nucleic acid comprising an expression construct comprising a transgene encoding a prosaposin (PSAP) protein flanked by two adeno-associated virus (AAV) inverted terminal repeats (ITRs), wherein the PSAP protein is encoded by the nucleic acid sequence in SEQ ID NO: 17.

10. The rAAV vector of claim 9, wherein the transgene is operably linked to a promoter.

11. The rAAV vector of claim 10, wherein the promoter comprises a chicken beta-actin (CBA) promoter.

12. The rAAV vector of claim 9, wherein each ITR sequence is a wild-type AAV2 ITR sequence.

13. A plasmid comprising the rAAV vector of claim 9.

14. A recombinant adeno-associated virus (rAAV) comprising:
 (i) an adeno-associated virus (AAV) capsid protein; and
 (ii) the rAAV vector of claim 9.

15. The rAAV of claim 14, wherein the AAV capsid protein is AAV9 capsid protein.

16. A recombinant adeno-associated virus (rAAV) vector comprising a nucleic acid comprising, in 5' to 3' order:
 (a) a 5' adeno-associated virus (AAV) inverted terminal repeat (ITR);
 (b) a CMV enhancer;
 (c) a chicken beta actin (CBA) promoter;
 (d) a transgene encoding a prosaposin (PSAP) protein, wherein the PSAP protein is encoded by the nucleic acid sequence in SEQ ID NO: 17;
 (e) a Woodchuck hepatitis virus Posttranscriptional Regulatory Element (WPRE);
 (f) a Bovine Growth Hormone polyA (bGH polyA) signal tail; and
 (g) a 3' AAV ITR.

17. A recombinant adeno-associated virus (rAAV) comprising:
 (i) an adeno-associated virus (AAV) capsid protein; and
 (ii) the rAAV vector of claim 16.

18. The rAAV of claim 17, wherein the AAV capsid protein is AAV9 capsid protein.

19. A method of producing an rAAV, the method comprising:
 (i) delivering to a cell a first vector encoding one or more adeno-associated virus (AAV) rep protein and/or one or more AAV cap protein, and the recombinant AAV (rAAV) vector of claim 16;
 (ii) culturing the cells under conditions allowing for packaging the rAAV; and
 (iii) harvesting the cultured host cell or culture medium for collection of the rAAV.

* * * * *

UNITED STATES PATENT AND TRADEMARK OFFICE
CERTIFICATE OF CORRECTION

| | |
|---|---|
| PATENT NO. | : 11,661,585 B2 |
| APPLICATION NO. | : 16/841539 |
| DATED | : May 30, 2023 |
| INVENTOR(S) | : Asa Abeliovich et al. |

It is certified that error appears in the above-identified patent and that said Letters Patent is hereby corrected as shown below:

In the Claims

Claim 6, at Column 384, Lines 64-65:
"one or more AAV virus cap protein;"
Should read:
-- one or more AAV cap protein; --

Claim 16, at Column 385, Line 25:
"A recombinant adeno-associated virus (AAV) vector"
Should read:
-- A recombinant adeno-associated virus (rAAV) vector --

Signed and Sealed this
First Day of October, 2024

Katherine Kelly Vidal
*Director of the United States Patent and Trademark Office*